US008143305B2

(12) United States Patent
Anilkumar et al.

(10) Patent No.: US 8,143,305 B2
(45) Date of Patent: Mar. 27, 2012

(54) 2,3-SUBSTITUTED INDOLE DERIVATIVES FOR TREATING VIRAL INFECTIONS

(75) Inventors: Gopinadhan N. Anilkumar, Edison, NJ (US); Frank Bennett, Cranford, NJ (US); Tin-Yau Chan, Edison, NJ (US); Kevin X. Chen, Edison, NJ (US); Mousumi Sannigrahi, Summit, NJ (US); Francisco Velazquez, Clinton, NJ (US); Srikanth Venkatraman, Edison, NJ (US); Qingbei Zeng, Edison, NJ (US); Jose S. Duca, Cranford, NJ (US); Charles A. Lesburg, Short Hills, NJ (US); Joseph A. Kozlowski, Princeton, NJ (US); F. George Njoroge, Warren, NJ (US); Stuart B. Rosenblum, West Orange, NJ (US); Neng-Yang Shih, Lexington, MA (US); Stephen J. Gavalas, Manhasset, NY (US); Yueheng Jiang, Whitehouse Station, NJ (US); Patrick A. Pinto, Morris Plains, NJ (US); Haiyan Pu, Livingston, NJ (US); Oleg B. Selyutin, West Windsor, NJ (US); Bancha Vibulbhan, Kenilworth, NJ (US); Li Wang, Nanuet, NY (US); Wanli Wu, New Haven, CT (US); Weiying Yang, Monmouth Junction, NJ (US); Yuhua Huang, Westfield, NJ (US); Hsueh-Cheng Huang, Scarsdale, NY (US); Robert Palermo, Seattle, WA (US); Boris Feld, New Milford, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 12/675,897

(22) PCT Filed: Aug. 27, 2008

(86) PCT No.: PCT/US2008/010130
§ 371 (c)(1),
(2), (4) Date: Oct. 22, 2010

(87) PCT Pub. No.: WO2009/032116
PCT Pub. Date: Mar. 12, 2009

(65) Prior Publication Data
US 2011/0033417 A1    Feb. 10, 2011

Related U.S. Application Data

(60) Provisional application No. 60/968,745, filed on Aug. 29, 2007.

(51) Int. Cl.
*A01N 43/38* (2006.01)
*A61K 31/40* (2006.01)
*C07D 209/04* (2006.01)

(52) U.S. Cl. ........ 514/412; 548/469; 546/122; 546/152; 546/255

(58) Field of Classification Search .................. 548/469; 514/412; 546/122, 152, 255
See application file for complete search history.

(56) References Cited

U.S. PATENT DOCUMENTS

| 3,632,805 | A | 1/1972 | Yamamoto at al. |
| 4,634,697 | A | 1/1987 | Hamashima |
| 4,812,561 | A | 3/1989 | Hamashima et al. |
| 4,933,443 | A | 6/1990 | Hamashima et al. |
| 5,017,380 | A | 5/1991 | Hamashima et al. |
| 6,800,434 | B2 | 10/2004 | Saksena et al. |
| 6,838,475 | B2 | 1/2005 | Arasappan et al. |
| 6,846,802 | B2 | 1/2005 | Chen et al. |
| 6,911,428 | B2 | 6/2005 | Zhu et al. |
| 6,914,122 | B2 | 7/2005 | Venkatraman et al. |
| 7,012,066 | B2 | 3/2006 | Saksena et al. |
| 2002/0160962 | A1 | 10/2002 | Saksena et al. |
| 2004/0077704 | A1 | 4/2004 | Beight et al. |
| 2005/0075331 | A1 | 4/2005 | Pratt et al. |
| 2005/0101770 | A1 | 5/2005 | Presta |
| 2005/0176648 | A1 | 8/2005 | Saksena et al. |
| 2005/0249702 | A1 | 11/2005 | Njoroge et al. |
| 2007/0274951 | A1 | 11/2007 | Tong et al. |

FOREIGN PATENT DOCUMENTS

| AU | 2002313410 B2 | 7/2002 |
| DE | 648639 C | 6/1937 |
| EP | 0449196 A2 | 10/1991 |
| FR | 2768146 A1 | 3/1999 |
| JP | 4-149429 | 5/2004 |
| WO | 96/37619 A1 | 11/1996 |
| WO | 98/14181 A1 | 4/1998 |
| WO | 98/17679 A1 | 4/1998 |
| WO | 98/22496 A2 | 5/1998 |
| WO | 99/07734 A2 | 2/1999 |
| WO | 02/30895 A1 | 4/2002 |

(Continued)

OTHER PUBLICATIONS

Beaulieu et al., "Inhibitors of the HCV NS5B polymerase: New hope for the treatment of hepatitis C infections", Current Opinion in Investigational Drugs, 2004. vol. 5. pp. 838-850. No. 8.
Behrens et al., "Identification and properties of the RNA-dependent RNA polymerase of hepatitis C virus", The EMBO Journal, 1996, vol. 15, pp. 12-22, No. 1.
Bioworld Today, 9 (217):4 Nov. 10, 1998, pp. 1-5.
Birnbock et al., "Sulfate Derivatives of 2-Phenylindols as Novel Steroid Sulfatase Inhibitors", Biochemical Pharmacology, 1990, vol. 39, pp. 1709-1713, No. 11.

(Continued)

*Primary Examiner* — Paul V. Ward
(74) *Attorney, Agent, or Firm* — Jeffrey P. Bergman; Sheldon O. Heber

(57) ABSTRACT

The present invention relates to 2,3-Substituted Indole Derivatives, compositions comprising at least one 2,3-Substituted Indole Derivative, and methods of using the 2,3-Substituted Indole Derivatives for treating or preventing a viral infection or a virus-related disorder in a patient.

12 Claims, No Drawings

FOREIGN PATENT DOCUMENTS

| WO | 02/068412 A1 | 9/2002 |
|---|---|---|
| WO | 2004/035571 A1 | 4/2004 |
| WO | 2004/106328 A1 | 12/2004 |
| WO | 2005/034941 A1 | 4/2005 |
| WO | 2005/084315 A2 | 9/2005 |
| WO | 2005/087731 A1 | 9/2005 |
| WO | 2005/111018 A1 | 11/2005 |
| WO | 2006/020082 A1 | 2/2006 |
| WO | 2006/032541 A1 | 3/2006 |
| WO | 2006/034337 A2 | 3/2006 |
| WO | 2006/046030 A2 | 5/2006 |
| WO | 2006/076529 A1 | 7/2006 |
| WO | 2007/029029 A2 | 3/2007 |
| WO | 2007/038209 A2 | 4/2007 |
| WO | 2007/084413 A2 | 7/2007 |
| WO | 2007/084435 A2 | 7/2007 |
| WO | 2008/082484 A1 | 7/2008 |

OTHER PUBLICATIONS

Bunker et al., "1,3-Diaryl-2-Carboxyindoles as Potent Non-Peptide Endothelin Antagonists", Bioorganic & Medicinal Chemistry Letters, 1996, vol. 6, pp. 1061-1066, No. 9.
Chemical and Pharmaceutical Bulletin, vol. 19, 1971, p. 263-270.
Denmark et al., "Palladium-Catalyzed Cross-Coupling Reactions of Silanolates; A Paradigm Shift in Silicon-Based Cross-Coupling Reactions", Chem. Eur. J., 2006, vol. 12, pp. 4954-4963.
Dimasi et al., "Characterization of Engineered Hepatitis C Virus NS3 Protease Inhibitors Affinity Selected from Human Pancreatic Secretory Trypsin Inhibitor and Minibody Repertoires", Journal of Virology, 1997. vol. 71, pp. 7461-7469, No. 10.
Elzouki et al., "Serine protease inhibitors in patients with chronic viral hepatitis", Journal of Hepatology, 1997, vol. 27, pp. 42-48.
Ferrari et al., "Characterization of Soluble Hepatitis C Virus RNA-Dependent RNA Polymerase Expressed in *Escherichia coli*", Journal of Virology. 1999, vol. 73, pp. 1649-1654, No. 2.
Fonseca et al., "Synthesis and antiviral evaluation of benzimidazoles, quinoxalines and indoles from dehydroabietic acid", Bioorganic & Medicinal Chemistry, 2004, vol. 12, pp. 103-112.
Forbes et al., "Synthesis, Biological Activity, and Molecular Modeling Studies of Selective 5-HT2C/2B Receptor Antagonists", J. Med. Chem., 1996, vol. 39, pp. 4966-4977, No. 25.
Goldsmith et al, "Studies in the Benzindole Series", J. Org. Chem, 1952, vol. 18, pp. 507-514.
Gopalsamy et al, "Design and synthesis of 2,3,4,9-tetrahydro-1H-carbazole and 1,2,3,4-tetrahydro-cyclopenta[b] indole derivatives as non-nucleoside inhibitors of hepatitis C virus NS5B RNA-dependent RNA polymerase". Bioorganic & Medicinal Chemistry Letters, 2006, vol. 16, pp. 2532-2534.
Humphrey et al., "Practical Methodologies for the Synthesis of Indoles", Chem. Rev., 2006, vol. 106, pp. 2875-2911.
International Search Report for International Application No. PCT/US2007/025754, mailed May 13, 2008, (4 pages).
Written Opinion for PCT/US2007/025754, filed Dec. 17, 2007, (7 pages).
International Search Report for International Application No. PCT/US2007/025765, mailed May 13, 2008, (6 pages).
Written Opinion for PCT/US2007/025765, filed Dec. 17, 2007. (8 pages).
International Search Report for International Application No. PCT/US2007/025757, mailed Mar. 6, 2009, (8 pages).
Written Opinion for PCT/US2007/025757, filed Dec. 17, 2007 (12 pages).
International Search Report for International Application No. PCT/US2008/010130, mailed Jan. 22, 2009. (5 pages).
Written Opinion for PCT/US2008/010130, filed Aug. 27, 2008 (9 pages).
International Search Report for International Application No. PCT/US2008/010149, mailed Feb. 2, 2009, (5 pages).
Written Opinion for PCT/US2008/010149, filed Aug. 27, 2008 (6 pages).
International Search Report for International Application No. PCT/US2008/083351, mailed Feb. 27, 2009, (3 pages).
Written Opinion for PCT/US2008/083351, filed Nov. 13, 2008 (5 pages).
International Search Report for International Application No. PCT/US2008/010147, mailed May 4, 2009. (3 pages).
Written Opinion for PCT/US2008/010147, filed Aug. 27, 2008 (6 pages).
International Search Report for International Application No. PCT/US2008/083358. mailed Mar. 6, 2009, (2 pages).
Written Opinion for PCT/US2008/083358, filed Nov. 13, 2008 (5 pages).
International Search Report for International Application No. PCT/US2008/010148, mailed Dec. 9, 2008, (3 pages).
Written Opinion for PCT/US2008/010148, filed Aug. 27, 2008 (7 pages).
International Search Report for International Application No. PCT/US2009/046822, mailed Oct. 7, 2009, (5 pages).
Written Opinion for PCT/US2009/046822, filed Jun. 10, 2009 (8 pages).
Ingallinella et al., "Potent Peptide Inhibitors of Human Hepatitis C Virus NS3 Protease are Obtained by Optimizing the Cleavage Products", Biochemistry, 1998, vol. 37, pp. 8906-8914.
Journal of Heterocyclic Chemistry. vol. 12, 1975, pp. 351-358.
Journal of Medicinal Chemistry, vol. 23, No. 7, 1980, pp. 764-773.
Journal of Organic Chemistry, vol. 27, 1962, pp. 3782-3786.
Landro et al., "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", Biochemistry, 1997, vol. 36, pp. 9340-9348.
Lindsay et al., "SmI2-Promoted Radical Addition Reactions with N-(2-indolyiacyl)oxazolidinones: Synthesis of Bisindole Compounds", Journal of Organic Chemistry, 2007, vol. 72, pp. 4181-4188, No. 11.
Llinas-Brunet et al., "Peptide-Based Inhibitors of the Hepatitis C Virus Serine Protease", Bioorganic & Medicinal Chemistry Letters, 1998, vol. 8, pp. 1713-1718.
Malcolm et al., "SCH 503034, a Mechanism-Based Inhibitor of Hepatitis C Virus NS3 Protease, Suppresses Polyprotein Maturation and Enhances the Antiviral Activity of Alpha Interferon in Replicon Cells", Antimicrobial Agents and Chemotherapy, 2006, vol. 50, pp. 1013-1020, No. 3.
Martin, et al., "Affinity selection of a camelized VH domain antibody inhibitor of hepatitis C virus NS3 protease", Protein Engineering, 1997, vol. 10, pp. 607-614, No. 5.
Martin et al., "Design of Selective Eglin Inhibitors of HCV NS3 Proteinase", Biochemistry, 1998. vol. 37, pp. 11459-11468.
Mijratake et al., "Synthesis of Duocarmycin SA by Way of Methyl 4-(Methoxycarbonyl)oxy-3H-pyrrolo[3,2-f] quinoline-2-carboxylate as a Tricyclic Heteroaromatic Intermediate", Chem. Pharm. Bulletin, 1998, vol. 46, pp. 400-412. No. 3.
Ni et al., "Progress and development of small molecule HCV antivirals", Current Opinion in Drug Discovery & Development. 2004, vol. 7, pp. 446-459, No. 4.
Rawal et al., "Photocyclization of Pyrrole Analogues of Stilbene an Expedient Approach to Anti-tumour Agent CC-1065". Journal Chem. Soc. Chem. Commun., 1984, pp. 1526-1527.
Sechi et al., "Design and Synthesis of Novel Indole β-Diketo Acid Derivatives as HIV-1 Integrase Inhibitors", J. Med Chem., 2004, vol. 47, pp. 5298-5310, No. 21.
Silvestri et al., "Synthesis and biological evaluation of 5H-indolo [3,2-b][1,5]benzothiazepine derivatives, designed as conformationally constrained analogues of the human immunodeficiency virus type 1 reverse transcriptase inhibitor L-737,126", Antiviral Chemistry & Chemotherapy, 1998, vol. 9, pp. 139-148.
Tan et al., "Hepatitis C Therapeutics Current Status and Emerging Strategies", Nature Reviews. 2002, vol. 1. pp. 867-881.

2,3-SUBSTITUTED INDOLE DERIVATIVES FOR TREATING VIRAL INFECTIONS

FIELD OF THE INVENTION

The present invention relates to 2,3-Substituted Indole Derivatives, compositions comprising at least one 2,3-Substituted Indole Derivative, and methods of using the 2,3-Substituted Indole Derivatives for treating or preventing a viral infection or a virus-related disorder in a patient.

BACKGROUND OF THE INVENTION

HCV is a (+)-sense single-stranded RNA virus that has been implicated as the major causative agent in non-A, non-B hepatitis (NANBH). NANBH is distinguished from other types of viral-induced liver disease, such as hepatitis A virus (HAV), hepatitis B virus (HBV), hepatitis delta virus (HDV), as well as from other forms of liver disease such as alcoholism and primary biliary cirrhosis.

Hepatitis C virus is a member of the hepacivirus genus in the family Flaviviridae. It is the major causative agent of non-A, non-B viral hepatitis and is the major cause of transfusion-associated hepatitis and accounts for a significant proportion of hepatitis cases worldwide. Although acute HCV infection is often asymptomatic, nearly 80% of cases resolve to chronic hepatitis. About 60% of patients develop liver disease with various clinical outcomes ranging from an asymptomatic carrier state to chronic active hepatitis and liver cirrhosis (occurring in about 20% of patients), which is strongly associated with the development of hepatocellular carcinoma (occurring in about 1-5% of patients). The World Health Organization estimates that 170 million people are chronically infected with HCV, with an estimated 4 million living in the United States.

HCV has been implicated in cirrhosis of the liver and in induction of hepatocellular carcinoma. The prognosis for patients suffering from HCV infection remains poor as HCV infection is more difficult to treat than other forms of hepatitis. Current data indicates a four-year survival rate of below 50% for patients suffering from cirrhosis and a five-year survival rate of below 30% for patients diagnosed with localized resectable hepatocellular carcinoma. Patients diagnosed with localized unresectable hepatocellular carcinoma fare even worse, having a five-year survival rate of less than 1%.

HCV is an enveloped RNA virus containing a single-stranded positive-sense RNA genome approximately 9.5 kb in length. The RNA genome contains a 5'-nontranslated region (5' NTR) of 341 nucleotides, a large open reading frame (ORF) encoding a single polypeptide of 3,010 to 3,040 amino acids, and a 3'-nontranslated region (3'-NTR) of variable length of about 230 nucleotides. HCV is similar in amino acid sequence and genome organization to flaviviruses and pestiviruses, and therefore HCV has been classified as a third genus of the family Flaviviridae.

The 5' NTR, one of the most conserved regions of the viral genome, contains an internal ribosome entry site (IRES) which plays a pivotal role in the initiation of translation of the viral polyprotein. A single long open reading frame encodes a polyprotein, which is co- or post-translationally processed into structural (core, E1, E2 and p7) and nonstructural (NS2, NS3, NS4A, NS4B, NS5A, and NS5B) viral proteins by either cellular or viral proteinases. The 3' NTR consists of three distinct regions: a variable region of about 38 nucleotides following the stop codon of the polyprotein, a polyuridine tract of variable length with interspersed substitutions of cytidines, and 98 nucleotides (nt) at the very 3' end which are highly conserved among various HCV isolates. By analogy to other plus-strand RNA viruses, the 3'-NTR is thought to play an important role in viral RNA synthesis. The order of the genes within the genome is: $NH_2$—C-E1-E2-p7-NS2-NS3-NS4A-NS4B-NS5A-NS5B-COOH.

Processing of the structural proteins core (C), envelope protein 1 and (E1, E2), and the p7 region is mediated by host signal peptidases. In contrast, maturation of the nonstructural (NS) region is accomplished by two viral enzymes. The HCV polyprotein is first cleaved by a host signal peptidase generating the structural proteins C/E1, E1/E2, E2/p7, and p7/NS2. The NS2-3 proteinase, which is a metalloprotease, then cleaves at the NS2/NS3 junction. The NS3/4A proteinase complex (NS3 being a serine protease and NS4A acting as a cofactor of the NS3 protease), is then responsible for processing all the remaining cleavage junctions. RNA helicase and NTPase activities have also been identified in the NS3 protein. One-third of the NS3 protein functions as a protease, and the remaining two-thirds of the molecule acts as the helicase/ATPase that is thought to be involved in HCV replication. NS5A may be phosphorylated and acts as a putative cofactor of NS5B. The fourth viral enzyme, NS5B, is a membrane-associated RNA-dependent RNA polymerase (RdRp) and a key component responsible for replication of the viral RNA genome. NS5B contains the "GDD" sequence motif, which is highly conserved among all RdRps characterized to date.

Replication of HCV is thought to occur in membrane-associated replication complexes. Within these, the genomic plus-strand RNA is transcribed into minus-strand RNA, which in turn can be used as a template for synthesis of progeny genomic plus-strands. At least two viral enzymes appear to be involved in this reaction: the NS3 helicase/NTPase, and the NS5B RNA-dependent RNA polymerase. While the role of NS3 in RNA replication is less clear, NS5B is the key enzyme responsible for synthesis of progeny RNA strands. Using recombinant baculoviruses to express NS5B in insect cells and a synthetic nonviral RNA as a substrate, two enzymatic activities have been identified as being associated with it: a primer-dependent RdRp and a terminal transferase (TNTase) activity. It was subsequently confirmed and further characterized through the use of the HCV RNA genome as a substrate. Other studies have shown that NS5B with a C-terminal 21 amino-acid truncation expressed in *Escherichia coli* is also active for in vitro RNA synthesis. On certain RNA templates, NS5B has been shown to catalyze RNA synthesis via a de novo initiation mechanism, which has been postulated to be the mode of viral replication in vivo. Templates with single-stranded 3' termini, especially those containing a 3'-terminal cytidylate moiety, have been found to direct de novo synthesis efficiently. There has also been evidence for NS5B to utilize di- or tri-nucleotides as short primers to initiate replication.

It is well-established that persistent infection of HCV is related to chronic hepatitis, and as such, inhibition of HCV replication is a viable strategy for the prevention of hepatocellular carcinoma. Present treatment approaches for HCV infection suffer from poor efficacy and unfavorable side-effects and there is currently a strong effort directed to the discovery of HCV replication inhibitors that are useful for the treatment and prevention of HCV related disorders. New approaches currently under investigation include the development of prophylactic and therapeutic vaccines, the identification of interferons with improved pharmacokinetic characteristics, and the discovery of agents designed to inhibit the function of three major viral proteins: protease, helicase and polymerase. In addition, the HCV RNA genome itself, particularly the IRES element, is being actively exploited as an antiviral target using antisense molecules and catalytic ribozymes.

Particular therapies for HCV infection include α-interferon monotherapy and combination therapy comprising α-interferon and ribavirin. These therapies have been shown to be effective in some patients with chronic HCV infection. The use of antisense oligonucleotides for treatment of HCV infection has also been proposed as has the use of free bile acids, such as ursodeoxycholic acid and chenodeoxycholic acid, and conjugated bile acids, such as tauroursodeoxycholic acid. Phosphonoformic acid esters have also been proposed as potentially for the treatment of various viral infections including HCV. Vaccine development, however, has been hampered by the high degree of viral strain heterogeneity and immune evasion and the lack of protection against reinfection, even with the same inoculum.

The development of small-molecule inhibitors directed against specific viral targets has become a major focus of anti-HCV research. The determination of crystal structures for NS3 protease, NS3 RNA helicase, and NS5B polymerase has provided important structural insights that should assist in the rational design of specific inhibitors.

NS5B, the RNA-dependent RNA polymerase, is an important and attractive target for small-molecule inhibitors. Studies with pestiviruses have shown that the small molecule compound VP32947 (3-[((2-dipropylamino)ethyl)thio]-5H-1,2,4-triazino[5,6-b]indole) is a potent inhibitor of pestivirus replication and most likely inhibits the NS5B enzyme since resistant strains are mutated in this gene. Inhibition of RdRp activity by (−)β-L-2′,3′-dideoxy-3′-thiacytidine 5′-triphosphate (3TC; lamivudine triphosphate) and phosphonoacetic acid also has been observed.

Despite the intensive effort directed at the treatment and prevention of HCV and related viral infections, there exists a need in the art for non-peptide, small-molecule compounds having desirable or improved physicochemical properties that are useful for inhibiting viruses and treating viral infections and virus-related disorders.

SUMMARY OF THE INVENTION

In one aspect, the present invention provides compounds of formula (I):

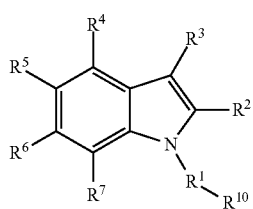

(I)

and pharmaceutically acceptable salts, solvates, esters and prodrugs thereof, wherein:

$R^1$ is a bond, $-[C(R^{12})_2]_r-$, $-[C(R^{12})_2]_r-O-[C(R^{12})_2]_q-$, $-[C(R^{12})_2]_r-N(R^9)-[C(R^{12})_2]_q-$, $-[C(R^{12})_2]_q-CH=CH-[C(R^{12})_2]_q-$, $-[C(R^{12})_2]_q-C\equiv C-[C(R^{12})_2]_q-$, or $-[C(R^{12})_2]_q-SO_2-[C(R^{12})_2]_q-$;

$R^2$ is $-[C(R^{12})_2]_q-C(O)N(R^9)SOR^{11}$, $-[C(R^{12})_2]_q-C(O)N(R^9)SO_2R^{11}$, $-[C(R^{12})_2]_q-C(O)N(R^9)SO_2N(R^9)_2$,

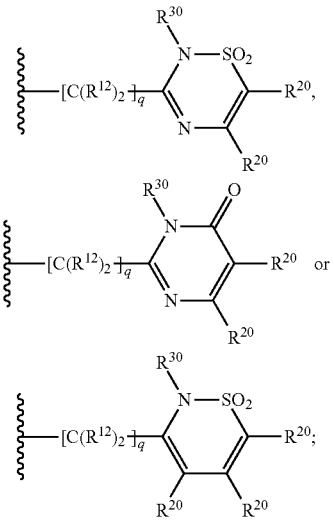

$R^3$ is:

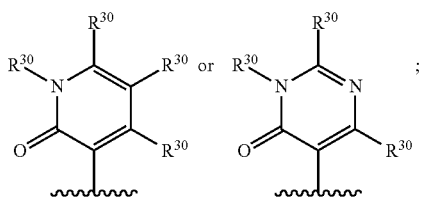

$R^4$, $R^5$, $R^6$ and $R^7$ are each, independently, H, alkyl, alkenyl, alkynyl, aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, $-[C(R^{12})_2]_q$-haloalkyl, $-[C(R^{12})_2]_q$-hydroxyalkyl, halo, $-OH$, $-OR^9$, $-CN$, $-[C(R^{12})_2]_q-C(O)R^8$, $-[C(R^{12})_2]_q-C(O)OR^9$, $-[C(R^{12})_2]_q-C(O)N(R^9)_2$, $-[C(R^{12})_2]_q-OR^9$, $-[C(R^{12})_2]_q-N(R^9)_2$, $-[C(R^{12})_2]_q-NHC(O)R^8$, $-[C(R^{12})_2]_q-NR^8C(O)N(R^9)_2$, $-[C(R^{12})_2]_q-NHSO_2R^{11}$, $-[C(R^{12})_2]_q-S(O)_pR^{11}$, $-[C(R^{12})_2]_q-SO_2N(R^9)_2$ or $-SO_2N(R^9)C(O)N(R^9)_2$;

each occurrence of $R^8$ is independently H, alkyl, alkenyl, alkynyl, $-[C(R^{12})_2]_q$-aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, haloalkyl or hydroxyalkyl;

each occurrence of $R^9$ is independently H, alkyl, alkenyl, alkynyl, $-[C(R^{12})_2]_q$-O-alkyl, $-[C(R^{12})_2]_q-N(alkyl)_2$, $-[C(R^{12})_2]_q$-aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, haloalkyl or hydroxyalkyl;

$R^{10}$ is H, cycloalkyl, cycloalkenyl, heterocycloalkyl, heterocycloalkenyl, aryl, heteroaryl, wherein a cycloalkyl, cycloalkenyl, heterocycloalkyl, heterocycloalkenyl, aryl or heteroaryl group can be optionally and independently substituted with up to 4 substituents, which are each independently selected from H, alkyl, alkenyl, alkynyl, aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$- heteroaryl, —[C(R$^{12}$)$_2$]$_q$-haloalkyl, —[C(R$^{12}$)$_2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$; —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$, such that when R$^1$ is a bond, R$^{10}$ is not H;

each occurrence of R$^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally and independently substituted with up to 4 substituents, which are each independently selected from —H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$alkyl, —[C(R$^{12}$)$_2$]$_q$—NHSO$_2$cycloalkyl, —[C(R$^{12}$)$_2$]$_q$—NHSO$_2$aryl, —[C(R$^{12}$)$_2$]$_q$—SO$_2$N(R$^9$)$_2$ and —SO$_2$N(R$^9$)C(O)NR$^9$)$_2$;

each occurrence of R$^{12}$ is independently H, halo, —N(R$^9$)$_2$, —OR$^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally and independently substituted with up to 4 substituents, which are each independently selected from alkyl, halo, haloalkyl, hydroxyalkyl, —OH, —CN, —C(O)alkyl, —C(O)Oalkyl, —C(O)NH-alkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two R$^{12}$ groups, together with the carbon atoms to which they are attached, join to form a cycloalkyl, heterocycloalkyl or C=O group;

each occurrence of R$^{20}$ is independently alkyl, aryl, cycloalkyl, heterocycloalkyl or heteroaryl, or both R$^{20}$ groups and the carbon atoms to which they are attached, join to form a cycloalkyl, cycloheteroalkyl, aryl or heteroaryl group wherein a cycloalkyl, cycloheteroalkyl, aryl or heteroaryl group can be substituted with up to 4 groups, which are each independently selected from alkyl, alkenyl, alkynyl, halo, —OH, —OR$^9$, —CN, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-haloalkyl, —[C(R$^{12}$)$_2$]$_q$-hydroxyalkyl, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^2$)$_2$]$_q$—NR$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$;

each occurrence of R$^{30}$ is independently H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)NR$^9$)$_2$, —[C(R$^{12}$)$_2$]—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ or —SO$_2$N(R$^9$)C(O)N(R$^9$)$_2$, or two adjacent R$^{30}$ groups, together with the carbon atoms to which they are attached, join to form a –3- to 7-membered ring selected from aryl, cycloalkyl, heteroaryl and heterocycloalkyl;

each occurrence of p is independently 0, 1 or 2;

each occurrence of q is independently an integer ranging from 0 to 4; and each occurrence of r is independently an integer ranging from 1 to 4.

In another aspect, the present invention provides compounds of formula (II):

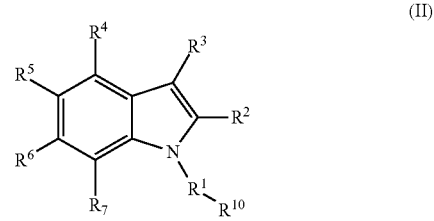

and pharmaceutically acceptable salts, solvates, esters and prodrugs thereof, wherein:

R$^1$ is a bond, —[C(R$^{12}$)$_2$]$_r$—, —[C(R$^{12}$)$_2$]$_r$—O—[C(R$^{12}$)$_2$]$_q$—, —[C(R$^{12}$)$_2$]$_r$—N(R$^9$)—[C(R$^{12}$)$_2$]$_q$—, —[C(R$^{12}$)$_2$]$_q$—CH=CH—[C(R$^{12}$)$_2$]$_q$—, —[C(R$^{12}$)$_2$]$_q$—C≡C—[C(R$^{12}$)$_2$]$_q$, or —[C(R$^{12}$)$_2$]$_q$—SO$_2$—[C(R$^{12}$)$_2$]$_q$—;

R$^2$ is —[C(R$^{12}$)$_2$]$_q$—C(O)NR$^9$)SOR$^{11}$, —[C(R$^{12}$)$_2$]$_q$—C(O)NR$^9$)SO$_2$R$^{11}$, —[C(R$^{12}$)$_2$]$_q$—C(O)N(R$^9$)SO$_2$NR$^9$)$_2$,

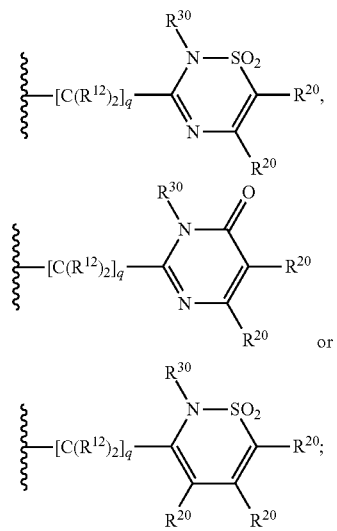

R$^3$ is

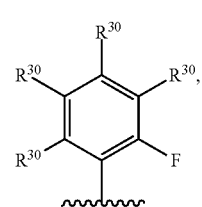

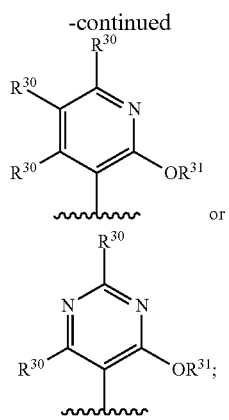

$R^4$, $R^5$, $R^6$ and $R^7$ are each, independently, H, alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, —OH, —OR$^9$, —CN, —[C($R^{12}$)$_2$]$_q$—C(O)R$^8$, —[C($R^{12}$)$_2$]$_q$—C(O)OR$^9$, —[C($R^{12}$)$_2$]$_q$—C(O)N(R$^9$)$_2$, —[C($R^{12}$)$_2$]$_q$—OR$^9$, —[C($R^{12}$)$_2$]$_q$—N(R$^9$)$_2$, —[C($R^{12}$)$_2$]$_q$—NHC(O)R$^8$, —[C($R^{12}$)$_2$]$_q$—NR$^8$C(O)N(R$^9$)$_2$, —[C($R^{12}$)$_2$]$_q$—NHSO$_2$R$^{11}$, —[C($R^{12}$)$_2$]$_q$—S(O)$_p$R$^{11}$, —[C($R^{12}$)$_2$]$_q$—SO$_2$N(R$^9$)$_2$ or —SO$_2$N(R$^9$)C(O)N(R$^9$)$_2$;

each occurrence of $R^8$ is independently H, alkyl, alkenyl, alkynyl, —[C($R^{12}$)$_2$]$_q$-aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, haloalkyl or hydroxyalkyl;

each occurrence of $R^9$ is independently H, alkyl, alkenyl, alkynyl, —[C($R^{12}$)$_2$]$_q$—O-alkyl, —[C($R^{12}$)$_2$]$_q$—N(alkyl)$_2$, —[C($R^{12}$)$_2$]$_q$-aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, haloalkyl or hydroxyalkyl;

$R^{10}$ is H, cycloalkyl, cycloalkenyl, heterocycloalkyl, heterocycloalkenyl, aryl, heteroaryl, wherein a cycloalkyl, cycloalkenyl, heterocycloalkyl, heterocycloalkenyl, aryl or heteroaryl group can be optionally and independently substituted with up to 4 substituents, which are each independently selected from —H, alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, —OH, —OR$^9$, —CN, —[C($R^{12}$)$_2$]$_q$—C(O)R$^8$, —[C($R^{12}$)$_2$]$_q$—C(O)OR$^9$, —[C($R^{12}$)$_2$]$_q$—C(O)N(R$^9$)$_2$, —[C($R^{12}$)$_2$]$_q$—OR$^9$, —[C($R^{12}$)$_2$]$_q$—NR$^9$)$_2$, —[C($R^{12}$)$_2$]$_q$—NHC(O)R$^8$, —[C($R^{12}$)$_2$]$_q$—NR$^8$C(O)N(R$^9$)$_2$, —[C($R^{12}$)$_2$]$_q$—NHSO$_2$R$^{11}$, —[C($R^{12}$)$_2$]$_q$—S(O)$_p$R$^{11}$, —[C($R^{12}$)$_2$]$_q$—SO$_2$N(R$^9$)$_2$ and —SO$_2$N(R$^9$)C(O)N(R$^9$)$_2$, such that when $R^1$ is a bond, $R^{10}$ is not H;

each occurrence of $R^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally and independently substituted with up to 4 substituents, which are each independently selected from —H, alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, —OH, —OR$^9$, —CN, —[C($R^{12}$)$_2$]$_q$—C(O)R$^8$, —[C($R^{12}$)$_2$]$_g$—C(O)R$^8$, —[C($R^{12}$)$_2$]$_q$—C(O)N(R$^9$)$_2$, —[C($R^{12}$)$_2$]$_q$—OR$^9$, —[C($R^{12}$)$_2$]$_q$—N(R$^9$)$_2$, —[C($R^{12}$)$_2$]$_q$—NHC(O)R$^8$, —[C($R^{12}$)$_2$]$_q$—NR$^8$C(O)N(R$^9$)$_2$, —[C($R^{12}$)$_2$]$_q$—NHSO$_2$alkyl, —[C($R^{12}$)$_2$]$_q$—NHSO$_2$cycloalkyl, —[C($R^{12}$)$_2$]$_q$—NHSO$_2$aryl, —[C($R^{12}$)$_2$]$_q$—SO$_2$N(R$^9$)$_2$ and —SO$_2$N(R$^9$)C(O)N(R$^9$)$_2$;

each occurrence of $R^{12}$ is independently H, halo, —N(R$^9$)$_2$, —OR$^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally and independently substituted with up to 4 substituents, which are each independently selected from alkyl, halo, haloalkyl, hydroxyalkyl, —OH, —CN, —C(O)alkyl, —C(O)Oalkyl, —C(O)NH-alkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two $R^{12}$ groups, together with the carbon atoms to which they are attached, join to form a cycloalkyl, heterocycloalkyl or C═O group;

each occurrence of $R^{20}$ is independently alkyl, aryl, cycloalkyl, heterocycloalkyl or heteroaryl, or both $R^{20}$ groups and the carbon atoms to which they are attached, join to form a cycloalkyl, cycloheteroalkyl, aryl or heteroaryl group wherein a cycloalkyl, cycloheteroalkyl, aryl or heteroaryl group can be substituted with up to 4 groups, which are each independently selected from alkyl, alkenyl, alkynyl, halo, —OH, —OR$^9$, —CN, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-haloalkyl, —[C($R^{12}$)$_2$]$_q$-hydroxyalkyl, —[C($R^{12}$)$_2$]$_q$—C(O)R$^8$, —[C($R^{12}$)$_2$]$_q$—C(O)OR$^9$, —[C($R^{12}$)$_2$]$_q$—C(O)N(R$^9$)$_2$, —[C($R^{12}$)$_2$]$_q$—OR$^9$, —[C($R^{12}$)$_2$]$_q$—N(R$^9$)$_2$, —[C($R^{12}$)$_2$]$_q$—NHC(O)R$^8$, —[C($R^{12}$)$_2$]$_q$—NR$^8$C(O)N(R$^9$)$_2$, —[C($R^{12}$)$_2$]$_q$—NHSO$_2$R$^{11}$, —[C($R^{12}$)$_2$]$_q$—S(O)$_p$R$^{11}$, —[C($R^{12}$)$_2$]$_q$—SO$_2$N(R$^9$)$_2$ and —SO$_2$N(R$^9$)C(O)N(R$^9$)$_2$;

each occurrence of $R^{30}$ is independently selected from —H, alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, —OH, —OR$^9$, —CN, —[C($R^{12}$)$_2$]$_q$—C(O)R$^8$, —[C($R^{12}$)$_2$]$_q$—C(O)OR$^9$, —[C($R^{12}$)$_2$]$_q$—C(O)N(R$^9$)$_2$, —[C($R^{12}$)$_2$]$_q$—OR$^9$, —[C($R^{12}$)$_2$]$_q$—N(R$^9$)$_2$, —[C($R^{12}$)$_2$]$_q$—NHC(O)R$^8$, —[C($R^{12}$)$_2$]$_q$—NR$^8$C(O)N(R$^9$)$_2$, —[C($R^{12}$)$_2$]$_q$—NHSO$_2$R$^{11}$, —[C($R^{12}$)$_2$]$_q$—S(O)$_p$R$^{11}$, —[C($R^{12}$)$_2$]$_q$—SO$_2$N(R$^9$)$_2$ and —SO$_2$N(R$^9$)C(O)N(R$^9$)$_2$, or two adjacent $R^{30}$ groups, together with the carbon atoms to which they are attached, join to form a −3- to 7-membered ring selected from aryl, cycloalkyl, heteroaryl and heterocycloalkyl;

$R^{31}$ is alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl or —[C($R^{12}$)$_2$]$_q$-hydroxyalkyl;

each occurrence of p is independently 0, 1 or 2;
each occurrence of q is independently an integer ranging from 0 to 4; and
each occurrence of r is independently an integer ranging from 1 to 4.

The compounds of formulas (I) and (II) (herein referred to collectively as the "2,3-Substituted Indole Derivatives") and pharmaceutically acceptable salts, solvates, esters and prodrugs thereof can be useful for treating or preventing a viral infection or a virus-related disorder in a patient.

Also provided by the invention are methods for treating or preventing a viral infection or a virus-related disorder in a patient, comprising administering to the patient an effective amount of at least one 2,3-Substituted Indole Derivative.

The present invention further provides pharmaceutical compositions comprising an effective amount of at least one 2,3-Substituted Indole Derivative or a pharmaceutically acceptable salt, solvate thereof, and a pharmaceutically acceptable carrier. The compositions can be useful for treating or preventing a viral infection or a virus-related disorder in a patient.

The details of the invention are set forth in the accompanying detailed description below.

Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

In an embodiment, the present invention provides 2,3-Substituted Indole Derivatives, pharmaceutical compositions comprising at least one 2,3-Substituted Indole Derivative, and methods of using the 2,3-Substituted Indole Derivatives for treating or preventing a viral infection in a patient.

DEFINITIONS AND ABBREVIATIONS

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc. . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "alkyl" as used herein, refers to an aliphatic hydrocarbon group, wherein one of the aliphatic hydrocarbon group's hydrogen atoms is replaced with a single bond. An alkyl group can be straight or branched and can contain from about 1 to about 20 carbon atoms. In one embodiment, an alkyl group contains from about 1 to about 12 carbon atoms. In another embodiment, an alkyl group contains from about 1 to about 6 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or optionally substituted by one or more substituents which may be the same or different, each substituent being independently selected from the group consisting of halo, alkenyl, alkynyl, —O-aryl, aryl, heteroaryl, cycloalkyl, cycloalkenyl, cyano, —OH, —O-alkyl, —O-haloalkyl, -alkylene-O-alkyl, alkylthio, —NH$_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)-cycloalkyl, —C(O)alkyl, —C(O)NH$_2$, —C(O)NH-alkyl, —C(O)OH and —C(O)O-alkyl. In one embodiment, an alkyl group is unsubstituted. In another embodiment, an alkyl group is a straight chain alkyl group. In another embodiment, an alkyl group is a branched alkyl group.

The term "alkenyl" as used herein, refers to an aliphatic hydrocarbon group having at least one carbon-carbon double bond, wherein one of the aliphatic hydrocarbon group's hydrogen atoms is replaced with a single bond. An alkenyl group can be straight or branched and can contain from about 2 to about 15 carbon atoms. In one embodiment, an alkenyl group contains from about 2 to about 10 carbon atoms. In another embodiment, an alkenyl group contains from about 2 to about 6 carbon atoms. Non-limiting examples of illustrative alkenyl groups include ethenyl, propenyl, n-butenyl, 3-methylbut-2-enyl, n-pentenyl, octenyl and decenyl. An alkenyl group may be unsubstituted or optionally substituted by one or more substituents which may be the same or different, each substituent being independently selected from the group consisting of halo, alkyl, alkynyl, —O-aryl, aryl, cycloalkyl, cycloalkenyl, cyano, —OH, —O-alkyl, —O-haloalkyl, -alkylene-O-alkyl, alkylthio, —NH$_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)-cycloalkyl, —C(O)alkyl, —C(O)NH$_2$, —C(O)NH-alkyl, —C(O)OH and —C(O)O-alkyl. In one embodiment, an alkenyl group is unsubstituted. In another embodiment, an alkenyl group is a straight chain alkenyl group. In another embodiment, an alkenyl group is a branched alkenyl group.

The term "alkynyl" as used herein, refers to an aliphatic hydrocarbon group having at least one carbon-carbon triple bond, wherein one of the aliphatic hydrocarbon group's hydrogen atoms is replaced with a single bond. An alkynyl group can be straight or branched and can contain from about 2 to about 15 carbon atoms. In one embodiment, an alkynyl group contains from about 2 to about 10 carbon atoms. In another embodiment, an alkynyl group contains from about 2 to about 6 carbon atoms. Non-limiting examples of illustrative alkynyl groups include ethynyl, propynyl, 2-butynyl and 3-methylbutynyl. An alkynyl group may be unsubstituted or optionally substituted by one or more substituents which may be the same or different, each substituent being independently selected from the group consisting of halo, alkyl, alkenyl, —O-aryl, aryl, cycloalkyl, cycloalkenyl, cyano, —OH, —O-alkyl, -alkylene-O-alkyl, —O-haloalkyl, -alkylthio, —NH$_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)-cycloalkyl, —C(O)alkyl, —C(O)NH$_2$, —C(O)NH-alkyl, —C(O)OH and —C(O)O-alkyl. In one embodiment, an alkynyl group is unsubstituted. In another embodiment, an alkynyl group is a straight chain alkynyl group. In another embodiment, an alkynyl group is a branched alkynyl group.

The term "alkylene" as used herein, refers to an alkyl group, as defined above, wherein one of the alkyl group's hydrogen atoms is replaced with a bond. Illustrative examples of alkylene include, but are not limited to, —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH$_2$CH(CH$_3$)CH$_2$— and —CH$_2$CH$_2$CH(CH$_3$)—. In one embodiment, an alkylene group is a straight chain alkylene group. In another embodiment, an alkylene group is a branched alkylene group.

"Aryl" means an aromatic monocyclic or multicyclic ring system having from about 6 to about 14 ring carbon atoms. In one embodiment, an aryl group has from about 6 to about 10 ring carbon atoms. An aryl group can be optionally substituted with one or more "ring system substituents" which may be the same or different, and are as defined herein below. Non-limiting examples of illustrative aryl groups include phenyl and naphthyl. In one embodiment, an aryl group is unsubstituted. In another embodiment, an aryl group is a phenyl group.

The term "cycloalkyl" as used herein, refers to a non-aromatic mono- or multicyclic ring system having from about 3 to about 10 ring carbon atoms. In one embodiment, a cycloalkyl has from about 5 to about 10 ring carbon atoms. In another embodiment, a cycloalkyl has from about 5 to about 7 ring carbon atoms. Non-limiting examples of illustrative monocyclic cycloalkyls include cyclopropyl, cyclopentyl, cyclohexyl, cycloheptyl and the like. Non-limiting examples of illustrative multicyclic cycloalkyls include 1-decalinyl, norbornyl, adamantyl and the like. A cycloalkyl group can be optionally substituted with one or more "ring system substituents" which may be the same or different, and are as defined herein below. In one embodiment, a cycloalkyl group is unsubstituted.

The term "cycloalkenyl" as used herein, refers to a non-aromatic mono- or multicyclic ring system comprising from about 3 to about 10 ring carbon atoms and containing at least one endocyclic double bond. In one embodiment, a cycloalkenyl contains from about 5 to about 10 ring carbon atoms. In another embodiment, a cycloalkenyl contains 5 or 6 ring carbon atoms. Non-limiting examples of illustrative monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. In one embodiment, a cycloalkenyl group is unsubstituted.

The term "halo" as used herein, means —F, —Cl, —Br or —I. In one embodiment, halo refers to —Cl or —F.

The term "haloalkyl" as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of illustrative haloalkyl groups include —CH$_2$F, —CHF$_2$, —CF$_3$, —CH$_2$Cl and —CCl$_3$.

The term "hydroxyalkyl" as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of illustrative hydroxyalkyl groups include hydroxymethyl, 2-hydroxyethyl, 3-hydroxypropyl, 4-hydroxybutyl and —CH(OH)CH$_2$CH$_3$.

The term "heteroaryl" as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is monocyclic and has 5 or 6 ring atoms and at least one nitrogen ring atom. A heteroaryl group can be optionally substituted by one or more "ring system substituents" which may be the same or different, and are as defined herein below. A heteroaryl group is joined via a ring carbon atom and any nitrogen atom of a heteroaryl can be optionally oxidized to the corresponding N-oxide. The term "heteroaryl" also encompasses a heteroaryl group, as defined above, which has been fused to a benzene ring. Non-limiting examples of illustrative heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. In one embodiment, a heteroaryl group is a 6-membered heteroaryl group. In another embodiment, a heteroaryl group is a 5-membered heteroaryl group.

Unless otherwise indicated, the group:

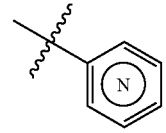

represents a 6-membered heteroaryl group containing 1 or 2 ring nitrogen atoms and no other ring heteroatoms. Examples of such a group include, but are not limited to pyridyl, pyrimidinyl, pyridazinyl and pyrazinyl. In one embodiment, this group has 1 ring nitrogen atom. In another embodiment, this group has 2 ring nitrogen atoms. This group may be optionally and The term "heterocycloalkyl" as used herein, refers to a non-aromatic saturated monocyclic or multicyclic ring system comprising 3 to about 10 ring atoms, wherein from 1 to 4 of the ring atoms are independently O, S or N and the remainder of the ring atoms are carbon atoms. In one embodiment, a heterocycloalkyl group has from about 5 to about 10 ring atoms. In another embodiment, a heterocycloalkyl group has 5 or 6 ring atoms. There are no adjacent oxygen and/or sulfur atoms present in the ring system. Any —NH group in a heterocycloalkyl ring may exist protected such as, for example, as an —N(Boc), —N(CBz), —N(Tos) group and the like; such protected heterocycloalkyl groups are considered part of this invention. A heterocycloalkyl group can be optionally substituted by one or more "ring system substituents" which may be the same or different, and are as defined herein below. The nitrogen or sulfur atom of the heterocyclyl can be optionally oxidized to the corresponding N-oxide, S-oxide or S,S-dioxide. Non-limiting examples of illustrative monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. A ring carbon atom of a heterocycloalkyl group may be functionalized as a carbonyl group. An illustrative example of such a heterocycloalkyl group is pyrrolidonyl:

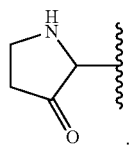

In one embodiment, a heterocycloalkyl group is a 6-membered heterocycloalkyl group. In another embodiment, a heterocycloalkyl group is a 5-membered heterocycloalkyl group.

The term "heterocycloalkenyl" as used herein, refers to a heterocycloalkyl group, as defined above, wherein the heterocycloalkyl group contains from 3 to 10 ring atoms, and at least one endocyclic carbon-carbon or carbon-nitrogen double bond. In one embodiment, a heterocycloalkenyl group has from 5 to 10 ring atoms. In another embodiment, a heterocycloalkenyl group is monocyclic and has 5 or 6 ring atoms. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of illustrative heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. A ring carbon atom of a heterocyclenyl group may be functionalized as a carbonyl group. An illustrative example of such a heterocyclenyl group is:

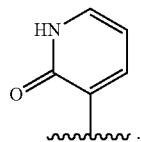

In one embodiment, a heterocycloalkenyl group is a 6-membered heterocycloalkenyl group. In another embodiment, a heterocycloalkenyl group is a 5-membered heterocycloalkenyl group.

The term "ring system substituent" as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, —OH, hydroxyalkyl, —O-alkyl, -alkylene-O-alkyl, —O-aryl, aralkoxy, acyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —OC(O)-alkyl, —OC(O)-aryl, —OC(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkylene-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

The term "substituted," as used herein, means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" as used herein, means optional substitution with the specified groups, radicals or moieties.

The terms "purified", "in purified form" or "in isolated and purified form" as used herein, for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, R[11], etc.) occurs more than one time in any constituent or in Formula (I) or (II), its definition on each occurrence is independent of its definition at every other occurrence, unless otherwise noted.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" as used herein, refers to a compound (e.g, a drug precursor) that is transformed in vivo to provide a 2,3-Substituted Indole Derivative or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a 2,3-Substituted Indole Derivative or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as O-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl, and the like.

Similarly, if a 2,3-Substituted Indole Derivative contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, P(O) (OH)$_2$, —P(O)(O($C_1$-$C_6$)alkyl)$_2$ or glycosyl (the radical resulting from the removal of a hydroxyl group of the hemiacetal form of a carbohydrate), and the like.

If a 2,3-Substituted Indole Derivative incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) allyl, ($C_3$-$C_7$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino($C_1$-$C_4$)alkyl or mono-N- or di-N,N—($C_1$-$C_6$)alkylaminoalkyl, —C(Y$^4$)Y$^5$ wherein Y$^4$ is H or methyl and Y$^5$ is mono-N- or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates.

Non-limiting examples of illustrative solvates include ethanolates, methanolates, and the like. "Hydrate" is a solvate wherein the solvent molecule is $H_2O$.

One or more compounds of the invention may optionally be converted to a solvate. Preparation of Solvates is Generally Known. Thus, for Example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

The term "effective amount" or "therapeutically effective amount" is meant to describe an amount of compound or a composition of the present invention that is effective to treat or prevent a viral infection or a virus-related disorder.

Metabolic conjugates, such as glucuronides and sulfates which can undergo reversible conversion to the 2,3-Substituted Indole Derivatives are contemplated in the present invention.

The 2,3-Substituted Indole Derivatives may form salts, and all such salts are contemplated within the scope of this invention. Reference to a 2,3-Substituted Indole Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a 2,3-Substituted Indole Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a 2,3-Substituted Indole Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, choline, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

The 2,3-Substituted Indole Derivatives may contain asymmetric or chiral centers, and, therefore, exist in different stereoisomeric forms. It is intended that all stereoisomeric forms of the 2,3-Substituted Indole Derivatives as well as mixtures thereof, including racemic mixtures, form part of the present invention. In addition, the present invention embraces all geometric and positional isomers. For example, if a 2,3-Substituted Indole Derivative incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the 2,3-Substituted Indole Derivatives may be atropisomers (e.g., substituted biaryls) and are considered as part of this invention. Enantiomers can also be separated by use of chiral HPLC column.

The straight — line as a bond generally indicates a mixture of, or either of, the possible isomers, non-limiting example(s) include, containing (R)- and (S)-stereochemistry. For example,

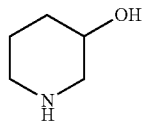

means containing both

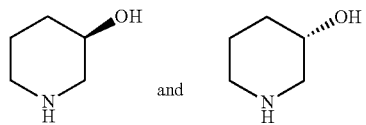

A dashed line (-----) represents an optional bond.
Lines drawn into the ring systems, such as, for example:

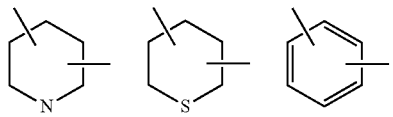

indicate that the indicated line (bond) may be attached to any of the substitutable ring atoms, non limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

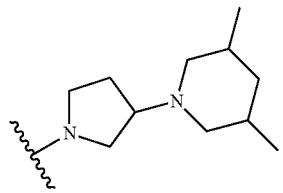

represents

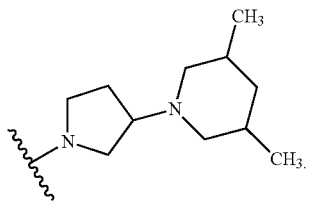

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a 2,3-Substituted Indole Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Such compounds are useful as therapeutic, diagnostic or research reagents. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled 2,3-Substituted Indole Derivatives (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled 2,3-Substituted Indole Derivatives can generally be prepared by following procedures analogous to those disclosed in the Schemes and/or in the Examples herein below, by substituting an appropriate isotopically labelled reagent for a non-isotopically labelled reagent.

Polymorphic forms of the 2,3-Substituted Indole Derivatives, and of the salts, solvates, hydrates, esters and prodrugs of the 2,3-Substituted Indole Derivatives, are intended to be included in the present invention.

The following abbreviations are used below and have the following meanings: Bn is benzyl; Bu is butyl; CDI is N,N'-carbonyldiimidazole; DABCO is 1,4-Diazabicyclo[2.2.2]octane; dba is dibenzylideneacetone; DBU is 1,8-Diazabicyclo[5.4.0]undec-7-ene; DCM is dichloromethane; DIEA is diethylamine; DIPEA is diisopropylethylamine; DME is dimethoxyethane; DMF is dimethylformamide; DMSO is dimethylsulfoxide; dppf is 1,1'-bis(diphenylphosphino)ferrocene; EDCI is 1-(3-dimethylaminopropyl)-3-ethylcarbodiimide; Et is ethyl; Et$_3$N is triethylamine; EtOAc is ethyl acetate; HATU is N-(diethylamino)-1H-1,2,3-triazolo[4,5-b]pyridine-1-yl-methylene]-N-methylmethanaminium hexafluorophosphate N-oxide; HPLC is high performance liquid chromatography; Me is methyl; MeOH is methanol; MS is mass spectrometry; NBS is N-bromosuccinimide; NIS is N-iodosuccinimide; PPA is polyphosphoric acid; TBAF is tetra-n-butylammonium fluoride; THF is tetrahydrofuran; TLC is thin layer chromatography and TMS is trimethylsilyl.

The 2,3-Substituted Indole Derivatives of Formula
(I)

The present invention provides 2,3-Substituted Indole Derivatives having the formula:

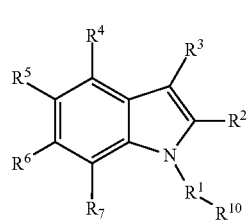

(I)

and pharmaceutically acceptable salts, solvates, esters and prodrugs thereof, wherein $R^1$, $R^2$, $R^3$, $R^4$, $R^5$, $R^6$, $R^7$ and $R^{10}$ are defined above for the compounds of formula (I).

In one embodiment, $R^1$ is bond.

In another embodiment, $R^1$ is —[C(R$^{12}$)$_2$]$_r$—.

In another embodiment, $R^1$ is —[C(R$^{12}$)$_2$]$_r$—O—[C(R$^{12}$)$_2$]$_q$—.

In still another embodiment, $R^1$ is —[C(R$^{12}$)$_2$]$_r$—N(R$^9$)—[C(R$^{12}$)$_2$]$_q$—.

In yet another embodiment, $R^1$ is —[C(R$^{12}$)$_2$]$_q$—CH=CH—[C(R$^{12}$)$_2$]$_q$—.

In another embodiment, $R^1$ is —[C(R$^{12}$)$_2$]$_q$—C≡C—[C(R$^{12}$)$_2$]$_q$—.

In a further embodiment, $R^1$ is —[C(R$^{12}$)$_2$]$_q$—SO$_2$—[C(R$^{12}$)$_2$]$_q$—.

In one embodiment, $R^1$ is —CH$_2$—, —CH$_2$CH$_2$—, —CH(CH$_3$)— or

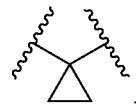

In another embodiment, $R^1$ is —CH$_2$—.

In another embodiment, $R^1$ is

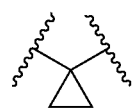

In one embodiment, $R^{10}$ is aryl or heteroaryl.

In another embodiment, $R^{10}$ is aryl.

In another embodiment, $R^{10}$ is H.

In another embodiment, $R^{10}$ is cycloalkyl.

In another embodiment, $R^{10}$ is cycloalkenyl.

In still another embodiment, $R^{10}$ is heterocycloalkenyl.

In another embodiment, $R^{10}$ is heteroaryl.

In another embodiment, $R^{10}$ is heterocycloalkyl.

In another embodiment, $R^{10}$ is phenyl.

In another embodiment, $R^{10}$ is phenyl, which is substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$.

In yet another embodiment, $R^{10}$ is pyridyl.

In a further embodiment, $R^{10}$ is

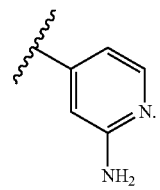

In another embodiment, —$R^{10}$ is:

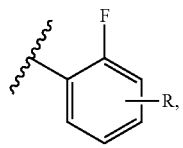

wherein R represents up to 2 optional and additional phenyl substituents, each independently selected from halo, —O-alkyl, alkyl, —$CF_3$, —CN, —$NHSO_2$-alkyl, —$NO_2$, —C(O)$NH_2$, —C(O)OH, —$NH_2$, —$SO_2$-alkyl, —$SO_2$NH-alkyl, —S-alkyl, —$CH_2NH_2$, —$SO_2NH_2$, —NHC(O)-alkyl, —C(O)O-alkyl, —C(O)-heterocycloalkyl and heteroaryl.

In one embodiment, $R^{10}$ is:

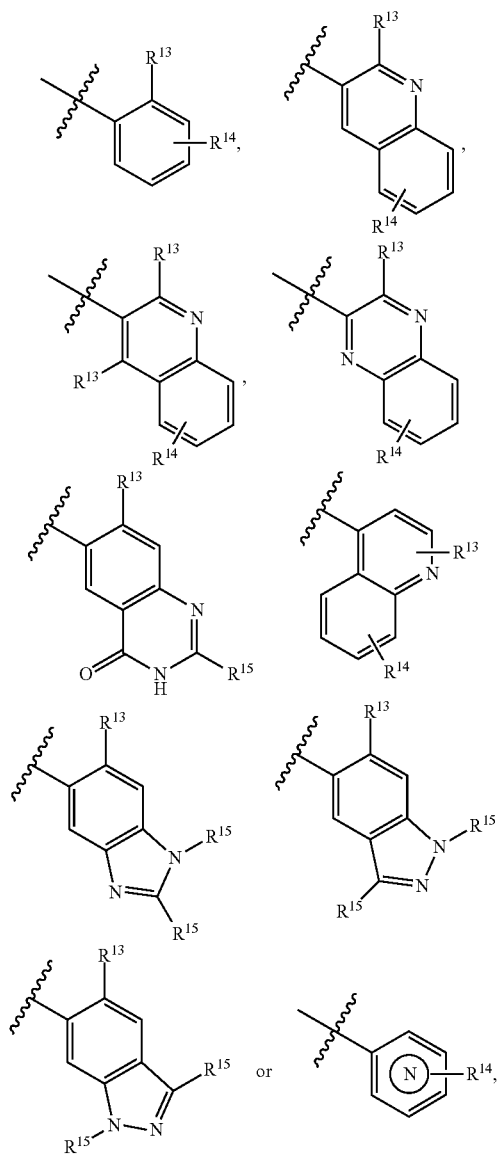

wherein $R^{13}$ is H, F, Br or Cl; $R^{14}$ represents up to 4 optional and additional substituents, each independently selected from alkyl, cycloalkyl, $CF_3$, —CN, halo, —O-alkyl, —O-haloalkyl, —$NHSO_2$-alkyl, —$NO_2$, —C(O)$NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; each occurrence of $R^{15}$ is independently alkyl, cycloalkyl, $CF_3$, —CN, halo, —O-alkyl, —O-haloalkyl, —$NHSO_2$-alkyl, —$NO_2$, —C(O)$NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl; and

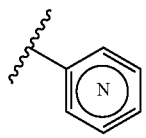

represents a pyridyl group, wherein the ring nitrogen atom can be at any of the five unsubstituted ring atom positions.

In another embodiment, $R^{10}$ is

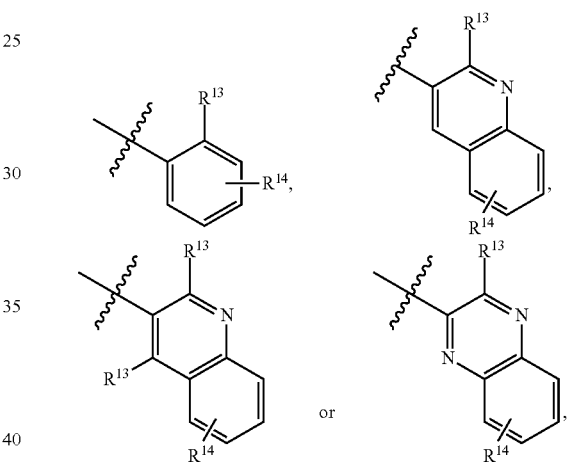

or wherein $R^{13}$ is F or Cl and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl.

In yet another embodiment, $R^{10}$ is:

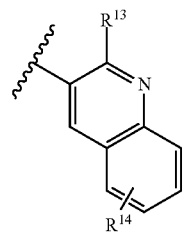

wherein $R^{13}$ is F or Cl and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$alkyl, —$SO_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In a further embodiment, R$^{10}$ is:

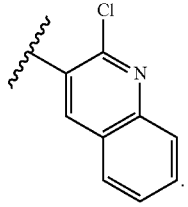

In another embodiment, R$^1$ is —CH$_2$— or

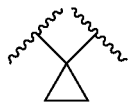

and R$^{10}$ is

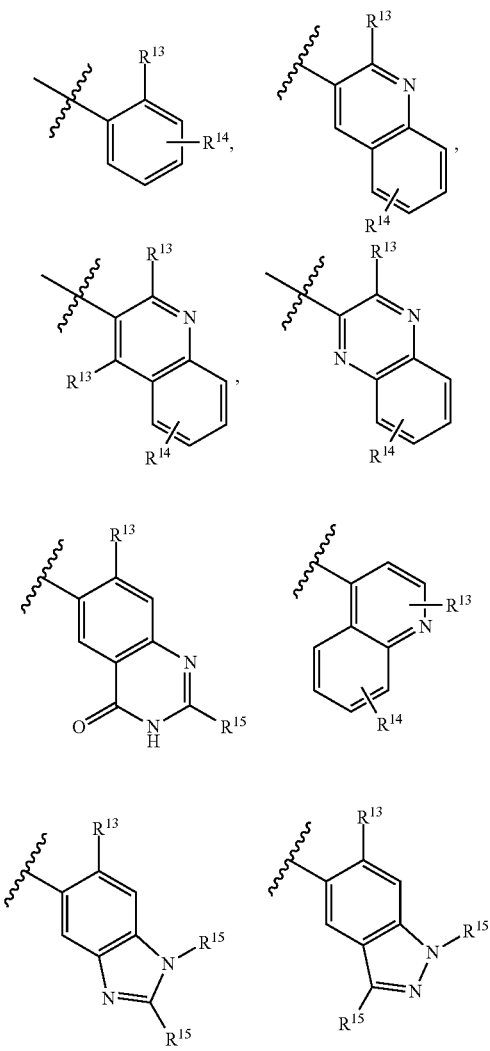

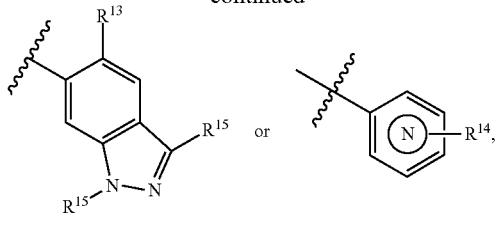

wherein R$^{13}$ is F or Cl; R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of R$^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In still another embodiment, R$^1$ is —CH$_2$— or and

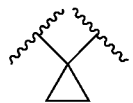

R$^{10}$ is

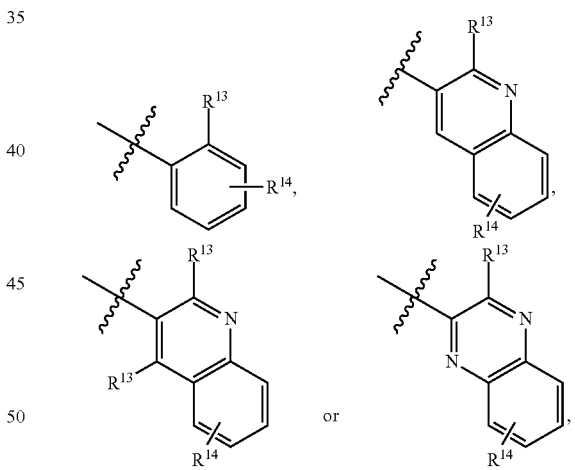

wherein R$^{13}$ is F or Cl and R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In one embodiment, —R$^1$-R$^{10}$ is benzyl.

In another embodiment, —R$^1$-R$^{10}$ is benzyl, wherein the phenyl moiety of the benzyl group is substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]—NH$_2$.

In still another embodiment, —$R^1$-$R^{10}$ is

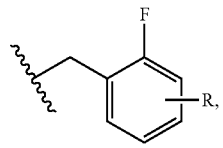

wherein R represents up to 2 optional and additional phenyl substituents, each independently selected from halo, —O-alkyl, alkyl, —$CF_3$, —CN, —$NHSO_2$-alkyl, —$NO_2$, —C(O)$NH_2$, —C(O)OH, —$NH_2$, —$SO_2$-alkyl, —$SO_2$NH-alkyl, —S-alkyl, —$CH_2NH_2$, —$SO_2NH_2$, —NHC(O)-alkyl, —C(O)O-alkyl, —C(O)-heterocycloalkyl and heteroaryl.

In another embodiment, —$R^1$-$R^{10}$ is

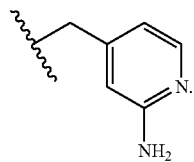

In still another embodiment, —$R^1$-$R^{10}$ is alkyl.

In yet another embodiment, —$R^1$-$R^{10}$ is —$R^1$-$R^{10}$ is benzyl, wherein the phenyl moiety of the benzyl group is substituted with 1 or 2 fluorine atoms.

In yet another embodiment, —$R^1$-$R^{10}$ is —$R^1$-$R^{10}$ is benzyl, wherein the phenyl moiety of the benzyl group is substituted with 1 or 2 methyl groups.

In yet another embodiment, —$R^1$-$R^{10}$ is $R^1$-$R^{10}$ is benzyl, wherein the phenyl moiety of the benzyl group is substituted with one fluorine atom and one methyl group.

In another embodiment, —$R^1$-$R^{10}$ is haloalkyl.

In a further embodiment, —$R^1$-$R^{10}$ is —$CH_2$-cycloalkyl.

In one embodiment, $R^2$ is —C(O)$NHSO_2R^{11}$ or —C(O)$NHSO_2N(R^9)_2$.

In another embodiment, $R^2$ is —C(O)$NHSO_2R^{11}$ or —C(O)$NHSO_2N(R^9)_2$, wherein $R^9$ is H, alkyl, -alkyl-N(alkyl)$_2$, aryl, cycloalkyl, heteroaryl or heterocycloalkyl and $R^{11}$ is alkyl, -alkyl-N(alkyl)$_2$, aryl, cycloalkyl, haloalkyl, heteroaryl, heterocycloalkyl or hydroxyalkyl.

In another embodiment, $R^2$ is —[C($R^{12})_2]_q$—C(O)N($R^9$)$SO_2R^{11}$.

In another embodiment, $R^2$ is —[C($R^{12})_2]_q$—C(O)N($R^9$)$SOR^{11}$.

In still another embodiment, $R^2$ is —[C($R^{12})_2]_q$—C(O)N($R^9$)$SO_2N(R^{11})_2$.

In another embodiment, $R^2$ is

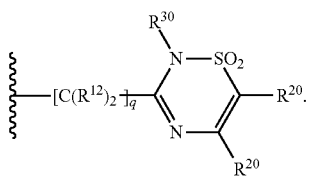

In another embodiment, $R^2$ is

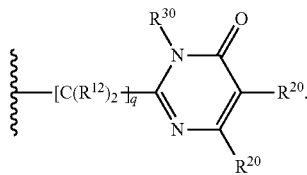

In yet another embodiment, $R^2$ is

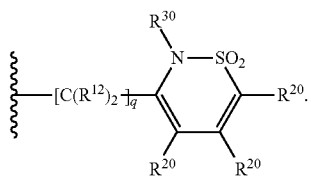

In another embodiment, $R^2$ is —C(O)N($R^9$)$SO_2R^{11}$.
In another embodiment, $R^2$ is —C(O)$NHSO_2R^{11}$.
In another embodiment, $R^2$ is —C(O)$NHSO_2R^{11}$ and $R^{11}$ is —[C($R^{12})_2]_q$-alkyl.
In yet another embodiment, $R^2$ is —C(O)$NHSO_2R^{11}$ and $R^{11}$ is —[C($R^{12})_2]_q$-aryl.
In another embodiment, $R^2$ is —C(O)$NHSO_2R^{11}$ and $R^{11}$ is —[C($R^{12})_2]_q$-cycloalkyl. In a further embodiment, $R^2$ is —C(O)$NHSO_2R^{11}$ and $R^{11}$ is —[C($R^{12})_2]_q$-heterocycloalkyl.
In another embodiment, $R^2$ is —C(O)$NHSO_2R^{11}$ and $R^{11}$ is —[C($R^{12})_2]_q$-heteroaryl.
In another embodiment, $R^2$ is —C(O)$NHSO_2R^{11}$ and $R^{11}$ is —[C($R^{12})_2]_q$-haloalkyl.
In still another embodiment, $R^2$ is —C(O)$NHSO_2R^{11}$ and $R^{11}$ is —[C($R^{12})_2]_q$-hydroxyalkyl.
In still another embodiment, $R^2$ is —C(O)$NHSO_2R^{11}$ and $R^{11}$ is alkyl.
In yet another embodiment, $R^2$ is —C(O)$NHSO_2R^{11}$ and $R^{11}$ is aryl.
In another embodiment, $R^2$ is —C(O)$NHSO_2R^{11}$ and $R^{11}$ is cycloalkyl.
In a further embodiment, $R^2$ is —C(O)$NHSO_2R^{11}$ and $R^{11}$ is heterocycloalkyl.
In another embodiment, $R^2$ is —C(O)$NHSO_2R^{11}$ and $R^{11}$ is heteroaryl.
In another embodiment, $R^2$ is —C(O)$NHSO_2R^{11}$ and $R^{11}$ is haloalkyl.
In still another embodiment, $R^2$ is —C(O)$NHSO_2R^{11}$ and $R^{11}$ is hydroxyalkyl.
In another embodiment, $R^2$ is —C(O)$NHSO_2R^{11}$ and $R^{11}$ is —[C($R^{12})_2]_q$-phenyl.
In another embodiment, $R^2$ is —C(O)$NHSO_2R^{11}$ and $R^{11}$ is benzyl.
In another embodiment, $R^2$ is —C(O)$NHSO_2R^{11}$ and $R^{11}$ is naphthyl.
In yet another embodiment, $R^2$ is —C(O)$NHSO_2R^{11}$ and $R^{11}$ is —$NH_2$ or —N($CH_3$)$_2$.
In another embodiment, $R^2$ is —C(O)$NHSO_2CH_3$.
In another embodiment, $R^2$ is —C(O)$NHSO_2CH_2CH_3$.
In another embodiment, $R^2$ is —C(O)$NHSO_2R^{11}$, and $R^{11}$ is alkyl, aryl, cycloalkyl, haloalkyl, heteroaryl, heterocycloalkyl or hydroxyalkyl.

In one embodiment, $R^2$ is —C(O)$NHSO_2R^{11}$ and $R^{11}$ is alkyl, cycloalkyl or aryl.

In one embodiment, $R^2$ is —C(O)$NHSO_2N(R^9)_2$ and $R^9$ is H, alkyl, aryl, cycloalkyl, heteroaryl or heterocycloalkyl.

In another embodiment, $R^2$ is —C(O)$NHSO_2N(R^9)_2$ and $R^9$ is H, alkyl, aryl, cycloalkyl, heteroaryl or heterocycloalkyl.

In another embodiment, $R^2$ is —C(O)NHSO$_2$N($R^9$)$_2$ and $R^9$ is —[C($R^{12}$)$_2$]$_q$—O-alkyl or —[C($R^{12}$)$_2$]$_q$—N(alkyl)$_2$.

In still another embodiment, $R^2$ is —C(O)NHSO$_2$N($R^9$)$_2$ and $R^9$ is —(CH$_2$)$_2$—N(CH$_3$)$_2$ or —(CH$_2$)$_3$—N(CH$_3$)$_2$.

In another embodiment, $R^2$ is —C(O)NHSO$_2$N($R^9$)$_2$ and $R^9$ is H, alkyl or cycloalkyl.

In another embodiment, $R^2$ is —C(O)NHSO$_2$$R^{11}$ and $R^{11}$ is methyl, ethyl, isopropyl, cyclopropyl or phenyl.

In another embodiment, $R^2$ is —C(O)NHSO$_2$N($R^9$)$_2$ and $R^9$ is H, methyl, ethyl or cyclopropyl.

In still another embodiment, $R^2$ is —C(O)NHSO$_2$$R^{11}$ and $R^{11}$ is cyclopropyl.

In another embodiment, $R^2$ is —C(O)NHSO$_2$N($R^9$)$_2$ and $R^9$ is H or methyl.

In still another embodiment, $R^2$ is —C(O)NHSO$_2$$R^{11}$ and $R^{11}$ is phenyl, which is optionally substituted with up to 3 groups independently selected from: alkyl, F, Cl, methyl, —NH$_2$, —NO$_2$, methoxy, —SO$_2$NH$_2$, —COON, —[C($R^{12}$)$_2$]$_q$—C(O)O-alkyl, —OH, —NHSO$_2$-alkyl, —[C($R^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C($R^{12}$)$_2$]$_q$—NHC(O)-alkyl, pyrazolyl or —OCH$_2$C(O)NH$_2$.

In yet another embodiment, $R^2$ is —C(O)NHSO$_2$$R^{11}$ and $R^{11}$ is —[C($R^{12}$)$_2$]$_q$—NHSO$_2$-alkyl, —[C($R^{12}$)$_2$]—O-alkyl, or —[C($R^{12}$)$_2$]-alkyl.

In yet another embodiment, $R^2$ is —C(O)NHSO$_2$$R^{11}$ and $R^{11}$ is imidazolyl, pyridyl, thienyl, furanyl, benzofuranyl, benzo[1,3]dioxolyl, tetrahydropyranyl,

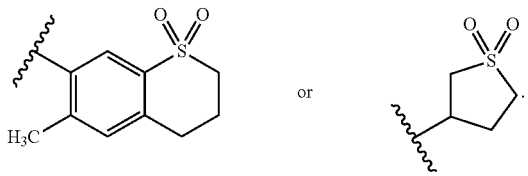

In yet another embodiment, $R^2$ is —C(O)NHSO$_2$$R^{11}$ and $R^{11}$ is cyclopropyl, cyclobutyl, cyclopentyl or cyclohexyl.

In one embodiment, $R^3$ is

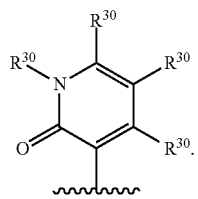

In another embodiment, $R^3$ is

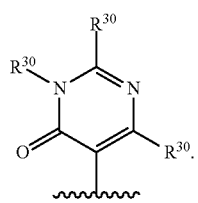

In another embodiment, $R^3$ is

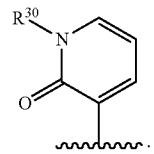

In another embodiment, $R^3$ is

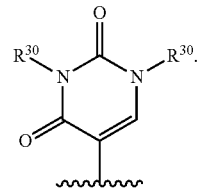

In one embodiment, $R^4$ is H.
In another embodiment, $R^4$ is H or F.
In another embodiment, $R^4$ is F.
In another embodiment, $R^5$ is H.
In another embodiment, $R^6$ is H.
In another embodiment, $R^6$ is H or F.
In another embodiment, $R^6$ is F.
In still another embodiment, $R^7$ is H.
In another embodiment, $R^4$ and $R^7$ are each H.
In yet another embodiment, $R^4$, $R^6$ and $R^7$ are each H.
In another embodiment, $R^4$, $R^5$, $R^6$ and $R^7$ are each H.
In a further embodiment, $R^4$, $R^6$ and $R^7$ are each H and $R^5$ is other than H.
In another embodiment, $R^4$, $R^6$ and $R^7$ are each H and $R^5$ is alkyl.
In another embodiment, $R^4$, $R^6$ and $R^7$ are each H and $R^5$ is halo.
In another embodiment, $R^4$, $R^6$ and $R^7$ are each H and $R^5$ is methyl.
In a further embodiment, $R^4$, $R^6$ and $R^7$ are each H and $R^5$ is Cl.
In another embodiment, $R^4$ and $R^7$ are each H and $R^5$ and $R^6$ are other than H.
In another embodiment, $R^4$ and $R^7$ are each independently H, alkyl, halo or —OH; $R^5$ is H, alkyl, —O-alkyl, —O-haloalkyl, cycloalkyl, halo, haloalkyl, —OH, hydroxyalkyl, —NH$_2$ or —CN; and $R^6$ is H, alkyl, —O-alkyl, —O-haloalkyl, cycloalkyl, halo, haloalkyl, —OH, hydroxyalkyl, —NH$_2$ or —CN.

In another embodiment, $R^5$ is other than H.
In still another embodiment, $R^5$ is alkyl.
In yet another embodiment, $R^5$ is halo.
In still another embodiment, $R^5$ is methyl.
In another embodiment, $R^5$ is ethyl.
In another embodiment, $R^6$ is H.
In another embodiment, $R^6$ is other than H.
In a further embodiment, $R^6$ is alkyl.
In yet another embodiment, $R^6$ is halo.
In still another embodiment, $R^6$ is methyl.
In another embodiment, $R^6$ is F.
In one embodiment, $R^4$ is H or F; $R^5$ is methyl or ethyl; $R^6$ is H or F; and $R^7$ is H.

In one embodiment, $R^2$ is —C(O)NHSO$_2$R$^{11}$ or —C(O)NHSO$_2$N(R$^9$)$_2$, and $R^3$ is:

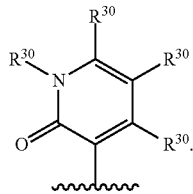

In one embodiment, $R^2$ is —C(O)NHSO$_2$R$^{11}$ or —C(O)NHSO$_2$N(R$^9$)$_2$;
$R^3$ is:

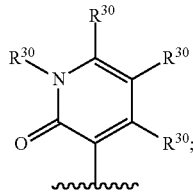

and two adjacent $R^{30}$ groups and the carbon atoms to which they are attached, join to form a benzene ring.

In one embodiment, $R^2$ is —C(O)NHSO$_2$R$^{11}$ or —C(O)NHSO$_2$N(R$^9$)$_2$; and
$R^3$ is

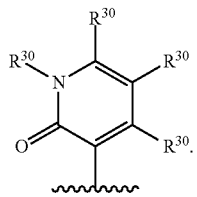

In one embodiment, $R^2$ is —C(O)NHSO$_2$R$^{11}$ and $R^3$ is

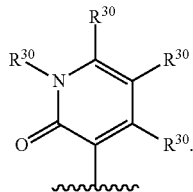

In one embodiment, $R^2$ is —C(O)NHSO$_2$CH$_3$, and $R^3$ is

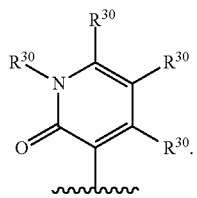

In one embodiment, $R^2$ is —C(O)NHSO$_2$R$^{11}$; $R^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$; and $R^3$ is

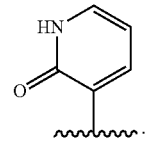

In one embodiment, $R^2$ is —C(O)NHSO$_2$R$^1$ and $R^3$ is

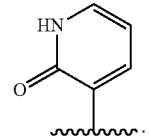

In one embodiment, $R^2$ is —C(O)NHSO$_2$CH$_3$, and $R^3$ is

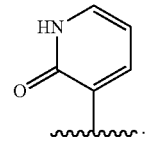

In one embodiment, $R^2$ is —C(O)NHSO$_2$R$^{11}$, R$^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$; and $R^3$ is

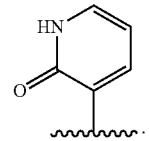

In another embodiment, $R^2$ is —C(O)NHSO$_2$R$^{11}$ or —C(O)NHSO$_2$N(R$^9$)$_2$;
$R^3$ is:

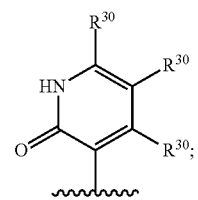

and $R^4$ and $R^7$ are each independently H, halo or hydroxy.

In another embodiment, $R^2$ is $—C(O)NHSO_2R^{11}$ or $—C(O)NHSO_2N(R^9)_2$;

$R^3$ is:

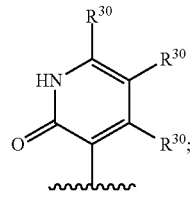

and $R^5$ is H, alkyl, —O-alkyl, cycloalkyl, halo, haloalkyl, —OH, hydroxyalkyl, —$NH_2$ or —CN.

In another embodiment, $R^2$ is $—C(O)NHSO_2R^{11}$ or $—C(O)NHSO_2N(R^9)_2$;

$R^3$ is

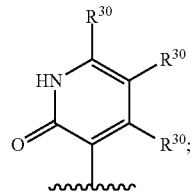

and $R^5$ is alkyl, cycloalkyl, halo or hydroxy.

In another embodiment, $R^2$ is $—C(O)NHSO_2R^{11}$ or $—C(O)NHSO_2N(R^9)_2$;

$R^3$ is:

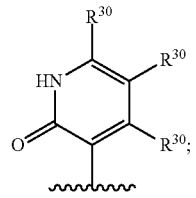

and $R^6$ is H, alkyl, —O-alkyl, cycloalkyl, halo, haloalkyl, —OH, hydroxyalkyl, —$NH_2$ or —CN.

In another embodiment, $R^2$ is $—C(O)NHSO_2R^{11}$ or $—C(O)NHSO_2N(R^9)_2$;

$R^3$ is

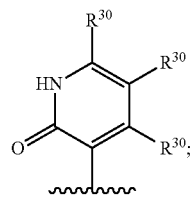

and $R^6$ is alkyl, cycloalkyl, halo or hydroxy.

In still another embodiment, $R^1$ is $—[C(R^{12})_2]_r—$; $R^2$ is $—C(O)NHSO_2R^{11}$ or $—C(O)NHSO_2NR^9)_2$; $R^3$ is:

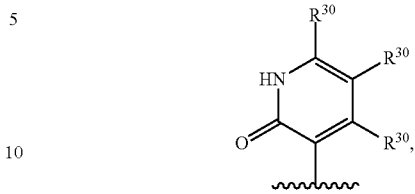

and $R^{10}$ is aryl or heteroaryl;

In one embodiment, $R^1$ is $—[C(R^{12})_2]_r—$; $R^2$ is $—C(O)NHSO_2R^{11}$ or $—C(O)NHSO_2N(R^9)_2$;

and $R^3$ is:

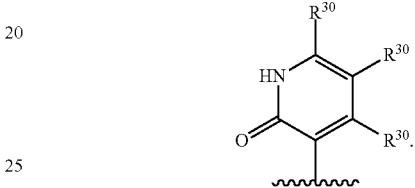

In another embodiment, $R^1$ is $—[C(R^{12})_2]_r—$; $R^2$ is $—C(O)NHSO_2R^{11}$ or $—C(O)NHSO_2N(R^9)_2$; $R^3$ is:

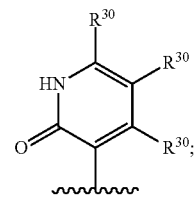

and $R^{10}$ is phenyl, naphthyl, pyridyl, quinolinyl or quinoxalinyl, each of which can be optionally substituted as set forth in claim 1;

In one embodiment, $R^1$ is $—[C(R^{12})_2]_r—$; $R^2$ is $—C(O)NHSO_2R^{11}$ or $—C(O)NHSO_2N(R^9)_2$;

$R^3$ is:

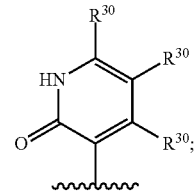

and $R^{10}$ is:

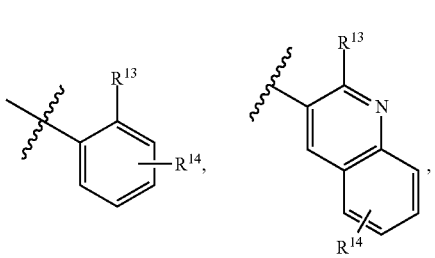

-continued

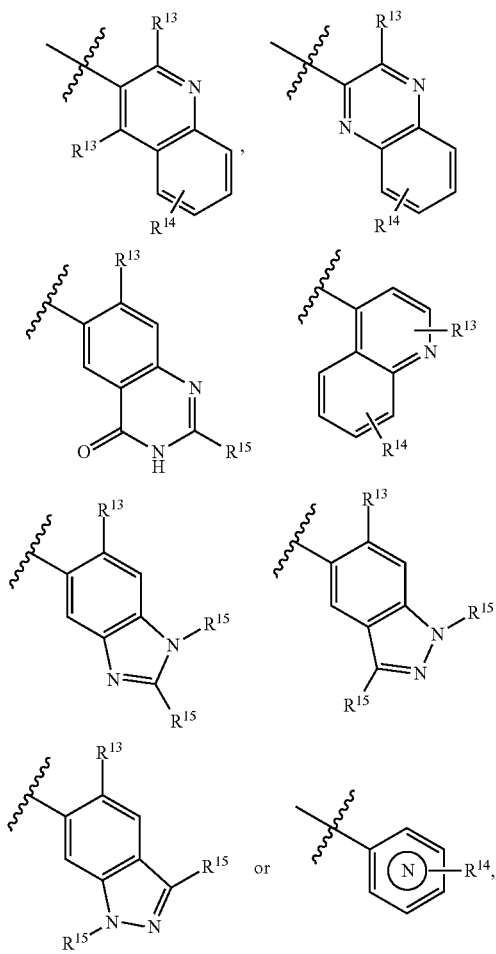

wherein $R^{13}$ is F or Cl; $R^{14}$ represents up to 4 optional and additional substituents, each independently selected from alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In yet another embodiment, $R^1$ is —[C(R$^{12}$)$_2$]$_1$—; $R^2$ is —C(O)NHSO$_2$R$^{11}$ or —C(O)NHSO$_2$N(R$^9$)$_2$; $R^3$ is:

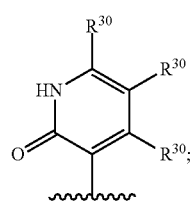

and $R^{10}$ is:

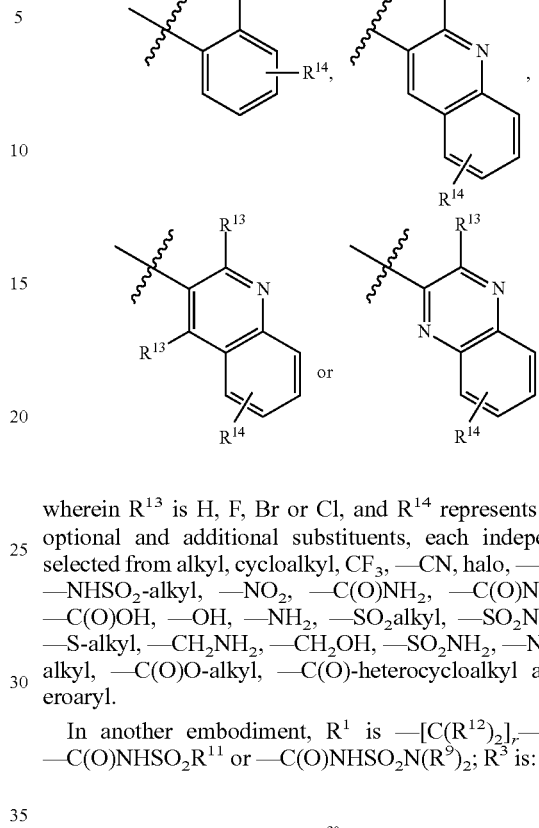

wherein $R^{13}$ is H, F, Br or Cl, and $R^{14}$ represents up to 4 optional and additional substituents, each independently selected from alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In another embodiment, $R^1$ is —[C(R$^{12}$)$_2$]$_r$—; $R^2$ is —C(O)NHSO$_2$R$^{11}$ or —C(O)NHSO$_2$N(R$^9$)$_2$; $R^3$ is:

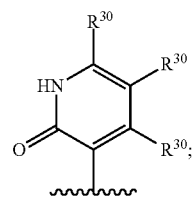

$R^5$ is H, alkyl, —O-alkyl, cycloalkyl, halo, haloalkyl, —OH, hydroxyalkyl, —NH$_2$ or —CN; $R^6$ is H, alkyl, —O-alkyl, cycloalkyl, halo, haloalkyl, —OH, hydroxyalkyl, —NH$_2$ or —CN; and $R^{10}$ is phenyl, naphthyl, pyridyl, quinolinyl or quinoxalinyl, each of which can be optionally substituted as set forth in claim 1.

In a further embodiment, $R^1$ is —[C(R$^{12}$)$_2$]$_1$ —; $R^2$ is —C(O)NHSO$_2$R$^{11}$ or —C(O)NHSO$_2$N(R$^9$)$_2$; $R^3$ is:

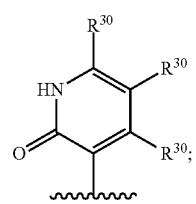

$R^5$ is H, methyl, ethyl or cyclopropyl; $R^6$ is H, F or —OH; and $R^{10}$ is phenyl, naphthyl, pyridyl, quinolinyl or quinoxalinyl, each of which can be optionally substituted as set forth in claim 1.

In another embodiment, $R^1$ is $-[C(R^{12})_2]_r-$; $R^2$ is $-C(O)NHSO_2R^{11}$ or $-C(O)NHSO_2N(R^9)_2$; $R^3$ is:

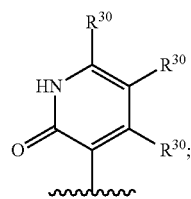

$R^9$ is H, methyl or ethyl; $R^{10}$ is phenyl, naphthyl, pyridyl, quinolinyl or quinoxalinyl, each of which can be optionally substituted as set forth in claim 1; and $R^{11}$ is methyl, ethyl, cyclopropyl or phenyl.

In one embodiment, $R^1$ is $-[C(R^{12})_2]_r-$; $R^2$ is $-C(O)NHSO_2R^{11}$ or $-C(O)NHSO_2N(R^9)_2$; $R^3$ is:

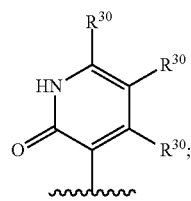

$R^9$ is H, methyl or ethyl; $R^{10}$ is phenyl, naphthyl, pyridyl, quinolinyl or quinoxalinyl, each of which can be optionally substituted as set forth in claim 1; and $R^{11}$ is methyl, cyclopropyl or phenyl.

In another embodiment, $R^1$ is $-[C(R^{12})_2]_r-$; $R^2$ is $-C(O)NHSO_2R^{11}$ or $-C(O)NHSO_2N(R^9)_2$; and $R^3$ is

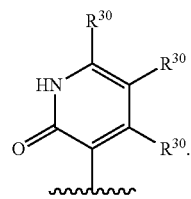

In another embodiment, $R^1$ is $-CH_2-$, $-CH_2CH_2-$, $-CH(CH_3)-$ or

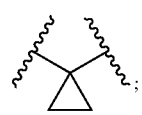

$R^2$ is $-C(O)NHSO_2R^{11}$ or $-C(O)NHSO_2N(R^9)_2$; and $R^3$ is:

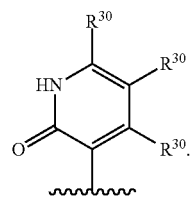

In another embodiment, $R^1$ is $-CH_2-$ or

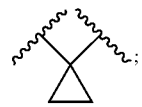

$R^2$ is $-C(O)NHSO_2R^{11}$ or $-C(O)NHSO_2N(R^9)_2$; and $R^3$ is

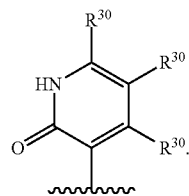

In one embodiment, $R^1$ is $-CH_2-$ or

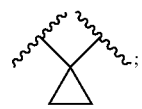

$R^2$ is $-C(O)NHSO_2R^{11}$ or $-C(O)NHSO_2N(R^9)_2$; $R^3$ is

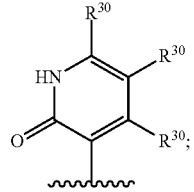

and
$R^{10}$ is aryl or heteroaryl.

In one embodiment, $R^1$ is $-CH_2-$ or

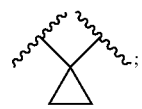

$R^2$ is $-C(O)NHSO_2R^{11}$ or $-C(O)NHSO_2N(R^9)_2$; $R^3$ is

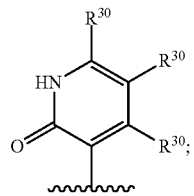

and
$R^{10}$ is phenyl, naphthyl, pyridyl, quinolinyl or quinoxalinyl, each of which can be optionally substituted as set forth in formula (I).

In one embodiment, $R^1$ is —CH$_2$— or

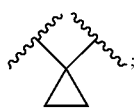

$R^2$ is —C(O)NHSO$_2$R$^{11}$ or —C(O)NHSO$_2$N(R$^9$)$_2$; $R^3$ is

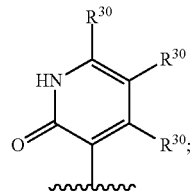

and
$R^{10}$ is

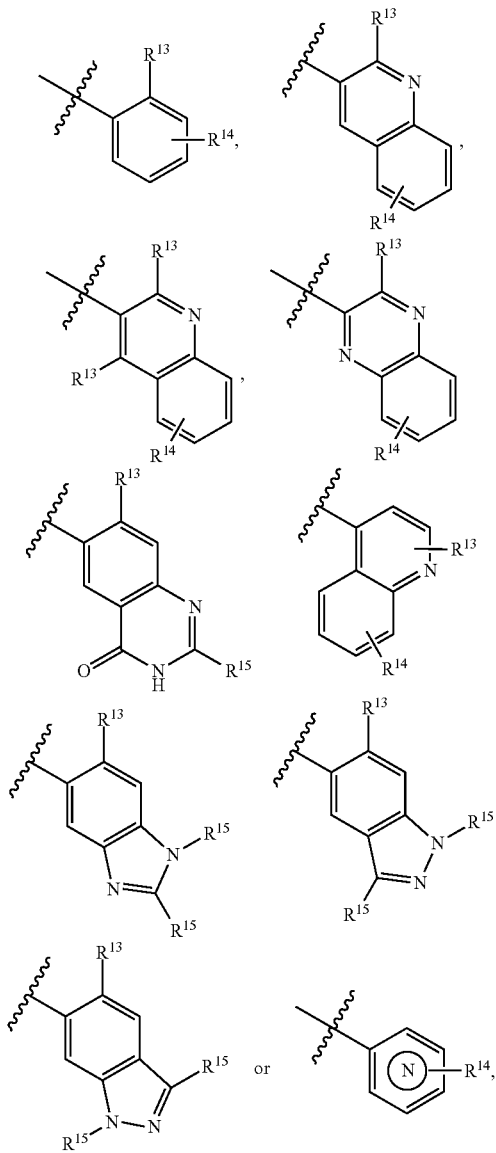

wherein $R^{13}$ is F or Cl; $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of $R^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In another embodiment, $R^1$ is —CH$_2$— or

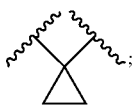

$R^2$ is —C(O)NHSO$_2$R$^{11}$ or —C(O)NHSO$_2$N(R$^9$)$_2$; $R^3$ is

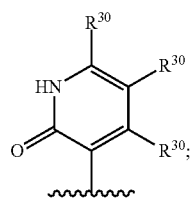

and
$R^{10}$ is


wherein $R^{13}$ is F or Cl and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In another embodiment, $R^1$ is —$CH_2$— or

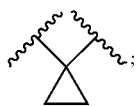

$R^2$ is —C(O)$NHSO_2R^{11}$ or —C(O)$NHSO_2N(R^9)_2$; $R^3$ is

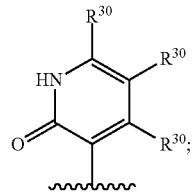

$R^5$ is alkyl, cycloalkyl, halo or —OH; $R^6$ is alkyl, cycloalkyl, halo or —OH; and $R^{10}$ is

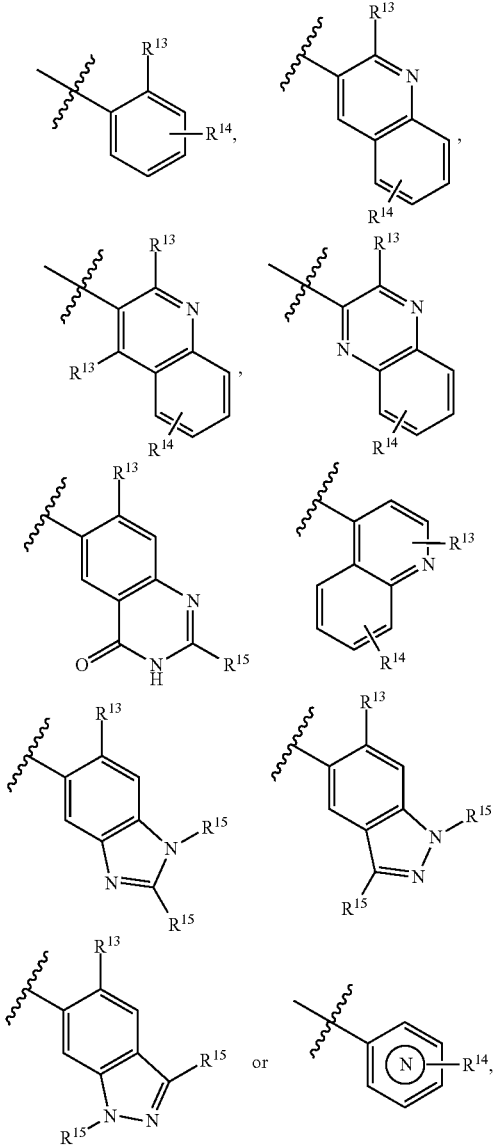

wherein $R^{13}$ is F or Cl; $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl.

In another embodiment, $R^1$ is —$CH_2$— or

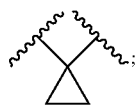

$R^2$ is —C(O)$NHSO_2R^{11}$ or —C(O)$NHSO_2N(R^9)_2$; $R^3$ is $R^5$ is alkyl, cycloalkyl, halo or —OH; $R^6$ is alkyl, cycloalkyl, halo or —OH; and $R^{10}$ is

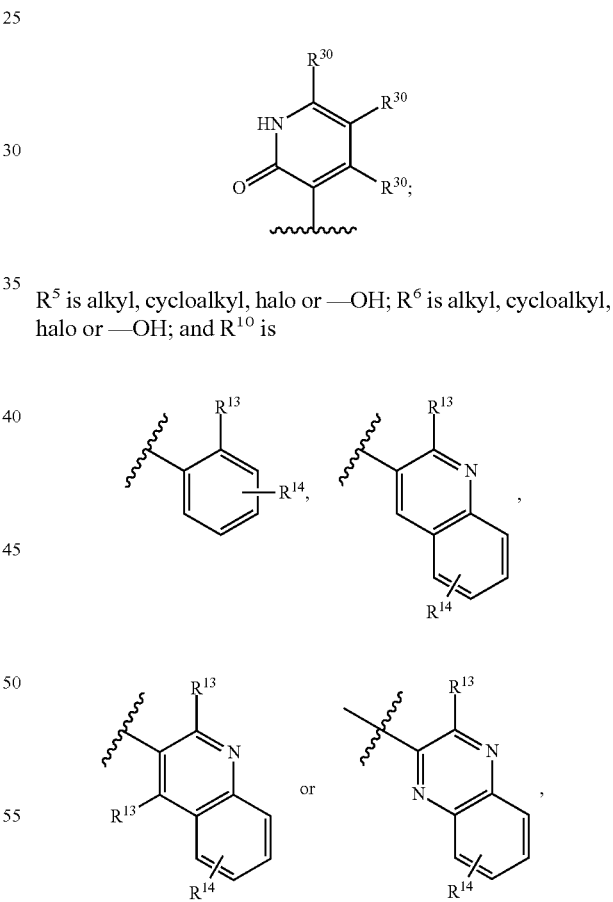

wherein $R^{13}$ is F or Cl and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl.

In one embodiment, $R^1$ is —CH$_2$— or

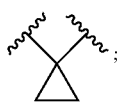

$R^2$ is —C(O)NHSO$_2$R$^{11}$ or —C(O)NHSO$_2$N(R$^9$)$_2$; $R^3$ is

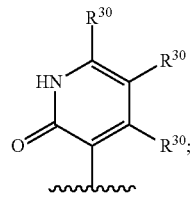

$R^5$ is methyl, ethyl or cyclopropyl; $R^6$ is H, F or —OH; and $R^{10}$ is

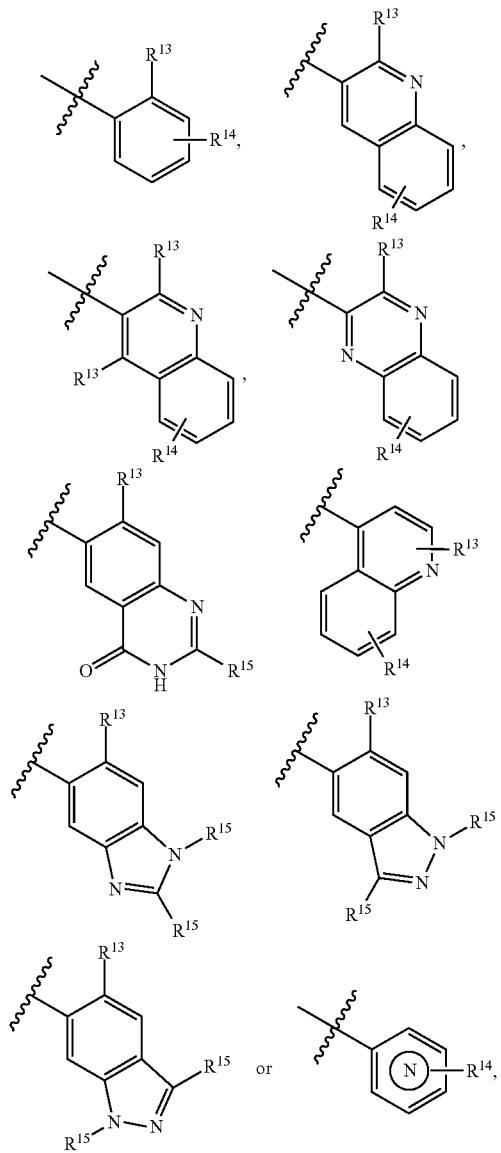

wherein $R^{13}$ is F or Cl; $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of $R^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In another embodiment, $R^1$ is —CH$_2$— or

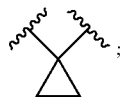

$R^2$ is —C(O)NHSO$_2$R$^{11}$ or —C(O)NHSO$_2$N(R$^9$)$_2$; $R^3$ is

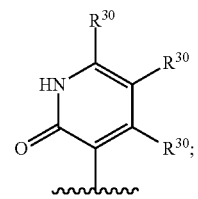

$R^5$ is methyl, ethyl or cyclopropyl; $R^6$ is H, F or —OH; and $R^{10}$ is

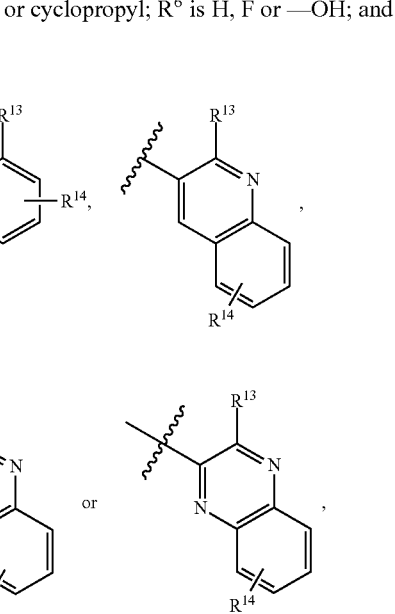

wherein $R^{13}$ is F or Cl and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In still another embodiment, $R^1$ is —CH$_2$— or

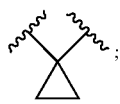

$R^2$ is —C(O)NHSO$_2$R$^{11}$ or —C(O)NHSO$_2$N(R$^9$)$_2$; $R^3$ is

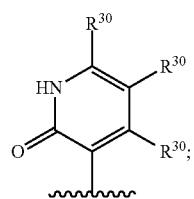

$R^9$ is H, methyl or ethyl; $R^{10}$ is

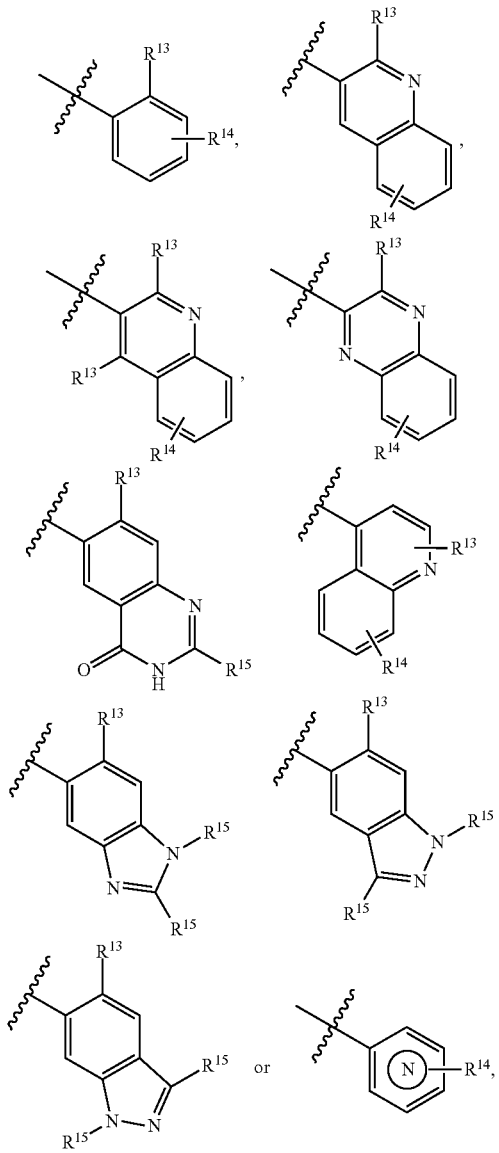

wherein $R^{11}$ is methyl, ethyl, cyclopropyl or phenyl; $R^{13}$ is F or Cl; $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of $R^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In a further embodiment, $R^1$ is —CH$_2$— or

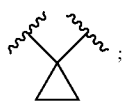

$R^2$ is —C(O)NHSO$_2$R$^{11}$ or —C(O)NHSO$_2$N(R$^9$)$_2$; $R^3$ is

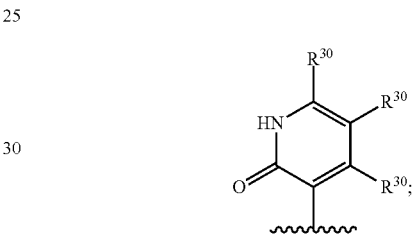

$R^9$ is H, methyl or ethyl; $R^{10}$ is

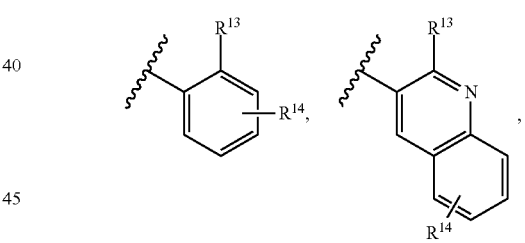

wherein $R^{13}$ is F or Cl and $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and $R^{11}$ is methyl, ethyl, cyclopropyl or phenyl.

In another embodiment, $R^1$ is —$CH_2$— or

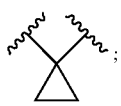

$R^2$ is —$C(O)NHSO_2R^{11}$ or —$C(O)NHSO_2N(R^9)_2$; $R^3$ is

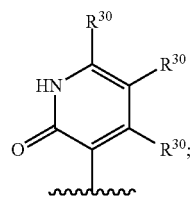

$R^9$ is H, methyl or ethyl; $R^{10}$ is

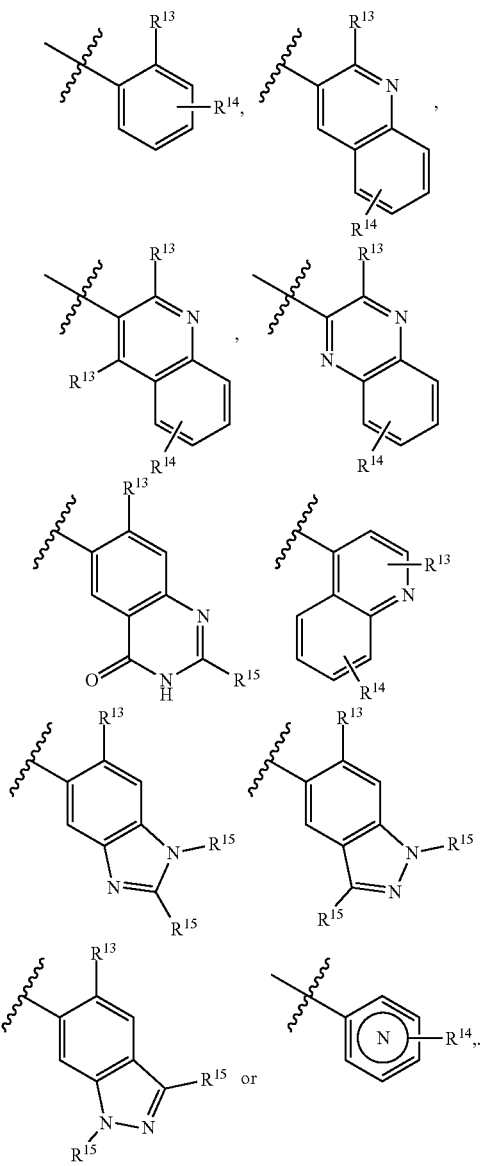

wherein $R^{11}$ is methyl, ethyl or phenyl; $R^{13}$ is F or Cl; $R^{14}$ represents up to 4 optional and additional substituents, each independently selected from alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl.

In another embodiment, $R^1$ is —$CH_2$— or

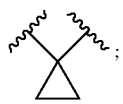

$R^2$ is —$C(O)NHSO_2R^{11}$ or —$C(O)NHSO_2N(R^9)_2$; $R^3$ is

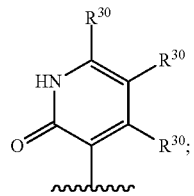

$R^9$ is H, methyl or ethyl; $R^{10}$ is

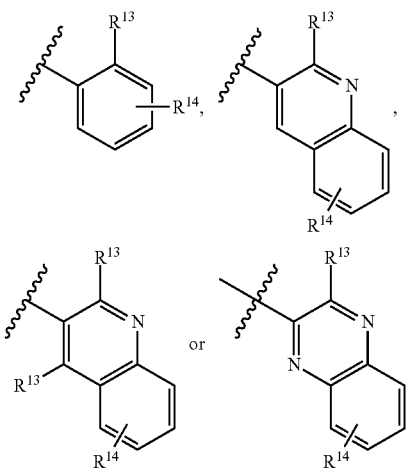

wherein $R^{13}$ is F or Cl and $R^{14}$ represents up to 4 optional and additional substituents, each independently selected from alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and $R^{11}$ is methyl, ethyl or phenyl.

In one embodiment, R$^1$-R$^{10}$ is

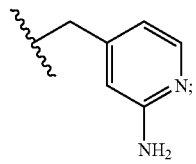

R$^2$ is —C(O)NHSO$_2$R$^{11}$; and R$^3$ is

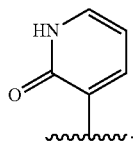

In one embodiment, R$^1$-R$^{10}$ is

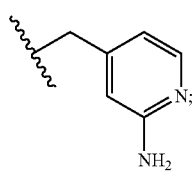

R$^2$ is —C(O)NHSO$_2$CH$_3$; and R$^3$ is

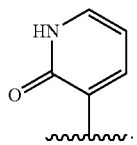

In one embodiment, R$^1$-R$^{10}$ is

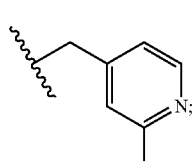

R$^2$ is —C(O)NHSO$_2$R$^{11}$, R$^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_y$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_1$—NHC(O)-alkyl, pyrazolyl or —OCH$_2$C(O)NH$_2$; and R$^3$ is

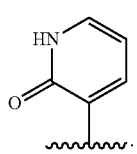

In one embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; R$^2$ is —C(O)NHSO$_2$R$^{11}$; and R$^3$ is

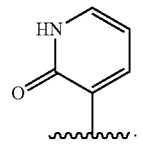

In one embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$, R$^2$ is —C(O)NHSO$_2$CH$_3$; and R$^3$ is

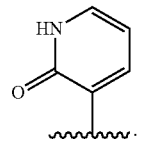

In one embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$; and R$^3$ is

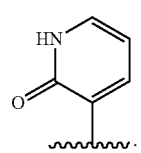

In one embodiment, R$^1$-R$^{10}$ is

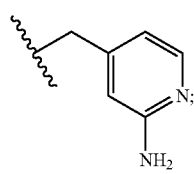

R$^2$ is —C(O)NHSO$_2$R$^{11}$; R$^3$ is

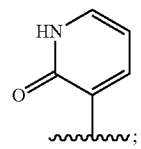

R$^4$, R$^6$ and R$^7$ are each H; and R$^5$ is other than H.

In another embodiment, $R^1$-$R^{10}$ is

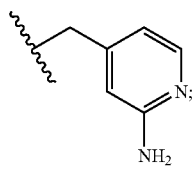

$R^2$ is —C(O)NHSO$_2$CH$_3$; $R^3$ is

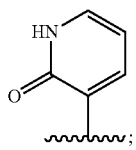

$R^4$, $R^6$ and $R^7$ are each H; and $R^5$ is other than H.

In another embodiment, $R^1$-$R^{10}$ is

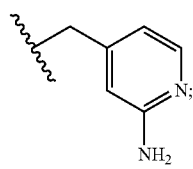

$R^2$ is —C(O)NHSO$_2$R$^{11}$, R$^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]—NHC(O)-alkyl, pyrazolyl or —OCH$_2$C(O)NH$_2$; $R^3$ is

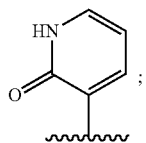

$R^4$, $R^6$ and $R^7$ are each H; and $R^5$ is other than H.

In one embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; $R^2$ is —C(O)NHSO$_2$R$^{11}$; $R^3$ is

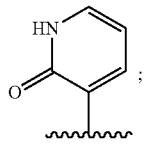

$R^4$, $R^6$ and $R^7$ are each H; and $R^5$ is other than H.

In another embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; $R^2$ is —C(O)NHSO$_2$CH$_3$; $R^3$ is

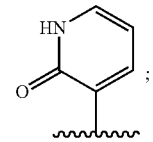

$R^4$, $R^6$ and $R^7$ are each H; and $R^5$ is other than H.

In another embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; $R^2$ is —C(O)NHSO$_2$R$^{11}$, R$^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$; $R^3$ is

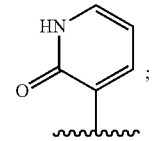

$R^4$, $R^6$ and $R^7$ are each H; and $R^5$ is other than H.

In one embodiment, $R^1$-$R^{10}$ is

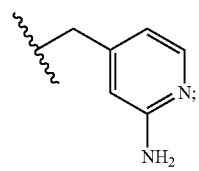

$R^2$ is —C(O)NHSO$_2$R$^{11}$; $R^3$ is

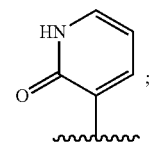

$R^4$ is H or F; $R^5$ is methyl or ethyl; $R^6$ is H or F; and $R^7$ is H.

In another embodiment, $R^1$-$R^{10}$ is

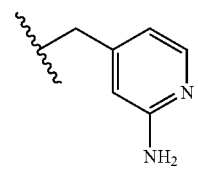

$R^2$ is —C(O)NHSO$_2$CH$_3$; $R^3$ is

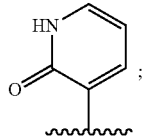

$R^4$ is H or F; $R^5$ is methyl or ethyl; $R^6$ is H or F; and $R^7$ is H.

In another embodiment, $R^1$-$R^{10}$ is

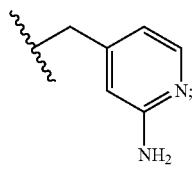

$R^2$ is —C(O)NHSO$_2$R$^{11}$, R$^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$; $R^3$ is

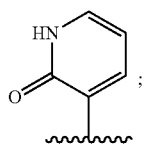

$R^4$ is H or F; $R^5$ is methyl or ethyl; $R^6$ is H or F; and $R^7$ is H.

In one embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; $R^2$ is —C(O)NHSO$_2$R$^{11}$; $R^3$ is

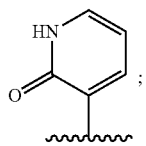

$R^4$ is H or F; $R^5$ is methyl or ethyl; $R^6$ is H or F; and $R^7$ is H.

In another embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; $R^2$ is —C(O)NHSO$_2$CH$_3$; $R^3$ is

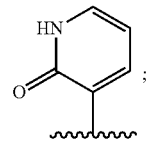

$R^4$ is H or F; $R^5$ is methyl or ethyl; $R^6$ is H or F; and $R^7$ is H.

In another embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; $R^2$ is —C(O)NHSO$_2$R$^{11}$, R$^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$; $R^3$ is

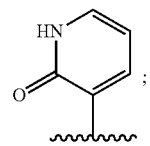

$R^4$ is H or F; $R^5$ is methyl or ethyl; $R^6$ is H or F; and $R^7$ is H.

In one embodiment, $R^1$ is —CH$_2$—; $R^2$ is —C(O)NHSO$_2$CH$_3$ or —C(O)NHSO$_2$-cyclopropyl; $R^3$ is

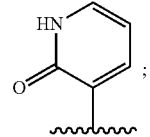

$R^4$ is H or F; $R^5$ is methyl or ethyl; $R^6$ is H or F; $R^7$ is H; and —R$^{10}$ is:

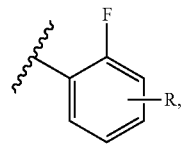

wherein R represents up to 2 optional and additional phenyl substituents, each independently selected from halo, —O-alkyl, alkyl, —CF$_3$, —CN, —NHSO$_2$-alkyl, —NO$_2$, —C(O)NH$_2$, —C(O)OH, —NH$_2$, —SO$_2$-alkyl, —SO$_2$NH-alkyl, —S-alkyl, —CH$_2$NH$_2$, —SO$_2$NH$_2$, —NHC(O)-alkyl, —C(O)O-alkyl, —C(O)-heterocycloalkyl and heteroaryl.

In one embodiment, $R^2$ is —C(O)NHSO$_2$R$^{11}$ or —C(O)NHSO$_2$N(R$^9$)$_2$, wherein R$^9$ is H, alkyl, aryl, cycloalkyl, heteroaryl or heterocycloalkyl and R$^{11}$ is alkyl, aryl, cycloalkyl, haloalkyl, heteroaryl, heterocycloalkyl or hydroxyalkyl.

In another embodiment, $R^2$ is —C(O)NHSO$_2$R$^{11}$ or —C(O)NHSO$_2$N(R$^9$)$_2$, wherein R$^9$ is H, alkyl, aryl, cycloalkyl, heteroaryl or heterocycloalkyl and R$^{11}$ is alkyl, aryl, cycloalkyl, haloalkyl, heteroaryl, heterocycloalkyl or hydroxyalkyl; and $R^3$ is:

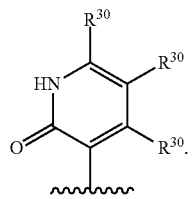

In another embodiment, $R^2$ is —C(O)NHSO$_2$R$^{11}$ or —C(O)NHSO$_2$N(R$^9$)$_2$, wherein R$^9$ is H, alkyl, aryl, cycloalkyl, heteroaryl or heterocycloalkyl and R$^{11}$ is alkyl, aryl, cycloalkyl, haloalkyl, heteroaryl, heterocycloalkyl or hydroxyalkyl; and R$^1$ is —[C(R$^{12}$)$_2$]$_r$—. In still another embodiment, $R^2$ is —C(O)NHSO$_2$R$^{11}$ or —C(O)NHSO$_2$N (R$^9$)$_2$, wherein R$^9$ is H, alkyl, aryl, cycloalkyl, heteroaryl or heterocycloalkyl and R$^{11}$ is alkyl, aryl, cycloalkyl, haloalkyl, heteroaryl, heterocycloalkyl or hydroxyalkyl; and R$^1$ is —CH$_2$—, —CH$_2$CH$_2$—, —CH(CH$_3$)— or

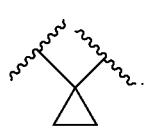

In another embodiment, $R^2$ is —C(O)NHSO$_2$R$^{11}$ or —C(O)NHSO$_2$N(R$^9$)$_2$, wherein R$^9$ is H, alkyl, aryl, cycloalkyl, heteroaryl or heterocycloalkyl and R$^{11}$ is alkyl, aryl, cycloalkyl, haloalkyl, heteroaryl, heterocycloalkyl or hydroxyalkyl; and wherein R$^4$ and R$^7$ are each independently H, alkyl, halo or —OH, R$^5$ is H, alkyl, —O-alkyl, —O-haloalkyl, cycloalkyl, halo, haloalkyl, —OH, hydroxyalkyl, —NH$_2$ or —CN, and R$^6$ is H, alkyl, —O-alkyl, —O-haloalkyl, cycloalkyl, halo, haloalkyl, —OH, hydroxyalkyl, —NH$_2$ or —CN.

In yet another embodiment, $R^2$ is —C(O)NHSO$_2$R$^{11}$ or —C(O)NHSO$_2$N(R$^9$)$_2$, wherein R$^9$ is H, alkyl, aryl, cycloalkyl, heteroaryl or heterocycloalkyl and R$^{11}$ is alkyl, aryl, cycloalkyl, haloalkyl, heteroaryl, heterocycloalkyl or hydroxyalkyl; and R$^{10}$ is aryl or heteroaryl.

In yet another embodiment, $R^2$ is —C(O)NHSO$_2$R$^{11}$ or —C(O)NHSO$_2$N(R$^9$)$_2$, wherein R$^9$ is H, alkyl, aryl, cycloalkyl, heteroaryl or heterocycloalkyl and R$^{11}$ is alkyl, aryl, cycloalkyl, haloalkyl, heteroaryl, heterocycloalkyl or hydroxyalkyl; and R$^{10}$ is:

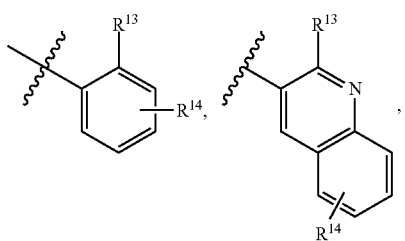

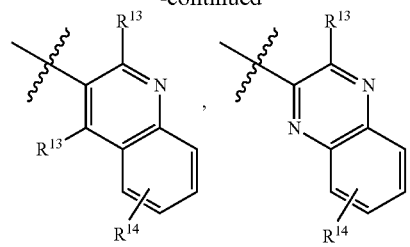

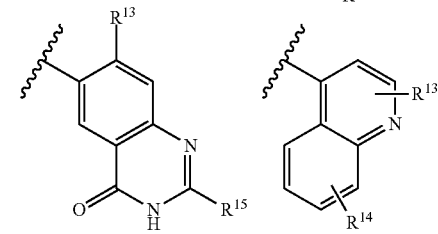

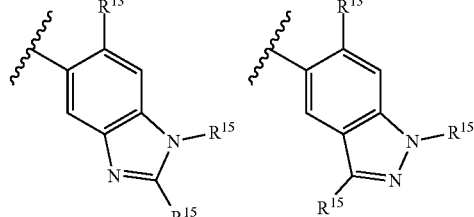

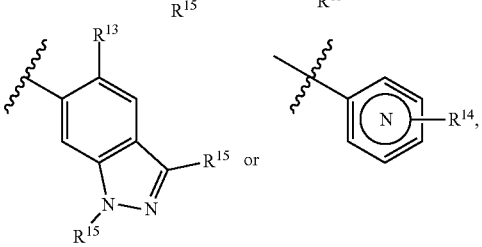

wherein R$^{13}$ is H, F, Br or Cl; R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; each occurrence of R$^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl; and

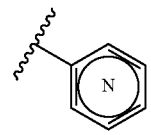

represents a pyridyl group, wherein the ring nitrogen atom can be at any of the five unsubstituted ring atom positions.

In another embodiment, $R^2$ is —C(O)NHSO$_2$R$^{11}$ or —C(O)NHSO$_2$N(R$^9$)$_2$, wherein R$^9$ is H, alkyl, aryl, cycloalkyl, heteroaryl or heterocycloalkyl and R$^{11}$ is alkyl, aryl, cycloalkyl, haloalkyl, heteroaryl, heterocycloalkyl or hydroxyalkyl; and R$^{10}$ is:

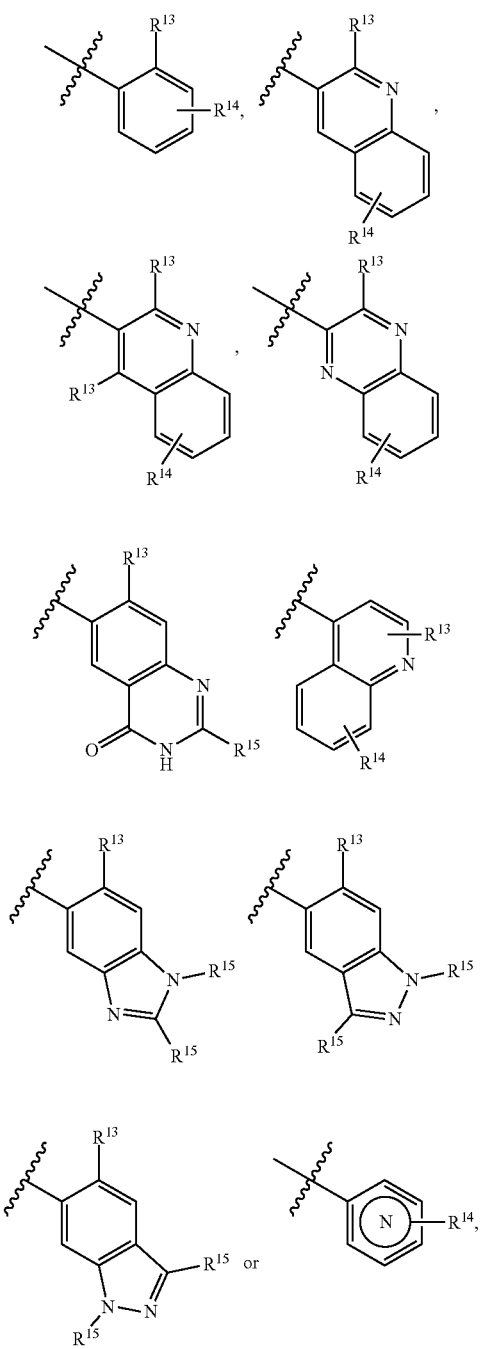

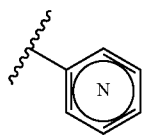

represents a pyridyl group, wherein the ring nitrogen atom can be at any of the five unsubstituted ring atom positions.

In another embodiment, $R^2$ is —C(O)NHSO$_2$R$^{11}$ or —C(O)NHSO$_2$N(R$^9$)$_2$, wherein R$^9$ is H, alkyl, aryl, cycloalkyl, heteroaryl or heterocycloalkyl and R$^{11}$ is alkyl, aryl, cycloalkyl, haloalkyl, heteroaryl, heterocycloalkyl or hydroxyalkyl; $R^{10}$ is:

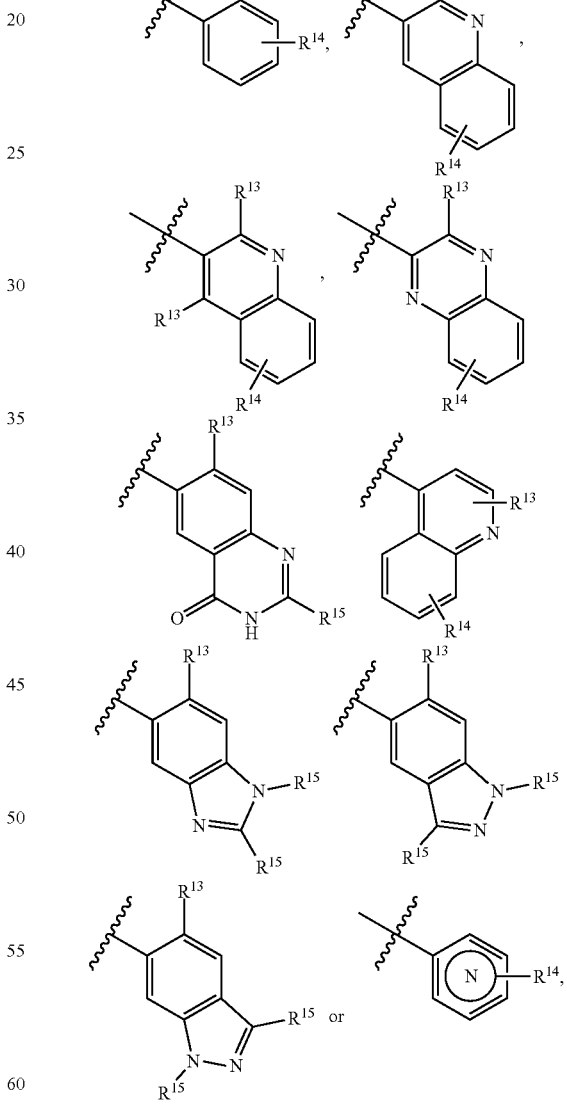

wherein $R^{13}$ is H, F, Br or Cl; $R^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; each occurrence of R$^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl; and wherein $R^{13}$ is H, F, Br or Cl; $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; each occurrence of R$^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl;

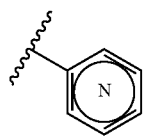

represents a pyridyl group, wherein the ring nitrogen atom can be at any of the five unsubstituted ring atom positions; and R$^4$ and R$^7$ are each independently H, halo or —OH; R$^5$ is H, alkyl, —O-alkyl, —O-haloalkyl, cycloalkyl, halo, haloalkyl, —OH, hydroxyalkyl, —NH$_2$ or —CN; and R$^6$ is H, alkyl, —O-alkyl, —O-haloalkyl, cycloalkyl, halo, haloalkyl, —OH, hydroxyalkyl, —NH$_2$ or —CN.

In yet another embodiment, R$^2$ is —C(O)NHSO$_2$R$^{11}$ or —C(O)NHSO$_2$N(R$^9$)$_2$, wherein R$^9$ is H, alkyl, aryl, cycloalkyl, heteroaryl or heterocycloalkyl and R$^{11}$ is alkyl, aryl, cycloalkyl, haloalkyl, heteroaryl, heterocycloalkyl or hydroxyalkyl; R$^{10}$ is:

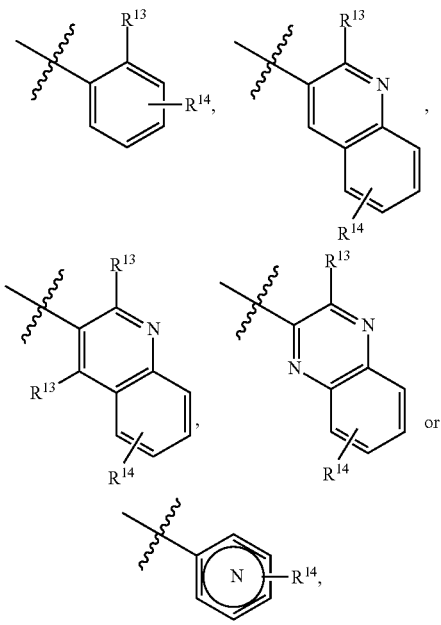

wherein R$^{13}$ is H, F, Br or Cl; R$^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl;

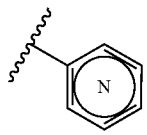

represents a pyridyl group, wherein the ring nitrogen atom can be at any of the five unsubstituted ring atom positions; and R$^4$ and R$^7$ are each independently H, halo or —OH; R$^5$ is H, alkyl, —O-alkyl, —O-haloalkyl, cycloalkyl, halo, haloalkyl, —OH, hydroxyalkyl, —NH$_2$ or —CN; and R$^6$ is H, alkyl, —O-alkyl, —O-haloalkyl, cycloalkyl, halo, haloalkyl, —OH, hydroxyalkyl, —NH$_2$ or —CN.

In one embodiment, R$^1$ is —[C(R$^{12}$)$_2$]$_r$—; R$^2$ is —C(O)NHSO$_2$R$^{11}$ or —C(O)NHSO$_2$N(R$^9$)$_2$, wherein R$^9$ is H, alkyl, -alkyl-N(alkyl)$_2$, aryl, cycloalkyl, heteroaryl or heterocycloalkyl and R$^{11}$ is alkyl, -alkyl-N(alkyl)$_2$, aryl, cycloalkyl, haloalkyl, heteroaryl, heterocycloalkyl or hydroxyalkyl; and R$^3$ is:

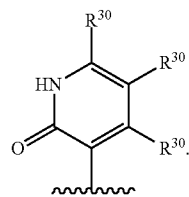

In another embodiment, R$^1$ is —CH$_2$—, —CH$_2$CH$_2$—, —CH(CH$_3$)— or

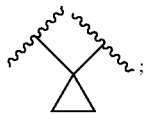

R$^2$ is —C(O)NHSO$_2$R$^{11}$ or —C(O)NHSO$_2$N(R$^9$)$_2$, wherein R$^9$ is H, alkyl, -alkyl-N(alkyl)$_2$, aryl, cycloalkyl, heteroaryl or heterocycloalkyl and R$^{11}$ is alkyl, -alkyl-N(alkyl)$_2$, aryl, cycloalkyl, haloalkyl, heteroaryl, heterocycloalkyl or hydroxyalkyl; and R$^3$ is:

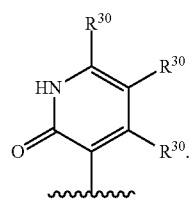

In another embodiment, R$^1$ is —CH$_2$—; R$^2$ is —C(O)NHSO$_2$R$^{11}$ or —C(O)NHSO$_2$N(R$^9$)$_2$, wherein R$^9$ is H, alkyl, -alkyl-N(alkyl)$_2$, aryl, cycloalkyl, heteroaryl or heterocycloalkyl and R$^{11}$ is alkyl, -alkyl-N(alkyl)$_2$, aryl, cycloalkyl, haloalkyl, heteroaryl, heterocycloalkyl or hydroxyalkyl; and R$^3$ is:

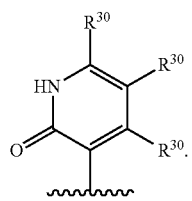

In still another embodiment, $R^1$ is —[C(R$^{12}$)$_2$]$_r$—; $R^2$ is —C(O)NHSO$_2$R$^{11}$ or —C(O)NHSO$_2$N(R$^9$)$_2$, wherein $R^9$ is H, alkyl, -alkyl-N(alkyl)$_2$, aryl, cycloalkyl, heteroaryl or heterocycloalkyl and $R^{11}$ is alkyl, -alkyl-N(alkyl)$_2$, aryl, cycloalkyl, haloalkyl, heteroaryl, heterocycloalkyl or hydroxyalkyl; $R^3$ is:

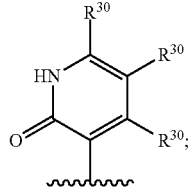

$R^4$ and $R^7$ are each independently H, alkyl, halo or —OH; $R^5$ is H, alkyl, —O-alkyl, —O-haloalkyl, cycloalkyl, halo, haloalkyl, —OH, hydroxyalkyl, —NH$_2$ or —CN; and $R^6$ is H, alkyl, —O-alkyl, —O-haloalkyl, cycloalkyl, halo, haloalkyl, —OH, hydroxyalkyl, —NH$_2$ or —CN.

In another embodiment, $R^1$ is —[C(R$^{12}$)$_2$]$_r$—, $R^2$ is —C(O)NHSO$_2$R$^{11}$ or —C(O)NHSO$_2$N(R$^9$)$_2$, wherein $R^9$ is H, alkyl, -alkyl-N(alkyl)$_2$, aryl, cycloalkyl, heteroaryl or heterocycloalkyl and $R^{11}$ is alkyl, -alkyl-N(alkyl)$_2$, aryl, cycloalkyl, haloalkyl, heteroaryl, heterocycloalkyl or hydroxyalkyl; $R^3$ is:

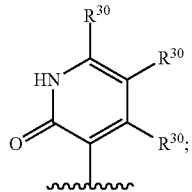

$R^4$ and $R^7$ are each independently H, alkyl, halo or —OH; $R^5$ is H, alkyl, —O-alkyl, —O-haloalkyl, cycloalkyl, halo, haloalkyl, —OH, hydroxyalkyl, —NH$_2$ or —CN; $R^6$ is H, alkyl, —O-alkyl, —O-haloalkyl, cycloalkyl, halo, haloalkyl, —OH, hydroxyalkyl, —NH$_2$ or —CN; and $R^{10}$ is aryl or heteroaryl.

In yet another embodiment, $R^1$ is —[C(R$^{12}$)$_2$]$_r$—; $R^2$ is —C(O)NHSO$_2$R$^{11}$ or —C(O)NHSO$_2$N(R$^9$)$_2$, wherein $R^9$ is H, alkyl, -alkyl-N(alkyl)$_2$, aryl, cycloalkyl, heteroaryl or heterocycloalkyl and $R^{11}$ is alkyl, -alkyl-N(alkyl)$_2$, aryl, cycloalkyl, haloalkyl, heteroaryl, heterocycloalkyl or hydroxyalkyl; $R^3$ is:

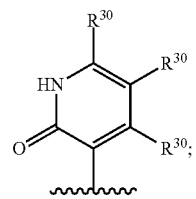

$R^4$ and $R^7$ are each independently H, alkyl, halo or —OH; $R^5$ is H, alkyl, —O-alkyl, —O-haloalkyl, cycloalkyl, halo, haloalkyl, —OH, hydroxyalkyl, —NH$_2$ or —CN; $R^6$ is H, alkyl, —O-alkyl, —O-haloalkyl, cycloalkyl, halo, haloalkyl, —OH, hydroxyalkyl, —NH$_2$ or —CN; and $R^{10}$ is:

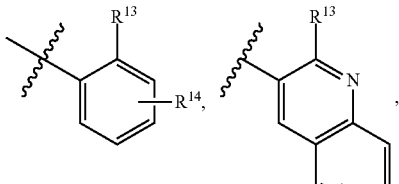

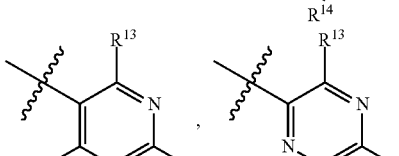

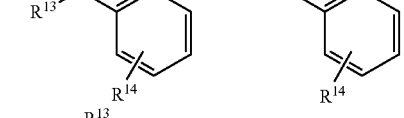

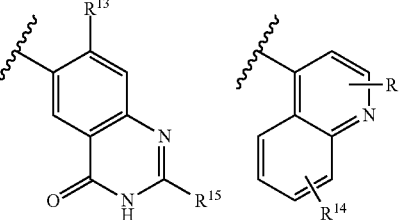

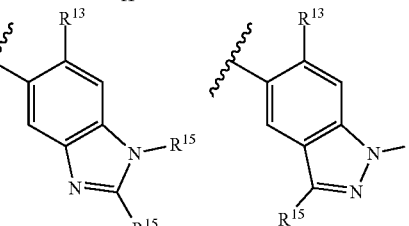

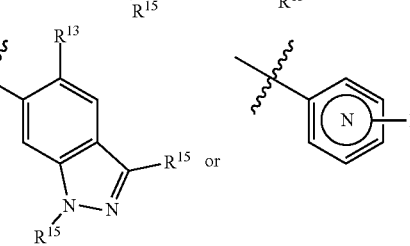

wherein $R^{13}$ is H, F, Br or Cl; $R^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; each occurrence of R$^{15}$ is independently alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl; and

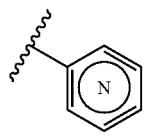

represents a pyridyl group, wherein the ring nitrogen atom can be at any of the five unsubstituted ring atom positions.

In another embodiment, R$^1$ is —[C(R$^{12}$)$_2$]$_r$—; R$^2$ is —C(O)NHSO$_2$R$^{11}$ or —C(O)NHSO$_2$N(R$^9$)$_2$, wherein R$^9$ is H, alkyl, -alkyl-N(alkyl)$_2$, aryl, cycloalkyl, heteroaryl or heterocycloalkyl and R$^{11}$ is alkyl, -alkyl-N(alkyl)$_2$, aryl, cycloalkyl, haloalkyl, heteroaryl, heterocycloalkyl or hydroxyalkyl; R$^3$ is:

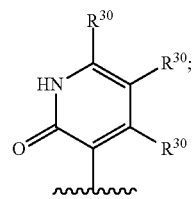

R$^4$ and R$^7$ are each independently H, alkyl, halo or —OH; R$^5$ is H, alkyl, —O-alkyl, —O-haloalkyl, cycloalkyl, halo, haloalkyl, —OH, hydroxyalkyl, —NH$_2$ or —CN; R$^6$ is H, alkyl, —O-alkyl, —O-haloalkyl, cycloalkyl, halo, haloalkyl, —OH, hydroxyalkyl, —NH$_2$ or —CN; and R$^{10}$ is:

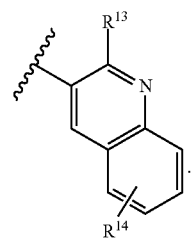

In a further embodiment, R$^1$ is [C(R$^{12}$)$_2$]$_r$—; R$^2$ is —C(O)NHSO$_2$R$^{11}$ or —C(O)NHSO$_2$N(R$^9$)$_2$, wherein R$^9$ is H, alkyl, -alkyl-N(alkyl)$_2$, aryl, cycloalkyl, heteroaryl or heterocycloalkyl and R$^{11}$ is alkyl, -alkyl-N(alkyl)$_2$, aryl, cycloalkyl, haloalkyl, heteroaryl, heterocycloalkyl or hydroxyalkyl; R$^3$ is:

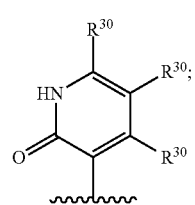

R$^4$ and R$^7$ are each independently H, alkyl, halo or —OH; R$^5$ is H, alkyl, —O-alkyl, —O-haloalkyl, cycloalkyl, halo, haloalkyl, —OH, hydroxyalkyl, —NH$_2$ or —CN; R$^6$ is H, alkyl, —O-alkyl, —O-haloalkyl, cycloalkyl, halo, haloalkyl, —OH, hydroxyalkyl, —NH$_2$ or —CN; and R$^{10}$ is:

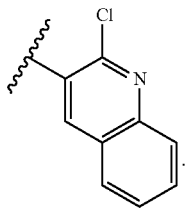

In another embodiment, R$^1$ is —[C(R$^{12}$)$_2$]$_r$—; R$^2$ is —C(O)NHSO$_2$R$^{11}$ or —C(O)NHSO$_2$N(R$^9$)$_2$, wherein R$^9$ is H, alkyl, -alkyl-N(alkyl)$_2$, aryl, cycloalkyl, heteroaryl or heterocycloalkyl and R$^{11}$ is alkyl, -alkyl-N(alkyl)$_2$, aryl, cycloalkyl, haloalkyl, heteroaryl, heterocycloalkyl or hydroxyalkyl; R$^3$ is:

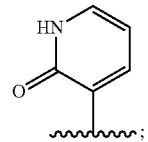

R$^4$ and R$^7$ are each independently H, alkyl, halo or —OH; R$^5$ is H, alkyl, —O-alkyl, —O-haloalkyl, cycloalkyl, halo, haloalkyl, —OH, hydroxyalkyl, —NH$_2$ or —CN; R$^6$ is H, alkyl, —O-alkyl, —O-haloalkyl, cycloalkyl, halo, haloalkyl, —OH, hydroxyalkyl, —NH$_2$ or —CN; and R$^{10}$ is:

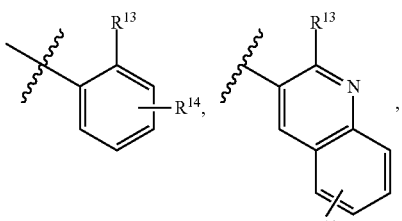

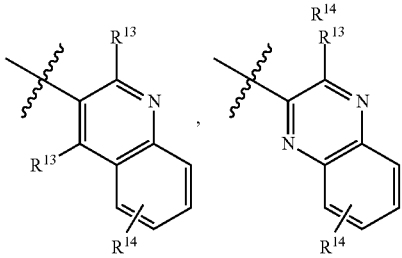

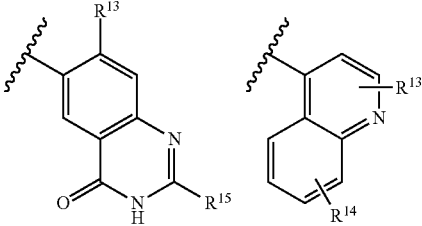

-continued

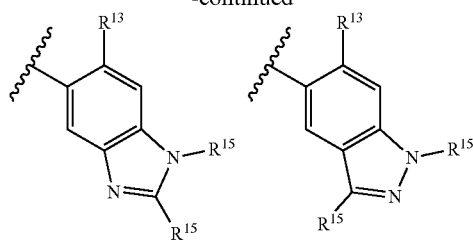

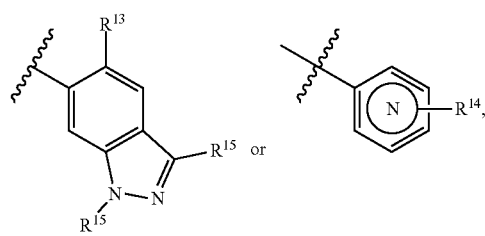

wherein $R^{13}$ is H, F, Br or Cl; $R^{14}$ represents up to 4 optional and additional substituents, each independently selected from alkyl, cycloalkyl, $CF_3$, —CN, halo, —O-alkyl, —O-haloalkyl, —$NHSO_2$-alkyl, —$NO_2$, —C(O)$NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2$OH, —$SO_2NH_2$, —NHC(O)-alkyl, —C(O)O-alkyl, —C(O)-heterocycloalkyl and heteroaryl; each occurrence of $R^{15}$ is independently alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2$OH, —$SO_2NH_2$, —NHC(O)-alkyl, —C(O)O-alkyl, —C(O)-heterocycloalkyl or heteroaryl; and

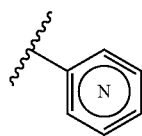

represents a pyridyl group, wherein the ring nitrogen atom can be at any of the five unsubstituted ring atom positions.

In one embodiment, for the compounds of formula (I), variables $R^1$, $R^2$, $R^3$, $R^4$, $R^5$, $R^5$, $R^6$, $R^7$ and $R^{10}$ are selected independently of each other.

In another embodiment, the compounds of formula (I) are in purified form.

In one embodiment, the compounds of formula (I) have the formula (Ia):

(Ia)

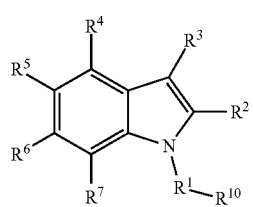

or a pharmaceutically acceptable salt, solvate, ester or prodrug thereof, wherein:
$R^1$ is —$CH_2$—, —$CH_2CH_2$—, —$CH(CH_3)$— or

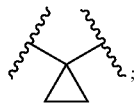

$R^2$ is —C(O)$NHSO_2R^{11}$, —C(O)$NHSO_2N(R^9)_2$, —C(O)N(alkyl)$SO_2R^{11}$ or —C(O)N(alkyl)$SO_2N(R^9)_2$;
$R^3$ is:

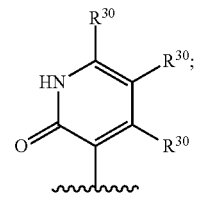

$R^4$, $R^5$, $R^6$ and $R^7$ are each, independently, H, alkyl, —[C($R^{12}$)$_2$]$_q$-cycloalkyl, —[C($R^{12}$)$_2$]$_q$-heterocycloalkyl, haloalkyl, halo, —OH, —$OR^9$ or —N($R^9$)$_2$;
each occurrence of $R^9$ is independently H, alkyl, -alkyl-N(alkyl)$_2$, cycloalkyl, heterocycloalkyl, haloalkyl or hydroxyalkyl;
$R^{10}$ is:

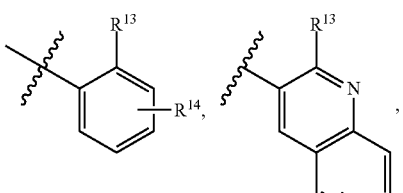

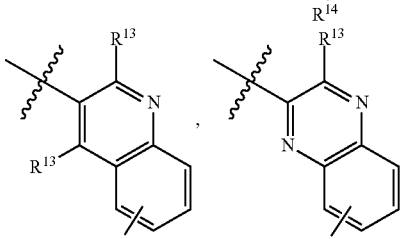

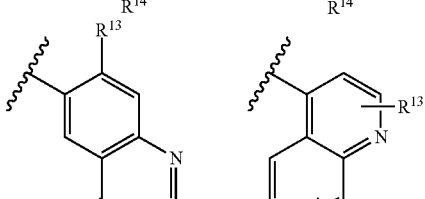

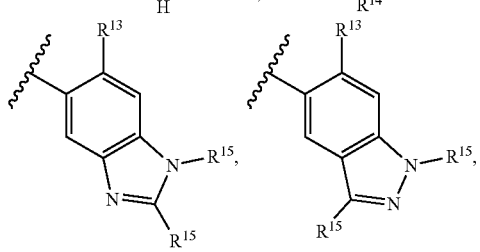

-continued

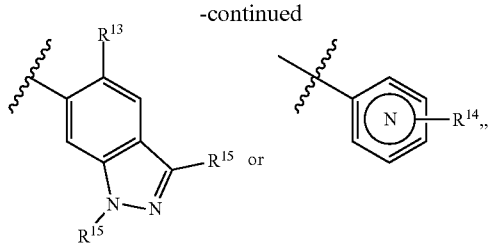

such that when $R^1$ is a bond, $R^{10}$ is not H;

each occurrence of $R^{11}$ is independently alkyl, -alkyl-N(alkyl)$_2$, aryl, cycloalkyl, haloalkyl, heteroaryl, heterocycloalkyl or hydroxyalkyl;

each occurrence of $R^{12}$ is independently H, halo, —N(alkyl)$_2$, —OH, —O-alkyl, alkyl, cycloalkyl or heterocycloalkyl, or two $R^{12}$ groups, together with the carbon atoms to which they are attached, join to form a cycloalkyl, heterocycloalkyl or C=O group;

$R^{13}$ is H, F, Br or Cl;

$R^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl;

each occurrence of $R^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl;

each occurrence of $R^{30}$ is independently, H, halo, —N(alkyl)$_2$, —OH, —O-alkyl, —O-haloalkyl, alkyl, cycloalkyl or heterocycloalkyl, or two adjacent $R^{30}$ groups, together with the carbon atoms to which they are attached, join to form a –3- to 7-membered ring selected from aryl, cycloalkyl, heteroaryl and heterocycloalkyl;

each occurrence of q is independently an integer ranging from 0 to 4;

each occurrence of r is independently an integer ranging from 1 to 4; and

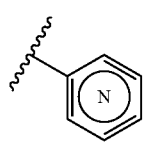

represents a pyridyl group, wherein the ring nitrogen atom can be at any of the five unsubstituted ring atom positions.

In one embodiment, for the compounds of formula (Ia),
$R^1$ is —CH$_2$—;
$R^2$ is —C(O)NHSO$_2$R$^{11}$ or —C(O)NHSO$_2$N(R$^9$)$_2$;
$R^3$ is:

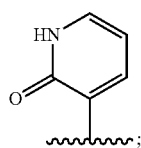

$R^4$, $R^5$, $R^6$ and $R^7$ are each independently H, alkyl, haloalkyl or halo;

each occurrence of $R^9$ is independently H, alkyl, cycloalkyl, heterocycloalkyl, haloalkyl or hydroxyalkyl; and each occurrence of $R^{11}$ is independently alkyl, aryl or cycloalkyl.

In another embodiment, for the compounds of formula (Ia),
$R^1$ is —CH$_2$—;
$R^2$ is —C(O)NHSO$_2$R$^{11}$ or —C(O)NHSO$_2$N(R$^9$)$_2$;
$R^3$ is:

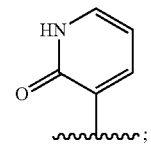

$R^4$, $R^5$, $R^6$ and $R^7$ are each independently H, alkyl, or halo;

each occurrence of $R^9$ is independently H, alkyl or cycloalkyl;

$R^{10}$ is:

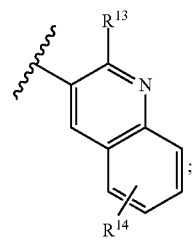

and each occurrence of $R^{11}$ is independently alkyl, aryl or cycloalkyl.

In one embodiment, for the compounds of formula (Ia), variables $R^1$, $R^2$, $R^3$, $R^4$, $R^5$, $R^5$, $R^6$, $R^7$ and $R^{10}$ are selected independently of each other.

In another embodiment, the compounds of formula (Ia) are in purified form.

The 2,3-Substituted Indole Derivatives of Formula (II)

The present invention also provides 2,3-Substituted Indole Derivatives having the formula:

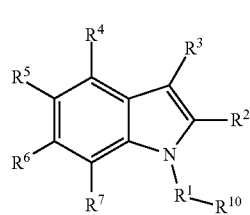

and pharmaceutically acceptable salts, solvates, esters and prodrugs thereof, wherein $R^1$, $R^2$, $R^4$, $R^5$, $R^6$, $R^7$ and $R^{10}$ are defined above for the compounds of formula (II).

In one embodiment, $R^1$ is bond.
In another embodiment, $R^1$ is $-[C(R^{12})_2]_r-$.
In another embodiment, $R^1$ is $-[C(R^{12})_2]_r-O-[C(R^{12})_2]_q-$.
In still another embodiment, $R^1$ is $-[C(R^{12})_2]_r-N(R^9)-[C(R^{12})_2]_q-$.
In yet another embodiment, $R^1$ is $-[C(R^{12})_2]_q-CH=CH-[C(R^{12})_2]_q-$.
In another embodiment, $R^1$ is $-[C(R^{12})_2]_r-C\equiv C-[C(R^{12})_2]_q-$.
In a further embodiment, $R^1$ is $-[C(R^{12})_2]_q-SO_2-[C(R^{12})_2]_q-$.
In one embodiment, $R^1$ is $-CH_2-$, $-CH_2CH_2-$, $-CH(CH_3)-$ or

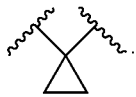

In another embodiment, $R^1$ is $-CH_2-$.
In another embodiment, $R^1$ is

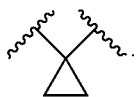

In one embodiment, $R^{10}$ is aryl.
In another embodiment, $R^{10}$ is $-H$.
In another embodiment, $R^{10}$ is cycloalkyl.
In another embodiment, $R^{10}$ is cycloalkenyl.
In still another embodiment, $R^{10}$ is heterocycloalkenyl.
In another embodiment, $R^{10}$ is heteroaryl.
In another embodiment, $R^{10}$ is heterocycloalkyl.
In another embodiment, $R^{10}$ is phenyl.
In another embodiment, $R^{10}$ is phenyl, which is substituted with from 1-4 groups independently selected from: halo, $-NH_2$, $-NHSO_2$-alkyl, haloalkyl, methoxy, $-O$-haloalkyl, $-[C(R^{12})_2]_q-NHC(O)NH$-alkyl, alkyl, $-OH$, $-CN$, $-C(O)NH_2$ or $-[C(R^{12})_2]_q-NH_2$.
In yet another embodiment, $R^{10}$ is pyridyl.
In a further embodiment, $R^{10}$ is

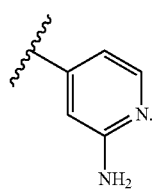

In another embodiment, $-R^{10}$ is:

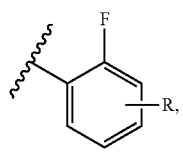

wherein R represents up to 2 optional and additional phenyl substituents, each independently selected from halo, $-O$-alkyl, alkyl, $-CF_3$, $-CN$, $-NHSO_2$-alkyl, $-NO_2$, $-C(O)NH_2$, $-C(O)OH$, $-NH_2$, $-SO_2$-alkyl, $-SO_2NH$-alkyl, $-S$-alkyl, $-CH_2NH_2$, $-SO_2NH_2$, $-NHC(O)$-alkyl, $-C(O)O$-alkyl, $-C(O)$-heterocycloalkyl and heteroaryl.

In another embodiment, $R^{10}$ is

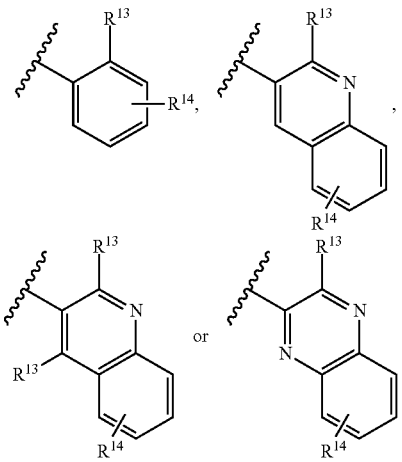

wherein $R^{13}$ is F or Cl and $R^{14}$ represents up to 4 optional and additional substituents, each independently selected from alkyl, cycloalkyl, $CF_3$, $-CN$, halo, $-O$-alkyl, $-NHSO_2$-alkyl, $-NO_2$, $-C(O)NH_2$, $-C(O)NH$-alkyl, $-C(O)OH$, $-OH$, $-NH_2$, $-SO_2$alkyl, $-SO_2NH$-alkyl, $-S$-alkyl, $-CH_2NH_2$, $-CH_2OH$, $-SO_2NH_2$, $-NHC(O)$-alkyl, $-C(O)O$-alkyl, $-C(O)$-heterocycloalkyl and heteroaryl.

In another embodiment, $R^1$ is $-CH_2-$, $-CH_2CH_2-$, $-CH(CH_3)-$ or

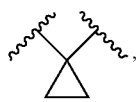

and $R^{10}$ is aryl or heteroaryl.

In another embodiment, $R^1$ is $-CH_2-$, $-CH_2CH_2-$, $-CH(CH_3)-$ or

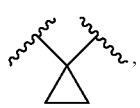

and $R^{10}$ is phenyl.

In another embodiment, $R^1$ is $-CH_2-$, $-CH_2CH_2-$, $-CH(CH_3)-$ or

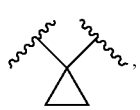

and $R^{10}$ is alkyl or cycloalkyl.

In another embodiment, $R^1$ is $-CH_2-$ and $R^{10}$ is aryl or heteroaryl.

In still another embodiment, $R^1$ is —CH$_2$— or

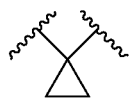

and $R^{10}$ is

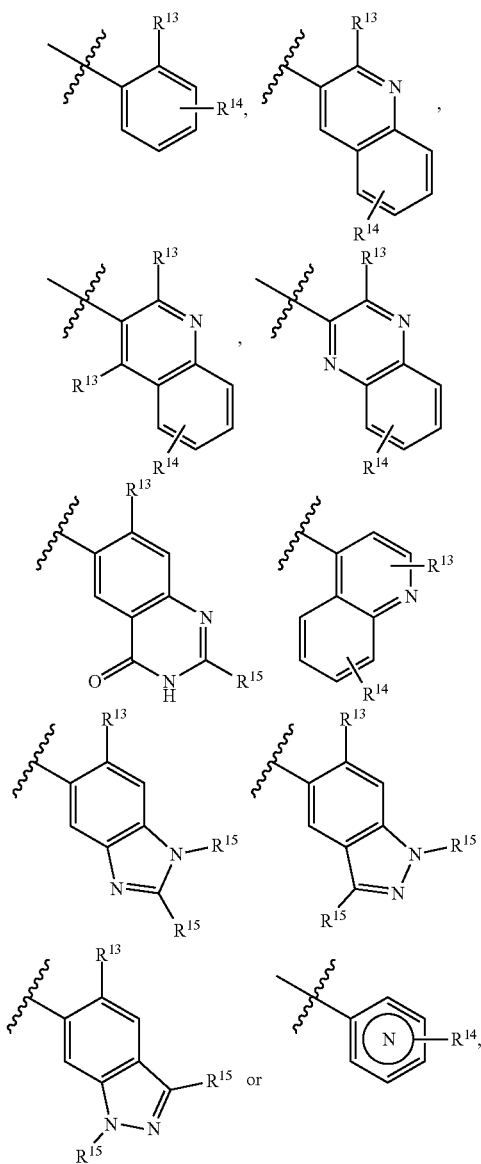

wherein $R^{13}$ is F or Cl; $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of $R^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In one embodiment, —R$^1$-R$^{10}$ is benzyl.

In another embodiment, —R$^1$-R$^{10}$ is benzyl, wherein the phenyl moiety of the benzyl group is substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$.

In still another embodiment, —R$^1$-R$^{10}$ is

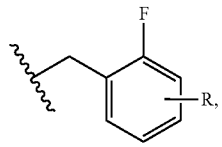

wherein R represents up to 2 optional and additional phenyl substituents, each independently selected from halo, —O-alkyl, alkyl, —CF$_3$, —CN, —NHSO$_2$-alkyl, —NO$_2$, —C(O)NH$_2$, —C(O)OH, —NH$_2$, —SO$_2$-alkyl, —SO$_2$NH-alkyl, —S-alkyl, —CH$_2$NH$_2$, —SO$_2$NH$_2$, —NHC(O)-alkyl, —C(O)O-alkyl, —C(O)-heterocycloalkyl and heteroaryl.

In another embodiment, —R$^1$-R$^{10}$ is

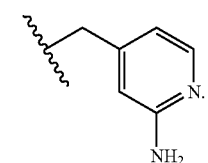

In still another embodiment, —R$^1$-R$^{10}$ is alkyl.

In yet another embodiment, —R$^1$-R$^{10}$ is —R$^1$-R$^{10}$ is benzyl, wherein the phenyl moiety of the benzyl group is substituted with 1 or 2 fluorine atoms.

In yet another embodiment, —R$^1$-R$^{10}$ is —R$^1$-R$^{10}$ is benzyl, wherein the phenyl moiety of the benzyl group is substituted with 1 or 2 methyl groups.

In yet another embodiment, —R$^1$-R$^{10}$ is —R$^1$-R$^{10}$ is benzyl, wherein the phenyl moiety of the benzyl group is substituted with one fluorine atom and one methyl group.

In another embodiment, —R$^1$-R$^{10}$ is haloalkyl.

In a further embodiment, —R$^1$-R$^{10}$ is —CH$_2$-cycloalkyl.

In another embodiment, —R$^1$-R$^{10}$ is other than H.

In another embodiment, $R^1$ is —CH$_2$— and $R^{10}$ is alkyl or cycloalkyl.

In another embodiment, $R^1$ is —CH$_2$— and $R^{10}$ is

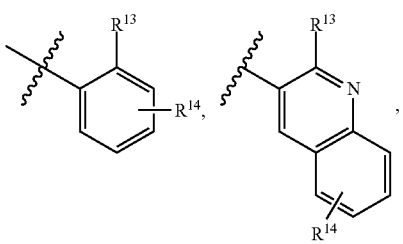

-continued

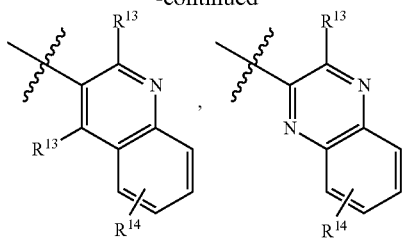

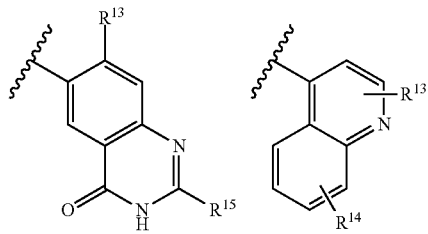

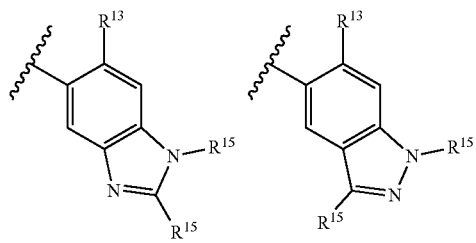

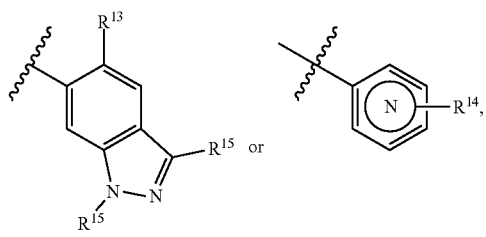

wherein $R^{13}$ is F or Cl; $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl.

In one embodiment, $R^2$ is —C(O)$NHSO_2R^{11}$ or —C(O)$NHSO_2N(R^9)_2$.

In another embodiment, $R^2$ is —[C(R$^{12}$)$_2$]$_q$—C(O)N(R$^9$)$SO_2R^{11}$.

In another embodiment, $R^2$ is —[C(R$^{12}$)$_2$]$_q$—C(O)N(R$^9$)$SOR^{11}$.

In still another embodiment, $R^2$ is —[C(R$^{12}$)$_2$]$_q$—C(O)N(R$^9$)$SO_2N(R^{11})_2$.

In another embodiment, $R^2$ is

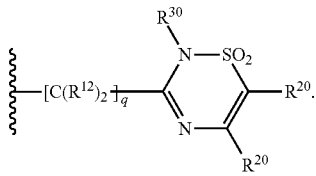

In another embodiment, $R^2$ is

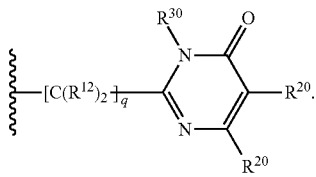

In yet another embodiment, $R^2$ is

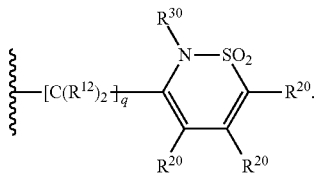

In another embodiment, $R^2$ is —C(O)N(R$^9$)$SO_2R^{11}$.
In another embodiment, $R^2$ is —C(O)$NHSO_2R^{11}$.
In another embodiment, $R^2$ is —C(O)$NHSO_2R^{11}$ and $R^{11}$ is —[C(R$^{12}$)$_2$]$_q$-alkyl.
In yet another embodiment, $R^2$ is —C(O)$NHSO_2R^{11}$ and $R^{11}$ is —[C(R$^{12}$)$_2$]$_y$-aryl.
In another embodiment, $R^2$ is —C(O)$NHSO_2R^{11}$ and $R^{11}$ is —[C(R$^{12}$)$_2$]$_q$-cycloalkyl.
In a further embodiment, $R^2$ is —C(O)$NHSO_2R^{11}$ and $R^{11}$ is —[C(R$^{12}$)$_2$]$_q$-heterocycloalkyl.
In another embodiment, $R^2$ is —C(O)$NHSO_2R^{11}$ and $R^{11}$ is —[C(R$^{12}$)$_2$]$_q$-heteroaryl.
In another embodiment, $R^2$ is —C(O)$NHSO_2R^{11}$ and $R^{11}$ is —[C(R$^{12}$)$_2$]$_q$-haloalkyl.
In still another embodiment, $R^2$ is —C(O)$NHSO_2R^{11}$ and $R^{11}$ is —[C(R$^{12}$)$_2$]$_q$-hydroxyalkyl.
In still another embodiment, $R^2$ is —C(O)$NHSO_2R^{11}$ and $R^{11}$ is alkyl.
In yet another embodiment, $R^2$ is —C(O)$NHSO_2R^{11}$ and $R^{11}$ is aryl.
In another embodiment, $R^2$ is —C(O)$NHSO_2R^{11}$ and $R^{11}$ is cycloalkyl.
In a further embodiment, $R^2$ is —C(O)$NHSO_2R^{11}$ and $R^{11}$ is heterocycloalkyl.
In another embodiment, $R^2$ is —C(O)$NHSO_2R^{11}$ and $R^{11}$ is heteroaryl.
In another embodiment, $R^2$ is —C(O)$NHSO_2R^{11}$ and $R^{11}$ is haloalkyl.
In still another embodiment, $R^2$ is —C(O)$NHSO_2R^{11}$ and $R^{11}$ is hydroxyalkyl.
In another embodiment, $R^2$ is —C(O)$NHSO_2R^{11}$ and $R^{11}$ is —[C(R$^{12}$)$_2$]$_y$-phenyl.
In another embodiment, $R^2$ is —C(O)$NHSO_2R^{11}$ and $R^{11}$ is benzyl.
In another embodiment, $R^2$ is —C(O)$NHSO_2R^{11}$ and $R^{11}$ is naphthyl.

In yet another embodiment, $R^2$ is —C(O)NHSO$_2$R$^{11}$ and R$^{11}$ is —NH$_2$ or —N(CH$_3$)$_2$.

In another embodiment, $R^2$ is —C(O)NHSO$_2$CH$_3$.

In another embodiment, $R^2$ is —C(O)NHSO$_2$CH$_2$CH$_3$.

In another embodiment, $R^2$ is —C(O)NHSO$_2$R$^{11}$, and R$^{11}$ is alkyl, aryl, cycloalkyl, haloalkyl, heteroaryl, heterocycloalkyl or hydroxyalkyl.

In one embodiment, $R^2$ is —C(O)NHSO$_2$R$^{11}$ and R$^{11}$ is alkyl, cycloalkyl or aryl.

In one embodiment, $R^2$ is —C(O)NHSO$_2$N(R$^9$)$_2$ and R$^9$ is H, alkyl, aryl, cycloalkyl, heteroaryl or heterocycloalkyl.

In another embodiment, $R^2$ is —C(O)NHSO$_2$N(R$^9$)$_2$ and R$^9$ is H, alkyl or cycloalkyl.

In another embodiment, $R^2$ is —C(O)NHSO$_2$R$^{11}$ and R$^{11}$ is methyl, ethyl, isopropyl, cyclopropyl or phenyl.

In another embodiment, $R^2$ is —C(O)NHSO$_2$N(R$^9$)$_2$ and R$^9$ is H, methyl, ethyl or cyclopropyl.

In yet another embodiment, $R^2$ is —C(O)NHSO$_2$N(R$^9$)$_2$ and R$^9$ is —[C(R$^{12}$)$_2$]-O-alkyl or —[C(R$^{12}$)$_2$]$_q$—N(allyl)$_2$.

In another embodiment, $R^2$ is —C(O)NHSO$_2$N(R$^9$)$_2$ and R$^9$ is —(CH$_2$)$_2$—N(CH$_3$)$_2$ or —(CH$_2$)$_3$—N(CH$_3$)$_2$.

In still another embodiment, $R^2$ is —C(O)NHSO$_2$R$^{11}$ and R$^{11}$ is cyclopropyl.

In another embodiment, $R^2$ is —C(O)NHSO$_2$N(R$^9$)$_2$ and R$^9$ is H or methyl.

In still another embodiment, $R^2$ is —C(O)NHSO$_2$R$^{11}$ and R$^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$.

In yet another embodiment, $R^2$ is —C(O)NHSO$_2$R$^{11}$ and R$^{11}$ is —[C(R$^{12}$)$_2$]$_q$—NHSO$_2$-alkyl, —[C(R$^{12}$)$_2$]—O-alkyl, or —[C(R$^{12}$)$_2$]-alkyl.

In yet another embodiment, $R^2$ is —C(O)NHSO$_2$R$^{11}$ and R$^{11}$ is imidazolyl, pyridyl, thienyl, furanyl, benzofuranyl, benzo[1,3]dioxolyl, tetrahydropyranyl,

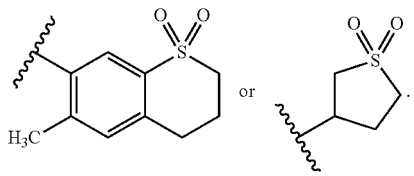

In yet another embodiment, $R^2$ is —C(O)NHSO$_2$R$^{11}$ and R$^{11}$ is cyclopropyl, cyclobutyl, cyclopentyl or cyclohexyl.

In one embodiment, $R^3$ is

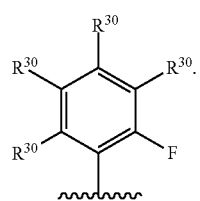

In another embodiment, $R^3$ is

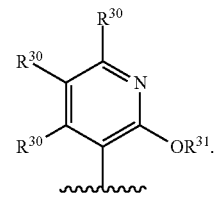

In another embodiment, $R^3$ is

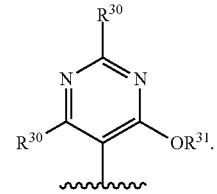

In another embodiment, $R^3$ is

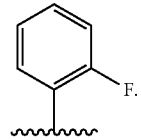

In one embodiment, $R^4$ is H.
In another embodiment, $R^4$ is H or F.
In another embodiment, $R^4$ is F.
In another embodiment, $R^5$ is H.
In another embodiment, $R^5$ is other than H.
In yet another embodiment, $R^6$ is H.
In another embodiment, $R^6$ is other than H.
In another embodiment, $R^6$ is H or F.
In a further embodiment, $R^6$ is F.
In one embodiment, $R^9$ is H and $R^{11}$ is methyl or ethyl.
In another embodiment, $R^9$ is H and $R^{11}$ is cyclopropyl.
In still another embodiment, $R^7$ is H.
In another embodiment, $R^4$ and $R^7$ are each independently H, halo or hydroxy.
In another embodiment, $R^4$ and $R^7$ are each independently H, F or hydroxy.
In another embodiment, $R^4$ and $R^7$ are each H.
In yet another embodiment, $R^4$, $R^6$ and $R^7$ are each H.
In another embodiment, $R^4$, $R^5$, $R^6$ and $R^7$ are each H.
In a further embodiment, $R^4$, $R^6$ and $R^7$ are each H and $R^5$ is other than H.
In another embodiment, $R^4$, $R^6$ and $R^7$ are each H and $R^5$ is alkyl.
In another embodiment, $R^4$, $R^6$ and $R^7$ are each H and $R^5$ is halo.
In another embodiment, $R^4$, $R^6$ and $R^7$ are each H and $R^5$ is methyl.
In a further embodiment, $R^4$, $R^6$ and $R^7$ are each H and $R^5$ is Cl.
In another embodiment, $R^4$ and $R^7$ are each H and $R^5$ and $R^6$ are other than H.
In another embodiment, $R^5$ is other than H.
In still another embodiment, $R^5$ is alkyl.
In yet another embodiment, $R^5$ is halo.
In still another embodiment, $R^5$ is methyl.
In another embodiment, $R^5$ is ethyl.

In another embodiment, $R^6$ is H.

In another embodiment, $R^6$ is other than H.

In a further embodiment, $R^6$ is alkyl.

In yet another embodiment, $R^6$ is halo.

In still another embodiment, $R^6$ is methyl.

In another embodiment, $R^6$ is F.

In one embodiment, $R^4$ is H or F; $R^5$ is methyl or ethyl; $R^6$ is H or F; and $R^7$ is H.

In one embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or NH$_2$; and $R^2$ is —C(O)NHSO$_2$R$^{11}$.

In one embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; and $R^2$ is —C(O)NHSO$_2$CH$_3$.

In another embodiment, $R^1$ is —CH$_2$—, —CH$_2$CH$_2$—, —CH(CH$_3$)— or

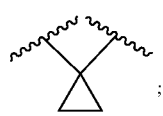

$R^2$ is —C(O)N(R$^9$)SO$_2$R$^{11}$; and $R^{10}$ is:

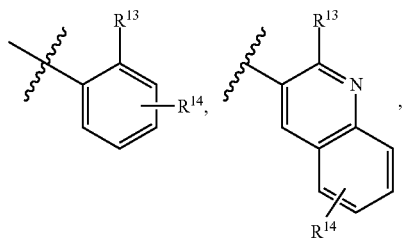

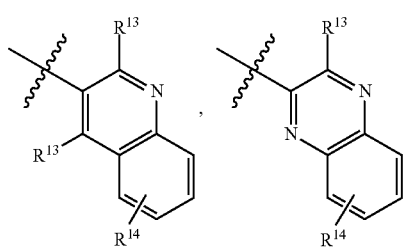

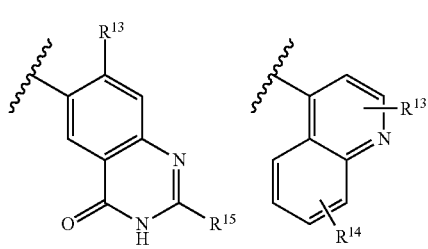

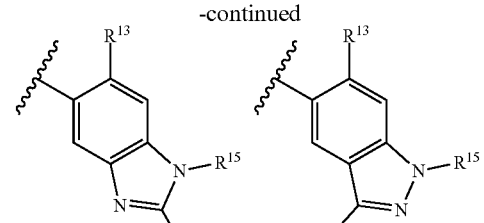

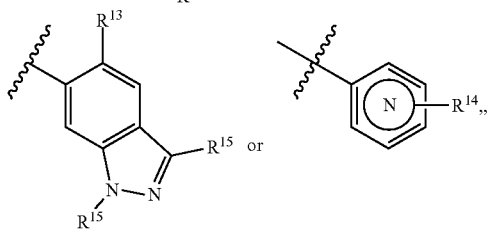

wherein $R^{13}$ is H, F, Br or Cl; $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of $R^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In another embodiment, $R^1$ is —CH$_2$—, —CH$_2$CH$_2$—, —CH(CH$_3$)— or

$R^2$ is —C(O)N(R$^9$)SO$_2$R$^{11}$; $R^5$ is alkyl, cycloalkyl, halo or —OH; $R^6$ is H, halo or —OH; and $R^{10}$ is:

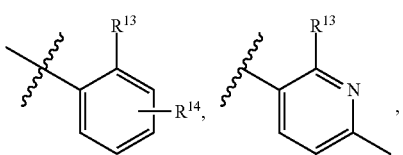

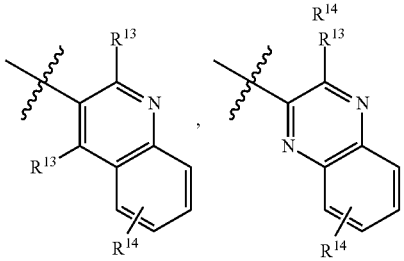

wherein R$^{13}$ is H, F, Br or Cl; R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of R$^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In another embodiment, R$^1$ is —CH$_2$—, —CH$_2$CH$_2$—, —CH(CH$_3$)— or

R$^2$ is —C(O)N(R$^9$)SO$_2$R$^{11}$; R$^5$ is methyl or ethyl; R$^6$ is H, F or Cl; and
R$^{10}$ is:

wherein R$^{13}$ is H, F, Br or Cl; R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of R$^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In another embodiment, R$^1$ is —CH$_2$—, —CH$_2$CH$_2$—, —CH(CH$_3$)— or

R$^2$ is —C(O)N(R$^9$)SO$_2$R$^{11}$; R$^5$ is methyl or ethyl; R$^6$ is H, F or Cl; R$^9$ is H;

$R^{10}$ is:

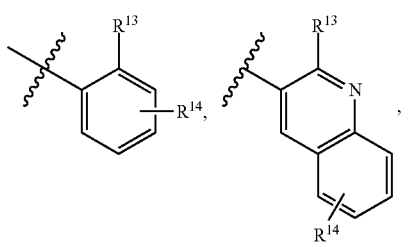

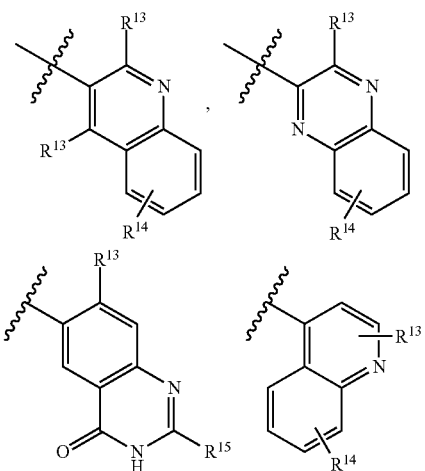

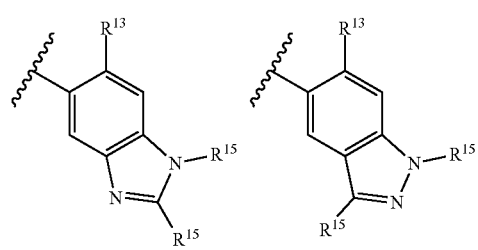

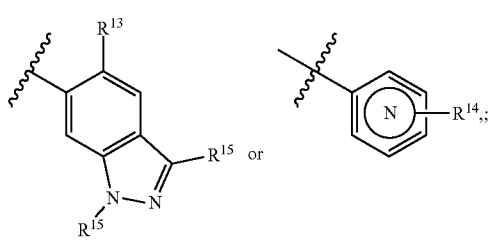

$R^{11}$ is methyl; $R^{13}$ is H, F, Br or Cl; $R^{14}$ represents up to 4 optional and additional substituents, each independently selected from alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl.

In another embodiment, $R^1$ is —$CH_2$—, —$CH_2CH_2$—, —$CH(CH_3)$— or

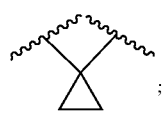

$R^2$ is —$C(O)N(R^9)SO_2R^{11}$; $R^5$ is methyl or ethyl; $R^6$ is H, F or Cl; $R^9$ is H;
$R^{10}$ is:

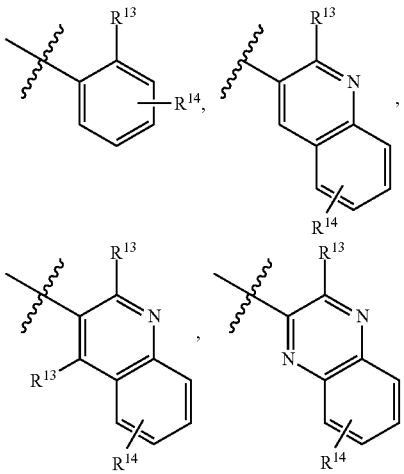

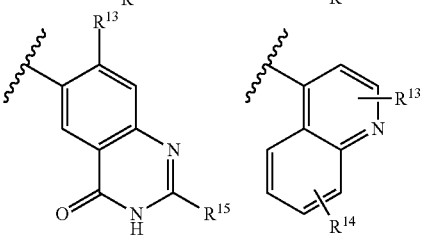

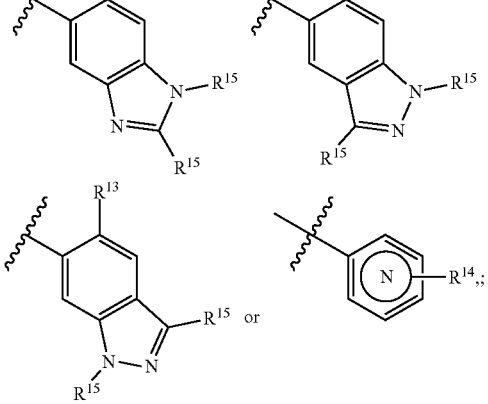

$R^{11}$ is cyclopropyl; $R^{13}$ is H, F, Br or Cl; $R^{14}$ represents up to 4 optional and additional substituents, each independently selected from alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and each occurrence of $R^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In one embodiment, R$^1$,

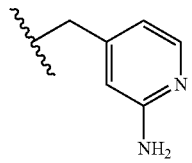

and R$^2$ is —C(O)NHSO$_2$R$^1$.

In one embodiment, R$^1$-R$^{10}$ is

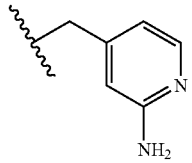

and R$^2$ is —C(O)NHSO$_2$CH$_3$.

In one embodiment, R$^1$-R$^{10}$ is

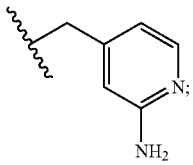

R$^2$ is —C(O)NHSO$_2$R$^{11}$; and R$^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$.

In one embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; R$^2$ is —C(O)NHSO$_2$R$^{11}$; and R$^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$.

In one embodiment, R$^1$-R$^{10}$ is

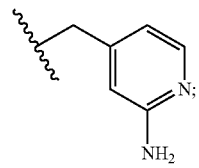

R$^2$ is —C(O)NHSO$_2$R$^{11}$; R$^4$, R$^6$ and R$^7$ are each H; and R$^5$ is other than H.

In another embodiment, R$^1$-R$^{10}$ is

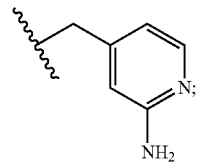

R$^2$ is —C(O)NHSO$_2$CH$_3$; R$^4$, R$^6$ and R$^7$ are each H; and R$^5$ is other than H.

In another embodiment, R$^1$-R$^{10}$ is

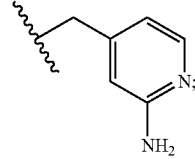

R$^2$ is —C(O)NHSO$_2$R$^{11}$, R$^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)alkyl, pyrazolyl or —OCH$_2$C(O)NH$_2$; R$^4$, R$^6$ and R$^7$ are each H; and R$^5$ is other than H.

In one embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; R$^2$ is —C(O)NHSO$_2$R$^{11}$; R$^4$, R$^6$ and R$^7$ are each H; and R$^5$ is other than H.

In another embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; R$^2$ is —C(O)NHSO$_2$CH$_3$; R$^4$, R$^6$ and R$^7$ are each H; and R$^5$ is other than H.

In another embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; R$^2$ is —C(O)NHSO$_2$R$^{11}$, R$^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, —OH, —NHSO$_2$-alkyl, —[C(R$^{12}$)$_2$]$_q$—SO$_2$- alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$; R$^4$, R$^6$ and R$^7$ are each H; and R$^5$ is other than H.

In one embodiment, R$^1$-R$^{10}$ is

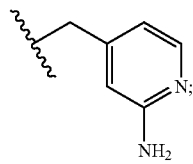

R$^2$ is —C(O)NHSO$_2$R$^{11}$; R$^4$ is H or F; R$^5$ is methyl or ethyl; R$^6$ is H or F; and R$^7$ is H.

In another embodiment, R$^1$-R$^{10}$ is

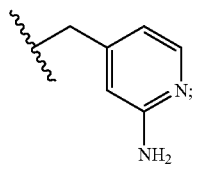

R$^2$ is —C(O)NHSO$_2$CH$_3$; R$^4$ is H or F; R$^5$ is methyl or ethyl; R$^6$ is H or F; and R$^7$ is H.

In another embodiment, R$^1$-R$^{10}$ is

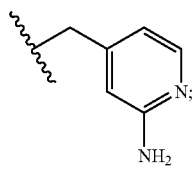

R$^2$ is —C(O)NHSO$_2$R$^{11}$, is phenyl, which is optionally substituted with up to 3 groups independently selected from: alkyl, F, Cl, methyl, —NH$_2$, —NO$_2$, methoxy, —SO$_2$NH$_2$, —COOH, [C(R$^{12}$)$_2$]$_q$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$; R$^4$ is H or F; R$^5$ is methyl or ethyl; R$^6$ is H or F; and R$^7$ is H.

In one embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; R$^2$ is —C(O)NHSO$_2$R$^{11}$; R$^4$ is H or F; R$^5$ is methyl or ethyl; R$^6$ is H or F; and R$^7$ is H.

In another embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]—NHC(O)NH-alkyl, alkyl, —OH, —CN, —C(O)NH$_2$ or —[C(R$^{12}$)$_2$]$_q$—NH$_2$; R$^2$ is —C(O)NHSO$_2$CH$_3$; R$^4$ is H or F; R$^5$ is methyl or ethyl; R$^6$ is H or F; and R$^7$ is H.

In another embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]—NHC(O)NH-alkyl, alkyl, —OH, —CN, —C(O)NH$_2$ or [C(R$^{12}$)$_2$]$_q$—NH$_2$; R$^2$ is —C(O)NHSO$_2$R$^{11}$, R$^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-allyl, —OH, —NHSO$_2$-alkyl, —[C(R$^{12}$)$_2$]$_q$—SO$_w$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$; R$^4$ is H or F; R$^5$ is methyl or ethyl; R$^6$ is H or F; and R$^7$ is H.

In one embodiment, R$^1$ is —CH$_2$—; R$^2$ is —C(O)NHSO$_2$CH$_3$ or —C(O)NHSO$_2$-cyclopropyl; R$^4$ is H or F; R$^5$ is methyl or ethyl; R$^6$ is H or F; R$^7$ is H; and —R$^{10}$ is:

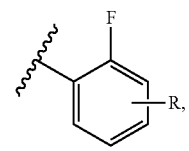

wherein R represents up to 2 optional and additional phenyl substituents, each independently selected from halo, —O-alkyl, alkyl, —CF$_3$, —CN, —NHSO$_2$-alkyl, —NO$_2$, —C(O)NH$_2$, —C(O)OH, —NH$_2$, —SO$_2$-alkyl, —SO$_2$NH-alkyl, —S-alkyl, —CH$_2$NH$_2$, —SO$_2$NH$_2$, —NHC(O)-alkyl, —C(O)O-alkyl, —C(O)-heterocycloalkyl and heteroaryl.

In another embodiment, R$^1$ is —CH$_2$—; R$^5$ is alkyl, cycloalkyl, halo or —OH; R$^6$ is H, halo or —OH; and R$^{10}$ is

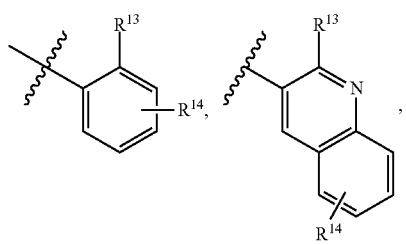

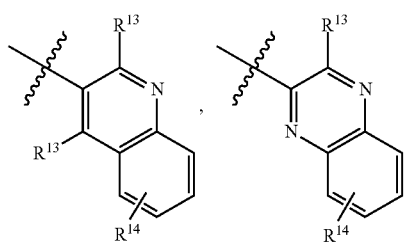

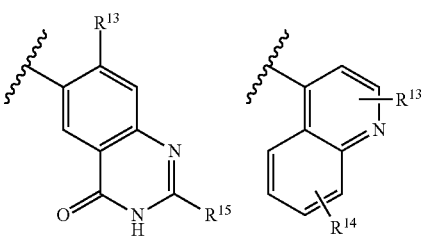

85

-continued

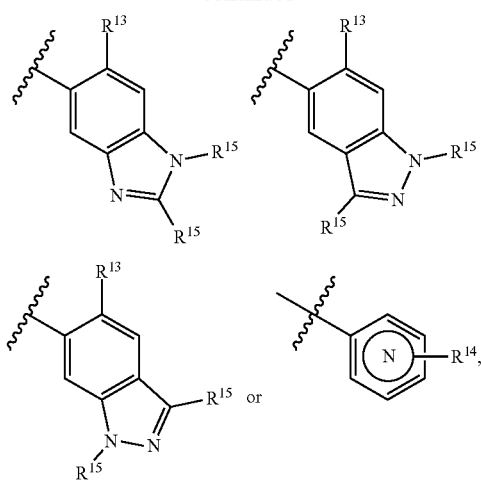

86

-continued

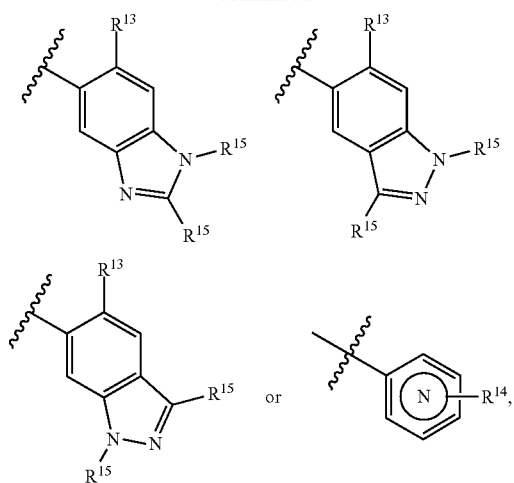

wherein $R^{13}$ is F or Cl; $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl.

In another embodiment, $R^1$ is —$CH_2$—; $R^5$ is methyl or ethyl; $R^6$ is H or F; and $R^{10}$ is wherein $R^{13}$ is F or Cl; $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl.

In still another embodiment, $R^1$ is —$CH_2$—; $R^9$ is H; $R^{10}$ is

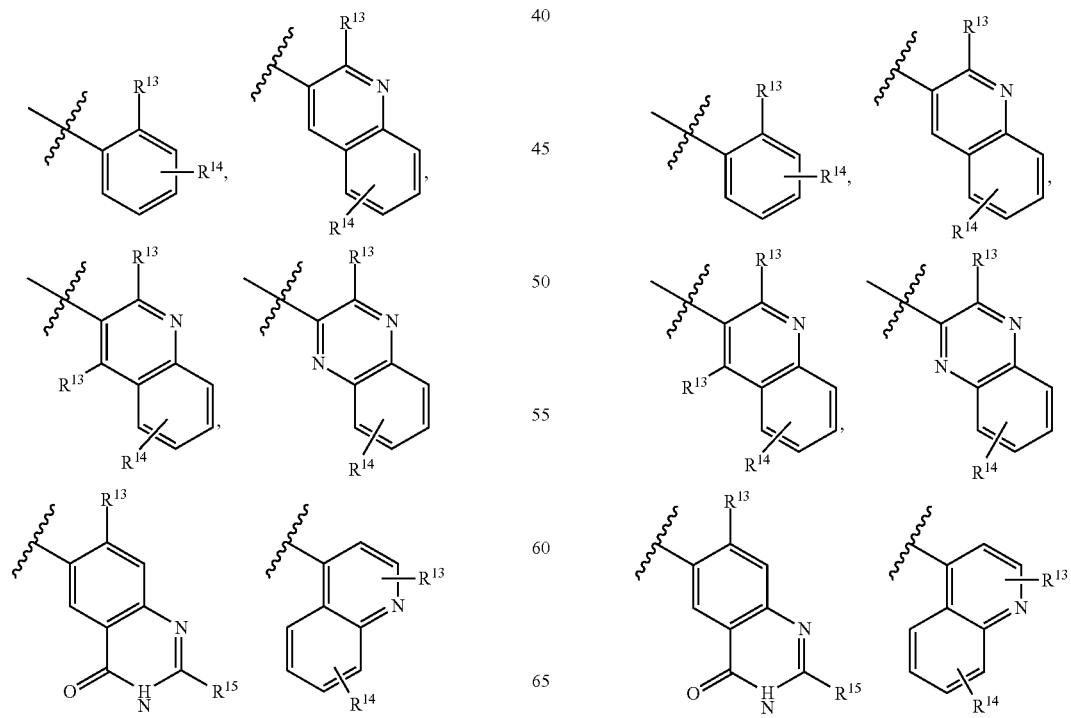

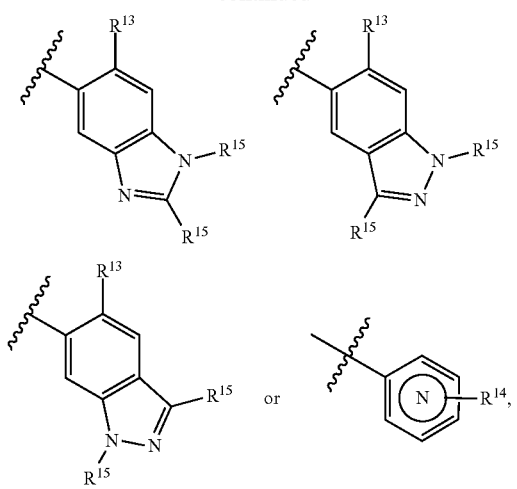

wherein $R^{13}$ is F or Cl; $R^{14}$ represents up to 4 optional and additional substituents, each independently selected from alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

$R^{11}$ is methyl.

In another embodiment, $R^1$ is —CH$_2$—; $R^9$ is H; $R^{10}$ is

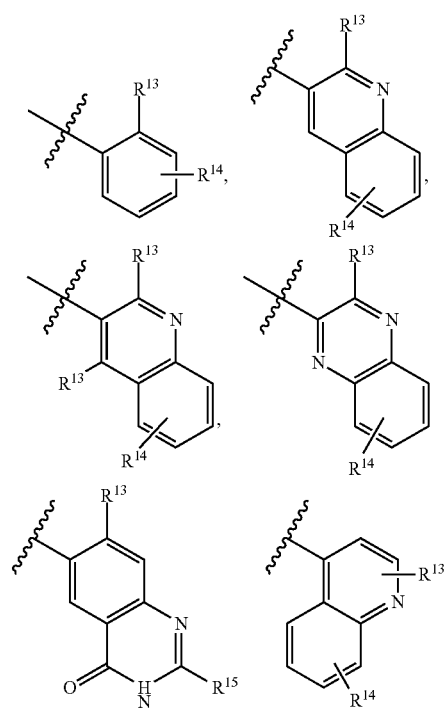

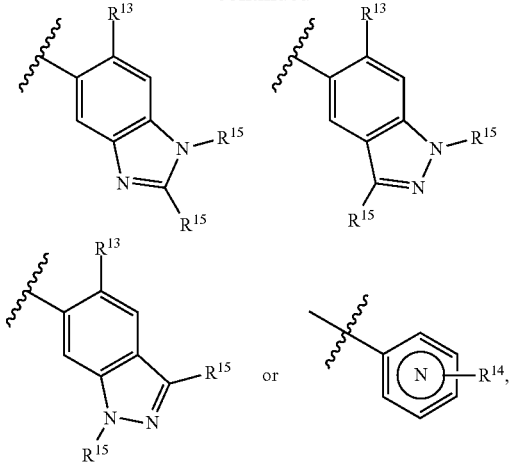

wherein $R^{13}$ is F or Cl; $R^{14}$ represents up to 4 optional and additional substituents, each independently selected from alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In one embodiment, $R^2$ is —C(O)NHSO$_2$R$^{11}$ or —C(O)NHSO$_2$N(R$^9$)$_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl.

In another embodiment, $R^2$ is —C(O)NHSO$_2$R$^{11}$ or —C(O)NHSO$_2$N(R$^9$)$_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl; and each occurrence of $R^{30}$ is independently, H, halo, —N(alkyl)$_2$, —OH, —O-alkyl, —O-haloalkyl, alkyl, cycloalkyl or heterocycloalkyl, or two adjacent $R^{30}$ groups, together with the carbon atoms to which they are attached, join to form an aryl, cycloalkyl, heteroaryl or heterocycloalkyl group.

In another embodiment, $R^2$ is —C(O)NHSO$_2$R$^{11}$ or —C(O)NHSO$_2$N(R$^9$)$_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl; and $R^1$ is —[C(R$^{12}$)$_2$]$_r$—.

In still another embodiment, $R^2$ is —C(O)NHSO$_2$R$^{11}$ or —C(O)NHSO$_2$N(R$^9$)$_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl; and $R^1$ is —CH$_2$—, —CH$_2$CH$_2$—, —CH(CH$_3$)— or

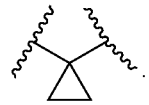

In another embodiment, $R^2$ is $—C(O)NHSO_2R^{11}$ or $—C(O)NHSO_2N(R^9)_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl; and wherein $R^4$ and $R^7$ are each independently H, alkyl, halo or —OH, $R^5$ is H, alkyl, —O-alkyl, —O-haloalkyl, cycloalkyl, halo, haloalkyl, —OH, hydroxyalkyl, —$NH_2$ or —CN, and $R^6$ is H, alkyl, —O-alkyl, —O-haloalkyl, cycloalkyl, halo, haloalkyl, —OH, hydroxyalkyl, —$NH_2$ or —CN.

In yet another embodiment, $R^2$ is $—C(O)NHSO_2R^{11}$ or $—C(O)NHSO_2N(R^9)_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl; and $R^{10}$ is aryl or heteroaryl.

In yet another embodiment, $R^2$ is $—C(O)NHSO_2R^{11}$ or $—C(O)NHSO_2N(R^9)_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl; and $R^{10}$ is:

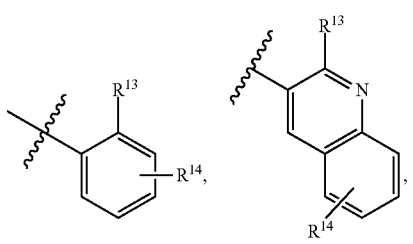

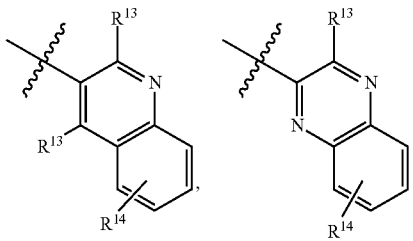

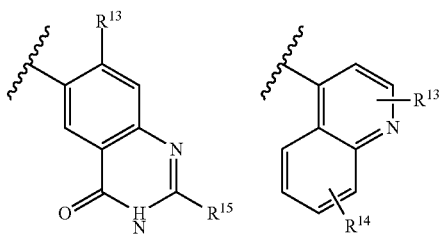

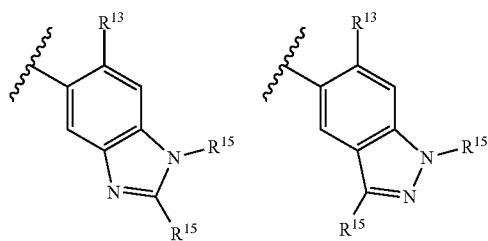

-continued

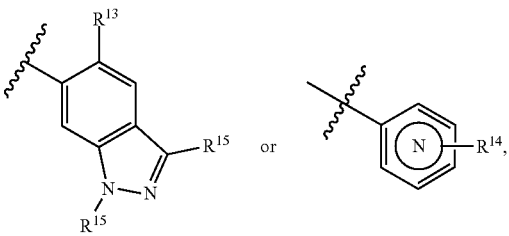

wherein $R^{13}$ is H, F, Br or Cl; $R^{14}$ represents up to 4 optional and additional substituents, each independently selected from alkyl, cycloalkyl, $CF_3$, —CN, halo, —O-alkyl, —O-haloalkyl, —$NHSO_2$-alkyl, —$NO_2$, —$C(O)NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; each occurrence of $R^{15}$ is independently alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl; and

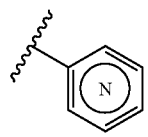

represents a pyridyl group, wherein the ring nitrogen atom can be at any of the five unsubstituted ring atom positions. In yet another embodiment, $R^2$ is $—C(O)NHSO_2R^{11}$ or $—C(O)NHSO_2N(R^9)_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl; $R^{10}$ is:

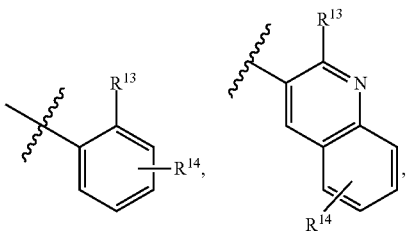

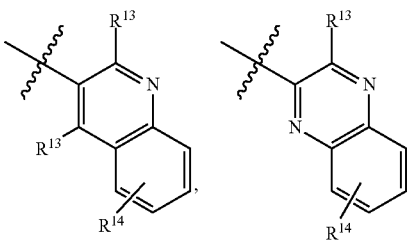

-continued

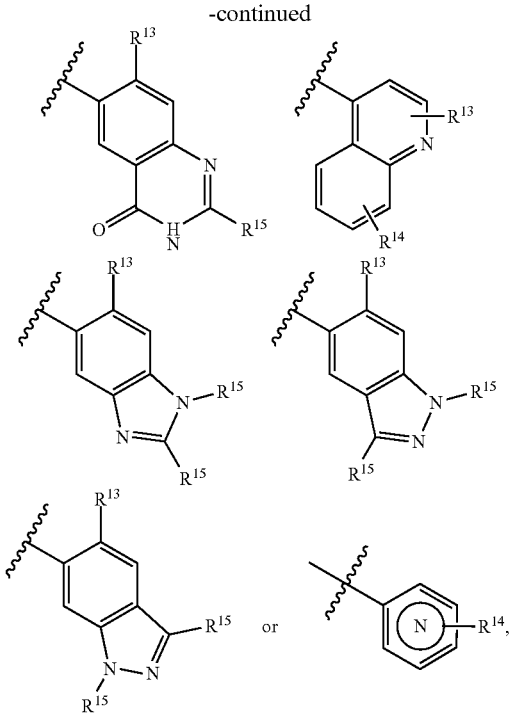

wherein $R^{13}$ is H, F, Br or Cl; $R^{14}$ represents up to 4 optional and additional substituents, each independently selected from alkyl, cycloalkyl, $CF_3$, —CN, halo, —O-alkyl, —O-haloalkyl, —$NHSO_2$-alkyl, —$NO_2$, —$C(O)NH_2$, —C(O)NH-alkyl, —C(O)OH, —OH, —$NH_2$, —$SO_2$alkyl, —$SO_2NH$-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; each occurrence of $R^{15}$ is independently alkyl, cycloalkyl, $CF_3$, —CN, halo, —O-alkyl, —$NHSO_2$-alkyl, —$NO_2$, —$C(O)NH_2$, —C(O)NH-alkyl, —C(O)OH, —OH, —$NH_2$, —$SO_2$alkyl, —$SO_2NH$-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl;

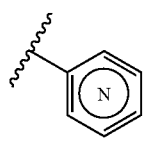

represents a pyridyl group, wherein the ring nitrogen atom can be at any of the five unsubstituted ring atom positions; and $R^4$ and $R^7$ are each independently H, halo or —OH; $R^5$ is H, alkyl, —O-alkyl, —O-haloalkyl, cycloalkyl, halo, haloalkyl, —OH, hydroxyalkyl, —$NH_2$ or —CN; and $R^6$ is H, alkyl, —O-alkyl, —O-haloalkyl, cycloalkyl, halo, haloalkyl, —OH, hydroxyalkyl, —$NH_2$ or —CN.

In one embodiment, $R^2$ is —$C(O)NHSO_2R^{11}$ or —$C(O)NHSO_2N(R^9)_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl.

In another embodiment, $R^2$ is —$C(O)NHSO_2R^{11}$ or —$C(O)NHSO_2N(R^9)_2$; $R^9$ is H, alkyl, aryl, cycloalkyl, heteroaryl or heterocycloalkyl; $R^{11}$ is alkyl, aryl, cycloalkyl, haloalkyl, heteroaryl, heterocycloalkyl or hydroxyalkyl; and each occurrence of $R^{30}$ is independently, H, halo, —$N(alkyl)_2$, —OH, —O-alkyl, —O-haloalkyl, alkyl, cycloalkyl or heterocycloalkyl, or two adjacent $R^{30}$ groups, together with the carbon atoms to which they are attached, join to form an aryl, cycloalkyl, heteroaryl or heterocycloalkyl group.

In another embodiment, $R^2$ is —$C(O)NHSO_2R^{11}$ or —$C(O)NHSO_2N(R^9)_2$; $R^3$ is:

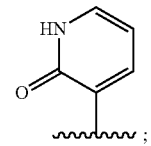

$R^9$ is H, alkyl, aryl, cycloalkyl, heteroaryl or heterocycloalkyl; $R^{11}$ is alkyl, aryl, cycloalkyl, haloalkyl, heteroaryl, heterocycloalkyl or hydroxyalkyl; and each occurrence of $R^{30}$ is independently, H, halo, —$N(alkyl)_2$, —OH, —O-alkyl, —O-haloalkyl, alkyl, cycloalkyl or heterocycloalkyl, or two adjacent $R^{30}$ groups, together with the carbon atoms to which they are attached, join to form an aryl, cycloalkyl, heteroaryl or heterocycloalkyl group.

In still another embodiment, $R^1$ is —$[C(R^{12})_2]_n$—; $R^2$ is —$C(O)NHSO_2R^{11}$ or —$C(O)NHSO_2N(R^9)_2$; $R^3$ is:

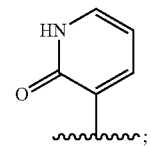

$R^9$ is H, alkyl, aryl, cycloalkyl, heteroaryl or heterocycloalkyl; $R^{11}$ is alkyl, aryl, cycloalkyl, haloalkyl, heteroaryl, heterocycloalkyl or hydroxyalkyl; and each occurrence of $R^{30}$ is independently, H, halo, —$N(alkyl)_2$, —OH, —O-alkyl, —O-haloalkyl, alkyl, cycloalkyl or heterocycloalkyl, or two adjacent $R^{30}$ groups, together with the carbon atoms to which they are attached, join to form an aryl, cycloalkyl, heteroaryl or heterocycloalkyl group.

In another embodiment, $R^1$ is —$CH_2$—, —$CH_2CH_2$—, —$CH(CH_3)$— or

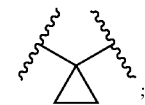

$R^2$ is —$C(O)NHSO_2R^{11}$ or —$C(O)NHSO_2N(R^9)_2$; $R^3$ is:

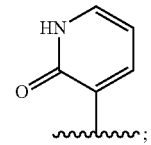

$R^9$ is H, alkyl, aryl, cycloalkyl, heteroaryl or heterocycloalkyl; $R^{11}$ is alkyl, aryl, cycloalkyl, haloalkyl, heteroaryl, heterocycloalkyl or hydroxyalkyl; and each occurrence of $R^{30}$ is independently, H, halo, —$N(alkyl)_2$, —OH, —O-alkyl, —O-haloalkyl, alkyl, cycloalkyl or heterocycloalkyl, or two adjacent $R^{30}$ groups, together with the carbon atoms to which they are attached, join to form an aryl, cycloalkyl, heteroaryl or heterocycloalkyl group.

In yet another embodiment, $R^1$ is —$CH_2$—; $R^2$ is —C(O)NHSO$_2$R$^{11}$ or —C(O)NHSO$_2$N(R$^9$)$_2$; $R^3$ is:

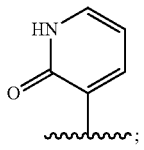

$R^9$ is H, alkyl, aryl, cycloalkyl, heteroaryl or heterocycloalkyl; $R^{11}$ is alkyl, aryl, cycloalkyl, haloalkyl, heteroaryl, heterocycloalkyl or hydroxyalkyl; and each occurrence of $R^{30}$ is independently, H, halo, —N(alkyl)$_2$, —OH, —O-alkyl, —O-haloalkyl, alkyl, cycloalkyl or heterocycloalkyl, or two adjacent $R^{30}$ groups, together with the carbon atoms to which they are attached, join to form an aryl, cycloalkyl, heteroaryl or heterocycloalkyl group.

In a further embodiment, $R^1$ is —[C(R$^{12}$)$_2$]$_r$—; $R^2$ is —C(O)NHSO$_2$R$^{11}$ or —C(O)NHSO$_2$N(R$^9$)$_2$; $R^3$ is:

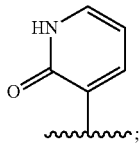

$R^4$ and $R^7$ are each independently H, halo or —OH; $R^5$ is H, alkyl, —O-alkyl, —O-haloalkyl, cycloalkyl, halo, haloalkyl, —OH, hydroxyalkyl, —NH$_2$ or —CN; $R^6$ is H, alkyl, —O-alkyl, —O-haloalkyl, cycloalkyl, halo, haloalkyl, —OH, hydroxyalkyl, —NH$_2$ or —CN; $R^9$ is H, alkyl, aryl, cycloalkyl, heteroaryl or heterocycloalkyl; $R^{11}$ is alkyl, aryl, cycloalkyl, haloalkyl, heteroaryl, heterocycloalkyl or hydroxyalkyl; and each occurrence of $R^{30}$ is independently, H, halo, —N(alkyl)$_2$, —OH, —O-alkyl, —O-haloalkyl, alkyl, cycloalkyl or heterocycloalkyl, or two adjacent $R^{30}$ groups, together with the carbon atoms to which they are attached, join to form an aryl, cycloalkyl, heteroaryl or heterocycloalkyl group.

In one embodiment, $R^1$ is —[C(R$^{12}$)$_2$]$_r$—; $R^2$ is —C(O)NHSO$_2$R$^{11}$ or —C(O)NHSO$_2$N(R$^9$)$_2$; $R^3$ is:

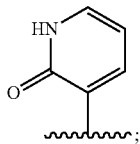

$R^4$ and $R^7$ are each independently H, halo or —OH; $R^5$ is H, alkyl, —O-alkyl, —O-haloalkyl, cycloalkyl, halo, haloalkyl, —OH, hydroxyalkyl, —NH$_2$ or —CN; $R^6$ is H, alkyl, —O-alkyl, —O-haloalkyl, cycloalkyl, halo, haloalkyl, —OH, hydroxyalkyl, —NH$_2$ or —CN; $R^9$ is H, alkyl, aryl, cycloalkyl, heteroaryl or heterocycloalkyl; $R^{11}$ is alkyl, aryl, cycloalkyl, haloalkyl, heteroaryl, heterocycloalkyl or hydroxyalkyl; and each occurrence of $R^{30}$ is independently, H, halo, —N(alkyl)$_2$, —OH, —O-alkyl, —O-haloalkyl, alkyl, cycloalkyl or heterocycloalkyl, or two adjacent $R^{30}$ groups, together with the carbon atoms to which they are attached, join to form an aryl, cycloalkyl, heteroaryl or heterocycloalkyl group; and $R^{10}$ is aryl or heteroaryl In another embodiment, $R^1$ is —[C(R$^{12}$)$_2$]$_r$—; $R^2$ is —C(O)NHSO$_2$R$^{11}$ or —C(O)NHSO$_2$N(R$^9$)$_2$; $R^3$ is:

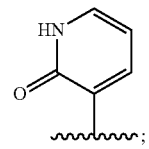

$R^4$ and $R^7$ are each independently H, halo or —OH; $R^5$ is H, alkyl, —O-alkyl, —O-haloalkyl, cycloalkyl, halo, haloalkyl, —OH, hydroxyalkyl, —NH$_2$ or —CN; $R^6$ is H, alkyl, —O-alkyl, —O-haloalkyl, cycloalkyl, halo, haloalkyl, —OH, hydroxyalkyl, —NH$_2$ or —CN; $R^9$ is H, alkyl, aryl, cycloalkyl, heteroaryl or heterocycloalkyl; $R^{11}$ is alkyl, aryl, cycloalkyl, haloalkyl, heteroaryl, heterocycloalkyl or hydroxyalkyl; and each occurrence of $R^{30}$ is independently, H, halo, —N(alkyl)$_2$, —OH, —O-alkyl, —O-haloalkyl, alkyl, cycloalkyl or heterocycloalkyl, or two adjacent $R^{30}$ groups, together with the carbon atoms to which they are attached, join to form an aryl, cycloalkyl, heteroaryl or heterocycloalkyl group; and $R^{10}$ is:

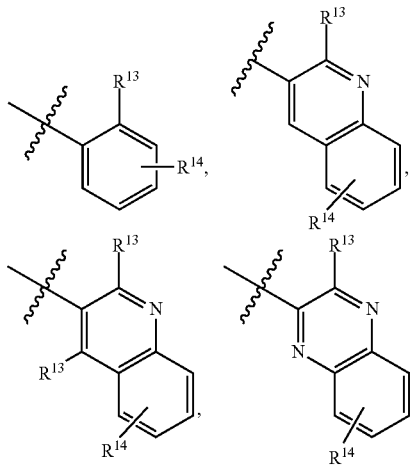

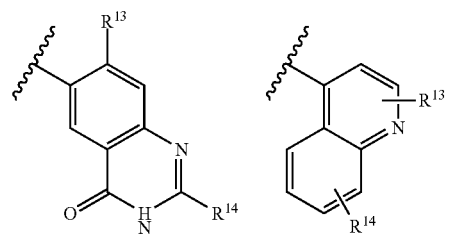

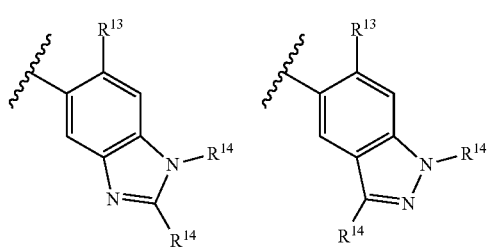

-continued

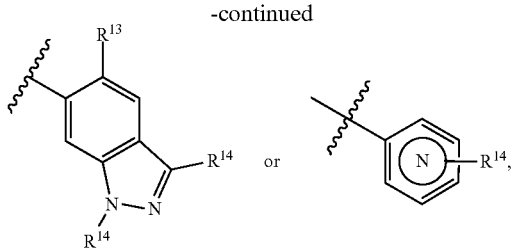

wherein $R^{13}$ is H, F, Br or Cl; $R^{14}$ represents up to 4 optional and additional substituents, each independently selected from alkyl, cycloalkyl, $CF_3$, —CN, halo, —O-alkyl, —O-haloalkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; each occurrence of $R^{15}$ is independently alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl; and

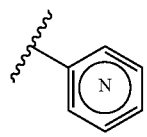

represents a pyridyl group, wherein the ring nitrogen atom can be at any of the five unsubstituted ring atom positions.

In another embodiment, $R^1$ is —[C($R^{12}$)$_2$]$_r$—; $R^2$ is —C(O)$NHSO_2R^{11}$ or —C(O)$NHSO_2N(R^9)_2$; $R^3$ is:

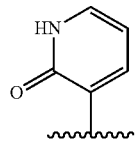

$R^4$ and $R^7$ are each independently H, halo or —OH; $R^5$ is H, alkyl, —O-alkyl, —O-haloalkyl, cycloalkyl, halo, haloalkyl, —OH, hydroxyalkyl, —$NH_2$ or —CN; $R^6$ is H, alkyl, —O-alkyl, —O-haloalkyl, cycloalkyl, halo, haloalkyl, —OH, hydroxyalkyl, —$NH_2$ or —CN; $R^9$ is H, alkyl, aryl, cycloalkyl, heteroaryl or heterocycloalkyl; $R^{11}$ is alkyl, aryl, cycloalkyl, haloalkyl, heteroaryl, heterocycloalkyl or hydroxyalkyl; and each occurrence of $R^{30}$ is independently, H, halo, —N(alkyl)$_2$, —OH, —O-alkyl, —O-haloalkyl, alkyl, cycloalkyl or heterocycloalkyl, or two adjacent $R^{30}$ groups, together with the carbon atoms to which they are attached, join to form an aryl, cycloalkyl, heteroaryl or heterocycloalkyl group; and $R^{10}$ is:

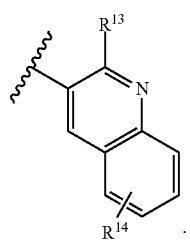

In still another embodiment, $R^1$ is —[C($R^{12}$)$_2$]$_r$—; $R^2$ is —C(O)$NHSO_2R^{11}$ or —C(O)$NHSO_2N(R^9)_2$; $R^3$ is:

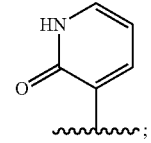

$R^4$ and $R^7$ are each independently H, halo or —OH; $R^5$ is H, alkyl, —O-alkyl, —O-haloalkyl, cycloalkyl, halo, haloalkyl, —OH, hydroxyalkyl, —$NH_2$ or —CN; $R^6$ is H, alkyl, —O-alkyl, —O-haloalkyl, cycloalkyl, halo, haloalkyl, —OH, hydroxyalkyl, —$NH_2$ or —CN; $R^9$ is H, alkyl, aryl, cycloalkyl, heteroaryl or heterocycloalkyl; $R^{11}$ is alkyl, aryl, cycloalkyl, haloalkyl, heteroaryl, heterocycloalkyl or hydroxyalkyl; and each occurrence of $R^{30}$ is independently, H, halo, —N(alkyl)$_2$, —OH, —O-alkyl, —O-haloalkyl, alkyl, cycloalkyl or heterocycloalkyl, or two adjacent $R^{30}$ groups, together with the carbon atoms to which they are attached, join to form an aryl, cycloalkyl, heteroaryl or heterocycloalkyl group; and $R^{10}$ is:

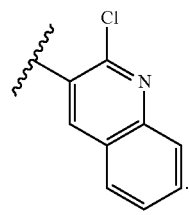

In one embodiment, for the compounds of formula (I), variables $R^1$, $R^2$, $R^3$, $R^4$, $R^5$, $R^5$, $R^6$, $R^7$ and $R^{10}$ are selected independently of each other.

In another embodiment, the compounds of formula (II) are in purified form.

In one embodiment, the compounds of formula (II) have the formula (IIa):

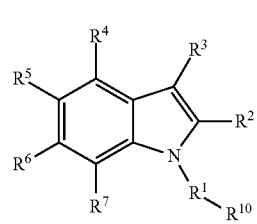

(IIa)

or a pharmaceutically acceptable salt, solvate, ester or prodrug thereof,
wherein:
$R^1$ is —$CH_2$—, —$CH_2CH_2$—, —CH($CH_3$)— or

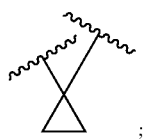

$R^2$ is —C(O)$NHSO_2R^{11}$, —C(O)$NHSO_2N(R^9)_2$, —C(O)N(alkyl)$SO_2R^{11}$ or —C(O)N(alkyl)$SO_2N(R^9)_2$;

$R^3$ is:

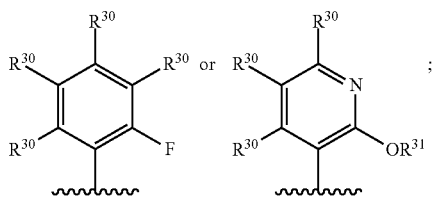

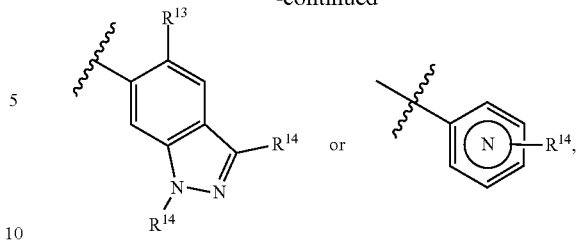

$R^4$, $R^5$, $R^6$ and $R^7$ are each, independently, H, alkyl, cycloalkyl, heterocycloalkyl, haloalkyl, halo, —OH, —OH, —O-alkyl, —O-haloalkyl, —NH$_2$, —NH-alkyl or —N(alkyl)$_2$;

each occurrence of $R^9$ is independently H, alkyl, cycloalkyl, heterocycloalkyl, haloalkyl or hydroxyalkyl;

$R^{10}$ is:

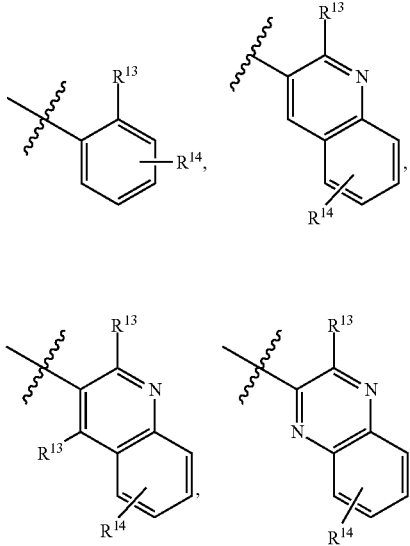

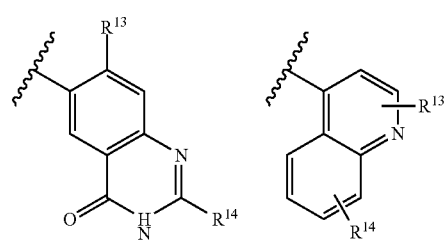

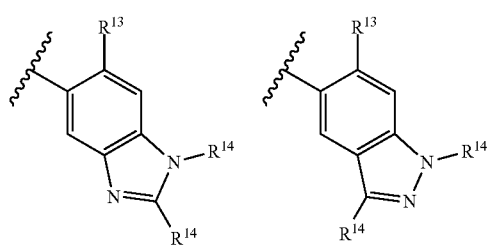

such that when $R^1$ is a bond, $R^{10}$ is not H;

each occurrence of $R^{11}$ is independently alkyl, aryl, cycloalkyl, haloalkyl, heteroaryl, heterocycloalkyl or hydroxyalkyl;

$R^{13}$ is H, F, Br or Cl;

$R^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl;

each occurrence of $R^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl;

each occurrence of $R^{30}$ is independently, H, halo, —N(alkyl)$_2$, —OH, —O-alkyl, —O-haloalkyl, alkyl, cycloalkyl or heterocycloalkyl, or two adjacent $R^{30}$ groups, together with the carbon atoms to which they are attached, join to form an aryl, cycloalkyl, heteroaryl or heterocycloalkyl group;

each occurrence of q is independently an integer ranging from 0 to 4;

each occurrence of r is independently an integer ranging from 1 to 4; and

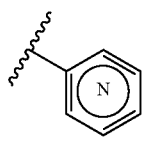

represents a pyridyl group, wherein the ring nitrogen atom can be at any of the five unsubstituted ring atom positions.

In one embodiment, for the compounds of formula (IIa), variables $R^1$, $R^2$, $R^3$, $R^4$, $R^5$, $R^5$, $R^6$, $R^7$ and $R^{10}$ are selected independently of each other.

In another embodiment, the compounds of formula (IIa) are in purified form.

Non-limiting illustrative examples of the 2,3-Substituted Indole Derivatives include compounds 1-641 as set forth in the following table and in the Examples section below.

| Compound No. | STRUCTURE | M + H |
|---|---|---|
| 1 | 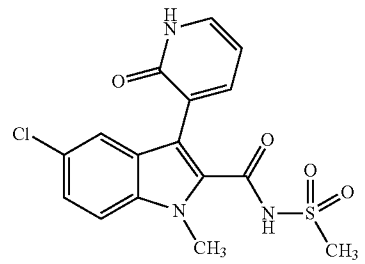 | 380.8 |
| 2 | 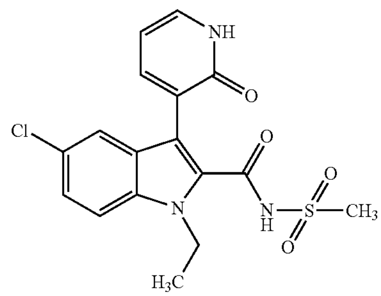 | 394.9 |
| 3 | 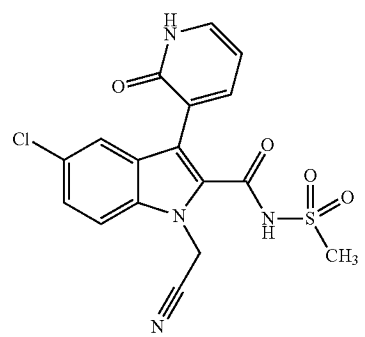 | 405.8 |
| 4 | 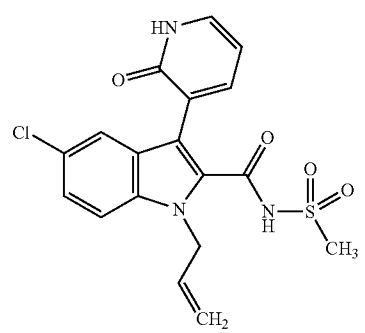 | 406.9 |
| 5 | 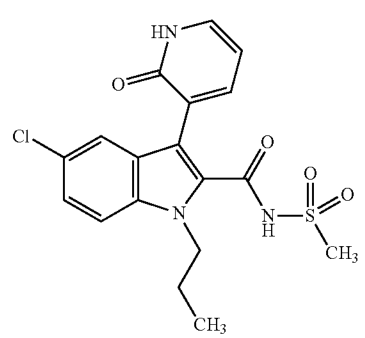 | 408.9 |

| Compound No. | STRUCTURE | M + H |
|---|---|---|
| 6 | 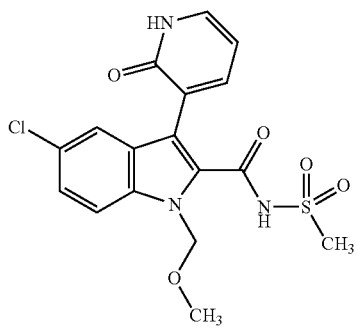 | 410.9 |
| 7 | 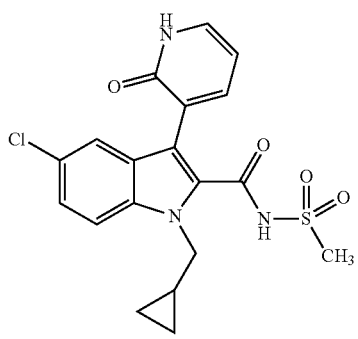 | 420.9 |
| 8 | 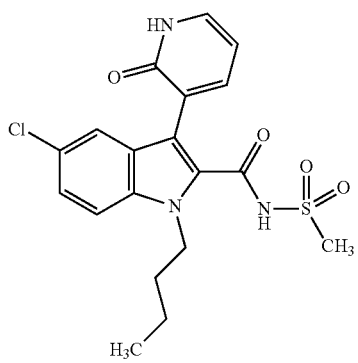 | 422.9 |
| 9 | 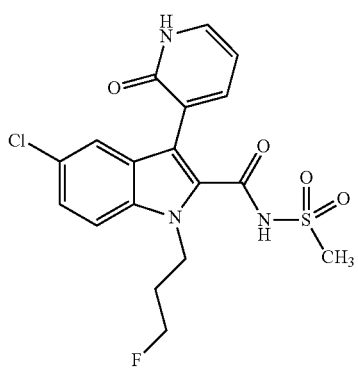 | 426.9 |

-continued
| Compound No. | STRUCTURE | M + H |
|---|---|---|
| 10 | 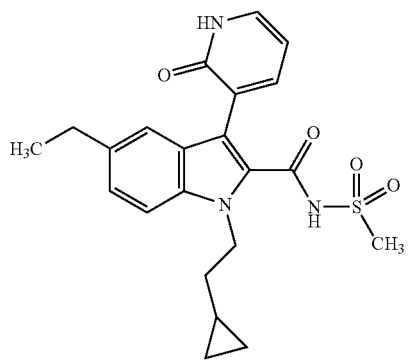 | 428.5 |
| 11 | 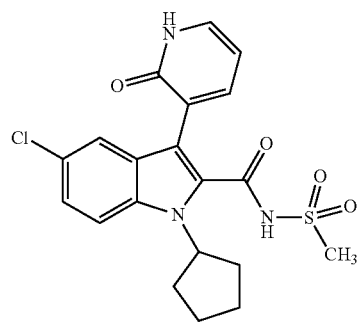 | 434.9 |
| 12 | 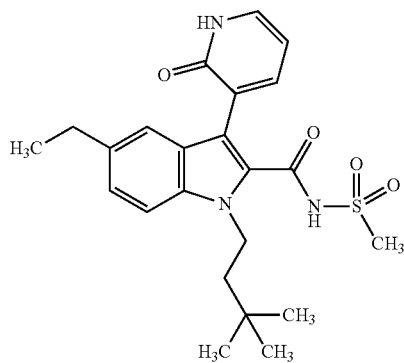 | 444.6 |
| 13 | 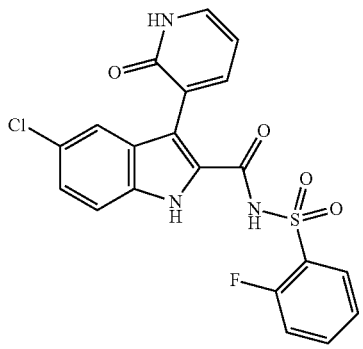 | 446.9 |

-continued

| Compound No. | STRUCTURE | M + H |
|---|---|---|
| 14 | 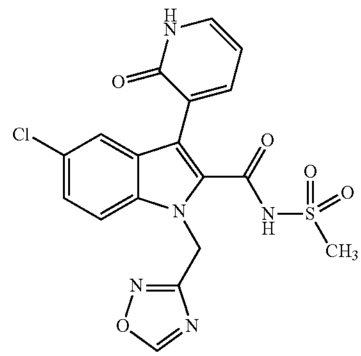 | 448.9 |
| 15 | 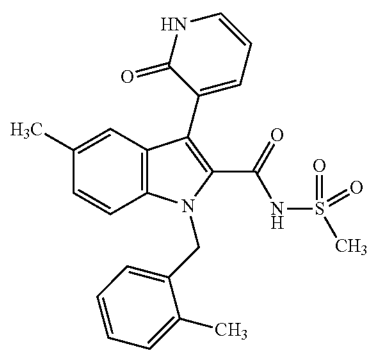 | 450.5 |
| 16 | 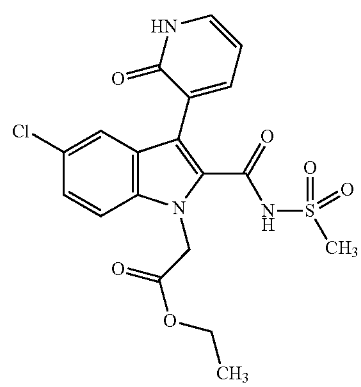 | 452.9 |
| 17 | 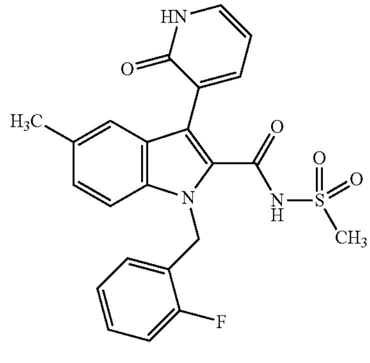 | 454.5 |

-continued
| Compound No. | STRUCTURE | M + H |
|---|---|---|
| 18 | 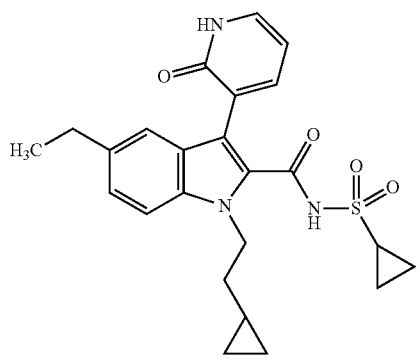 | 454.6 |
| 19 | 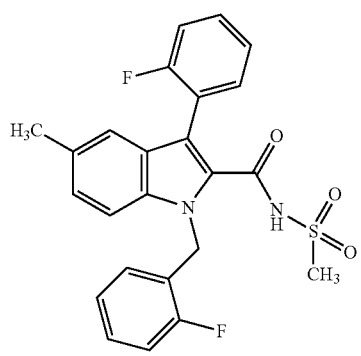 | 455.5 |
| 20 | 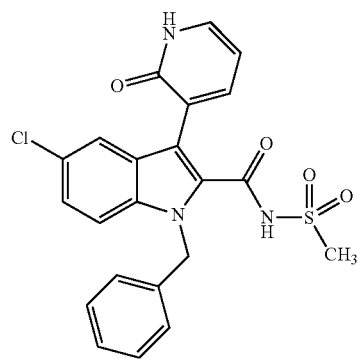 | 456.9 |
| 21 | 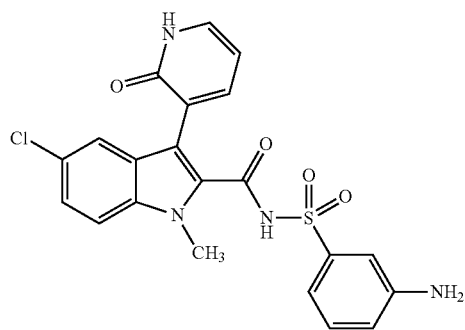 | 457.9 |

-continued
| Compound No. | STRUCTURE | M + H |
|---|---|---|
| 22 | 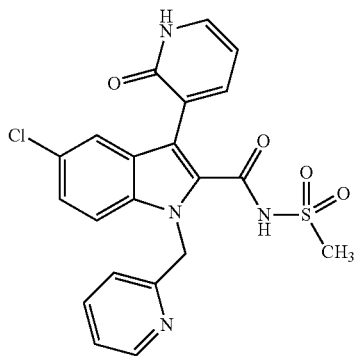 | 457.9 |
| 23 | 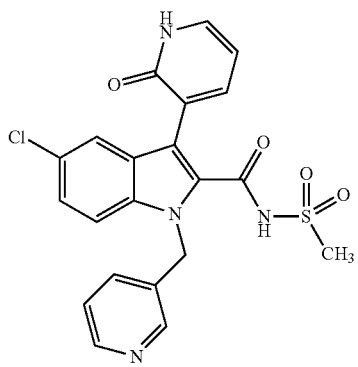 | 457.9 |
| 24 | 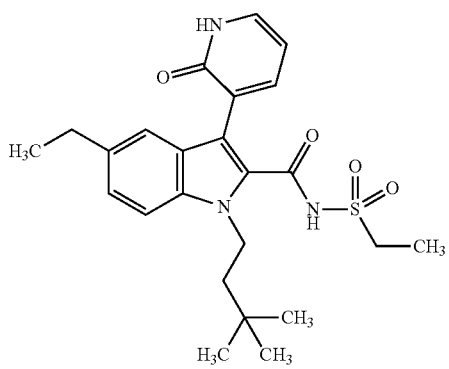 | 458.6 |
| 25 | 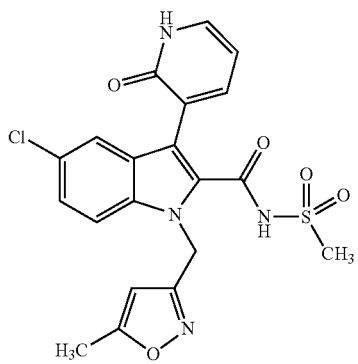 | 461.9 |

| Compound No. | STRUCTURE | M + H |
|---|---|---|
| 26 | 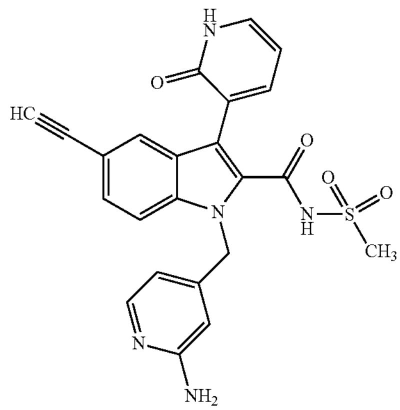 | 462.5 |
| 27 | 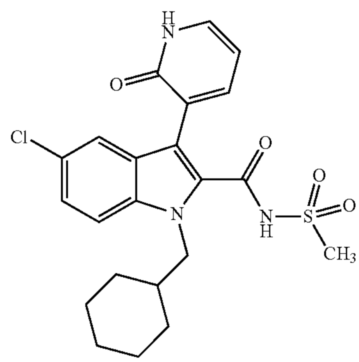 | 463.0 |
| 28 | 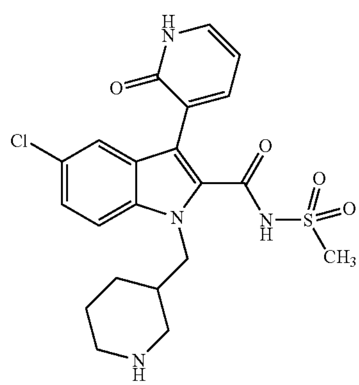 | 464.0 |
| 29 | 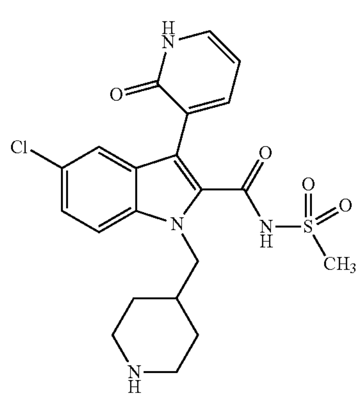 | 464.0 |

-continued

| Compound No. | STRUCTURE | M + H |
|---|---|---|
| 30 | 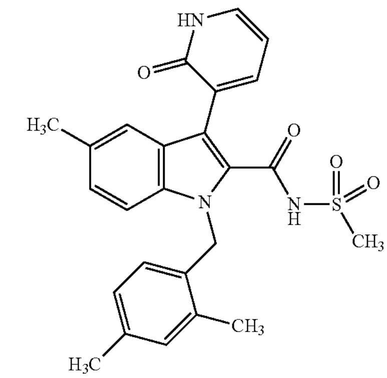 | 464.6 |
| 31 | 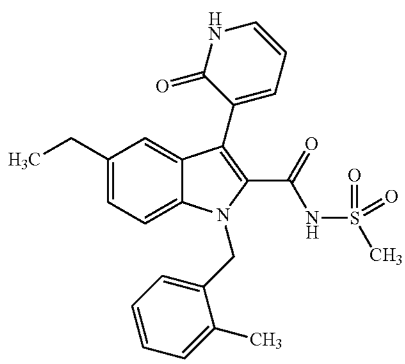 | 464.6 |
| 32 | 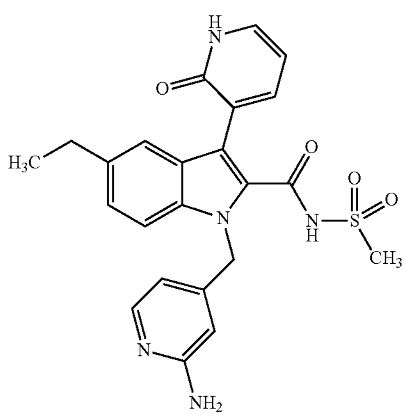 | 466.5 |
| 33 | 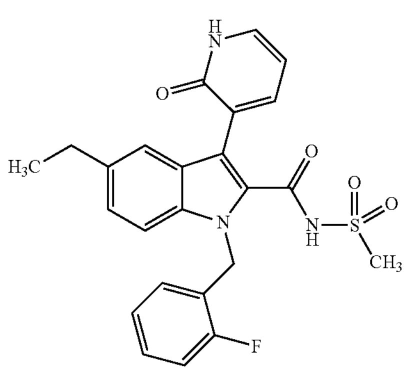 | 468.5 |

| Compound No. | STRUCTURE | M + H |
|---|---|---|
| 34 | 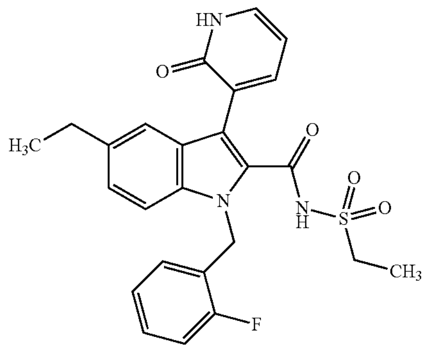 | 468.5 |
| 35 | 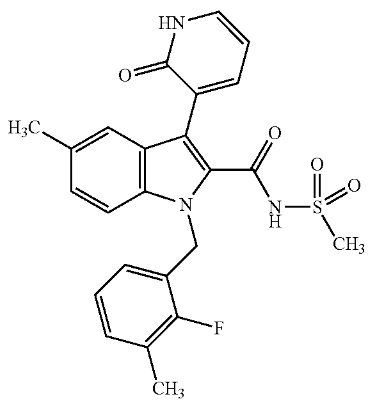 | 468.5 |
| 36 | 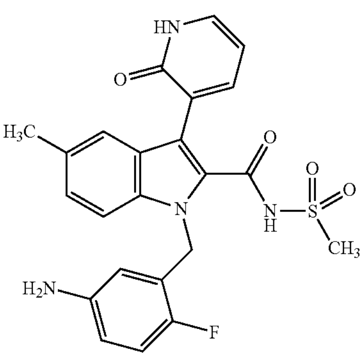 | 469.5 |
| 37 | 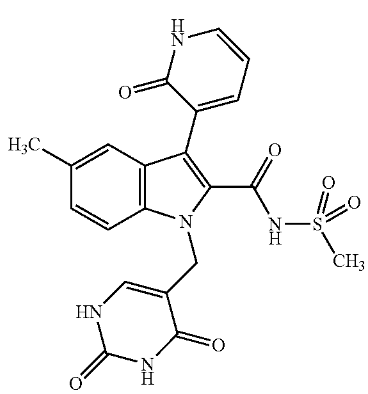 | 470.5 |

-continued
| Compound No. | STRUCTURE | M + H |
|---|---|---|
| 38 | 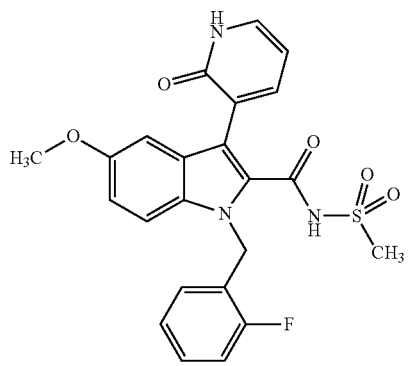 | 470.5 |
| 39 | 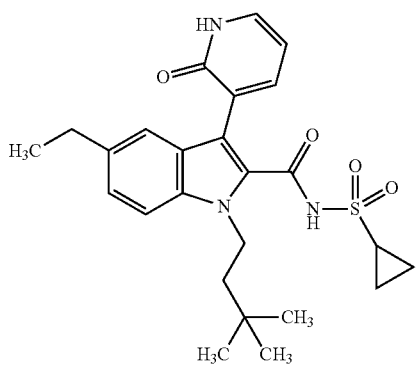 | 470.6 |
| 40 | 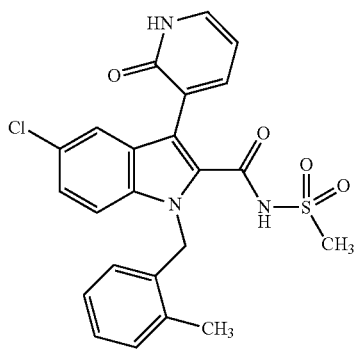 | 471.0 |
| 41 | 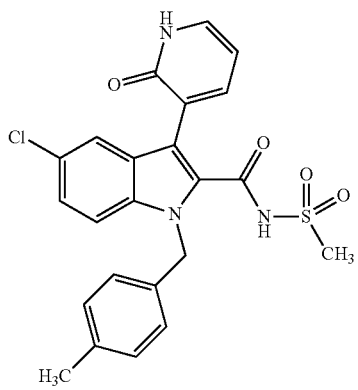 | 471.0 |

-continued

| Compound No. | STRUCTURE | M + H |
|---|---|---|
| 42 | 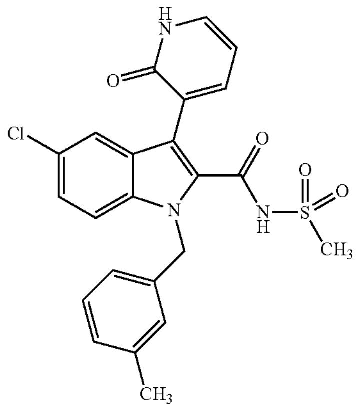 | 471.0 |
| 43 | 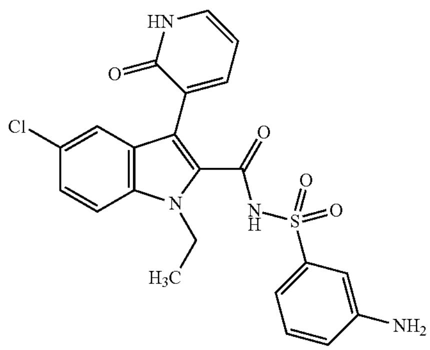 | 471.9 |
| 44 | 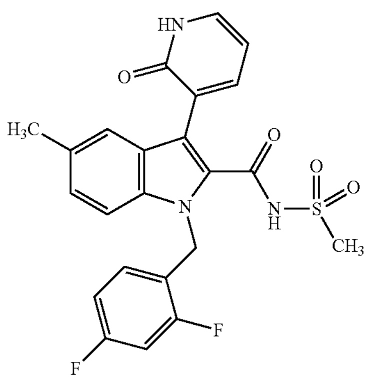 | 472.5 |
| 45 | 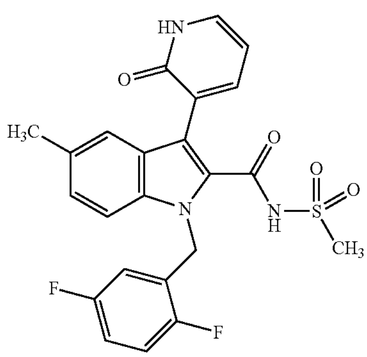 | 472.5 |

-continued

| Compound No. | STRUCTURE | M + H |
|---|---|---|
| 46 | (structure) | 472.5 |
| 47 | (structure) | 472.9 |
| 48 | (structure) | 472.9 |
| 49 | (structure) | 472.9 |

-continued

| Compound No. | STRUCTURE | M + H |
|---|---|---|
| 50 | 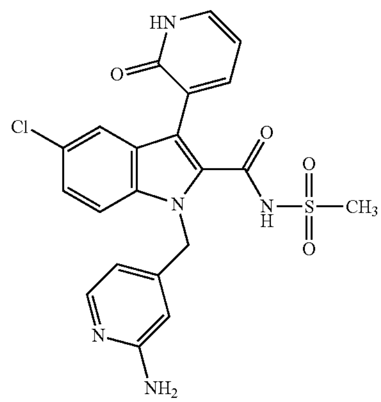 | 472.9 |
| 51 | 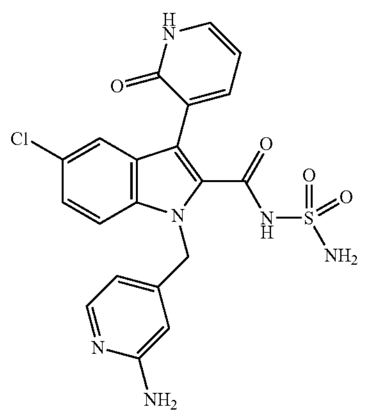 | 473.9 |
| 52 | 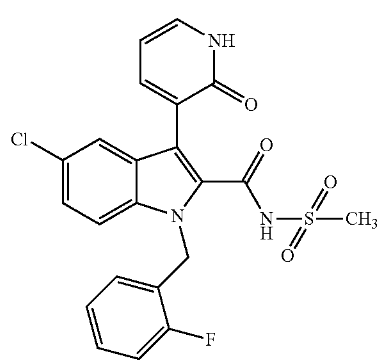 | 474.9 |
| 53 | 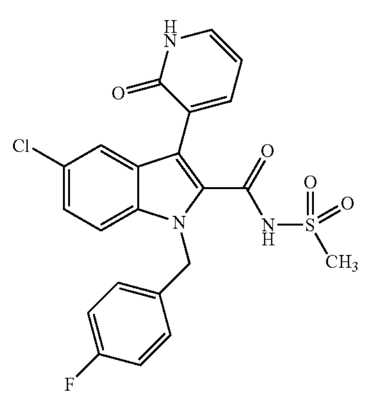 | 474.9 |

-continued
| Compound No. | STRUCTURE | M + H |
|---|---|---|
| 54 | 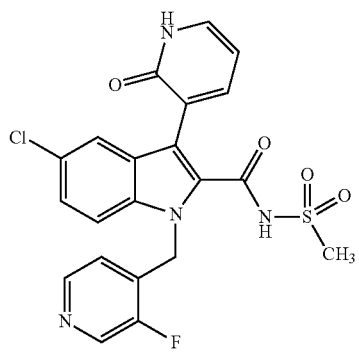 | 475.9 |
| 55 | 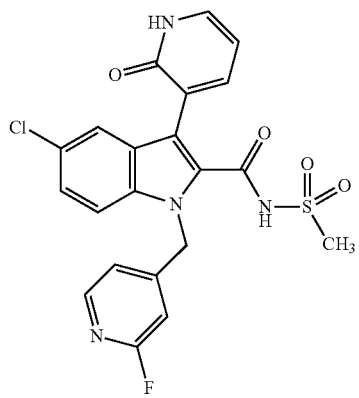 | 475.9 |
| 56 | 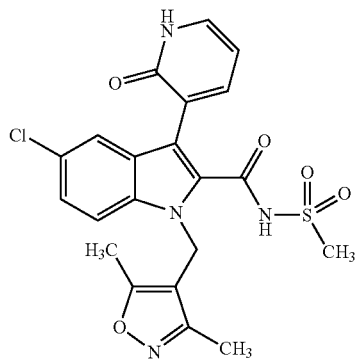 | 475.9 |
| 57 | 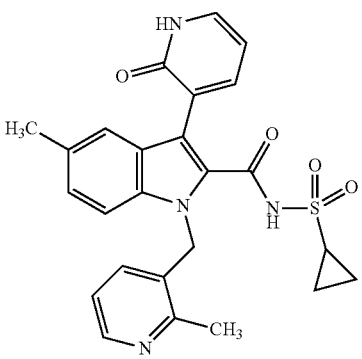 | 477.6 |

-continued

| Compound No. | STRUCTURE | M + H |
|---|---|---|
| 58 | 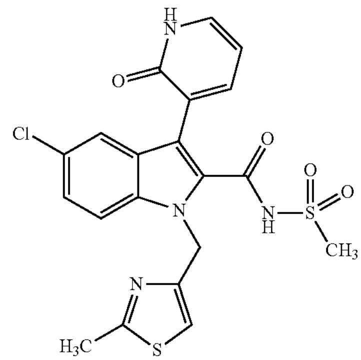 | 478.0 |
| 59 | 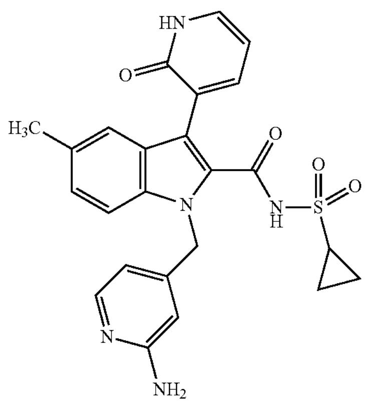 | 478.5 |
| 60 | 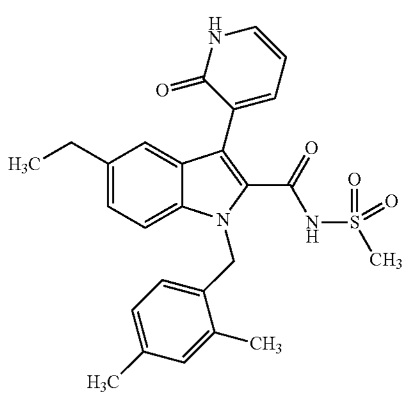 | 478.6 |
| 61 | 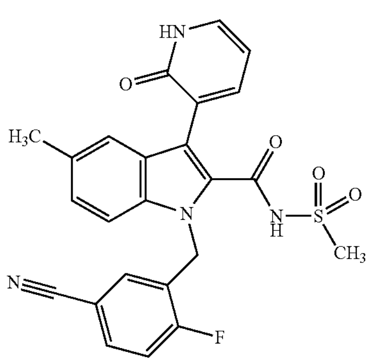 | 479.5 |

-continued

| Compound No. | STRUCTURE | M + H |
|---|---|---|
| 62 | (5-acetyl-3-(2-oxo-1,2-dihydropyridin-3-yl)-1-((2-aminopyridin-4-yl)methyl)-1H-indole-2-carboxylic acid methanesulfonamide) | 480.5 |
| 63 | (1-(2-fluorobenzyl)-5-methyl-3-(2-oxo-1,2-dihydropyridin-3-yl)-1H-indole-2-carboxylic acid cyclopropanesulfonamide) | 480.5 |
| 64 | (1-(2,4-dimethylbenzyl)-5-methoxy-3-(2-oxo-1,2-dihydropyridin-3-yl)-1H-indole-2-carboxylic acid methanesulfonamide) | 480.6 |
| 65 | (1-((2-aminopyridin-4-yl)methyl)-3-(2-oxo-1,2-dihydropyridin-3-yl)-5-propyl-1H-indole-2-carboxylic acid methanesulfonamide) | 480.6 |

-continued

| Compound No. | STRUCTURE | M + H |
|---|---|---|
| 66 | 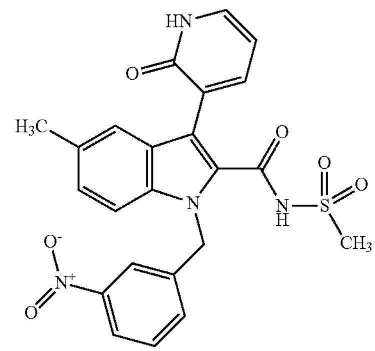 | 481.5 |
| 67 | 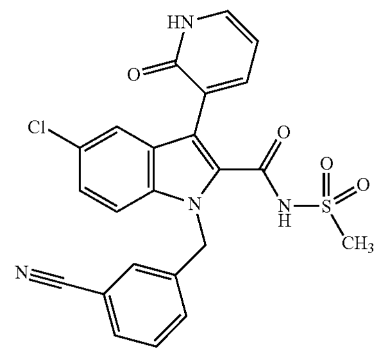 | 481.9 |
| 68 | 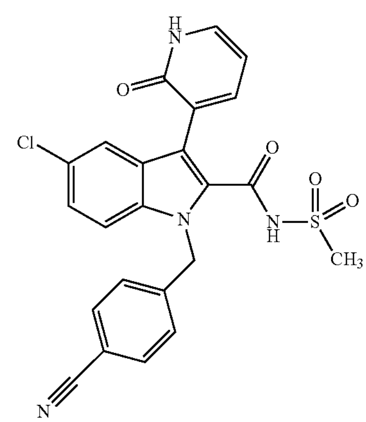 | 481.9 |
| 69 | 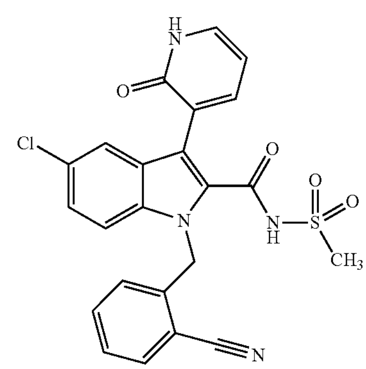 | 481.9 |

-continued

| Compound No. | STRUCTURE | M + H |
|---|---|---|
| 70 | 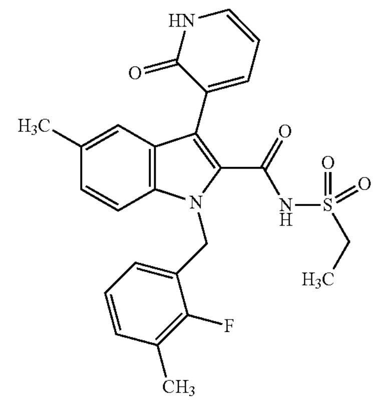 | 482.6 |
| 71 | 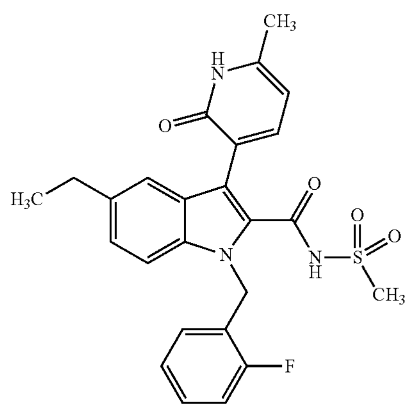 | 482.6 |
| 72 | 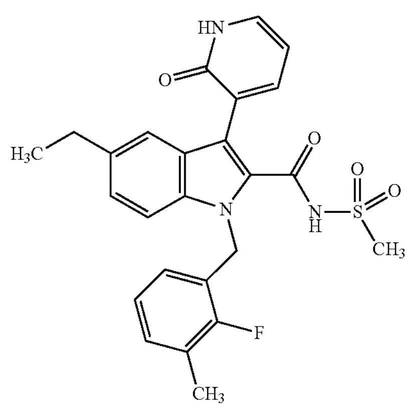 | 482.6 |
| 73 | 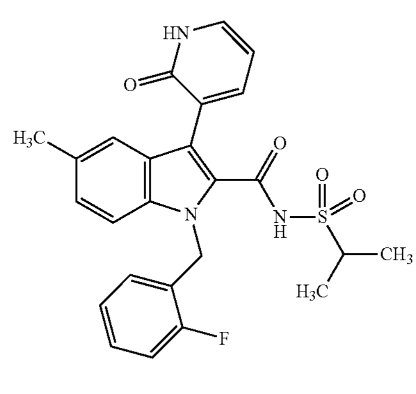 | 482.6 |

-continued
| Compound No. | STRUCTURE | M + H |
|---|---|---|
| 74 | 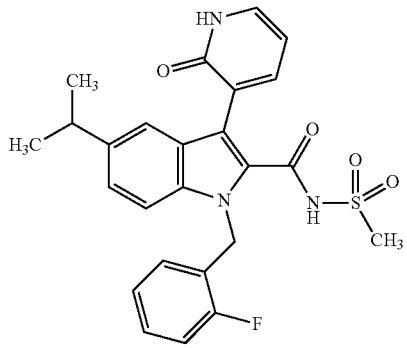 | 482.6 |
| 75 | 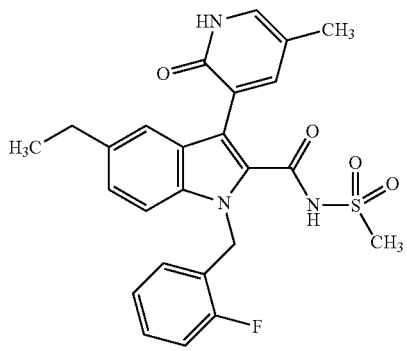 | 482.6 |
| 76 | 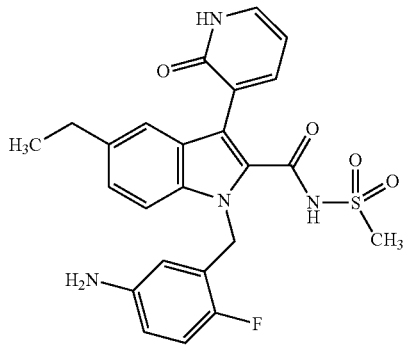 | 483.5 |
| 77 | 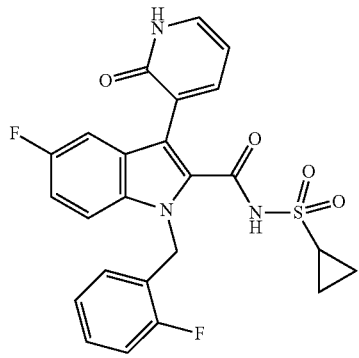 | 484.5 |

| Compound No. | STRUCTURE | M + H |
|---|---|---|
| 78 | 5-ethoxy-3-(2-oxo-1,2-dihydropyridin-3-yl)-1-(2-fluorobenzyl)-N-(methylsulfonyl)-1H-indole-2-carboxamide | 484.5 |
| 79 | 5-chloro-3-(2-oxo-1,2-dihydropyridin-3-yl)-1-(2,4-dimethylbenzyl)-N-(methylsulfonyl)-1H-indole-2-carboxamide | 485.0 |
| 80 | 5-chloro-3-(2-oxo-1,2-dihydropyridin-3-yl)-1-(2,5-dimethylbenzyl)-N-(methylsulfonyl)-1H-indole-2-carboxamide | 485.0 |
| 81 | 5-chloro-3-(2-oxo-1,2-dihydropyridin-3-yl)-1-(3,4-dimethylbenzyl)-N-(methylsulfonyl)-1H-indole-2-carboxamide | 485.0 |

-continued

| Compound No. | STRUCTURE | M + H |
|---|---|---|
| 82 | 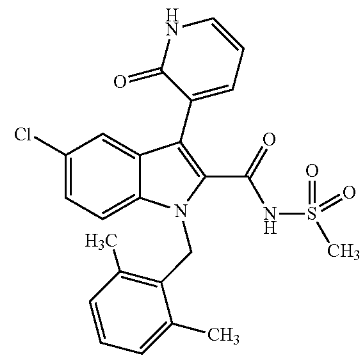 | 485.0 |
| 83 | 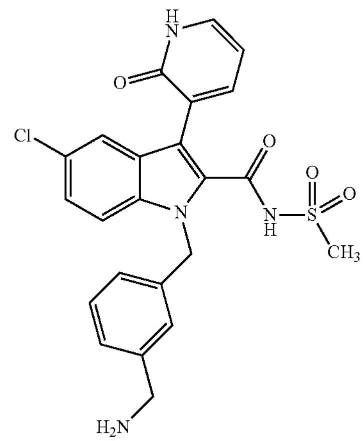 | 486.0 |
| 84 | 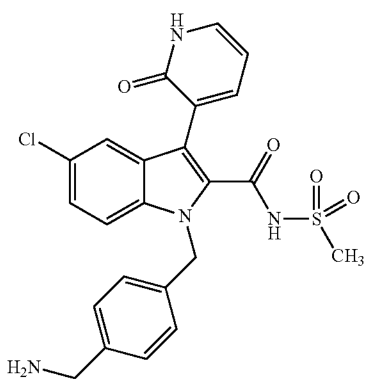 | 486.0 |
| 85 | 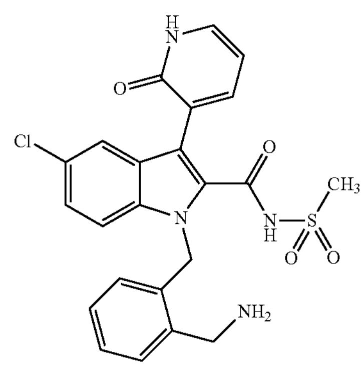 | 486.0 |

| Compound No. | STRUCTURE | M + H |
|---|---|---|
| 86 | 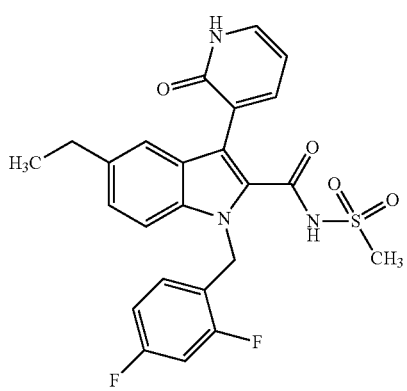 | 486.5 |
| 87 | 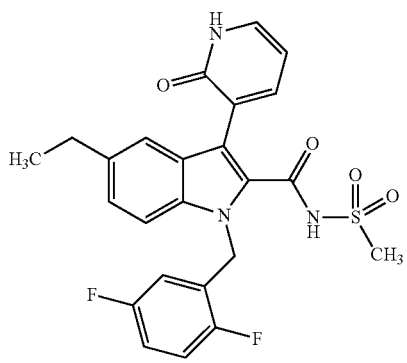 | 486.5 |
| 88 | 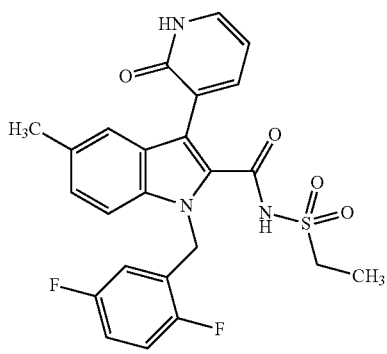 | 486.5 |
| 89 | 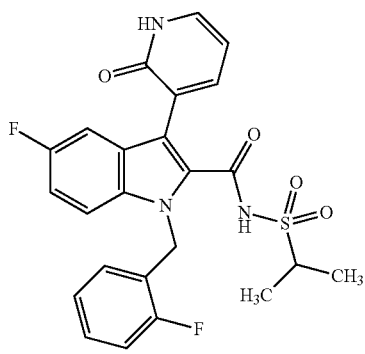 | 486.5 |

| Compound No. | STRUCTURE | M + H |
|---|---|---|
| 90 | 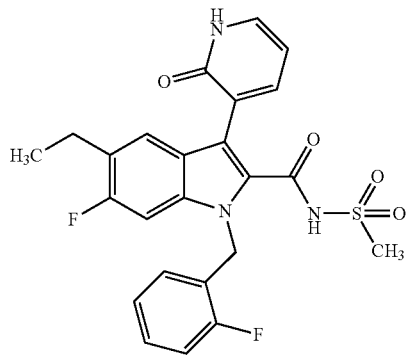 | 486.5 |
| 91 | 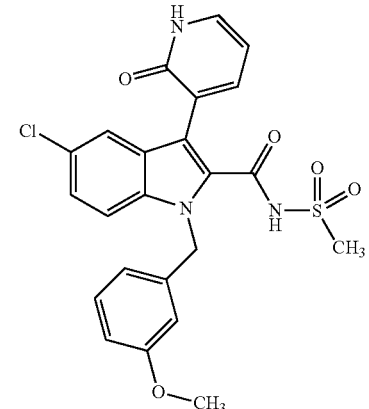 | 486.9 |
| 92 | 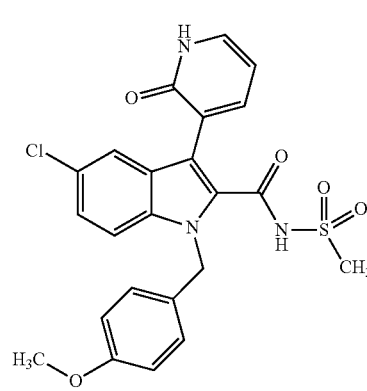 | 486.9 |
| 93 | 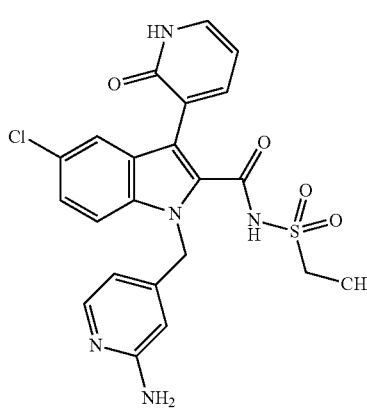 | 487.0 |

| Compound No. | STRUCTURE | M + H |
|---|---|---|
| 94 | 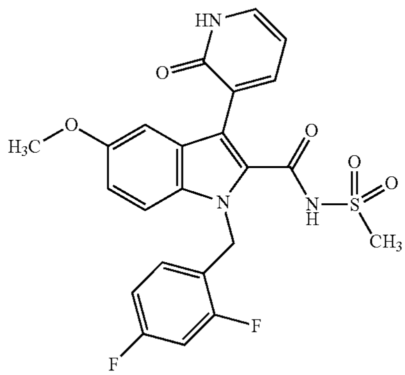 | 488.5 |
| 95 | 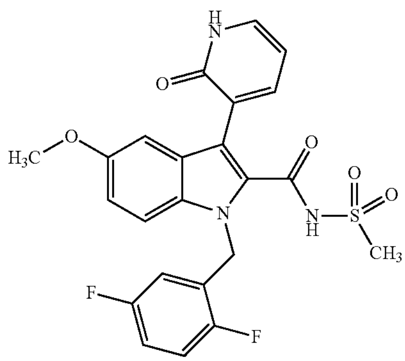 | 488.5 |
| 96 | 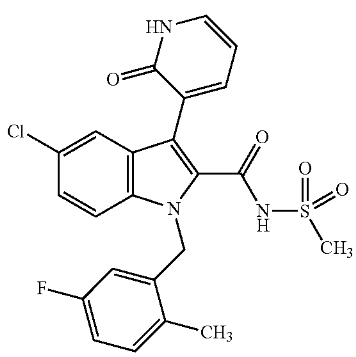 | 488.9 |
| 97 | 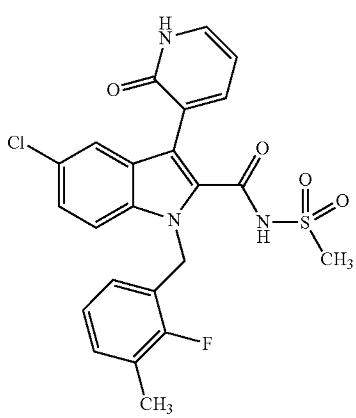 | 488.9 |

-continued

| Compound No. | STRUCTURE | M + H |
|---|---|---|
| 98 | 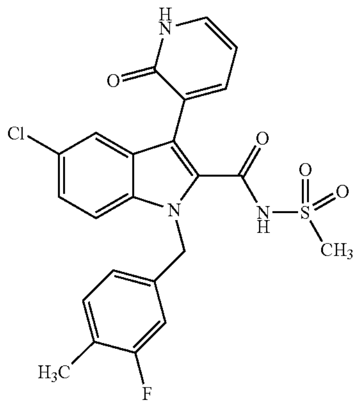 | 488.9 |
| 99 | 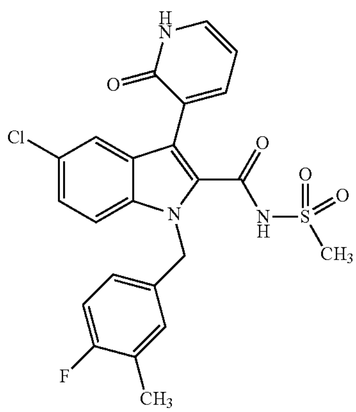 | 488.9 |
| 100 | 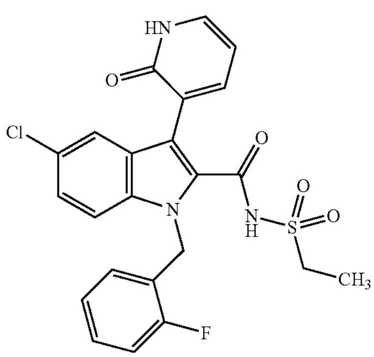 | 488.9 |
| 101 | 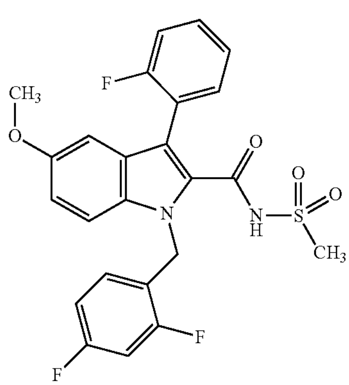 | 489.5 |

-continued
| Compound No. | STRUCTURE | M + H |
|---|---|---|
| 102 | 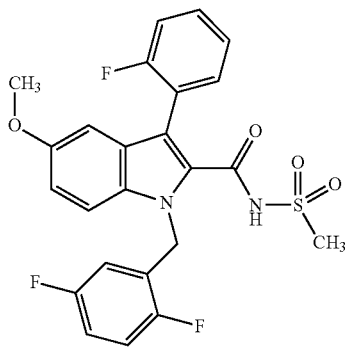 | 489.5 |
| 103 | 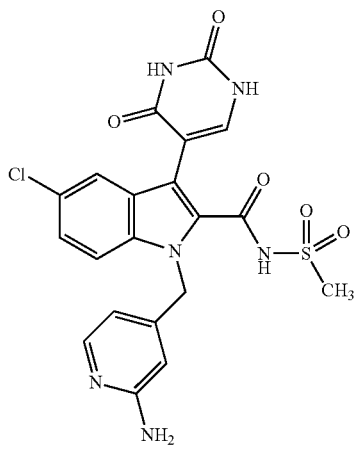 | 489.9 |
| 104 | 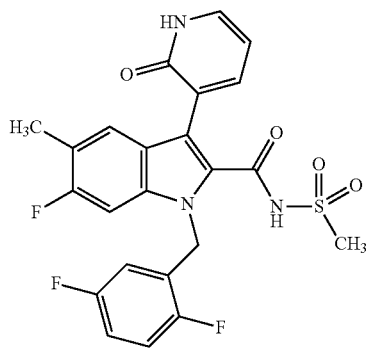 | 490.5 |
| 105 | 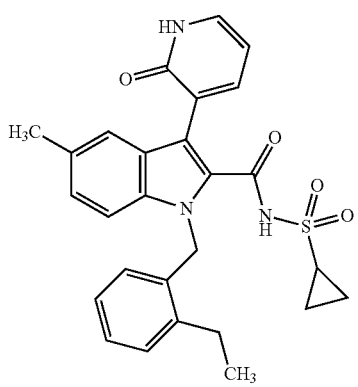 | 490.6 |

-continued

| Compound No. | STRUCTURE | M + H |
|---|---|---|
| 106 | 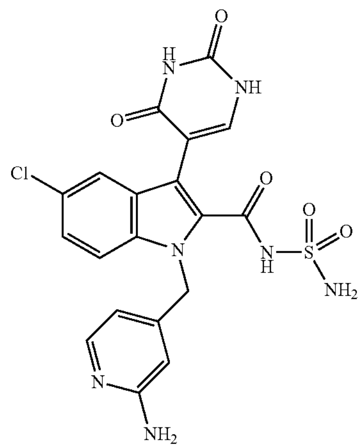 | 490.9 |
| 107 | 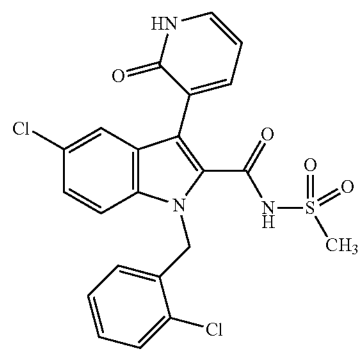 | 491.4 |
| 108 | 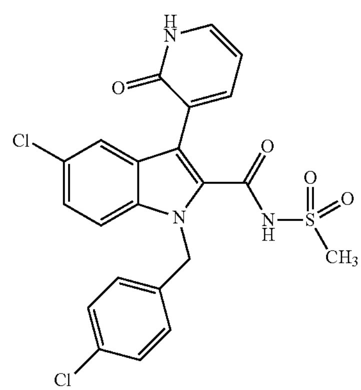 | 491.4 |
| 109 | 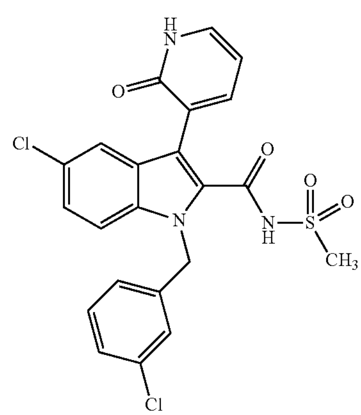 | 491.4 |

-continued

| Compound No. | STRUCTURE | M + H |
|---|---|---|
| 110 | 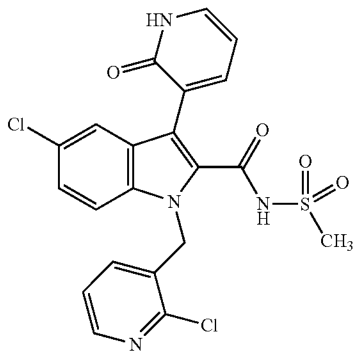 | 492.4 |
| 111 | 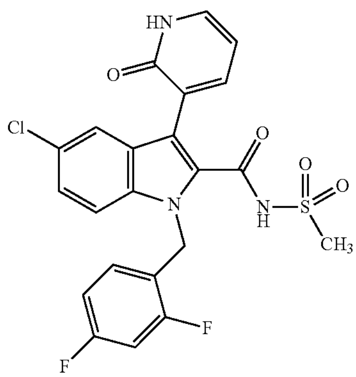 | 492.9 |
| 112 | 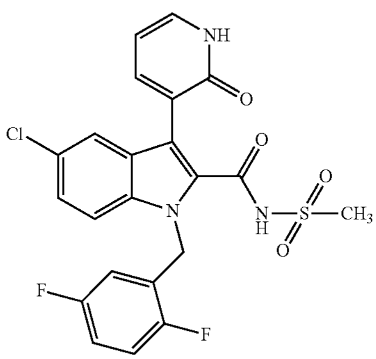 | 492.9 |
| 113 | 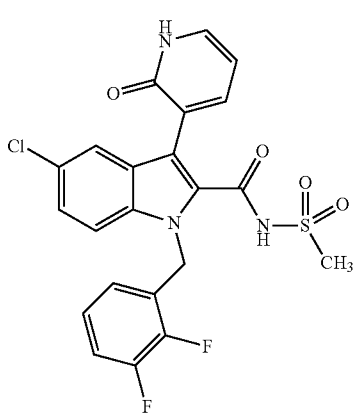 | 492.9 |

-continued
| Compound No. | STRUCTURE | M + H |
|---|---|---|
| 114 | 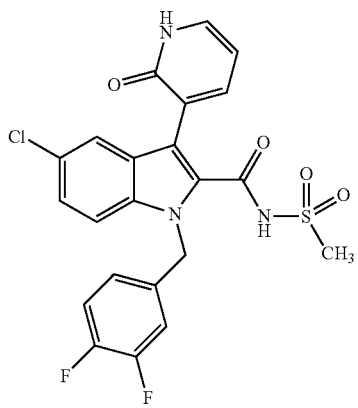 | 492.9 |
| 115 | 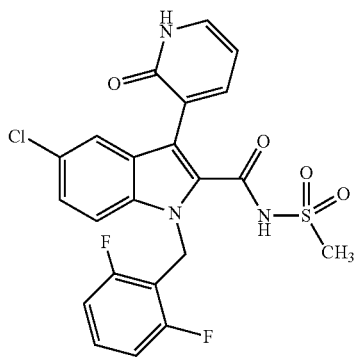 | 492.9 |
| 116 | 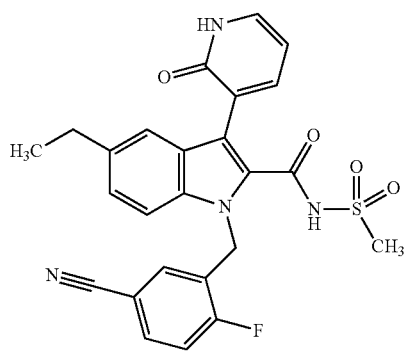 | 493.5 |
| 117 | 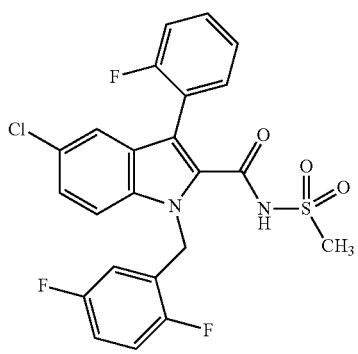 | 493.9 |

-continued
| Compound No. | STRUCTURE | M + H |
|---|---|---|
| 118 | 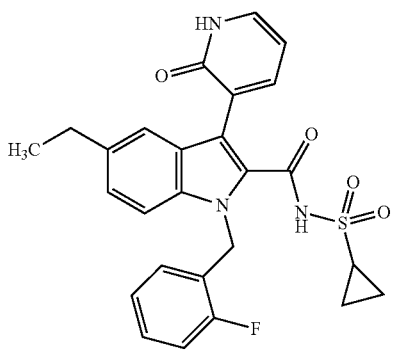 | 494.6 |
| 119 | 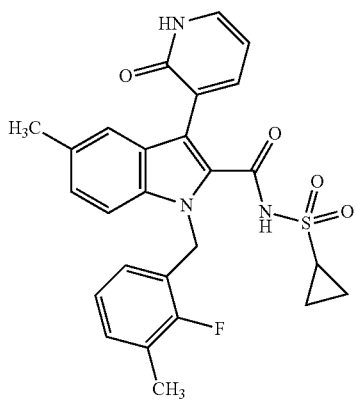 | 494.6 |
| 120 | 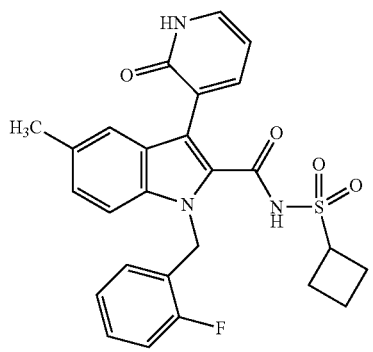 | 494.6 |
| 121 | 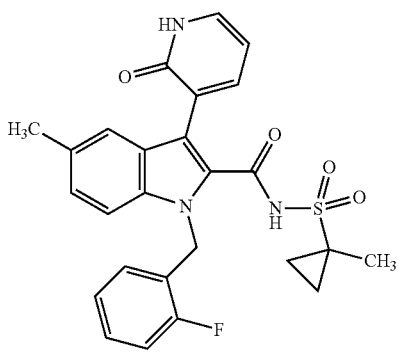 | 494.6 |

-continued

| Compound No. | STRUCTURE | M + H |
|---|---|---|
| 122 | 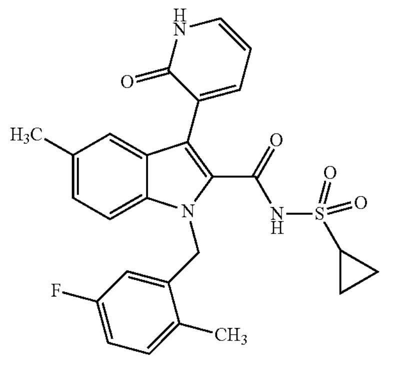 | 494.6 |
| 123 | 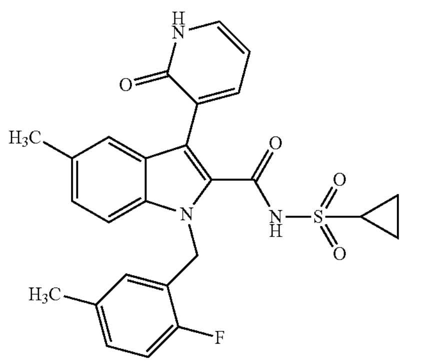 | 494.6 |
| 124 | 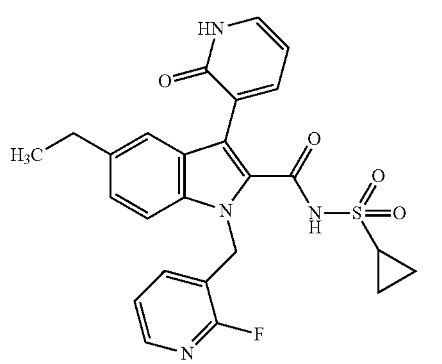 | 495.5 |
| 125 | 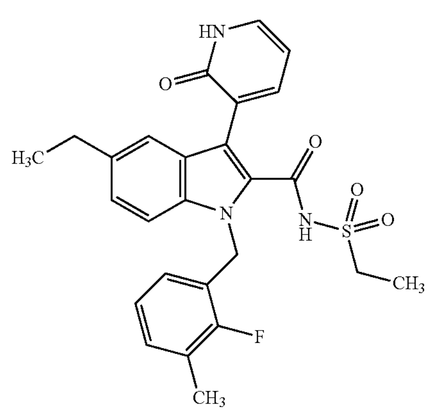 | 496.6 |

| Compound No. | STRUCTURE | M + H |
|---|---|---|
| 126 | 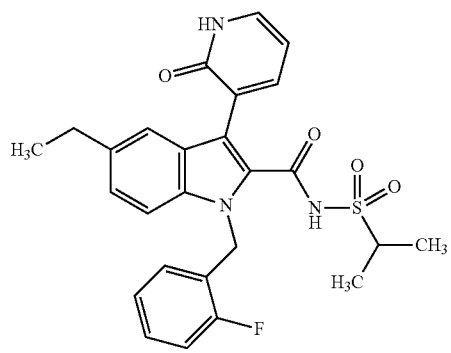 | 496.6 |
| 127 | 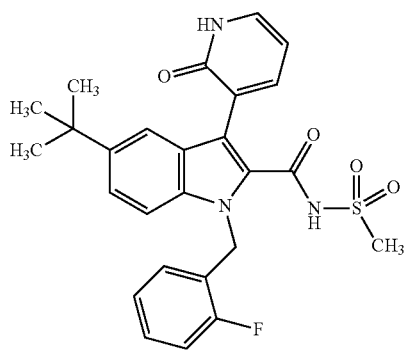 | 496.6 |
| 128 | 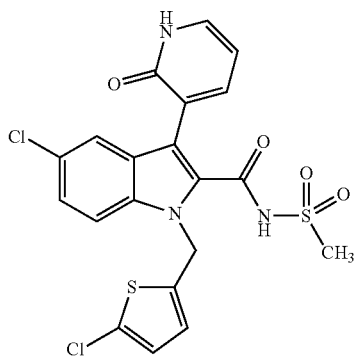 | 497.4 |
| 129 | 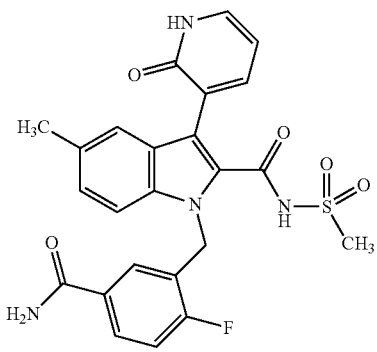 | 497.5 |

-continued

| Compound No. | STRUCTURE | M + H |
|---|---|---|
| 130 | 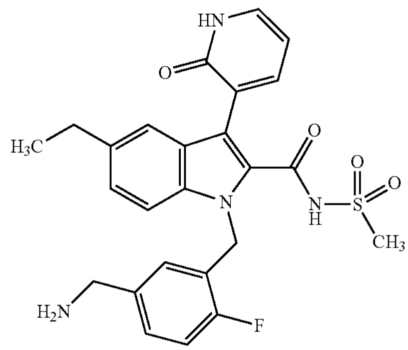 | 497.6 |
| 131 | 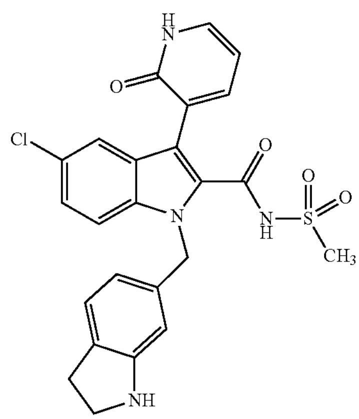 | 498.0 |
| 132 | 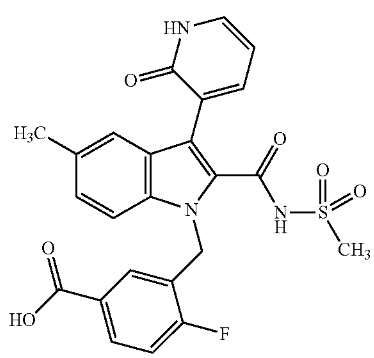 | 498.5 |
| 133 | 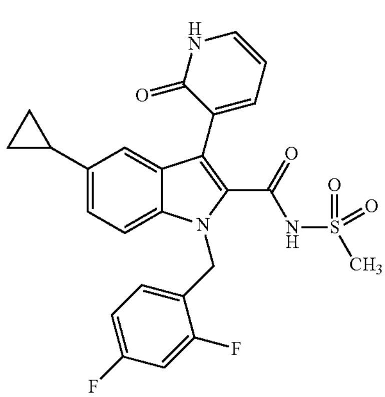 | 498.5 |

-continued
| Compound No. | STRUCTURE | M + H |
|---|---|---|
| 134 | 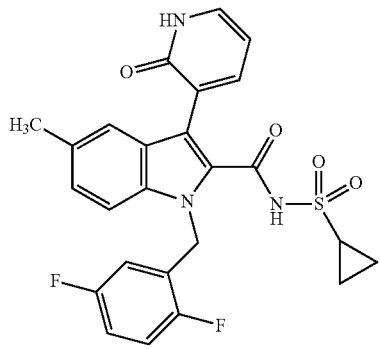 | 498.5 |
| 135 | 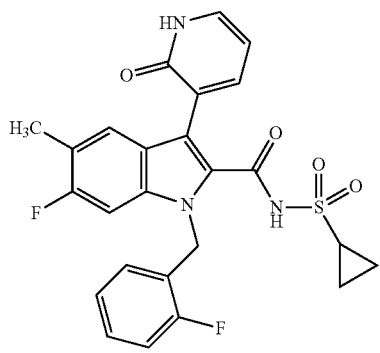 | 498.5 |
| 136 | 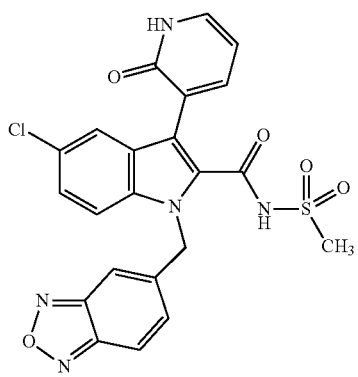 | 498.9 |
| 137 | 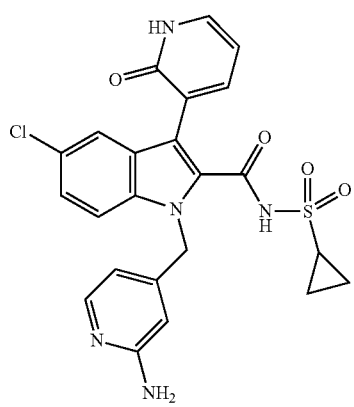 | 499.0 |

-continued

| Compound No. | STRUCTURE | M + H |
|---|---|---|
| 138 | 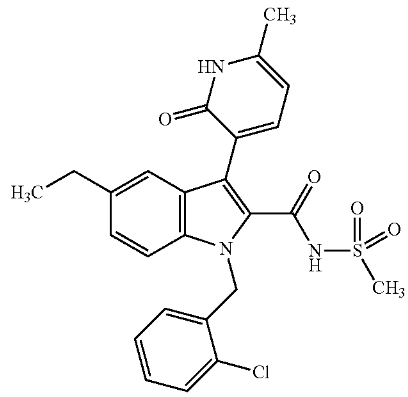 | 499.0 |
| 139 | 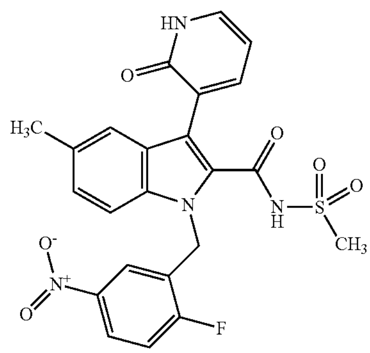 | 499.5 |
| 140 | 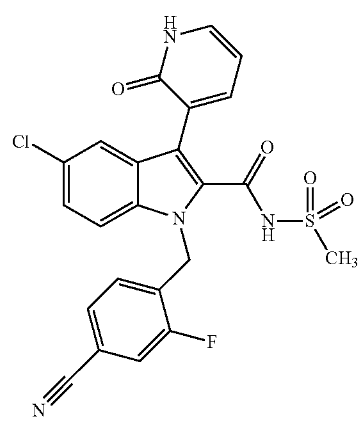 | 499.9 |
| 141 | 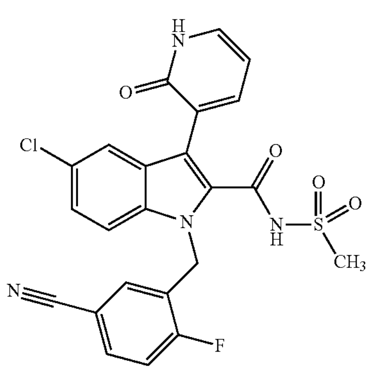 | 499.9 |

-continued
| Compound No. | STRUCTURE | M + H |
|---|---|---|
| 142 | 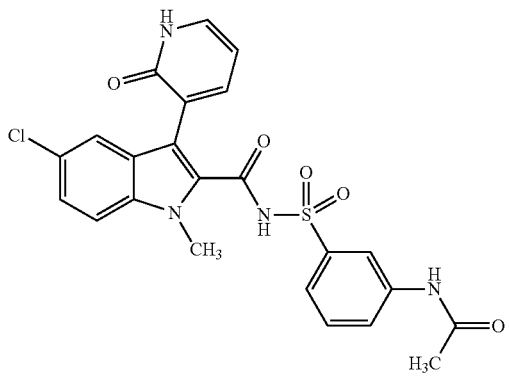 | 499.9 |
| 143 | 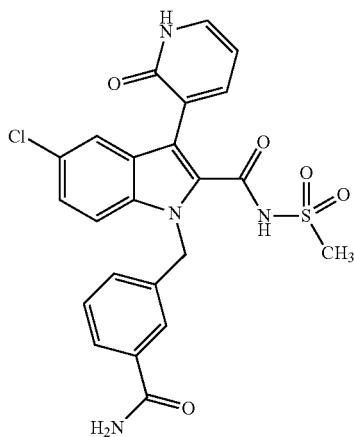 | 499.9 |
| 144 | 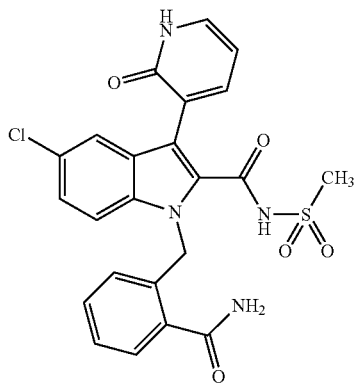 | 499.9 |

-continued
| Compound No. | STRUCTURE | M + H |
|---|---|---|
| 145 | 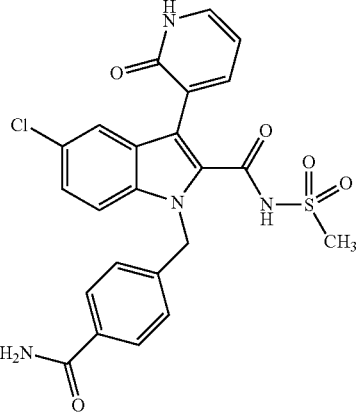 | 499.9 |
| 146 | 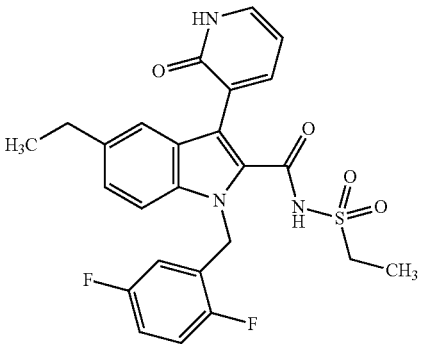 | 500.5 |
| 147 | 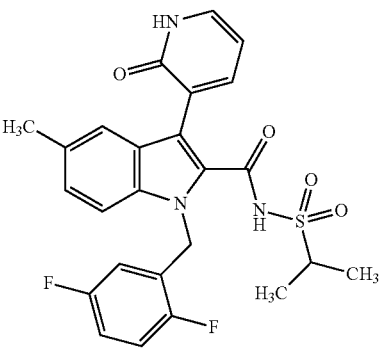 | 500.5 |
| 148 | 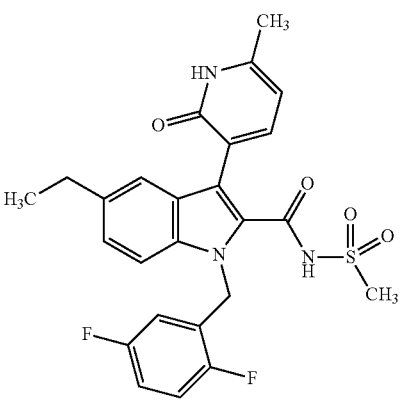 | 500.5 |

US 8,143,305 B2

-continued

| Compound No. | STRUCTURE | M + H |
|---|---|---|
| 149 | 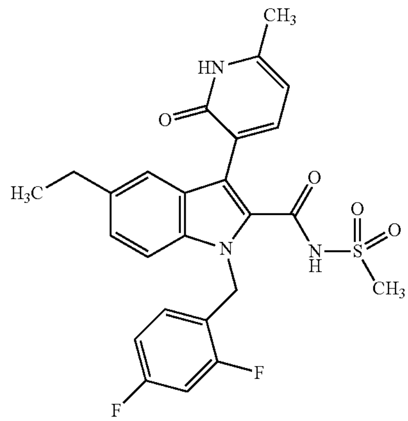 | 500.5 |
| 150 | 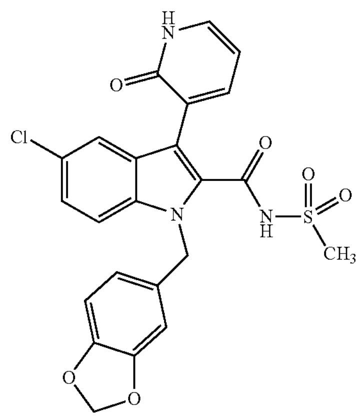 | 500.9 |
| 151 | 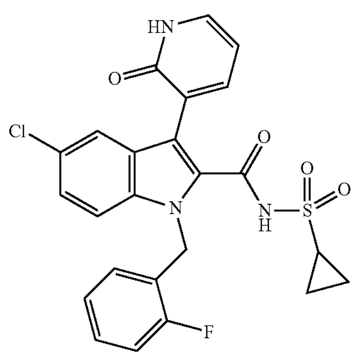 | 501.0 |
| 152 | 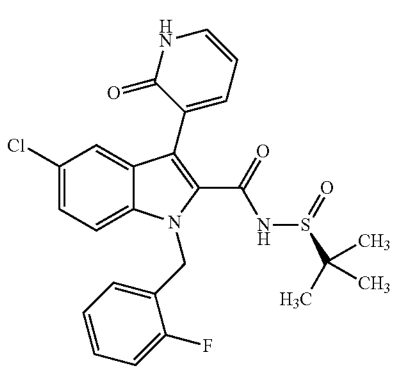 | 501.0 |

-continued
| Compound No. | STRUCTURE | M + H |
|---|---|---|
| 153 | 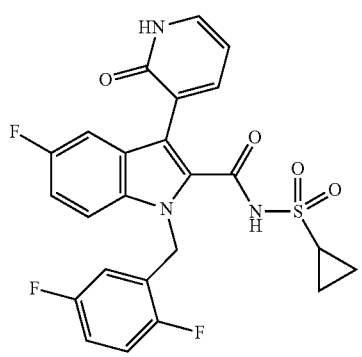 | 502.5 |
| 154 | 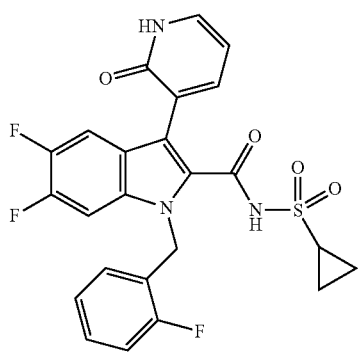 | 502.5 |
| 155 | 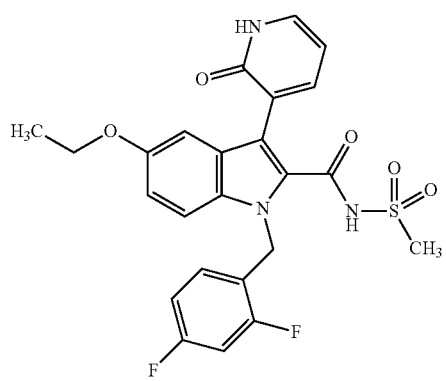 | 502.5 |
| 156 | 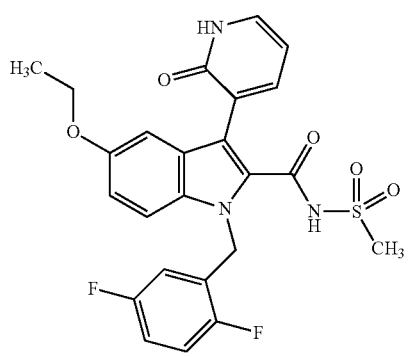 | 502.5 |

-continued
| Compound No. | STRUCTURE | M + H |
|---|---|---|
| 157 | 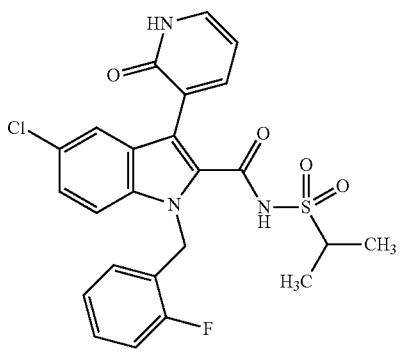 | 503.0 |
| 158 | 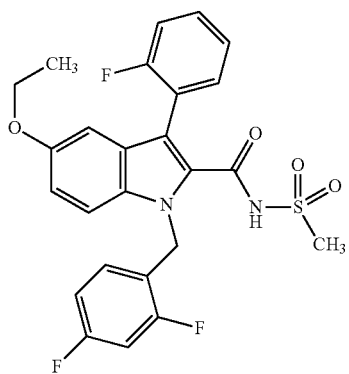 | 503.5 |
| 159 | 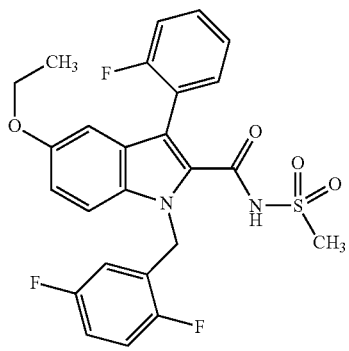 | 503.5 |
| 160 | 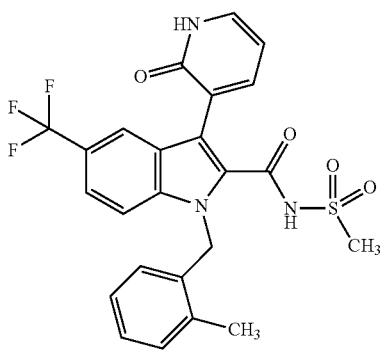 | 504.5 |

-continued

| Compound No. | STRUCTURE | M + H |
|---|---|---|
| 161 | 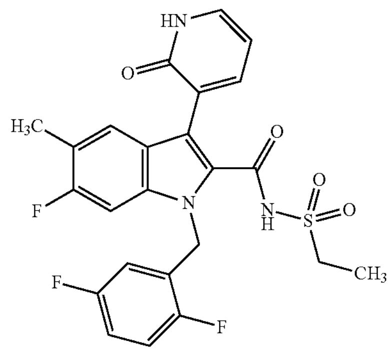 | 504.5 |
| 162 | 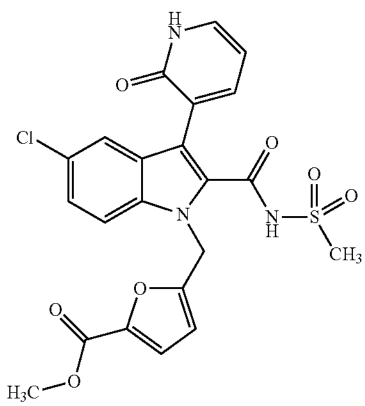 | 504.9 |
| 163 | 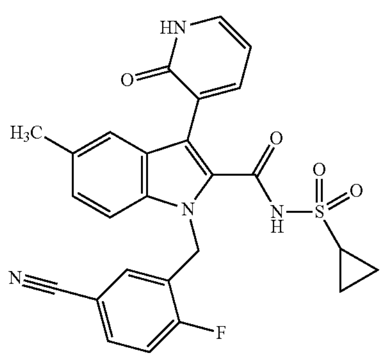 | 505.5 |
| 164 | 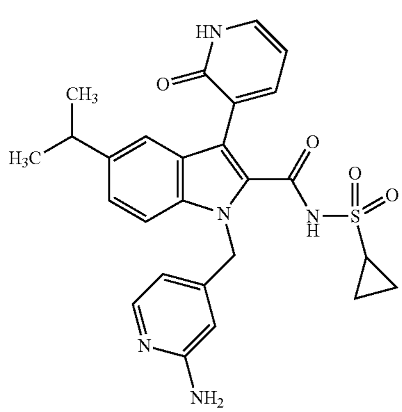 | 506.6 |

-continued

| Compound No. | STRUCTURE | M + H |
|---|---|---|
| 165 | 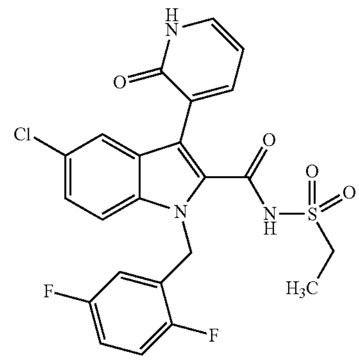 | 506.9 |
| 166 | 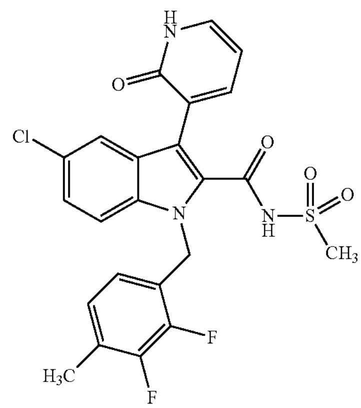 | 506.9 |
| 167 | 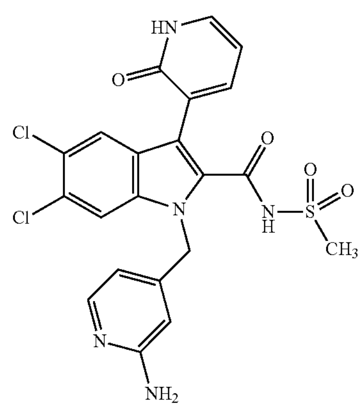 | 507.4 |
| 168 | 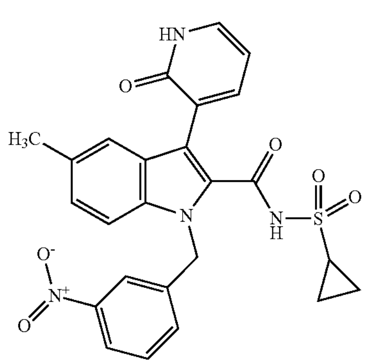 | 507.5 |

-continued

| Compound No. | STRUCTURE | M + H |
|---|---|---|
| 169 | 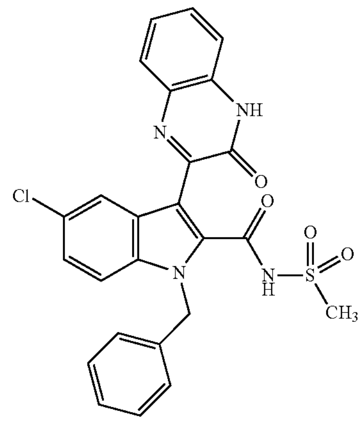 | 508.0 |
| 170 | 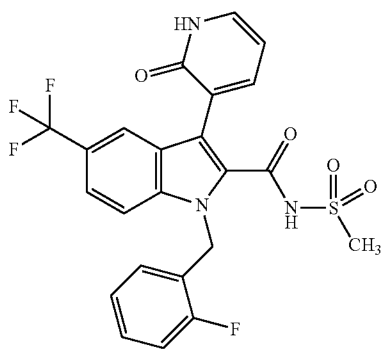 | 508.5 |
| 171 | 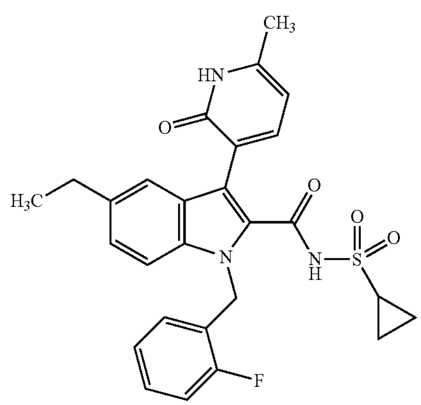 | 508.6 |
| 172 | 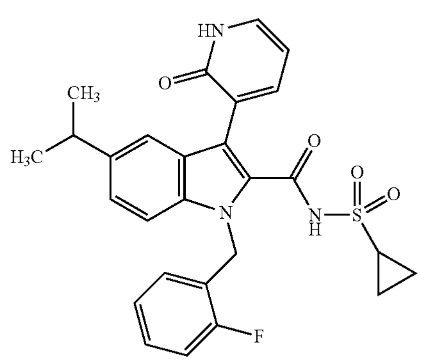 | 508.6 |

| Compound No. | STRUCTURE | M + H |
|---|---|---|
| 173 | 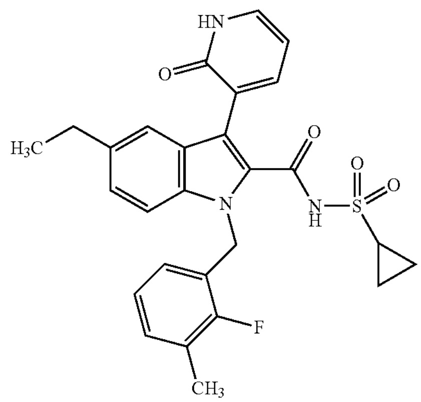 | 508.6 |
| 174 | 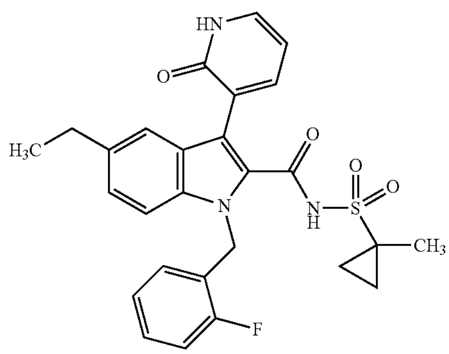 | 508.6 |
| 175 | 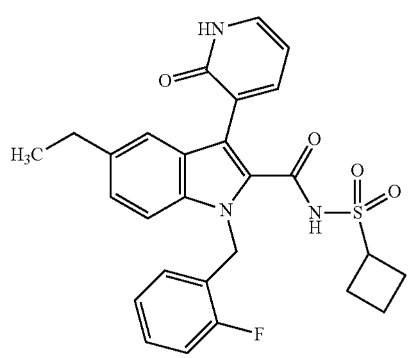 | 508.6 |
| 176 | 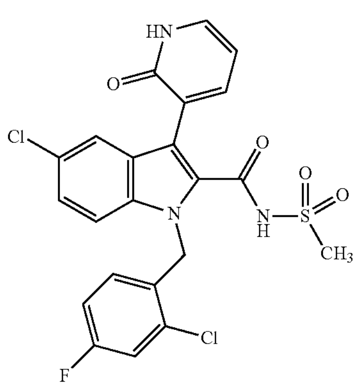 | 509.4 |

| Compound No. | STRUCTURE | M + H |
|---|---|---|
| 177 | 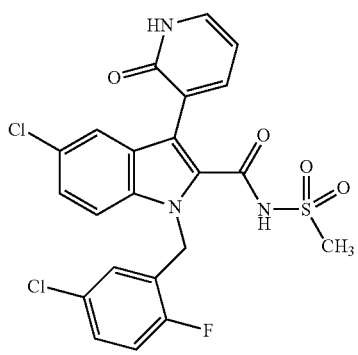 | 509.4 |
| 178 | 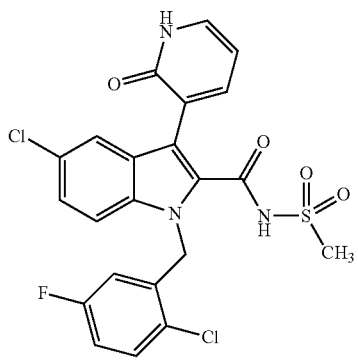 | 509.4 |
| 179 | 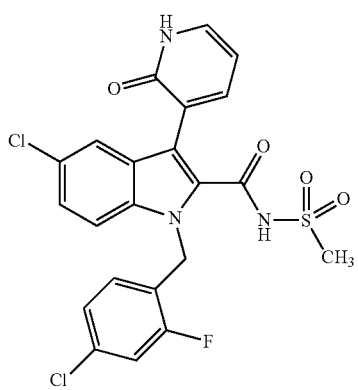 | 509.4 |
| 180 | 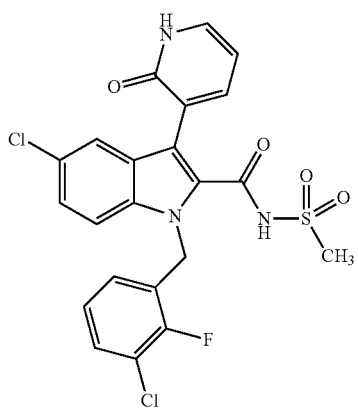 | 509.4 |

-continued

| Compound No. | STRUCTURE | M + H |
|---|---|---|
| 181 | 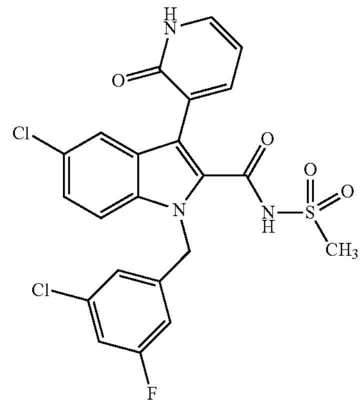 | 509.4 |
| 182 | 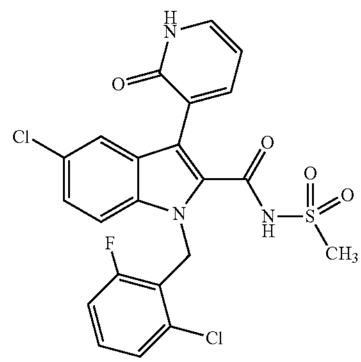 | 509.4 |
| 183 | 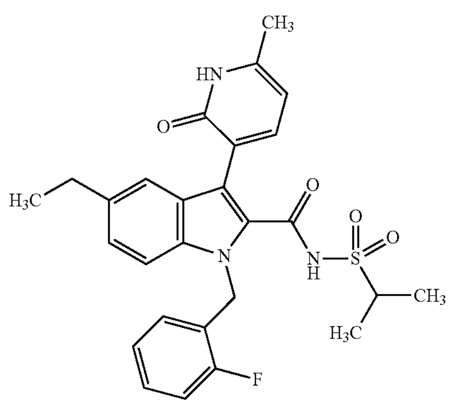 | 510.6 |
| 184 | 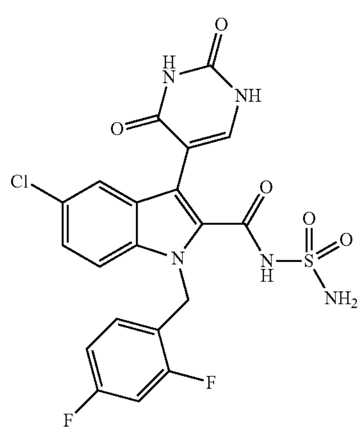 | 510.9 |

-continued

| Compound No. | STRUCTURE | M + H |
|---|---|---|
| 185 | 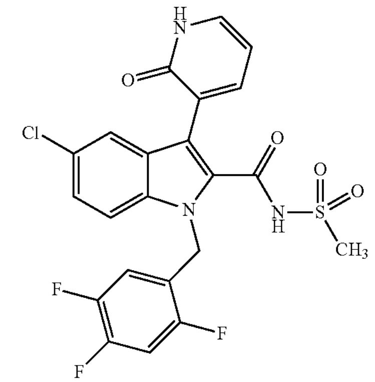 | 510.9 |
| 186 | 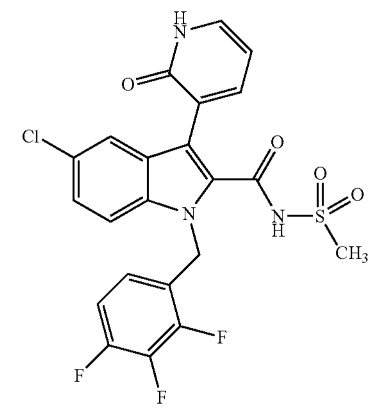 | 510.9 |
| 187 | 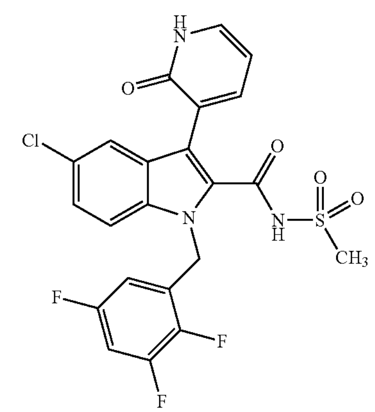 | 510.9 |
| 188 | 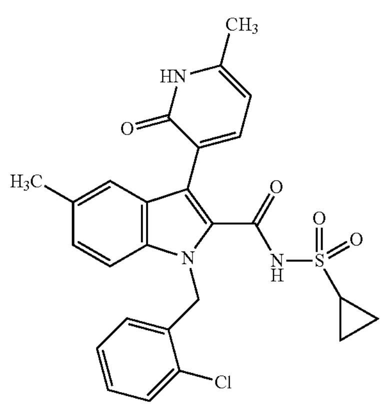 | 511.0 |

-continued

| Compound No. | STRUCTURE | M + H |
|---|---|---|
| 189 | 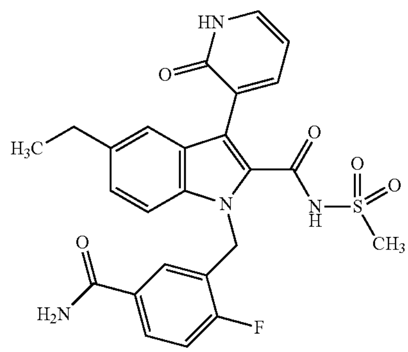 | 511.5 |
| 190 | 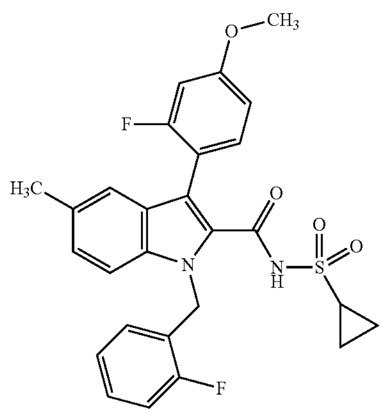 | 511.6 |
| 191 | 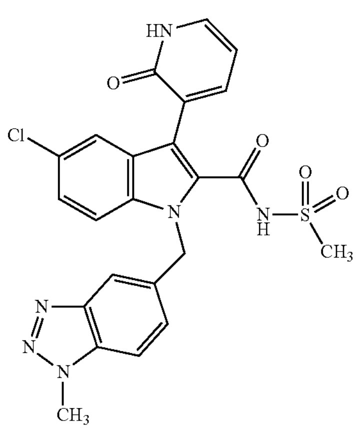 | 512.0 |

-continued
| Compound No. | STRUCTURE | M + H |
|---|---|---|
| 192 | 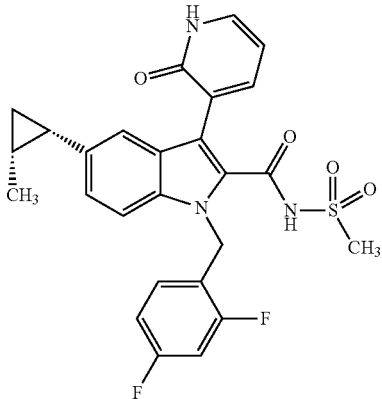 | 512.6 |
| 193 | 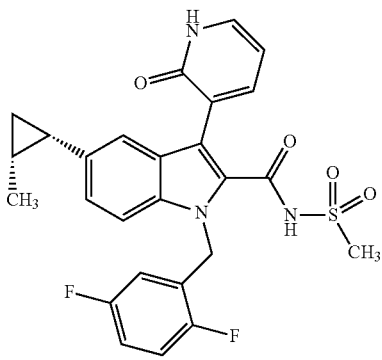 | 512.6 |
| 194 | 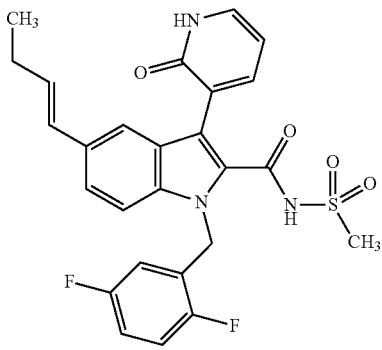 | 512.6 |
| 195 | 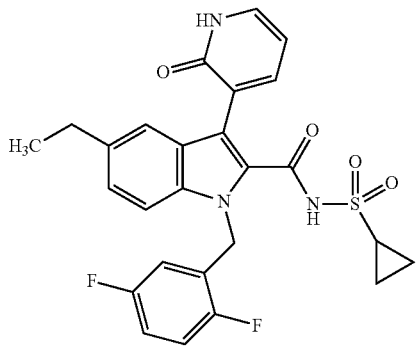 | 512.6 |

-continued

| Compound No. | STRUCTURE | M + H |
|---|---|---|
| 196 | 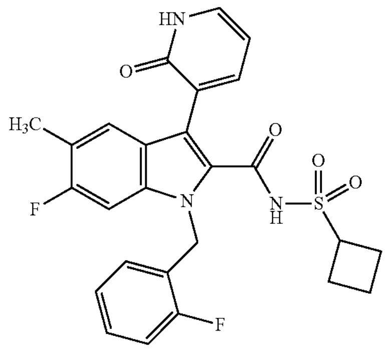 | 512.6 |
| 197 | 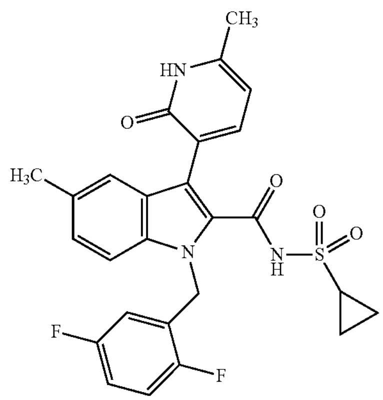 | 512.6 |
| 198 | 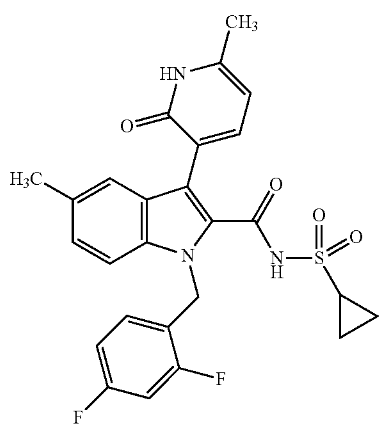 | 512.6 |
| 199 | 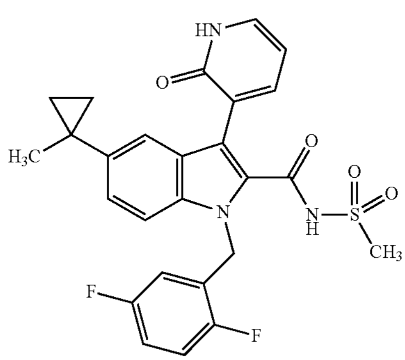 | 512.6 |

-continued
| Compound No. | STRUCTURE | M + H |
|---|---|---|
| 200 | 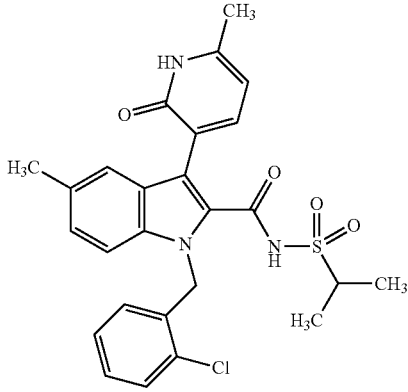 | 513.0 |
| 201 | 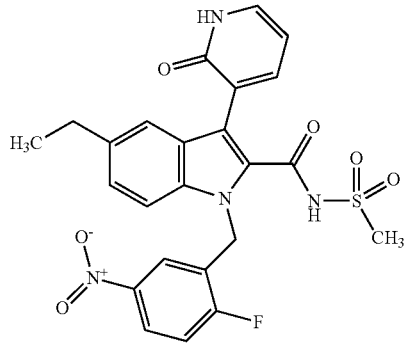 | 513.5 |
| 202 | 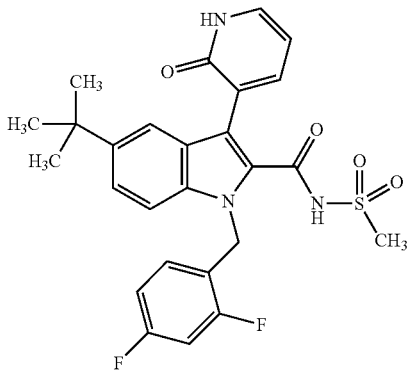 | 514.6 |
| 203 | 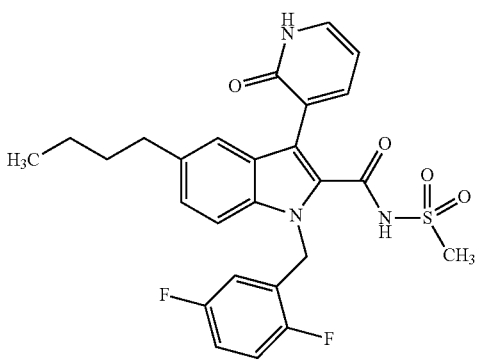 | 514.6 |

-continued
| Compound No. | STRUCTURE | M + H |
|---|---|---|
| 204 | 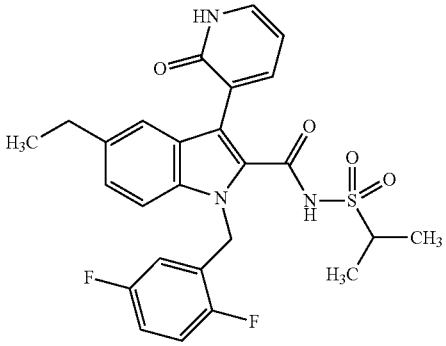 | 514.6 |
| 205 | 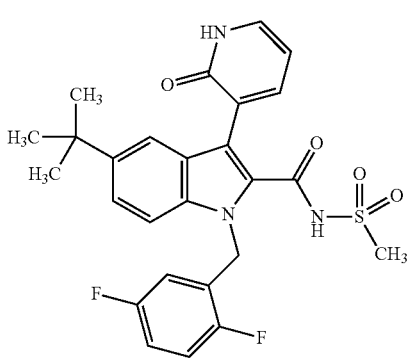 | 514.6 |
| 206 | 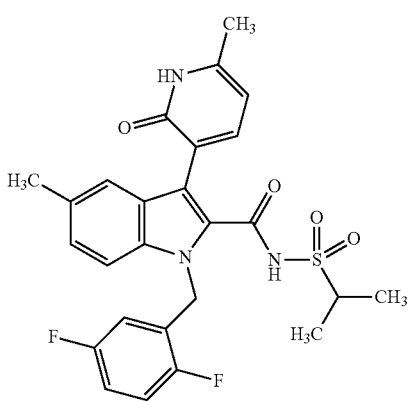 | 514.6 |
| 207 | 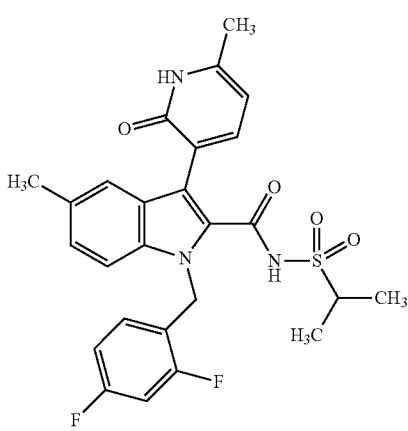 | 514.6 |

-continued
| Compound No. | STRUCTURE | M + H |
|---|---|---|
| 208 | 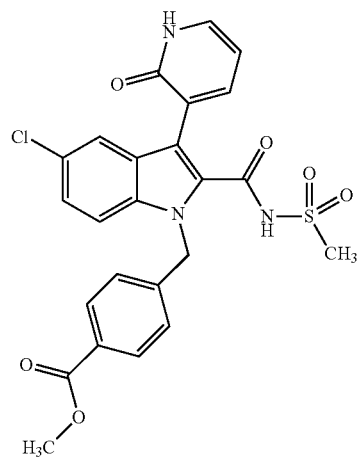 | 515.0 |
| 209 | 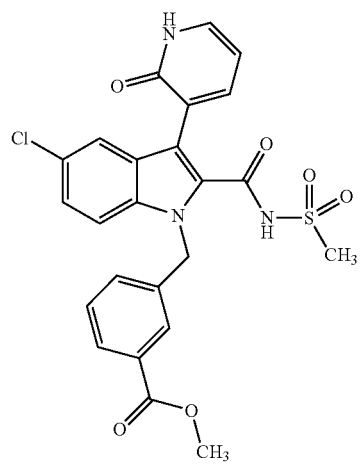 | 515.0 |
| 210 | 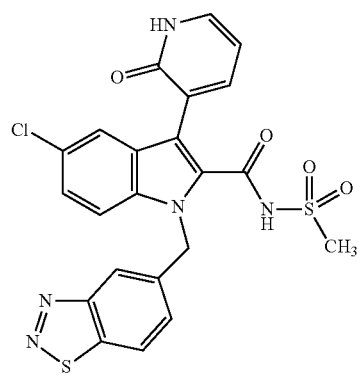 | 515.0 |

-continued

| Compound No. | STRUCTURE | M + H |
|---|---|---|
| 211 | 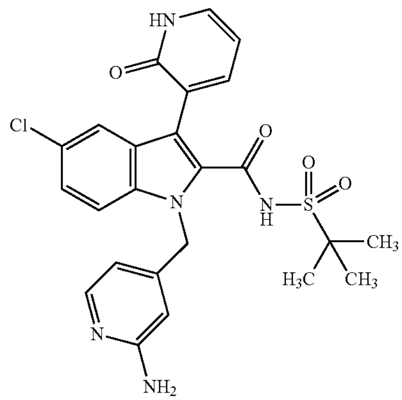 | 515.0 |
| 212 | 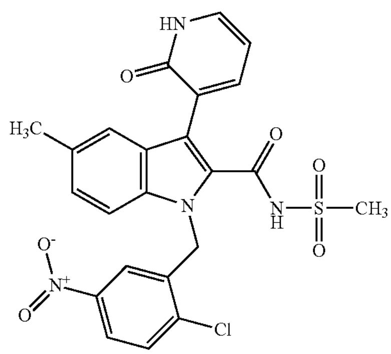 | 515.9 |
| 213 | 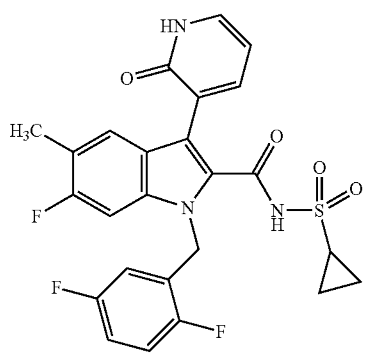 | 516.5 |
| 214 | 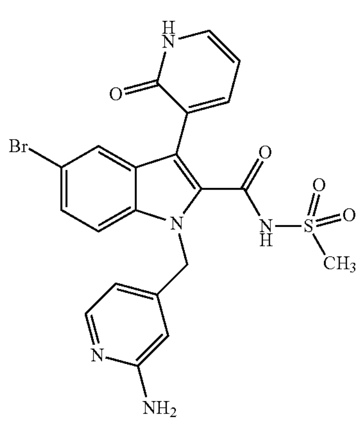 | 517.4 |

-continued

| Compound No. | STRUCTURE | M + H |
|---|---|---|
| 215 | 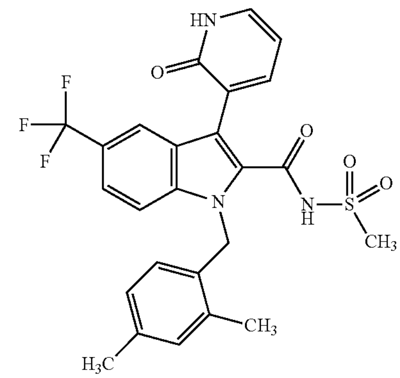 | 518.5 |
| 216 | 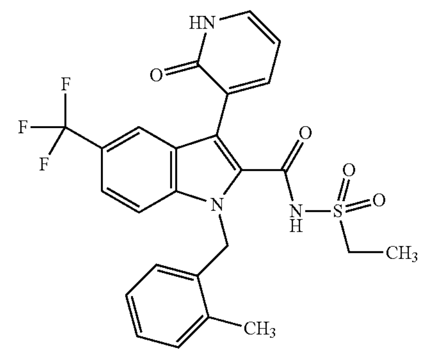 | 518.5 |
| 217 | 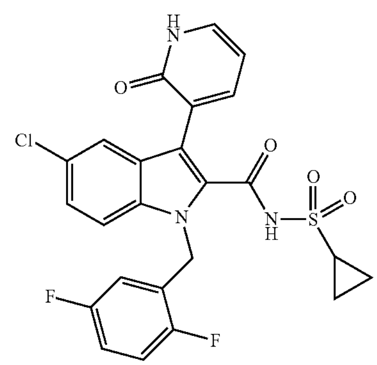 | 518.9 |
| 218 | 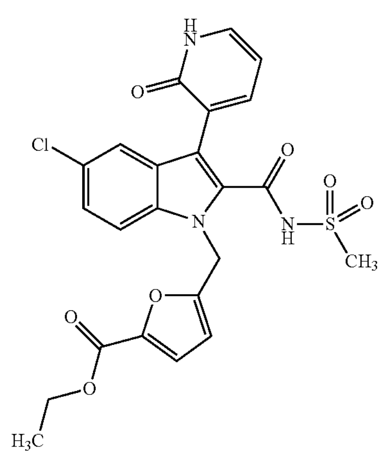 | 518.9 |

-continued

| Compound No. | STRUCTURE | M + H |
|---|---|---|
| 219 | 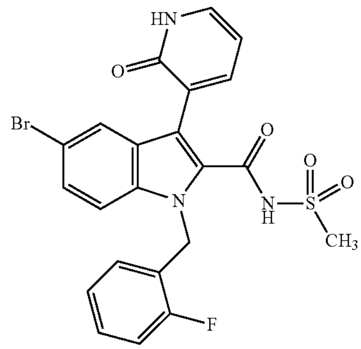 | 519.4 |
| 220 | 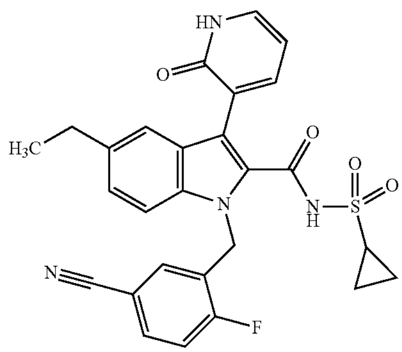 | 519.6 |
| 221 | 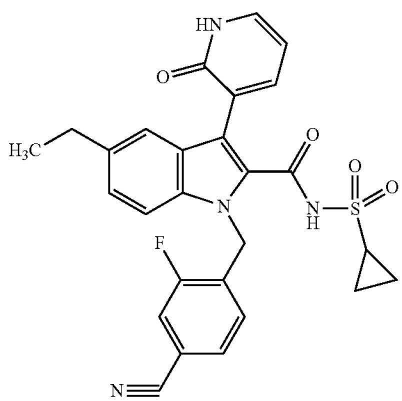 | 519.6 |
| 222 | 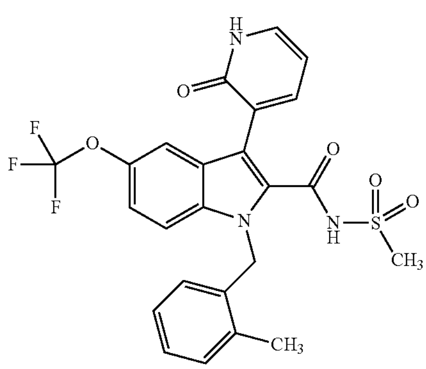 | 520.5 |

-continued
| Compound No. | STRUCTURE | M + H |
|---|---|---|
| 223 | 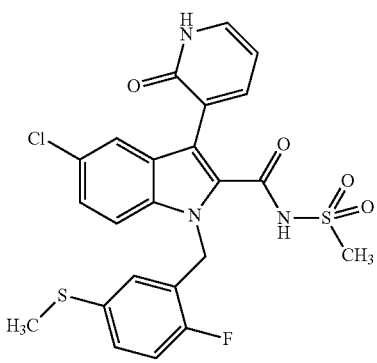 | 521.0 |
| 224 | 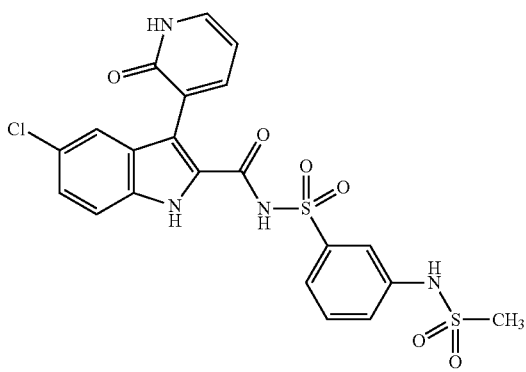 | 522.0 |
| 225 | 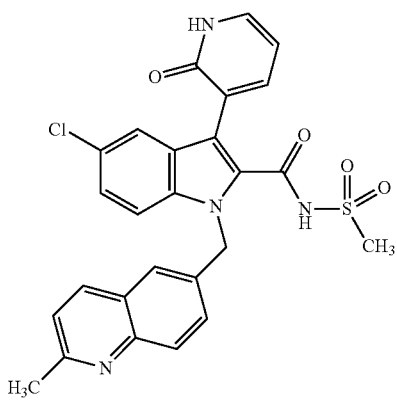 | 522.0 |
| 226 | 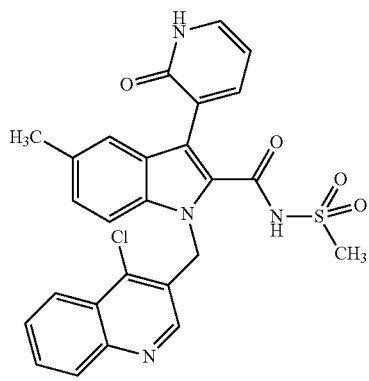 | 522.0 |

-continued
| Compound No. | STRUCTURE | M + H |
|---|---|---|
| 227 | 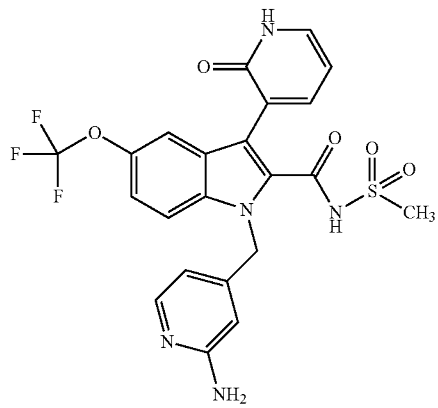 | 522.5 |
| 228 | 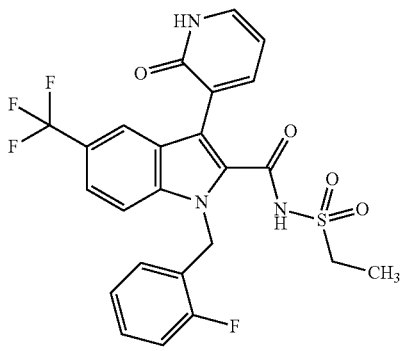 | 522.5 |
| 229 | 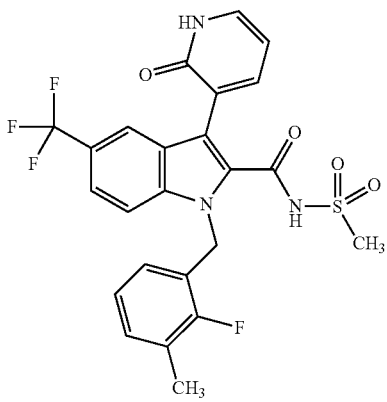 | 522.5 |
| 230 | 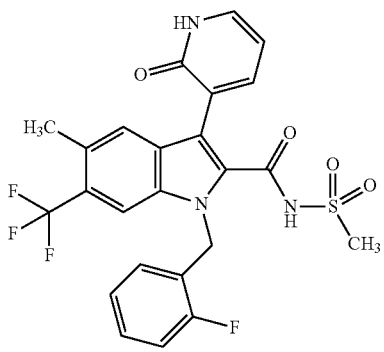 | 522.5 |

-continued

| Compound No. | STRUCTURE | M + H |
|---|---|---|
| 231 | 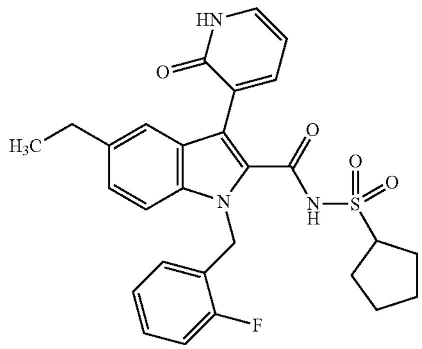 | 522.6 |
| 232 | 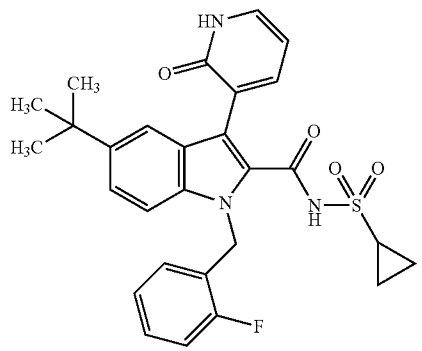 | 522.6 |
| 233 | 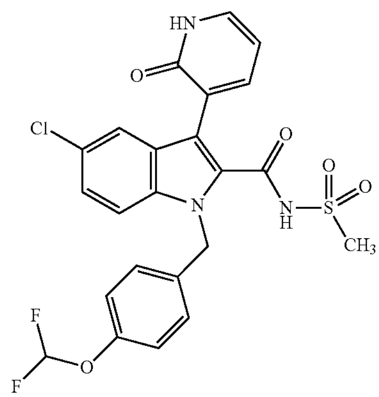 | 522.9 |
| 234 | 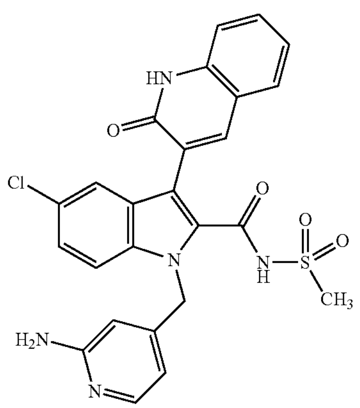 | 523.0 |

| Compound No. | STRUCTURE | M + H |
|---|---|---|
| 235 | 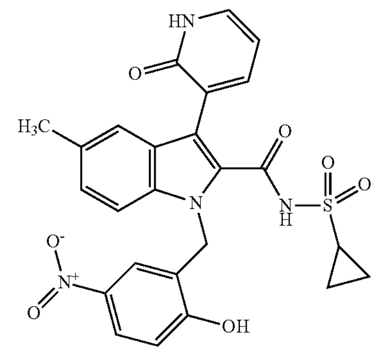 | 523.5 |
| 236 | 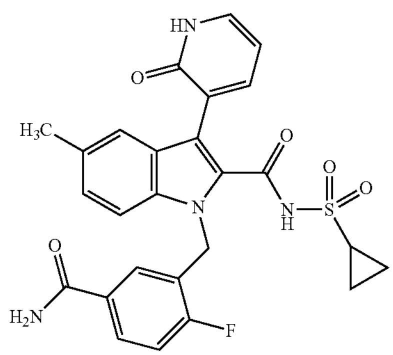 | 523.6 |
| 237 | 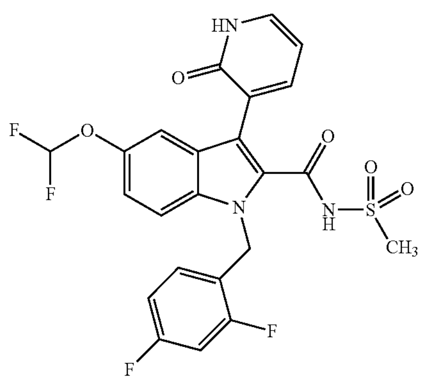 | 524.5 |
| 238 | 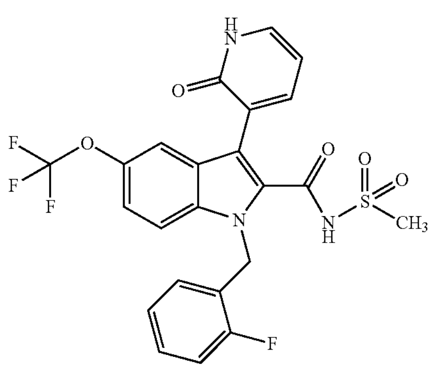 | 524.5 |

-continued

| Compound No. | STRUCTURE | M + H |
|---|---|---|
| 239 | 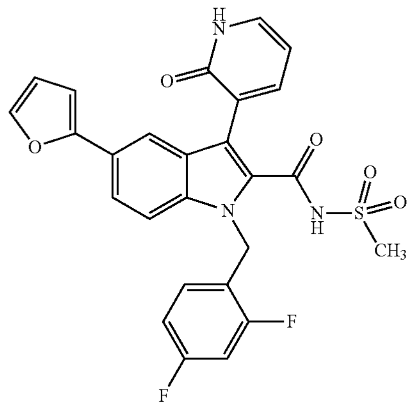 | 524.5 |
| 240 | 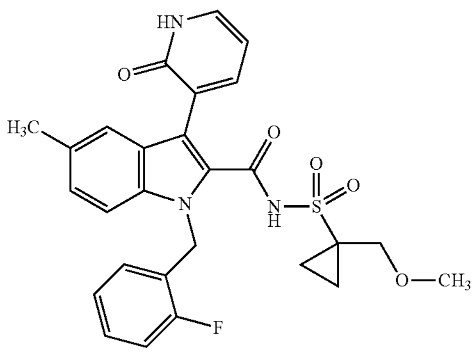 | 524.6 |
| 241 | 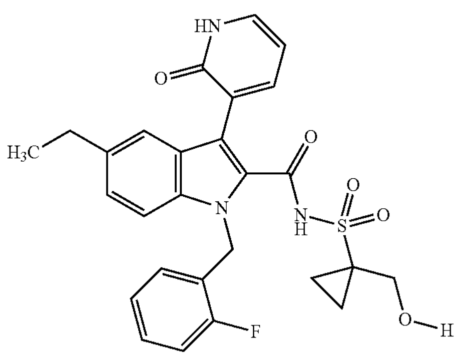 | 524.6 |
| 242 | 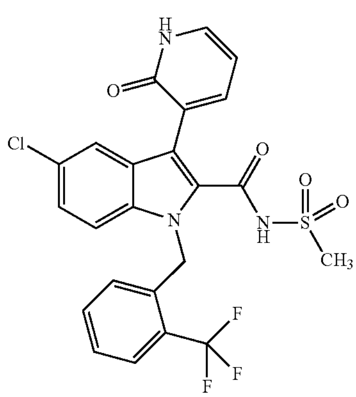 | 524.9 |

| Compound No. | STRUCTURE | M + H |
|---|---|---|
| 243 | 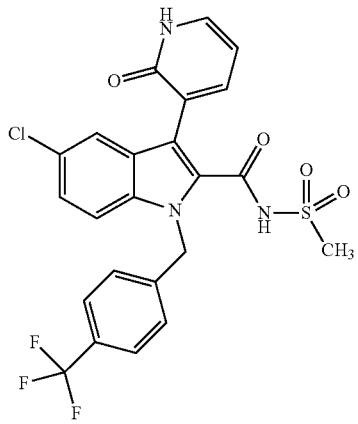 | 524.9 |
| 244 | 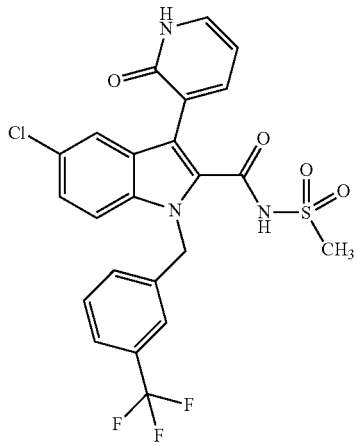 | 524.9 |
| 245 | 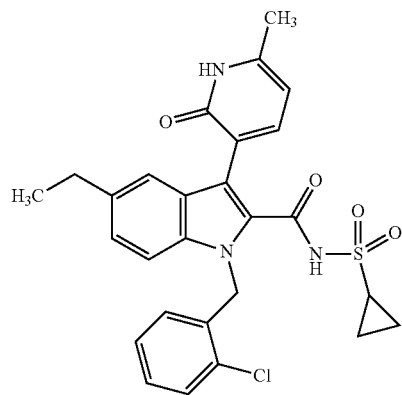 | 525.0 |

| Compound No. | STRUCTURE | M + H |
|---|---|---|
| 246 | 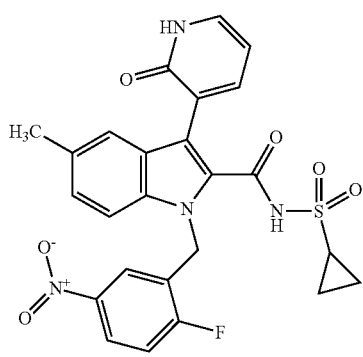 | 525.5 |
| 247 | 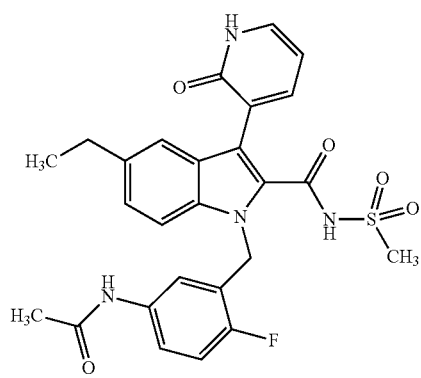 | 525.6 |
| 248 | 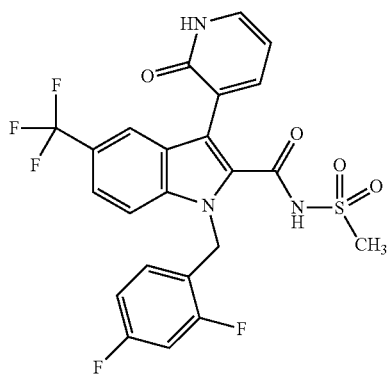 | 526.5 |
| 249 | 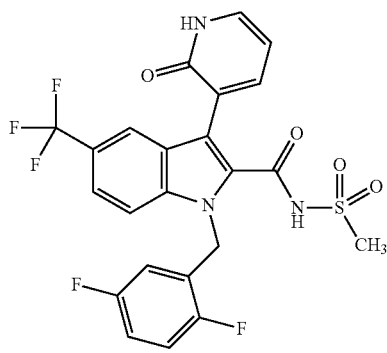 | 526.5 |

-continued

| Compound No. | STRUCTURE | M + H |
|---|---|---|
| 250 | 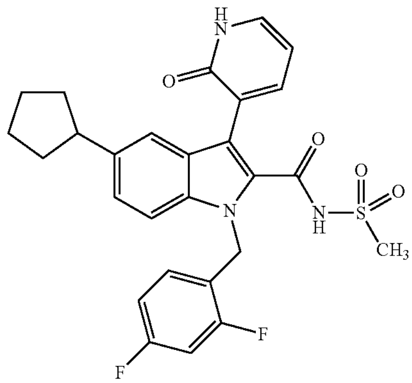 | 526.6 |
| 251 | 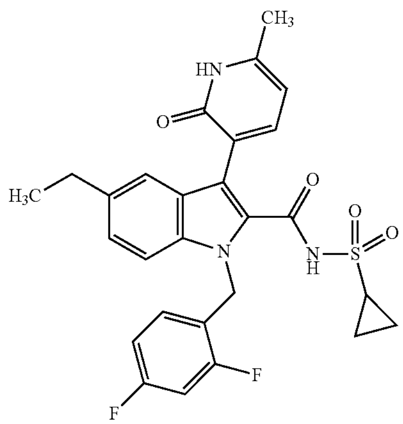 | 526.6 |
| 252 | 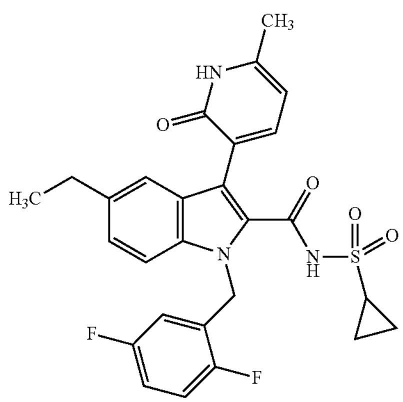 | 526.6 |
| 253 | 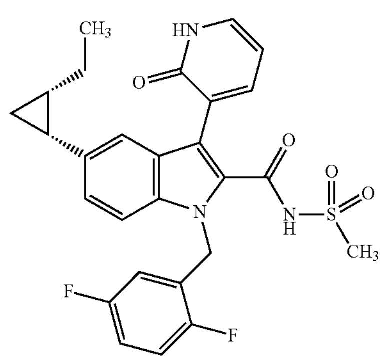 | 526.6 |

-continued

| Compound No. | STRUCTURE | M + H |
|---|---|---|
| 254 | 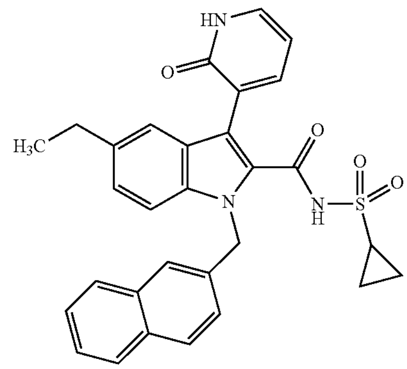 | 526.6 |
| 255 | 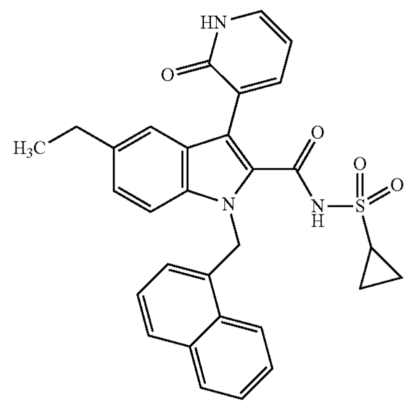 | 526.6 |
| 256 | 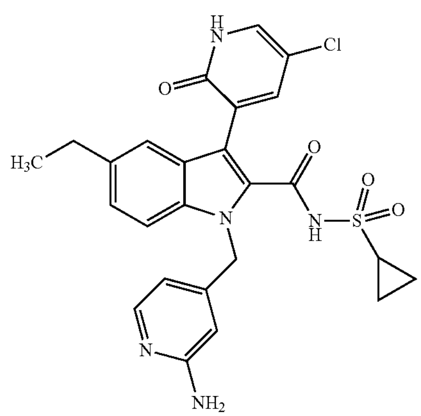 | 527.0 |
| 257 | 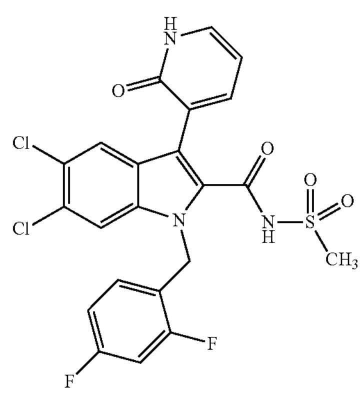 | 527.3 |

| Compound No. | STRUCTURE | M + H |
|---|---|---|
| 258 | 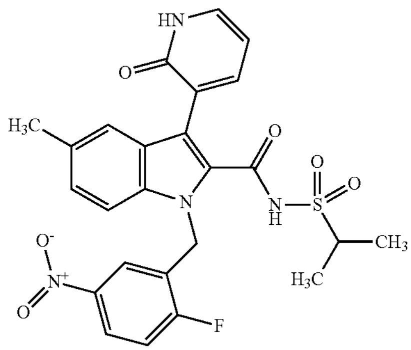 | 527.5 |
| 259 | 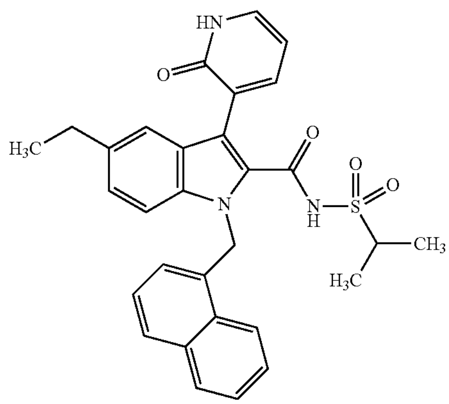 | 528.6 |
| 260 | 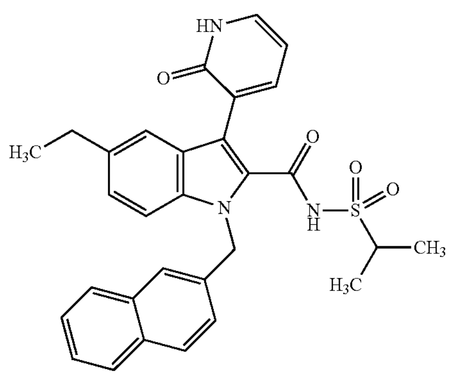 | 528.6 |
| 261 | 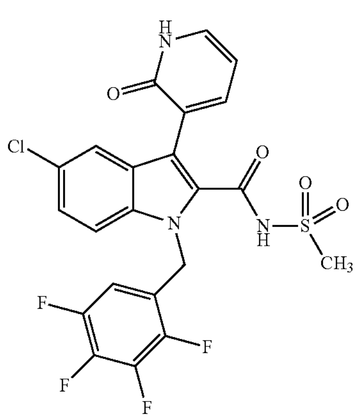 | 528.9 |

-continued
| Compound No. | STRUCTURE | M + H |
|---|---|---|
| 262 | 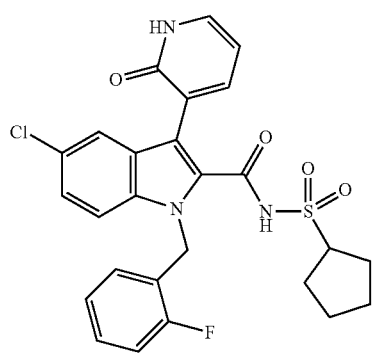 | 529.0 |
| 263 | 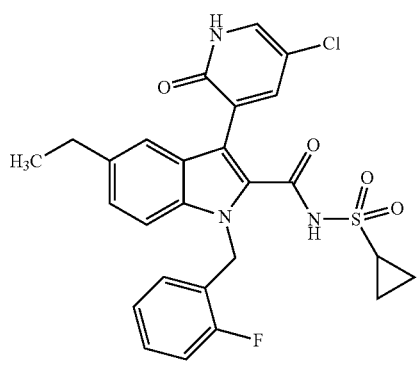 | 529.0 |
| 264 | 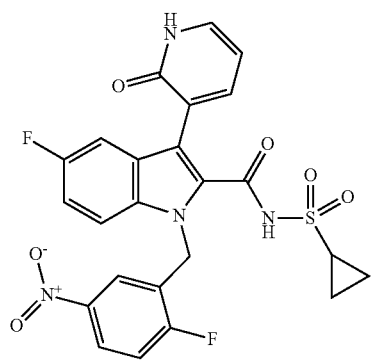 | 529.5 |
| 265 | 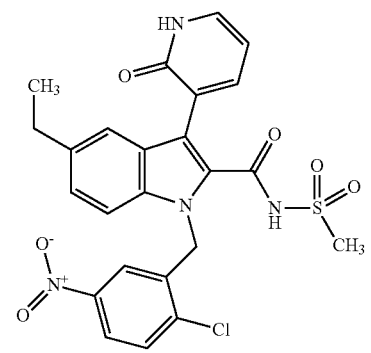 | 530.0 |

| Compound No. | STRUCTURE | M + H |
|---|---|---|
| 266 | 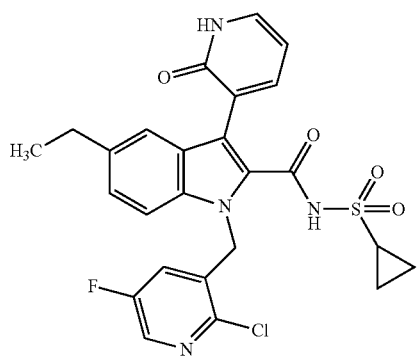 | 530.0 |
| 267 | 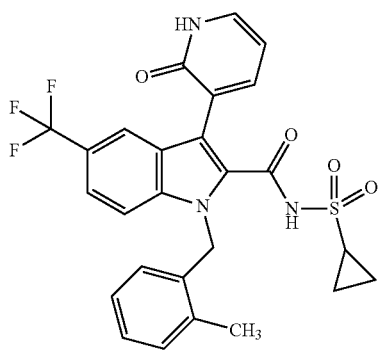 | 530.5 |
| 268 | 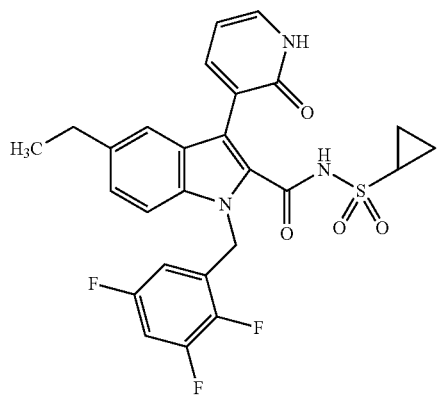 | 530.5 |
| 269 | 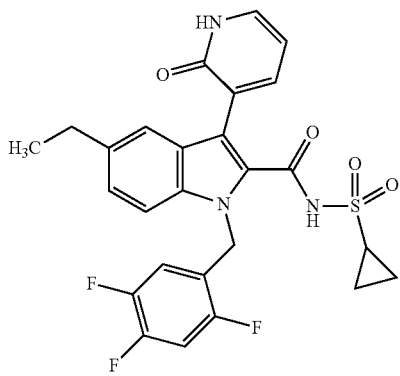 | 530.5 |

-continued
| Compound No. | STRUCTURE | M + H |
|---|---|---|
| 270 | 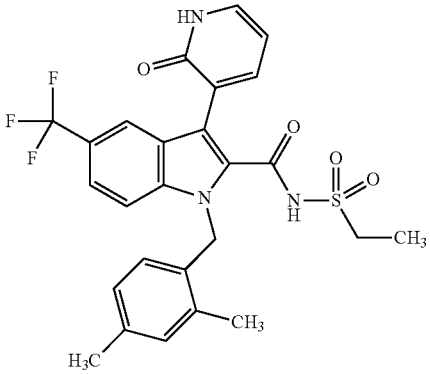 | 532.6 |
| 271 | 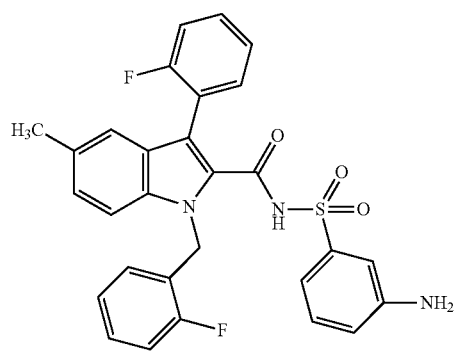 | 532.6 |
| 272 | 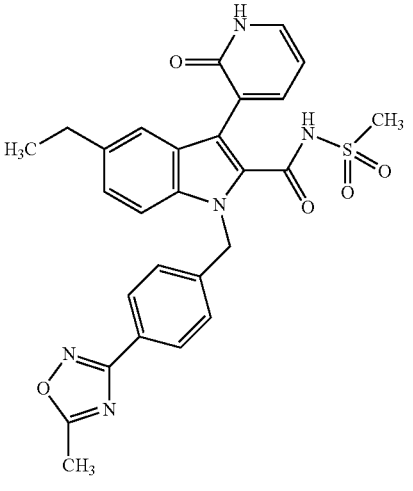 | 532.6 |
| 273 | 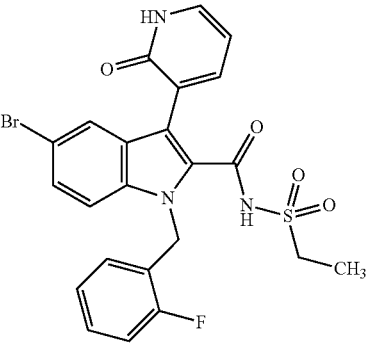 | 533.4 |

| Compound No. | STRUCTURE | M + H |
|---|---|---|
| 274 | 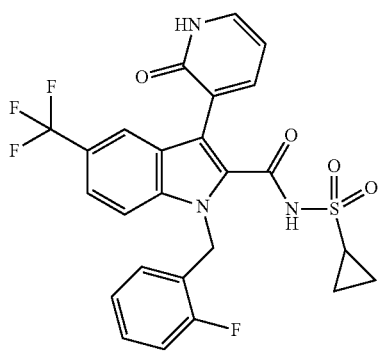 | 534.5 |
| 275 | 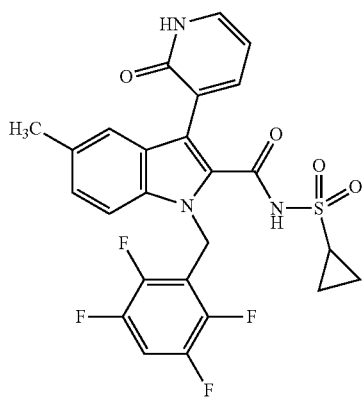 | 534.5 |
| 276 | 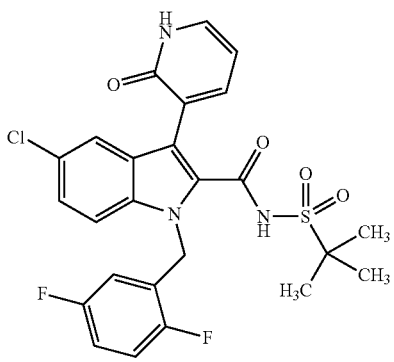 | 535.0 |
| 277 | 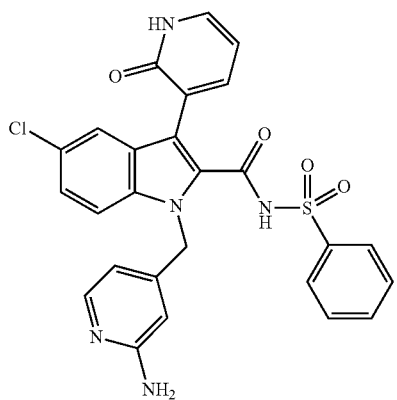 | 535.0 |

| Compound No. | STRUCTURE | M + H |
|---|---|---|
| 278 | 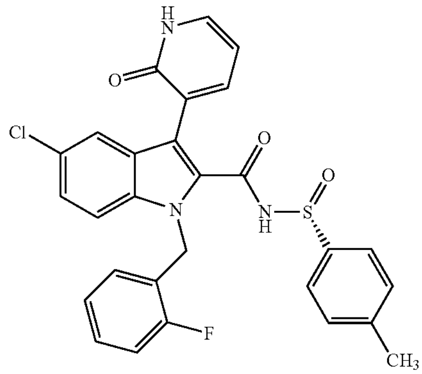 | 535.0 |
| 279 | 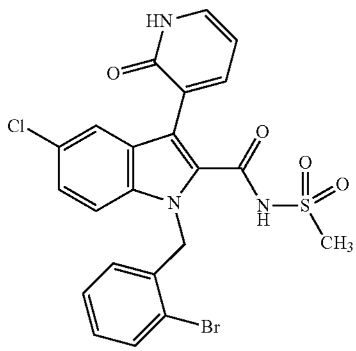 | 535.8 |
| 280 | 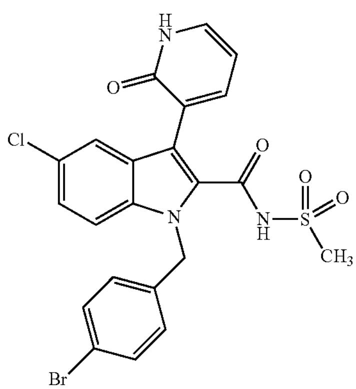 | 535.8 |
| 281 | 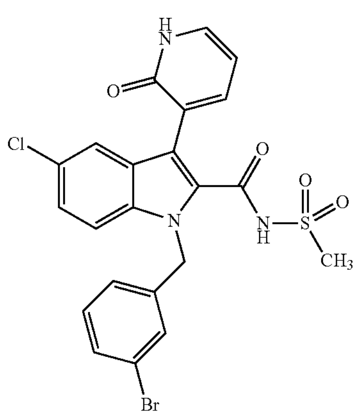 | 535.8 |

-continued

| Compound No. | STRUCTURE | M + H |
|---|---|---|
| 282 | 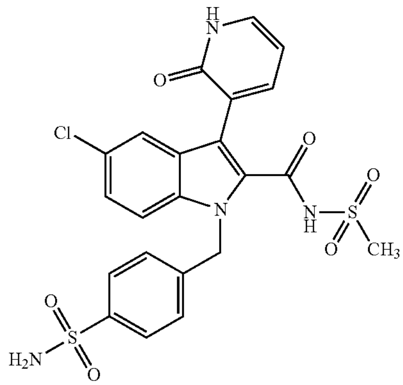 | 536.0 |
| 283 | 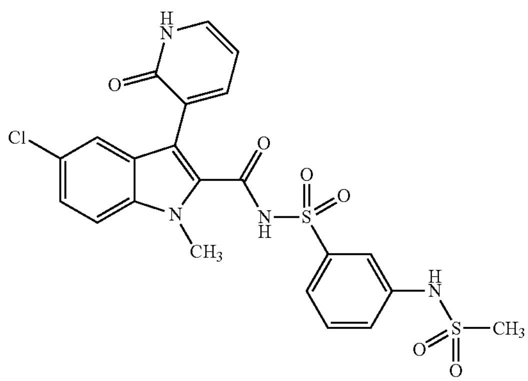 | 536.0 |
| 284 | 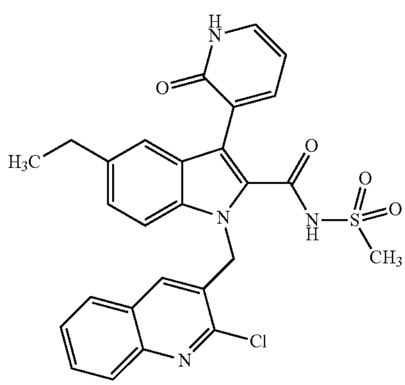 | 536.0 |
| 285 | 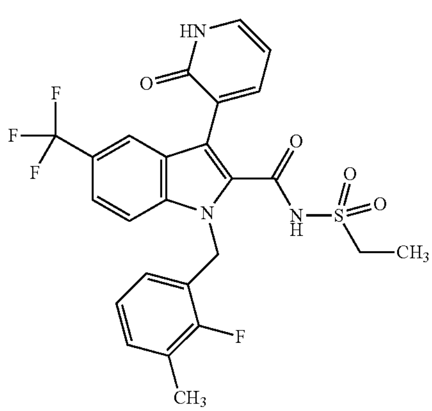 | 536.5 |

| Compound No. | STRUCTURE | M + H |
|---|---|---|
| 286 | 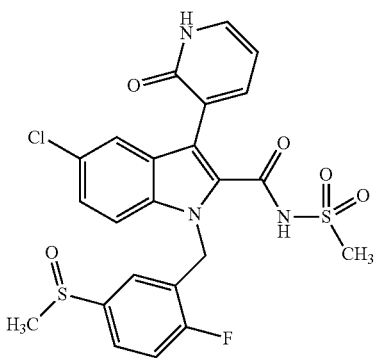 | 537.0 |
| 287 | 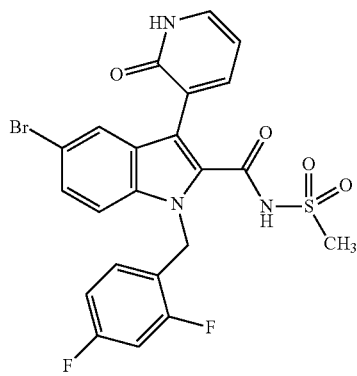 | 537.4 |
| 288 | 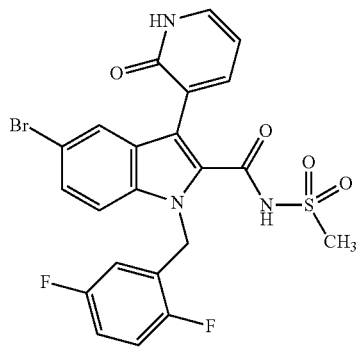 | 537.4 |
| 289 | 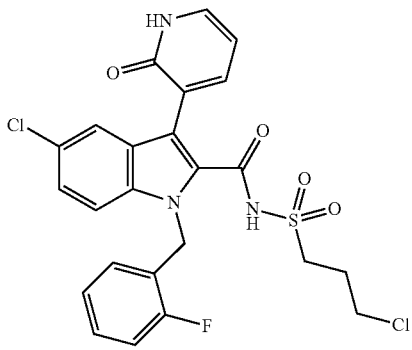 | 537.4 |

-continued
| Compound No. | STRUCTURE | M + H |
|---|---|---|
| 290 | 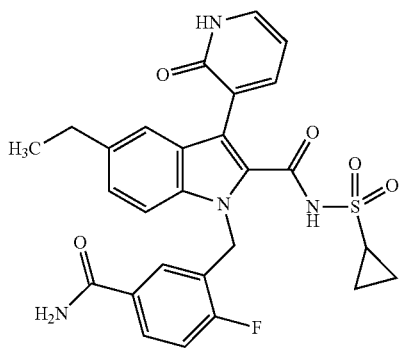 | 537.6 |
| 291 | 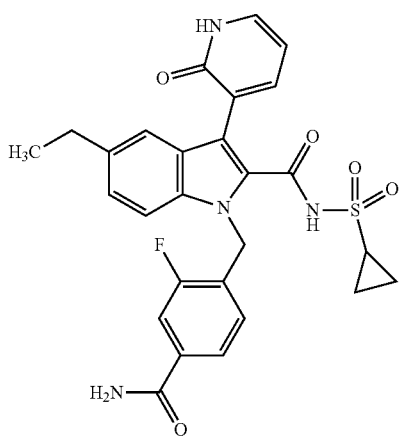 | 537.6 |
| 292 | 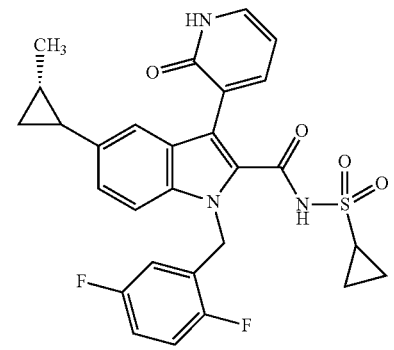 | 538.6 |
| 293 | 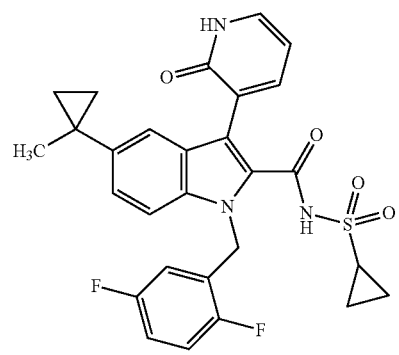 | 538.6 |

-continued
| Compound No. | STRUCTURE | M + H |
|---|---|---|
| 294 | 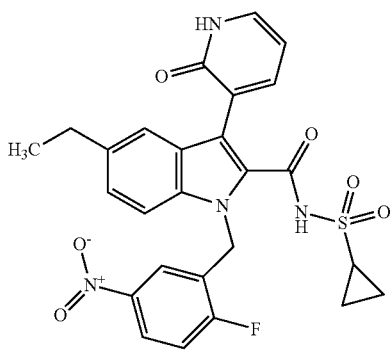 | 539.6 |
| 295 | 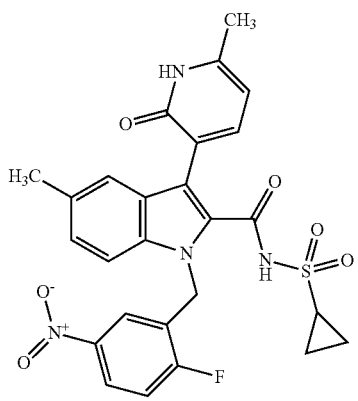 | 539.6 |
| 296 | 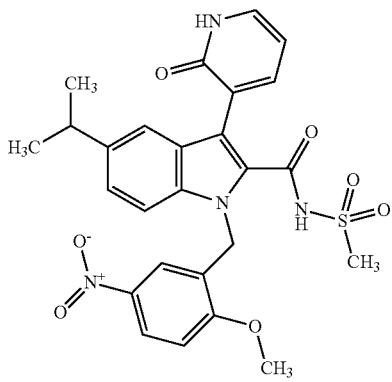 | 539.6 |
| 297 | 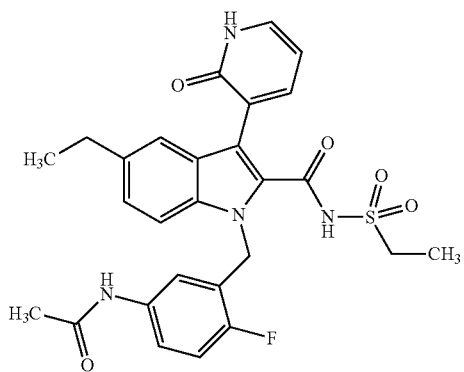 | 539.6 |

-continued

| Compound No. | STRUCTURE | M + H |
|---|---|---|
| 298 | 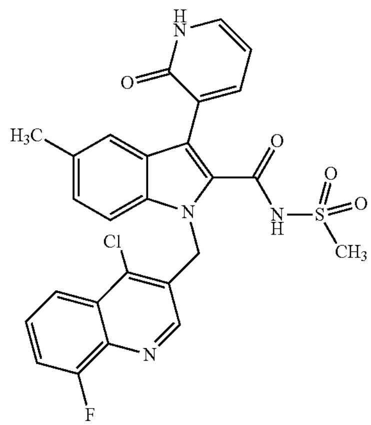 | 540.0 |
| 299 | 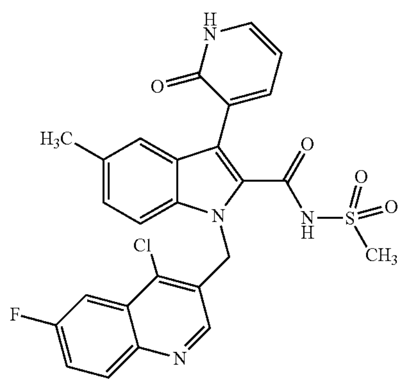 | 540.0 |
| 300 | 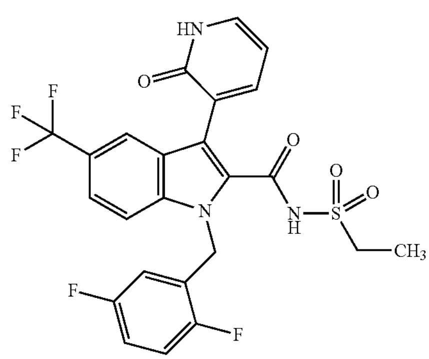 | 540.5 |
| 301 | 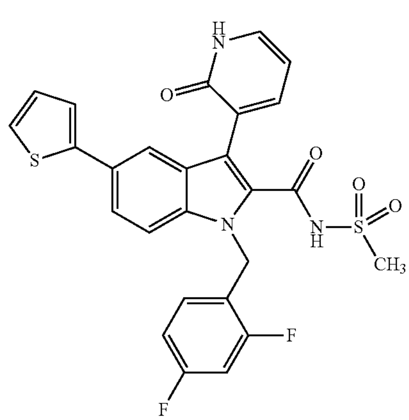 | 540.6 |

| Compound No. | STRUCTURE | M + H |
|---|---|---|
| 302 | 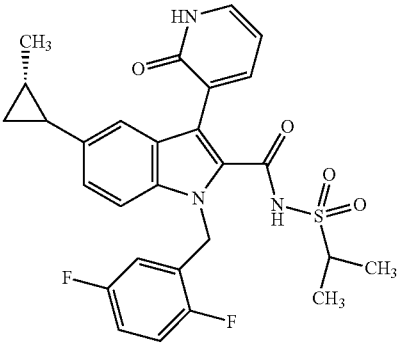 | 540.6 |
| 303 | 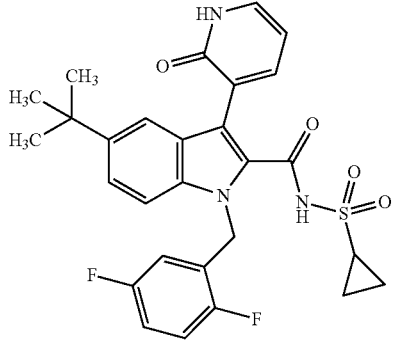 | 540.6 |
| 304 | 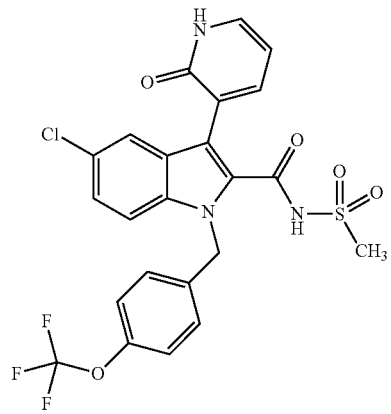 | 540.9 |
| 305 | 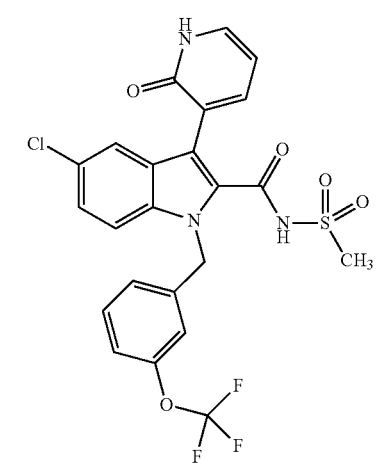 | 540.9 |

-continued
| Compound No. | STRUCTURE | M + H |
|---|---|---|
| 306 | 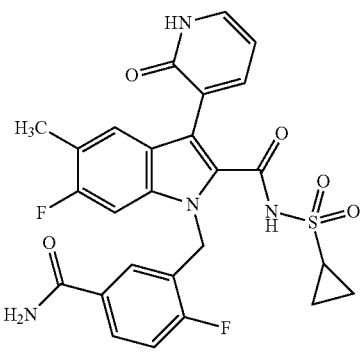 | 541.5 |
| 307 | 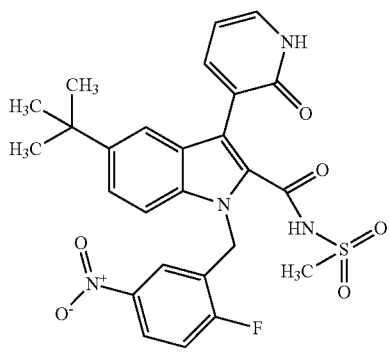 | 541.6 |
| 308 | 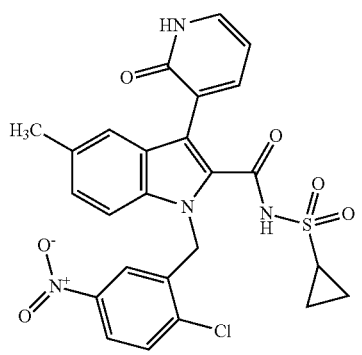 | 542.0 |
| 309 | 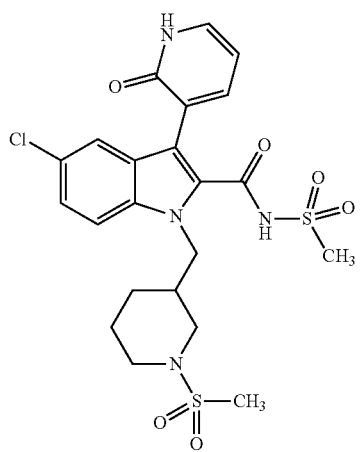 | 542.0 |

-continued

| Compound No. | STRUCTURE | M + H |
|---|---|---|
| 310 | 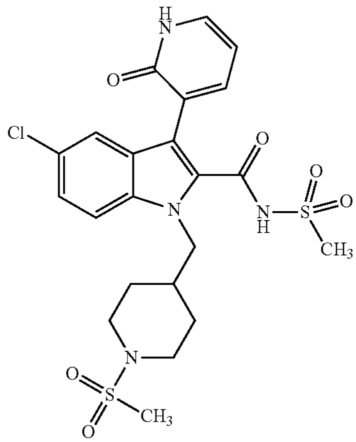 | 542.0 |
| 311 | 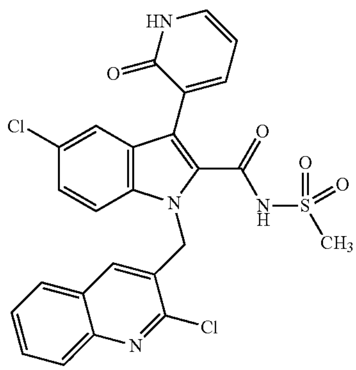 | 542.4 |
| 312 | 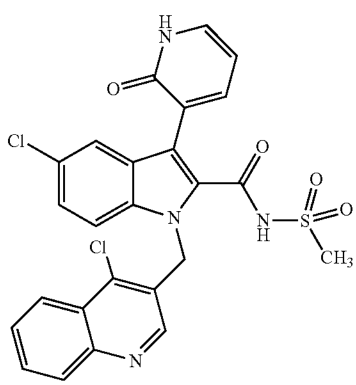 | 542.4 |
| 313 | 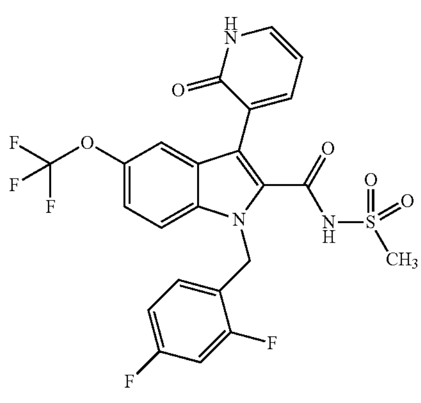 | 542.5 |

-continued

| Compound No. | STRUCTURE | M + H |
|---|---|---|
| 314 | 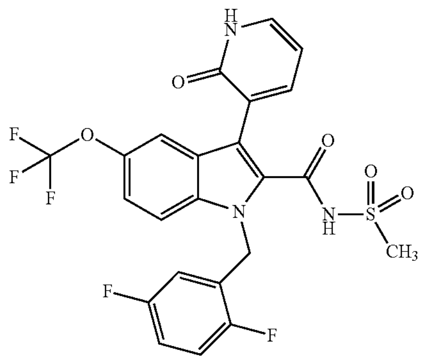 | 542.5 |
| 315 | 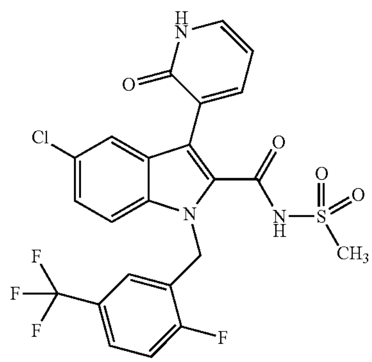 | 542.9 |
| 316 | 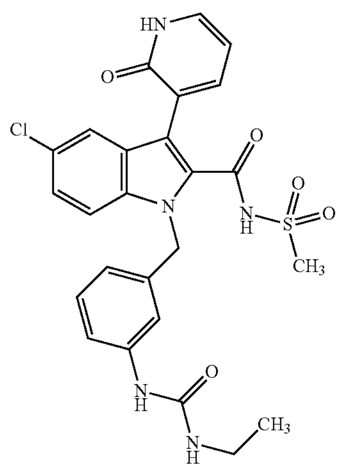 | 543.0 |
| 317 | 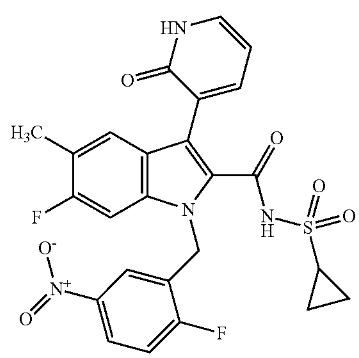 | 543.5 |

-continued
| Compound No. | STRUCTURE | M + H |
|---|---|---|
| 318 | 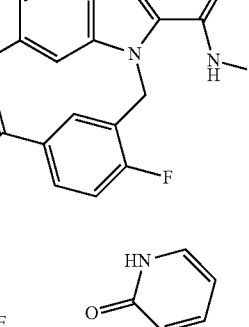 | 543.6 |
| 319 | 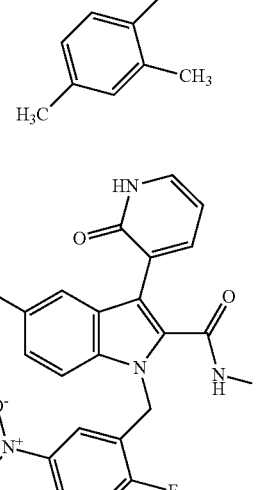 | 544.6 |
| 320 | 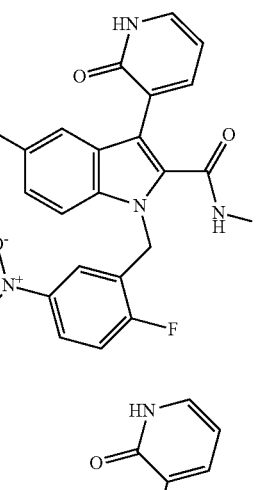 | 545.9 |
| 321 | 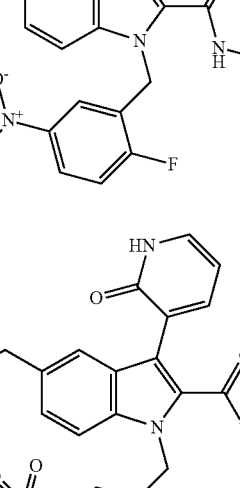 | 546.6 |

-continued
| Compound No. | STRUCTURE | M + H |
|---|---|---|
| 322 | 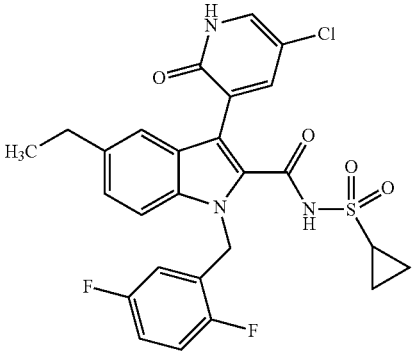 | 547.0 |
| 323 | 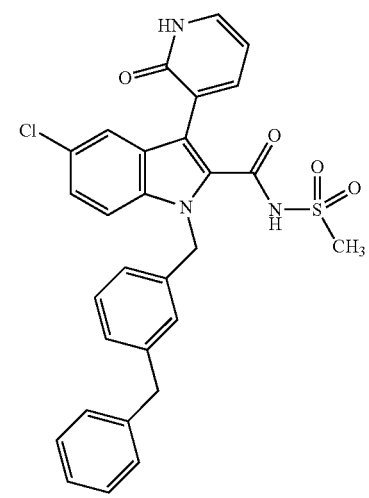 | 547.0 |
| 324 | 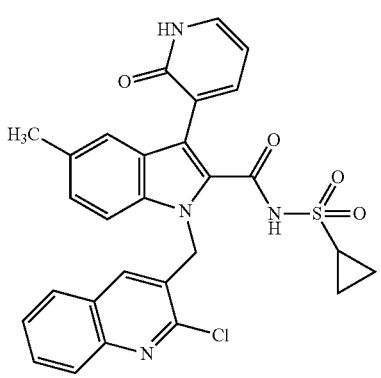 | 548.0 |
| 325 | 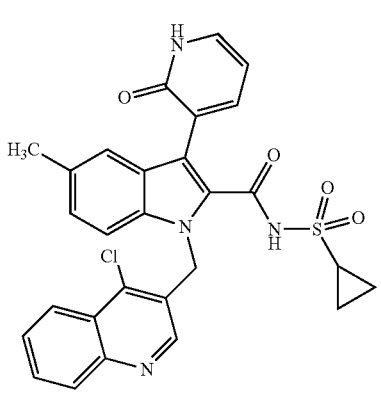 | 548.0 |

| Compound No. | STRUCTURE | M + H |
|---|---|---|
| 326 | 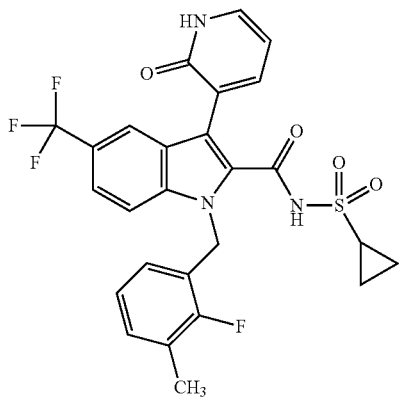 | 548.5 |
| 327 | 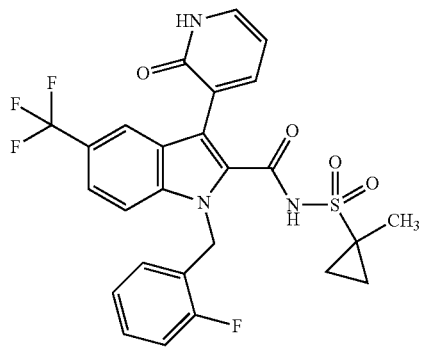 | 548.5 |
| 328 | 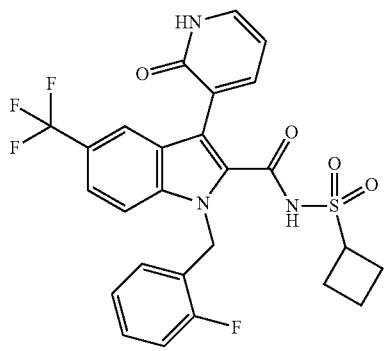 | 548.5 |
| 329 | 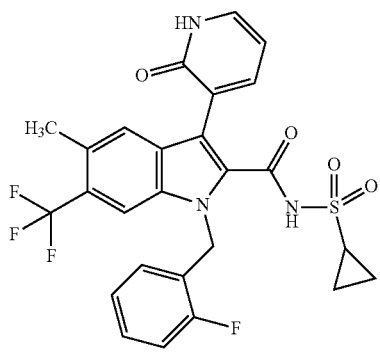 | 548.5 |

-continued
| Compound No. | STRUCTURE | M + H |
|---|---|---|
| 330 | 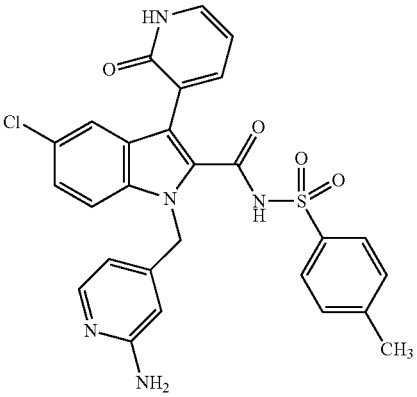 | 549.0 |
| 331 | 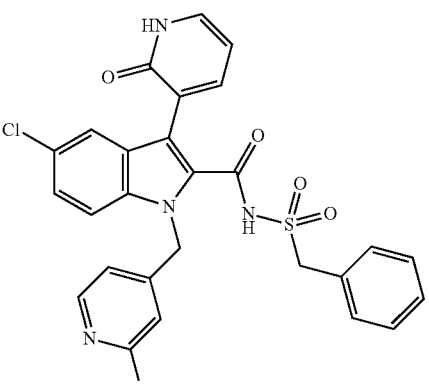 | 549.0 |
| 332 | 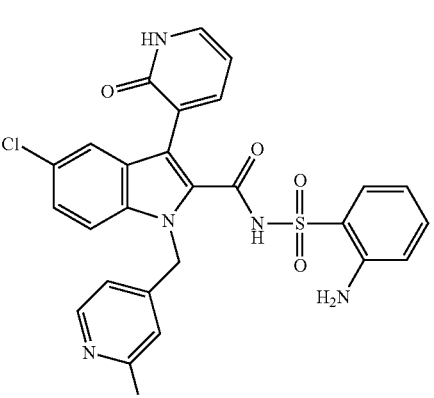 | 550.0 |
| 333 | 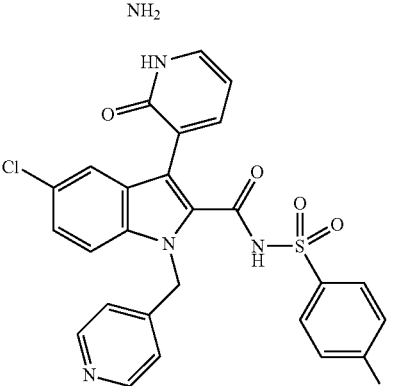 | 550.0 |

-continued
| Compound No. | STRUCTURE | M + H |
|---|---|---|
| 334 | 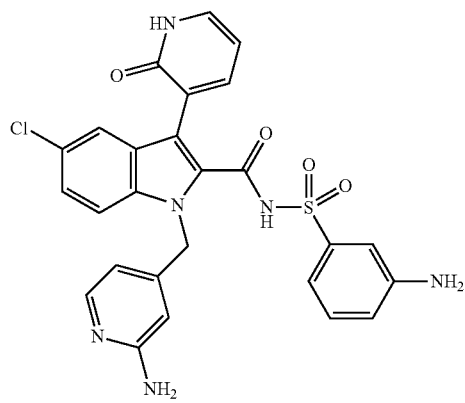 | 550.0 |
| 335 | 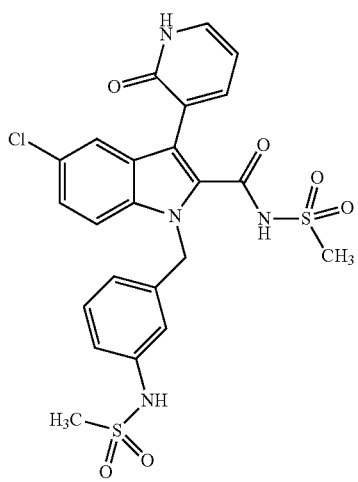 | 550.0 |
| 336 | 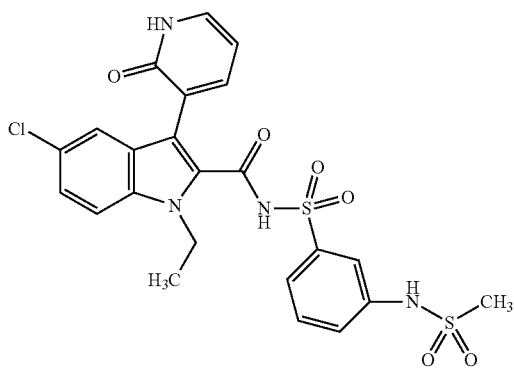 | 550.0 |

| Compound No. | STRUCTURE | M + H |
|---|---|---|
| 337 | 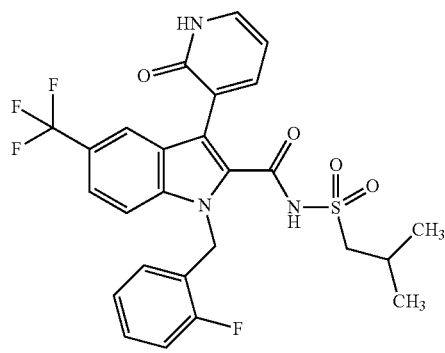 | 550.5 |
| 338 | 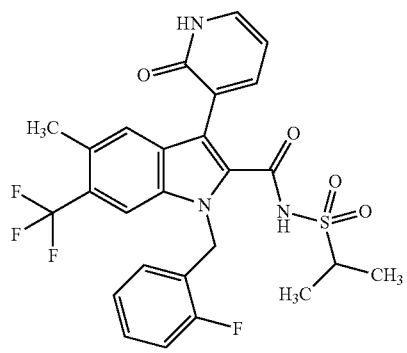 | 550.5 |
| 339 | 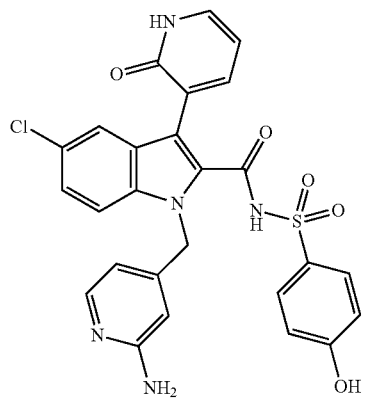 | 551.0 |
| 340 | 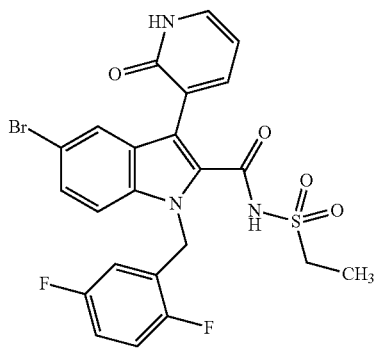 | 551.4 |

| Compound No. | STRUCTURE | M + H |
|---|---|---|
| 341 | 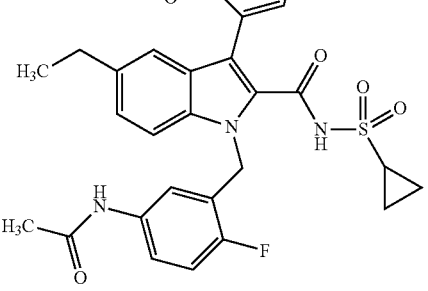 | 551.6 |
| 342 | 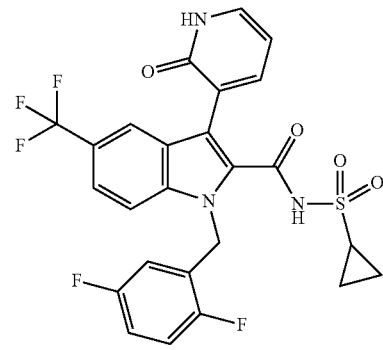 | 552.5 |
| 343 | 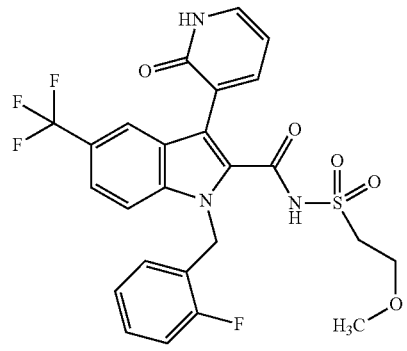 | 552.5 |
| 344 | 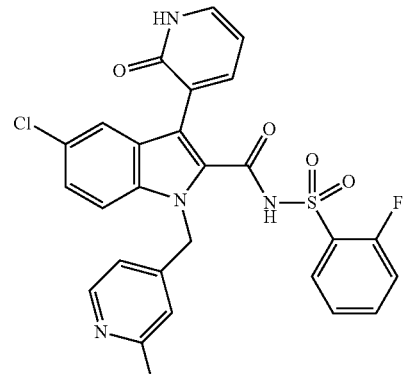 | 553.0 |

-continued
| Compound No. | STRUCTURE | M + H |
|---|---|---|
| 345 | 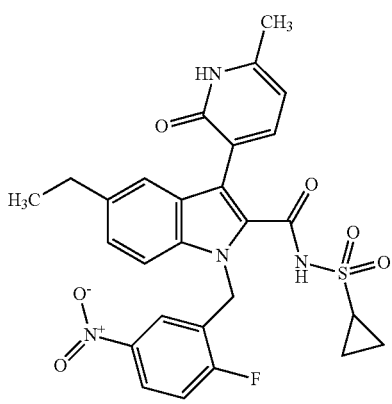 | 553.6 |
| 346 | 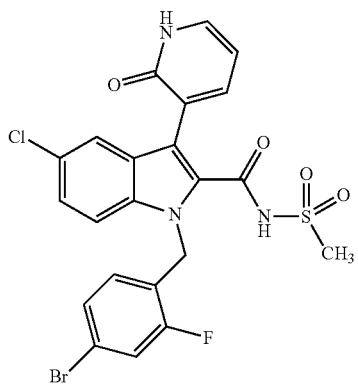 | 553.8 |
| 347 | 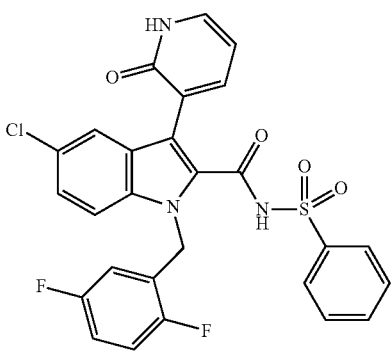 | 555.0 |
| 348 | 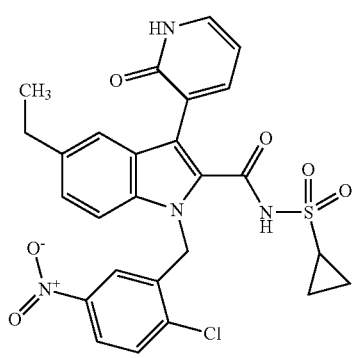 | 556.0 |

-continued

| Compound No. | STRUCTURE | M + H |
|---|---|---|
| 349 | 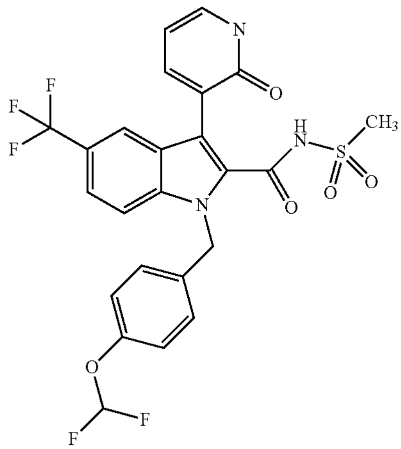 | 556.5 |
| 350 | 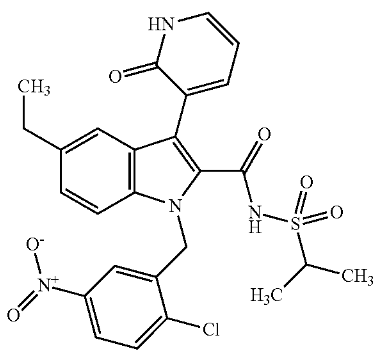 | 558.0 |
| 351 | 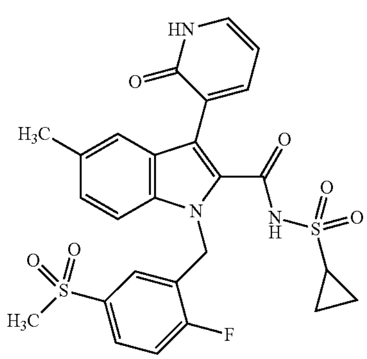 | 558.6 |

| Compound No. | STRUCTURE | M + H |
|---|---|---|
| 352 | 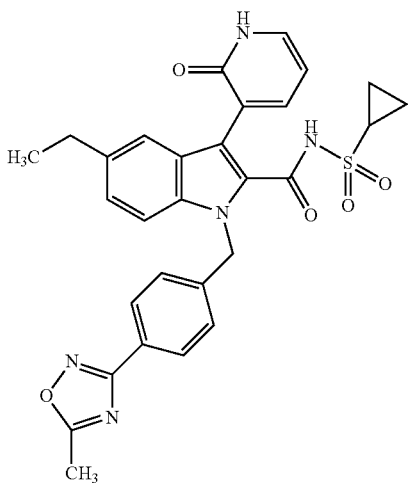 | 558.6 |
| 353 | 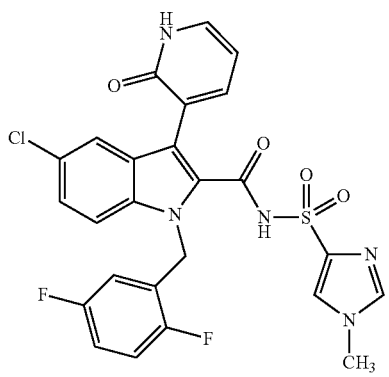 | 559.0 |
| 354 | 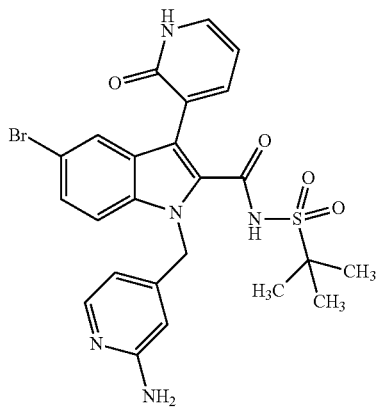 | 559.5 |

-continued

| Compound No. | STRUCTURE | M + H |
|---|---|---|
| 355 | 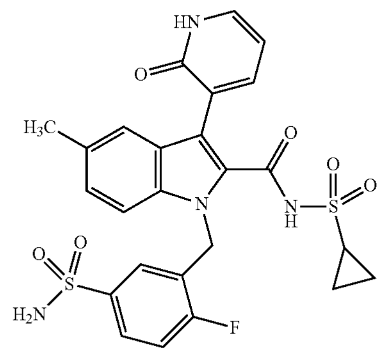 | 559.6 |
| 356 | 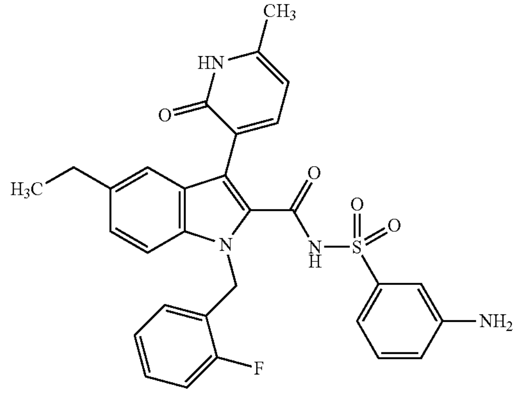 | 559.6 |
| 357 | 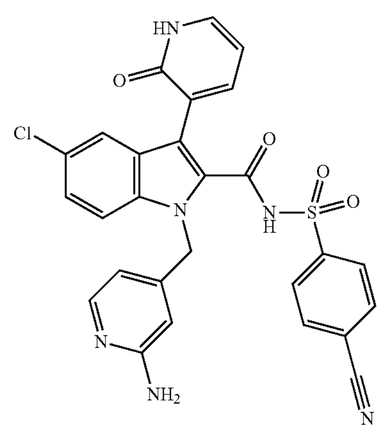 | 560.0 |
| 358 | 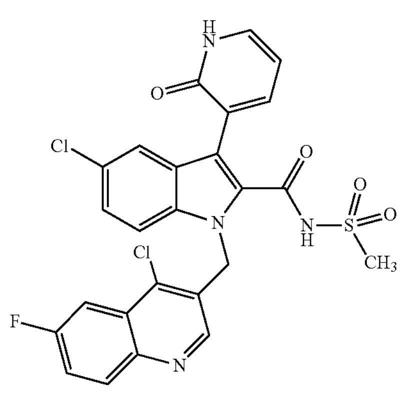 | 560.4 |

-continued
| Compound No. | STRUCTURE | M + H |
|---|---|---|
| 359 | 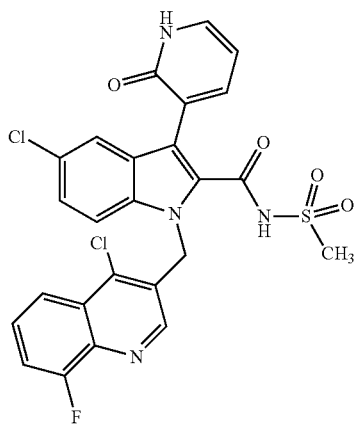 | 560.4 |
| 360 | 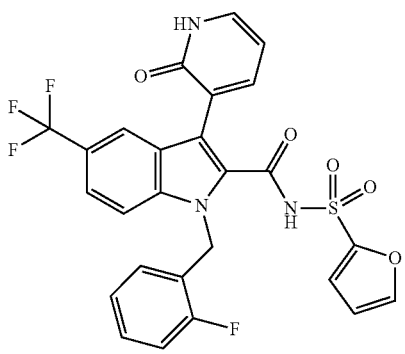 | 560.5 |
| 361 | 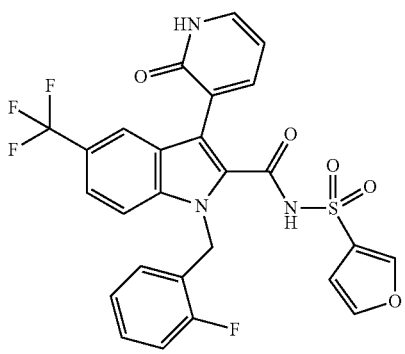 | 560.5 |
| 362 | 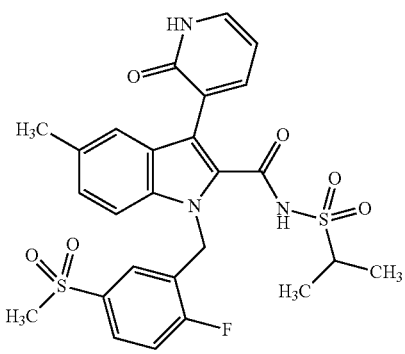 | 560.6 |

| Compound No. | STRUCTURE | M + H |
|---|---|---|
| 363 | 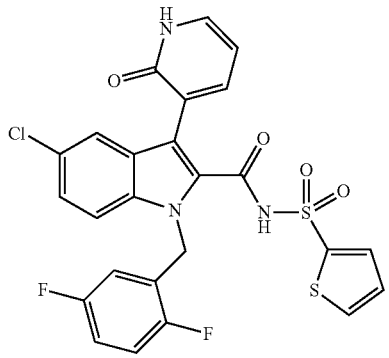 | 561.0 |
| 364 | 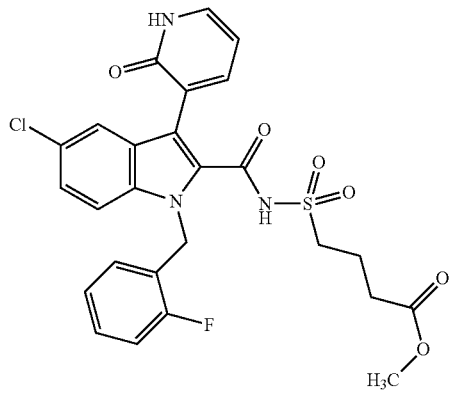 | 561.0 |
| 365 | 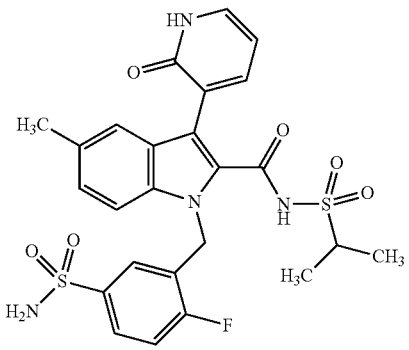 | 561.6 |
| 366 | 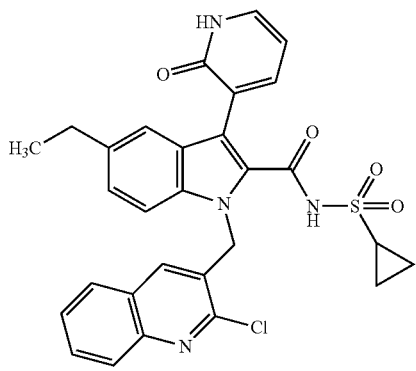 | 562.1 |

| Compound No. | STRUCTURE | M + H |
|---|---|---|
| 367 | 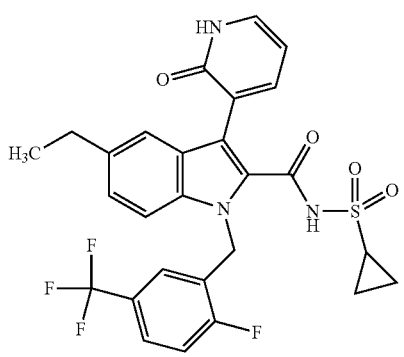 | 562.6 |
| 368 | 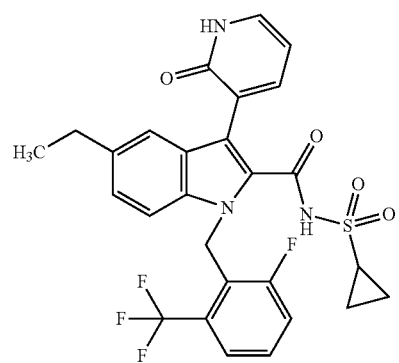 | 562.6 |
| 369 | 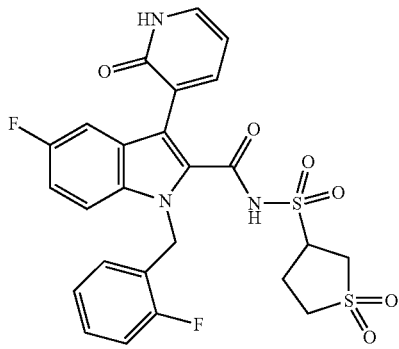 | 562.6 |
| 370 | 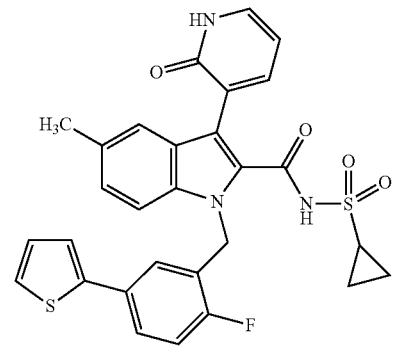 | 562.7 |

| Compound No. | STRUCTURE | M + H |
|---|---|---|
| 371 | 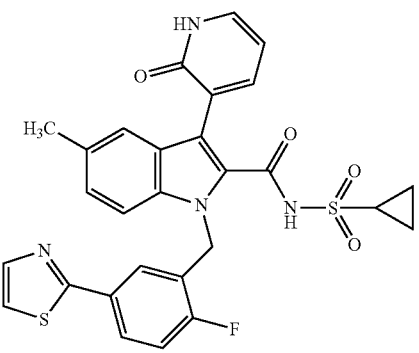 | 563.6 |
| 372 | 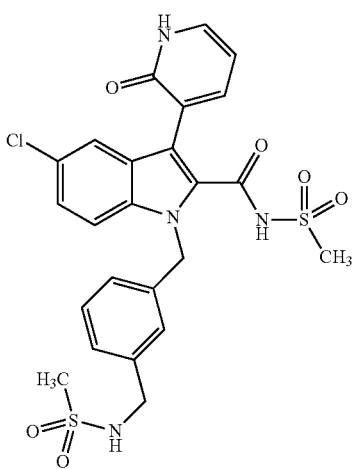 | 564.1 |
| 373 | 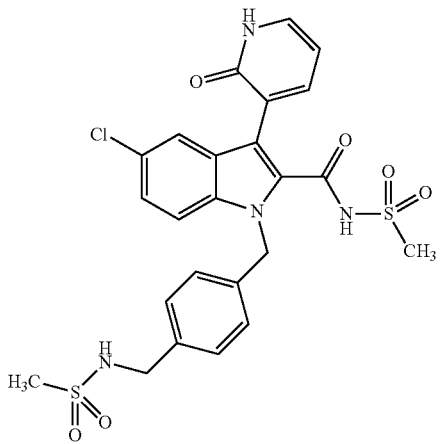 | 564.1 |

-continued

| Compound No. | STRUCTURE | M + H |
|---|---|---|
| 374 | 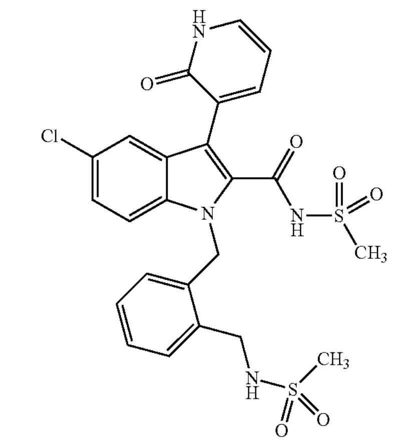 | 564.1 |
| 375 | 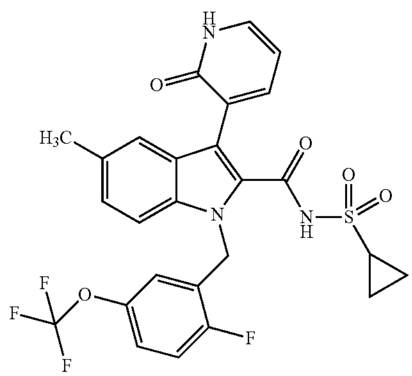 | 564.5 |
| 376 | 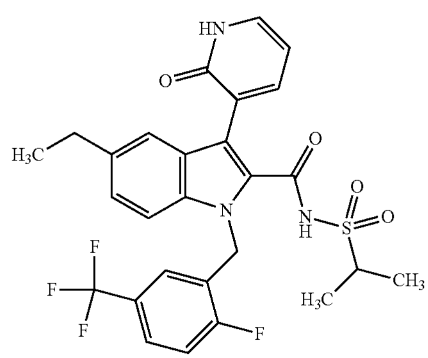 | 564.6 |
| 377 | 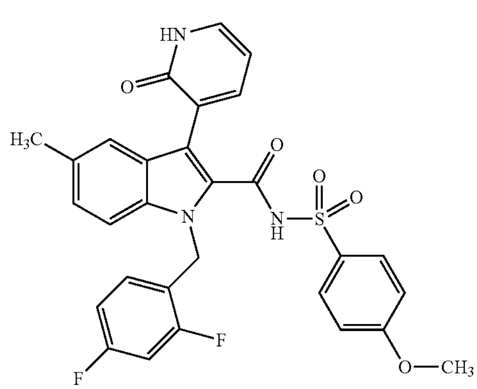 | 564.6 |

-continued
| Compound No. | STRUCTURE | M + H |
|---|---|---|
| 378 | 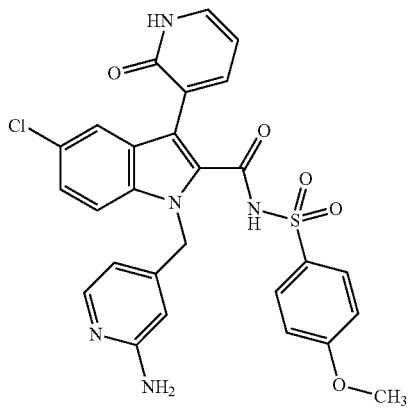 | 565.0 |
| 379 | 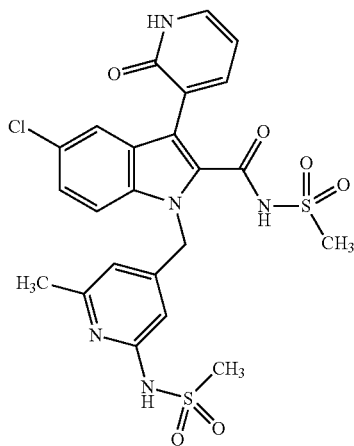 | 565.0 |
| 380 | 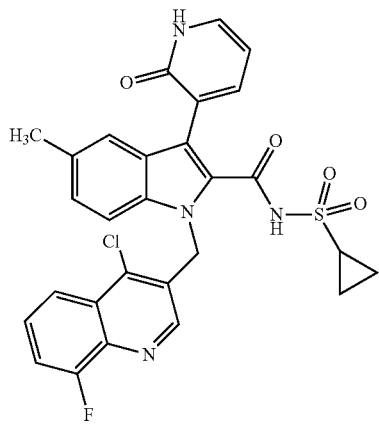 | 566.0 |

| Compound No. | STRUCTURE | M + H |
|---|---|---|
| 381 | 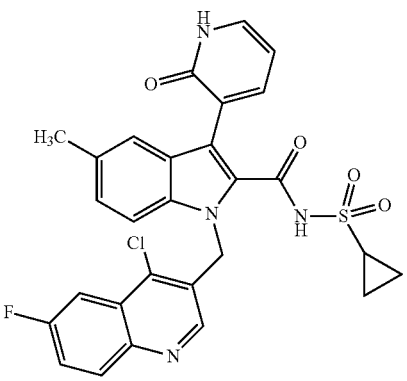 | 566.0 |
| 382 | 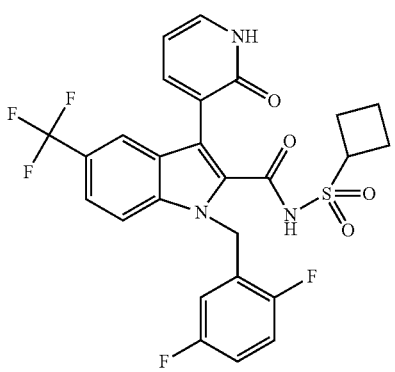 | 566.5 |
| 383 | 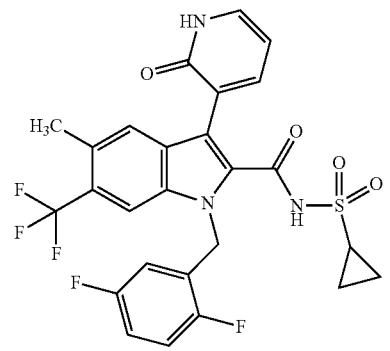 | 566.5 |
| 384 | 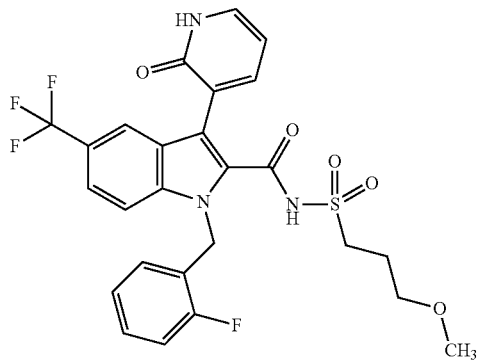 | 566.5 |

-continued
| Compound No. | STRUCTURE | M + H |
|---|---|---|
| 385 | 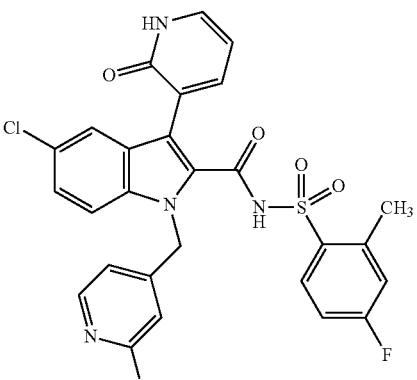 | 567.0 |
| 386 | 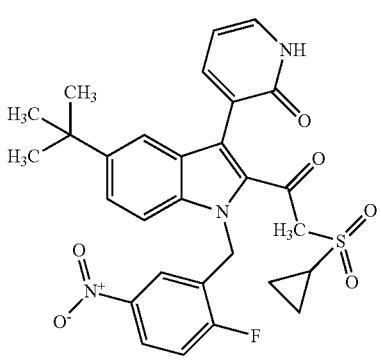 | 567.6 |
| 387 | 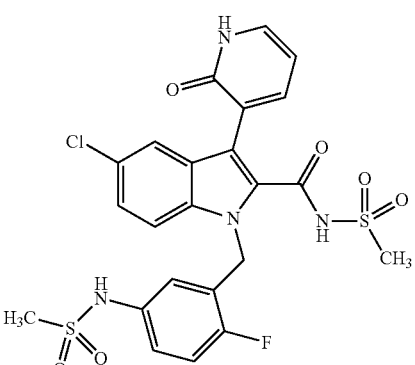 | 568.0 |
| 388 | 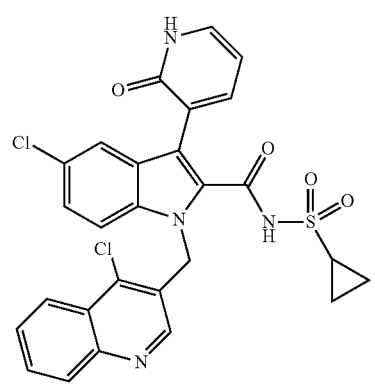 | 568.5 |

-continued
| Compound No. | STRUCTURE | M + H |
|---|---|---|
| 389 | 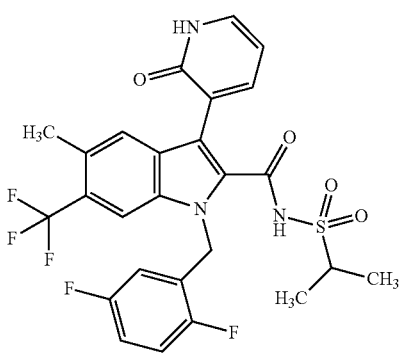 | 568.5 |
| 390 | 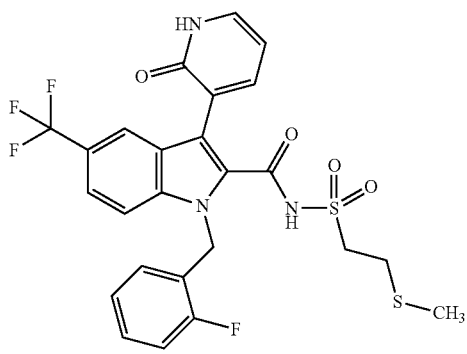 | 568.6 |
| 391 | 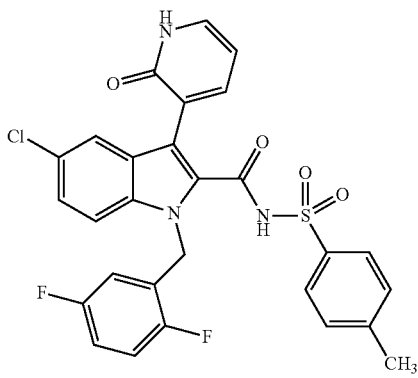 | 569.0 |
| 392 | 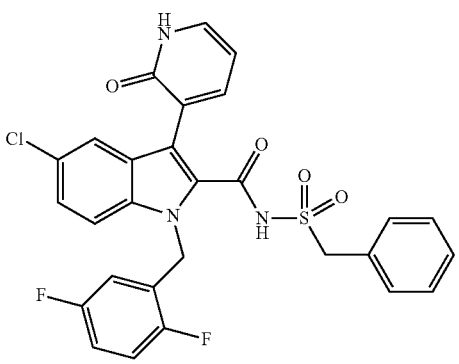 | 569.0 |

| Compound No. | STRUCTURE | M + H |
|---|---|---|
| 393 | 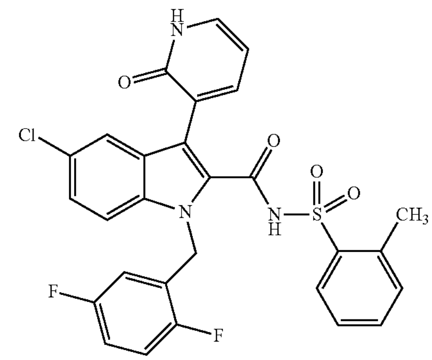 | 569.0 |
| 394 | 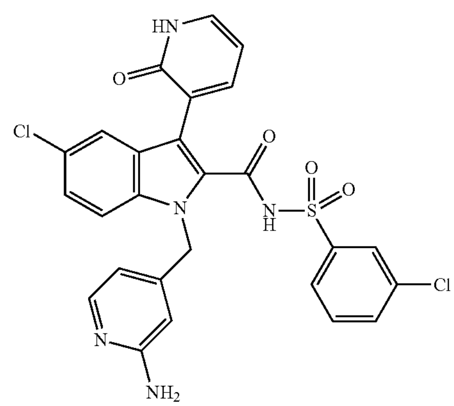 | 569.4 |
| 395 | 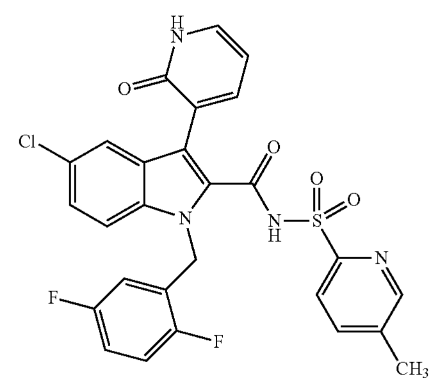 | 570.0 |
| 396 | 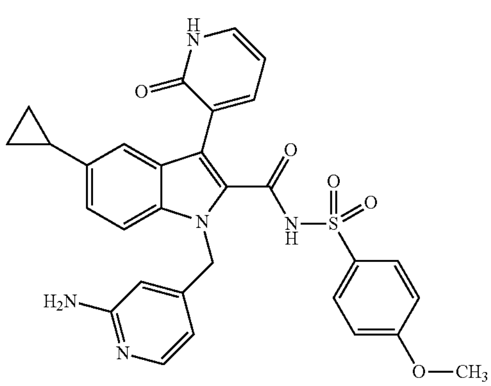 | 570.6 |

-continued

| Compound No. | STRUCTURE | M + H |
|---|---|---|
| 397 | 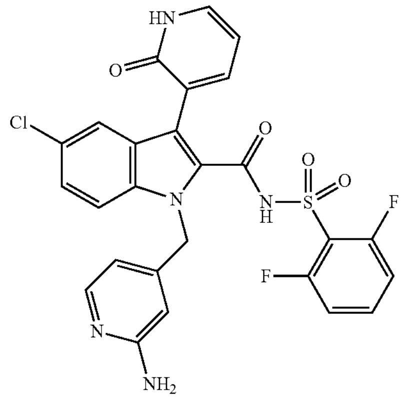 | 571.0 |
| 398 | 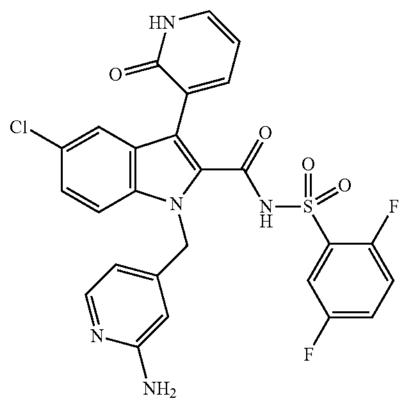 | 571.0 |
| 399 | 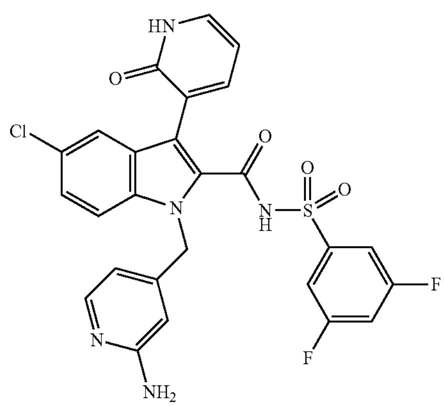 | 571.0 |
| 400 | 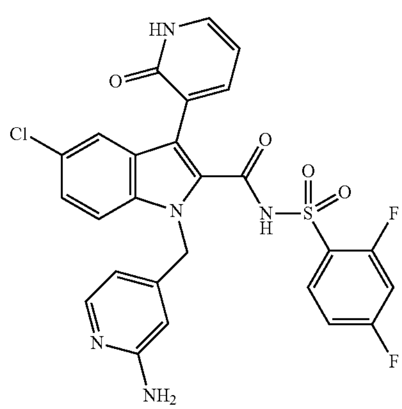 | 571.0 |

-continued
| Compound No. | STRUCTURE | M + H |
|---|---|---|
| 401 | 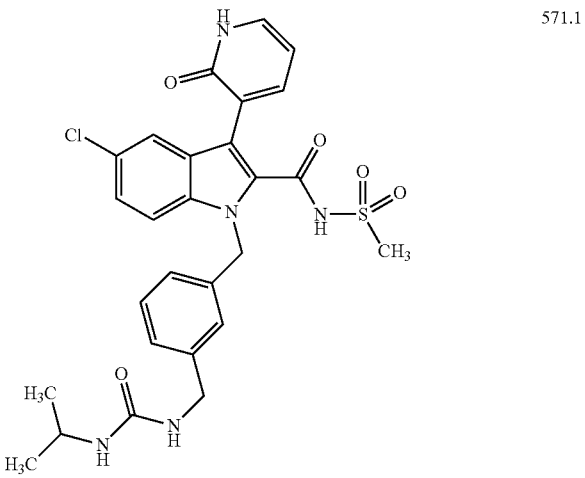 | 571.1 |
| 402 | 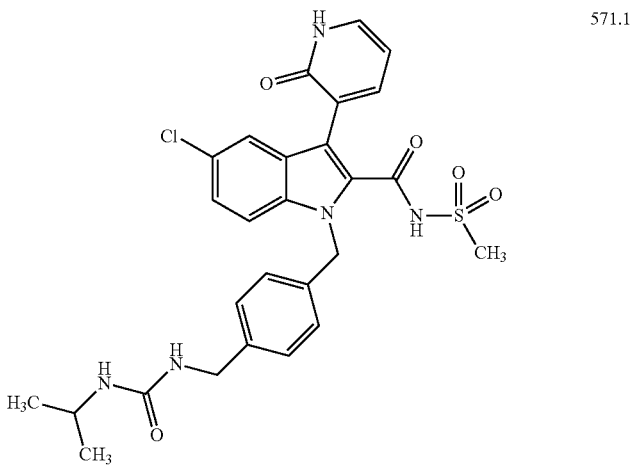 | 571.1 |
| 403 | 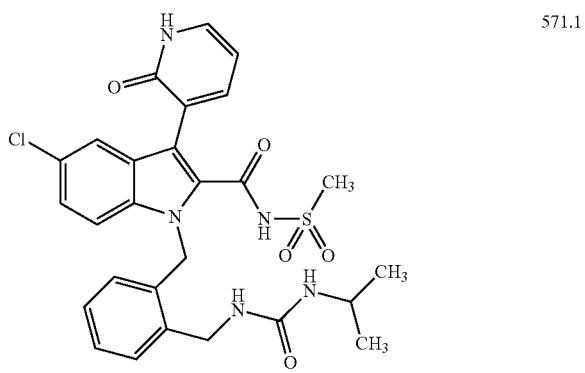 | 571.1 |

| Compound No. | STRUCTURE | M + H |
|---|---|---|
| 404 | 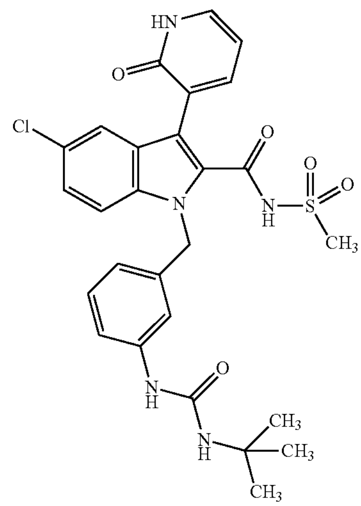 | 571.1 |
| 405 | 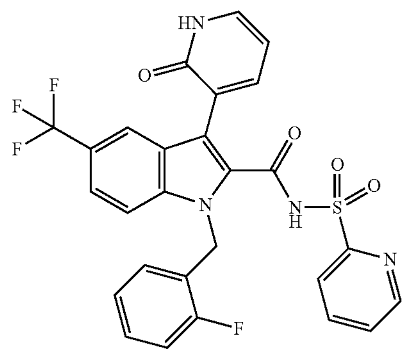 | 571.5 |
| 406 | 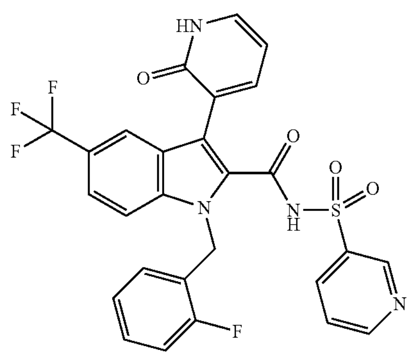 | 571.5 |
| 407 | 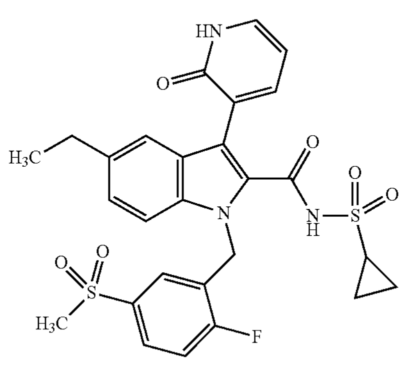 | 572.7 |

| Compound No. | STRUCTURE | M + H |
|---|---|---|
| 408 | 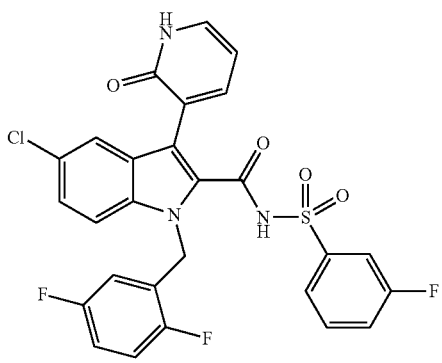 | 573.0 |
| 409 | 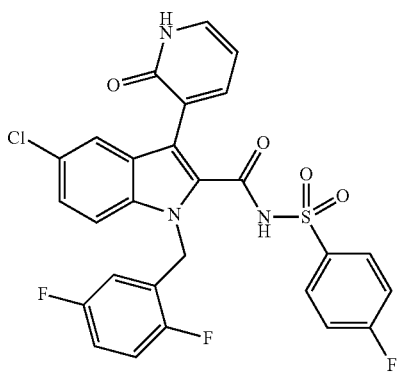 | 573.0 |
| 410 | 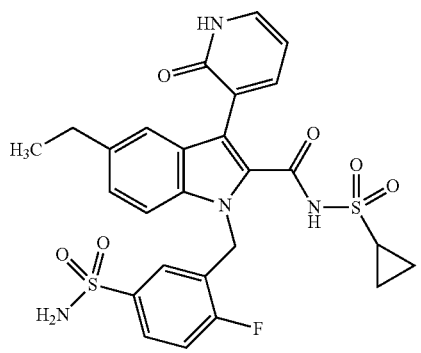 | 573.6 |
| 411 | 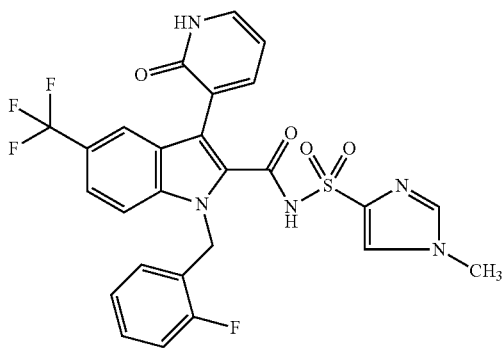 | 574.5 |

| Compound No. | STRUCTURE | M + H |
|---|---|---|
| 412 | 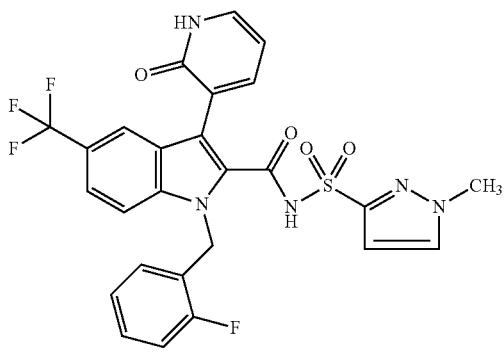 | 574.5 |
| 413 | 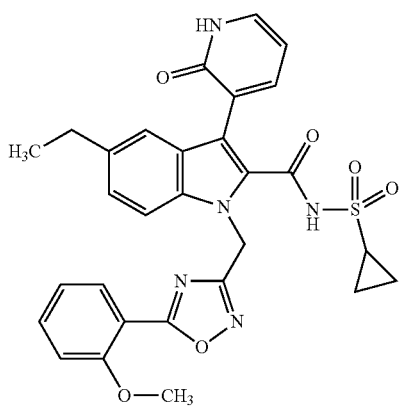 | 574.6 |
| 414 | 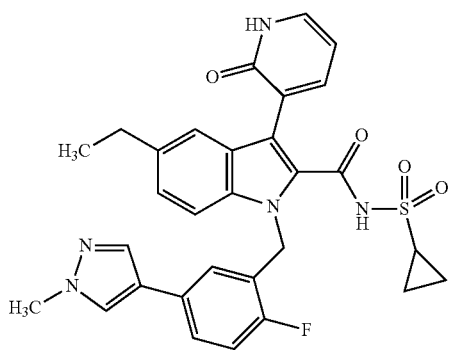 | 574.7 |
| 415 | 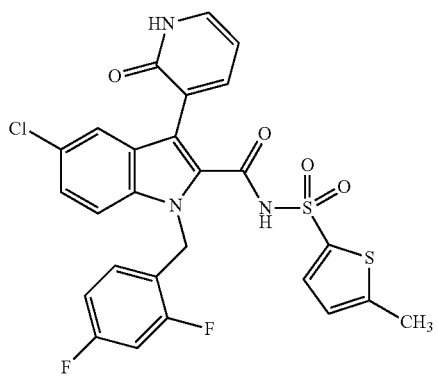 | 575.0 |

| Compound No. | STRUCTURE | M + H |
|---|---|---|
| 416 | 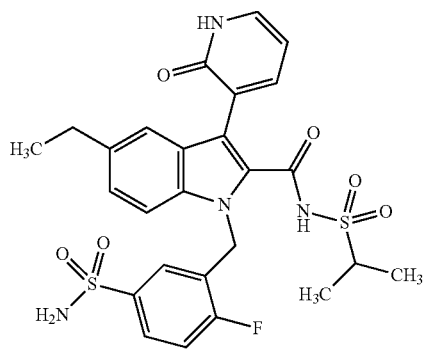 | 575.7 |
| 417 | 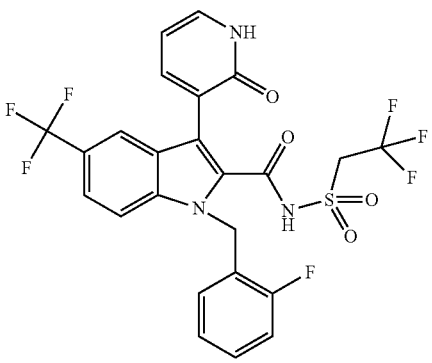 | 576.5 |
| 418 | 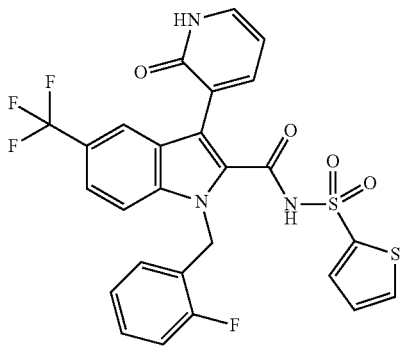 | 576.6 |
| 419 | 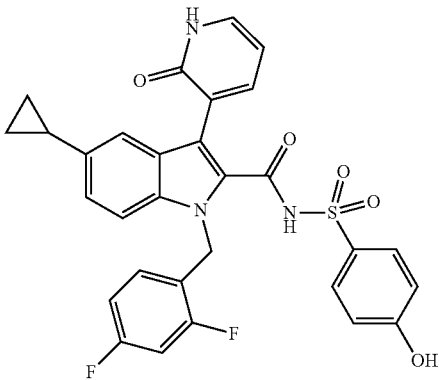 | 576.6 |

-continued
| Compound No. | STRUCTURE | M + H |
|---|---|---|
| 420 | 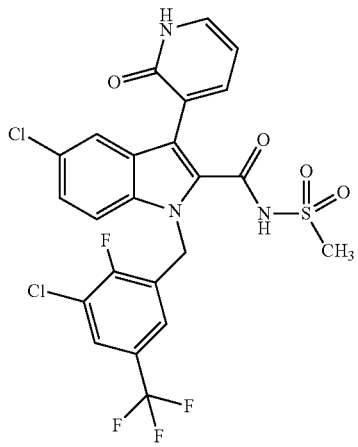 | 577.4 |
| 421 | 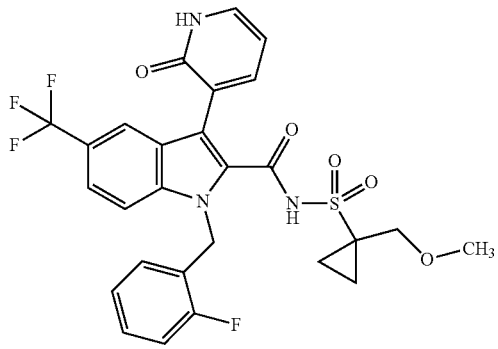 | 578.6 |
| 422 | 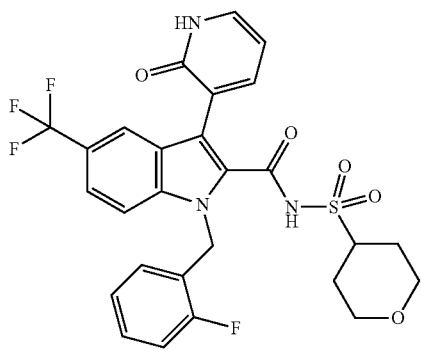 | 578.6 |

-continued

| Compound No. | STRUCTURE | M + H |
|---|---|---|
| 423 | 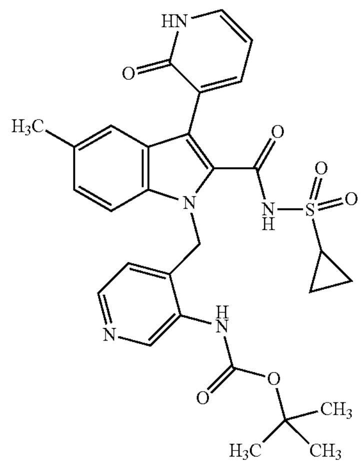 | 578.7 |
| 424 | 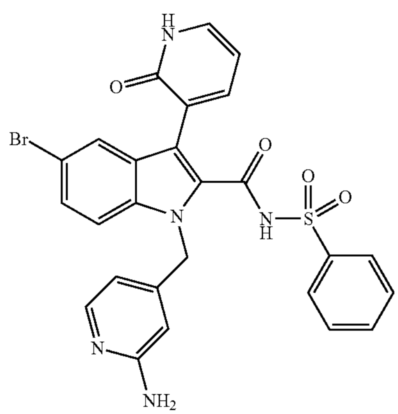 | 579.4 |
| 425 | 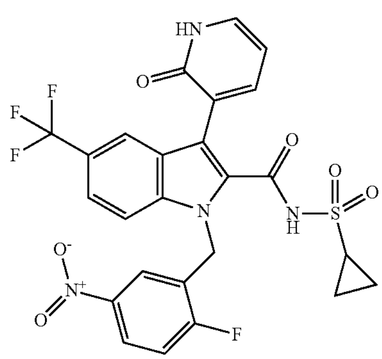 | 579.5 |

-continued

| Compound No. | STRUCTURE | M + H |
|---|---|---|
| 426 | 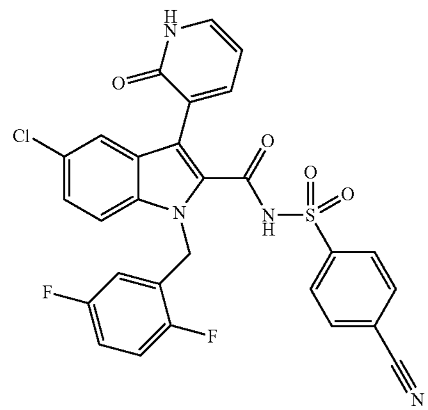 | 580.0 |
| 427 | 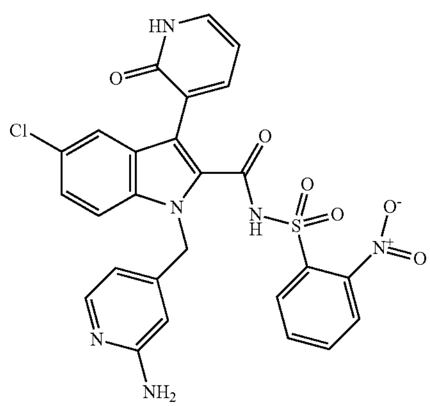 | 580.0 |
| 428 | 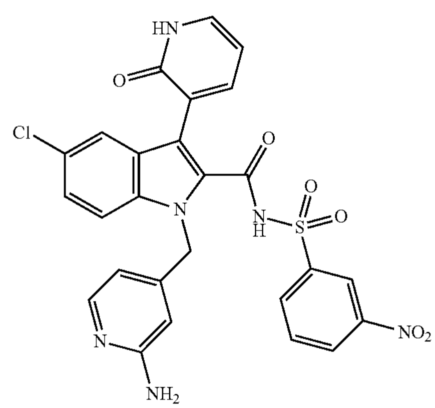 | 580.0 |
| 429 | 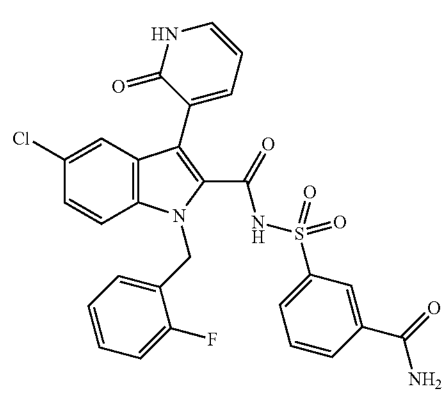 | 580.0 |

-continued

| Compound No. | STRUCTURE | M + H |
|---|---|---|
| 430 | 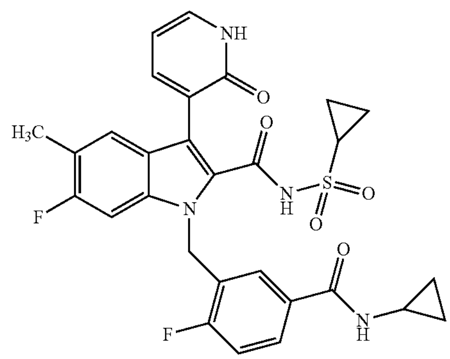 | 581.6 |
| 431 | 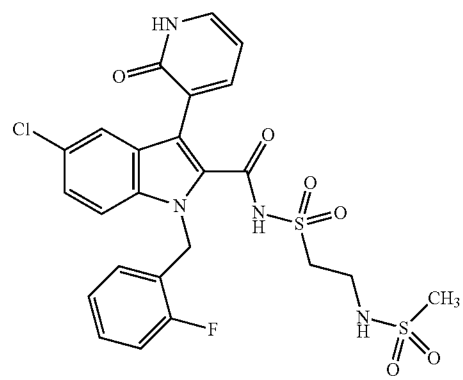 | 582.0 |
| 432 | 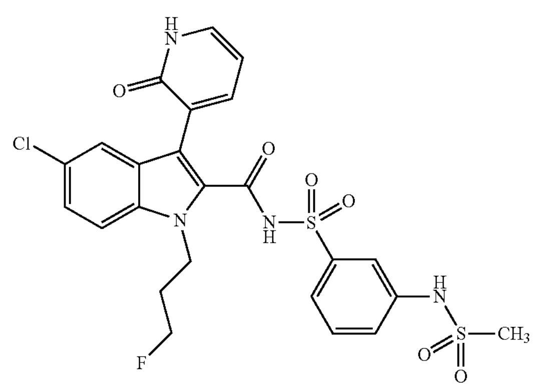 | 582.0 |
| 433 | 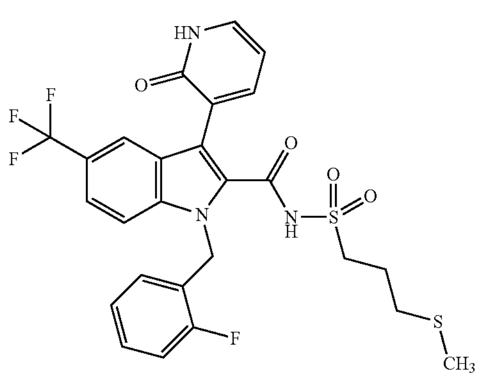 | 582.6 |

| Compound No. | STRUCTURE | M + H |
|---|---|---|
| 434 | 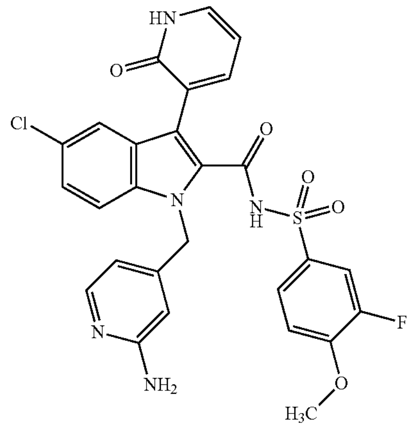 | 583.0 |
| 435 | 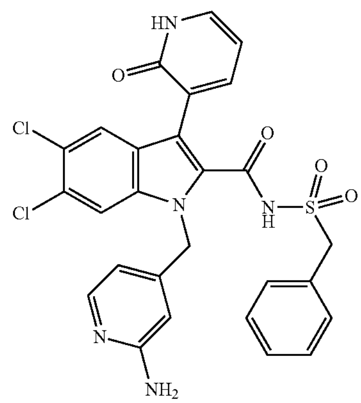 | 583.5 |
| 436 | 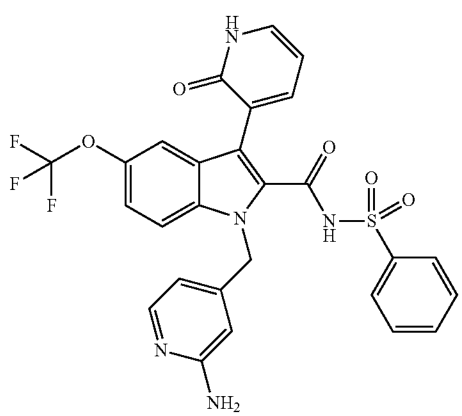 | 584.6 |
| 437 | 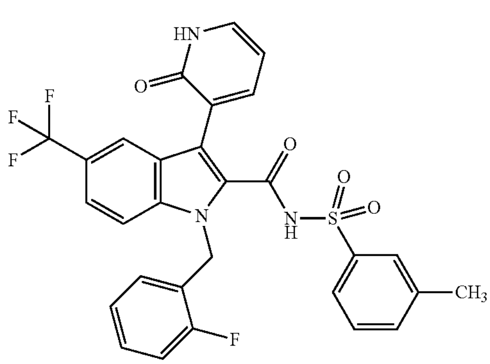 | 584.6 |

US 8,143,305 B2

-continued

| Compound No. | STRUCTURE | M + H |
|---|---|---|
| 438 | 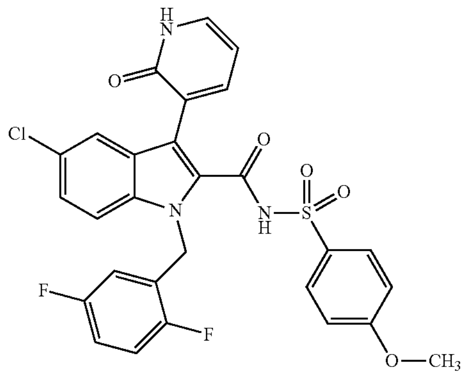 | 585.0 |
| 439 | 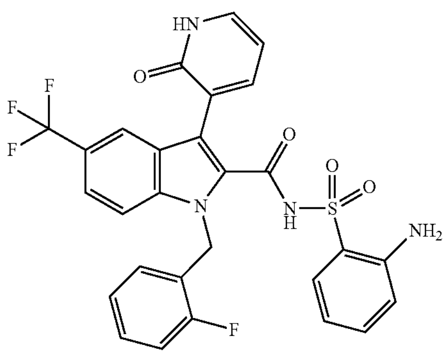 | 585.6 |
| 440 | 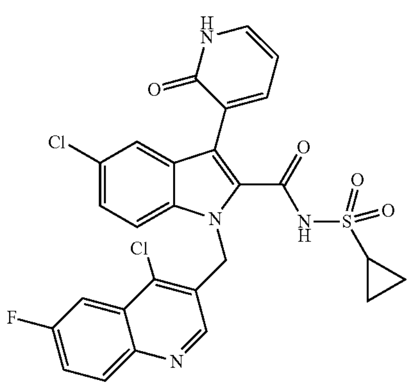 | 586.4 |
| 441 | 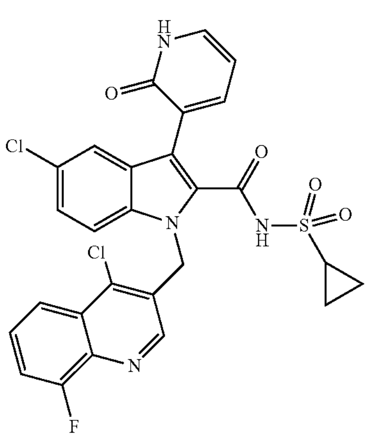 | 586.4 |

-continued
| Compound No. | STRUCTURE | M + H |
|---|---|---|
| 442 | 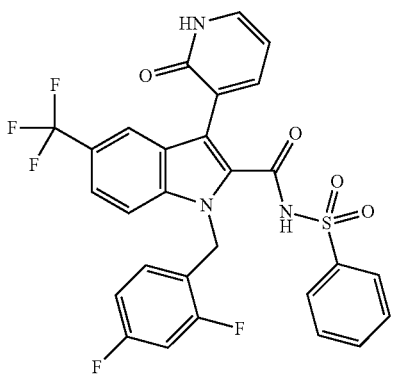 | 588.5 |
| 443 | 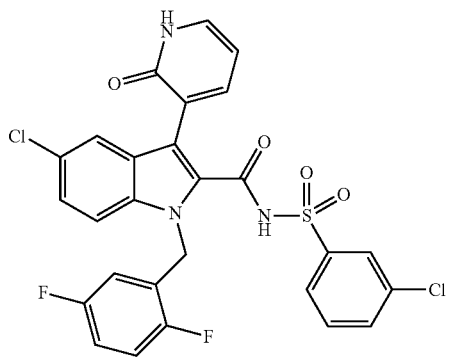 | 589.4 |
| 444 | 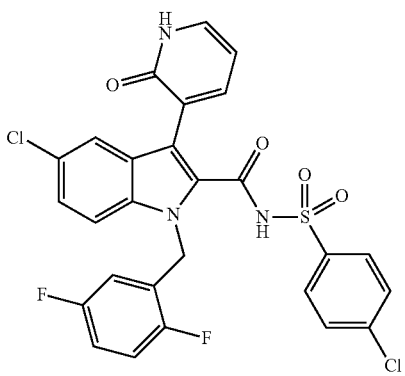 | 589.4 |
| 445 | 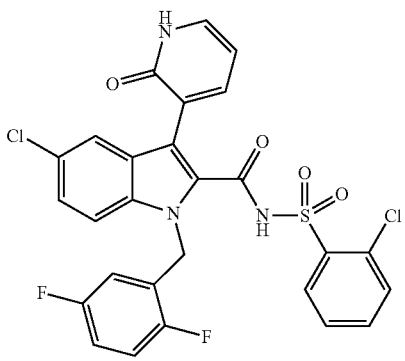 | 589.4 |

-continued

| Compound No. | STRUCTURE | M + H |
|---|---|---|
| 446 | 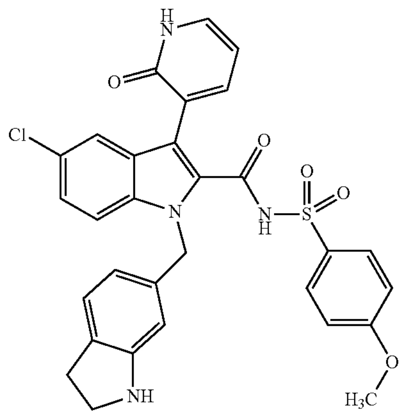 | 590.1 |
| 447 | 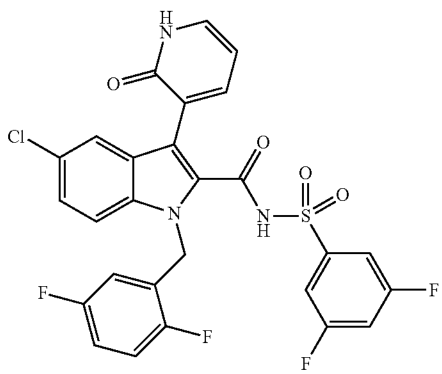 | 591.0 |
| 448 | 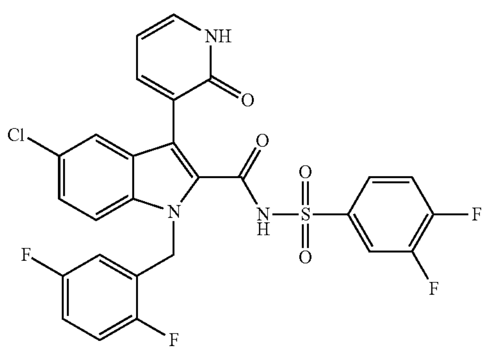 | 591.0 |
| 449 | 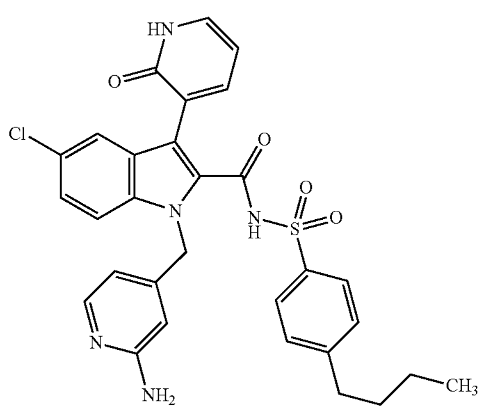 | 591.1 |

| Compound No. | STRUCTURE | M + H |
|---|---|---|
| 450 | 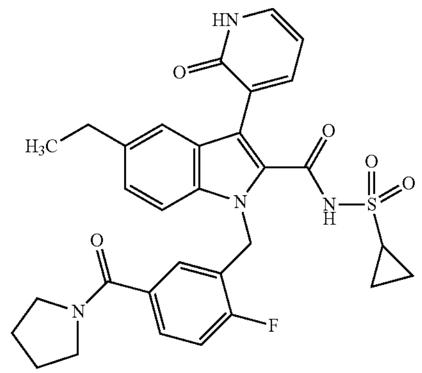 | 591.7 |
| 451 | 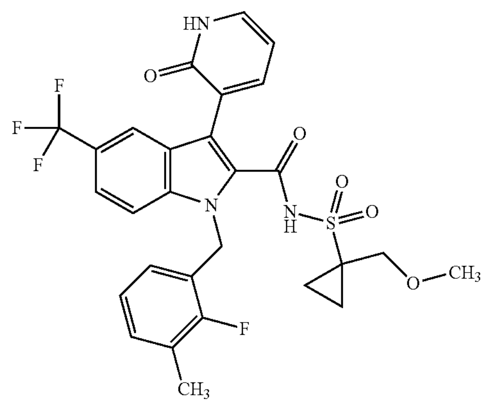 | 592.6 |
| 452 | 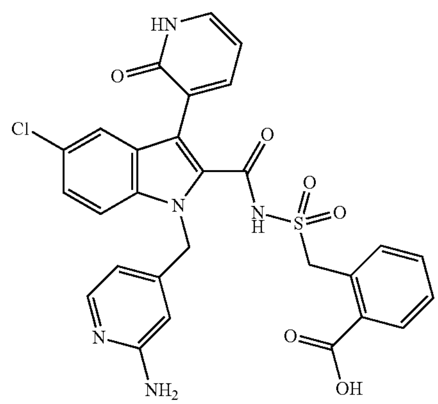 | 593.0 |
| 453 | 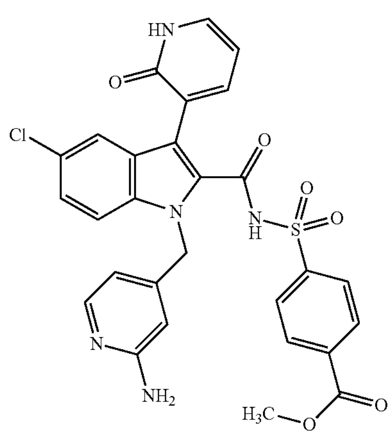 | 593.0 |

| Compound No. | STRUCTURE | M + H |
|---|---|---|
| 454 | 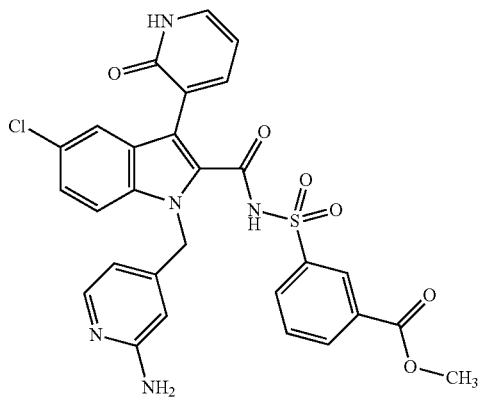 | 593.0 |
| 455 | 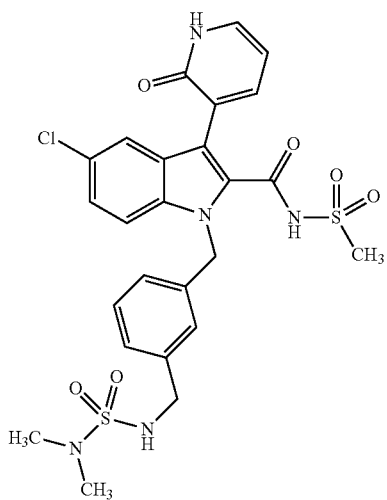 | 593.1 |
| 456 | 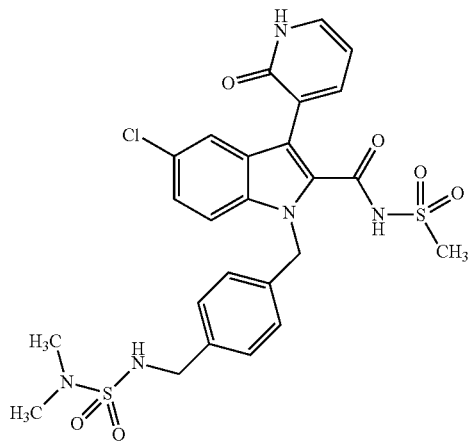 | 593.1 |

-continued

| Compound No. | STRUCTURE | M + H |
|---|---|---|
| 457 | 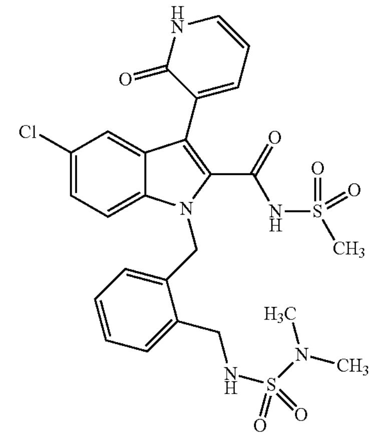 | 593.1 |
| 458 | 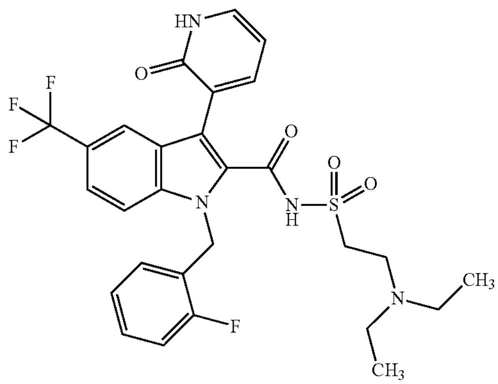 | 593.6 |
| 459 | 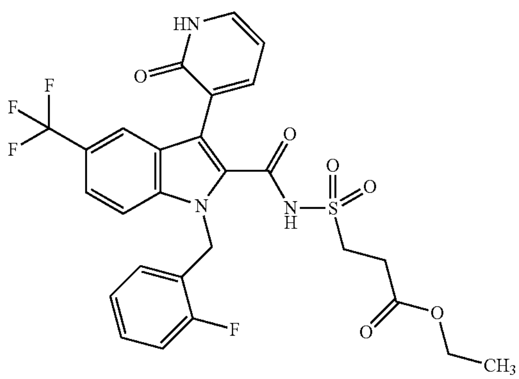 | 594.6 |
| 460 | 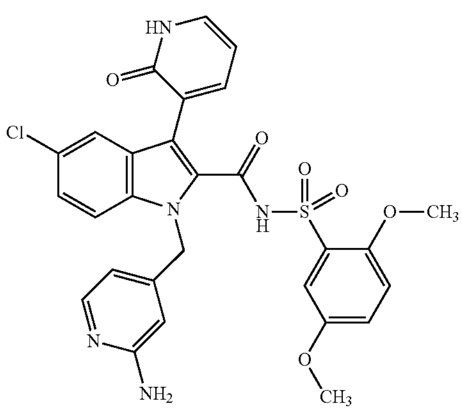 | 595.1 |

-continued

| Compound No. | STRUCTURE | M + H |
|---|---|---|
| 461 | 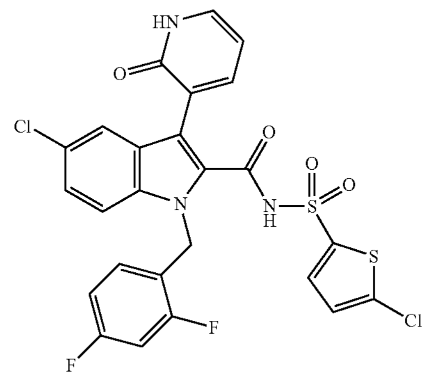 | 595.4 |
| 462 | 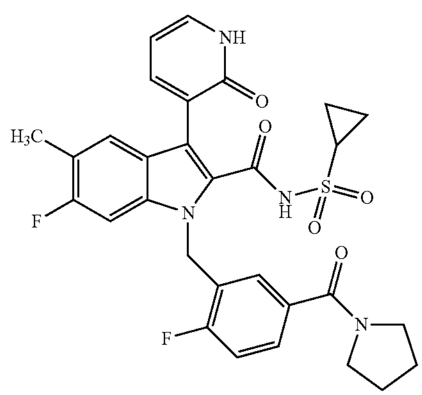 | 595.6 |
| 463 | 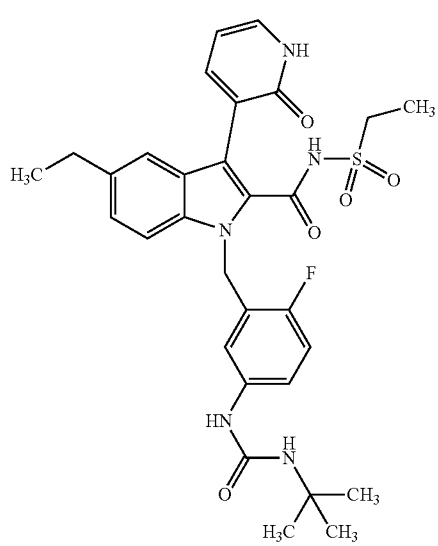 | 596.7 |

-continued

| Compound No. | STRUCTURE | M + H |
|---|---|---|
| 464 | 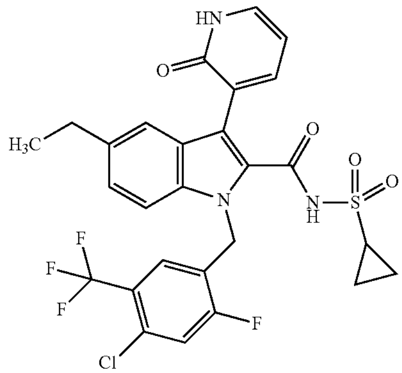 | 597.0 |
| 465 | 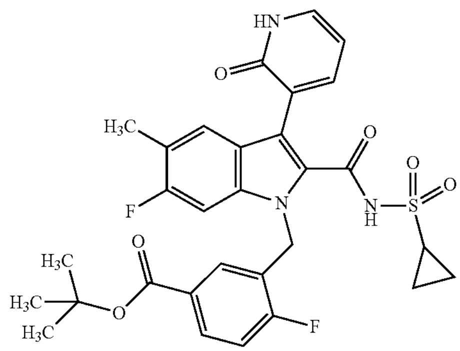 | 598.6 |
| 466 | 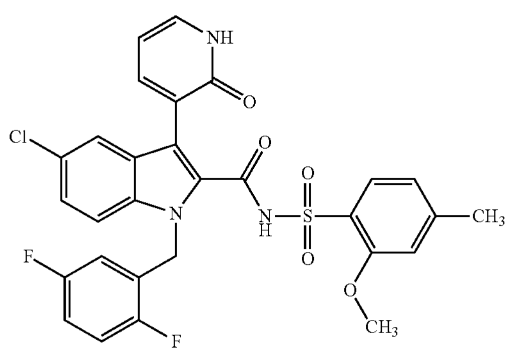 | 599.0 |
| 467 | 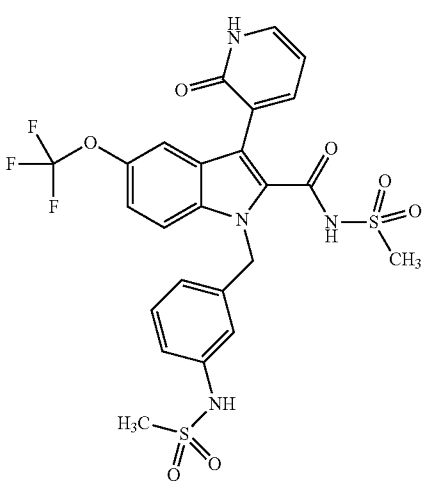 | 599.6 |

| Compound No. | STRUCTURE | M + H |
|---|---|---|
| 468 | 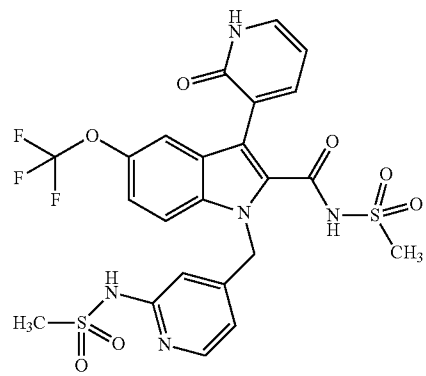 | 600.6 |
| 469 | 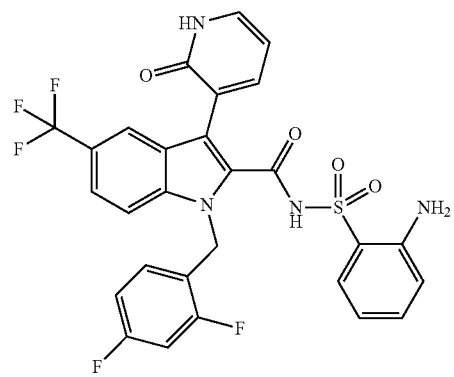 | 603.5 |
| 470 | 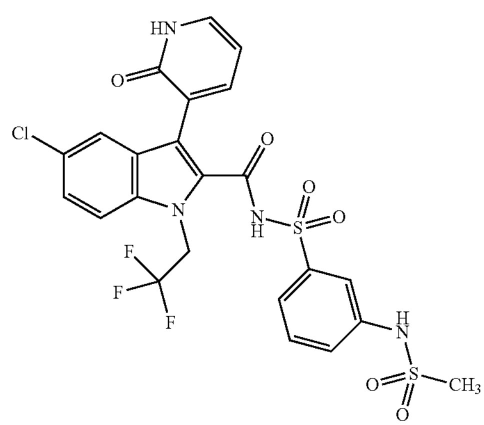 | 604.0 |
| 471 | 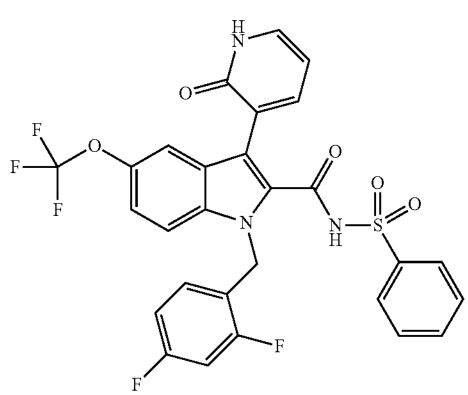 | 604.5 |

| Compound No. | STRUCTURE | M + H |
|---|---|---|
| 472 | 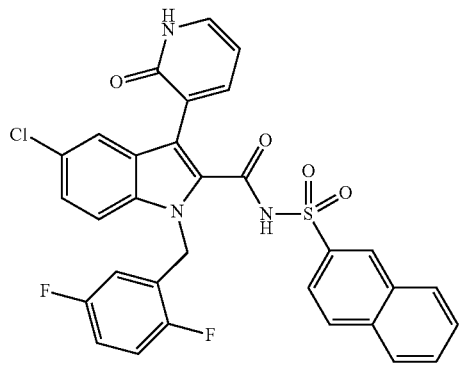 | 605.0 |
| 473 | 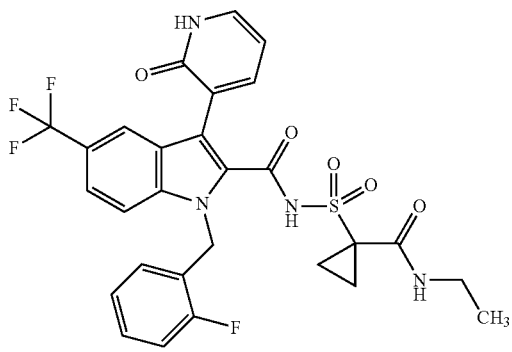 | 605.6 |
| 474 | 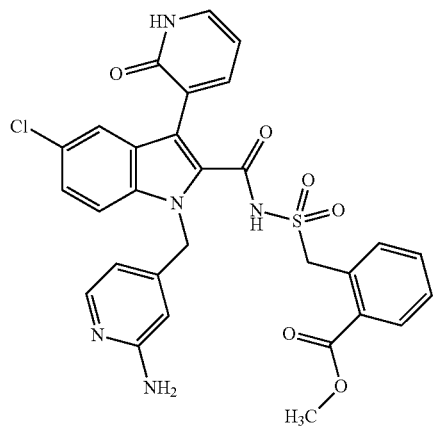 | 607.1 |
| 475 | 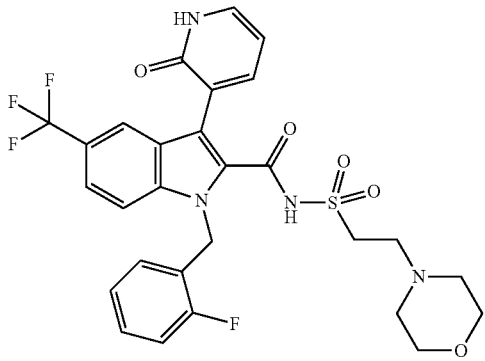 | 607.6 |

| Compound No. | STRUCTURE | M + H |
|---|---|---|
| 476 | 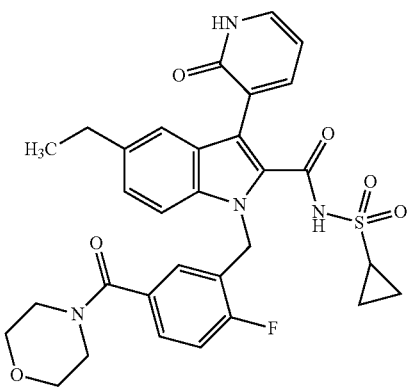 | 607.7 |
| 477 | 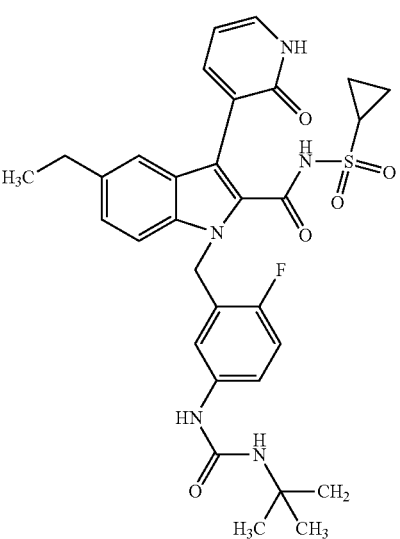 | 608.7 |
| 478 | 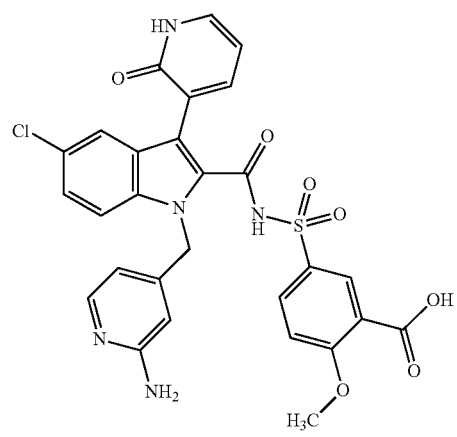 | 609.0 |

345
-continued
| Compound No. | STRUCTURE | M + H |
|---|---|---|
| 479 | 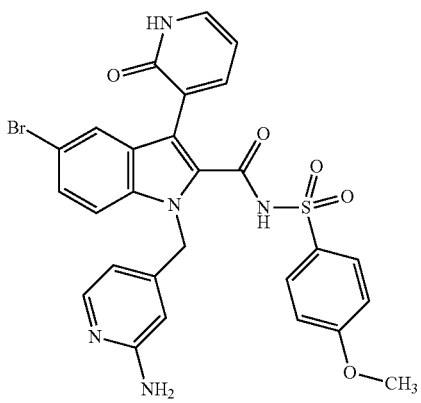 | 609.5 |
| 480 | 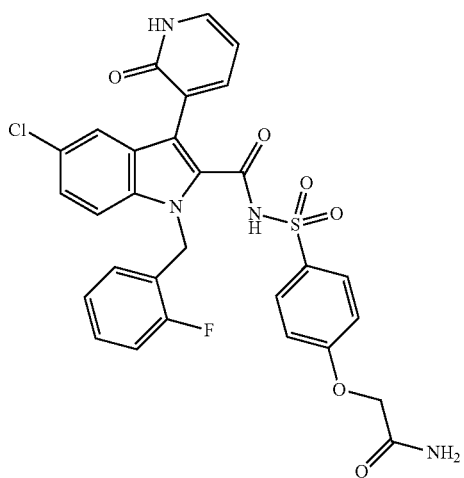 | 610.0 |
| 481 | 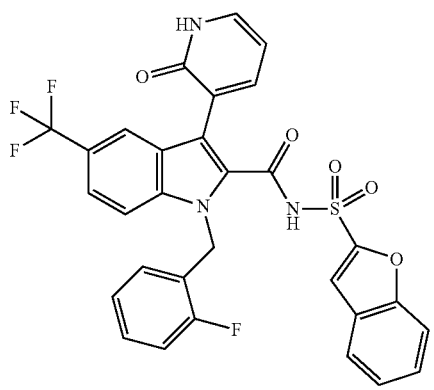 | 610.6 |

-continued

| Compound No. | STRUCTURE | M + H |
|---|---|---|
| 482 | 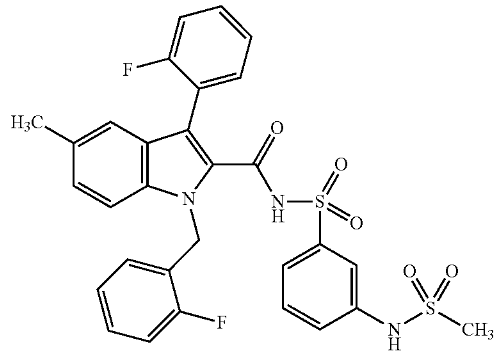 | 610.7 |
| 483 | 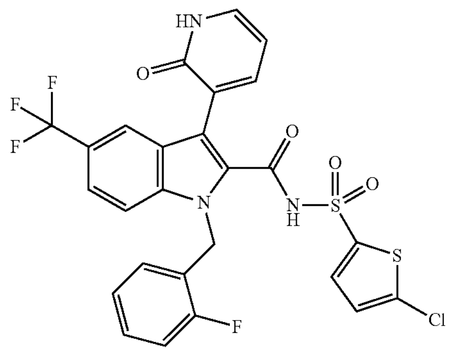 | 611.0 |
| 484 | 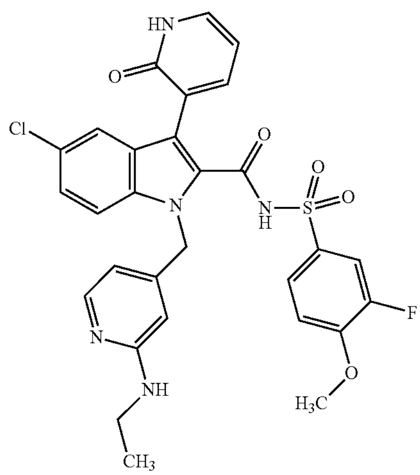 | 611.1 |
| 485 | 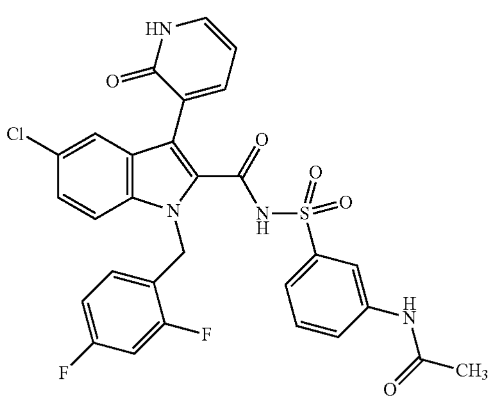 | 612.0 |

-continued
| Compound No. | STRUCTURE | M + H |
|---|---|---|
| 486 | 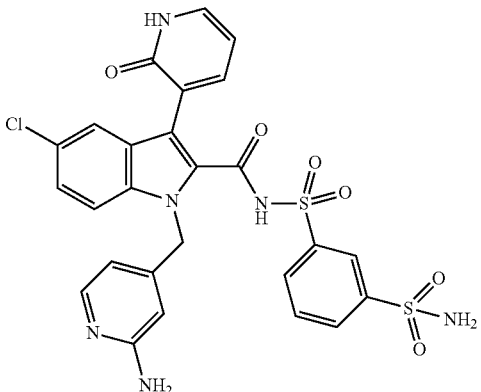 | 614.1 |
| 487 | 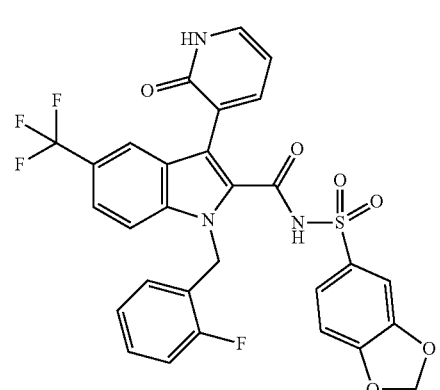 | 614.5 |
| 488 | 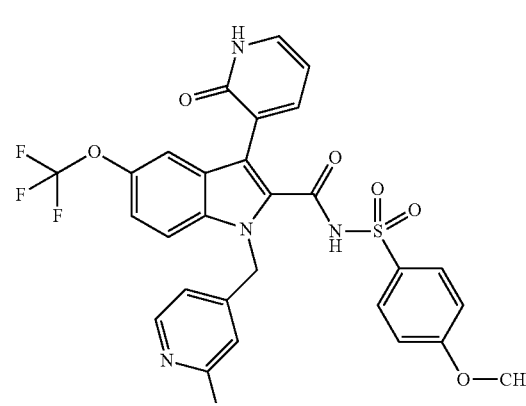 | 614.6 |
| 489 | 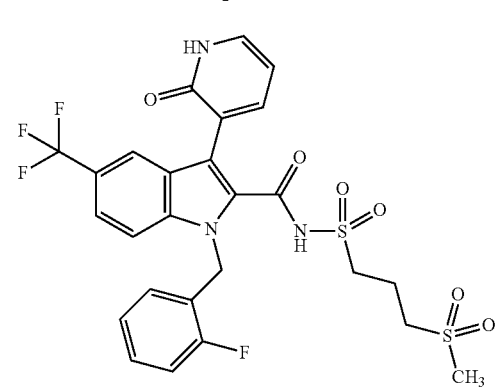 | 614.6 |

-continued
| Compound No. | STRUCTURE | M + H |
|---|---|---|
| 490 | 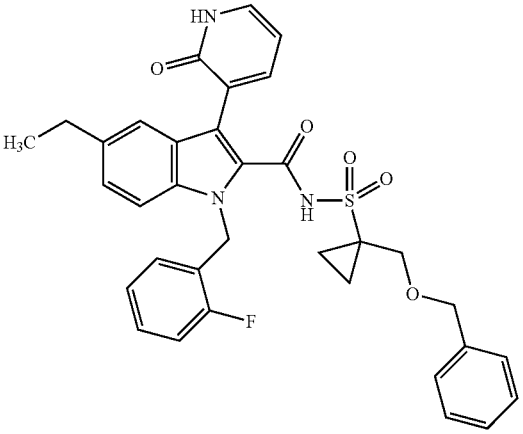 | 614.7 |
| 491 | 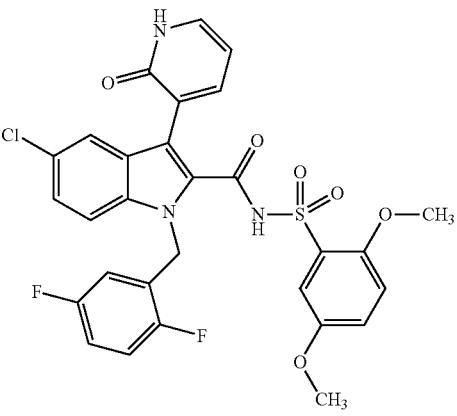 | 615.0 |
| 492 | 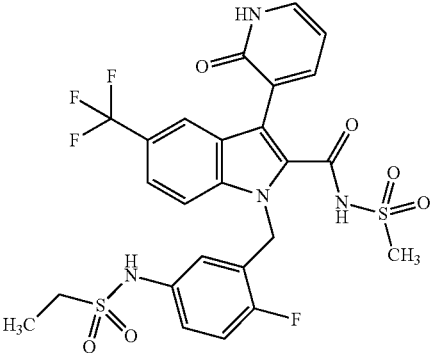 | 615.6 |
| 493 | 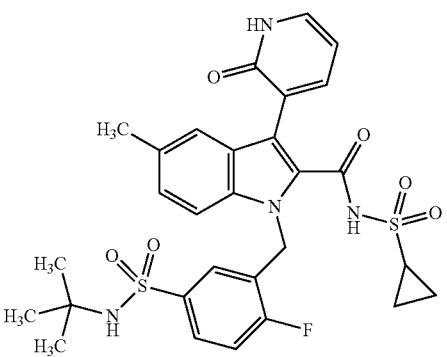 | 615.7 |

-continued

| Compound No. | STRUCTURE | M + H |
|---|---|---|
| 494 | 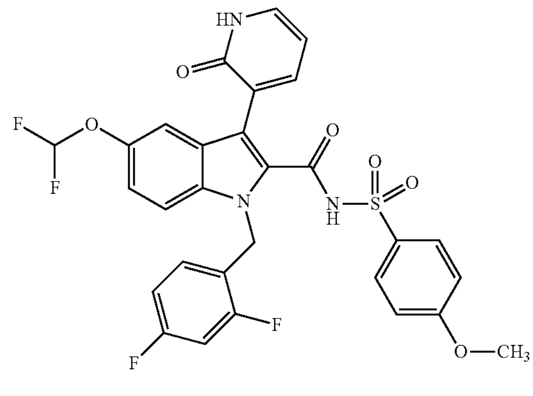 | 616.6 |
| 495 | 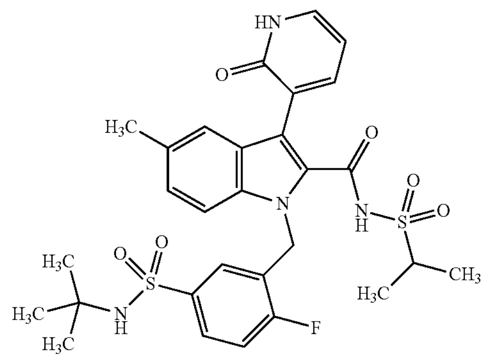 | 617.7 |
| 496 | 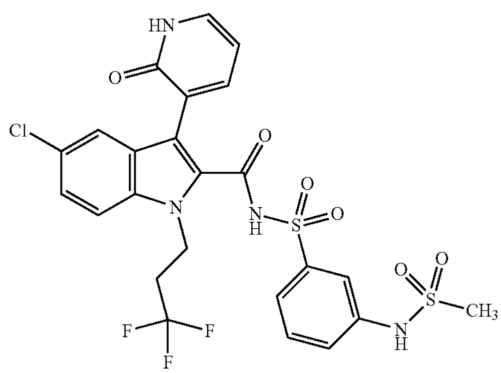 | 618.0 |
| 497 | 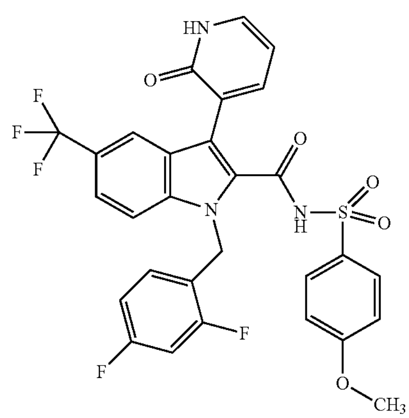 | 618.6 |

| Compound No. | STRUCTURE | M + H |
|---|---|---|
| 498 | 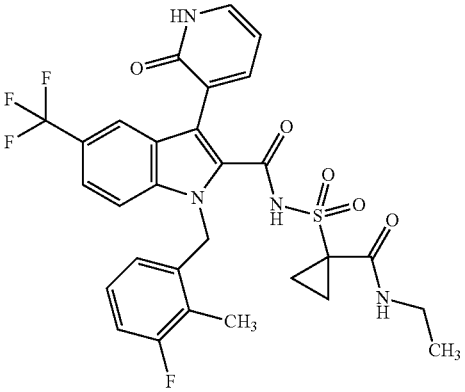 | 619.6 |
| 499 | 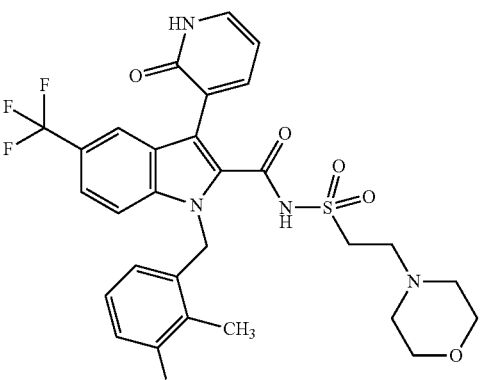 | 621.6 |
| 500 | 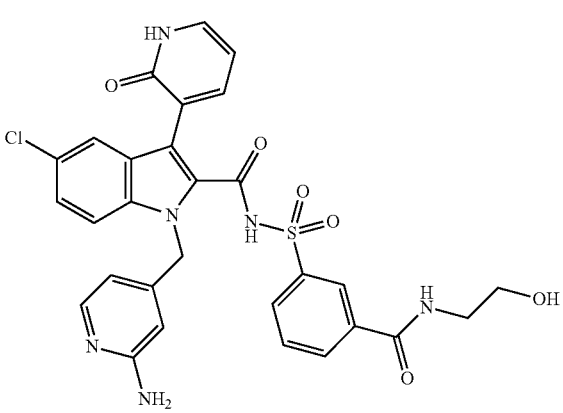 | 622.1 |
| 501 | 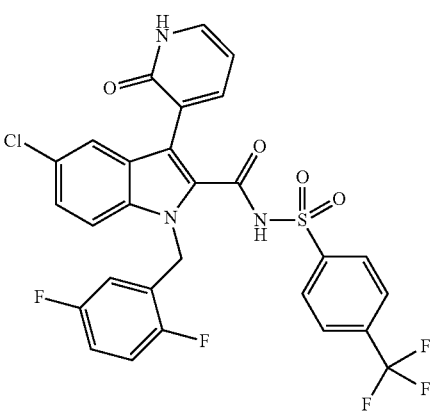 | 623.0 |

| Compound No. | STRUCTURE | M + H |
|---|---|---|
| 502 | 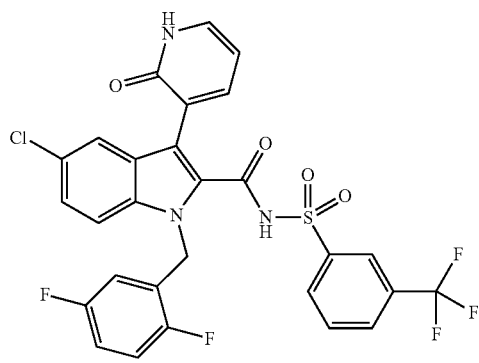 | 623.0 |
| 503 | 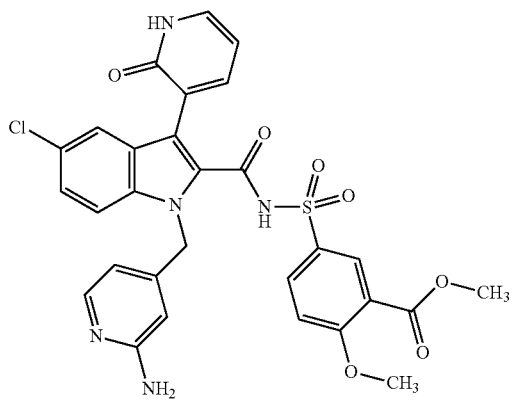 | 623.1 |
| 504 | 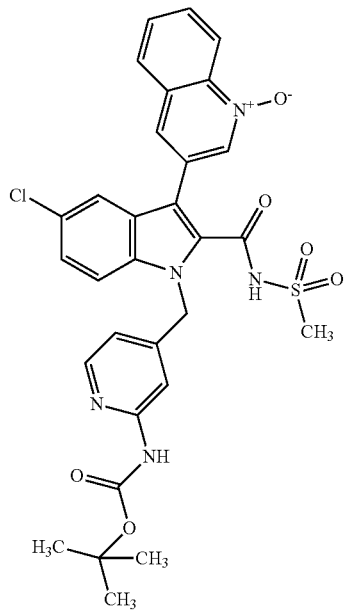 | 623.1 |

-continued
| Compound No. | STRUCTURE | M + H |
|---|---|---|
| 505 | 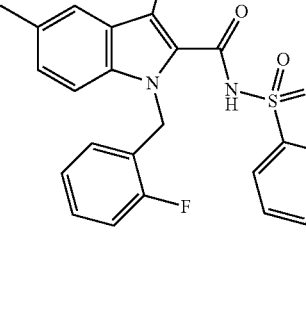 | 623.7 |
| 506 | 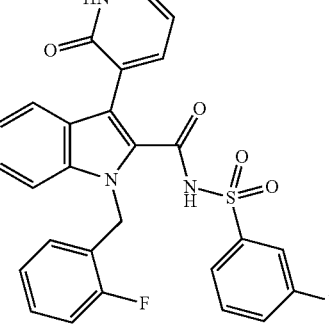 | 624.1 |
| 507 | 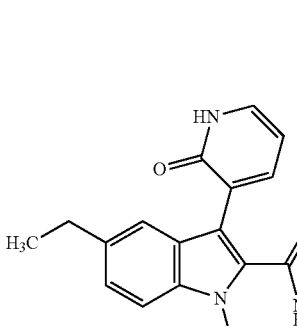 | 624.5 |
| 508 | 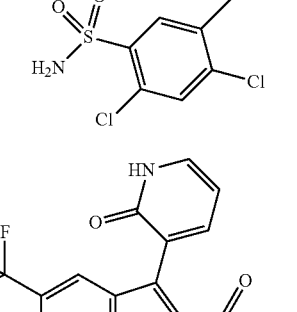 | 624.6 |

-continued
| Compound No. | STRUCTURE | M + H |
|---|---|---|
| 509 | 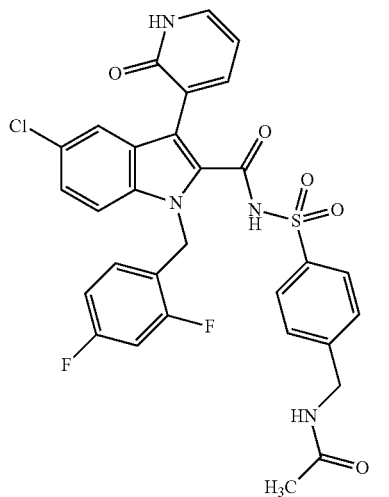 | 626.1 |
| 510 | 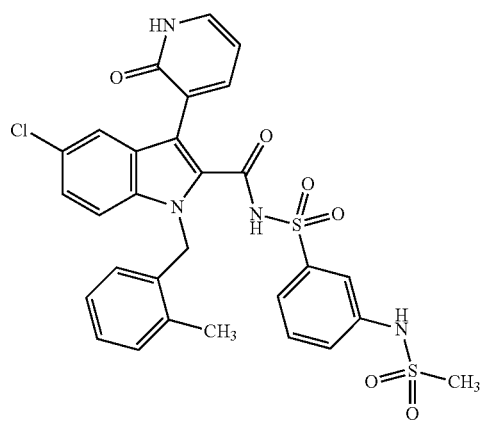 | 626.1 |
| 511 | 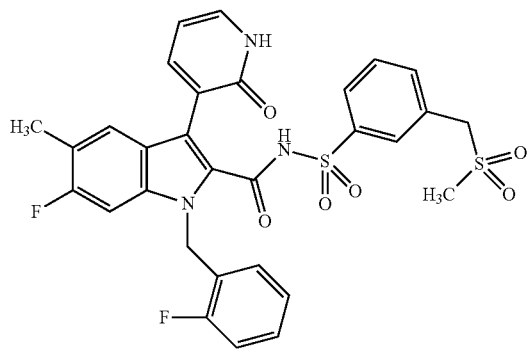 | 626.7 |

| Compound No. | STRUCTURE | M + H |
|---|---|---|
| 512 | 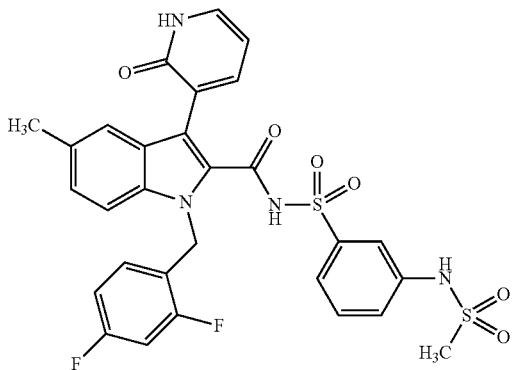 | 627.7 |
| 513 | 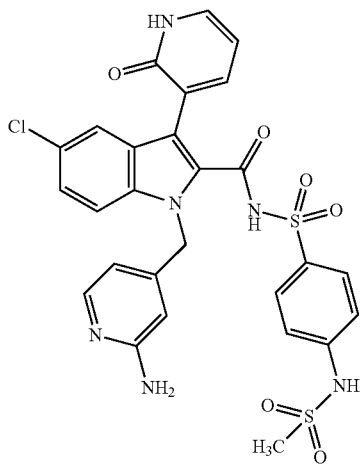 | 628.1 |
| 514 | 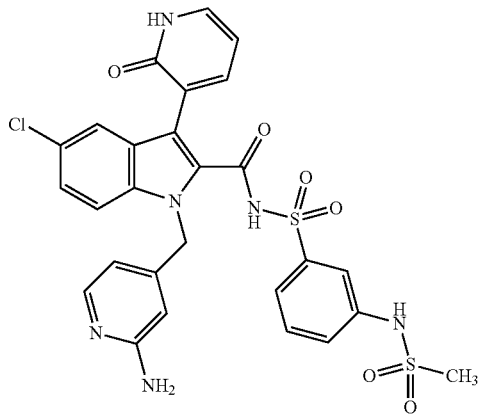 | 628.1 |

-continued
| Compound No. | STRUCTURE | M + H |
|---|---|---|
| 515 | 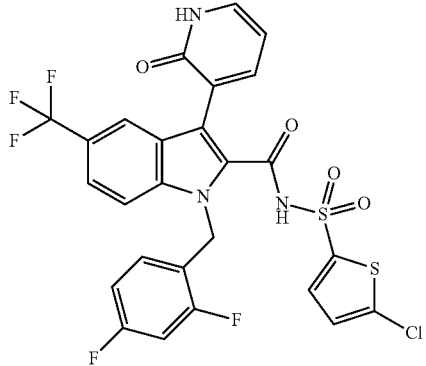 | 629.0 |
| 516 | 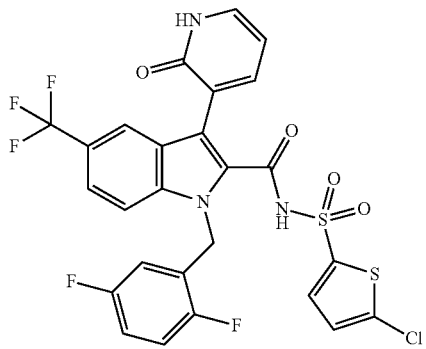 | 629.0 |
| 517 | 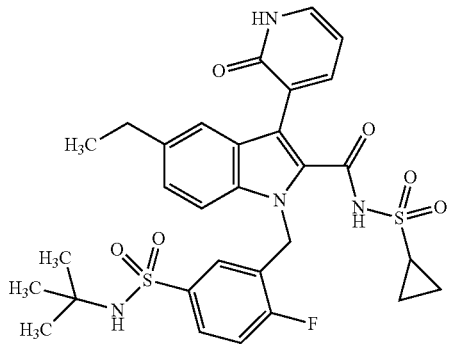 | 629.7 |
| 518 | 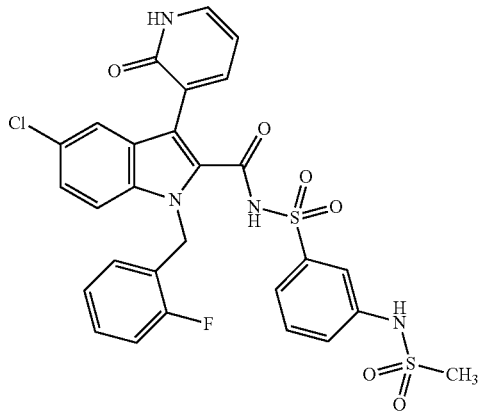 | 630.1 |

-continued

| Compound No. | STRUCTURE | M + H |
|---|---|---|
| 519 | 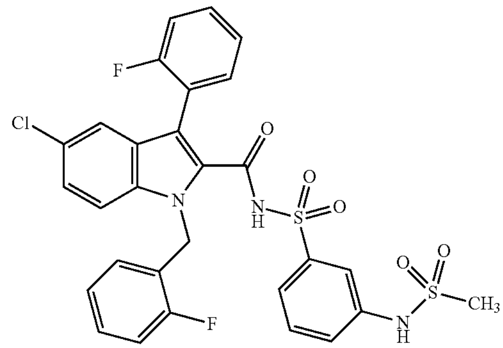 | 631.1 |
| 520 | 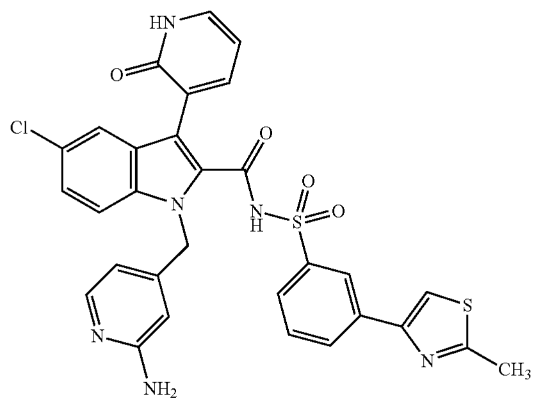 | 632.1 |
| 521 | 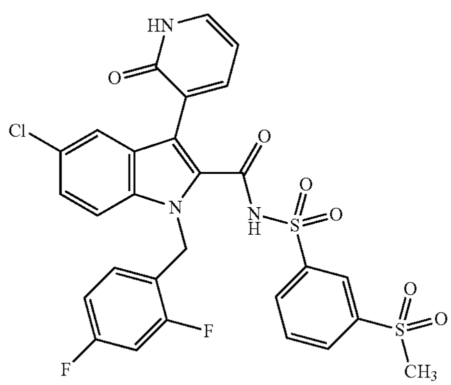 | 633.1 |
| 522 | 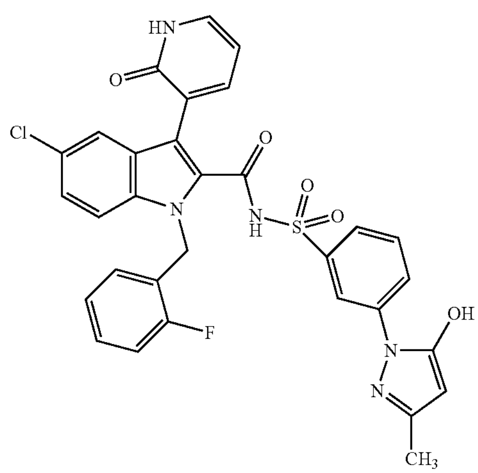 | 633.1 |

-continued

| Compound No. | STRUCTURE | M + H |
|---|---|---|
| 523 | 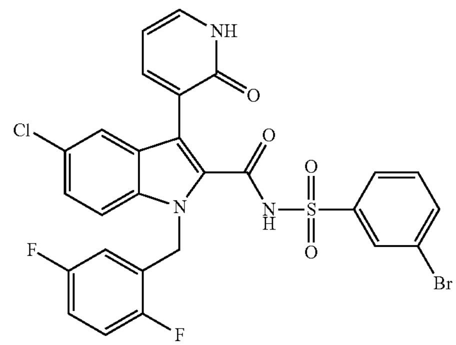 | 633.9 |
| 524 | 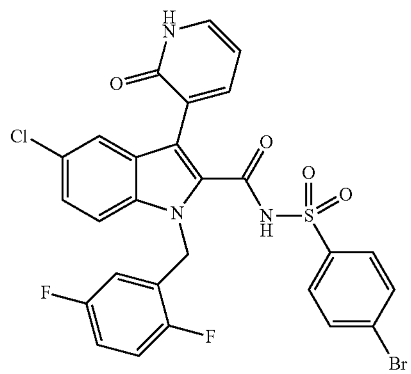 | 633.9 |
| 525 | 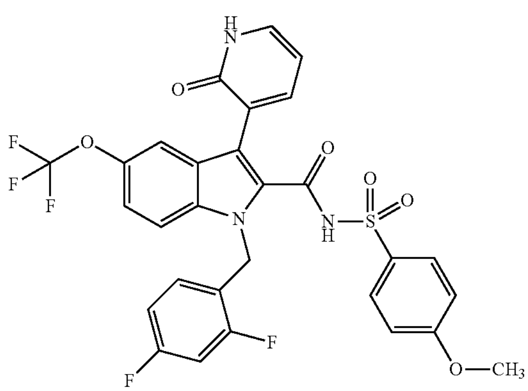 | 634.6 |
| 526 | 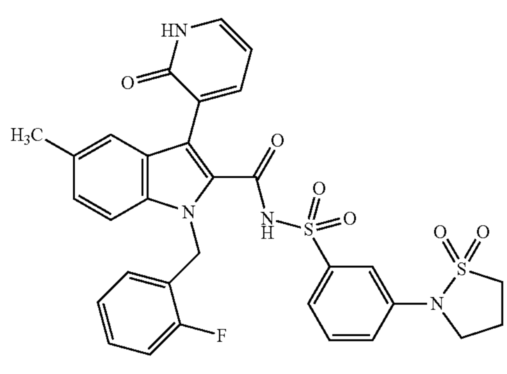 | 635.7 |

-continued
| Compound No. | STRUCTURE | M + H |
|---|---|---|
| 527 | 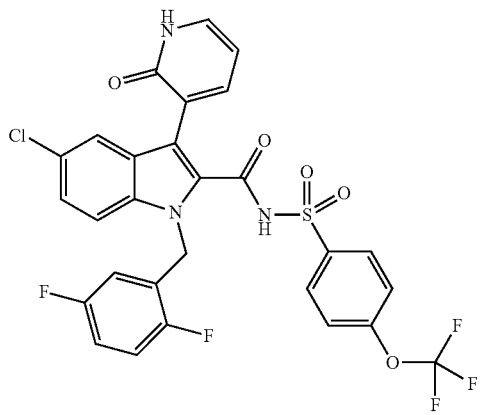 | 639.0 |
| 528 | 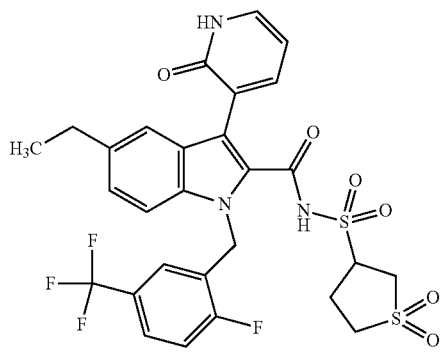 | 640.6 |
| 529 | 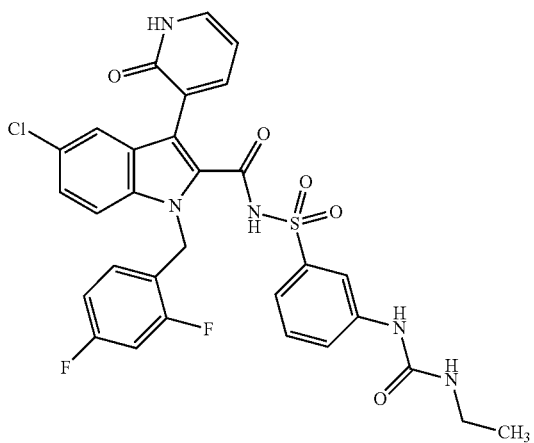 | 641.1 |

-continued

| Compound No. | STRUCTURE | M + H |
|---|---|---|
| 530 | 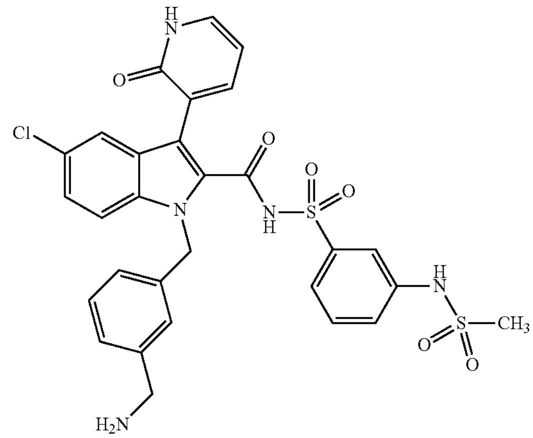 | 641.1 |
| 531 | 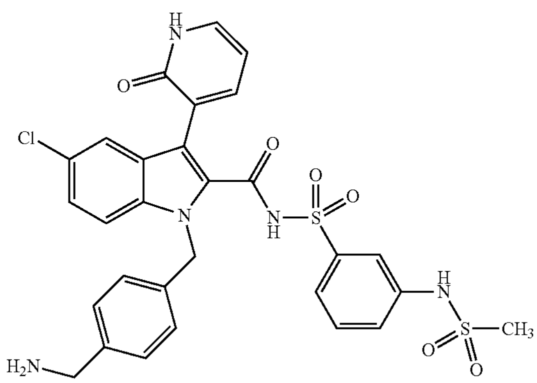 | 641.1 |
| 532 | 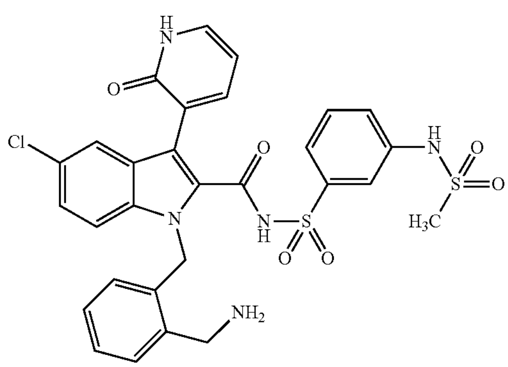 | 641.1 |
| 533 | 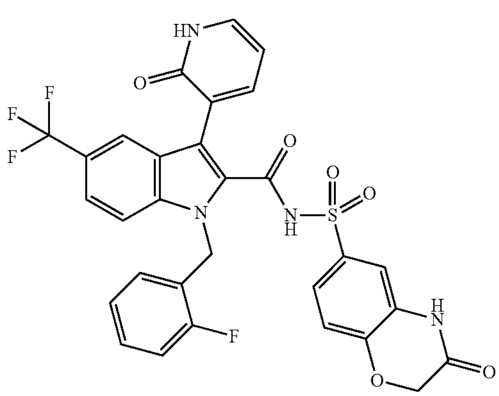 | 641.6 |

-continued

| Compound No. | STRUCTURE | M + H |
|---|---|---|
| 534 | 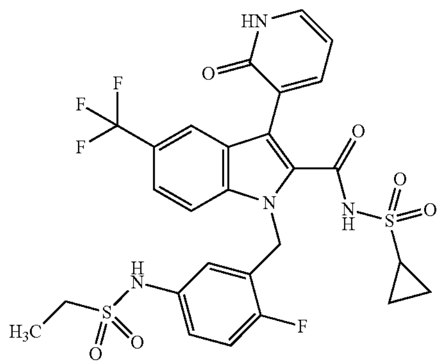 | 641.6 |
| 535 | 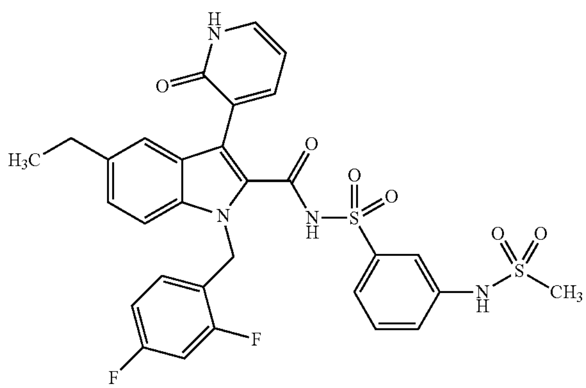 | 641.7 |
| 536 | 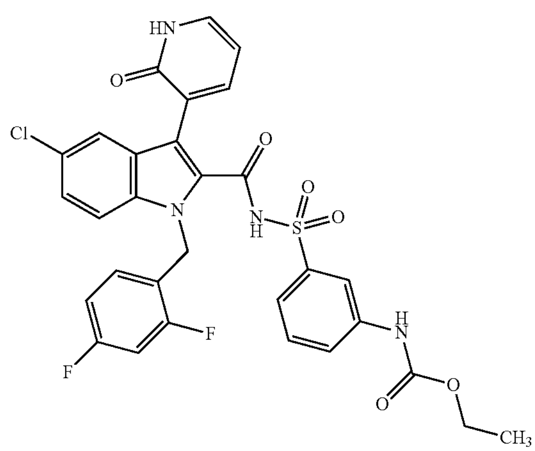 | 642.1 |
| 537 | 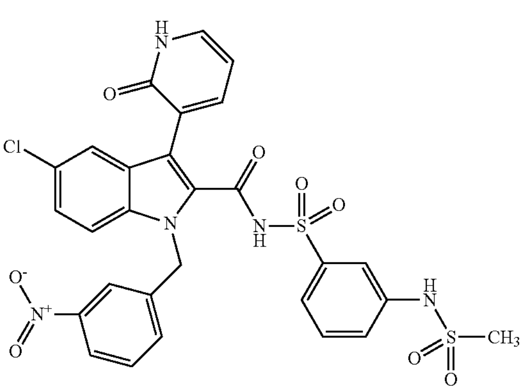 | 643.1 |

| Compound No. | STRUCTURE | M + H |
|---|---|---|
| 538 | 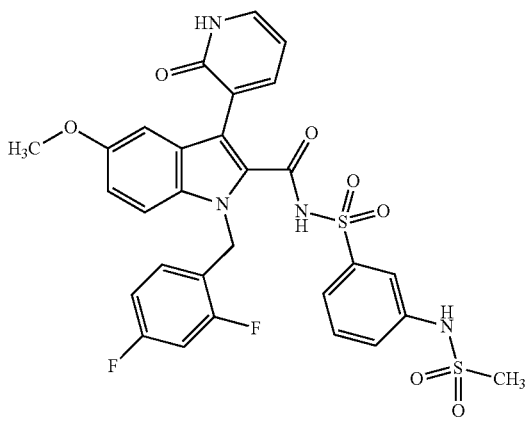 | 643.7 |
| 539 | 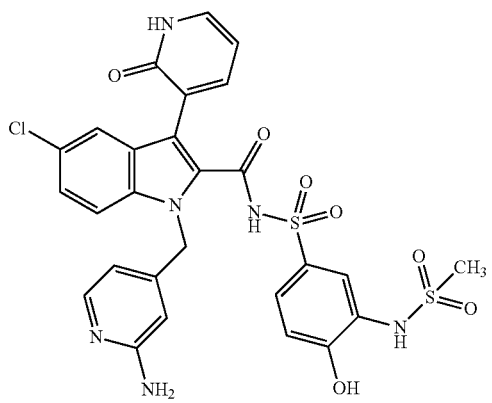 | 644.1 |
| 540 | 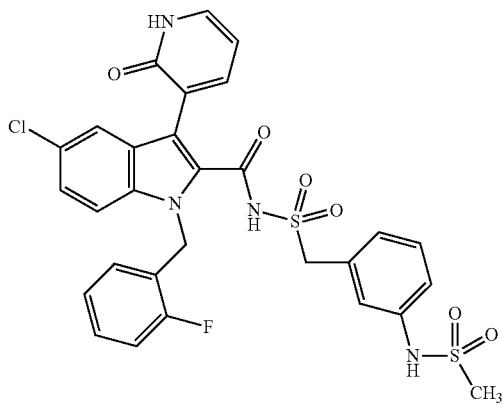 | 644.1 |

-continued

| Compound No. | STRUCTURE | M + H |
|---|---|---|
| 541 | 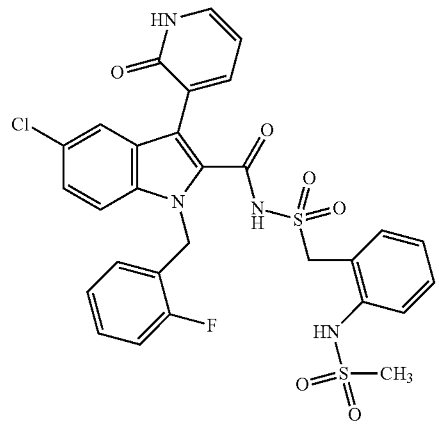 | 644.1 |
| 542 | 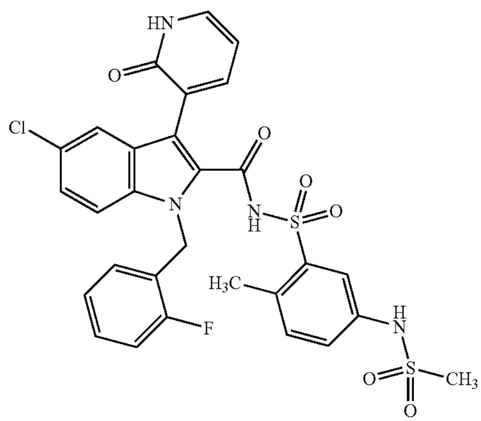 | 644.1 |
| 543 | 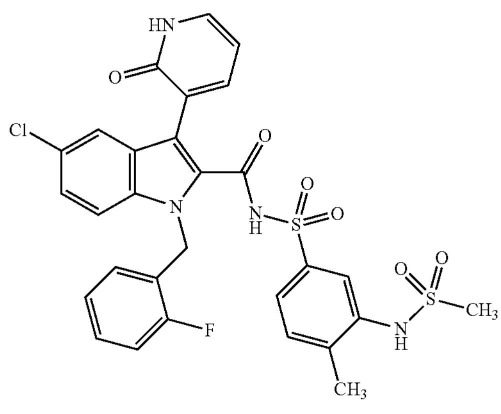 | 644.1 |
| 544 | 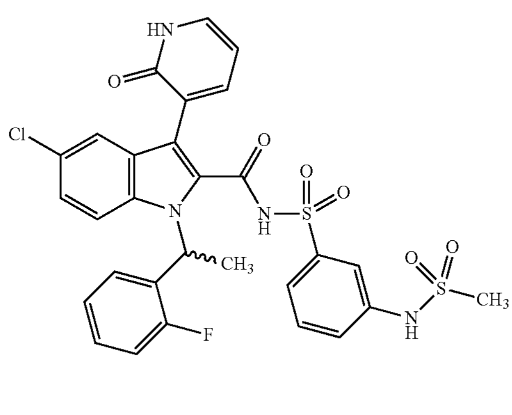 | 644.1 |

| Compound No. | STRUCTURE | M + H |
|---|---|---|
| 545 | 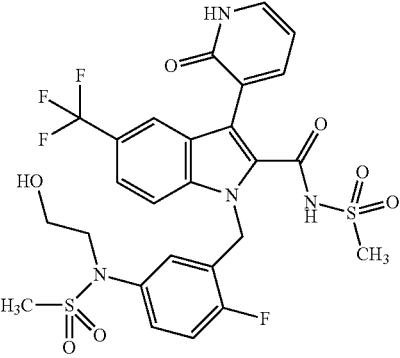 | 645.6 |
| 546 | 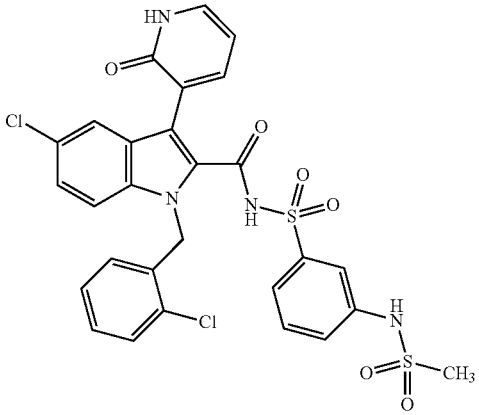 | 646.5 |
| 547 | 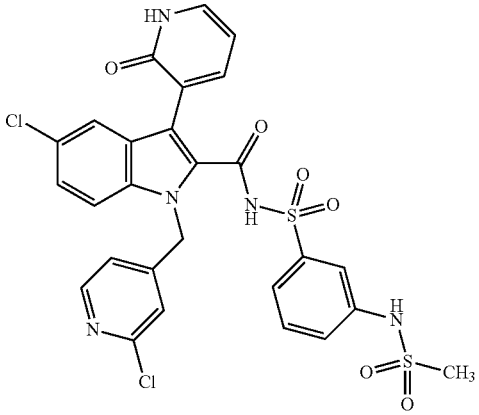 | 647.5 |

| Compound No. | STRUCTURE | M + H |
|---|---|---|
| 548 | 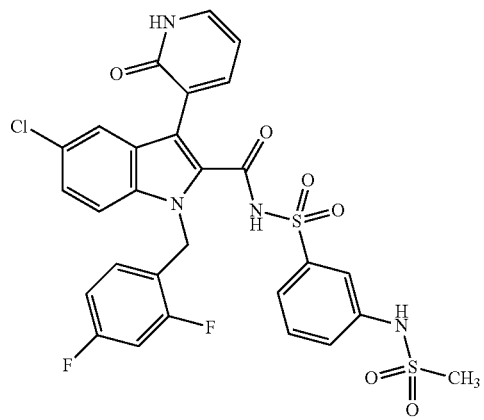 | 648.1 |
| 549 | 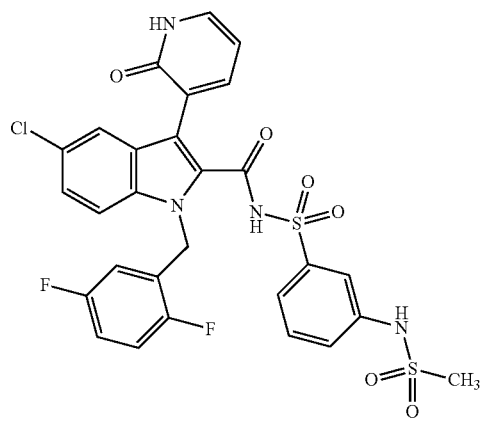 | 648.1 |
| 550 | 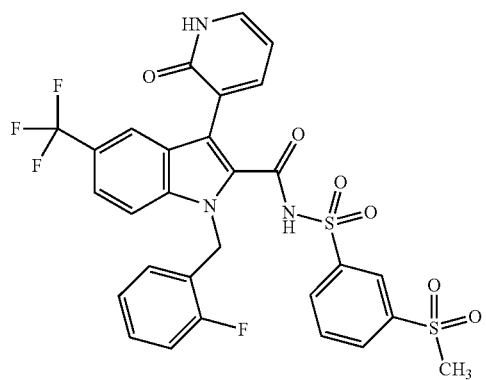 | 648.6 |

-continued

| Compound No. | STRUCTURE | M + H |
|---|---|---|
| 551 | 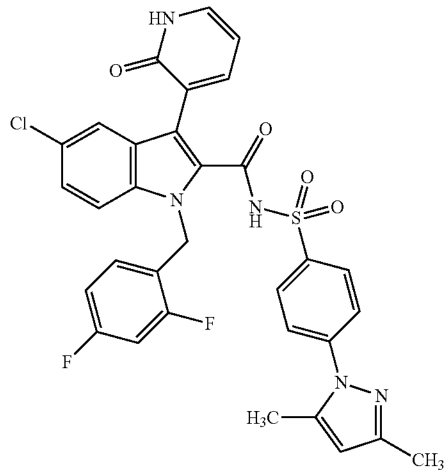 | 649.1 |
| 552 | 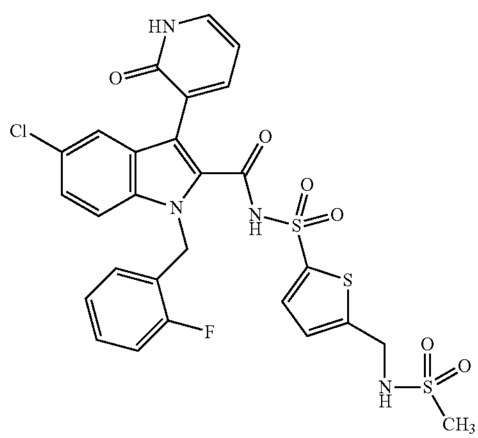 | 650.1 |
| 553 | 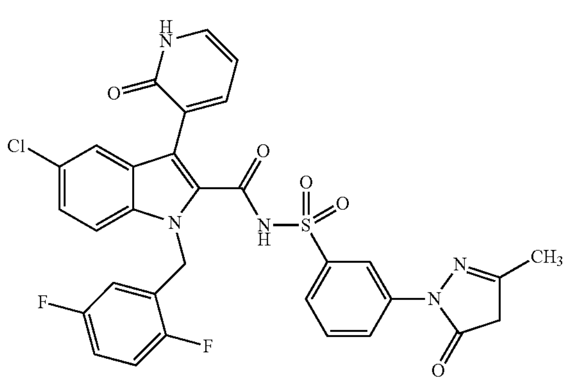 | 651.1 |

| Compound No. | STRUCTURE | M + H |
|---|---|---|
| 554 | 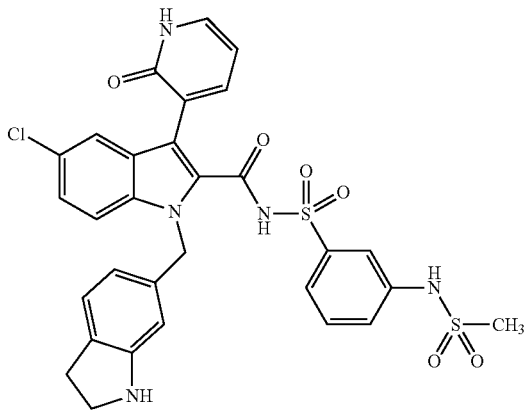 | 653.2 |
| 555 | 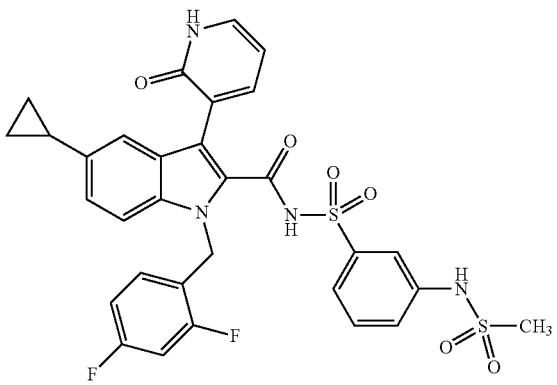 | 653.7 |
| 556 | 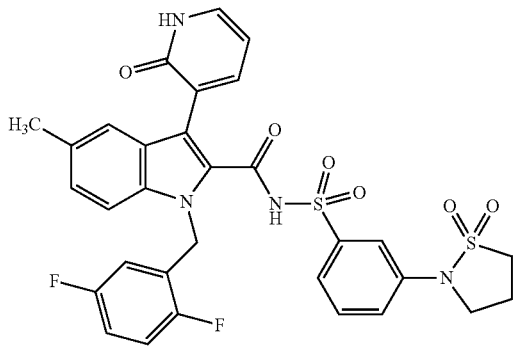 | 653.7 |

US 8,143,305 B2
389                                                                                     390
-continued
| Compound No. | STRUCTURE | M + H |
|---|---|---|
| 557 | 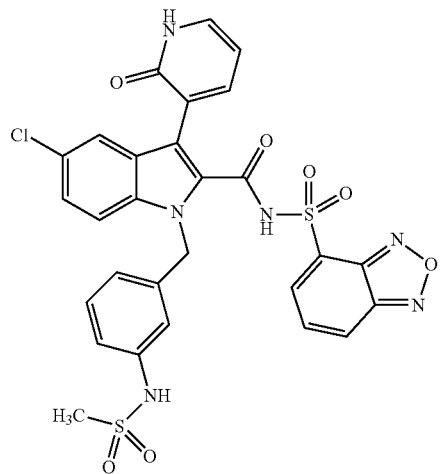 | 654.1 |
| 558 | 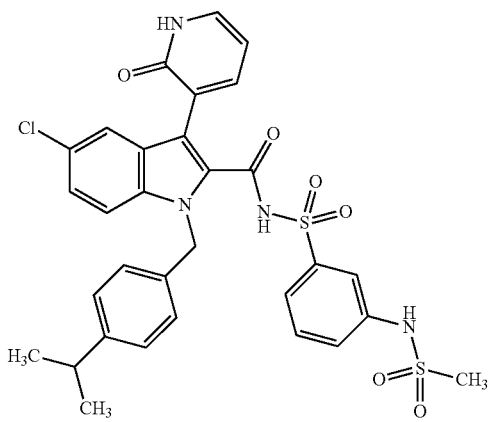 | 654.2 |
| 559 | 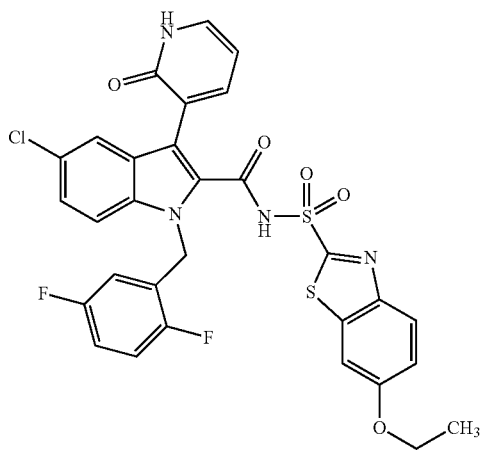 | 656.1 |

-continued
| Compound No. | STRUCTURE | M + H |
|---|---|---|
| 560 | 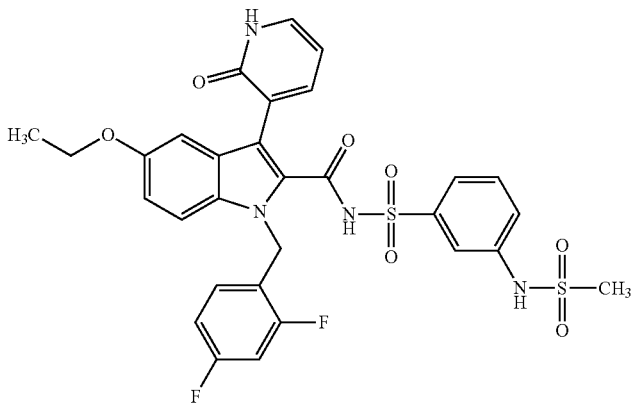 | 657.7 |
| 561 | 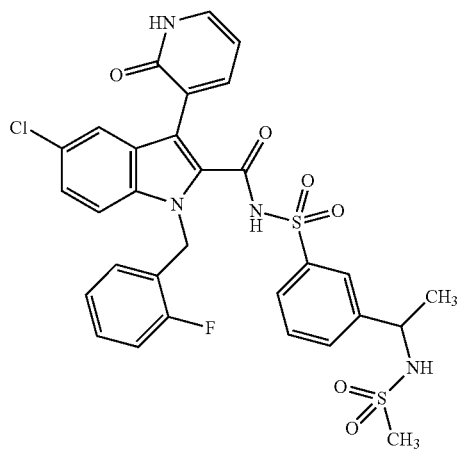 | 658.1 |
| 562 | 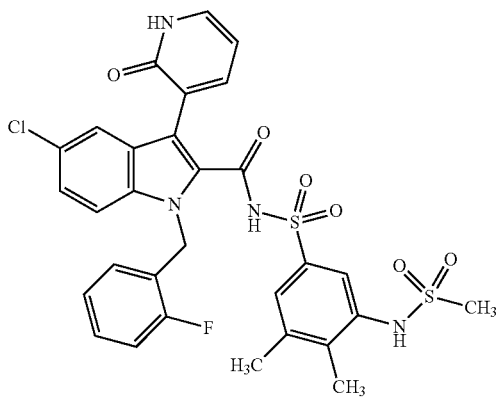 | 658.1 |

-continued

| Compound No. | STRUCTURE | M + H |
|---|---|---|
| 563 | 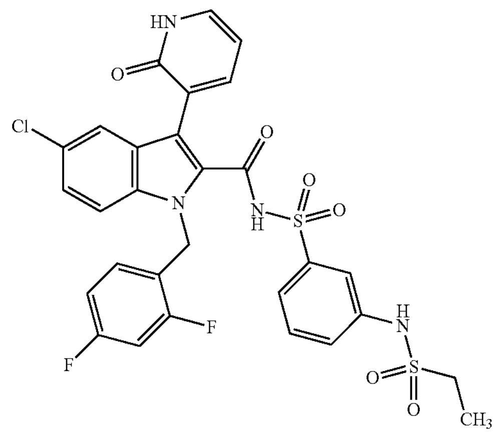 | 662.1 |
| 564 | 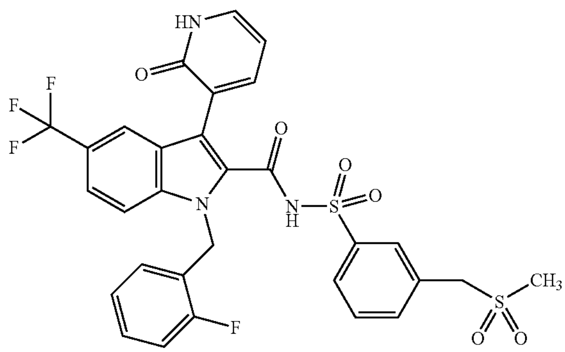 | 662.7 |
| 565 | 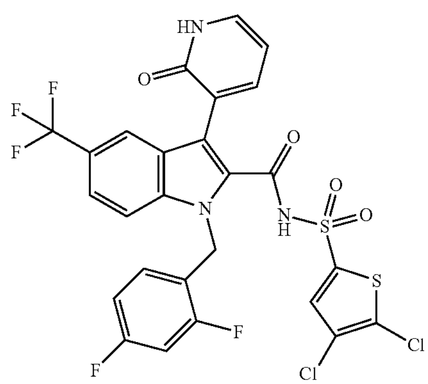 | 663.4 |
| 566 | 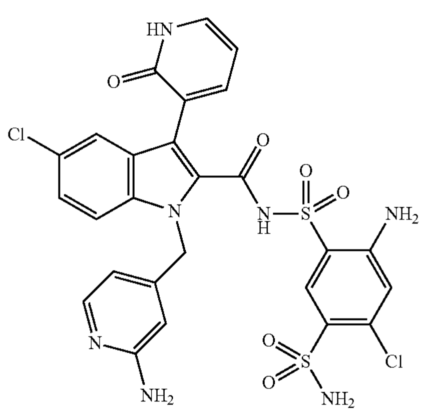 | 663.5 |

| Compound No. | STRUCTURE | M + H |
|---|---|---|
| 567 | 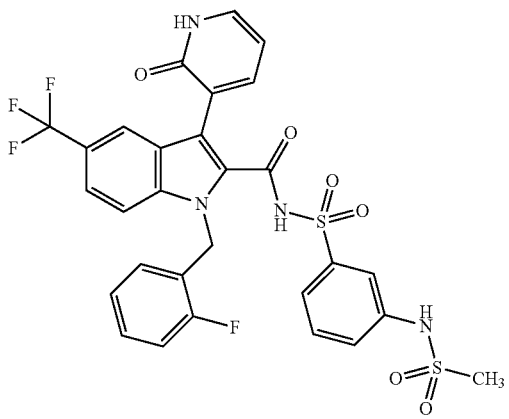 | 663.6 |
| 568 | 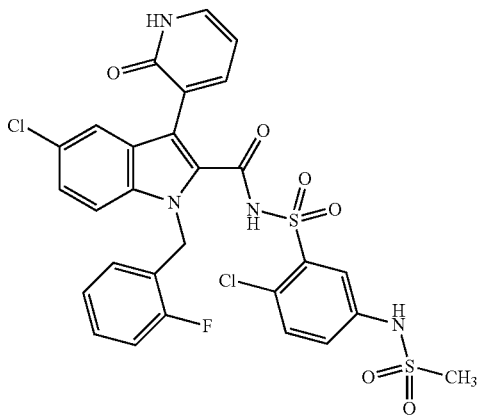 | 664.5 |
| 569 | 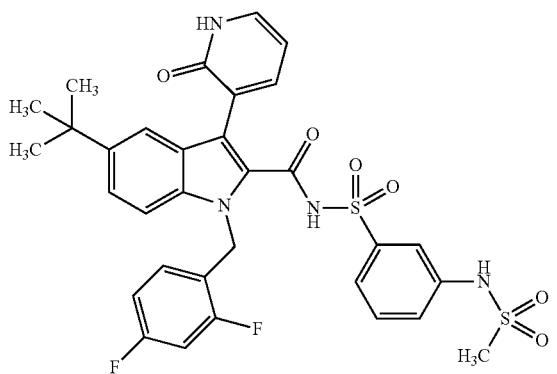 | 669.7 |

-continued
| Compound No. | STRUCTURE | M + H |
|---|---|---|
| 570 | 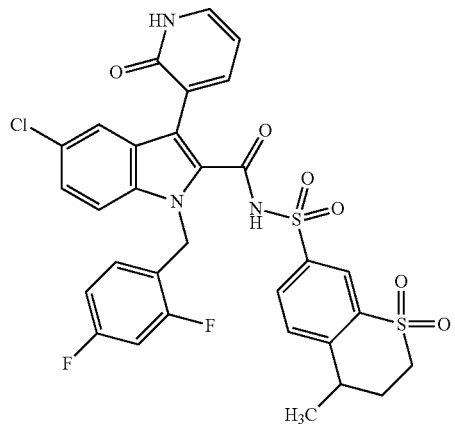 | 673.1 |
| 571 | 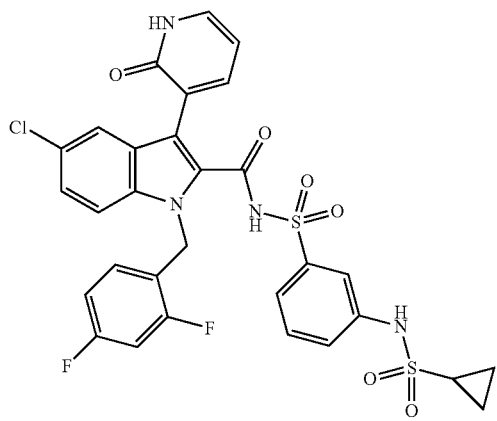 | 674.1 |
| 572 | 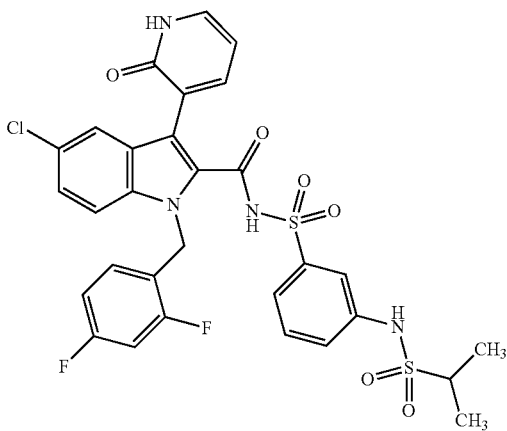 | 676.1 |

-continued
| Compound No. | STRUCTURE | M + H |
|---|---|---|
| 573 | 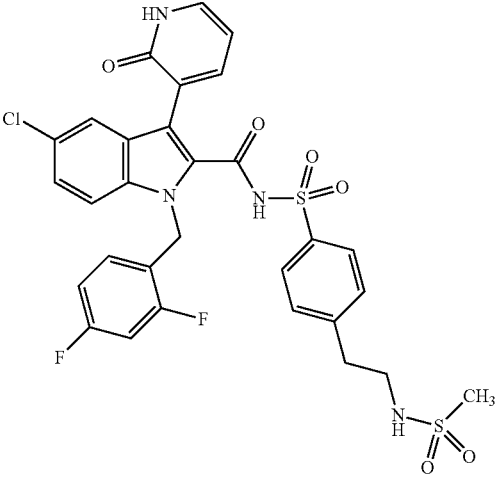 | 676.1 |
| 574 | 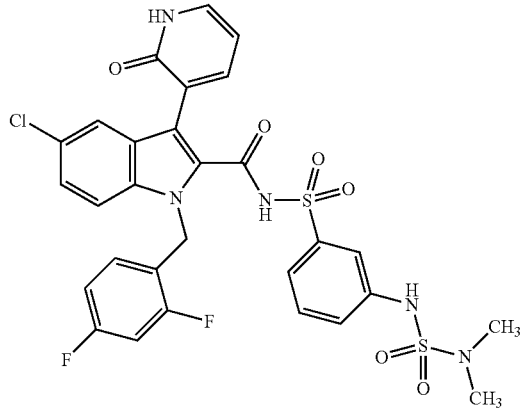 | 677.1 |
| 575 | 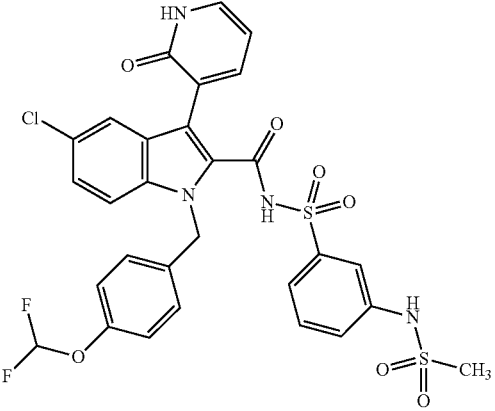 | 678.1 |

| Compound No. | STRUCTURE | M + H |
|---|---|---|
| 576 | 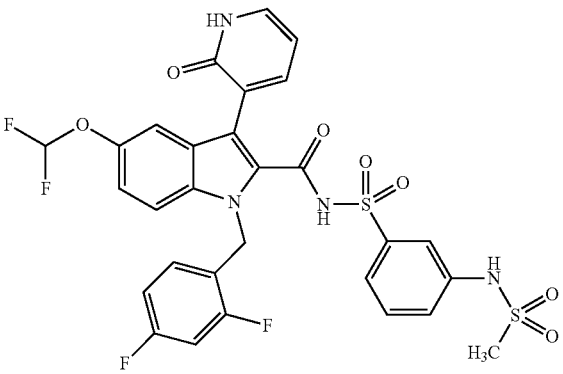 | 679.6 |
| 577 | 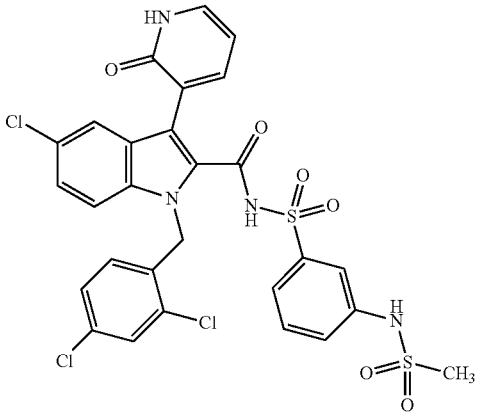 | 681.0 |
| 578 | 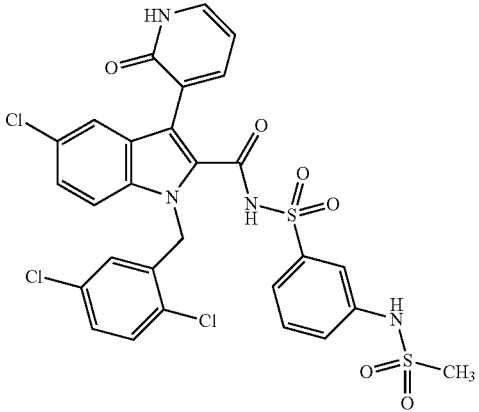 | 681.0 |

-continued
| Compound No. | STRUCTURE | M + H |
|---|---|---|
| 579 | 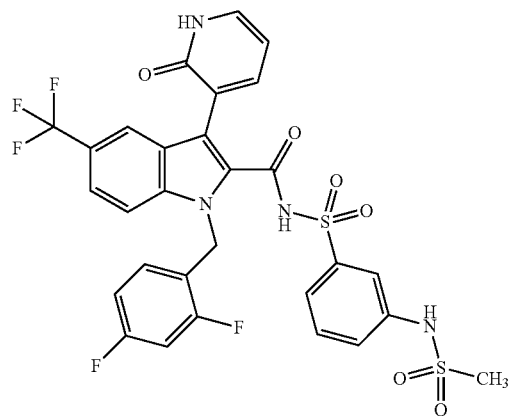 | 681.6 |
| 580 | 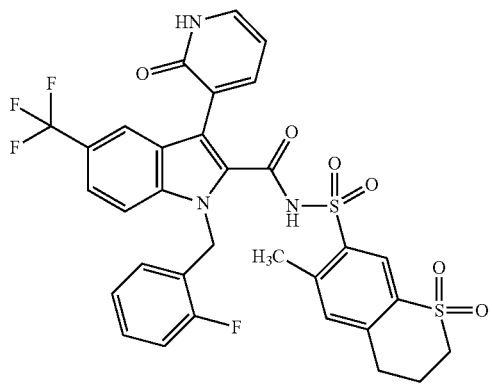 | 688.7 |
| 581 | 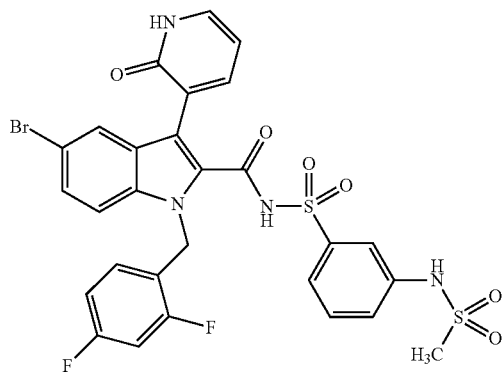 | 692.5 |

-continued
| Compound No. | STRUCTURE | M + H |
|---|---|---|
| 582 | 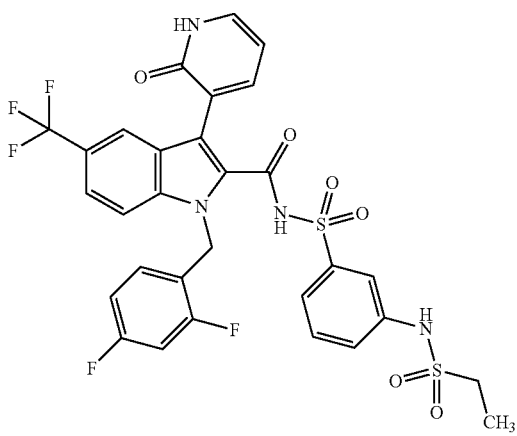 | 695.7 |
| 583 | 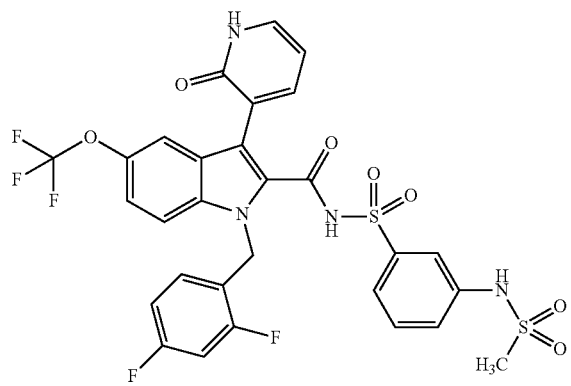 | 697.6 |
| 584 | 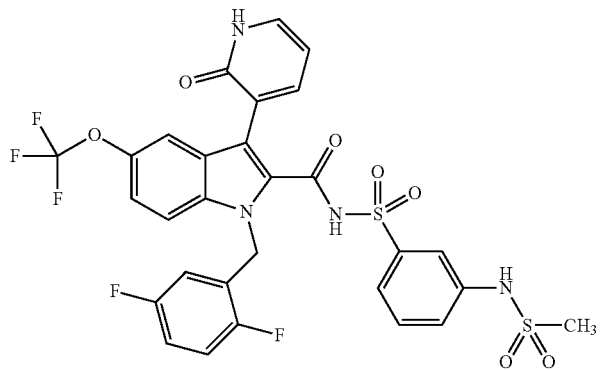 | 697.6 |

-continued
| Compound No. | STRUCTURE | M + H |
|---|---|---|
| 585 | 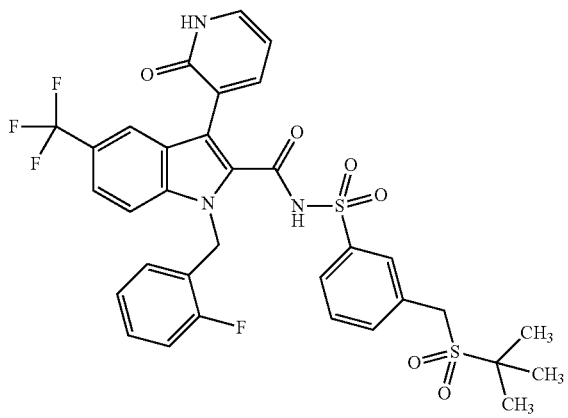 | 704.7 |
| 586 | 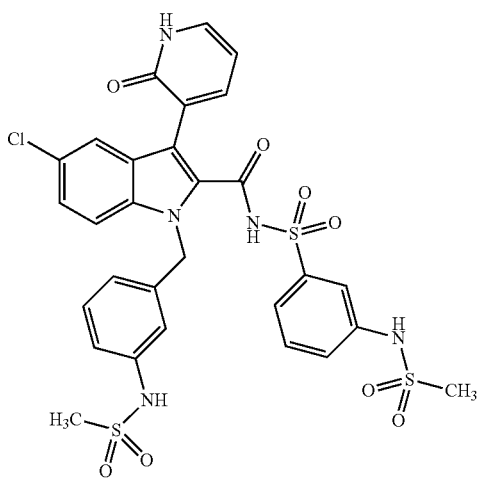 | 705.2 |
| 587 | 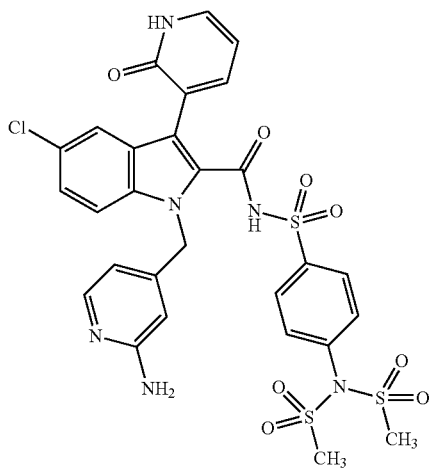 | 706.2 |

-continued
| Compound No. | STRUCTURE | M + H |
|---|---|---|
| 588 | 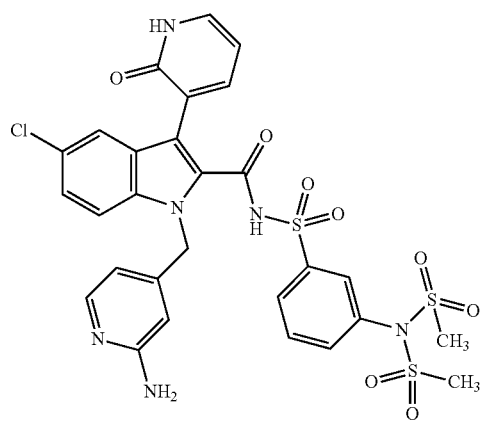 | 706.2 |
| 589 | 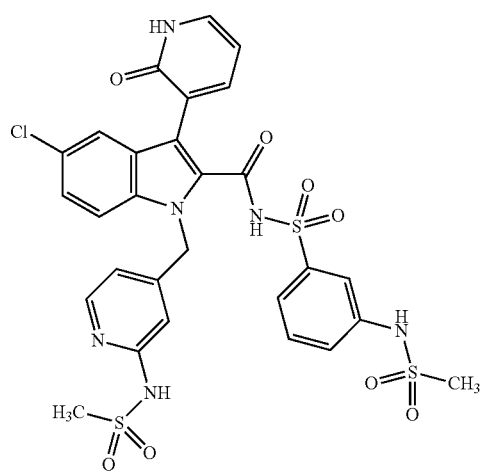 | 706.2 |
| 590 | 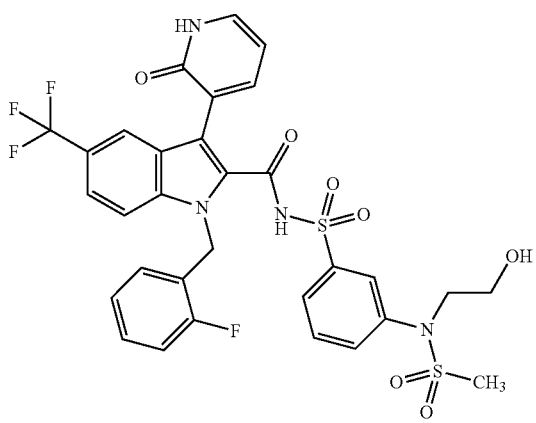 | 707.7 |

-continued

| Compound No. | STRUCTURE | M + H |
|---|---|---|
| 591 | 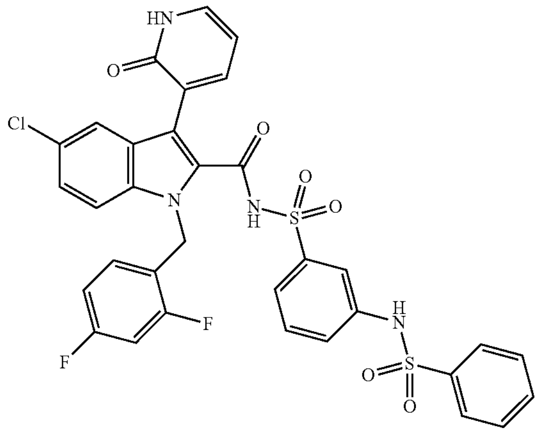 | 710.2 |
| 592 | 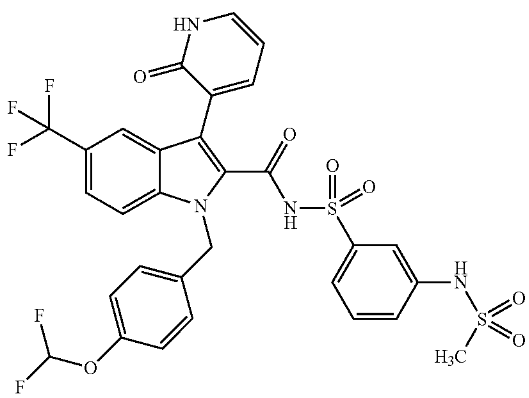 | 711.7 |
| 593 | 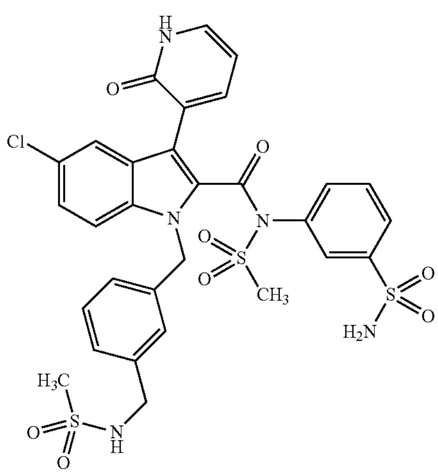 | 719.2 |

| Compound No. | STRUCTURE | M + H |
|---|---|---|
| 594 | 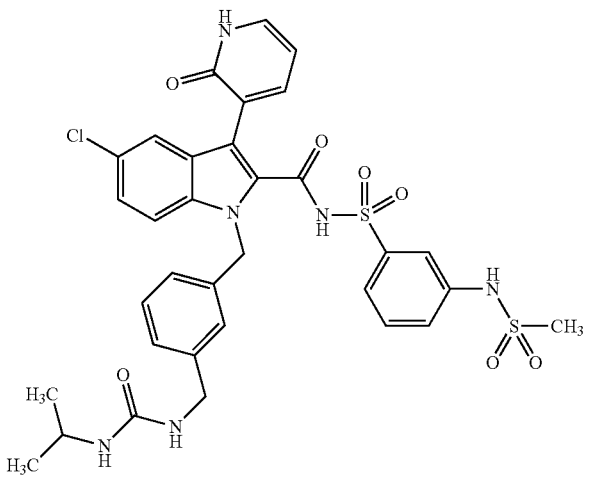 | 726.2 |
| 595 | 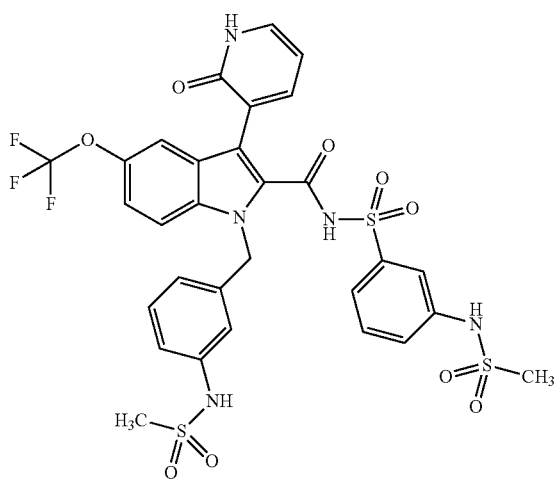 | 754.8 |
| 596 | 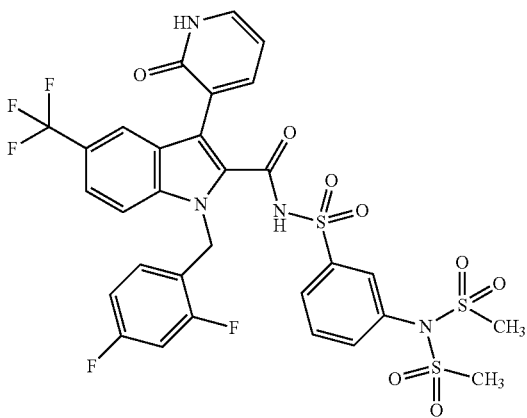 | 759.7 |

| Compound No. | STRUCTURE | M + H |
| --- | --- | --- |
| 597 | 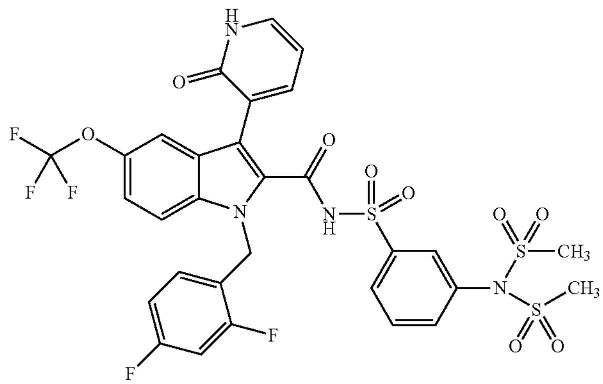 | 775.7 |
| 598 | 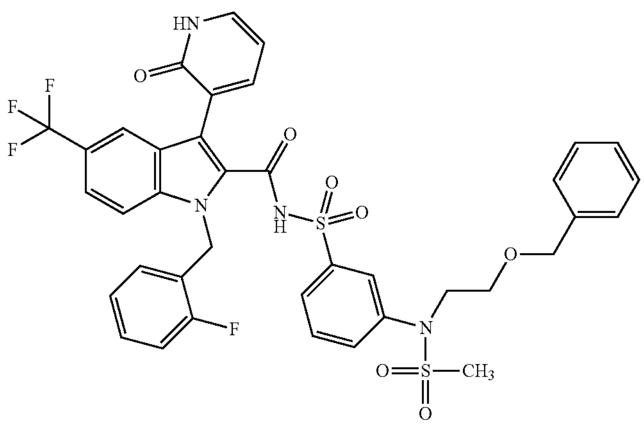 | 797.8 |
| 599 | 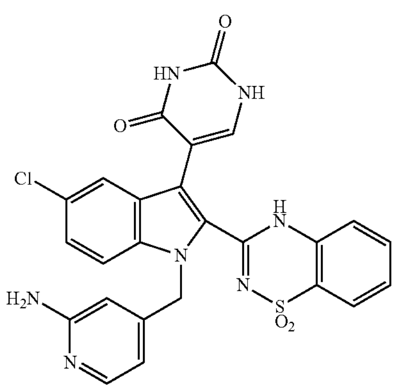 | 548.3 |
| 600 | 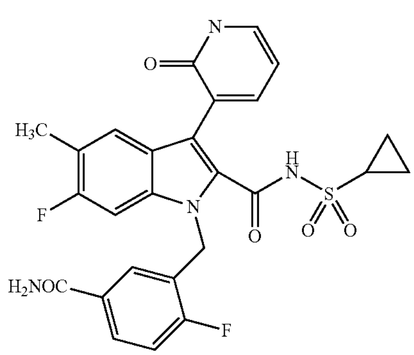 | 541.3 |

| Compound No. | STRUCTURE | M + H |
|---|---|---|
| 601 | 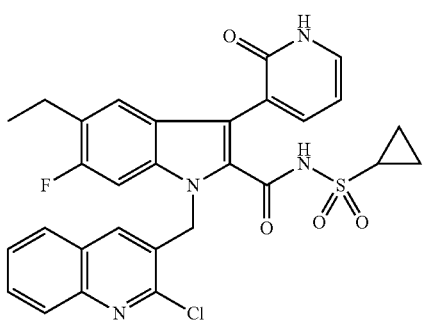 | NA |
| 602 | 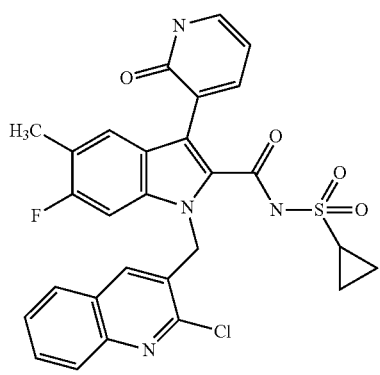 | 566.0 |
| 603 | 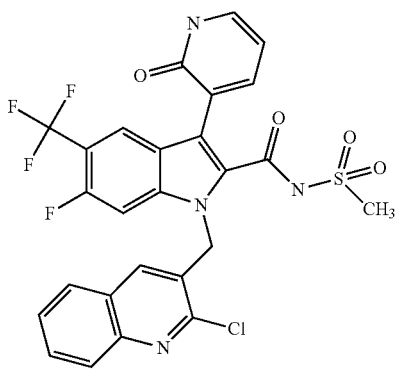 | 594.0 |
| 604 | 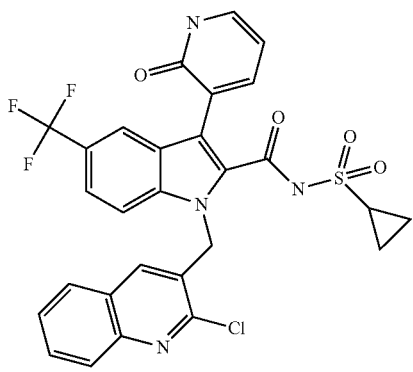 | 620.0 |

| Compound No. | STRUCTURE | M + H |
|---|---|---|
| 605 | 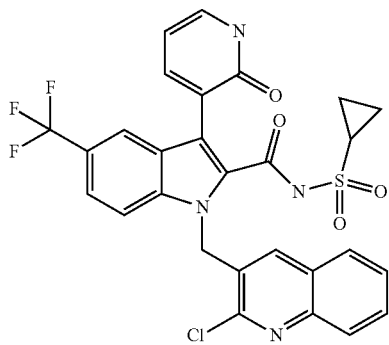 | 602.0 |
| 606 | 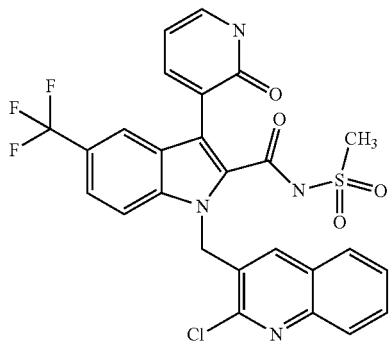 | 576.0 |
| 607 | 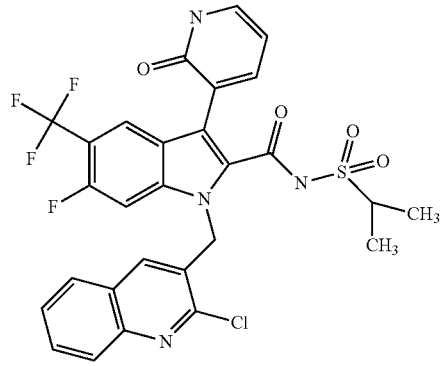 | 622.0 |
| 608 | 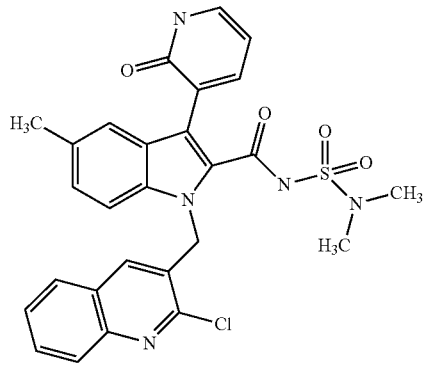 | 551.0 |

-continued
| Compound No. | STRUCTURE | M + H |
|---|---|---|
| 609 | 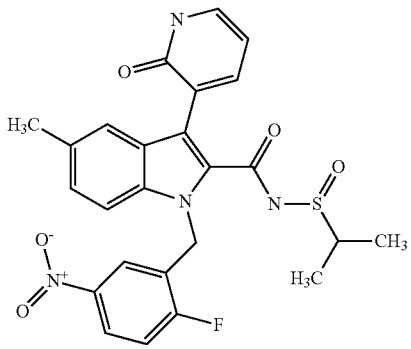 | 511.5 |
| 610 | 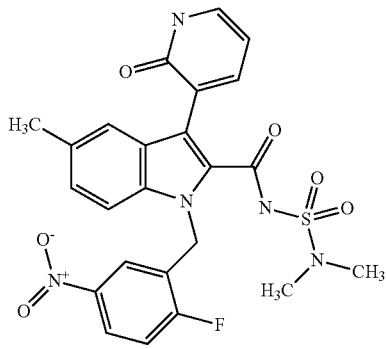 | 528.5 |
| 611 | 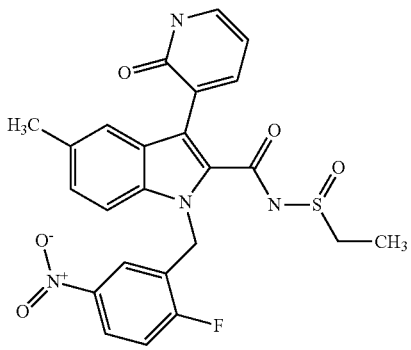 | 497.5 |
| 612 | 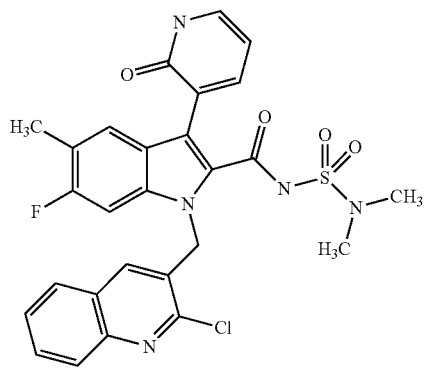 | 569.0 |

-continued
| Compound No. | STRUCTURE | M + H |
|---|---|---|
| 613 | 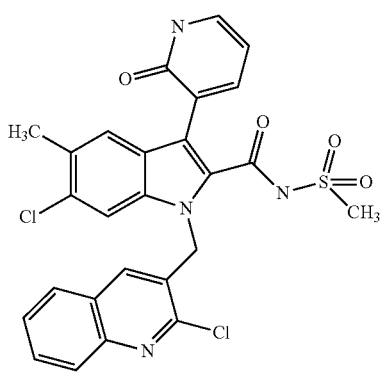 | 556.4 |
| 614 | 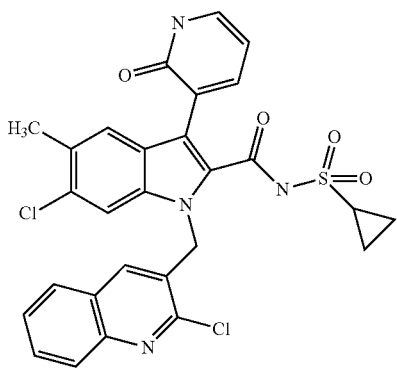 | 582.5 |
| 615 | 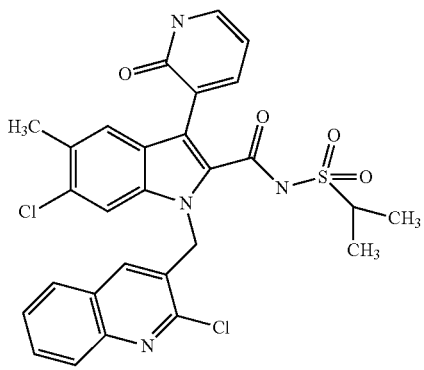 | 584.5 |
| 616 | 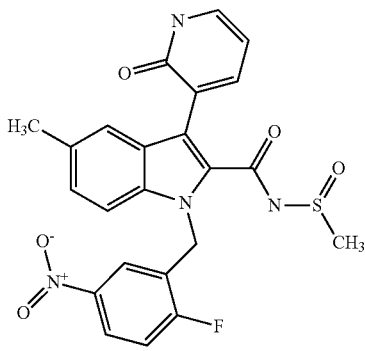 | 483.5 |

-continued

| Compound No. | STRUCTURE | M + H |
|---|---|---|
| 617 | 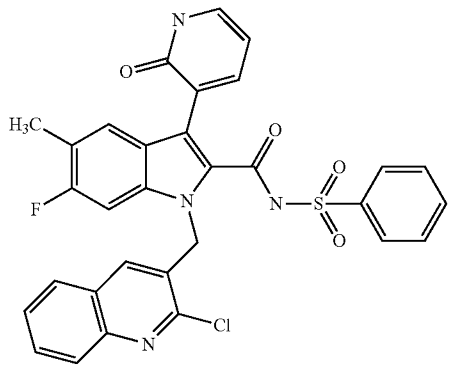 | 602.1 |
| 618 | 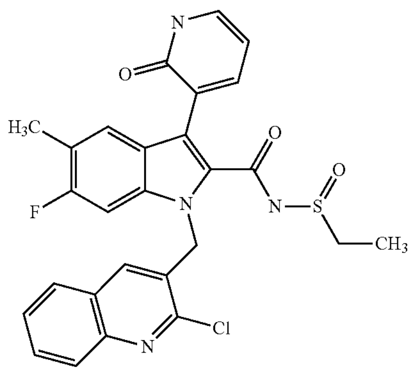 | 538.0 |
| 619 | 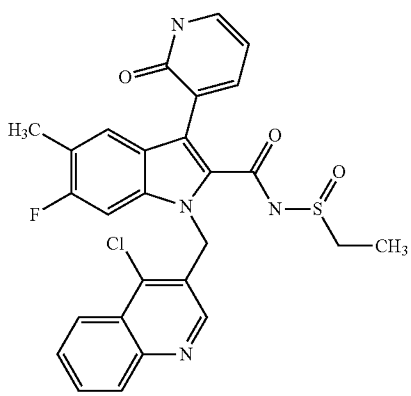 | 538.0 |
| 620 | 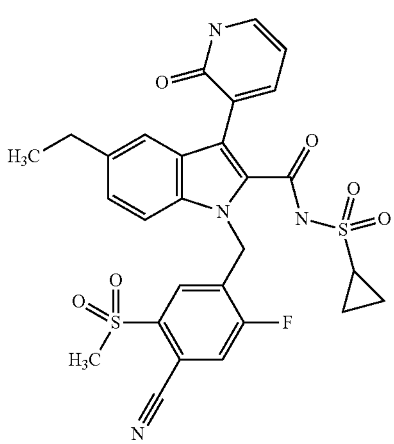 | 597.7 |

-continued
| Compound No. | STRUCTURE | M + H |
|---|---|---|
| 621 | 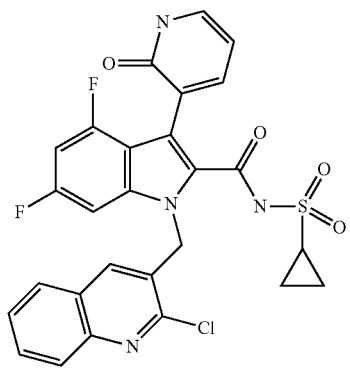 | 570.0 |
| 622 | 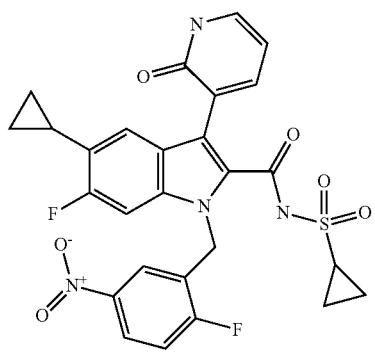 | 569.6 |
| 623 | 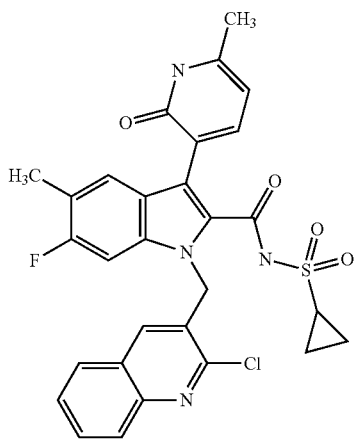 | 580.1 |
| 624 | 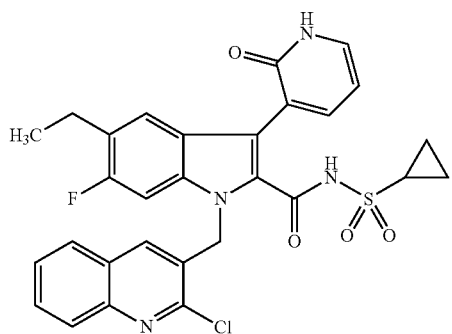 | 580.1 |

-continued
| Compound No. | STRUCTURE | M + H |
|---|---|---|
| 625 | 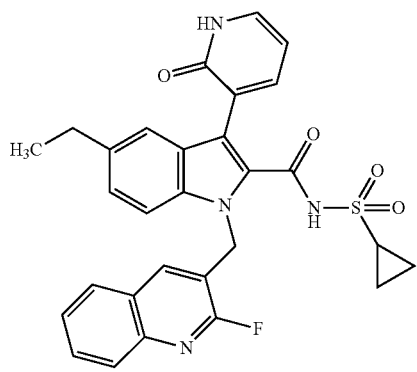 | 545.6 |
| 626 | 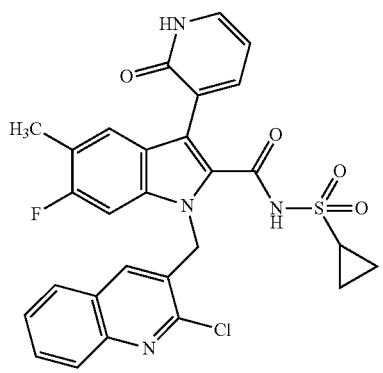 | 566.0 |
| 627 | 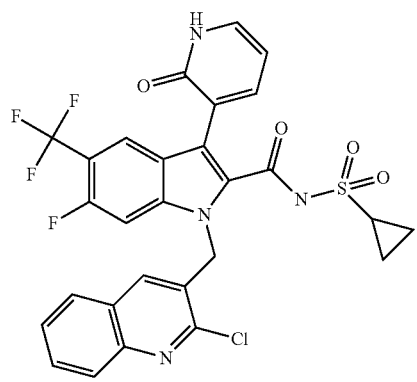 | 620.0 |
| 628 | 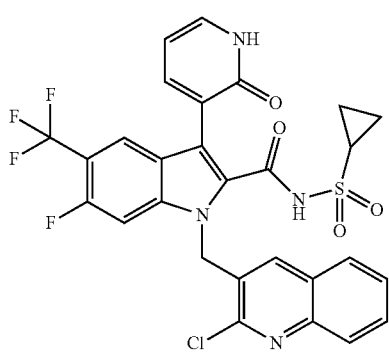 | 602.0 |

-continued

| Compound No. | STRUCTURE | M + H |
|---|---|---|
| 629 | 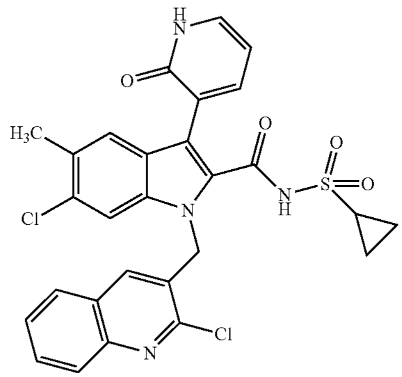 | 582.5 |
| 630 | 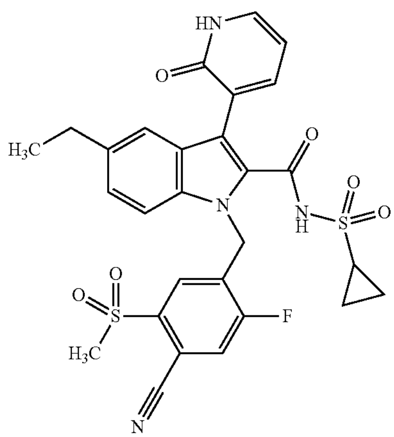 | 597.7 |
| 631 | 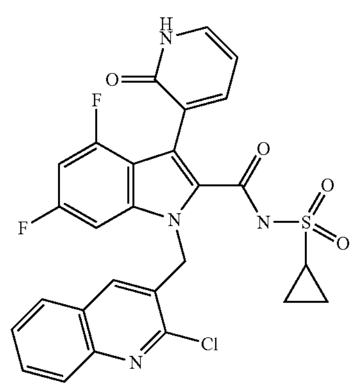 | 570.0 |
| 632 | 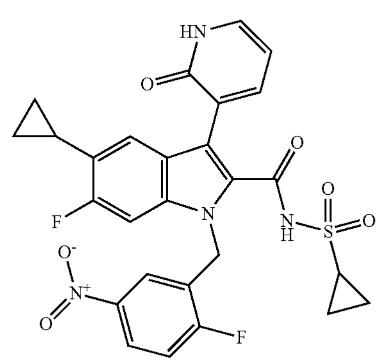 | 569.6 |

-continued
| Compound No. | STRUCTURE | M + H |
|---|---|---|
| 633 | 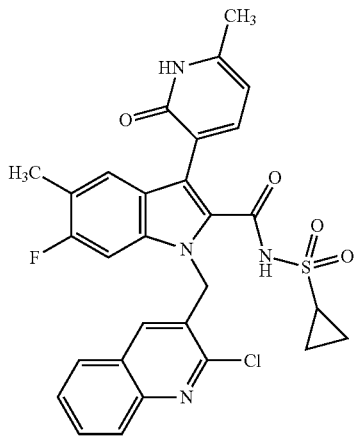 | 580.1 |
| 634 | 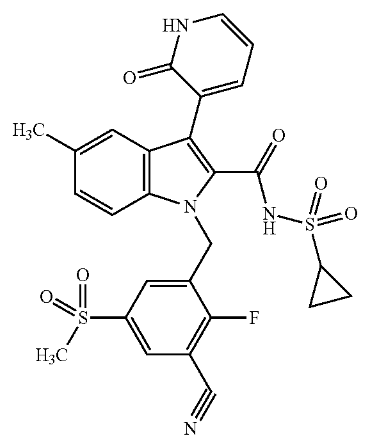 | 583.6 |
| 635 | 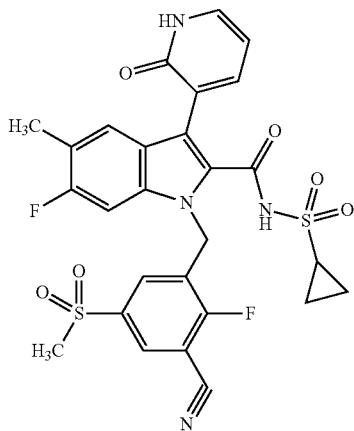 | 601.6 |

-continued
| Compound No. | STRUCTURE | M + H |
|---|---|---|
| 636 | 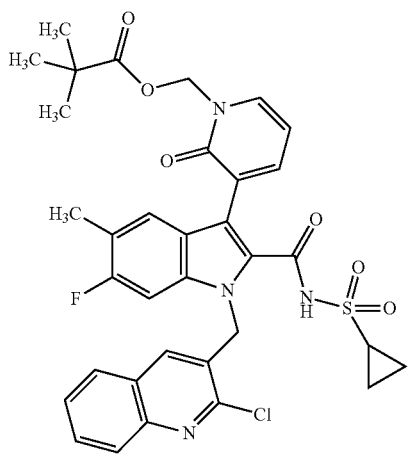 | 680.2 |
| 637 | 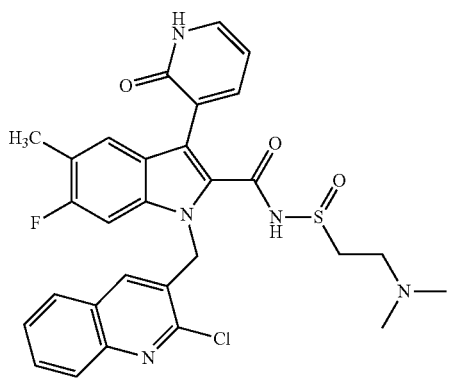 | NA |
| 638 | 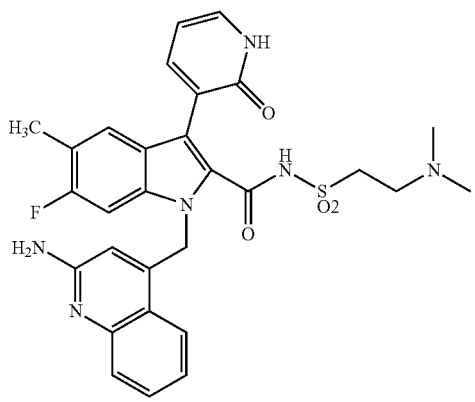 | NA |

-continued
| Compound No. | STRUCTURE | M + H |
|---|---|---|
| 639 | 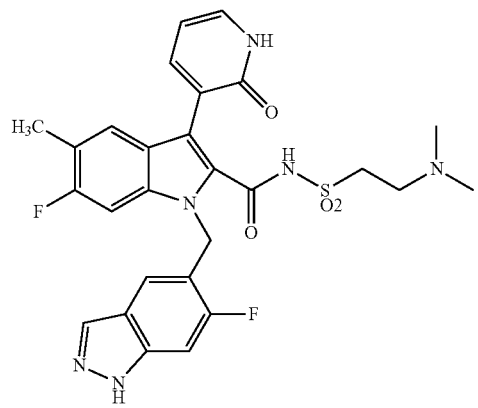 | NA |
| 640 | 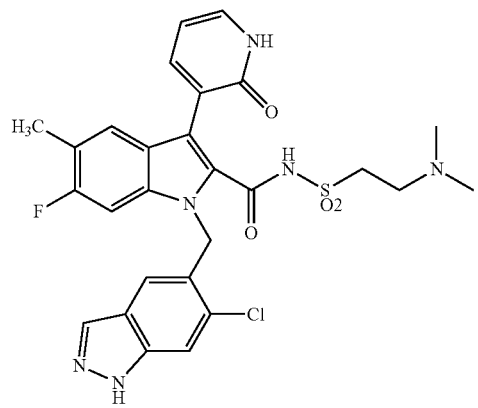 | NA |
| 641 | 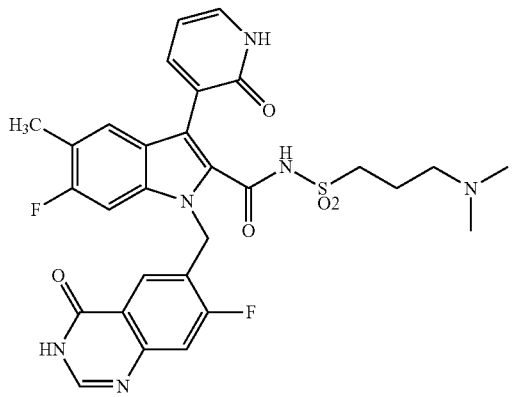 | NA |
NA = not available and pharmaceutically acceptable salts, solvates, esters and prodrugs thereof.

Methods for Making the 2,3-Substituted Indole Derivatives

Methods useful for making the 2,3-Substituted Indole Derivatives are set forth in the Examples below and generalized in Schemes 1-6. Examples of commonly known methodologies useful for the synthesis of indoles are set forth, for example, in G. R. Humphrey and J. T. Kuethe, *Chemical Reviews* 106:2875-2911, 2006.

Scheme 1 shows a method useful for making compounds of formula iv, which are useful intermediates for making the 2,3-Substituted Indole Derivatives.

Scheme 1

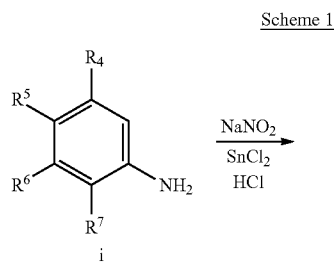

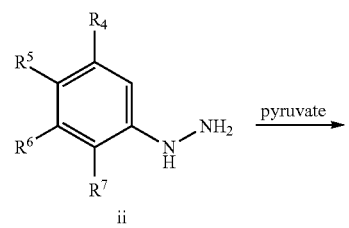

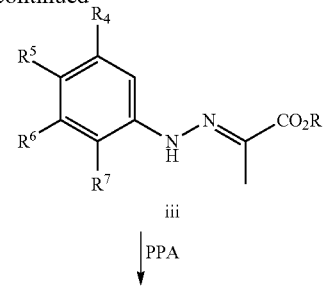

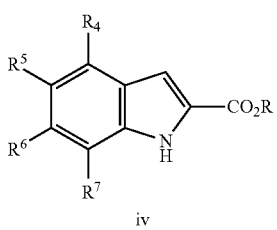

iv wherein $R^4$-$R^7$ are defined above for the compounds of formula (I) and R is H, alkyl or aryl.

An aniline compound of formula i can be converted to an indole compound of formula iv using various indole syntheses that are well-known to those skilled in the art of organic synthesis, including but not limited to, a Fischer indole synthesis through intermediates of type ii and iii, the method set forth in Nazare et al., *Angew. Chem.*, 116:4626-4629 (2004). The compounds of formula iv can be further elaborated to provide the 2,3-Substituted Indole Derivatives using the method described below in Scheme 4.

Scheme 2 shows methods useful for making compounds of formulas viii and x, which are useful intermediates for making of the 2,3-Substituted Indole Derivatives.

Scheme 2

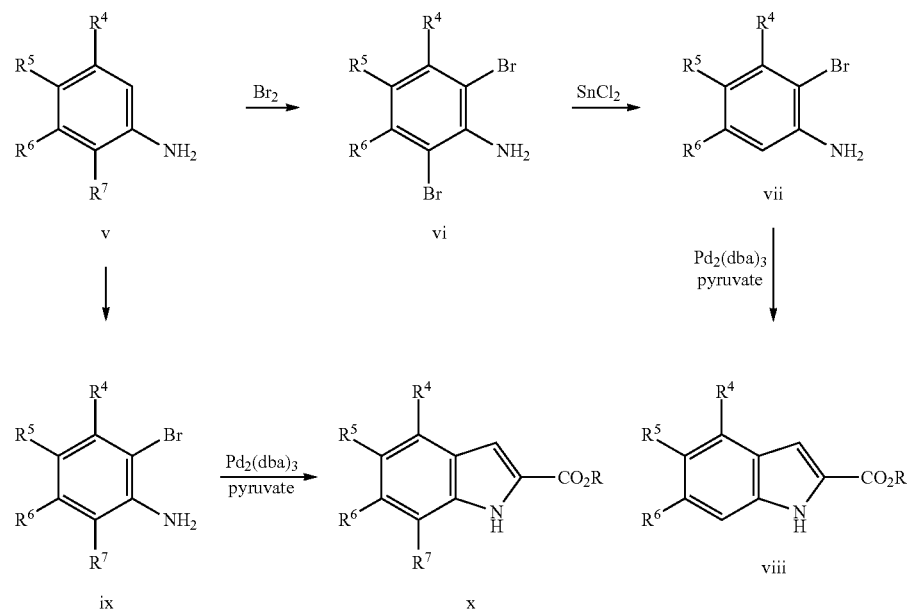

wherein R⁴-R⁷ are defined above for the compounds of formula (I) and R is H, alkyl or aryl.

A benzene derivative of formula v, wherein R⁷ is H, can be di-brominated to provide compound vi. Selective de-bromination provides the corresponding monobromo analog vii, which under palladium catalyzed cyclization conditions provides the desired intermediate viii, wherein R⁷ is H. Alternatively a compound of formula v, wherein R⁷ is other than H, can be monobrominated to provide compound 1x. A compound of formula ix can then undergo under palladium catalyzed cyclization conditions provides the desired intermediate x, wherein R⁷ is other than H.

Scheme 3 illustrates methods by which intermediate compounds of formula xi can be further derivatized to provide the 2,3-Substituted Indole Derivatives, which are intermediates to the title 2,3-Substituted Indole Derivatives.

cross-coupling method. Suitable cross-coupling methods include, but not limited to, a Stille coupling (see Choshi et al., *J. Org. Chem.*, 62:2535-2543 (1997), and Scott et al., *J. Am. Chem. Soc.*, 106:4630 (1984)), a Suzuki coupling (see Miyaura et al., *Chem. Rev.*, 95:2457 (1995)), a Negishi coupling (see Thou et al., *J. Am. Chem. Soc.*, 127:12537-12530 (2003)), a silanoate-based coupling (see Denmark et al., *Chem. Eur. J.* 12:4954-4963 (2006)) and a Kumada coupling (see Kumada, *Pure Appl. Chem.*, 52:669 (1980) and Fu et al., *Angew. Chem.* 114:4363 (2002)) to provide a compound of formula F. The carboxy protecting group, PG, can then be removed from the compound of formula xiv and the resulting carboxylic acid can be derivatized using the methods described below in order to make the appropriate R² groups and make the compounds of formula xv, which correspond to the compounds of formula (I), wherein R² is —C(O)OH.

Scheme 3

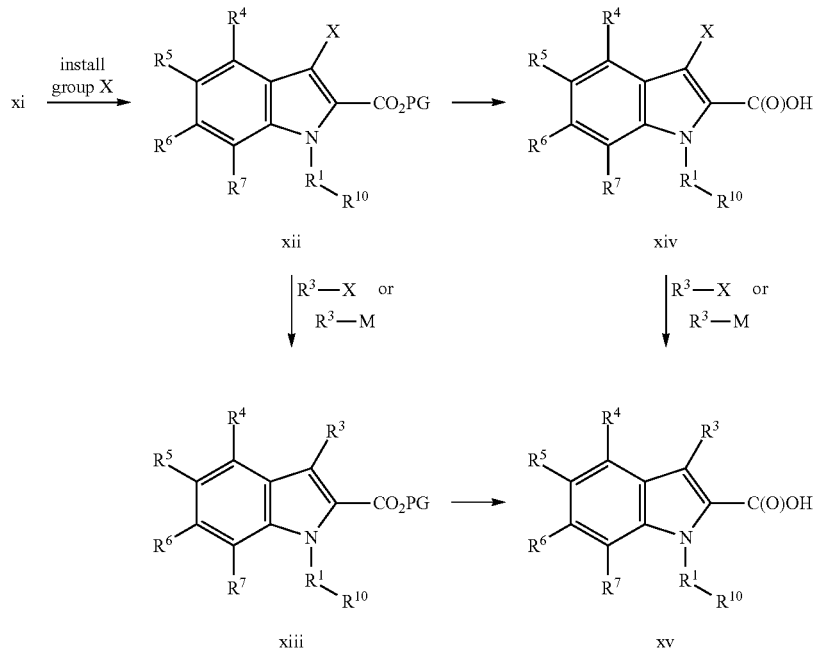

wherein R¹, R³, R⁴-R⁷ and R¹⁰ are defined above for the compounds of formula (I); PG is a carboxy protecting group; and X is halo, —O-triflate, —B(OH)₂, —Si(alkyl)₂OH, —Sn(alkyl)₃, —MgBr, —MgCl, —ZnBr, or —ZnCl; and M is any metal which can participate in an organometallic cross-coupling reaction.

An intermediate compound of formula xi can be converted to a 3-substituted indole of formula xii using methods well-known to one skilled in the art of organic synthesis. A compound of formula xii, wherein X is halo or —O-triflate can then be coupled with an appropriate compound of formula R³-M (wherein M is —B(OH)₂, —Si(alkyl)₂OH, —Sn(alkyl)₃, —MgBr, —MgCl, —ZnBr, —ZnCl, or any metal which can participate in an organometallic cross-coupling reaction) using an organometallic cross-coupling method. Alternatively, a compound of formula xii, wherein X is —B(OH)₂, —Si(alkyl)₂OH, —Sn(alkyl)₃, —MgBr, —MgCl, —ZnBr, —ZnCl, or any metal which can participate in an organometallic cross-coupling reaction, can then be coupled with an appropriate compound of formula R³-M (wherein M is halo or —O-triflate) using an organometallic Alternatively, a compound of formula xii can first be deprotected and the R² group attached using the above methods to provide a compound of formula xiii. A compound of formula xiii can then be cross-coupled with a compound of R³—X or R³-M as described above to provide the compounds of formula xv. Scheme 4 shows a method useful for making the 2,3-Substituted Indole Derivatives, wherein R² is —C(O)N(R⁹)SO₂R¹¹.

Scheme 4

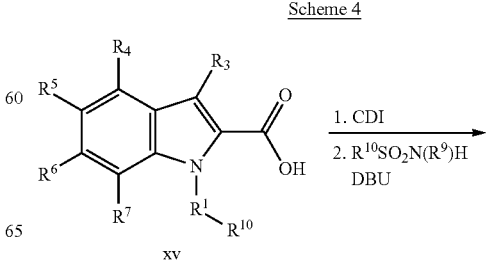

-continued

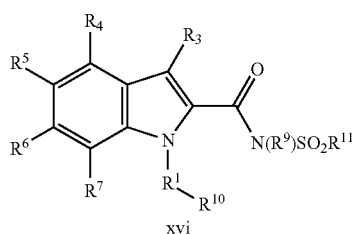
xvi wherein $R^1$, $R^2$, $R^3$, $R^4$, $R^5$, $R^6$, $R^7$, $R^{10}$, etc. and G are as defined for the 2,3-Substituted Indole Derivatives.

A 2-carboxy indole compound of formula xv can be coupled with a compound of formula $R^{11}SO_2NH(R^9)$ in the presence of carbonyldiimidazole (CDT) and 1,8-diazabicyclo[5.4.0]undec-7-ene (DBU) to provide the compounds of formula xvi, which correspond to the 2,3-Substituted Indole Derivatives wherein $R^2$ is $—C(O)NHSO_2R^{11}$.

Scheme 5 shows a method useful for making the 2,3-Substituted Indole Derivatives, wherein $R^2$ is:

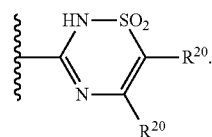

Scheme 5

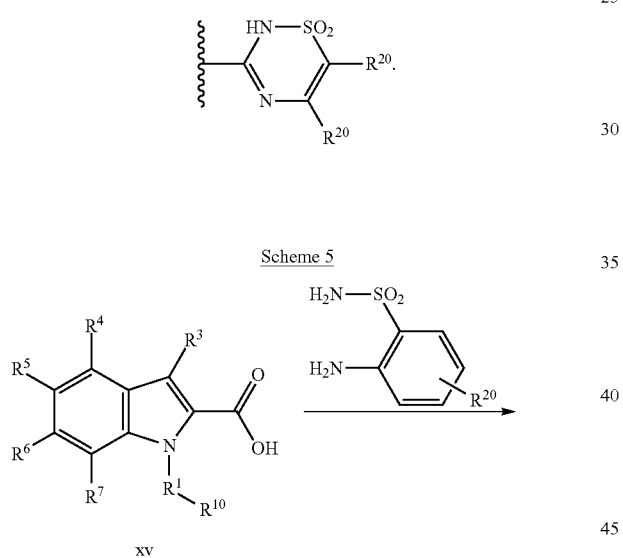

wherein $R^1$, $R^3$, $R^4$-$R^7$, $R^{10}$ and $R^{20}$ are defined above for the compounds of formulas (I) and (II).

A 2-carboxy indole compound of formula xv can be reacted with a 2-amino sulfonamide to provide the compounds of formula xvii, which correspond to the 2,3-Substituted Indole Derivatives wherein $R^2$ is:

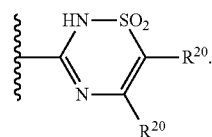

Scheme 6 shows a method useful for making the 2,3-Substituted Indole Derivatives, wherein $R^3$ is 1H-pyridin-2-one-3-yl.

Scheme 6

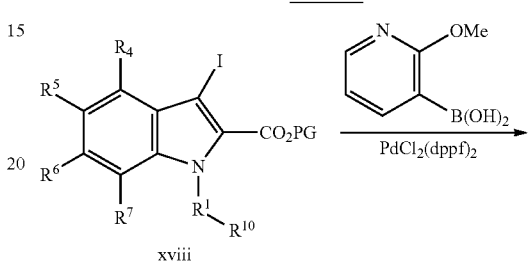

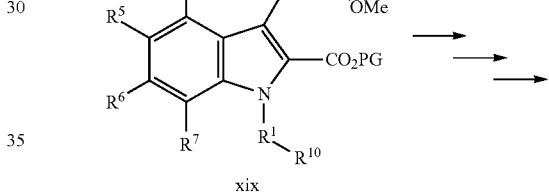

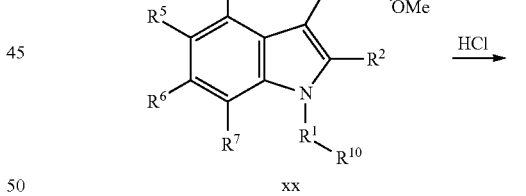

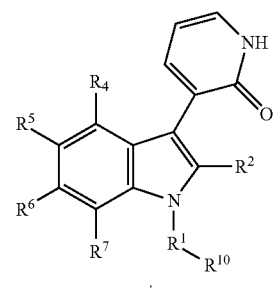
xxi wherein $R^1$, $R^2$, $R^4$-$R^7$ and $R^{10}$ are defined above for the compounds of formulas (I) and (II).

A 3-iodoindole compound of formula xviii can be coupled with 2-hydroxypyridine-3-boronic acid using a Suzuki coupling reaction to provide the R³-substituted indole compounds of formula xix. A compound of formula xix can be further elaborated using methods set forth above in Schemes 1-6 to provide the compounds of formula xx. The 2-hydroxypyridyl moiety of a compound of formula xx can then be reacted with strong acid, such as hydrochloric acid to provide the compounds of formula xxi, which correspond to the 2,3-Substituted Indole Derivatives, wherein R³ is 1H-pyridin-2-one-3-yl.

The starting material and reagents depicted in Schemes 1-6 are either available from commercial suppliers such as Sigma-Aldrich (St. Louis, Mo.) and Acros Organics Co. (Fair Lawn, N.J.), or can be prepared using methods well-known to those of skill in the art of organic synthesis.

One skilled in the art will recognize that the synthesis of 2,3-Substituted Indole Derivatives may require the need for the protection of certain functional groups (i.e., derivatization for the purpose of chemical compatibility with a particular reaction condition). Suitable protecting groups for the various functional groups of the 2,3-Substituted Indole Derivatives and methods for their installation and removal may be found in Greene et al., *Protective Groups in Organic Synthesis*, Wiley-Interscience, New York, (1999).

One skilled in the art will recognize that one route will be optimal depending on the choice of appendage substituents. Additionally, one skilled in the art will recognize that in some cases the order of steps has to be controlled to avoid functional group incompatibilities. One skilled in the art will recognize that a more convergent route (i.e. non-linear or preassembly of certain portions of the molecule) is a more efficient method of assembly of the target compounds. Methods suitable for the preparation of 2,3-Substituted Indole Derivatives are set forth above in Schemes 1-6.

The starting materials and the intermediates prepared using the methods set forth in Schemes 1-6 may be isolated and purified if desired using conventional techniques, including but not limited to filtration, distillation, crystallization, chromatography and the like. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. ¹H NMR spectra were obtained on a Bruker Avance 500 (500 MHz) and are reported as ppm down field from Me₄Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH₃CN, 5 min—95% CH₃CN, 5-7 min—95% CH₃CN, 7 min—stop. The retention time and observed parent ion are given. Flash column chromatography was performed using pre-packed normal phase silica from Biotage, Inc. or bulk silica from Fisher Scientific.

Example 1

Preparation of Compound 600

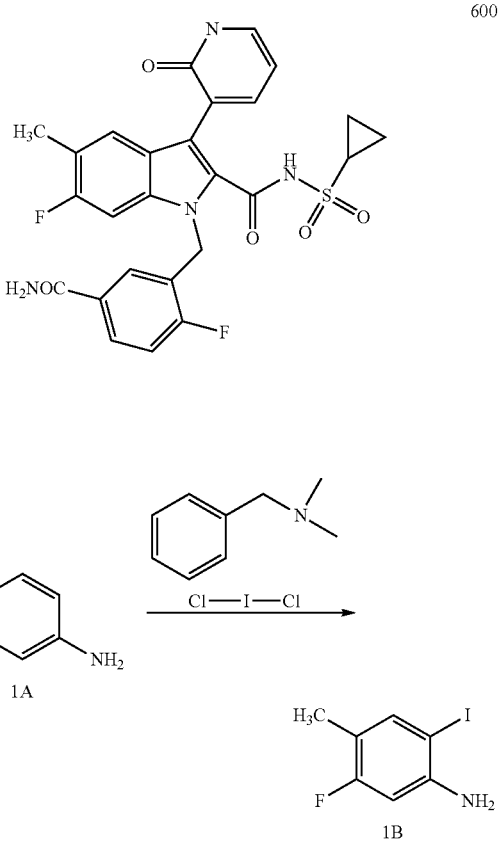

Step 1:

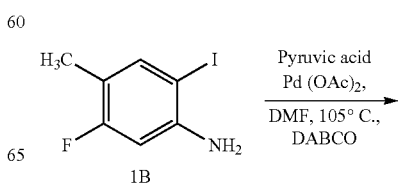

To a solution of 3-Fluoro-4-methyl-phenylamine (1A) (8.0 g, 64 mmol) in dicholoromethane (500 mL) and MeOH (100 mL) was added benzyltrimethylammonium dichloroiodate (23.8 g, 67.4 mmol) and calcium carbonate (12.8 g, 133 mmol). The suspension was allowed to stir at room temperature for 1 h, the solids were removed by filtration and the filtrate was concentrated. The concentrated crude was redissolved in CH₂Cl₂, washed successively with 5% NaHSO₄, saturated NaHCO₃, water, brine and dried over MgSO₄. The organic layer was concentrated and the crude was purified using chromatography over SiO₂ (330 g, flash column) using 0 to 20% ethyl acetate in hexane to provide compound 1B (13.4 g, 87%). ¹H NMR (400 MHz, CDCl₃): δ2.12 (s, 3H), 4.2 (broad S, 2H), 6.51 (d, J=10.8 Hz, 1H), 7.43 (d, J=8.4 Hz, 1H).

Step 2:

-continued

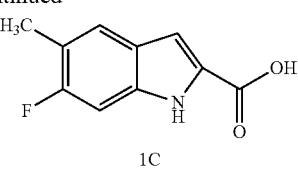
1C

A solution of the 5-fluoro, 4-methyl iodo aniline (1B) (13.4 g, 53.5 mmol), Pd(OAc)$_2$ (607 mg, 2.7 mmol), pyruvic acid (14.28 g, 162.0 mmol) and DABCO (18.2 g, 162 mmol) in DMF (120 mL) was degassed and heated to 105° C. for 4 h, cooled to room temperature and partitioned between ethyl acetate and water. The aqueous layer was extracted two more times with ethyl acetate. The organic layer was washed with brine, dried over MgSO$_4$, concentrated and the brown solid was washed with ethyl acetate/hexanes and filtered to provide compound 1C as a white solid (8.3 g, 83%) which was used directly in the next step. $^1$H NMR (400 MHz, d$_6$-DMSO): δ2.0 (broad s, 1H), 2.25 (s, 3H), 7.0 (s, 1H), 7.15 (d, J=11 Hz, 1H), 7.49 (d, J=7.3 Hz, 1H), 11.7 (s, 1H).

Step 3:

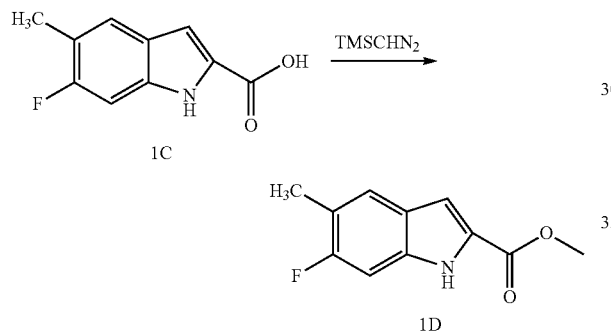

To a cooled solution of 6-Fluoro-5-Methyl-1H-indole-2-carboxylic acid in MeOH/toluene (1C) (200 mL, 1:1) was added TMS-diazomethane (2.0 M solution in diethylether, 1.05 eq.) dropwise and the reaction was allowed to warm up to room temperature over 1 h. The reaction mixture was concentrated and purified using triturating with CH$_2$Cl$_2$ and hexane and collecting the solids by filtration to obtain 6-Fluoro-5-Methyl-1H-indole-2-carboxylic acid methyl ester 1D (3.5 g). The concentrated filtrate was purified using chromatography over SiO$_2$ using 0 to 40% ethyl acetate in hexanes to provide an additional amount of 6-Fluoro-5-Methyl-1H-indole-2-carboxylic acid methyl ester 1D (1.0 g). Overall yield (60%). $^1$H NMR (400 MHz, d$_6$-DMSO): δ2.26 (s, 3H), 3.83 (s, 3H), 7.07 (s, 1H), 7.08 (d, J=10.2 Hz, 1H), 7.49 (d, J=8.1 Hz, 1H), 11.9 (s, 1H).

Step 4:

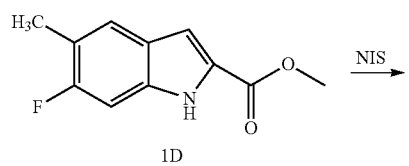

-continued

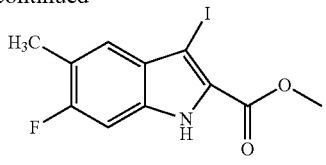
1E

To a solution of 6-Fluoro-5-Methyl-1H-indole-2-carboxylic acid methyl ester 1D (3.53 g, 17.03 mmol) in CHCl$_3$/THF (100 mL, 5:1) was added MS (3.83 g, 17.03 mmol) and the reaction mixture was allowed to stir at room temperature overnight. The reaction mixture was concentrated and redissolved in Ethyl acetate and washed with 1M Na$_2$S$_2$O$_3$, saturated NaHCO$_3$, water and brine. The organic layer was dried over MgSO$_4$, filtered, concentrated and the product was triturated using ethyl acetate/hexanes and filtered to provide compound 1E (5.34 g, 94.1%). $^1$H NMR (400 MHz, CDCl$_3$): δ2.39 (s, 3H), 3.97 (s, 3H), 7.07 (d, J=9.5 Hz, 1H), 7.32 (d, J=7.3 Hz, 1H), 9.1 (s, 1H).

Step 5:

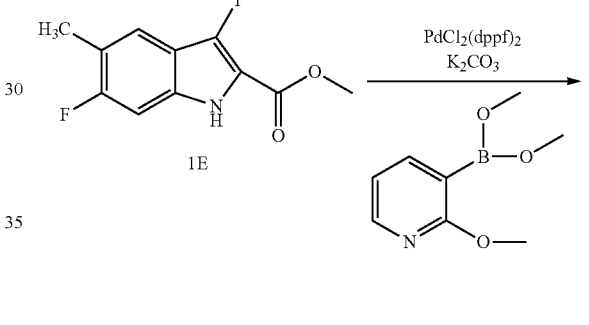

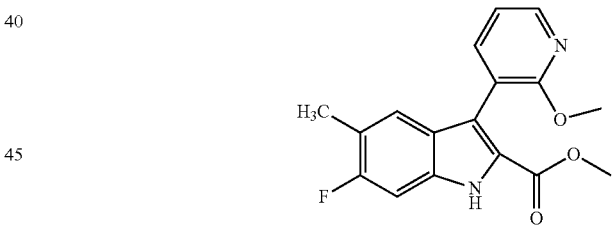
1F 2-methoxy-3-pyridine boronic acid (2.94 g, 19.23 mmol) was added to a solution of 6-Fluoro-3-iodo-5-methyl-1H-indole-2-carboxylic acid methyl ester 1E (5.34 g, 16.03 mmol) in 1, 2 dimethoxyethane (105 mL). The mixture was degassed and PdCl$_2$(dppf)$_2$ (1.3 g, 1.60 mmol) was added to the reaction mixture. After the resulting orange solution was allowed to stir at room temperature for 30 minutes, a solution of K$_2$CO$_3$ (8.86 g in 64 mL of H$_2$O) was added. The resulting brown solution was allowed to stir at 90° C. for 4 h, cooled to room temperature and diluted using ethyl acetate. The organic layer was washed with water, brine and dried over MgSO$_4$. The concentrated filtrate was purified over SiO$_2$ using 0 to 30% ethyl acetate in hexanes to provide compound 1F as a white solid (4.14 g, 82%). $^1$H NMR (400 MHz, d$_6$-DMSO): δ2.06 (s, 3H), 3.68 (s, 3H), 3.76 (s, 3H), 7.08 (m, 1H), 7.19 (m, 2H), 7.65 (d, J=10.0 Hz, 1H), 8.20 (m, 1H).

Step 6:

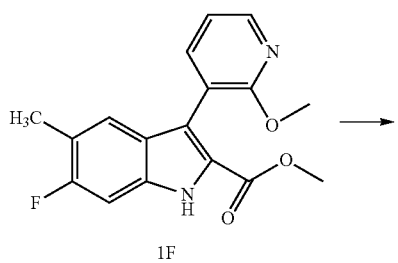

1F

To 6-Fluoro-3-(2-Methoxy-pyridin-3-yl)-5-methyl-1H-2-carboxylic acid methyl ester 1F (4.14 g, 13.17 mmol) was added 4N HCl in dioxane (40 mL) and the reaction mixture was heated at 80° C. for 12 h, cooled, and concentrated to provide 6-Fluoro-3-(2-hydroxy-pyridin-3-yl)-5-methyl-1H-2-carboxylic acid methyl ester. To the crude from last step was added LiOH (1.65 g, 39.51 mmol) in THF/MeOH/H$_2$O (75 mL, 2:2:1) and the slurry was heated at 65° C. for 12 hours, cooled, washed with 1 N HCl and water. The product was filtered, washed with ethyl acetate and dried in vacuo to provide 6-Fluoro-3-(2-hydroxy-pyridin-3-yl)-5-methyl-1H-2-carboxylic acid (3.59 g, 95.2% over 2 steps) and used directly in the next step. To the hydroxy acid (3.59 g, 12.54 mmol) from the previous step in DMF (70.0 mL) was added EDCI.HCl (4.8 g, 25.08 mmol) and Et$_3$N (8.73 mL, 62.7 mmol) and the reaction mixture was allowed to stir at room temperature for 12 hours. The reaction mixture was diluted with ethyl acetate, the slurry was washed with water and filtered. The ethyl acetate layer was washed with 1N HCl, brine, dried over MgSO$_4$ and concentrated in vacuo and the crude was added to the filtrate from the prior step and dried in vacuo to provide 9-Fluoro-10-methyl-7H-5-oxa-4,7-diaza-benzo[c]fluoren-6-one 1G as a white solid (3.36 g, 75%). $^1$H NMR (400 MHz, d$_6$-DMSO): δ 2.40 (s, 3H), 7.28 (d, J=10 Hz, 1H), 7.54 (m, 1H), 8.40 (m, 2H), 8.87 (d, J=7.2 Hz, 1H).

Step 7:

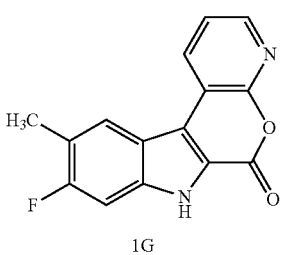

1G

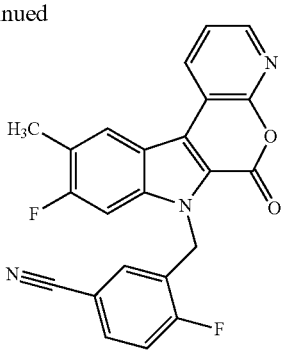

1H

To a solution of 9-Fluoro-10-methyl-7H-5-oxa-4,7-diaza-benzo[c]fluoren-6-one 1G (167 mg, 0.622 mmol) in DMF (3.0 mL) was added 3-Bromomethyl-4-fluoro-benzonitrile (160.0 mg, 0.747 mmol) and CsCO$_3$ (243 mg, 0.747 mmol) at room temperature and the reaction mixture was allowed to stir overnight. The reaction mixture was diluted with ethyl acetate, washed with water and brine, dried over MgSO$_4$, filtered and concentrated in vacuo. The concentrated crude was purified using chromatography over SiO$_2$ using 0 to 30% ethyl acetate in hexane to provide 4-Fluoro-3-(9-fluoro-10-methyl-6-oxo-6H-5-oxa-4,7-diaza-benzo[c]fluoren-7-ylmethyl)-benzonitrile 1H (200 mg, 80%). M.S. found for C23H13F2N3O2: 402.9 (M+H)$^+$.

Step 8:

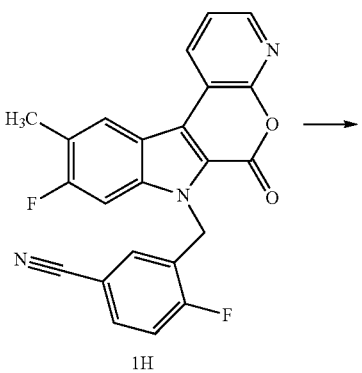

1H

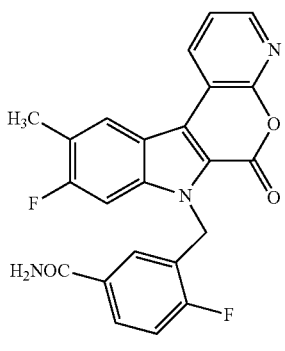

1I

To a solution of 4-Fluoro-3-(9-fluoro-10-methyl-6-oxo-6H-5-oxa-4,7-diaza-benzo[c]fluoren-7-ylmethyl)-benzonitrile 1H (126 mg, 0.313 mmol) in AcOH (1.0 mL) was added H$_2$SO$_4$ (4 drops). The reaction mixture was heated at 100° C. for 12 h and concentrated in vacuo. The solids were washed with water and ethyl acetate and dried under high vacuum to provide compound 1I as a white solid (124.0 mg, 94%). M.S. found for C23H15F2N3O3: 420.1 (M+H)$^+$.

Step 9:

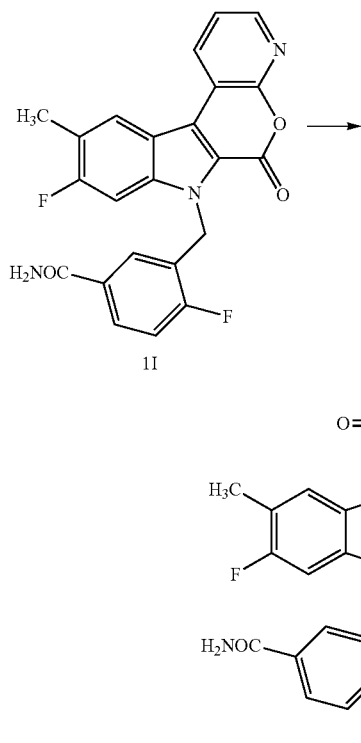

A slurry of 9-Fluoro-10-methyl-7H-5-oxa-4,7-diaza-benzo[c]fluoren-6-one A9 (34 mg, 0.08 mmol) and cyclopropyl sulfonamide (20.0 mg, 0.165 mmol) in anhydrous DMF (3.0 mL) was treated with NaH (16.0 mg, 0.4 mmol, 60% suspension in mineral oil). The reaction mixture was heated overnight at 40° C. The pH of the cooled (room temperature) reaction mixture was adjusted to pH=3 with 1N HCl and extracted with ethyl acetate. The ethyl acetate layer was washed with water, brine and filtered through $Na_2SO_4$. The concentrated crude was purified using HPLC using a C-18 column eluting with 20-90% $CH_3CN/H_2O$ gradient to provide compound 600. M.S. found for $C_{26}H_{22}F_2N_4O_5S$: 541.3 $(M+H)^+$.

Example 2

Preparation of Compound 601

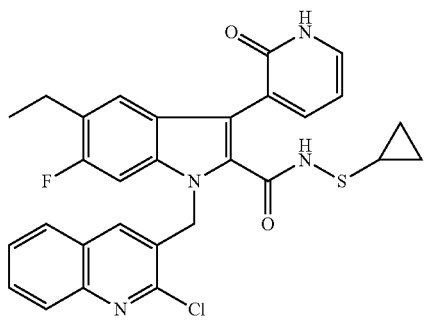

Step 1:

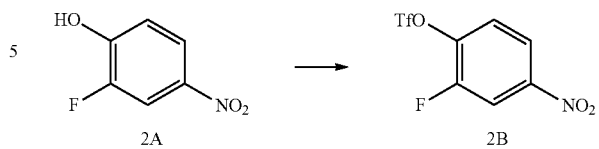

A solution of 2-fluoro-4-nitro-phenol (2A) (2.53 g; 16.1 mmol) in 60 mL of dry dichloromethane and 5 mL of dry THF was ice cooled and treated with pyridine (10 mL) and triflic anhydride (1.1 eq, 5.0 g, d 1.677). The mixture was allowed to stir for 10 min and treated with a catalytic amount of 4-dimethylamino pyridine (tip of spatula). The cooling bath was removed and the reaction was allowed to stir for 1 hour. TLC (10% ethyl acetate in hexanes) showed no more starting material left and the mixture was diluted with ethyl acetate (300 mL) and washed with aq saturated sodium bicarbonate (80 mL) and brine (80 mL). The organic layer was dried over magnesium sulfate, filtered and concentrated in vacuo. The residue was purified on silica gel (Biotage 40-M column; gradient: 0 to 10% ethyl acetate in hexanes) to provide compound 2B (4.0 g; 87%) as a colorless oil.

Step 2:

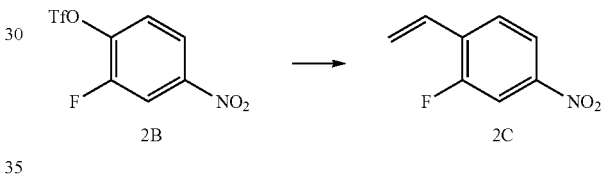

A solution of trifluoro-methanesulfonic acid 2-fluoro-4-nitro-phenyl ester (2B) (13.2 g; 45.64 mmol) in 225 mL of THF was treated with lithium chloride (7.0 eq, 13.5 g) and tributyl(vinyl)tin (2.0 eq, 26.6 mL, d 1.085). The mixture was degassed (vacuum/nitrogen flush) and tetrakis(triphenylphosphine)palladium was added (10 mol %, 5.26 g). The reaction mixture was heated to 80° C. and stirred overnight. TLC (5% ethyl acetate in hexanes) showed complete consumption of starting material. The mixture was diluted with water (100 mL) and extracted with 1:1 ether/ethyl acetate (900 mL). The organic layer was washed with 10% aqueous ammonium hydroxide (100 mL), water (100 mL) and brine (100 mL). The organic layer was dried over magnesium sulfate, filtered and concentrated in vacuo. The residue was adsorbed on silica gel and purified on a Biotage 40-S column (gradient: 0 to 4% ethyl acetate in hexanes) to provide compound 2C (7.6 g; 99%) as a slightly yellow oil which contains some stannane impurities (ca. 1.4 g)

Step 3:

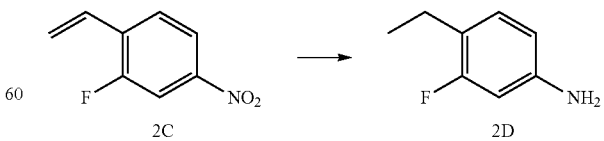

A solution of 2-fluoro-4-nitro-1-vinyl-benzene (2C) (42.65 mmol) in 140 mL of methanol was treated with a catalytic amount of 10% palladium on carbon (aprox 1.0 g). The mixture was hydrogenated at 35 psi for 2 hours. TLC (10% ethyl acetate in hexanes) showed complete consumption of starting material. The mixture was diluted with dichloromethane (100 mL) and filtered thru a short path of celite. The solids were washed with dichloromethane (100 mL). The filtrate, which contains the product 2D, was used for next reaction.

Step 4:

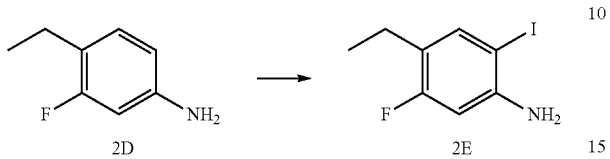

A solution of 4-ethyl-3-fluoro-phenylamine (2D) (the filtrate solution from previous step) was treated with benzyltrimethylammonium dichloroiodate (1.1 eq, 16.3 g) and calcium carbonate (2.0 eq, 8.53 g). The suspension was allowed to stir at room temp for 1 hour. TLC (10% ethyl acetate in hexanes) showed complete consumption of starting material. The solids were removed by filtration (whatman #1) and the filtrate was concentrated in vacuo. The residue was partitioned between 800 mL of 1:1 ether/ethyl acetate and aqueous 5% sodium hydrogen sulfate (200 mL). The organic layer was washed with water (200 mL) and brine (200 mL). The organic layer was dried over magnesium sulfate, filtered and concentrated in vacuo. The residue was adsorbed on silica gel and chromatographed on a Biotage 65-M column (gradient: 0 to 10% ether in hexanes) to provide compound 2E (8.5 g; 76%) as a yellow oil which contains some stannane impurities from a previous step.

Step 5:

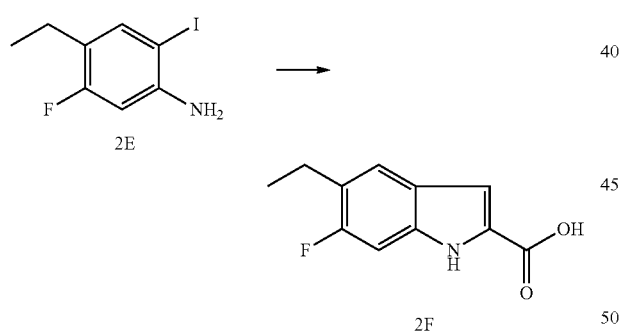

A solution of 4-ethyl-5-fluoro-2-iodo-phenylamine (2E) (7.29 g; 27.50 mmol) in 60 mL of dry DMF was treated with pyruvic acid (3.0 eq, 7.26 g, d 1.267) and DABCO (3.0 eq, 9.24 g). The mixture was degassed (vacuum/nitrogen flush) and palladium(II) acetate (0.05 eq, 308 mg) was added. The resulting solution was heated to 105° C. for 3 hours. The volatiles were removed in vacuo (high vacuum pump) and the residue was partitioned between ethyl acetate (200 mL) and water (200 mL). The aqueous layer was back extracted with ethyl acetate (4×100 mL). The combined organic layers were washed with brine, dried over magnesium sulfate, filtered and concentrated in vacuo to provide the crude product 2F as a dark brown oil. No further purification was carried out.

Step 6:

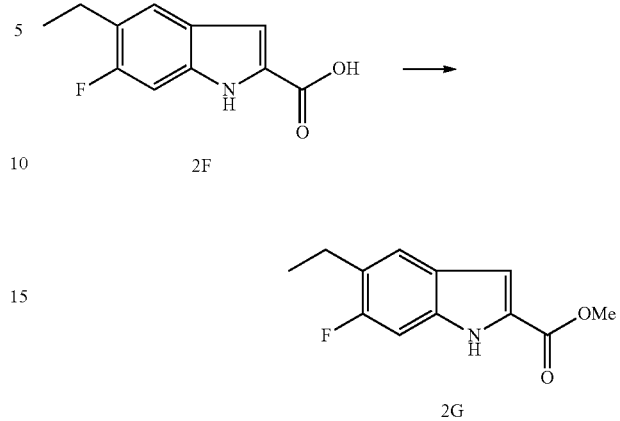

To an ice-cooled solution of 5-ethyl-6-fluoro-1H-indole-2-carboxylic acid (2F) (27.5 mmol) in 300 mL of 2:1 toluene/methanol was slowly added a solution of TMS-diazomethane in ether (2.0 eq, 27.5 mL of 2.0M). After addition was completed the cooling bath was removed and the reaction mixture was allowed to stir for 1 hour. The mixture was concentrated in vacuo to provide the crude product as a brown solid. The mixture was adsorbed on silica gel and purified on a Biotage 65-M column (gradient: 10 to 50% dichloromethane in hexanes) to provide compound 2G (3.0 g; 50% for two steps) as a white solid.

Step 7:

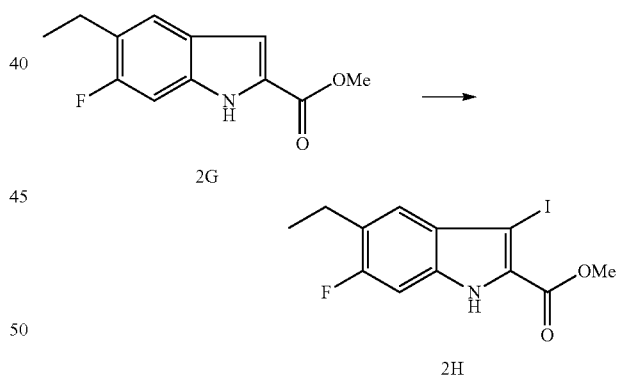

A solution of 5-ethyl-6-fluoro-1H-indole-2-carboxylic acid methyl ester (2G) (2.6 g; 11.75 mmol) in 60 mL of 1:1 THF-chloroform was ice-cooled and treated with N-iodosuccinimide (1.15 eq, 3.04 g). The cooling bath was removed and the mixture was allowed to stir for 2 hours. TLC (20% ethyl acetate in hexanes) showed almost complete consumption of starting material. The reaction mixture was diluted with ethyl acetate (300 mL) and washed with aq saturated sodium bicarbonate (2×60 mL) and brine (50 mL). The organic layer was dried over magnesium sulfate, filtered and concentrated in vacuo to provide the crude product 2H (4.0 g; 99%) as a slightly yellow solid which was used without further purification.

Step 8:

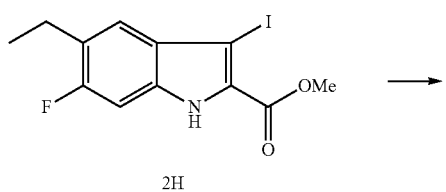

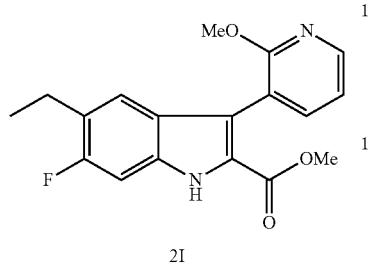

2-Methoxypyridine-3-boronic acid (1.5 eq, 2.69 g) was added to a solution of 5-ethyl-6-fluoro-3-iodo-1H-indole-2-carboxylic acid methyl ester (2I1) (11.75 mmol) in 120 mL of 1,2-dimethoxyethane. The mixture was degassed (vacuum/argon flush) and palladium catalyst (10 mol %, 960 mg of PdCl$_2$(dppf)$_2$) was added and the resulting orange solution was allowed to stir for 10 min at room temp. A solution of potassium carbonate (4.0 eq, 23.5 mL of aqueous 2M soln) was added and the resulting brown mixture was allowed to stir at 85° C. for 2 h at which point TLC (20% ethyl acetate in hexanes) showed almost complete consumption of starting material. The reaction mixture was cooled to room temp and diluted with ethyl acetate (300 mL), washed with aq saturated sodium bicarbonate (100 mL) and brine (100 mL). The organic layer was dried over magnesium sulfate, filtered and concentrated in vacuo. The crude product was adsorbed on silica gel and purified on a Biotage 65-M column (gradient: 0 to 15% ethyl acetate in 1:1 hexanes-dichloromethane) to provide compound 2I (3.3 g; 86%) as a white solid.

Step 9:

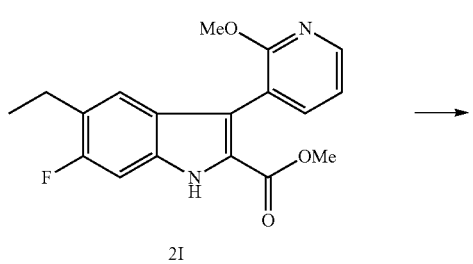

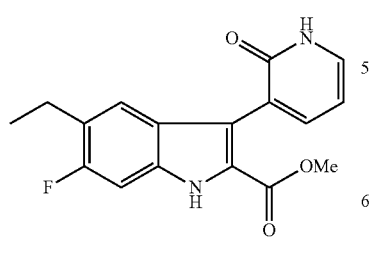

The 5-ethyl-6-fluoro-3-(2-methoxy-pyridin-3-yl)-1H-indole-2-carboxylic acid methyl ester (2I) (3.3 g; 10.05 mmol) was partially dissolved in 10 mL of methanol followed by addition of 40 mL of 4M HCl solution in dioxane. The resulting solution was heated in a sealed tube at 85° C. for 3 hours. TLC (40% acetone in 1:1 DCM-hexanes) showed aprox 40% conversion. All the volatiles were removed in vacuo and the residue was re-dissolved in 4M HCl soln in dioxane (40 mL). The mixture was heated in a sealed tube (90° C.) for 3 hours. TLC showed some starting material left. All the volatiles were again removed in vacuo and the residue was adsorbed on silica gel. Purification on a Biotage 40-M column (gradient: 20 to 60% acetone in 1:1 DCM-hexanes) gave the product 2J (2.0 g; 63%) as a slightly yellow solid.

Step 10:

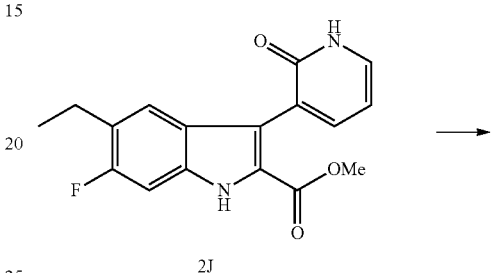

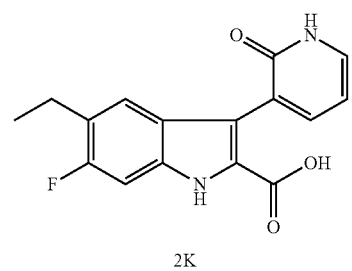

A solution of 5-ethyl-6-fluoro-3-(2-oxo-1,2-dihydro-pyridin-3-yl)-1H-indole-2-carboxylic acid methyl ester (2J) (1.9 g; 6.04 mmol) in 100 mL of 6:1:1 THF/water/methanol was treated with lithium hydroxide monohydrate (2.5 eq, 634 mg). The reaction mixture was allowed to stir at 50° C. and monitored by TLC (50% acetone in 1:1 DCM-hexanes). All the starting material had been consumed after 3 h (the product precipitated in the reaction mixture). The mixture was treated with aqueous 1M HCl (100 mL) and the product 2K (1.80 g; 99%) was recovered by filtration (whatman #1) as a white solid.

Step 11:

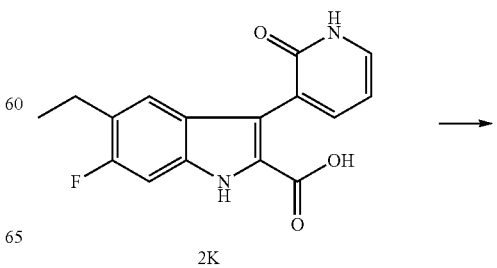

-continued

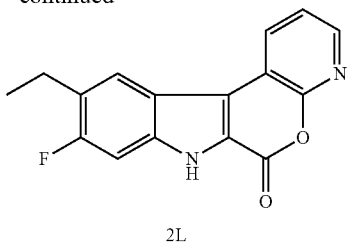

2L

The 5-ethyl-6-fluoro-3-(2-oxo-1,2-dihydro-pyridin-3-yl)-1H-indole-2-carboxylic acid (2K) (500 mg; 1.665 mmol) was suspended in dry DMF (40 mL) and treated with EDCI (2.0 eq, 638 mg) and triethylamine (10.0 eq, 2.33 mL, d 0.72). The mixture was stirred overnight at room temperature. The mixture was concentrated to dryness in vacuo (high vacuum pump). The residue was treated with methanol (10 mL) to make a homogenous suspension. The product was recovered by filtration (whatman #1) and washed with methanol (2×5 mL). The product 2L (282 mg; 60%) was thus obtained as a white solid.

Step 12:

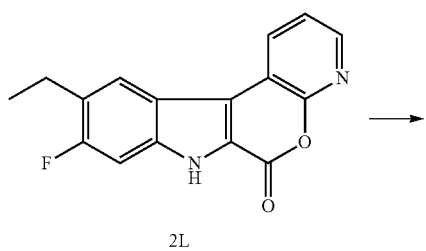

2L

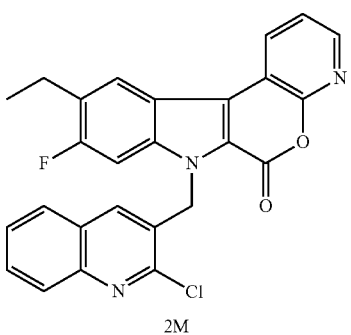

2M

The lactone 2L (40 mg, 0.141 mmol) was suspended in 2 mL of dry DMF and treated with 2-chloro-3-chloromethyl-quinoline (1.2 eq, 36 mg) and cesium carbonate (2.0 eq, 92 mg). A catalytic amount of tetrabutylammonium iodide (tip of spatula) was added and the mixture was allowed to stir at room temp. TLC (30% ethyl acetate in hexanes) showed complete consumption of starting material after 1 hour. The mixture was diluted with 50 mL of 4:1 DCM-THF and washed with water (10 mL). The organic layer was concentrated in vacuo to provide the crude product 2M (65 mg, 99%) which was used without further purification.

Step 13:

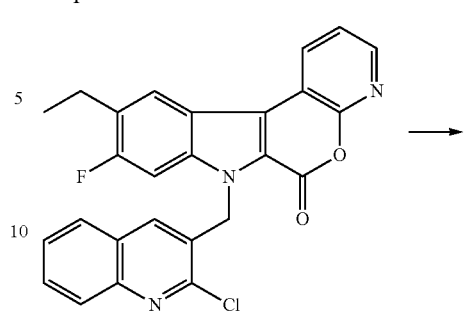

2M

601

The lactone 2M (65 mg; 0.141 mmol) was suspended in 3 mL of dry DMF followed by addition of cyclopropane sulfonamide (1.2 eq, 20 mg) and sodium hydride (2.0 eq, 11 mg of 60% suspension in mineral oil). The mixture was allowed to stir at room temp and eventually became a homogeneous solution (after 15 min). TLC (30% ethyl acetate in hexanes) showed complete consumption of starting material after 20 minutes. The reaction was quenched by addition of 5 drops of aq 1M HCl and further diluted with 5 mL of DMF. The solution was injected into an semi-prep HPLC system under the following conditions: Delta Pak Column, C18, 5 micrometer, 300A; 300×30 mm I.D.; Flow rate: 30 mL/min; Gradient: 40% acetonitrile (0.01% TFA) in water (0.01% TFA) for 10 min then increase to 90% over 20 min and stay for 10 minutes. The fraction containing the product (27 min) according to MS analysis was concentrated in vacuo to provide compound 601 (42 mg; 52%) as a white solid. Some of the product (23 mg) was dissolved in THF (3 mL) and treated with aqueous 1M NaOH solution (1.2 eq, 0.047 mL of aq. 1M soln). The mixture was allowed to stir for 10 min and then concentrated in vacuo to provide the sodium salt of compound 601 (23.8 mg).

Example 3

Preparation of Compound 271

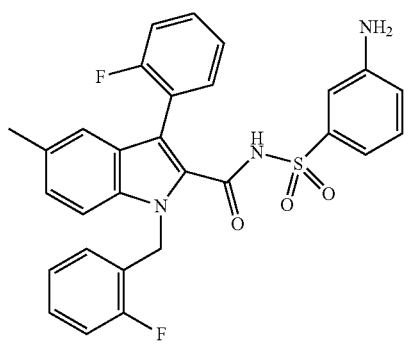

271

Step 1:

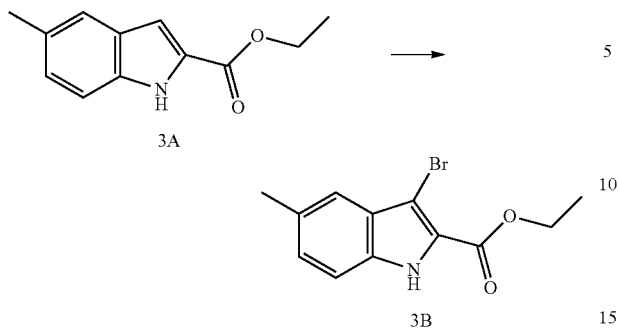

To a solution of 5-methyl-1H-indole-2-carboxylic acid ethyl ester, 3A (10.17 g, 50.03 mmol) in THF (100 mL) in a room temperature water bath was slowly added NBS (8.91 g, 50.06 mmol). The resulting solution was allowed to stir at room temperature for 3.5 h before water (800 mL) was added. The resulting mixture was allowed to stir at room temperature for 20 min and then filtered. The solid was washed with water (2×100 mL), dried in vacuo to provide the crude product 3B as a tan powder (13.8 g, 98% yield). $^1$H NMR (500 MHz, CDCl3): δ8.91 (s, 1H), 7.44 (q, J=0.95 Hz & 0.63 Hz, 1H), 7.28 (d, J=8.51 Hz, 1H), 7.21 & 7.19 (dd, J=1.58 Hz & 8.51 Hz, 1H), 4.46 (q, J=6.94 Hz & 7.25 Hz, 2H), 2.47 (s, 3H), 1.45 (t, J=7.25 Hz, 3H).

Step 2:

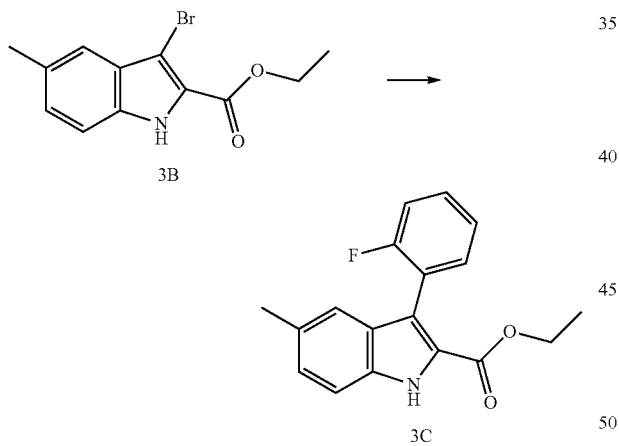

To a solution of 3-bromo-5-methyl-1H-indole-2-carboxylic acid ethyl ester, 3B (5.00 g, 17.72 mmol) in DME (80 mL) were added 2-fluorophenylboronic acid (3.72 g, 26.58 mmol) and [1,1'-bis(diphenylphosphino)ferrocene]-dichloropalladium(II) dichloromethane (1:1) complex (1.45 g, 1.77 mmol). A solution of sodium carbonate (17 mL of 1.5 M, 25.5 mmol) was added to the above mixture via a syringe. The reaction mixture was de-gassed, and then stirred at reflux for 6 hours. The reaction mixture was then cooled to room temperature, and filtered through a pad of celite. The filtrate was concentrated under reduced pressure, and the residue purified using flash chromatography on silica gel to provide compound 3C as a white solid (4.79 g, 90% yield). M.S. found for $C_{18}H_{16}FNO_2$: 298.3 (M+H)$^+$.

Step 3:

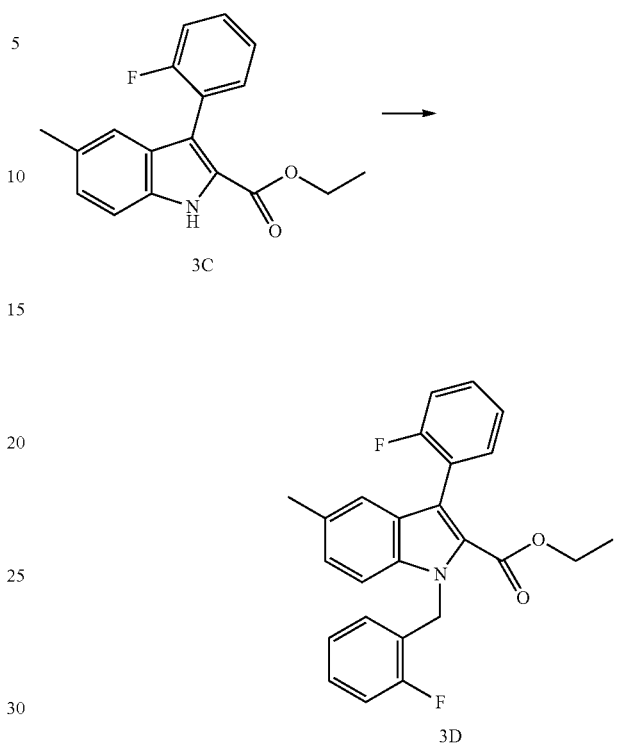

A suspension of 3-(2-fluoro-phenyl)-5-methyl-1H-indole-2-carboxylic acid ethyl ester, 3C (860 mg, 2.88 mmol), 2-fluorobenzylchloride (570 mg, 3.94 mmol), and cesium carbonate (2.10 g, 6.47 mmol) in DMF (3 mL) was allowed to stir at room temperature for 16 hours. The reaction mixture was diluted with ethyl acetate (300 mL), and washed with water (3×80 mL). The separated organic layer was dried over sodium sulfate, filtered and concentrated in vacuo. The residue was purified using flash chromatography on silica gel to provide compound 3D as a colorless oil (0.95 g, 81% yield). M.S. found for $C_{25}H_{21}F_2NO_2$: 406.2 (M+H)$^+$.

Step 4:

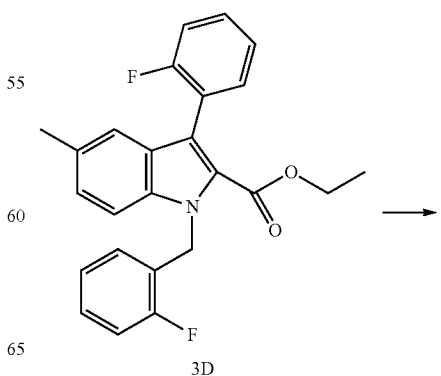

-continued

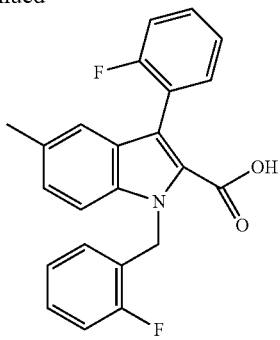

3E

To a solution of 1-(2-fluoro-benzyl)-3-(2-fluoro-phenyl)-5-methyl-1H-indole-2-carboxylic acid ethyl ester, 3D (950 mg, 2.34 mmol) in THF (20 mL) was added with an aqueous solution of lithium hydroxide (3.5 mL of 1 M, 3.5 mmol). The resulting solution was maintained at reflux for 5 days before cooled to room temperature. After concentration under reduced pressure, the residue was dissolved into methanol (10 mL), neutralized with 1.0 M HCl aqueous solution (8 mL, 8.0 mmol), and then was concentrated again under reduced pressure. The residue was extracted with ethyl acetate (2×50 mL). The combined organic layer was concentrated and dried on house vacuum to provide compound 3E (910 mg, ~100% yield). M.S. found for $C_{23}H_{17}F_2NO_2$: 378.2 $(M+H)^+$.

Step 5:

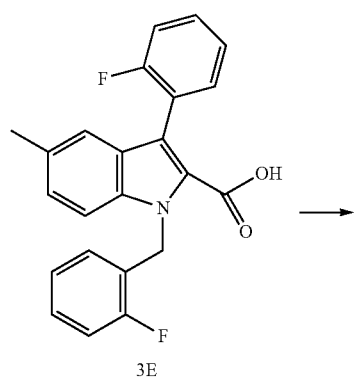

271

To a solution of 1-(2-fluoro-benzyl)-3-(2-fluoro-phenyl)-5-methyl-1H-indole-2-carboxylic acid, 3E (135 mg, 0.36 mmol) in THF (3 mL) was added 1,1'-carbonyldiimidazole (84 mg, 0.52 mmol). The reaction mixture was heated at reflux under nitrogen for 1 hour. The mixture was then cooled to room temperature, and 3-aminophenylsulfonamide (100 mg, 0.58 mmol) and DBU (90 mg, 0.58 mmol) were added. The reaction mixture was allowed to stir at reflux for 2.5 hours. The mixture was cooled down to room temperature, and concentrated in vacuo. The residue was purified using prep TLC on silica gel using 5% methanol in dichloromethane to provide compound 271 (113 mg, 59%). $^1$H NMR (500 MHz, CD3OD): δ7.48 (t, J=6.15 Hz, 1H), 7.43-7.38 (m, 2H), 7.34-7.13 (m, 9H), 7.03 (t, J=9.30 Hz, 1H), 6.95-6.91 (m, 2H), 6.73 (t, J=7.09 Hz, 1H), 5.65 (s, 2H), 3.68 (s, 3H), 2.40 (s, 2H). M.S. found for $C_{29}H_{23}F_2N_3O_3S$: 532.3 $(M+H)^+$ Example 4

Preparation of Compound 103

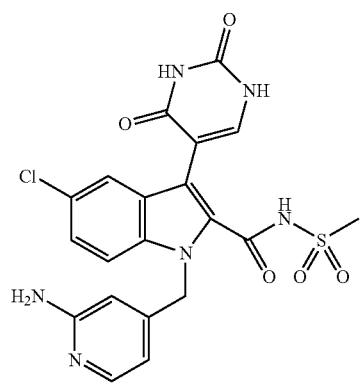

103

Step 1:

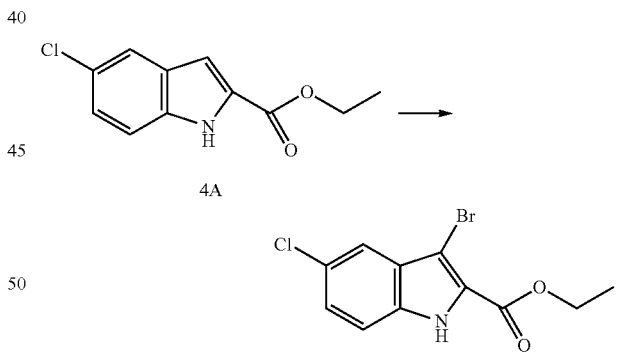

4A

4B

To a solution of ethyl 5-chloroindole-2-carboxylate, 4A (20 g, 89.6 mmol) in THF (200 mL) in a cooled water bath was added NBS (16.0 g, 89.9 mmol) slowly. The resulting reaction mixture was allowed to stir at room temperature for 18 h before water (700 mL) was added.

The mixture was continued to stir at room temperature for 20 min and then filtered. The solids were washed with water (2×100 mL), and dried to provide the crude product 4B (25.8 g, 90% yield). $^1$H NMR (500 MHz, CDCl3) δ9.06 (s, 1H), 7.66-7.65 (m, 1H), 7.35-7.31 (m, 2H), 4.47 (q, J=7.25 Hz, 2H), 1.46 (t, J=7.09 Hz, 3H).

Step 2:

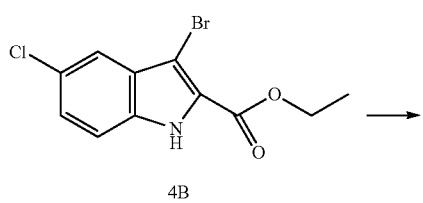
4B

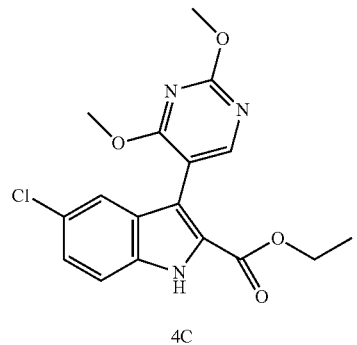
4C

To a mixture of 3-bromo-5-chloro-1H-indole-2-carboxylic acid ethyl ester, 4B (1.00 g, 3.31 mmol), 2,4-dimethoxypyrimidine-5-boronic acid (0.73 g, 3.97 mmol), [1,1'-bis(diphenylphosphino)ferrocene]dichloropalladium(II) with dichloromethane complex (1:1) (0.26 g, 0.32 mmol) in DME (15 mL) was added a solution of sodium carbonate (4.5 mL of 1.5 M, 6.75 mmol) via a syringe. The reaction mixture was allowed to stir at reflux for 6 h before cooled down to room temperature. The mixture was diluted with dichloromethane (50 mL), and was filtered through a pad of celite. The filtrate was concentrated under reduced pressure. The residue was purified using flash chromatography on silica gel (20% ethyl acetate in hexanes) to provide compound 4C as a white solid (0.47 g, 39% yield). M.S. found for $C_{17}H_{16}ClN_3O_4$: 362.2 (M+H)$^+$.

Step 3:

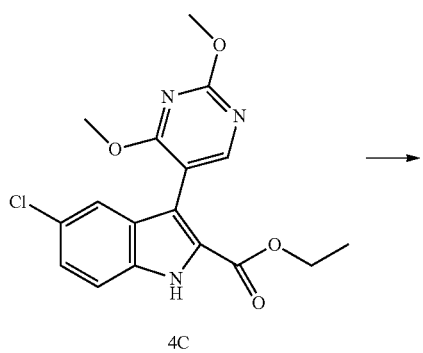
4C

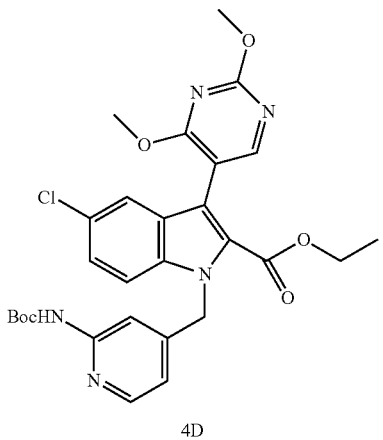
4D

To a solution of 5-chloro-3-(2,4-dimethoxy-pyrimidin-5-yl)-1H-indole-2-carboxylic acid ethyl ester, 4C (620 mg, 1.71 mmol) in DMF were added (4-bromomethyl-pyridin-2-yl)-carbamic acid tert-butyl ester (490 mg, 1.71 mmol) and cesium carbonate (1100 mg, 3.39 mmol). The resulting suspension was allowed to stir at room temperature for 17 hours. The mixture was then diluted with ethyl acetate (80 mL), and washed with water (3×50 mL). The organic layer was dried over sodium sulfate, filtered and concentrated in vacuo. The residue was purified using chromatography on silica gel using 30% ethyl acetate in hexanes to provide compound 4D (705 mg, 73% yield). M.S. found for $C_{28}H_{30}ClN_5O_6$: 568.3 (M+H)$^+$.

Step 4:

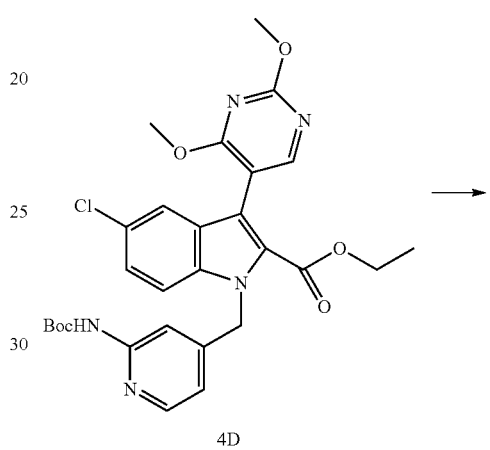
4D

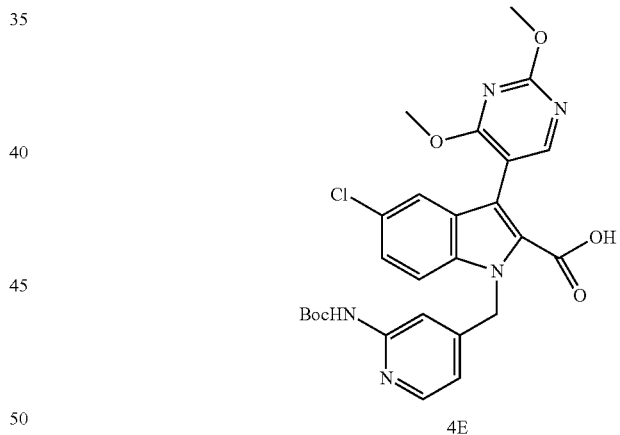
4E

To a solution of 1-(2-tert-butoxycarbonylamino-pyridin-4-ylmethyl)-5-chloro-3-(2,4-dimethoxy-pyrimidin-5-yl)-1H-indole-2-carboxylic acid ethyl ester, 4D (500 mg, 0.88 mmol) in THF (10 mL) was added an aqueous solution of lithium hydroxide (2.0 ml of 1 M, 2.9 mmol). The resulting reaction mixture was allowed to stir at reflux for 16 hours. The Reaction was then cooled and concentrated in vacuo. The residue was dissolved in methanol (80 mL), neutralized with 1.0 M HCl aqueous solution (2.5 mL, 2.5 mmol) and then concentrated again under reduced pressure. The residue was extracted with dichloromethane (3×30 mL). The combined organic layer was concentrated under reduced pressure, and dried on house vacuum to provide compound 4E (440 mg, 92%). M.S. found for $C_{26}H_{26}ClN_5O_6$: 540.3 (M+H)$^+$.

Step 5:

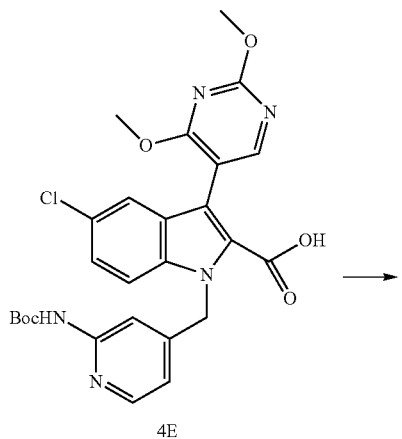

4E

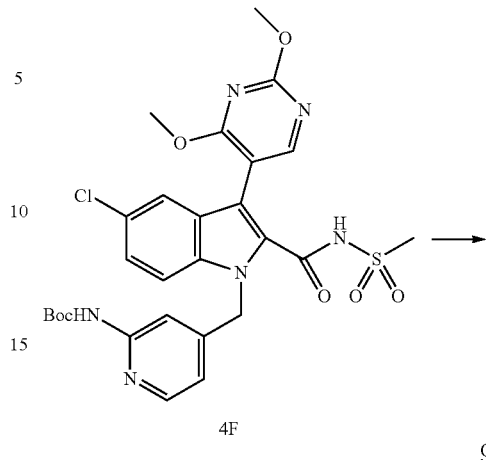

4F

Step 6:

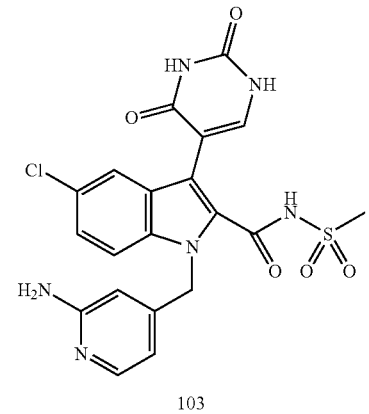

4F

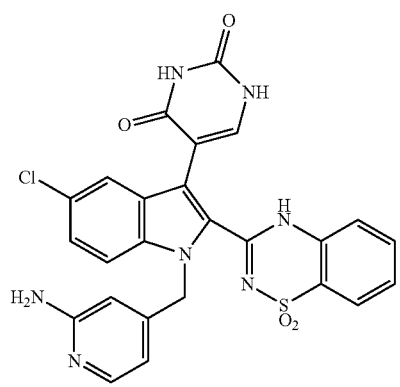

103

{4-[5-Chloro-3-(2,4-dimethoxy-pyrimidin-5-yl)-2-methanesulfonylaminocarbonyl-indol-1-ylmethyl]-pyridin-2-yl}-carbamic acid tert-butyl ester, 4F (5 mg, 0.0082 mmol) was dissolved in 4.0 M HCl in 1,4-dioxane (0.6 mL, 2.4 mmol). The resulting reaction mixture was allowed to stir at 80° C. in a sealed tube for 15 hours. temperature. The mixture was then cooled and concentrated in vacuo. The residue was washed with toluene (3×1 mL), and dried under in vacuo to provide compound 103 (3 mg, 75% yield). $^1$H NMR (500 MHz, CD3OD): δ 7.80 (d, J=6.31 Hz, 1H), 7.74 (s, 2H), 7.51 (d, J=8.83 Hz, 1H), 7.41 (d, J=8.20 Hz, 1H), 7.25-7.12 (m, 1H), 6.72 (d, J=6.31 Hz, 1H), 6.47 (s, 1H), 5.72 (s, 2H), 3.32 (s, 3H). M.S. found for $C_{20}H_{17}ClN_6O_5S$: 489.3 (M+H)$^+$.

Example 5

Preparation of Compound 599

A solution of 1-(2-tert-butoxycarbonylamino-pyridin-4-ylmethyl)-5-chloro-3-(2,4-dimethoxy-pyrimidin-5-yl)-1H-indole-2-carboxylic acid, 4E (38 mg, 0.070 mmol) and 1,1'-carbonyldiimidazole (13 mg, 0.080 mmol) in THF (4 mL) was allowed to stir at reflux for 1 h before cooled down to room temperature. Methylsulfonamide (10 mg, 0.11 mmol) and DBU (13 mg, 0.086 mmol) were then added. The resulting reaction mixture was allowed to stir at room temperature for 20 h before being concentrated under reduced pressure. The residue was diluted with ethyl acetate (100 mL), washed with aqueous 1.0 M HCl solution (2 mL) and then water (5 mL). The separated organic layer was dried over sodium sulfate, filtered and concentrated in vacuo. The residue was purified using preparative TLC on silica gel using 5% methanol in dichloromethane as the developing solvent to provide compound 4F (5 mg, 12%). M.S. found for $C_{27}H_{29}ClN_6O_7S$: 617.3 (M+H)$^+$.

Step 1:

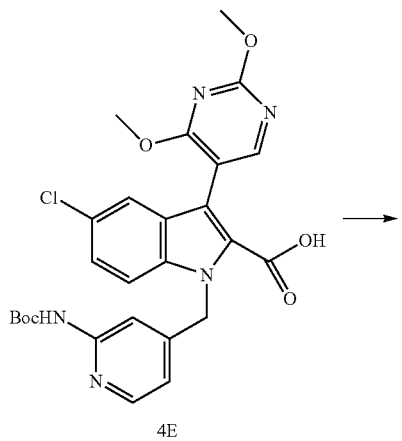

4E

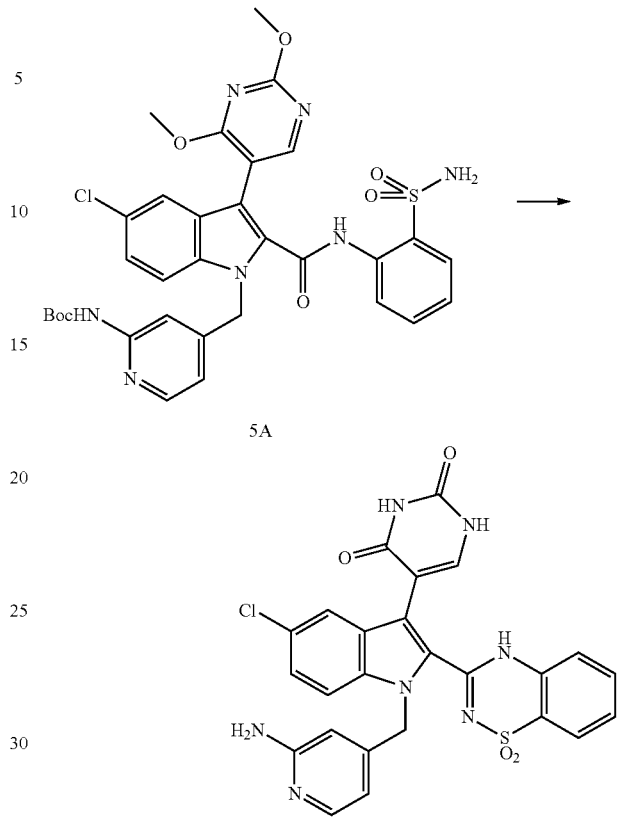

5A

To a solution of 1 42-tert-butoxycarbonylamino-pyridin-4-ylmethyl)-5-chloro-3-(2,4-dimethoxy-pyrimidin-5-yl)-1H-indole-2-carboxylic acid, 4E (120 mg, 0.22 mmol) in dichloromethane (4 mL) in an ice-water bath was added oxalyl chloride (0.2 mL, ~2.3 mmol) via a syringe. The mixture was allowed to stir at room temperature for 30 min and then at room temperature for 5 min before being concentrated under reduced pressure. The residue was dissolved into dichloromethane (4 mL), and 2-aminophenylsulfonamide (180 mg, 1.05 mmol) and triethylamine (0.3 mL) were added. The resulting reaction mixture was allowed to stir at room temperature for 20 h before concentrated under reduced pressure. The residue was purified using preparative TLC on silica gel using 10% methanol in dichloromethane as the developing solvent to provide compound 5A (30 mg, 19% yield). M.S. found for $C_{32}H_{32}ClN_7O_7S$: 694.4 (M+H)$^+$.

Step 2:

5A

599

{4-[5-Chloro-3-(2,4-dimethoxy-pyrimidin-5-yl)-2-(2-sulfamoyl-phenylcarbamoyl)-indol-1-ylmethyl]-pyridin-2-yl}-carbamic acid tert-butyl ester, 5A (30 mg, 0.043 mmol) was dissolved in 4.0 M HCl in 1,4-dioxane (1.0 mL, 4.0 mmol). The resulting solution was allowed to stir at 90° C. in a sealed tube for 17 h before being cooled down to room temperature. The mixture was concentrated under reduced pressure. The residue was purified using prep TLC on silica gel with 10% methanol in dichloromethane as the developing solvent to provide compound 599 (18 mg, 76% yield). $^1$H NMR (500 MHz, d$_6$-DMSO): δ12.35 (s, 1H), 11.28 (s, 1H), 11.13 (s, 1H), 7.84 (d, J=7.88 Hz, 1H), 7.72-7.69 (m, 3H), 7.57 (d, J=4.73 Hz, 1H), 7.50 (t, J=8.04 Hz, 1H), 7.39 (d, J=9.14 Hz, 1H), 7.32 (d, J=7.88 Hz, 1H), 6.15 (s, 1H), 6.11-6.08 (m, 1H), 5.76 (s, 1H), 5.67 (s, 2H), 4.04 (s, 2H). M.S. found for $C_{25}H_{18}ClN_7O_4S$: 548.3 (M+H)$^+$.

Example 6

Preparation of Compound 277

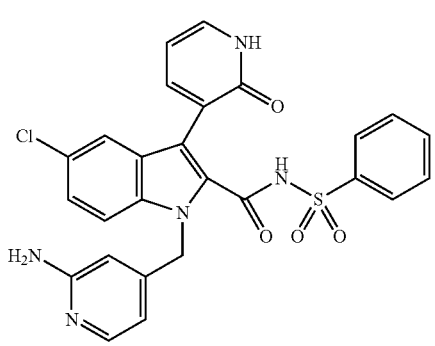

277

Step 1:

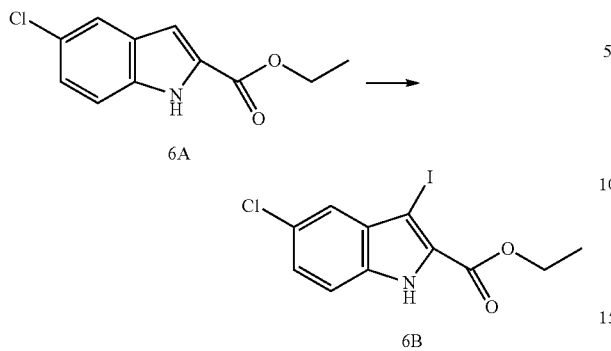

To a solution of 5-chloro-1H-indole-2-carboxylic acid ethyl ester, 6A (5.0 g, 22 mmol) in chloroform (25 mL) at room temperature was added N-iodosuccinimide (5.0 g, 22 mmol). The resulting suspension was allowed to stir at room temperature for 24 hours. The mixture was then concentrated under reduced pressure, and the residue dissolved into ethyl acetate (300 mL). The mixture was washed with water (100 mL) and brine respectively. The separated organic layer was dried over sodium sulfate, filtered and concentrated in vacuo to provide the crude product 6B (7.0 g, 91% yield). M.S. found for C11H9ClINO2: 350.2 (M+H)$^+$.

Step 2:

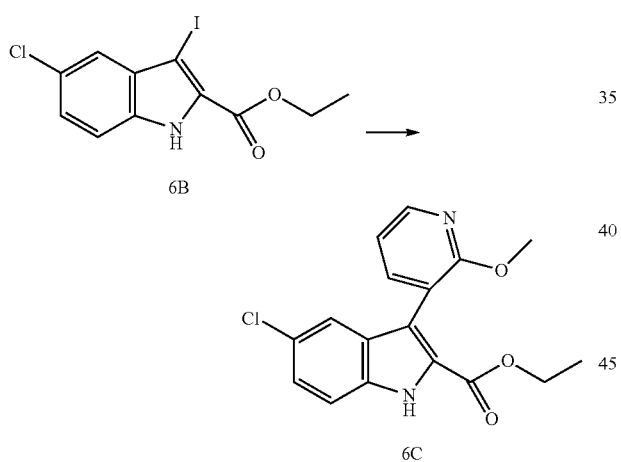

5-Chloro-3-iodo-1H-indole-2-carboxylic acid ethyl ester, 6B (3.0 g, 8.6 mmol) was dissolved into 1,2-dimethoxyethane (40 mL) and PdCl$_2$(dppf)$_2$ (0.7 g, 0.86 mmol) was added. The resulting mixture was refluxed at 90° C. for 0.5 hours. To the above mixture was added slowly a solution of 2-methoxy-3-pyridine boronic acid (2.9 g, 18.8 mmol) and potassium carbonate (2.4 g, 17.3 mmol) in water (10 mL). The resulting biphasic mixture was vigorously stirred at 90° C. for 1 h before it was cooled to room temperature. The reaction mixture was filtered and concentrated in vacuo. The residue was diluted with ethyl acetate (150 mL), and was washed with a solution of sodium sulfite (5 g) in water (50 mL). The aqueous layer was extracted with ethyl acetate (2×100 mL). The combined organic layer was dried over sodium sulfate, filtered and concentrated in vacuo. The residue was purified using flash chromatography to provide compound 6C (1.87 g, 66% yield). M.S. found for C17H15ClN2O3: 331.20 (M+H)$^+$.

Step 3:

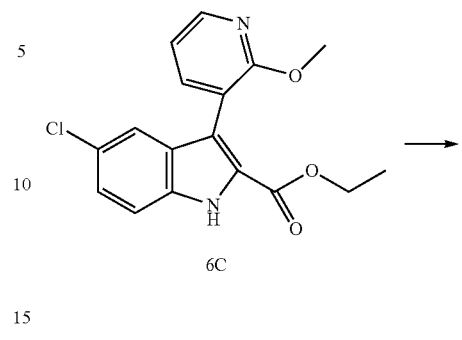

5-Chloro-3-(2-methoxy-pyridin-3-yl)-1H-indole-2-carboxylic acid ethyl ester, 6C (1.0 g, 3.0 mmol) was dissolved in DMF (15 mL) at room temperature. (4-bromomethyl-pyridin-2-yl)-carbamic acid tert-butyl ester (1.0 g, 3.6 mmol) and cesium carbonate (0.9 g, 4.5 mmol) were added sequentially and the resulting suspension stirred at room temperature for 20 hours. Ethyl acetate (200 mL) and water (100 mL) were added to the reaction mixture, and the layers were separated. The organic layer was washed with brine, and dried over sodium sulfate, filtered and concentrated in vacuo. The crude product was purified using flash chromatography to provide compound 6D (1.49 g, 93% yield). M.S. found for C29H30ClN3O5: 537.27 (M+H)$^+$; 437.17 (M-Boc+H)$^+$.

Step 4:

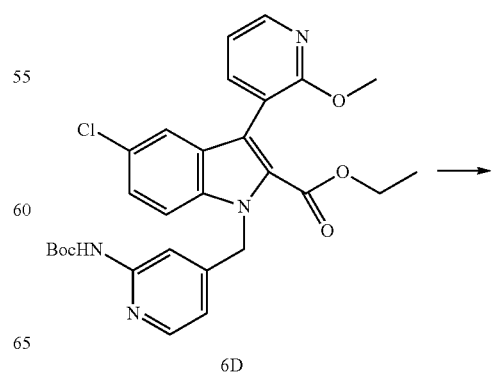

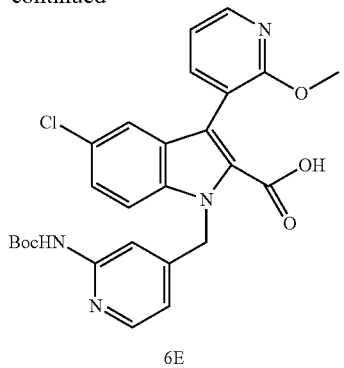

6E

To a solution of 1-(2-tert-butoxycarbonylamino-pyridin-4-ylmethyl)-5-chloro-3-(2-methoxy-pyridin-3-yl)-1H-indole-2-carboxylic acid ethyl ester, 6D (1.5 g, 2.79 mmol) in THF (20 mL) was added the solution of lithium hydroxide (0.3 g, 8.37 mmol) in water (5 mL). The resulting suspension was allowed to stir at 60° C. for 20 hours. The mixture was concentrated under reduced pressure. Ethyl acetate (150 mL) and water (100 mL) were added to the residue. The aqueous layer was acidified to pH=1~2 by adding aqueous 1N HCl solution, and was saturated with NaCl salts. The layers were separated, and the aqueous layer was further extracted with ethyl acetate (2×100 mL). The combined organic layer was dried over sodium sulfate, filtered and concentrated in vacuo to provide the crude product 6E (100% yield). $^1$H NMR (500 MHz, CDCl3) δ9.36 (s, 1H), 8.22 & 8.21 (dd, J=1.89 Hz & 5.04 Hz, 1H), 8.07 (s, 1H), 7.81 (d, J=5.68 Hz, 1H), 7.70 & 7.68 (dd, J=1.89 Hz & 7.25 Hz, 1H), 7.45 (d, J=1.89 Hz, 1H), 7.31 & 7.29 (dd, J=1.89 Hz & 8.83 Hz, 1H), 7.23 (d, J=8.83 Hz, 1H), 7.01 (q, J=5.04 Hz & 2.21 Hz, 1H), 6.36 (d, J=5.04 Hz, 1H), 5.85 (s, 2H), 3.80 (s, 3H), 1.46 (s, 9H).

Step 5:

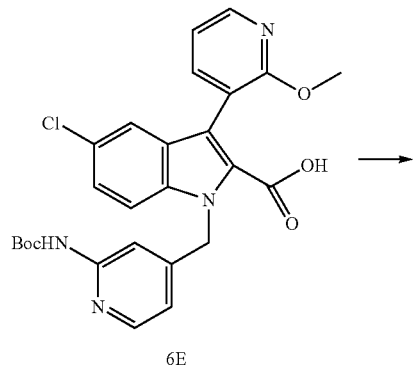

6E

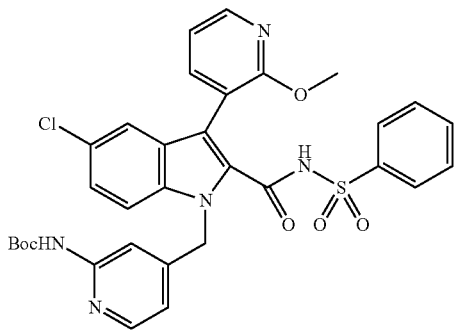

6F 1-(2-tert-Butoxycarbonylamino-pyridin-4-ylmethyl)-5-chloro-3-(2-methoxy-pyridin-3-yl)-1H-indole-2-carboxylic acid, 6E (400 mg, 0.79 mmol) was dissolved into tetrahydrofuran (30 mL) at room temperature. To the mixture was added carbonyl diimidazole (140 mg, 0.87 mmol). The resulting suspension was refluxed at 75° C. for 1 hour, and then cooled to room temperature to proved uncharacterized acylimidazole intermediate in THF (30 mL) solution. To the THF solution of the preceding intermediate (5 mL) were added benzenesulfonamide (30 mg, 0.19 mmol) and 1,8-diazabicyclo(5.4.0)undec-7-ene (30 uL). The resulting reaction mixture was allowed to stir at room temperature for 20 hours. Ethyl acetate (50 mL), tetrahydrofuran (10 mL) and 1% aqueous phosphoric acid (15 mL) were added to the reaction mixture, and the layers were separated. The aqueous layer was extracted with ethyl acetate/THF (3:1) (2×40 mL). The combined organic layer was dried over sodium sulfate, filtered and concentrated in vacuo. The residue was purified using flash chromatography to provide compound 6F (60 mg, 57% yield). M.S. found for C32H30ClN5O6S: 648.27 (M+H)$^+$.

Step 6:

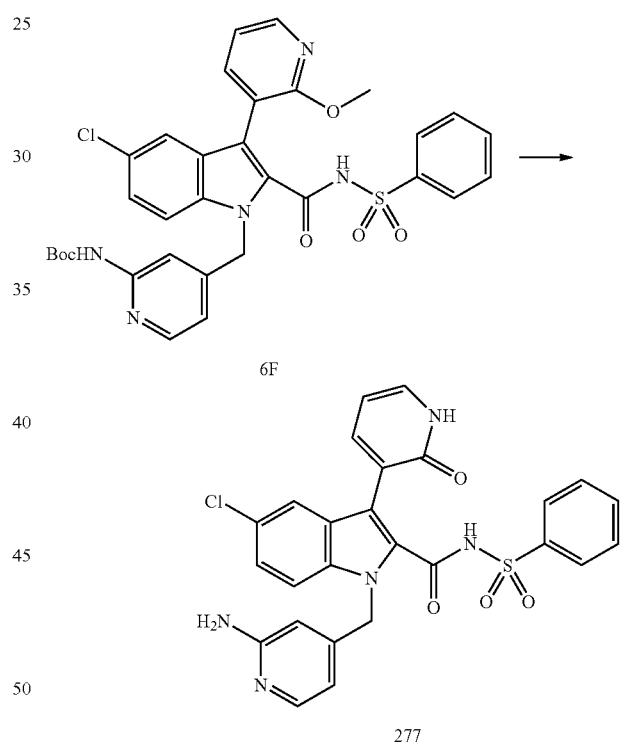

6F

277

To a solution of {-4-[2-benzenesulfonylaminocarbonyl-5-chloro-3-(2-methoxy-pyridin-3-yl)-indol-1-ylmethyl]-pyridin-2-yl}-carbamic acid tert-butyl ester, 6F (60 mg, 0.09 mmol) in methanol (3 mL) was added 4 N HCl in 1,4-dioxane (3 mL). The resulting reaction mixture was allowed to stir at 90° C. in a sealed tube for 2 hours. The mixture was concentrated under reduced pressure, and the residue was purified using flash chromatography to provide compound 277. $^1$H NMR (500 MHz, d$_6$-DMSO) δ7.88 (d, J=7.25 Hz, 2H), 7.84-7.79 (m, 2H), 7.66 (t, J=6.62 Hz, 2H), 7.54-7.48 (m, 4H), 7.37 (d, J=8.51 Hz, 1H), 6.76 (s, 1H), 6.56 (s, 1H), 6.19 (s, 1H), 5.64 (s, 2H). M.S. found for C$_{26}$H$_{20}$ClN$_5$O$_4$S: 534.17 (M+H)$^+$.

Example 7

Preparation of Compound 310

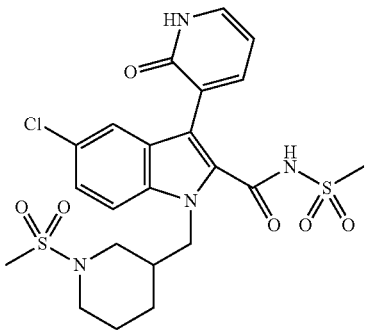
310

Step 1:

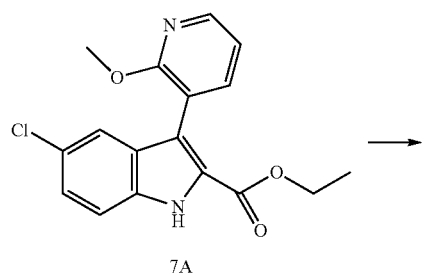
7A

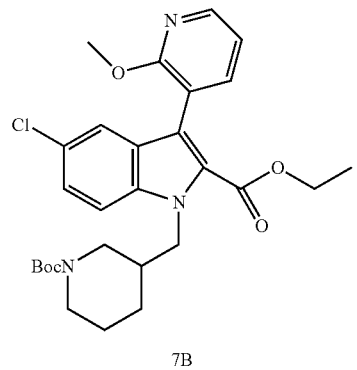
7B

To a solution of 5-chloro-3-(2-methoxy-pyridin-3-yl)-1H-indole-2-carboxylic acid ethyl ester, 7A (500 mg, 1.51 mmol) in DMF (3 mL) were added 1-N-boc-3-bromomethylpiperidine (500 mg, 1.78 mmol) and cesium carbonate. The resulting suspension was allowed to stir at 50° C. for 20 hours. The mixture was cooled down to room temperature, diluted with ethyl acetate (100 mL), and washed with water (3×20 mL). The organic layer was dried over sodium sulfate, filtered and concentrated in vacuo. The residue was purified using Combiflash chromatography on silica gel using 0-10% ethyl acetate in hexanes to provide compound 7B (780 mg, 97% yield). $^1$H NMR (500 MHz, CDCl3) δ 8.21 & 8.20 (dd, J=1.89 Hz & 5.04 Hz, 1H), 7.61 & 7.60 (dd, J=1.58 Hz & 7.25 Hz, 1H), 7.41 (d, J=1.58 Hz, 1H), 7.33 (d, J=8.51 Hz, 1H), 7.31 & 7.29 (dd, J=1.89 Hz & 8.83 Hz, 1H), 7.01 (q, J=5.04 Hz & 2.21 Hz, 1H), 4.48 (s, 2H), 4.14 (q, J=6.94 Hz & 7.25 Hz, 2H), 3.94 (d, J=13.24 Hz, 1H), 3.86 (s, 3H), 2.78-2.72 (m, 1H), 2.63 (t, J=11.67 Hz, 1H), 1.58 (s, 6H), 1.38 (s, 9H), 1.00 (t, J=7.09 Hz, 3H).

Step 2:

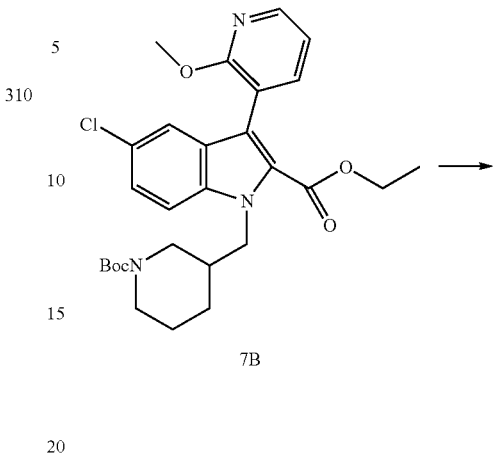
7B

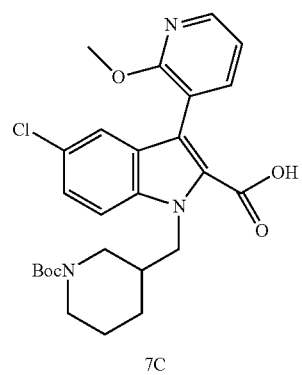
7C

To a solution of 1-(1-tert-butoxycarbonyl-piperidin-3-yl-methyl)-5-chloro-3-(2-methoxy-pyridin-3-yl)-1H-indole-2-carboxylic acid ethyl ester, 7B (370 mg, 0.70 mmol) in THF (50 mL) was added an aqueous solution of lithium hydroxide (2.0 mL of 1 M, 2.0 mmol). The resulting mixture was allowed to stir at reflux for 2 days before cooled down to room temperature. The mixture was concentrated under reduced pressure. The residue was dissolved into methanol (5 mL), neutralized with aqueous 1.0 M HCl solution (2.0 mL, 2.0 mmol) and then concentrated again under reduced pressure. The residue was triturated with ethyl acetate (3×30 mL), and the combined organic layer was concentrated and dried on house vacuum to provide compound 7C (290 mg, 83% yield).

Step 3:

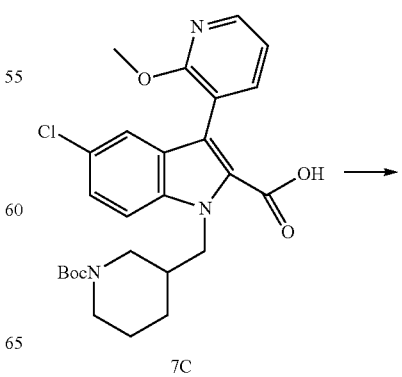
7C

-continued

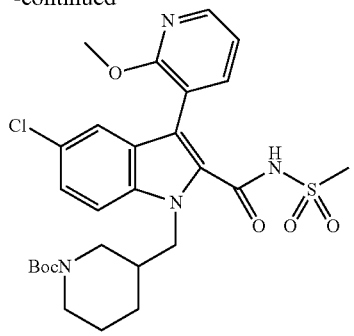

7D

To a solution of 1-(1-tert-butoxycarbonyl-piperidin-3-yl-methyl)-5-chloro-3-(2-methoxy-pyridin-3-yl)-1H-indole-2-carboxylic acid, 7C (290 mg, 0.58 mmol) in THF (5 mL) was added 1,1'-carbonyldiimidazole (150 mg, 0.92 mmol). The mixture was refluxed for 1.5 hours, cooled to room temperature and then methylsulfonamide (120 mg, 1.26 mmol) and DBU (190 mg, 1.25 mmol) were added. The resulting reaction mixture was allowed to stir at reflux for 3 h before cooled to room temperature. The mixture was concentrated under reduced pressure. The residue was purified using Combiflash chromatography on silica gel using 0-5% methanol in dichloromethane to provide compound 7D (280 mg, 84% yield). M.S. found for $C_{27}H_{33}ClN_4O_6S$: 577.3 $(M+H)^+$.

Step 4:

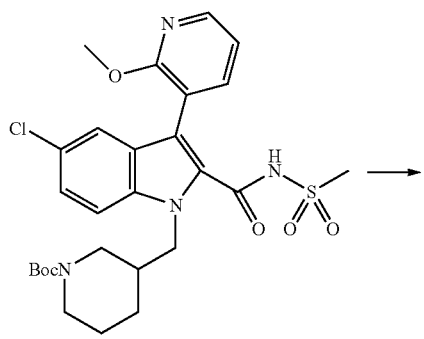

7D

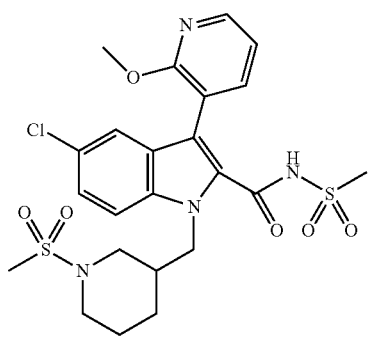

7E

A solution of 3-[5-Chloro-2-methanesulfonylaminocarbonyl-3-(2-methoxy-pyridin-3-yl)-indol-1-ylmethyl]-piperidine-1-carboxylic acid tert-butyl ester, 7D (85 mg, 0.15 mmol) in trifluoroacetic acid (2 mL) and dichloromethane (2 mL) was allowed to stir at room temperature for 4 hours. The mixture was then concentrated under reduced pressure, dissolved in dichloromethane (3 mL) and treated with triethylamine (0.5 mL) and methylsulfonyl-chloride (50 mg, 0.44 mmol). The resulting mixture was allowed to stir at room temperature for an additional 18 hours. The mixture was then concentrated under reduced pressure, and the residue was purified using Combiflash chromatography on silica gel using 0-5% methanol in dichloromethane to provide compound 7E (40 mg, 49% yield). M.S. found for $C_{23}H_{27}ClN_4O_6S_2$: 555.3 $(M+11)^+$.

Step 5:

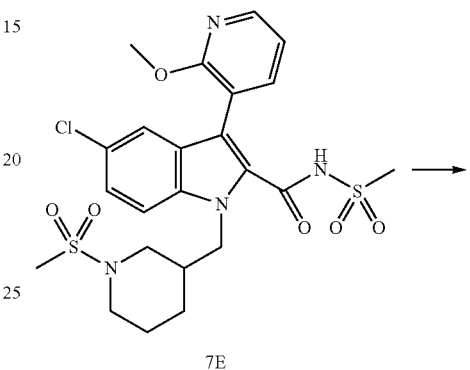

7E

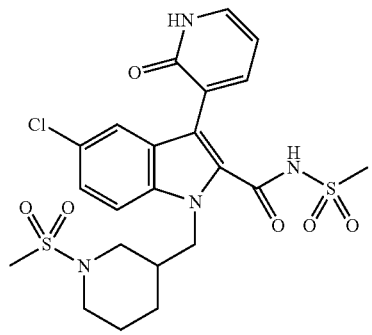

310

N-[5-Chloro-1-(1-methanesulfonyl-piperidin-3-ylmethyl)-3-(2-methoxy-pyridin-3-yl)-1H-indole-2-carbonyl]-methanesulfonamide, 7E (40 mg, 0.072 mmol) was dissolved in 4.0 N HCl in 1,4-dioxane (2.0 mL, 8.0 mmol). The mixture was allowed to stir at 90° C. in a sealed tube for 1 hour, cooled to room temperature, and then concentrated under reduced pressure. The residue was washed with methanol (2×3 mL), and was dried in vacuo to provide compound 310 as a white solid (26 mg, 67% yield). $^1$H NMR (500 MHz, $d_6$-DMSO): δ12.78 (s, 1H), 12.42 (s, 1H), 7.79-7.75 (m, 2H), 7.59 (s, 1H), 7.46 (s, 1H), 7.38 & 7.37 (dd, J=1.89 Hz & 8.51 Hz, 1H), 6.52 (t, J=6.94 Hz, 1H), 4.47-4.37 (m, 2H), 3.41 & 3.38 (dd, J=3.15 Hz & 11.67 Hz, 2H), 3.34 (s, 3H), 3.33 (s, 3H), 2.70-2.58 (m, 2H), 2.05-1.99 (m, 1H), 1.74-1.70 (m, 1H), 1.52-1.48 (m, 1H), 1.40 (q, J=11.67 Hz & 13.56 Hz, 1H), 1.09 (q, J=11.67 Hz & 11.03 Hz, 1H). M.S. found for $C_{22}H_{25}ClN_4O_6S_2$: 541.3 $(M+H)^+$.

Example 8

Preparation of Compound 273

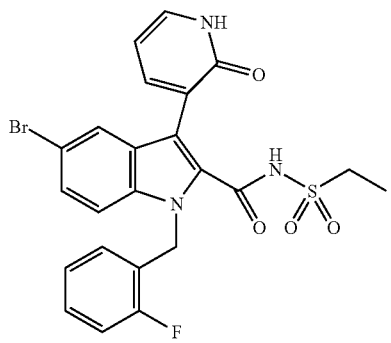

Step 1:

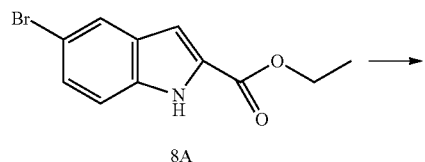

Ethyl 5-bromo 2-indole carboxylate, 8A (4.0 g, 14.9 mmol) was dissolved into acetone (200 mL) at room temperature. To the mixture was added N-iodosuccinimide (3.65 g, 15.4 mmol). The resulting suspension was allowed to stir at room temperature for 3 hours. The mixture was concentrated under reduced pressure, and the residue was dissovled into ethyl acetate (150 mL). The mixture was washed with saturated aqueous sodium thiosulfate solution (50 mL). The layers were separated, and the aqueous layer was extracted with ethyl acetate (2×100 mL). The combined organic layer was dried (magnesium sulfate), filtered and concentrated in vacuo to provide the crude product 8B (100% yield). $^1$H NMR (400 MHz, $d_6$-DMSO): δ 12.48 (s, 1H), 7.55 (s, 1H), 7.45-7.44 (m, 2H), 4.39 (q, J=6.59 Hz & 7.32 Hz, 2H), 1.38 (t, J=7.32 Hz, 3H).

Step 2:

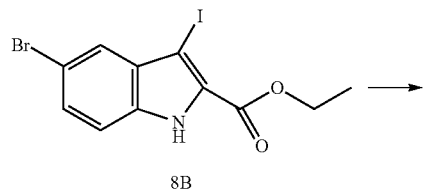

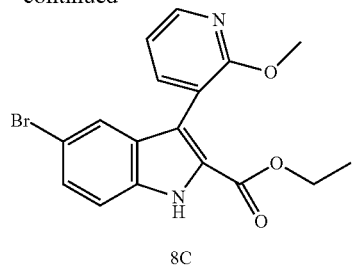

5-Bromo-3-iodo-1H-indole-2-carboxylic acid ethyl ester, 8B (8.66 g, 21.9 mmol) was dissolved into 1,2-dimethoxyethane (400 mL). And PdCl$_2$(dppf)$_2$ (1.80 g, 2.20 mmol) was added. The resulting mixture was de-gassed with nitrogen bubbling for 5 min before it was heated to 90° C. and allowed to stir for 15 minutes. In a second flask, the mixture of 2-methoxy-3-pyridine boronic acid (3.72 g, 24.3 mmol) and potassium carbonate (15.2 g, 110 mmol) in dimethoxyethane (100 mL) and water (100 mL) was de-gassed with nitrogen bubbling for 5 minutes. The mixture was then transferred in three portions to the first flask. The resulting bi-phasic mixture was vigorously stirred at 90° C. for 3.5 h before it was cooled to room temperature. The reaction was quenched by addition of a solution of sodium sulfite (15 g) in water (200 mL) at room temperature. Ethyl acetate (200 mL) was added, and the layers were separated. The aqueous layer was extracted with ethyl acetate (2×300 mL). The combined organic layer was dried (magnesium sulfate), filtered and concentrated in vacuo to provide the crude product 8C (100% yield). M.S. calc'd for C17H15BrN2O3: 375.22. Found: 377.00.

Step 3:

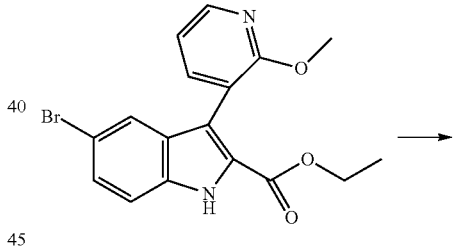

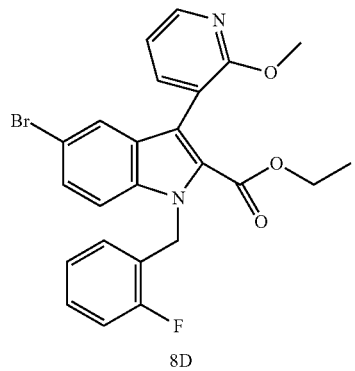

5-Bromo-3-(2-methoxy-pyridin-3-yl)-1H-indole-2-carboxylic acid ethyl ester, 8C (0.66 g, 1.59 mmol) was dissolved into DMF (50 mL) at room temperature. To the mixture were added 2-fluorobenzyl bromide (0.42 g, 2.23 mmol) and cesium carbonate (0.84 g, 2.40 mmol). The resulting suspension was allowed to stir at room temperature for 18 hours.

Ethyl acetate (200 mL) and water (100 mL) were added to the reaction mixture, and the layers were separated. The aqueous layer was extracted with ethyl acetate (2×100 mL). The combined organic layer was washed with water (2×100 mL). The separated organic layer was dried (magnesium sulfate), filtered and concentrated in vacuo to provide the crude product. The crude product was purified using flash chromatography to provide product 8D (0.32 g, 42% yield). M.S. calc'd for C24H20N2O3BrF: 483.33. Found: 485.3.

Step 4:

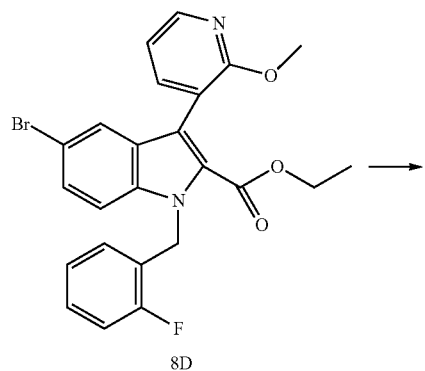

8D

To a solution of 5-bromo-1-(2-fluoro-benzyl)-3-(2-methoxy-pyridin-3-yl)-1H-indole-2-carboxylic acid ethyl ester, 8D (0.32 g, 0.66 mmol) in methanol (5 mL) was added lithium hydroxide monohydrate (110 mg, 2.64 mmol). And water (0.2 mL) was added to improve the solubility. The resulting suspension was allowed to stir at room temperature for 5 min before being placed in microwave reactor for 20 min (120° C., high power). The mixture was concentrated under reduced pressure. Ethyl acetate (50 mL) and water (50 mL) were added to the residue. The aqueous layer was acidified to pH=2 by adding aqueous 1N HCl solution, and was saturated with NaCl salts. The layers were separated, and the aqueous layer was further extracted with ethyl acetate (2×50 mL). The combined organic layer was dried (magnesium sulfate) and filtered and concentrated in vacuo to provide the crude product 8E (93% yield). M.S. calc'd for C22H16N2O3BrF: 455.28. Found: 456.01 (M+H)⁺.

Step 5:

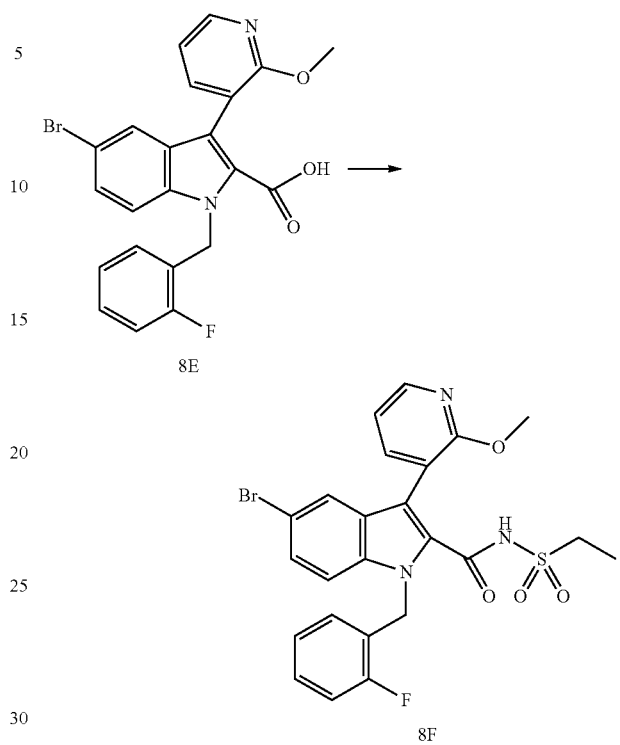

5-Bromo-1-(2-fluoro-benzyl)-3-(2-methoxy-pyridin-3-yl)-1H-indole-2-carboxylic acid, 8E (0.11 g, 0.24 mmol) was dissolved into tetrahydrofuran (5 mL) at room temperature. To the mixture was added carbonyl diimidazole (60 mg, 0.36 mmol). The resulting suspension was refluxed at 75° C. for 1.5 hours, and then cooled down to room temperature before adding ethane sulfonamide (77 mg, 0.75 mmol) and 1,8-diazabicyclo(5.4.0)undec-7-ene (0.12 mL, 0.75 mmol). The resulting reaction mixture was allowed to stir at room temperature for 48 hours. Ethyl acetate (80 mL), tetrahydrofuran (16 mL) and 1% aqueous phosphoric acid (25 mL) were added to the reaction mixture, and the layers were separated. The aqueous layer was extracted twice with ethyl acetate/THF (3:1) (60 mL). The combined organic layer was dried (magnesium sulfate), filtered and concentrated in vacuo. The crude product was purified using flash chromatography to provide 8F (80 mg, 60% yield). M.S. calc'd for C24H21N3O4FSBr: 546.41. Found: 547.93 (M+H)⁺.

Step 6:

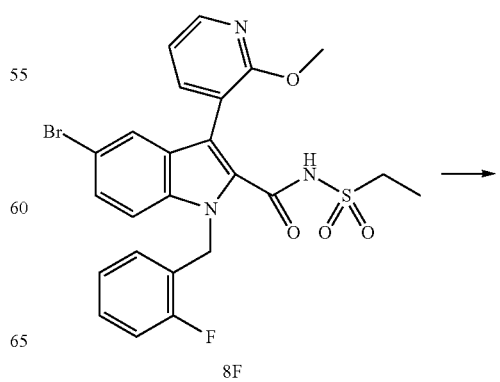

8F

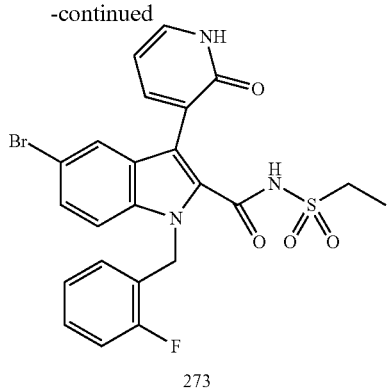

273

Ethanesulfonic acid [5-bromo-1-(2-fluoro-benzyl)-3-(2-oxo-1,2-dihydro-pyridin-3-yl)-1H-indole-2-carbonyl]-amide, 8F (80 mg, 0.15 mmol) was dissolved into 4N HCl in 1,4-dioxane (4 mL) in a tube. The reaction mixture was allowed to stir at 90° C. in the sealed tube for 1.5 hours. The reaction mixture was cooled down to room temperature before being concentrated under reduced pressure. The crude product was purified using reverse phase HPLC to provide compound 273 (55 mg, 71% yield). $^1$H NMR (500 MHz, d$_6$-DMSO): δ12.72 (bs, 2H), 7.82 & 7.80 (dd, J=1.89 Hz & 6.94 Hz, 1H), 7.66 (d, J=8.83 Hz, 2H), 7.57 (d, J=1.89 Hz, 1H), 7.49 & 7.48 (dd, J=1.58 Hz & 8.83 Hz, 1H), 7.33 (q, J=7.25 Hz & 7.88 Hz, 1H), 7.21 (t, J=9.14 Hz, 1H), 7.08 (t, J=7.57 Hz, 1H), 6.82 (t, J=7.72 Hz, 1H), 6.59 (t, J=6.62 Hz, 1H), 5.76 (s, 2H), 3.36-3.32 (m, 2H), 1.02 (t, J=7.25 Hz, 3H); $^{13}$C NMR (125 MHz, d$_6$-DMSO) δ163.04, 162.22, 160.79, 160.63, 158.66, 129.57, 129.51, 128.54, 128.51, 127.70, 127.56, 124.57, 124.44, 124.32, 122.69, 115.41, 115.24, 113.62, 113.27, 107.20, 54.84, 46.72, 7.36.

M.S. calc'd for C23H19BrFN3O4S: 532.38. Found: 534.3.

Example 9

Preparation of Compound 34

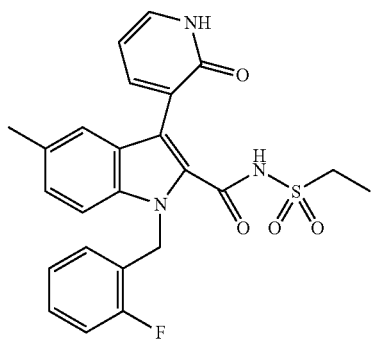

34

Step 1:

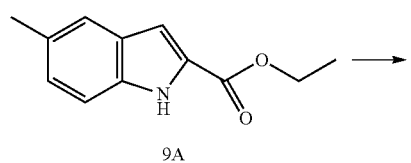

9A

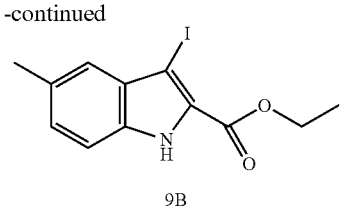

9B

To a solution of ethyl 5-methyl indole carboxylate, 9A (5.0 g, 24.6 mmol) in acetone (200 mL) was added N-iodosuccinimide (3.65 g, 15.4 mmol). The resulting suspension was allowed to stir at room temperature for 4 hours. The mixture was concentrated under reduced pressure, and the residue was dissolved into ethyl acetate (200 mL). The mixture was washed with saturated aqueous sodium thiosulfate solution (100 mL). The layers were separated, and the aqueous layer was extracted with ethyl acetate (2×100 mL). The combined organic layer was washed with water (200 mL), and was then dried (magnesium sulfate), filtered and concentrated in vacuo to provide the crude product 9B (7.62 g, 94% yield).

Step 2:

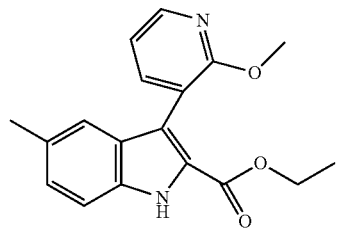

9B

9C

3-Iodo-5-methyl-1H-indole-2-carboxylic acid ethyl ester, 9B (7.62 g, 23.2 mmol) was dissolved into 1,2-dimethoxyethane (100 mL) and PdCl$_2$(dppf)$_2$ (1.89 g, 2.32 mmol) was added. The resulting mixture was de-gassed with nitrogen bubbling for 10 minutes. In a second flask, the mixture of 2-methoxy-3-pyridine boronic acid (4.26 g, 27.8 mmol) and potassium carbonate (16.0 g, 115.8 mmol) in dimethoxyethane (50 mL) and water (50 mL) was de-gassed with nitrogen bubbling for 5 minutes. The mixture was then transferred slowly to the first flask. The resulting biphasic mixture was allowed to stir at room temperature for 15 minutes, and then vigorously stirred at 90° C. for 4 hours. The reaction mixture was cooled to room temperature, and was quenched by addition of a solution of sodium sulfite (5 g) in water (100 mL) at room temperature. Ethyl acetate (200 mL) was added, and the layers were separated. The aqueous layer was extracted with ethyl acetate (2×300 mL). The combined organic layer was filtered through a pad of celite, dried over magnesium sulfate, and concentrated in vacuo to provide the crude product 9C (4.12 g, 57% yield). M.S. calc'd for C18H18N2O3: 310.35. Found: 311.15 (M+H)$^+$.

Step 3:

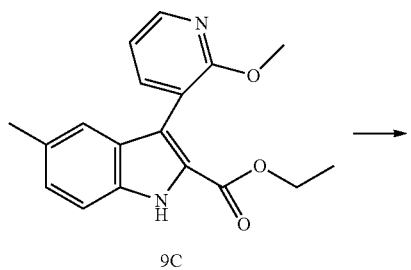

9C

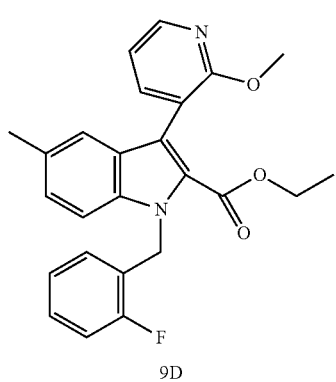

9D 3-(2-Methoxy-pyridin-3-yl)-5-methyl-1H-indole-2-carboxylic acid ethyl ester, 9C (0.70 g, 2.25 mmol) was dissolved into DMF (25 mL) at room temperature. To the mixture were added 2-fluorobenzyl bromide (0.68 g, 3.60 mmol) and cesium carbonate (1.60 g, 4.50 mmol). The resulting suspension was allowed to stir at room temperature for 18 hours. 300 mL of THF/ethyl acetate (1:3) and 50 mL of water were added to the reaction mixture, and the layers were separated. The aqueous layer was extracted with 100 mL of THF/ethyl acetate (1:3). The combined organic layer was washed with water (3×100 mL). The separated organic layer was dried over magnesium sulfate, filtered and concentrated in vacuo. The crude product obtained was purified using flash chromatography to provide compound 9D (0.75 g, 79% yield). M.S. calc'd for C25H23FN2O3: 418.46. Found: 419.27 (M+H)+.

Step 4:

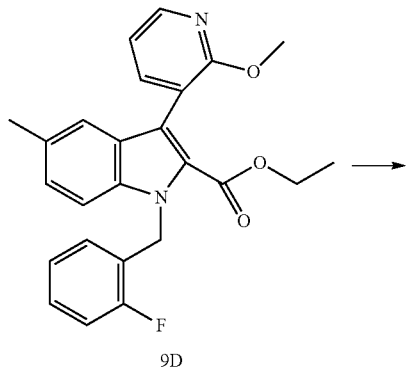

9D

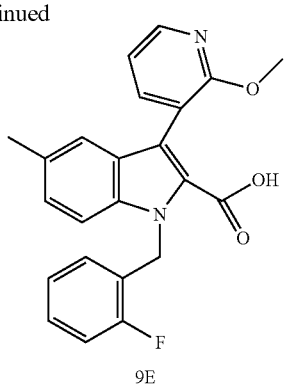

9E

To a solution of 1-(2-fluoro-benzyl)-3-(2-methoxy-pyridin-3-yl)-5-methyl-1H-indole-2-carboxylic acid ethyl ester, 9D (0.75 g, 1.79 mmol) in methanol (20 mL) was added lithium hydroxide monohydrate (220 mg, 5.24 mmol). Water (0.2 mL) was added to improve the solubility. The resulting suspension was allowed to stir at room temperature for 5 min before being placed in microwave reactor for 20 min (120° C., high power). The mixture was concentrated under reduced pressure, and 30 mL of water was added. The aqueous layer was acidified to pH=2 by adding aqueous 1N HCl solution, and the mixture was extracted three times with 100 mL of THF/ethyl acetate (3:1). The combined organic layer was dried over magnesium sulfate, filtered and concentrated in vacuo to provide the crude product 9E (0.70 g, 99% yield). M.S. calc'd for C23H19FN2O3: 390.41. Found: 391.2 (M+H)+.

Step 5:

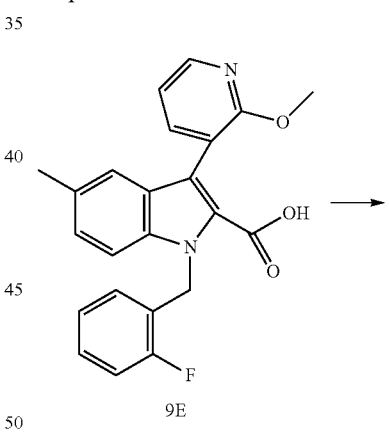

9E

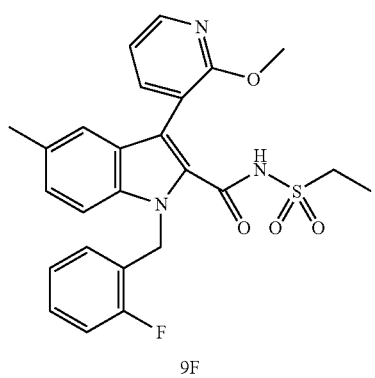

9F 1-(2-Fluoro-benzyl)-3-(2-methoxy-pyridin-3-yl)-5-methyl-1H-indole-2-carboxylic acid, 9E (140 mg, 0.36 mmol)

was dissolved into tetrahydrofuran (4 mL) at room temperature. To the mixture was added carbonyl diimidazole (87 mg, 0.54 mmol). The resulting suspension was refluxed at 75° C. for 1.5 hours, and then cooled down to room temperature before ethane sulfonamide (114 mg, 1.07 mmol) and 1,8-diazabicyclo(5.4.0)undec-7-ene (0.16 mL, 1.07 mmol) were added. The resulting reaction mixture was allowed to stir at room temperature for 48 hours. Ethyl acetate (100 mL), tetrahydrofuran (20 mL) and 1% aqueous phosphoric acid (25 mL) were added to the reaction mixture, and the layers were separated. The aqueous layer was extracted twice with ethyl acetate/THF (3:1) (60 mL). The combined organic layer was dried over magnesium sulfate, filtered and concentrated in vacuo. The crude product was purified using flash chromatography to provide compound 9F (120 mg, 70% yield). $^1$H NMR (500 MHz, d$_6$-DMSO) δ11.57 (s, 1H), 8.20 & 8.19 (dd, J=1.89 Hz & 5.04 Hz, 1H), 7.85 & 7.84 (dd, J=1.89 Hz & 7.25 Hz, 1H), 7.55 (d, J=8.51 Hz, 1H), 7.31-7.25 (m, 2H), 7.25-7.15 (m, 3H), 6.72 (t, J=6.94 Hz, 2H), 5.72 (s, 2H), 3.76 (s, 3H), 3.25 (q, J=7.25 Hz & 7.57 Hz, 2H), 2.36 (s, 3H), 0.88 (t, J=7.41 Hz, 3H). $^{13}$C NMR (125 MHz, d$_6$-DMSO) δ161.51, 160.45, 160.24, 151.47, 145.48, 140.09, 135.79, 130.14, 129.40, 128.29, 126.61, 125.56, 124.61, 119.47, 116.61, 115.91, 115.22, 115.06, 114.23, 110.74, 54.84, 52.89, 48.63, 20.97, 7.17. M.S. calc'd for C25H24FN3O4S: 481.54. Found: 482.3 (M+H)$^+$.

Step 6:

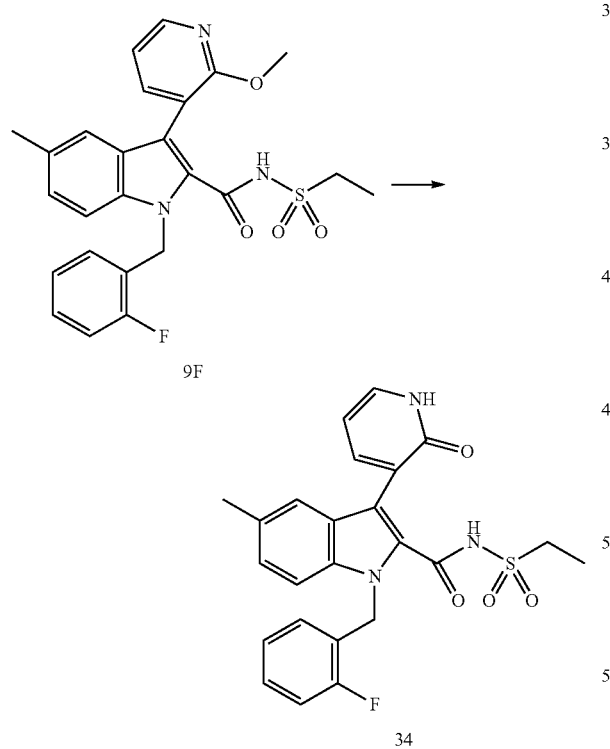

Ethanesulfonic acid [1-(2-fluoro-benzyl)-3-(2-methoxy-pyridin-3-yl)-5-methyl-1H-indole-2-carbonyl]-amide, 9F (120 mg, 0.25 mmol) was dissolved into 4N HCl in 1,4-dioxane (5 mL) in a tube. Water (0.2 mL) was added afterwards. The reaction mixture was allowed to stir at 90° C. in the sealed tube for 1.5 hours. The reaction mixture was cooled down to room temperature before being concentrated under reduced pressure. The crude product was purified using reverse phase HPLC to provide compound 34 (53 mg, 46% yield). $^1$H NMR (500 MHz, d$_6$-DMSO): δ12.75 (d, J=7.88 Hz, 2H), 7.80 d, J=4.41 Hz, 1H), 7.69 (s, 1H), 7.54-7.52 (m, 1H), 7.33-7.27 (m, 1H), 7.23-7.19 (m, 3H), 7.08-7.04 (m, 1H), 6.78 (s, 1H), 6.64 (s, 1H), 5.74 (s, 2H), 3.34-3.32 (m, 2H), 2.36 (s, 3H), 1.03-0.99 (m, 3H). $^{13}$C NMR (125 MHz, d$_6$-DMSO) δ162.59, 161.12, 160.55, 158.61, 144.16, 136.15, 135.57, 130.18, 129.28, 128.40, 127.14, 126.20, 124.88, 124.47, 119.62, 115.32, 115.15, 114.66, 110.74, 107.47, 66.92, 41.46, 20.94, 7.38. M.S. calc'd for C24H22FN3O4S: 467.51. Found: 468.3 (M+H)$^+$.

Example 10

Preparation of Compound 228

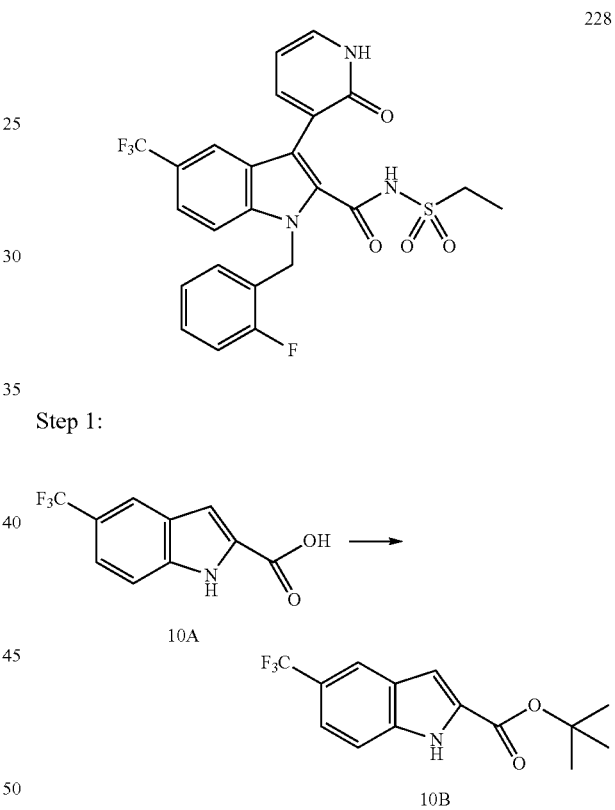

Step 1:

To a solution of 5-(trifluoromethyl)indole-2-carboxylic acid, 10A (1.6 g, 6.9 mmol) in toluene (5.0 mL) at room temperature was added N,N-dimethylformamide di-tert-butyl acetal (5.0 mL). The mixture was allowed to stir at 90° C. for 12 hours, and then was cooled to room temperature. Another aliquot of N,N-dimethylformamide di-tert butyl acetal (5 mL) was added. The reaction mixture was heated to 90° C. for another 12 hours, cooled to room temperature, and was diluted with ethyl acetate (10 mL). The mixture was washed with water (2×10 mL), and brine respectively. The separated organic layer was dried over MgSO$_4$, filtered and concentrated to provide compound 10B (1.2 g, 60% yield). $^1$H NMR (400 MHz, CDCl$_3$); δ9.17 (s, 1H), 7.97 (s, 1H), 7.51 (s, 2H), 7.21 (s, 1H), 1.63 (s, 9H).

Step 2:

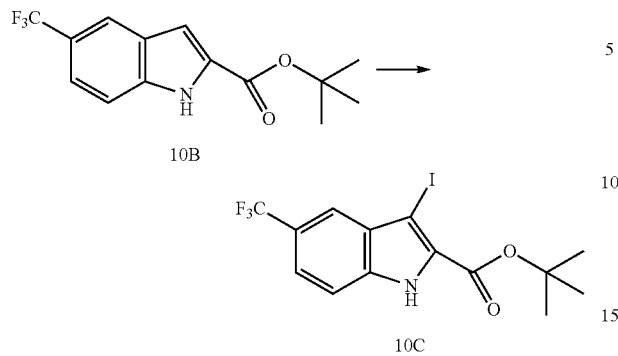

Step 4:

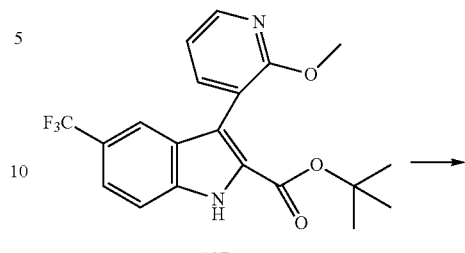

To a solution of 5-trifluoromethyl-1H-indole-2-carboxylic acid tert-butyl ester, 10B (1.2 g, 4.2 mmol) in CHCl$_3$ (25 mL) was added N-iodosuccinimide (946 mg, 4.2 mmol). The reaction mixture was allowed to stir at room temperature for 12 hours, before it was concentrated under reduced pressure. The residue was diluted into water (100 mL), and was extracted with EtOAc (200 mL). The separated organic layer was dried over MgSO$_4$, filtered, and concentrated in vacuo. The brown residue was taken in minimum amount of CH$_2$Cl$_2$ and triturated with hexanes. The product 10C was separated out as a brown solid after filtration, and dried in vacuo (1.23 g, 72% yield). $^1$H NMR (400 MHz, CDCl3); δ9.34 (s, 1H), 7.87 (s, 1H), 7.57 (d, J=8.06 Hz, 1H), 7.49 (d, J=8.79 Hz, 1H), 1.68 (s, 914).

Step 3:

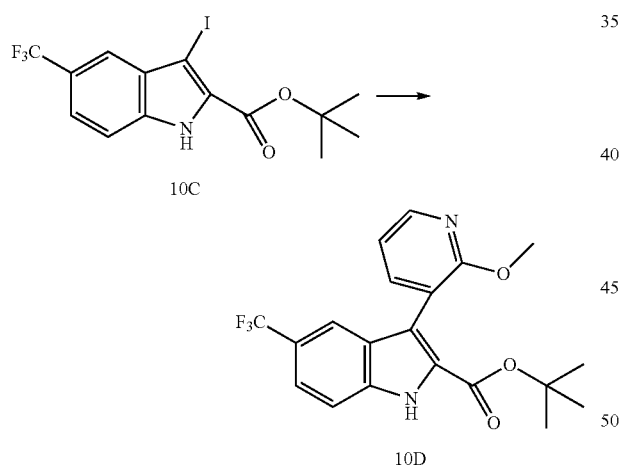

To a solution of 3-iodo-5-trifluoromethyl-1H-indole-2-carboxylic acid tert-butyl ester, 10C (1.23 g, 3.0 mmol) in DME (30 mL) under nitrogen atmosphere was added 2-methoxy-3-pyridyl boronic acid (0.48 g, 3.15 mmol) and Pd (dppf)$_2$Cl$_2$ (245 mg, 0.3 mmol). The resulting reaction was allowed to stir at room temperature under nitrogen for 0.5 hours. The reaction mixture was then treated with a solution of potassium carbonate (1.6 g, 12 mmol) in water (12 mL), and the resulting solution was allowed to stir at 90° C. for 1 hour. The reaction mixture was then diluted with EtOAc (200 mL), and the resulting solution was concentrated under reduced pressure. The residue was purified using flash column chromatography to provide compound 10D (820 mg, 70% yield). M.S. found for C20H19F3N2O3: 393.2 (M+H)$^+$.

To a solution of 3-(2-methoxy-pyridin-3-yl)-5-trifluoromethyl-1H-indole-2-carboxylic acid tert-butyl ester, 10D (400 mg, 1.02 mmol) in DMF (8 mL) were added 2-fluorobenzyl bromide (0.14 mL, 1.12 mmol) and cesium carbonate (365 mg, 1.12 mmol). The resulting mixture was allowed to stir at room temperature for 18 hours. Ethyl acetate (200 mL) and water (100 mL) were added to the reaction mixture, and the layers were separated. The organic layer was washed with water (2×100 mL) and brine (50 mL). The separated organic layer was dried over sodium sulfate, filtered and concentrated in vacuo to provide the crystallized product 10E (100% yield). M.S. found for C27H24F4N2O3: 501.11 (M+H)$^+$.

Step 5:

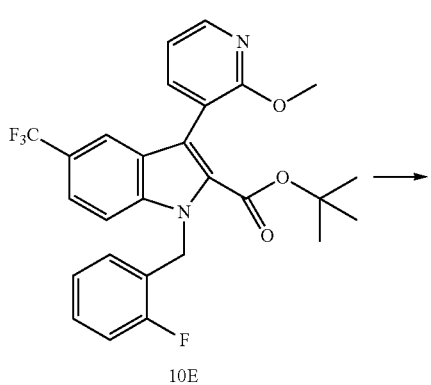

-continued

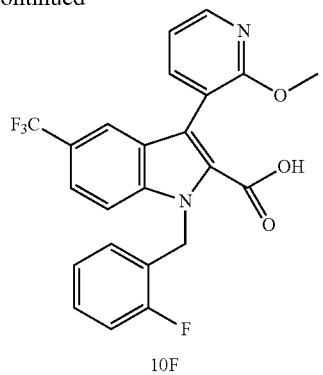

10F

To a solution of 1-(2-fluoro-benzyl)-3-(2-methoxy-pyridin-3-yl)-5-trifluoromethyl-1H-indole-2-carboxylic acid tert-butyl ester, 10E (510 mg, 1.02 mmol) in CH₂Cl₂ was added trifluoroacetic acid (3 mL). The reaction mixture was allowed to stir at room temperature for 18 hours. The solvent was removed under reduced pressure. The residue was dissolved into ethyl acetate (200 mL). The ethyl acetate solution was washed with water (4×50 mL) and brine. The separated organic layer was dried over sodium sulfate, filtered and concentrated in vacuo to provide compound 10F (100% yield). M.S. found for C23H16F4N2O3: 445.06 (M+H)⁺.

Step 6:

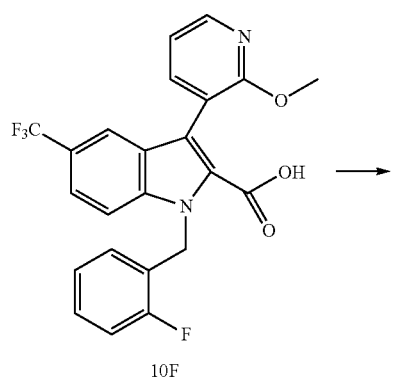

10F

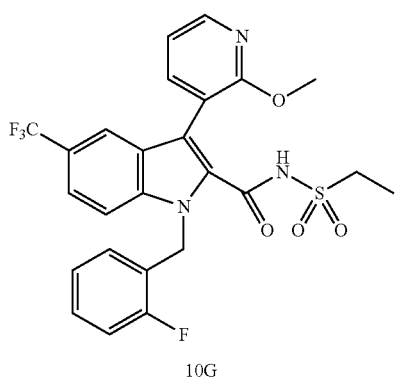

10G

To a solution of 1-(2-fluoro-benzyl)-3-(2-methoxy-pyridin-3-yl)-5-trifluoromethyl-1H-indole-2-carboxylic acid, 10F (100 mg, 0.23 mmol) in tetrahydrofuran (2 mL) was added carbonyl diimidazole (44 mg, 0.27 mmol). The resulting suspension was refluxed at 70° C. under argon for 1.5 hours, and then cooled down to room temperature. To the mixture were added ethane sulfonamide (37 mg, 0.34 mmol) and 1,8-diazabicyclo(5.4.0)undec-7-ene (67 uL, 0.45 mmol). The resulting reaction mixture was allowed to stir at room temperature for 48 hours. Ethyl acetate (100 mL) and 2% aqueous phosphoric acid (30 mL) were added to the reaction mixture, and the layers were separated. The organic layer was further washed with 2% aqueous phosphoric acid (2×30 mL), water (30 mL) and brine respectively. The organic layer was dried over sodium sulfate, filtered and concentrated in vacuo. The crude product was purified using flash chromatography to provide compound 10G (76 mg, 63% yield). M.S. found for C25H21F4N3O4S: 535.91 (M+H)⁺; 557.89 (M+Na)⁺.

Step 7:

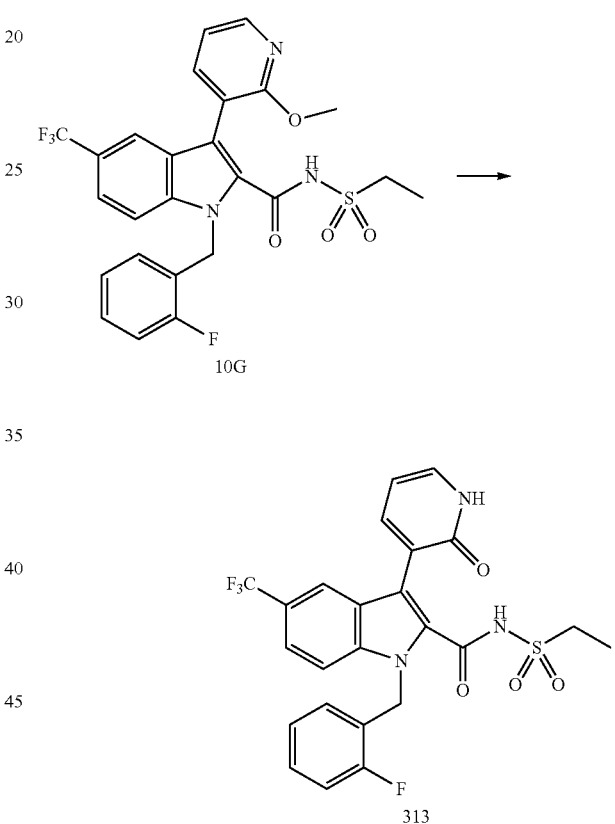

The solution of ethanesulfonic acid [1-(2-fluoro-benzyl)-3-(2-methoxy-pyridin-3-yl)-5-trifluoromethyl-1H-indole-2-carbonyl]-amide, 10G (76 mg, 0.14 mmol) in 4N HCl in 1,4-dioxane (4 mL) and 5 drops of water was allowed to stir at 90° C. in a sealed tube for 1.5 hours. The mixture was concentrated under reduced pressure, and the residue was purified using flash chromatography to provide compound 228 (37 mg, 51% yield). ¹H NMR (400 MHz, d₆-DMSO): δ7.92-7.76 (m, 4H), 7.64 (s, 2H), 7.33 (q, J=7.32 Hz, 11-1), 7.21 (t, J=9.52 Hz, 1H), 7.08 (t, J=7.32 Hz, 1H), 6.87 (t, J=7.69 Hz, 1H), 6.57 (s, 1H), 5.83 (s, 2H), 3.51-3.22 (m, 2H), 1.02 (t, J=7.32 Hz, 3H). M.S. found for C24H19F4N3O4S: 522.22 (M+H)⁺.

Example 11

Preparation of Compound 505

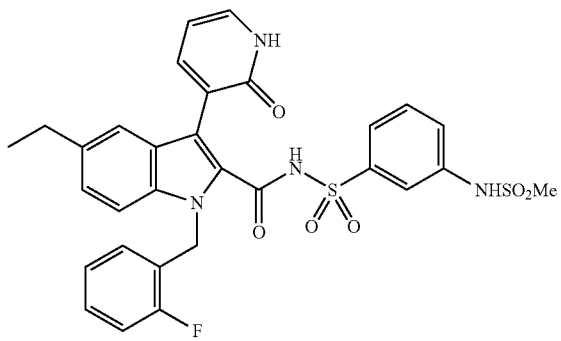

Step 1:

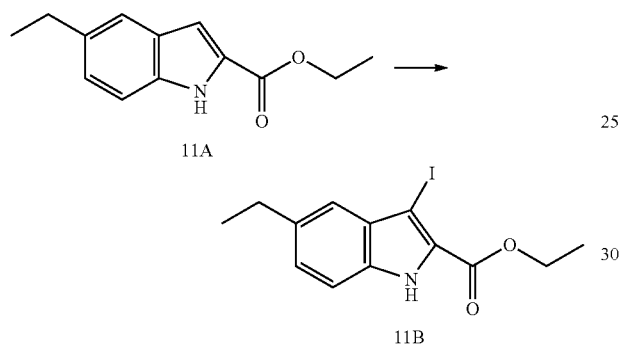

To a solution of 5-ethylindole-2-carboxylic acid ethyl ester, 11A (5.0 g, 23 mmol) in chloroform (100 mL) at room temperature was added N-iodosuccinimide (5.20 g, 23 mmol). The resulting suspension was allowed to stir at room temperature for 24 hours. The mixture was concentrated under reduced pressure, and the residue was dissolved into ethyl acetate (200 mL). The mixture was washed with water (100 mL) and brine (60 mL). The separated organic layer was dried over sodium sulfate, filtered and concentrated in vacuo to provide the crude product, 11B (7.35 g, 93% yield). M.S. found for C13H14INO2: 343.94 (M+H)+.

Step 2:

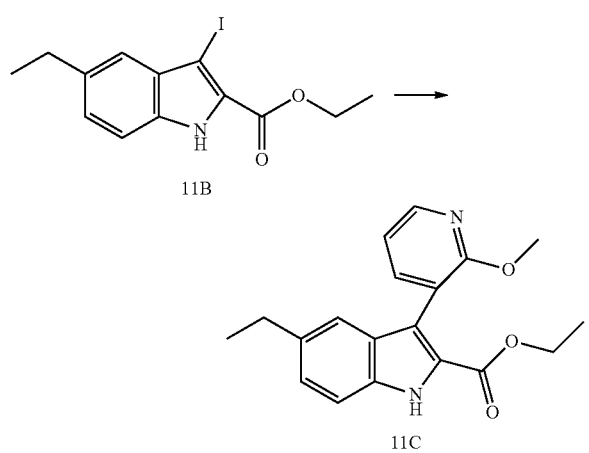

5-Ethyl-3-iodo-1H-indole-2-carboxylic acid ethyl ester, 11B (7.35 g, 21.4 mmol) was dissolved into 1,2-dimethoxyethane (150 mL). And PdCl$_2$(dppf)$_2$ (1.72 g, 0.21 mmol) was added. The resulting mixture was refluxed at 95° C. for 0.5 hours. To the mixture was added slowly the solution of 2-methoxy-3-pyridine boronic acid (9.60 g, 63 mmol) and potassium carbonate (8.7 g, 63 mmol) in water (50 mL). The resulting bi-phasic mixture was vigorously stirred at 95° C. for 1 h before it was cooled to room temperature. The reaction mixture was filtered and concentrated in vacuo. The residue was diluted with ethyl acetate (300 mL), and was washed with a solution of sodium sulfite (15 g) in water (200 mL). The aqueous layer was extracted with ethyl acetate (2×300 mL). The combined organic layer was dried over sodium sulfate, filtered and concentrated in vacuo. The residue was purified using flash chromatography to provide compound 11C (5.0 g, 74% yield). M.S. found for C19H20N2O3: 325.06 (M+H)+.

Step 3:

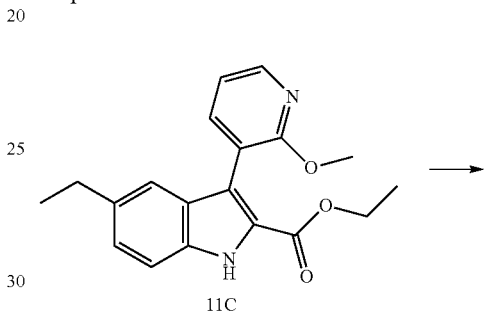

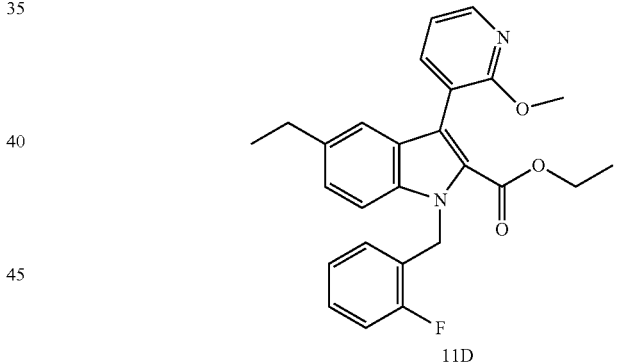

5-Ethyl-3-(2-methoxy-pyridin-3-yl)-1H-indole-2-carboxylic acid ethyl ester, 11C (500 mg, 1.54 mmol) was dissolved into DMF (20 mL) at room temperature. To the mixture were added 2-fluorobenzyl chloride (224 mg, 1.54 mmol) and cesium carbonate (502 mg, 1.54 mmol). The resulting suspension was allowed to stir at room temperature for 24 hours. Ethyl acetate (100 mL) and water (50 mL) were added to the reaction mixture, and the layers were separated. The aqueous layer was extracted with ethyl acetate (2×50 mL). The combined organic layer was washed with water (2×50 mL). The separated organic layer was dried over sodium sulfate, filtered and concentrated in vacuo. The crude product was purified using flash chromatography to provide compound 11D (665 mg, 100% yield).

Step 4:

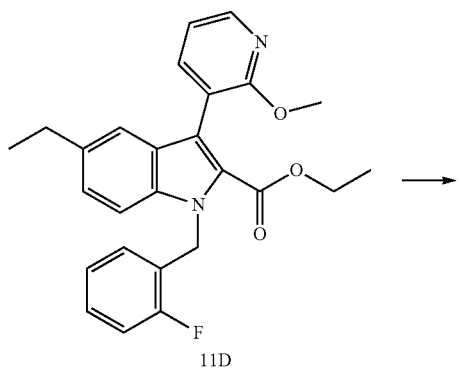

11D

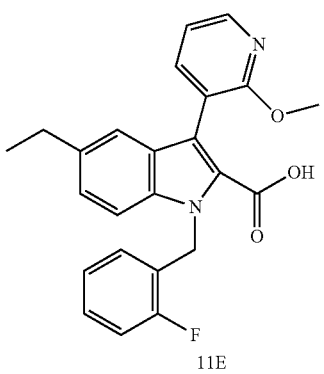

11E

To a solution of 5-ethyl-1-(2-fluoro-benzyl)-3-(2-methoxy-pyridin-3-yl)-1H-indole-2-carboxylic acid ethyl ester, 11D (665 mg, 1.54 mmol) in THF (50 mL) was added the solution of lithium hydroxide (220 mg, 9.24 mmol) in water (15 mL). The resulting suspension was allowed to stir at room temperature until the starting material was all consumed up. The mixture was concentrated under reduced pressure. Ethyl acetate (50 mL) and water (50 mL) were added to the residue. The aqueous layer was acidified to pH=2 by adding aqueous 1N HCl solution, and was saturated with NaCl salts. The layers were separated, and the aqueous layer was further extracted with ethyl acetate (2×50 mL). The combined organic layer was dried over sodium sulfate, filtered and concentrated in vacuo to provide the crude product 11E (620 mg, 100% yield). M.S. found for C24H21N2O3F: 405.28 (M+H)+.

Step 5:

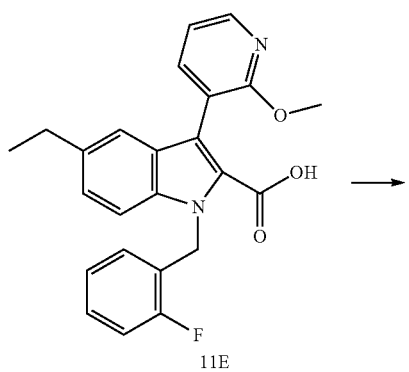

11E

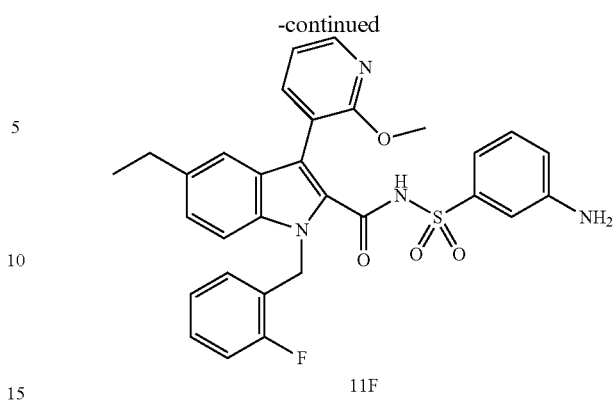

11F

5-Ethyl-1-(2-fluoro-benzyl)-3-(2-methoxy-pyridin-3-yl)-1H-indole-2-carboxylic acid, 11E (100 mg, 0.25 mmol) was dissolved into tetrahydrofuran (10 mL) at room temperature. To the mixture was added carbonyl diimidazole (49 mg, 0.30 mmol). The resulting suspension was refluxed at 75° C. for 1 hour, and then cooled down to room temperature before the addition of 3-aminobenzenesulfonamide (52 mg, 0.30 mmol) and 1,8-diazabicyclo(5.4.0)undec-7-ene (46 mg, 0.30 mmol). The resulting reaction mixture was allowed to stir at room temperature for 24 hours. The solvent was then evaporated under reduced pressure. Ethyl acetate (80 mL) and 1% aqueous phosphoric acid (25 mL) were added to the reaction mixture, and the layers were separated. The aqueous layer was extracted with ethyl acetate (2×60 mL). The combined organic layer was dried over sodium sulfate, filtered and concentrated in vacuo. The crude product was purified using flash chromatography to provide compound 11F (30 mg, 21% yield).

Step 7:

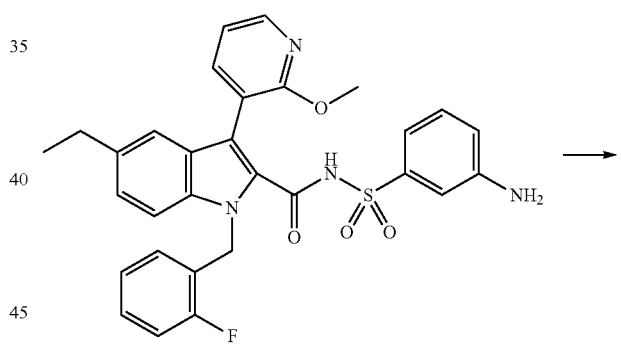

11F

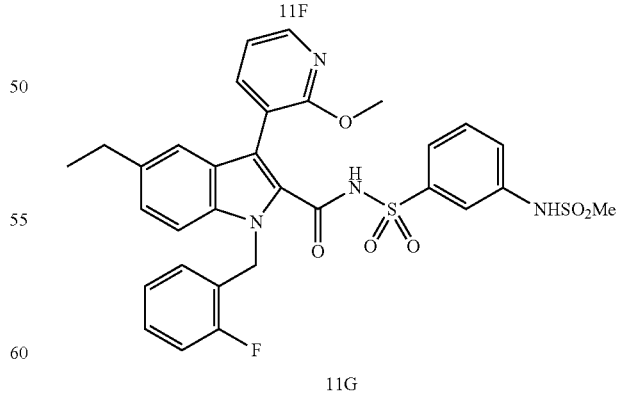

11G

To a solution of 3-amino-N-[5-ethyl-1-(2-fluoro-benzyl)-3-(2-methoxy-pyridin-3-yl)-1H-indole-2-carbonyl]-benzenesulfonamide, 11F (30 mg, 0.05 mmol) in THF (5 mL) and pyridine (1 mL) was slowly added ClSO2Me. The resulting reaction mixture was allowed to stir at room temperature for 24 hours, and then was diluted with ethyl acetate (50 mL). The mixture was washed with aqueous 1N HCl solution (20 mL) and brine (20 mL) respectively. The separated organic layer was dried over sodium sulfate, filtered and concentrated in vacuo. The crude product was purified using flash chromatography to provide compound 11G (30 mg, 94% yield).

Step 8:

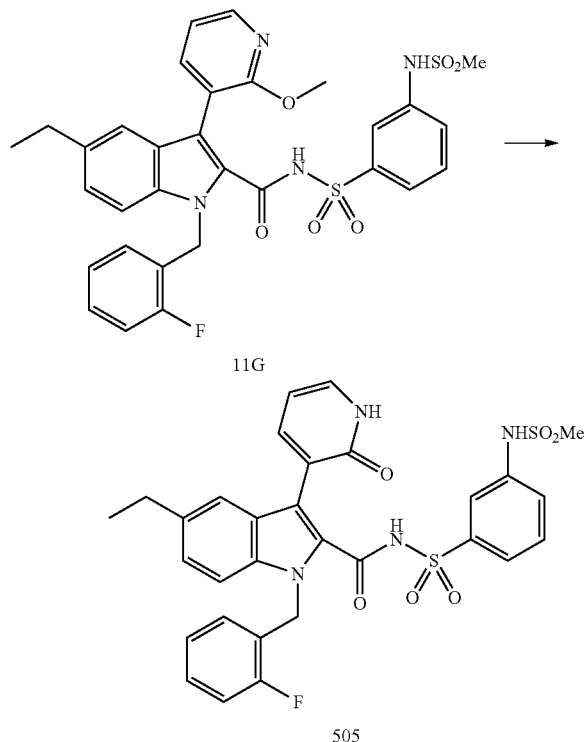

To a solution of N-[5-ethyl-1-(2-fluoro-benzyl)-3-(2-methoxy-pyridin-3-yl)-1H-indole-2-carbonyl]-3-methanesulfonylamino-benzenesulfonamide, 11G (30 mg, 0.05 mmol) in dioxane (3 mL) was added HCl (1 mL). The resulting reaction mixture was allowed to stir at 90° C. in a sealed tube for 2 hours. The mixture was concentrated under reduced pressure, and the residue was purified using flash chromatography to provide compound 505 (10 mg, 34% yield). $^1$H NMR (500 MHz, CD3OD): δ 7.87 (s, 1H), 7.77 (s, 1H), 7.67 (d, J=7.88 Hz, 1H), 7.59 (d, J=7.88 Hz, 1H), 7.54 (t, J=8.35 Hz, 1H), 7.47-7.35 (m, 3H), 7.27 (s, 1H), 7.22 (q, J=6.94 Hz & 6.62 Hz, 2H), 7.02 (t, J=9.46 Hz, 1H), 6.90 (t, J=7.57 Hz, 1H), 6.67 (s, 2H), 5.69 (s, 2H), 2.98 (s, 3H), 2.72 (q, J=7.25 Hz & 7.57 Hz, 2H), 1.24 (t, J=7.57 Hz, 3H). M.S. found for $C_{30}H_{27}FN_4O_6S_2$: 623.3 (M+H)$^+$ Example 12

Preparation of Compound 195

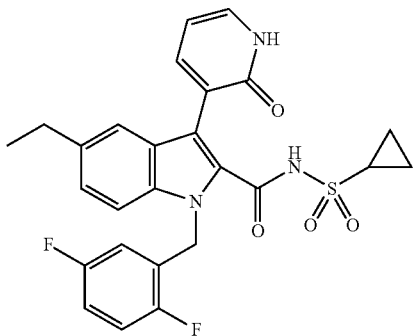

Step 1:

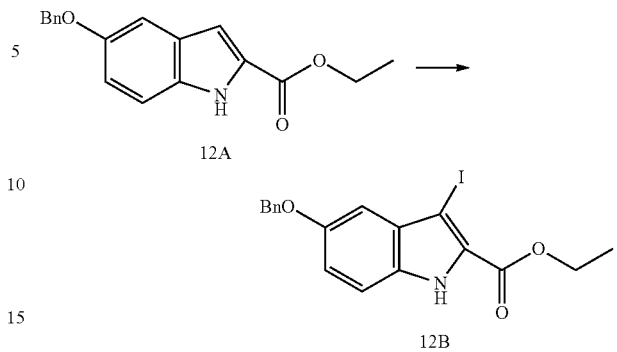

To a solution of ethyl 5-OBn indole carboxylate (12A, 10.0 g, 33.9 mmol) in acetone (300 mL) was added N-iodosuccinimide (8.0 g, 33.8 mmol). The resulting suspension was allowed to stir at room temperature for 4 hours. The mixture was concentrated under reduced pressure, and the residue was dissolved into ethyl acetate (300 mL). The mixture was washed with saturated aqueous sodium thiosulfate solution (200 mL). The layers were separated, and the aqueous layer was extracted with ethyl acetate (2×200 mL). The combined organic layer was dried over magnesium sulfate, filtered and concentrated in vacuo to provide the crude product 12B (100% yield). M.S. found for C18H16INO3: 421.89 (M+H)$^+$.

Step 2:

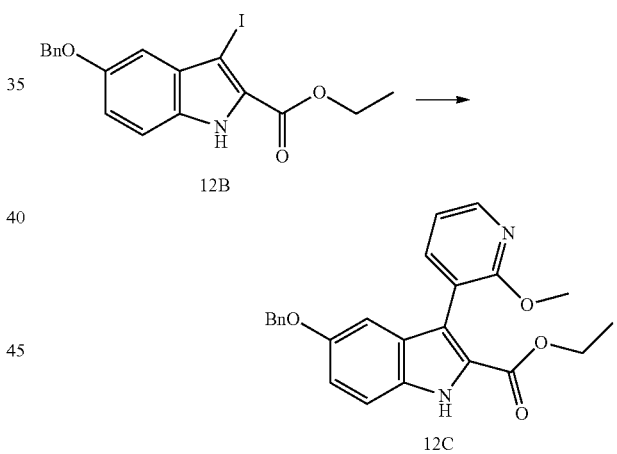

5-Benzyloxy-3-iodo-1H-indole-2-carboxylic acid ethyl ester, 12B (10.8 g, 24.1 mmol) was dissolved into 1,2-dimethoxyethane (300 mL). And PdCl$_2$(dppf)$_2$ (2.0 g, 2.45 mmol) was added. The resulting mixture was de-gassed with nitrogen bubbling for 5 min before it was heated to 90° C. and allowed to stir for 15 minutes. In a second flask, the mixture of 2-methoxy-3-pyridine boronic acid (4.3 g, 28.1 mmol) and potassium carbonate (16.7 g, 121 mmol) in dimethoxyethane (100 mL) and water (100 mL) was de-gassed with nitrogen bubbling for 5 minutes. The mixture was then transferred in three portions to the first flask. The resulting biphasic mixture was vigorously stirred at 90° C. for 3.5 h before it was cooled to room temperature. The reaction was quenched by addition of a solution of sodium sulfite (15 g) in water (200 mL) at room temperature. Ethyl acetate (300 mL) was added, and the layers were separated. The aqueous layer was extracted with ethyl acetate (2×300 mL). The combined organic layer was dried (magnesium sulfate), filtered and concentrated in vacuo to provide the crude product 12C (7.37 g, 76% yield). M.S. found for C24H22N2O4: 403.1 (M+H)+.

Step 3:

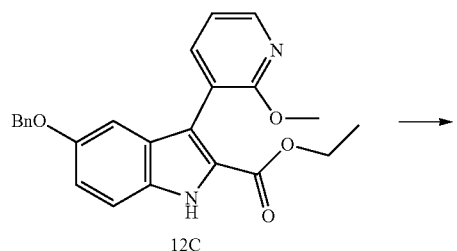

To a solution of 5-benzyloxy-3-(2-methoxy-pyridin-3-yl)-1H-indole-2-carboxylic acid ethyl ester, 12C (4.2 g, 10.4 mmol) in absolute EtOH was added 5% Pd—C (2.0 g). The flask was vacuumed, and then charged with H$_2$ gas. The reaction mixture was allowed to stir at room temperature for 3 hours. The palladium catalyst was filtered off through a pad of celite, and was washed with 100 mL of MeOH/THF (1:1). The filtrate collected was concentrated under reduced pressure to provide the crude product 12D (3.25 g, 100% yield). M.S. found for C17H16N2O4: 313.2 (M+H)+.

Step 4:

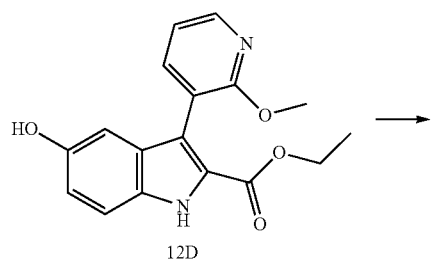

To the mixture of 5-hydroxy-3-(2-methoxy-pyridin-3-yl)-1H-indole-2-carboxylic acid ethyl ester, 12D (3.2 g, 10.4 mmol) and triethyl amine (4.0 mL, 28.7 mmol) in dichloromethane (100 mL) was added PhN(SO$_2$CF$_3$)$_2$ (5.4 g, 15.1 mmol). The resulting reaction mixture was allowed to stir at room temperature for 4 hours. The mixture was then diluted with dichloromethane (100 mL), and was washed with aqueous 1N sodium carbonate solution (2×100 mL). The separated aqueous solution was again extracted with dichloromethane (100 mL). The combined organic layer was dried over magnesium sulfate, filtered and concentrated in vacuo. The crude product was purified using flash chromatography to provide compound 12E (4.12 g, 88% yield). M.S. found for C18H15F3N2O6S: 445.2 (M+11)÷.

Step 5:

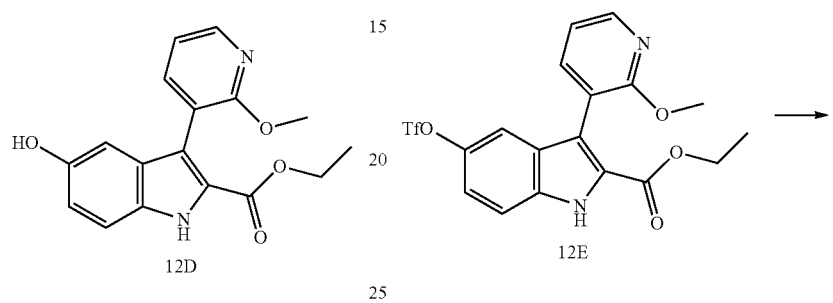

To a solution of 3-(2-methoxy-pyridin-3-yl)-5-trifluoromethanesulfonyloxy-1H-indole-2-carboxylic acid ethyl ester, 12E (1.0 g, 2.25 mmol), TMS acetylene (2.0 mL, 14.4 mmol) and nBu$_4$N$^+$I$^-$ (0.92 g, 2.49 mmol) in DMF (48 mL) were added PdCl$_2$(PPh$_3$)$_2$ (160 mg, 0.23 mmol), CuI (130 mg, 0.68 mmol) and triethylamine (2.1 mL, 15.1 mmol). The resulting reaction mixture was stirred in a sealed tube at 65° C. for 18 hours. The mixture was cooled down to room temperature, and was diluted with water (50 mL) and EtOAc (100 mL). The layers were separated, and the aqueous layer was extracted with EtOAc (2×50 mL). The combined organic layer was washed with water (2×100 mL) before it was dried over magnesium sulfate, filtered and concentrated in vacuo to provide the crude product 12F (100% yield). M.S. found for C22H24N2O3Si: 393.3 (M+H)+.

Step 6:

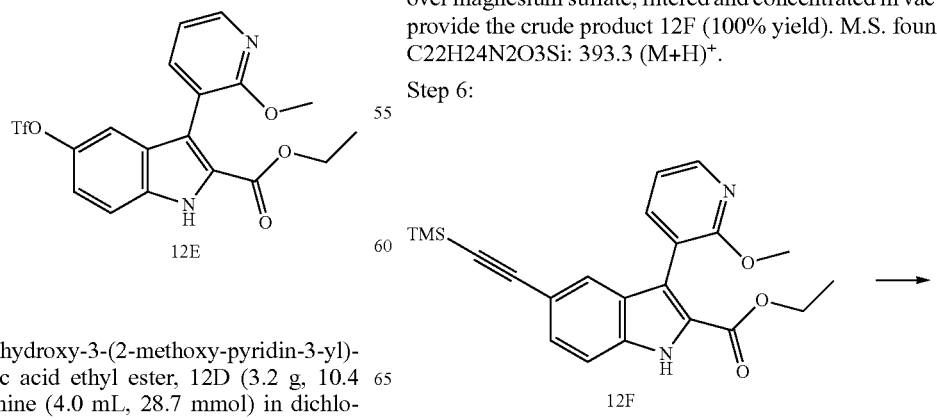

-continued

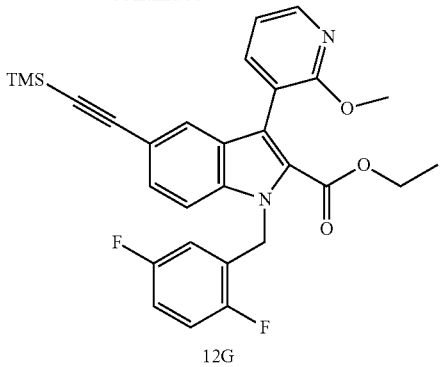
12G 3-(2-Methoxy-pyridin-3-yl)-5-trimethylsilanylethynyl-1H-indole-2-carboxylic acid ethyl ester, 12F (0.76 g, 1.94 mmol) was dissolved into DMF (40 mL) at room temperature. To the mixture were added 2,5-difluorobenzyl bromide (0.60 g, 2.9 mmol) and cesium carbonate (1.1 g, 3.38 mmol). The resulting suspension was allowed to stir at room temperature for 18 hours. 300 mL of THF/ethyl acetate (1:3) and 50 mL of water were added to the reaction mixture, and the layers were separated. The aqueous layer was extracted with ethyl acetate (2×50 mL). The combined organic layer was washed with water (2×100 mL). The separated organic layer was dried over magnesium sulfate, filtered and concentrated in vacuo to provide the crude product 12G (0.65 g, 81% yield). M.S. found for $C_{29}H_{28}F_2N_2O_3Si$: 519.3 (M+H)+.

Step 7:

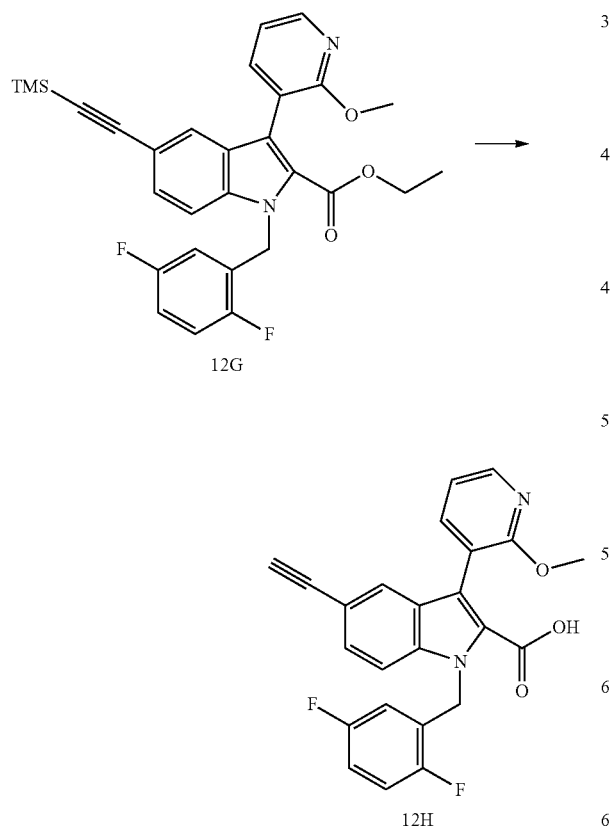

To a solution of 1-(2,5-difluoro-benzyl)-3-(2-methoxy-pyridin-3-yl)-5-trimethylsilanylethynyl-1H-indole-2-carboxylic acid ethyl ester, 12G (0.65 g, 1.25 mmol) in methanol (12 mL) and THF (5 mL) was added lithium hydroxide monohydrate (220 mg, 5.24 mmol). The resulting suspension was allowed to stir at room temperature for 5 min before being placed in microwave reactor for 20 min (120° C., high power). The mixture was concentrated under reduced pressure, and 30 mL of water was added. The aqueous layer was acidified to pH=2 by adding aqueous 1N HCl solution, and the mixture was extracted three times with 100 mL of THF/ethyl acetate (3:1). The combined organic layer was dried over magnesium sulfate, filtered and concentrated in vacuo to provide the crude product 12H (100% yield). $^1$H NMR (400 MHz, CDCl3) δ8.32 & 8.30 (dd, J=2.20 Hz & 5.13 Hz, 1H), 7.75 & 7.73 (dd, J=2.20 Hz & 7.32 Hz, 1H), 7.68 (s, 1H), 7.45 (d, J=9.52 Hz, 1H), 7.33 (d, J=8.79 Hz, 1H), 7.09-6.88 (m, 4H), 6.47-6.42 (m, 1H), 5.87 (s, 2H), 3.74 (s, 3H), 3.01 (s, 1H).

Step 8:

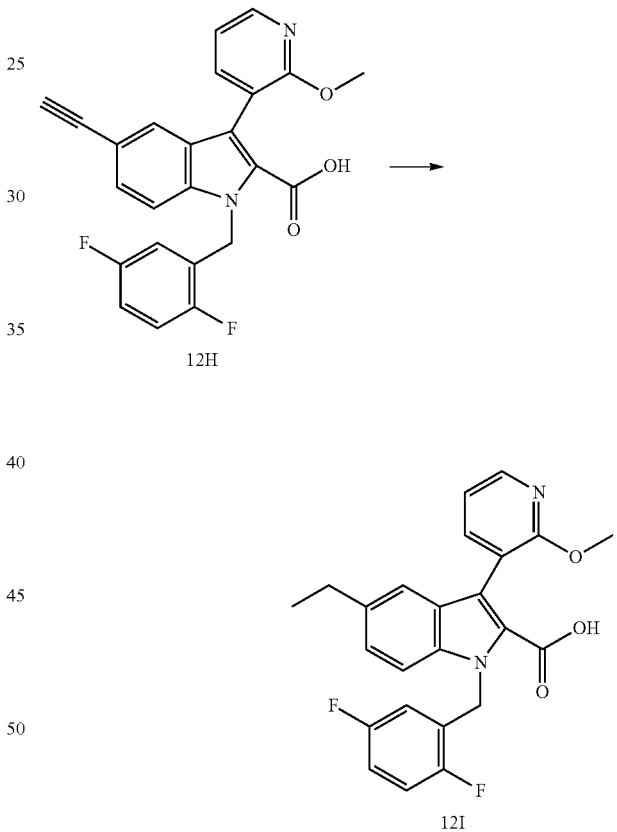

To a solution of 1-(2,5-difluoro-benzyl)-5-ethynyl-3-(2-methoxy-pyridin-3-yl)-1H-indole-2-carboxylic acid, 12I1 (0.57 g, 1.25 mmol) in absolute EtOH and THF was added 5% Pd—C (200 mg). The flask was vacuumed, and then charged with $H_2$ gas. The reaction mixture was allowed to stir at room temperature for 3 hours. The palladium catalyst was filtered off through a pad of celite, and was washed with 100 mL of MeOH/THF (1:1). The filtrate collected was concentrated under reduced pressure to provide the crude product 12I (100% yield). M.S. found for C24H20F2N2O3: 423.05 (M+H)+.

Step 9:

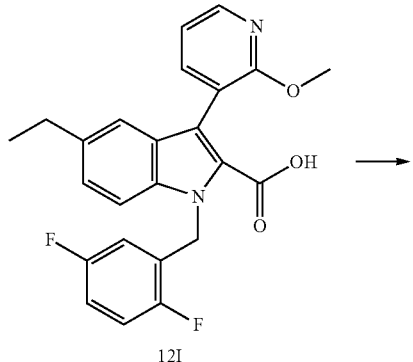

12I 1-(2,5-Difluoro-benzyl)-5-ethyl-3-(2-methoxy-pyridin-3-yl)-1H-indole-2-carboxylic acid, 12I (140 mg, 0.36 mmol) was dissolved into tetrahydrofuran (5 mL) at room temperature. To the mixture was added carbonyl diimidazole (78 mg, 0.48 mmol). The resulting suspension was refluxed at 75° C. for 1 hour, and then cooled down to room temperature before it was added cyclopropyl sulfonamide (89 mg, 0.74 mmol) and 1,8-diazabicyclo(5.4.0)undec-7-ene (0.12 mL, 0.80 mmol). The resulting reaction mixture was allowed to stir at room temperature for 18 hours. Ethyl acetate (150 mL) and 5% aqueous phosphoric acid (100 mL) were added, and the layers were separated. The aqueous layer was extracted twice with ethyl acetate (2×60 mL). The combined organic layer was dried over magnesium sulfate, filtered and concentrated in vacuo. The crude product was purified using flash chromatography to provide compound 12J (155 mg, 80% yield). M.S. found for C27H25F2N3O4S: 526.06 (M+H)$^+$.

Step 10:

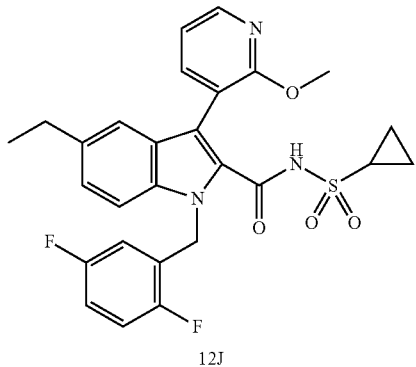

12J

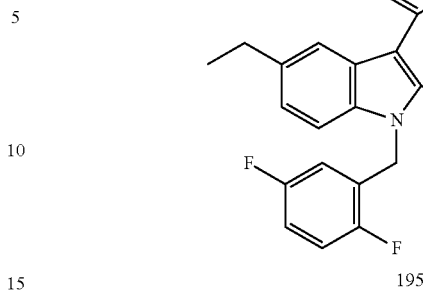

195

Cyclopropanesulfonic acid [1-(2,5-difluoro-benzyl)-5-ethyl-3-(2-methoxy-pyridin-3-yl)-1H-indole-2-carbonyl]-amide, 12J (155 mg, 0.30 mmol) was dissolved into 4N HCl in 1,4-dioxane (6 mL) in a tube. The reaction mixture was allowed to stir at 90° C. in the sealed tube for 2.5 hours. The reaction mixture was cooled down to room temperature before being concentrated under reduced pressure. The crude product was purified using reverse phase HPLC to provide compound 195 (57 mg, 38% yield). $^1$H NMR (500 MHz, d$_6$-DMSO): δ 12.79 (s, 1H), 12.73 (s, 1H), 7.82 (d, J=6.62 Hz, 1H), 7.69 (d, J=5.04 Hz, 1H), 7.57 (d, J=8.51 Hz, 1H), 7.33-7.15 (m, 4H), 6.64-6.60 (m, 2H), 5.73 (s, 2H), 2.96-2.91 (m, 1H), 2.66 (q, J=7.25 Hz & 7.57 Hz, 2H), 1.17 (t, J=7.57 Hz, 3H), 0.98 (d, J=5.99 Hz, 4H). M.S. found for C26H23F2N3O4S: 512.18 (M+H)$^+$.

Example 13

Preparation of Compound 192

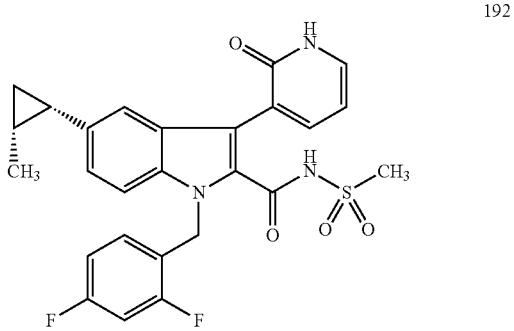

192

Step 1:

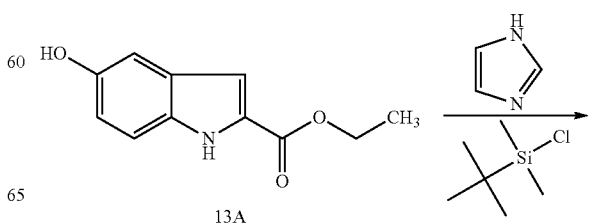

13A

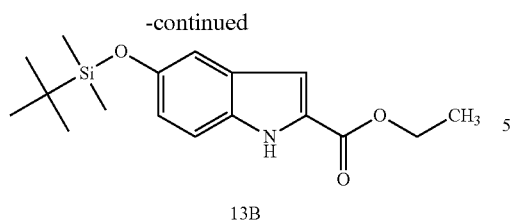

13B

A solution of ethyl 5-hydroxy-1H-indole-2-carboxylate (13A, 6.0 g; 29.24 mmol) in 300 mL of dichloromethane was treated with imidazole (4.0 eq, 7.96 g) and tert-butyldimethylsilyl chloride (2.0 eq, 8.82 g). The reaction was allowed to stir at room temp for 3 hours. A small sample (1 mL) was taken from reaction mixture, diluted with dichloromethane (10 mL) and washed with water. Evaporation of the solvent and NMR analysis showed all starting material had been consumed. The reaction mixture was diluted with dichloromethane (300 mL) and washed with water (2×100 mL) and brine (100 mL). The organic layer was dried over magnesium sulfate, filtered and concentrated to provide compound 13B (9.20 g; 98%) as a white solid.

Step 2:

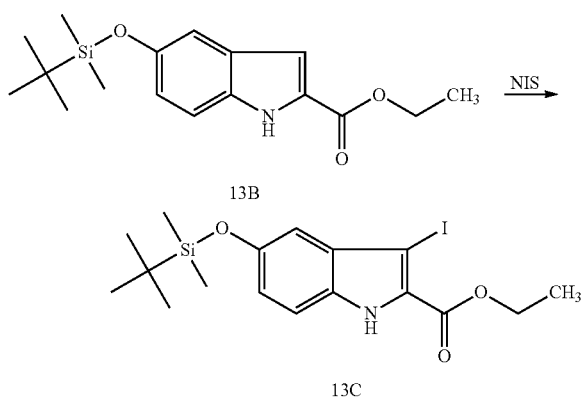

A solution of ethyl 5-tert-butyldimethylsilyloxy-1H-indole-2-carboxylate 13B (9.0 g) in 300 mL of chloroform was ice-cooled and treated with N-iodosuccinimide (1.1 eq, 6.97 g). The mixture was allowed to stir at 0° C. for 10 min and then at room temp for 2 hours. NMR analysis of a small aliquot showed complete conversion of starting material. The reaction mixture was diluted with dichloromethane (300 mL) and washed with aq saturated sodium thiosulfate (150 mL), aq saturated sodium bicarbonate (150 mL) and brine (100 mL). The organic layer was dried over magnesium sulfate, filtered and concentrated to provide compound 13C (11.58 g; 92%) as a white solid. M.S. found for $C_{17}H_{24}INO_3Si$: 446.36 (M+H)$^+$.

Step 3:

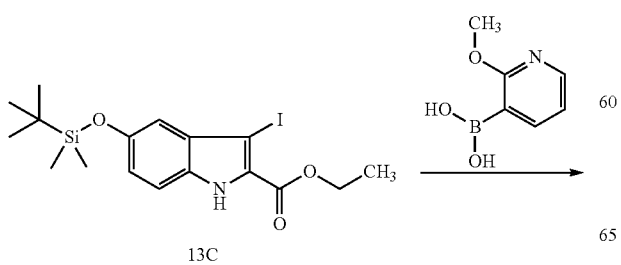

The 2-methoxy-3-pyridine boronic acid (1.05 eq, 3.27 g) was added to a solution of 13C (9.06 g; 20.345 mmol) in 100 mL of 1,2-dimethoxyethane. The mixture was degassed (vacuum/argon flush) and PdCl$_2$(dppf)$_2$ (10 mol %, 1.66 g) was added and the resulting orange solution was allowed to stir for 30 min at room temp. A solution of potassium carbonate (4.0 eq, 81 mL of aq 1M soln) was added and the resulting brown solution was allowed to stir at 90° C. for 2 hours. The reaction mixture was cooled to room temperature and concentrated. The residue was diluted with ethyl acetate (600 mL) and washed with aq saturated sodium bicarbonate (100 mL) and brine (100 mL). The organic layer was dried over magnesium sulfate, filtered and concentrated. The residue was divided into two equal portions and each was purified using silica gel chromatography (Biotage 75-M column; gradient: 0 to 30% ethyl acetate in hexanes) to provide compound 13D as a white solid (6.76 g; 65%). M.S. found for C23H30N2O4Si: 427.56 (M+H)$^+$.

Step 4:

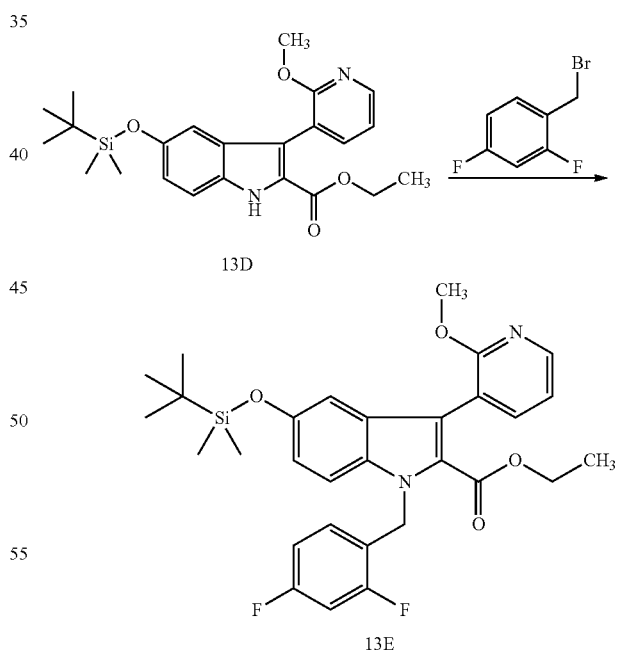

A solution of indole derivative 13D (6.5 g, 15.237 mmol) in 50 mL of dry THF was added to an ice-cooled suspension of sodium hydride (1.3 eq, 792 mg of 60% susp in mineral oil) in 50 mL of dry THF. The resulting solution was allowed to stir for 10 min followed by addition of 2,4-difluorobenzyl bromide (1.3 eq, 2.54 mL, d 1.613). A catalytic amount of tetrabutylammonium iodide (0.2 eq, 1.12 g) was added to the reaction mixture and stirring was continued for 18 h (temperature from 0 to 25° C.). The reaction was quenched by addition of water (10 mL) and the mixture was diluted with ethyl acetate (500 mL). The organic layer was washed with water (2×100 mL) and brine (80 mL), dried over magnesium sulfate, filtered and concentrated to provide the crude product 13E as a colorless foam contaminated with undesired bis-N,O-difluorobenzyl product. The crude mixture was used for next reaction without further any further purification. M.S. found for $C_{30}H_{34}N_2O_4Si$: 553.65 $(M+H)^+$.

Step 6:

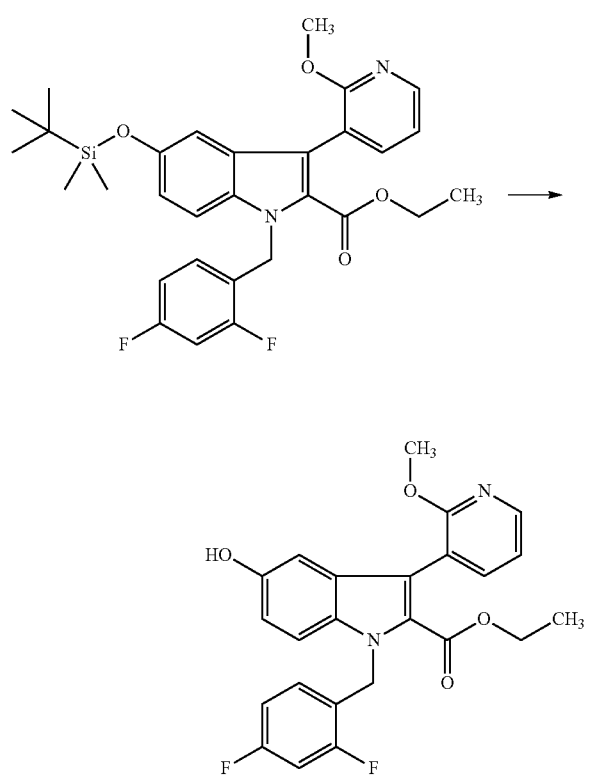

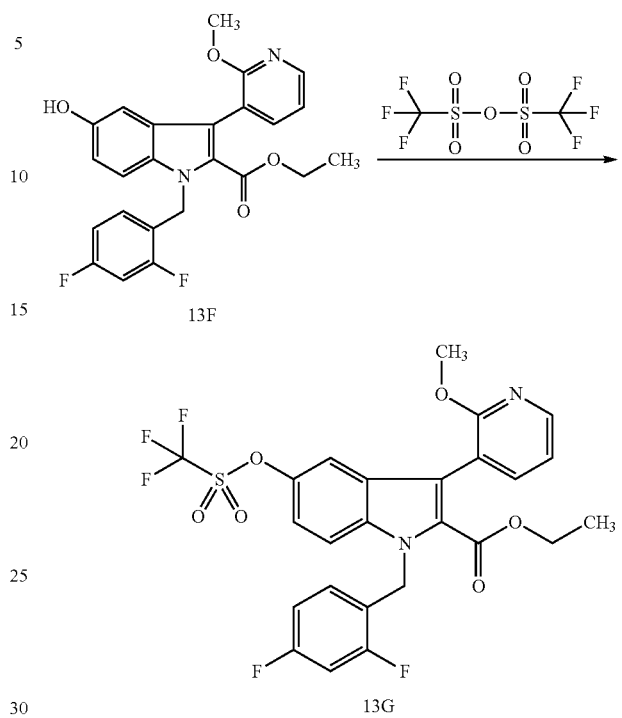

Step 5:

A solution of crude silylether 13E (15.237 mmol; 8.4 g) in 100 mL of THF (NOTE: 13E contains an impurity identified as the bis-N,O-difluorobenzyl compound) was ice-cooled and treated with ca 1.0 eq of TBAF (15 mL of 1.0M soln in THF). The mixture immediately turned yellow-green in color and TLC after 5 min (30% ethyl acetate in hexanes) showed no more starting material left. The mixture was diluted with ethyl acetate (500 mL) and washed with water (100 mL), aq saturated sodium bicarbonate (100 mL) and brine (100 mL). The organic layer was dried over magnesium sulfate, filtered and concentrated. The residue was purified using silica gel chromatography (Biotage 75-M column; gradient: 10 to 50% ethyl acetate in hexanes) to provide compound 13F as a white solid (5.8 g; 88% for two steps). $^1$H NMR (400 MHz, $d_6$-DMSO): δ9.09 (s, 1H), 8.17 & 8.16 (dd, J=2.20 & 5.13 Hz, 1H), 7.71 & 7.69 (dd, J=1.46 & 7.32 Hz, 1H), 7.45 (d, J=8.79 Hz, 1H), 7.26 (t, J=10.98 Hz, 1H), 7.10-7.06 (m, 1H), 6.97 (dt, J=8.79 & 2.20 Hz, 1H), 6.88 & 6.86 (dd, J=8.79 & 2.20 Hz, 1H), 6.76-6.71 (m, 1H), 6.67 (d, J=2.20 Hz, 1H), 5.77 (s, 2H), 3.99 (q, J=7.32 Hz, 2H), 3.75 (s, 3H), 0.85 (t, J=7.32 Hz, 3H).

A solution of 1-(2,4-Difluoro-benzyl)-5-hydroxy-3-(2-methoxy-pyridin-3-yl)-1H-indole-2-carboxylic acid ethyl ester 13F (2.0 g; 4.56 mmol) in 20 mL of dry dichloromethane was ice cooled and treated with pyridine (4 mL) and triflic anhydride (2.1 eq, 1.61 mL, d 1.677). The mixture was allowed to stir for 10 min and treated with a catalytic amount of 4-dimethylamino pyridine. The cooling bath was removed and the reaction was allowed to stir for 2 hours. TLC (10% ethyl acetate in hexanes) showed no more starting material left and the mixture was diluted with ethyl acetate (200 mL) and washed with water (50 mL) and brine (50 mL). The organic layer was dried over magnesium sulfate, filtered and concentrated. The residue was purified using silica gel chromatography (Biotage 40-M column; gradient: 0 to 20% ethyl acetate in hexanes) to provide compound 13G (2.50 g; 96%) as a colorless oil. MS found for $C_{25}H_{19}F_5N_2O_6S$: 571.12 $(M+H)^+$.

Step 7:

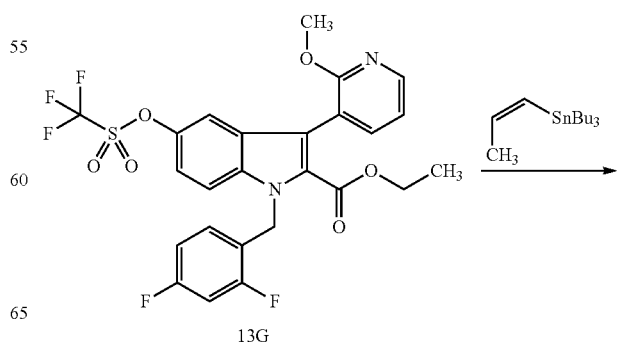

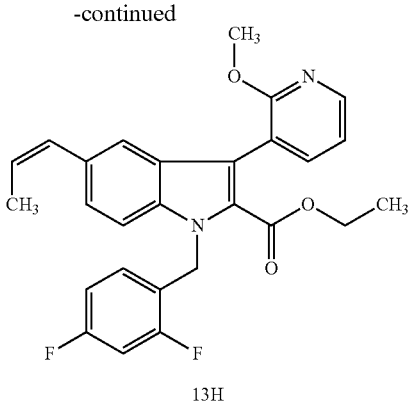

13H

A solution of 1-(2,4-difluoro-benzyl)-3-(2-methoxy-pyridin-3-yl)-5-trifluoromethanesulfonyloxy-1H-indole-2-carboxylic acid ethyl ester 13G (650 mg; 1.13 mmol) in 10 mL of THF was treated with lithium chloride (7.0 eq, 336 mg) and (Z)-1-propenyltributyl stannane (1.5 eq, 0.51 mL, d 1.1). The mixture was degassed (vacuum/nitrogen flush) and tetrakis (triphenylphosphine)palladium was added (10 mol %, 130 mg). The reaction mixture was heated to 70° C. and stirred overnight. TLC (10% ethyl acetate in hexanes) and MS analyses showed complete conversion of starting material. The mixture was diluted with ethyl acetate (80 mL) and washed successively with water (10 mL), 10% aq ammonium hydroxide (10 mL), water (10 mL), and brine (10 mL). The organic layer was dried over magnesium sulfate, filtered and concentrated in vacuo. The residue was purified using silica gel chromatography (Biotage 25-M column; gradient: 80 mL of hexanes then 0 to 25% ethyl acetate in hexanes) to provide compound 13H (400 mg; 77%) as a colorless oil. MS found for C27H24F2N2O3: 463.30 (M+H)+.

Step 8:

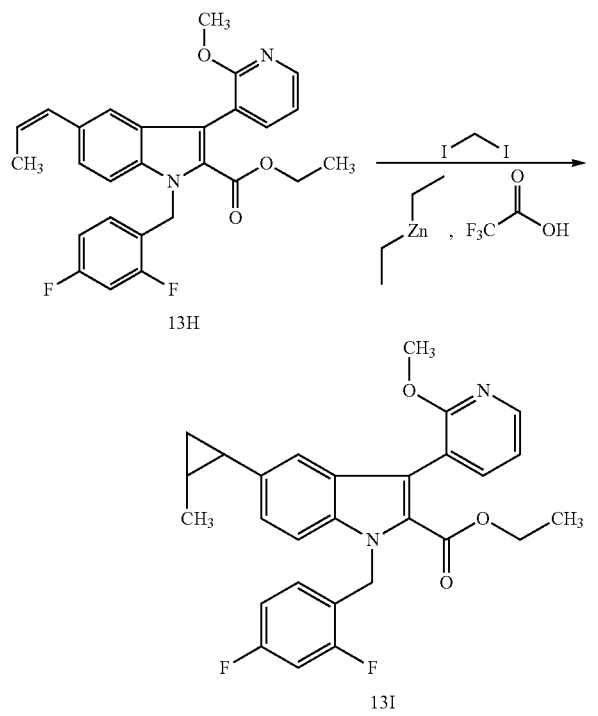

To a vigorously stirred solution of diethylzinc (10.0 eq, 3.9 mL of 1M soln in heptane) in 2 mL of dry dichloromethane at 0° C. (ice-water bath) was added dropwise a solution of trifluoroacetic acid (10.0 eq, 0.299 mL, d 1.480) in 0.5 mL of dichloromethane. The resulting mixture was allowed to stir for 10 min after which a solution of diiodomethane (10.0 eq, 0.31 mL, d 3.325) in 0.5 mL of dichloromethane was added dropwise. The mixture was allowed to stir for 10 min followed by addition of a solution of 1-(2,4-difluoro-benzyl)-3-(2-methoxy-pyridin-3-yl)-5-prop-Z-enyl-1H-indole-2-carboxylic acid ethyl ester 13H (180 mg; 0.389 mmol) in 1 mL of dry dichloromethane. The reaction was allowed to stir at 0° C. and monitored by TLC and MS analyses (NOTE: Rf of starting material and product is the same in different solvent systems). After 4 h the reaction was quenched by addition of aq saturated sodium bicarbonate (10 mL). The mixture was extracted with ethyl acetate (50 mL). The organic layer was washed with aq 1M HCl (10 mL), aq saturated sodium bicarbonate (10 mL), and brine (10 mL). The organic layer was dried over magnesium sulfate, filtered and concentrated. The residue was purified using silica gel chromatography (Biotage 12-S column, gradient: 0 to 20% ethyl acetate in hexanes) to provide compound 13I as a colorless oil. M.S. found for C28H26F2N2O3: 477.26 (M+H)+.

Step 9:

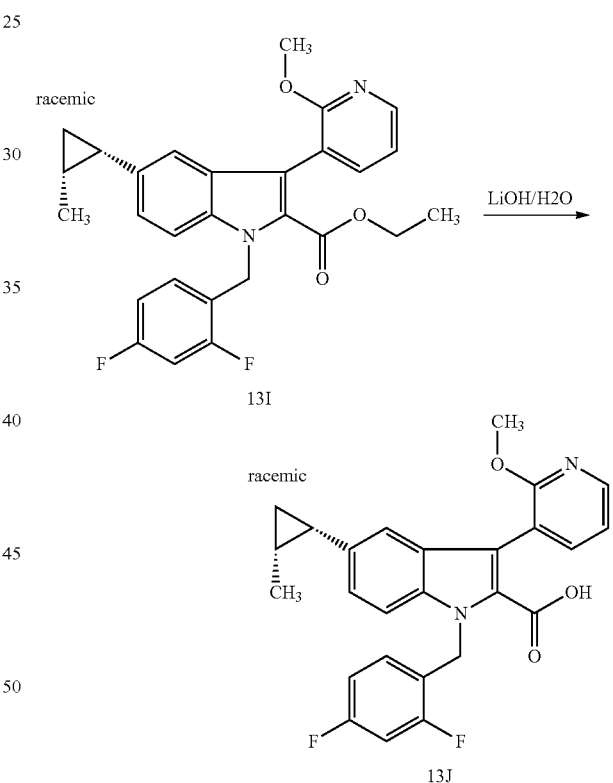

A solution of 1-(2,4-difluoro-benzyl)-3-(2-methoxy-pyridin-3-yl)-5-(2-cis-methyl-cyclopropyl)-1H-indole-2-carboxylic acid ethyl ester 13I (230 mg; 0.482 mmol) in 10 mL of a 5:1:1 THF/water/methanol mixture was treated with lithium hydroxide monohydrate (5.0 eq, 101 mg). The mixture was heated to 50° C. for 5 hours. TLC (20% ethyl acetate in hexanes) showed complete consumption of the starting material. The mixture was diluted with aq 1M HCl (40 mL) and the product was taken into dichloromethane (3×25 mL). The combined organic layers were dried over magnesium sulfate, filtered and concentrated to provide compound 13J (205 mg; 95% yield) as a white solid.

Step 10:

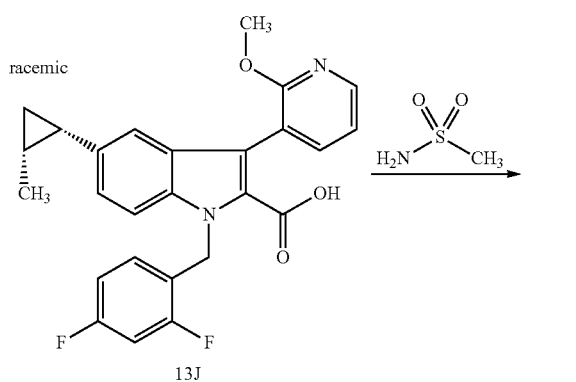

A solution of 1-(2,4-difluoro-benzyl)-3-(2-methoxy-pyridin-3-yl)-5-(2-cis-methyl-cyclopropyl)-1H-indole-2-carboxylic acid 13J (100 mg; 0.222 mmol) in 5 mL of dry THF was treated with carbonyl diimidazole (1.25 eq, 45 mg). The mixture was heated to 70° C. for 2 h and then cooled to room temp. Methanesulfonamide (1.25 eq, 26 mg) and DBU (1.5 eq, 0.049 mL, d 1.018) were added and the mixture was heated to 70° C. overnight. The mixture was diluted with ethyl acetate (60 mL) and washed with aq 1M HCl (10 mL) and brine (10 mL). The organic layer was dried over magnesium sulfate, filtered and concentrated in vacuo. The residue was purified using silica gel chromatography (Biotage 25-S silica gel column, gradient: 0 to 20% acetone in dichloromethane) to provide compound 13K (85 mg; 73%) as a white solid. M.S. found for C27H25F2N3O4S: 526.16 (M+H)$^+$.

Step 11:

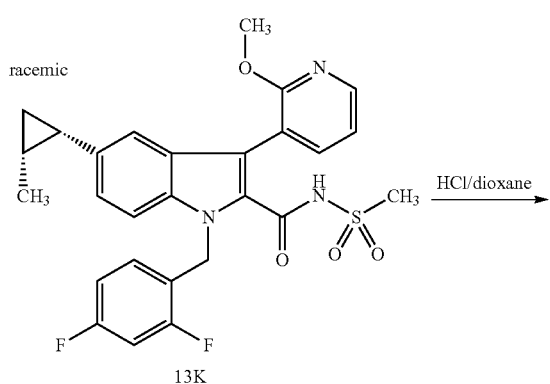

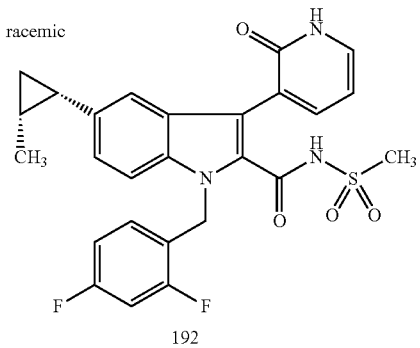

The N-[1-(2,4-Difluoro-benzyl)-3-(2-methoxy-pyridin-3-yl)-5-(2-methyl-cyclopropyl)-1H-indole-2-carbonyl]-methanesulfonamide 13K (0.152 mmol) was dissolved in 3 mL of 4M HCl soln in dioxane. Methanol was added (1 mL) and the solution was heated at 90° C. in a sealed tube for 2.5 hours. The reaction mixture was concentrated to provide the crude product as a white solid. A sample (1 mg) was dissolved in 0.5 mL of DMF and analyzed on analytical HPLC under the following conditions: Column: Delta Pak; C18, 5 micrometer, 300 A; 150×3.9 mm I.D.; Flow rate: 1 mL/min; Gradient: 40% acetonitrile in water for 5 min then increase to 80% over 25 minutes. The product was purified on semi-prep HPLC under the following conditions: Column: Delta Pak, C18, 5 micrometer, 300 A; 300×30 mm I.D.; Flow rate: 30 mL/min; Gradient: 50% acetonitrile in water for 20 min then increase to 80% over 30 min and stay there for 10 minutes. The fraction containing the product according to MS analysis was concentrated to remove acetonitrile and water to provide compound 192 (30 mg; 40%) as a white solid. MS found for C26H23F2N3O4S: 512.06 (M+H)$^+$. $^1$H NMR (400 MHz, d$_6$-DMSO): δ7.78 & 7.76 (dd, J=2.20 & 6.59 Hz, 1H), 7.64 (bs, 1H), 7.52 (d, J=8.06 Hz, 1H), 7.29-7.17 (m, 3H), 7.02-6.94 (m, 2H), 6.62-6.58 (m, 1H), 5.67 (s, 2H), 3.25 (s, 3H), 2.14-2.09 (m, 1H), 1.11-1.10 (m, 1H), 0.94-0.89 (m, 1H), 0.68-0.67 (m, 3H), 0.56-0.52 (m, 1H).

Example 14

Preparation of Compound 194

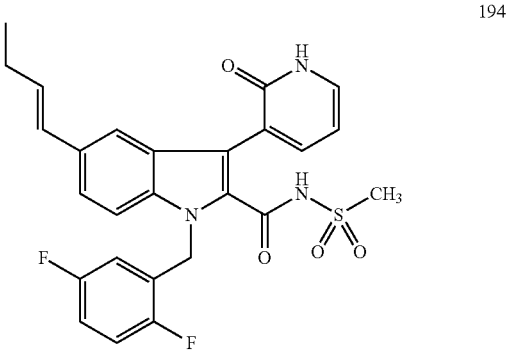

Step 1:

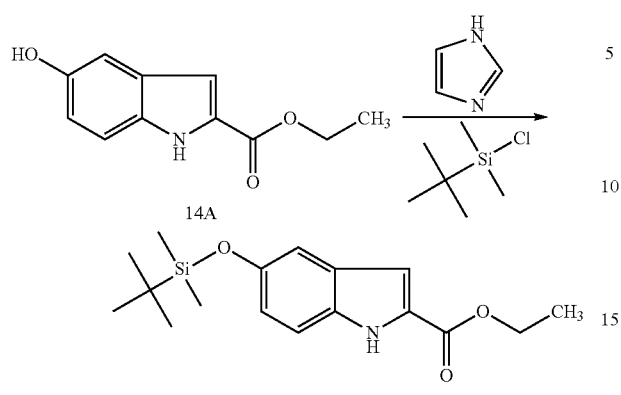

A solution of ethyl 5-hydroxy-1H-indole-2-carboxylate 14A (6.0 g; 29.24 mmol) in 300 mL of dichloromethane was treated with imidazole (4.0 eq, 7.96 g) and tert-butyldimethylsilyl chloride (2.0 eq, 8.82 g). The reaction was allowed to stir at room temp for 3 hours. A small sample (1 mL) was taken from reaction mixture, diluted with dichloromethane (10 mL) and washed with water. Evaporation of the solvent and NMR analysis showed all starting material had been consumed. The reaction mixture was diluted with dichloromethane (300 mL) and washed with water (2×100 mL) and brine (100 mL). The organic layer was dried over magnesium sulfate, filtered and concentrated to provide compound 14B (9.20 g; 98%) as a white solid.

Step 2:

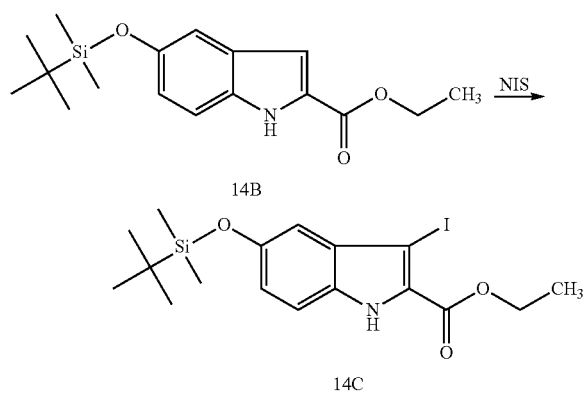

A solution of ethyl 5-tert-butyldimethylsilyloxy-1H-indole-2-carboxylate 14B (9.0 g) in 300 mL of chloroform was ice-cooled and treated with N-iodosuccinimide (1.1 eq, 6.97 g). The mixture was allowed to stir at 0° C. for 10 min and then at room temp for 2 hours. NMR analysis of a small aliquot showed complete conversion of starting material. The reaction mixture was diluted with dichloromethane (300 mL) and washed with aq saturated sodium thiosulfate (150 mL), aq saturated sodium bicarbonate (150 mL) and brine (100 mL). The organic layer was dried over magnesium sulfate, filtered and concentrated to provide compound 14C (11.58 g; 92%) as a white solid. M.S. found for C17H24INO3Si: 446.36 (M+H)$^+$.

Step 3:

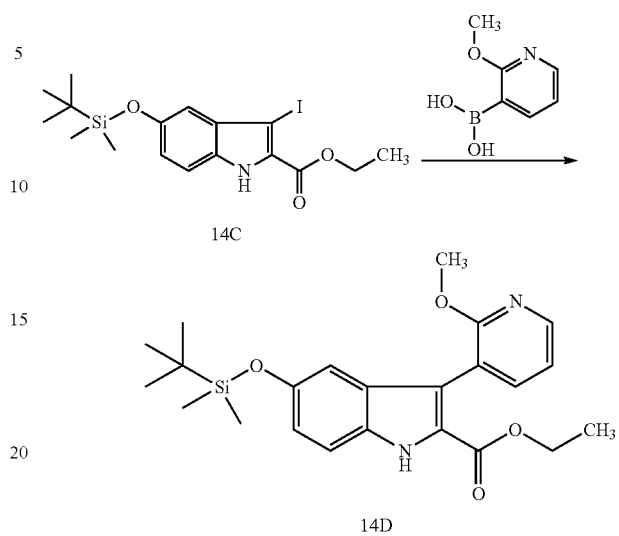

The 2-methoxy-3-pyridine boronic acid (1.05 eq, 3.27 g) was added to a solution of 14C (9.06 g; 20.345 mmol) in 100 mL of 1,2-dimethoxyethane. The mixture was degassed (vacuum/argon flush) and PdCl$_2$(dppf)$_2$ (10 mol %, 1.66 g) was added and the resulting orange solution was allowed to stir for 30 min at room temp. A solution of potassium carbonate (4.0 eq, 81 mL of aq 1M soln) was added and the resulting brown solution was allowed to stir at 90° C. for 2 hours. The reaction mixture was cooled to room temperature and concentrated. The residue was diluted with ethyl acetate (600 mL) and washed with aq saturated sodium bicarbonate (100 mL) and brine (100 mL). The organic layer was dried over magnesium sulfate, filtered and concentrated. The residue was divided into two equal portions and each was purified using silica gel chromatography (Biotage 75-M column; gradient: 0 to 30% ethyl acetate in hexanes) to provide compound 14D as a white solid (6.76 g; 65%). M.S. found for C23H30N2O4Si: 427.56 (M+H)$^+$.

Step 4:

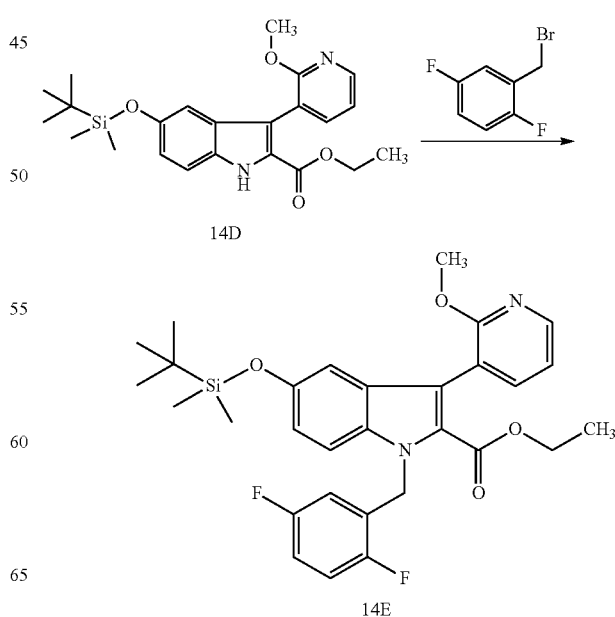

A solution of indole derivative 14D (6.5 g, 15.237 mmol) in 50 mL of dry THF was added to an ice-cooled suspension of sodium hydride (1.3 eq, 792 mg of 60% suspension in mineral oil) in 50 mL of dry THF. The resulting solution was allowed to stir for 10 min followed by addition of 2,5-difluorobenzyl bromide (1.3 eq, 2.54 mL, d 1.613). A catalytic amount of tetrabutylammonium iodide (0.2 eq, 1.12 g) was added to the reaction mixture and stirring was continued for 18 h (temperature from 0 to 25° C.). The reaction was quenched by addition of water (10 mL) and the mixture was diluted with ethyl acetate (500 mL) The organic layer was washed with water (2×100 mL) and brine (80 mL), dried over magnesium sulfate, filtered and concentrated to provide the crude product 14E as a colorless foam contaminated with undesired bis-N, O-difluorobenzyl product. The crude mixture was used for next reaction without further any further purification.

Step 5:

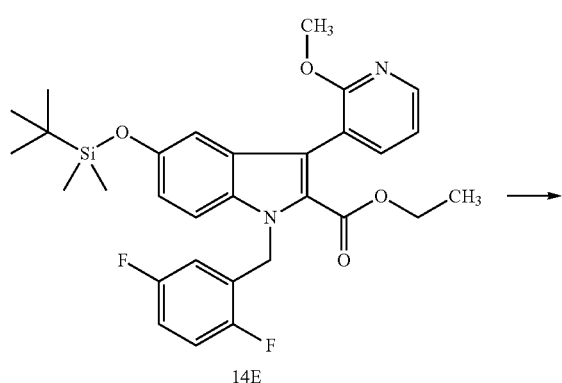

14E

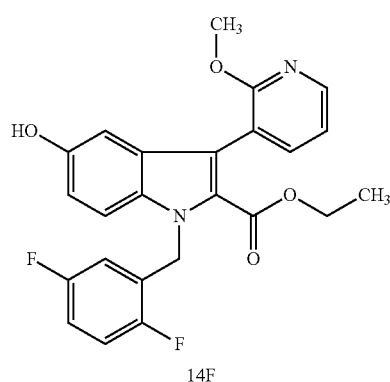

14F

A solution of crude silylether 14E (15.237 mmol; 8.4 g) in 100 mL of THF (NOTE: 14E contains an impurity identified as the bis-N,O-difluorobenzyl compound) was ice-cooled and treated with ca 1.0 eq of TBAF (15 mL of 1.0M soln in THF). The mixture immediately turned yellow-green in color and TLC after 5 min (30% ethyl acetate in hexanes) showed no more starting material left. The mixture was diluted with ethyl acetate (500 mL) and washed with water (100 mL), aq saturated sodium bicarbonate (100 mL) and brine (100 mL). The organic layer was dried over magnesium sulfate, filtered and concentrated. The residue was purified using silica gel chromatography (Biotage 75-M column; gradient: 10 to 50% ethyl acetate in hexanes) to provide compound 14F as a white solid (5.8 g; 88% for two steps).

Step 6:

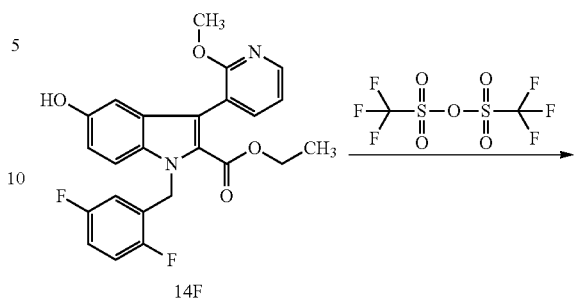

14F

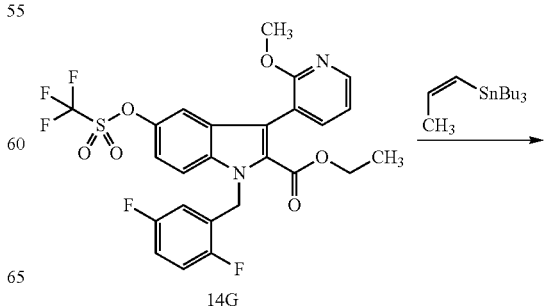

14G

A solution of 1-(2,5-Difluoro-benzyl)-5-hydroxy-3-(2-methoxy-pyridin-3-yl)-1H-indole-2-carboxylic acid ethyl ester 14F (2.0 g; 4.56 mmol) in 20 mL of dry dichloromethane was ice cooled and treated with pyridine (4 mL) and triflic anhydride (2.1 eq, 1.61 mL, d 1.677). The mixture was allowed to stir for 10 min and treated with a catalytic amount of 4-dimethylamino pyridine. The cooling bath was removed and the reaction was allowed to stir for 2 hours. TLC (10% ethyl acetate in hexanes) showed no more starting material left and the mixture was diluted with ethyl acetate (200 mL) and washed with water (50 mL) and brine (50 mL). The organic layer was dried over magnesium sulfate, filtered and concentrated. The residue was purified using silica gel chromatography (Biotage 40-M column; gradient: 0 to 20% ethyl acetate in hexanes) to provide compound 14G (2.50 g; 96%) as a colorless oil.

Step 7:

14G

-continued

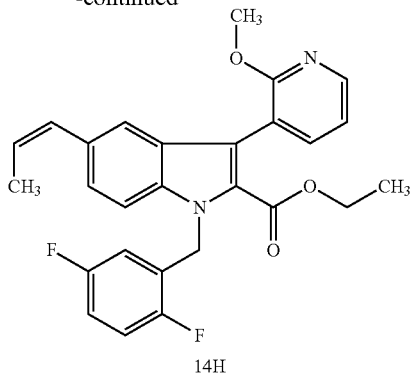

14H

A solution of 1-(2,5-difluoro-benzyl)-3-(2-methoxy-pyridin-3-yl)-5-trifluoromethanesulfonyloxy-1H-indole-2-carboxylic acid ethyl ester 14G (650 mg; 1.13 mmol) in 10 mL of THF was treated with lithium chloride (7.0 eq, 336 mg) and (Z)-1-propenyltributyl stannane (1.5 eq, 0.51 mL, d 1.1). The mixture was degassed (vacuum/nitrogen flush) and tetrakis(triphenylphosphine)palladium was added (10 mol %, 130 mg). The reaction mixture was heated to 70° C. and stirred overnight. TLC (10% ethyl acetate in hexanes) and MS analyses showed complete conversion of starting material. The mixture was diluted with ethyl acetate (80 mL) and washed successively with water (10 mL), 10% aq ammonium hydroxide (10 mL), water (10 mL), and brine (10 mL). The organic layer was dried over magnesium sulfate, filtered and concentrated in vacuo. The residue was purified using silica gel chromatography (Biotage 25-M column; gradient: 80 mL of hexanes then 0 to 25% ethyl acetate in hexanes) to provide compound 14H (400 mg; 77%) as a colorless oil.

Step 8:

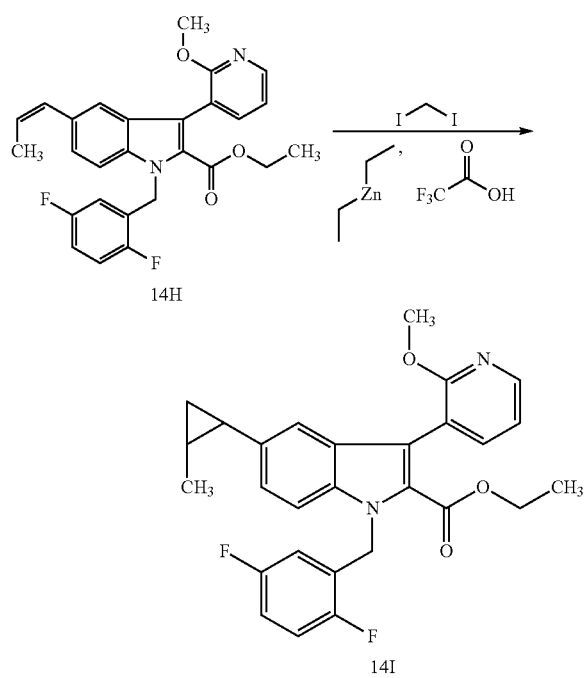

To a vigorously stirred solution of diethylzinc (10.0 eq, 3.9 mL of 1M soln in heptane) in 2 mL of dry dichloromethane at 0° C. (ice-water bath) was added dropwise a solution of trifluoroacetic acid (10.0 eq, 0.299 mL, d 1.480) in 0.5 mL of dichloromethane. The resulting mixture was allowed to stir for 10 min after which a solution of diiodomethane (10.0 eq, 0.31 mL, d 3.325) in 0.5 mL of dichloromethane was added dropwise. The mixture was allowed to stir for 10 min followed by addition of a solution of 1-(2,5-difluoro-benzyl)-3-(2-methoxy-pyridin-3-yl)-5-prop-Z-enyl-1H-indole-2-carboxylic acid ethyl ester 14H (180 mg; 0.389 mmol) in 1 mL of dry dichloromethane. The reaction was allowed to stir at 0° C. and monitored by TLC and MS analyses (NOTE: Rf of starting material and product is the same in different solvent systems). After 4 h the reaction was quenched by addition of aq saturated sodium bicarbonate (10 mL). The mixture was extracted with ethyl acetate (50 mL). The organic layer was washed with aq 1M HCl (10 mL), aq saturated sodium bicarbonate (10 mL), and brine (10 mL). The organic layer was dried over magnesium sulfate, filtered and concentrated. The residue was purified using silica gel chromatography (Biotage 12-S column, gradient: 0 to 20% ethyl acetate in hexanes) to provide compound 14I as a colorless oil.

Step 9:

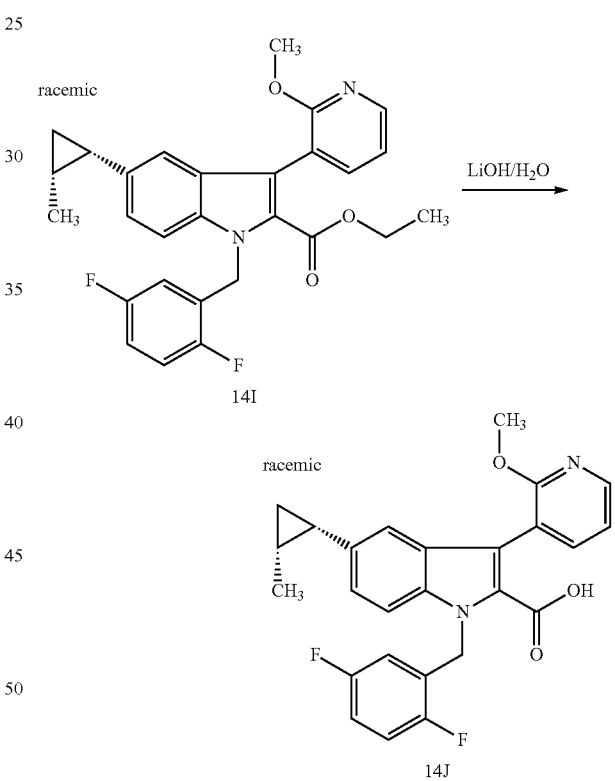

A solution of 1-(2,5-difluoro-benzyl)-3-(2-methoxy-pyridin-3-yl)-5-(2-cis-methyl-cyclopropyl)-1H-indole-2-carboxylic acid ethyl ester 14I (230 mg; 0.482 mmol) in 10 mL of a 5:1:1 THF/water/methanol mixture was treated with lithium hydroxide monohydrate (5.0 eq, 101 mg). The mixture was heated to 50° C. for 5 hours. TLC (20% ethyl acetate in hexanes) showed complete consumption of the starting material. The mixture was diluted with aq 1M HCl (40 mL) and the product was taken into dichloromethane (3×25 mL). The combined organic layers were dried over magnesium sulfate, filtered and concentrated to provide compound 14J (205 mg; 95%) as a white solid.

Step 10:

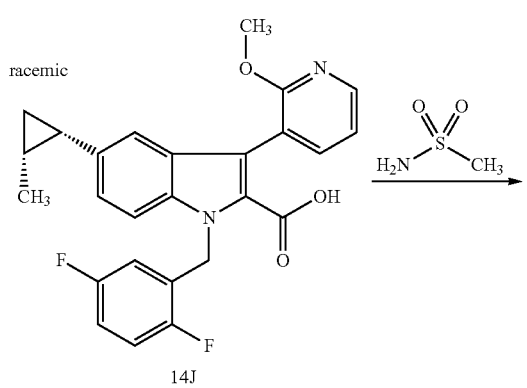

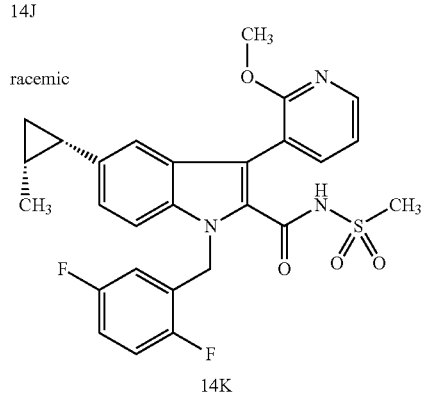

A solution of 1-(2,5-difluoro-benzyl)-3-(2-methoxy-pyridin-3-yl)-5-(2-cis-methyl-cyclopropyl)-1H-indole-2-carboxylic acid 14J (100 mg; 0.222 mmol) in 5 mL of dry THF was treated with carbonyl diimidazole (1.25 eq, 45 mg). The mixture was heated to 70° C. for 2 h and then cooled to room temp. Methanesulfonamide (1.25 eq, 26 mg) and DBU (1.5 eq, 0.049 mL, d 1.018) were added and the mixture was heated to 70° C. overnight. The mixture was diluted with ethyl acetate (60 mL) and washed with aq 1M HCl (10 mL) and brine (10 mL). The organic layer was dried over magnesium sulfate, filtered and concentrated in vacuo. The residue was purified using silica gel chromatography (Biotage 25-S silica gel column, gradient: 0 to 20% acetone in dichloromethane) to provide compound 14K (85 mg; 73%) as a white solid. M.S. found for C27H25F2N3O4S: 526.22 (M+H)+.

Step 11

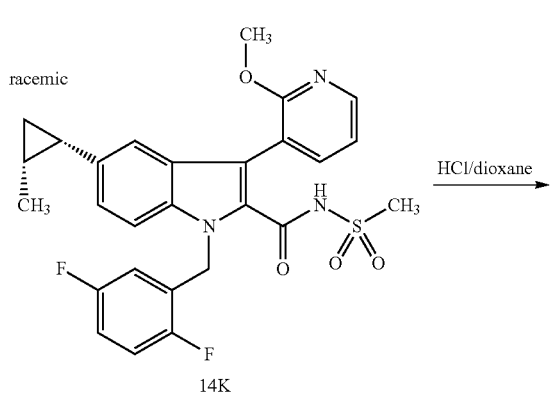

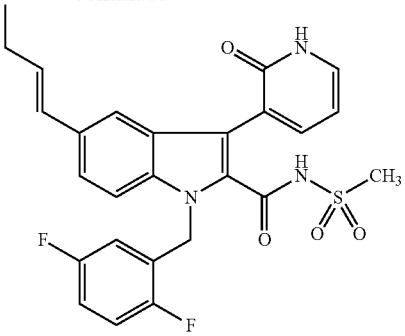

The N-[1-(2,4-Difluoro-benzyl)-3-(2-methoxy-pyridin-3-yl)-5-(2-methyl-cyclopropyl)-1H-indole-2-carbonyl]-methanesulfonamide 14K (0.152 mmol) was dissolved in 3 mL of 4M HCl soln in dioxane. Methanol was added (1 mL) and the solution was heated at 90° C. in a sealed tube for 2.5 hours. The reaction mixture was concentrated to provide the crude product as a white solid. A sample (1 mg) was dissolved in 0.5 mL of DMF and analyzed on analytical HPLC under the following conditions: Column: Delta Pak; C18, 5 micrometer, 300 A; 150×3.9 mm I.D.; Flow rate: 1 mL/min; Gradient: 40% acetonitrile in water for 5 min then increase to 80% over 25 minutes. The product was purified on semi-prep HPLC under the following conditions: Column: Delta Pak, C18, 5 micrometer, 300 A; 300×30 mm I.D.; Flow rate: 30 mL/min; Gradient: 50% acetonitrile in water for 20 min then increase to 80% over 30 min and stay there for 10 minutes. The fraction containing the product according to MS analysis was concentrated to remove acetonitrile and water to provide a major product as a white solid and a minor product, which was identified as Compound 194. $^1$H NMR (400 MHz, d$_6$-DMSO): δ 7.84 & 7.82 (dd, J=2.20 & 7.32 Hz, 1H), 7.65 (bs, 1H), 7.55 (d, J=8.79 Hz, 1H), 7.49 (d, J=8.79 Hz, 1H), 7.34 (bs, 1H), 7.31-7.25 (m, 11-1), 7.19-7.12 (m, 1H), 6.60 (t, J=6.59 Hz, 2H), 6.46-6.42 (m, 1H), 6.27-6.20 (m, 1H), 5.70 (s, 2H), 3.24 (s, 3H), 2.16 (quintet, J=6.59 & 7.32 Hz, 2H), 1.02 (t, J=7.32 Hz, 3H). M.S. found for C26H23F2N3O4S: 512.16 (M+H)+.

Example 15

Preparation of Compound 26

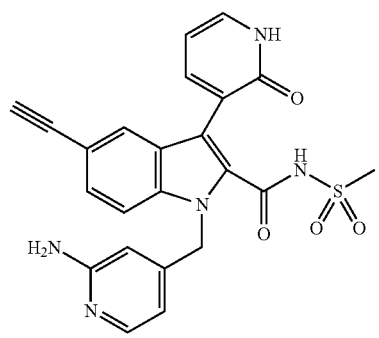

Step 1:

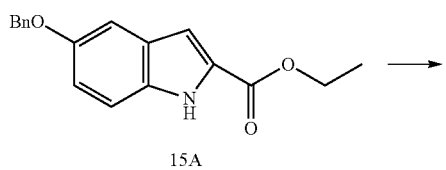

Ethyl 5-benzyloxyindole-2-carboxylate, 15A (5.0 g, 16.9 mmol) was dissolved into acetone (400 mL) at room temperature. To the mixture was added N-iodosuccinimide (4.0 g, 16.9 mmol). The resulting suspension was allowed to stir at room temperature for 3 hours. The mixture was concentrated under reduced pressure, and the residue was dissolved into ethyl acetate (300 mL). The mixture was washed with saturated aqueous sodium thiosulfate solution (100 mL). The layers were separated, and the aqueous layer was extracted with ethyl acetate (2×150 mL). The combined organic layer was dried over magnesium sulfate, filtered and concentrated in vacuo to provide the crude product 15B (100% yield). M.S. found for C18H16INO3: 421.89 (M+H)$^+$.

Step 2:

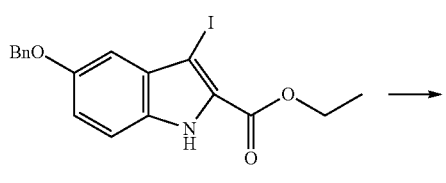

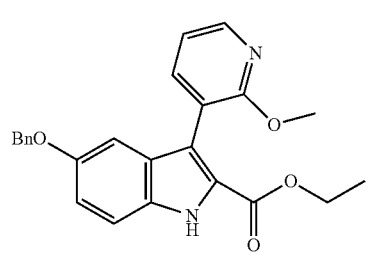

5-Benzyloxy-3-iodo-1H-indole-2-carboxylic acid ethyl ester, 15B (4.0 g, 9.48 mmol) was dissolved into 1,2-dimethoxyethane (90 mL). And PdCl$_2$(dppf)$_2$ (775 mg, 0.95 mmol) was added. The resulting mixture was de-gassed with argon bubbling for 5 min before it was heated to 90° C. and allowed to stir for 30 minutes. In a second flask, the mixture of 2-methoxy-3-pyridine boronic acid (1.95 g, 11.4 mmol) and potassium carbonate (6.6 g, 47.8 mmol) in dimethoxyethane (30 mL) and water (30 mL) was de-gassed with argon bubbling for 5 minutes. The mixture was then transferred in three portions to the first flask. The resulting bi-phasic mixture was vigorously stirred at 90° C. for 4 h before it was cooled to room temperature. The reaction was quenched by addition of a solution of sodium sulfite (10 g) in water (400 mL) at room temperature. Ethyl acetate (500 mL) was added, and the layers were separated. The aqueous layer was extracted with ethyl acetate (2×500 mL). The combined organic layer was dried over magnesium sulfate, filtered and concentrated in vacuo to provide the crude product 15C (3.2 g, 84% yield). M.S. found for C24H22N2O4: 403.2 (M+H)$^+$.

Step 3:

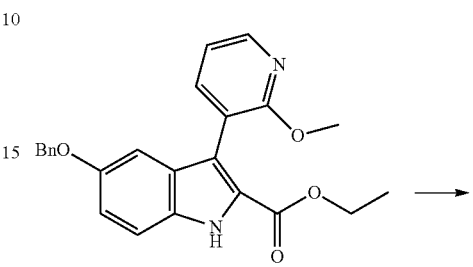

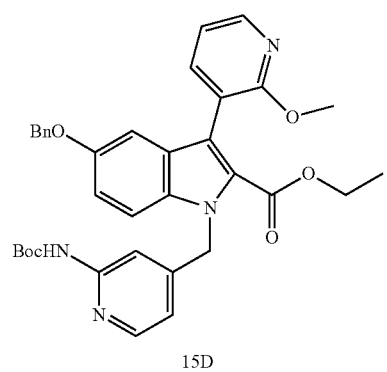

5-Benzyloxy-3-(2-methoxy-pyridin-3-yl)-1H-indole-2-carboxylic acid ethyl ester, 15C (2.0 g, 4.96 mmol) was dissolved into DMF (60 mL) at room temperature. To the mixture were added (4-bromomethyl-pyridin-2-yl)-carbamic acid tert-butyl ester (1.4 g, 4.88 mmol) and cesium carbonate (3.6 g, 11.0 mmol). The resulting suspension was allowed to stir at room temperature for 18 hours. Ethyl acetate (200 mL) and water (150 mL) were, and the layers were separated. The aqueous layer was extracted with ethyl acetate (2×150 mL). The combined organic layer was dried over magnesium sulfate, filtered and concentrated in vacuo to provide the crude product 15D (1.95 g, 65% yield). M.S. found for C35H36N4O6: 609.4 (M+H)$^+$.

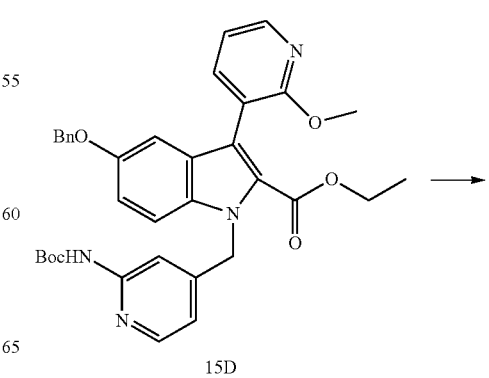

-continued

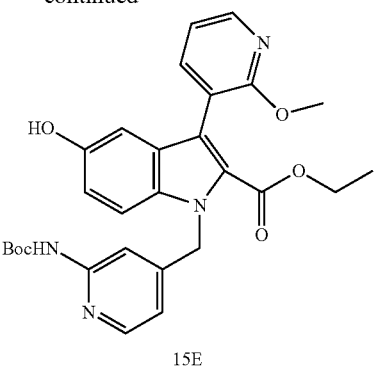

15E

Step 4:

To a solution of 5-benzyloxy-1-(2-tert-butoxycarbonylamino-pyridin-4-ylmethyl)-3-(2-methoxy-pyridin-3-yl)-1H-indole-2-carboxylic acid ethyl ester, 15D (1.90 g, 3.12 mmol) in EtOH was added 10% Pd—C (1.0 g). The flask was vacuumed, and then charged with $H_2$ gas. The reaction mixture was allowed to stir at room temperature under $H_2$ gas for 3 hours. The palladium catalyst was filtered off through a pad of celite, and was washed with 100 mL of MeOH/THF (1:1). The filtrate collected was concentrated under reduced pressure to provide the crude product 15E (1.54 g, 95% yield). M.S. found for C28H30N4O6: 519.5 $(M+H)^+$.

Step 5:

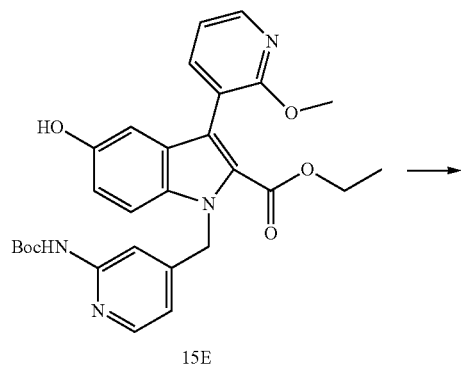

15E

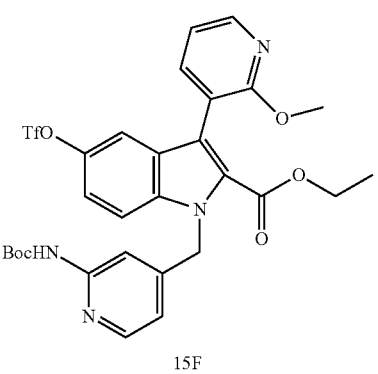

15F

To the mixture of 1-(2-tert-butoxycarbonylamino-pyridin-4-ylmethyl)-5-hydroxy-3-(2-methoxy-pyridin-3-yl)-1H-indole-2-carboxylic acid ethyl ester, 15E (1.54 g, 2.97 mmol) and triethyl amine (1.0 mL, 7.17 mmol) in dichloromethane (50 mL) was added PhN(SO$_2$CF$_3$)$_2$ (1.35 g, 3.78 mmol). The resulting reaction mixture was allowed to stir at 0° C. to room temperature for 18 hours. The mixture was then diluted with dichloromethane (100 mL), and was washed with aqueous 1N sodium carbonate solution (2×50 mL). The separated aqueous solution was extracted with dichloromethane (100 mL). The combined organic layer was dried over magnesium sulfate, filtered and concentrated in vacuo. The crude product was purified using flash chromatography to provide compound 15F (1.55 g, 80% yield). M.S. found for C29H29F3N4O8S: 651.5 $(M+H)^+$.

Step 6:

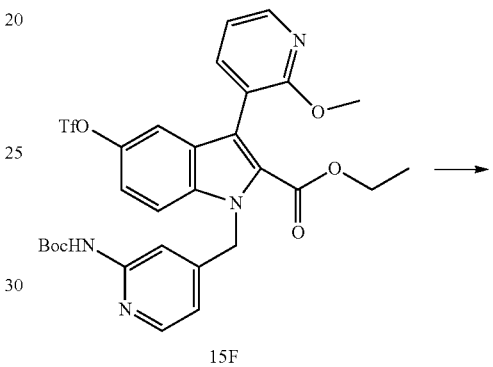

15F

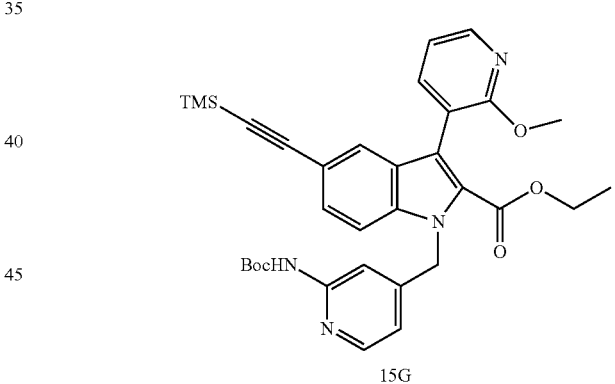

15G

To a solution of 1-(2-tert-butoxycarbonylamino-pyridin-4-ylmethyl)-3-(2-methoxy-pyridin-3-yl)-5-trifluoromethanesulfonyloxy-1H-indole-2-carboxylic acid ethyl ester, 15F (600 mg, 0.92 mmol), TMS acetylene (0.65 mL, 4.69 mmol) and nBu$_4$N$^+$I$^-$ (409 mg, 1.11 mmol) in DMF (20 mL) were added PdCl$_2$(PPh$_3$)$_2$ (65 mg, 0.09 mmol), CuI (53 mg, 0.28 mmol) and triethyl amine (0.65 mL, 4.66 mmol). The resulting reaction mixture was stirred in a sealed tube at 65° C. for 18 hours. The mixture was cooled down to room temperature, and was diluted with water (90 mL) and EtOAc (150 mL). The layers were separated, and the aqueous layer was extracted with EtOAc (2×90 mL). The combined organic layer was washed with water (2×50 mL) before it was dried over magnesium sulfate, filtered and concentrated in vacuo to provide the crude product 15G (514 mg, 93% yield). M.S. found for C33H38N4O5Si: 599.5 $(M+H)^+$.

Step 7:

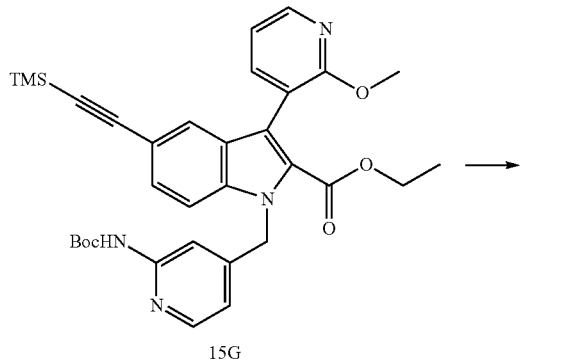

15G

To a solution of 1-(2-tert-butoxycarbonylamino-pyridin-4-ylmethyl)-3-(2-methoxy-pyridin-3-yl)-5-trimethylsilanyl-ethynyl-1H-indole-2-carboxylic acid ethyl ester, 15G (251 mg, 0.42 mmol) in water (3 mL) and THF (3 mL) was added aqueous 1 N lithium hydroxide solution (1.3 mL). The resulting suspension was allowed to stir at 70° C. for 18 hours. The mixture was cooled to room temperature, and the aqueous layer was acidified to pH=2 by adding aqueous 1N HCl solution. The mixture was diluted with ethyl acetate (50 mL) and water (30 mL), and the layers were separated. The aqueous layer was extracted twice with 50 mL of THF/ethyl acetate (1:1). The combined organic layer was dried over magnesium sulfate, filtered and concentrated in vacuo to provide the crude product 15H (191 mg, 91% yield). M.S. found for C28H26N4O5: 499.4 (M+H)+.

Step 8:

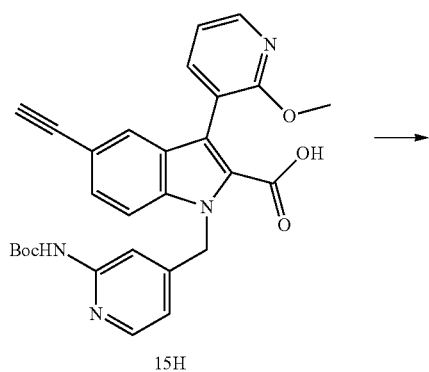

15H

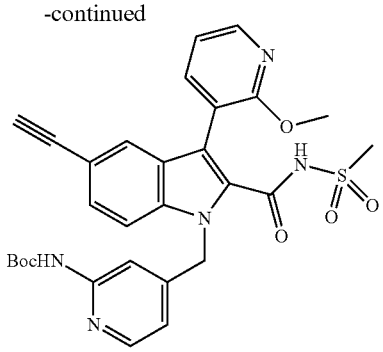

15I 1-(2-tert-Butoxycarbonylamino-pyridin-4-ylmethyl)-5-ethynyl-3-(2-methoxy-pyridin-3-yl)-1H-indole-2-carboxylic acid, 15H (128 mg, 0.26 mmol) was dissolved into tetrahydrofuran (5 mL) at room temperature. To the mixture was added carbonyl diimidazole (50 mg, 0.31 mmol). The resulting suspension was refluxed at 75° C. for 1 hour, and then cooled down to room temperature before methylsulfonamide (49 mg, 0.52 mmol) and 1,8-diazabicyclo(5.4.0)undec-7-ene (0.08 mL, 0.52 mmol) were added. The resulting reaction mixture was allowed to stir at room temperature for 24 hours. Ethyl acetate (50 mL), tetrahydrofuran (10 mL) and 1% aqueous phosphoric acid (15 mL) were added to the reaction mixture, and the layers were separated. The aqueous layer was extracted twice with ethyl acetate/THF (3:1) (40 mL). The combined organic layer was dried over magnesium sulfate, filtered and concentrated in vacuo. The crude product was purified using flash chromatography to provide compound 151 (80 mg, 54% yield). M.S. found for C29H29N5O6S: 576.20 (M+H)+.

Step 9:

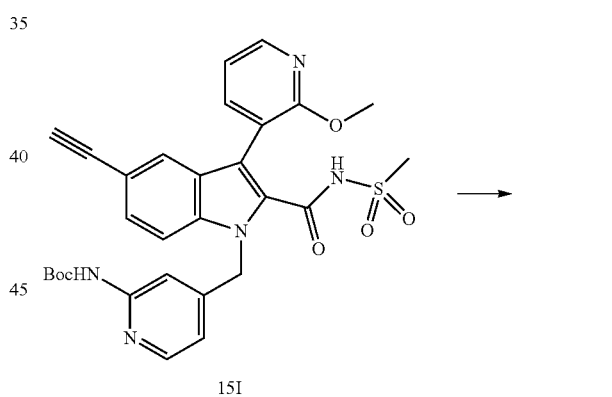

15I

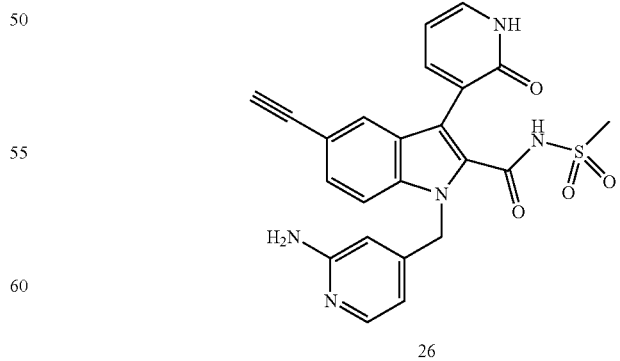

26

The solution of {4-[5-ethynyl-2-methanesulfonylaminocarbonyl-3-(2-methoxy-pyridin-3-yl)-indol-1-ylmethyl]-pyridin-2-yl}-carbamic acid tert-butyl ester, 151 (5 mg, 0.01 mmol) in chloroform was treated with TMSI (3.5 uL, 0.03 mmol). The reaction mixture was allowed to stir at 50° C. for 18 hours. The mixture was then cooled down to room temperature, and was quenched with MeOH (1 mL). The mixture was concentrated under reduced pressure to provide compound 26. M.S. found for C23H19N5O4S: 462.3 (M+H)+.

Example 16

Preparation of Compound 156

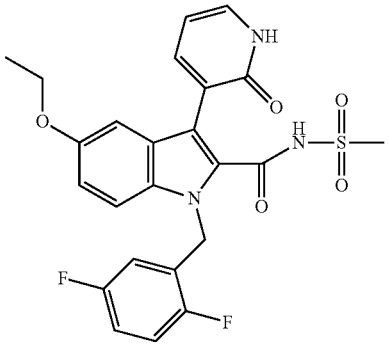

Step 1:

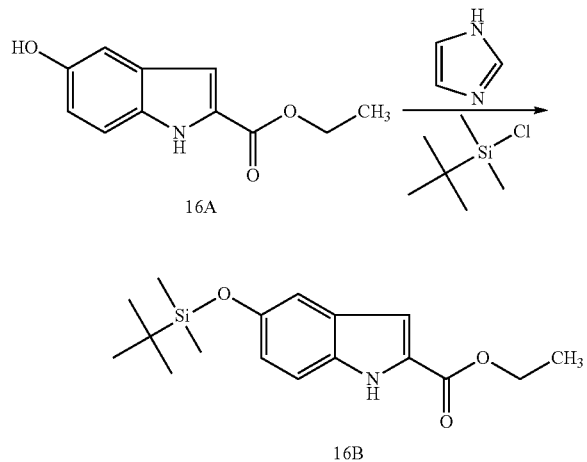

A solution of ethyl 5-hydroxy-1H-indole-2-carboxylate 16A (10.0 g; 48.73 mmol) in 300 mL of dichloromethane was treated with imidazole (4.0 eq, 13.27 g) and tert-butyldimethylsilyl chloride (2.0 eq, 14.69 g). The reaction was allowed to stir at room temp for 3 hours. A small sample (1 mL) was taken from reaction mixture, diluted with dichloromethane (10 mL) and washed with water. Evaporation of the solvent and NMR analysis showed all starting material had been consumed. The reaction mixture was diluted with dichloromethane (300 mL) and washed with water (2×200 mL) and brine (200 mL). The organic layer was dried over magnesium sulfate, filtered and concentrated to provide compound 16B (15.75 g) as a white solid.

Step 2:

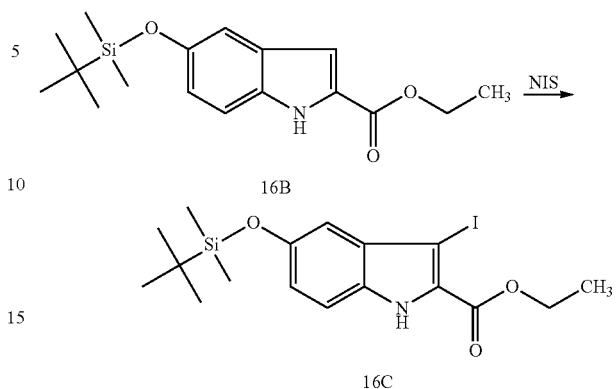

A solution of ethyl 5-tert-butyldimethylsilyloxy-1H-indole-2-carboxylate 16B (15.6 g) in 500 mL of chloroform was ice-cooled and treated with N-iodosuccinimide (1.1 eq, 12.06 g). The mixture was allowed to stir at 0° C. for 10 min and then at room temp for 2 hours. NMR analysis of a small aliquot showed complete conversion of starting material. The reaction mixture was diluted with dichloromethane (300 mL) and washed with aq saturated sodium thiosulfate (200 mL), aq saturated sodium bicarbonate (200 mL) and brine (200 mL). The organic layer was dried over magnesium sulfate, filtered and concentrated to provide compound 16C (19.47 g; 90%) as a white solid. M.S. found for C17H24INO3Si: 446.36 (M+H)+.

Step 3:

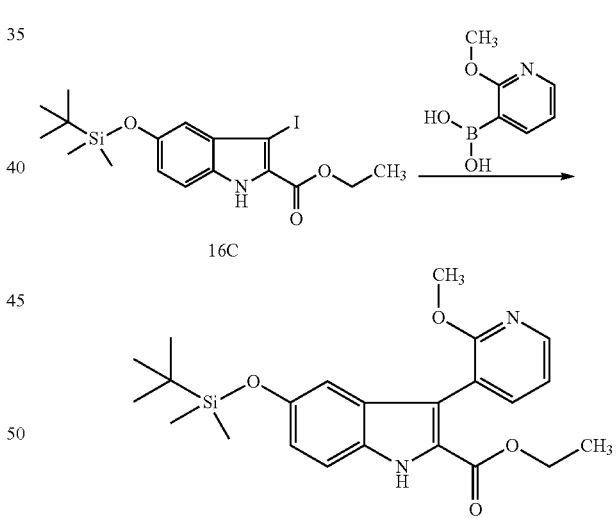

The 2-methoxy-3-pyridine boronic acid (1.05 eq, 6.99 g) was added to a solution of 16C (19.4 g; 43.55 mmol) in 500 mL of 1,2-dimethoxyethane. The mixture was degassed (vacuum/argon flush) and PdCl$_2$(dppf)$_2$ (5 mol %, 1.78 g) was added and the resulting orange solution was allowed to stir for 30 min at room temp. A solution of potassium carbonate (4.0 eq, 174 mL of aq 1M soln) was added and the resulting brown solution was allowed to stir at 90° C. for 2 hours. The reaction mixture was cooled to room temperature and concentrated. The residue was diluted with ethyl acetate (1 L) and washed with brine (200 mL). The organic layer was dried over magnesium sulfate, filtered and concentrated. The residue was divided into two equal portions and each was purified using silica gel chromatography (Biotage 75-M column; gradient: 0 to 35% ethyl acetate in hexanes) to provide compound 16D as a white solid (14.5 g; 80%). M.S. found for C23H30N2O4Si: 427.56 (M+H)⁺.

Step 4:

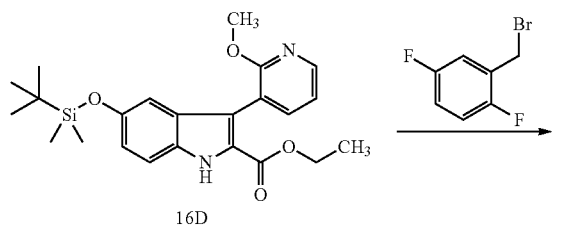

16D

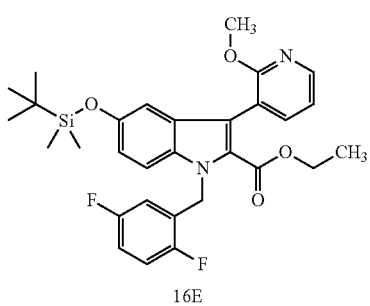

16E

A solution of indole derivative 16D (4.0 g, 9.376 mmol) in 90 mL of dry DMF was ice-cooled and treated with 2,5-difluorobenzyl bromide (1.1 eq, 1.32 mL, d 1.613) and cesium carbonate (3.0 eq, 9.16 g). The mixture turned yellow in color and the ice-water bath was removed. A catalytic amount of tetrabutylammonium iodide (approx 20 mg) was added. The reaction mixture was allowed to stir for 30 min where it became green in color and TLC (20% ethyl acetate in hexanes) showed no more starting materials left. The reaction was quenched by addition of water (10 mL) and the mixture was diluted with ethyl acetate (400 mL). The organic layer was washed with water (3×80 mL) and brine (80 mL), dried over magnesium sulfate, filtered and concentrated to provide the crude product 16E. The crude mixture was used for next reaction without further any further purification.

Step 5:

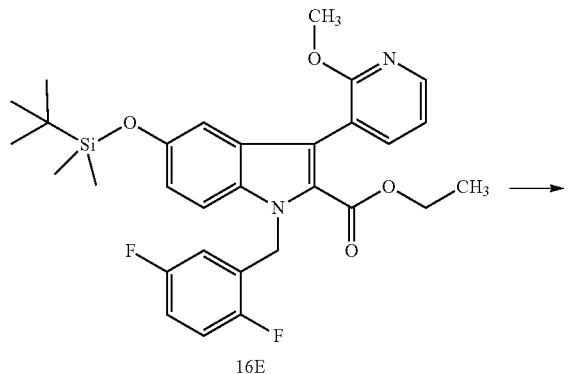

16E

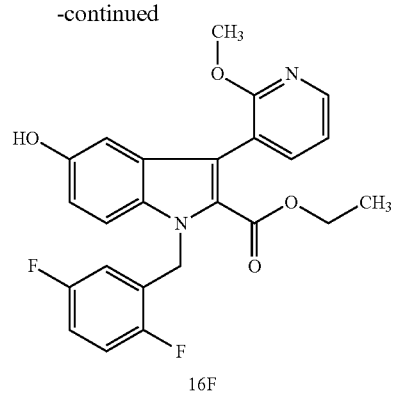

16F

A solution of crude silylether 16E (9.376 mmol) in 100 mL of THF was ice-cooled and treated with ca 1.0 eq of TBAF (9.3 mL of 1.0M soln in THF). The mixture immediately turned yellow-green in color and TLC after 5 min (20% ethyl acetate in hexanes) showed no more starting material left. The mixture was diluted with ethyl acetate (400 mL) and washed with water (100 mL), aq saturated sodium bicarbonate (100 mL) and brine (100 mL). The organic layer was dried over magnesium sulfate, filtered and concentrated. The residue was purified using silica gel chromatography (Biotage 75-M column; gradient: 10 to 50% ethyl acetate in hexanes) to provide compound 16F as a white solid (3.81 g; 94%). ¹H NMR (400 MHz, d₆-DMSO): δ9.12 (s, 1H), 8.18 & 8.17 (dd, J=1.46 & 5.13 Hz, 1H), 7.74 & 7.72 (dd, J=2.20 & 7.32 Hz, 1H), 7.46 (d, J=9.52 Hz, 1H), 7.31-7.25 (m, 1H), 7.16-7.07 (m, 1H), 6.87 (d, J=8.79 Hz, 1H), 6.67 (s, 1H), 6.40-6.35 (m, 1H), 5.80 (s, 2H), 3.99 (q, J=7.32 Hz, 2H), 3.75 (s, 3H), 0.845 (t, J=7.32 Hz, 3H).

Step 6:

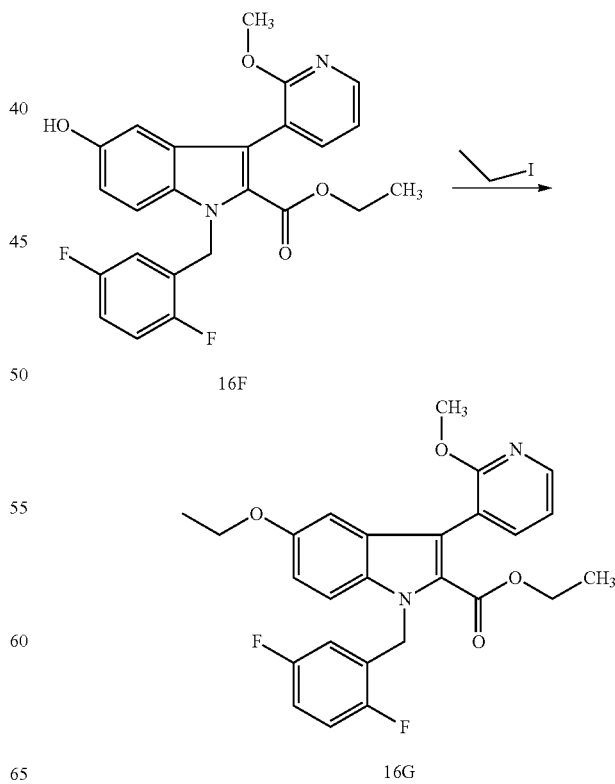

16F

16G

A solution of 1-(2,5-Difluoro-benzyl)-5-hydroxy-3-(2-methoxy-pyridin-3-yl)-1H-indole-2-carboxylic acid ethyl ester 16F (600 mg; 1.368 mmol) in 10 mL of dry DMF was ice cooled and treated with iodoethane (3.0 eq, 0.34 mL, d 1.950) and cesium carbonate (2.5 eq, 1.11 g). The resulting yellow solution was allowed to stir at 50° C. for 30 min at which time TLC (20% ethyl acetate in hexanes) showed no more starting material left and the mixture was diluted with ethyl acetate (100 mL) and washed with water (3×20 mL) and brine (10 mL). The organic layer was dried over magnesium sulfate, filtered and concentrated. The residue was purified using silica gel chromatography (Biotage 25-M column; gradient: 0 to 20% ethyl acetate in hexanes) to provide compound 16G (530 mg; 87%) as a white solid. MS found for C26H24F2N2O4: 467.13 (M+H)+.

Step 7:

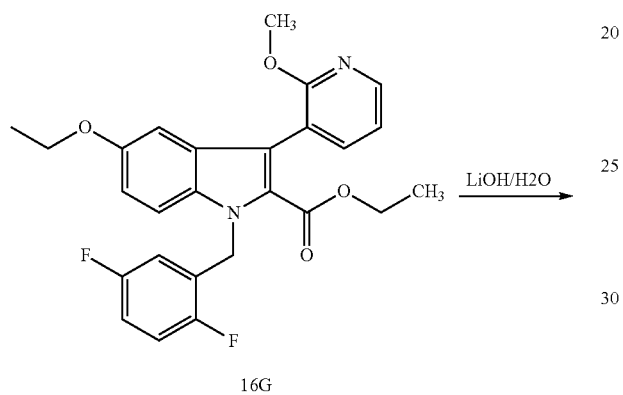

16G

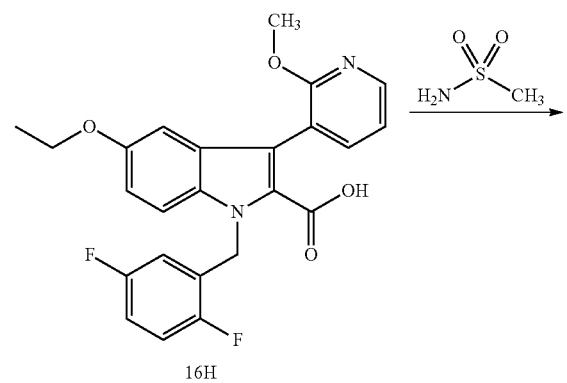

16H

Step 8:

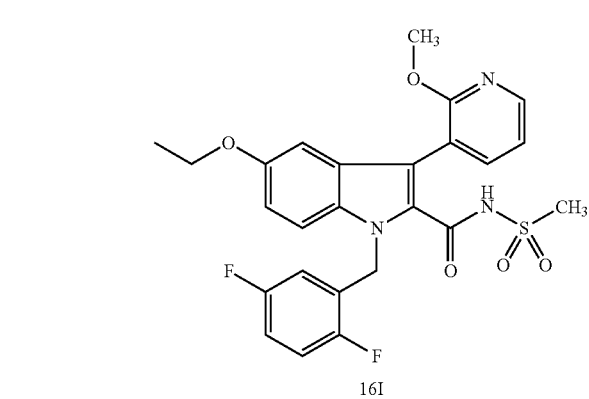

16I

A solution of 16H (150 mg; 0342 mmol) in 3 mL of dry THF was treated with carbonyl dimidazole (1.2 eq, 67 mg). The mixture was heated to 70° C. for 2 h and then cooled to room temp. Methanesulfonamide (1.3 eq, 43 mg) and DBU (1.3 eq, 0.079 mL, d 1.018) were added and the mixture was heated to 70° C. overnight. The mixture was diluted with ethyl acetate (100 mL) and washed with aq 1M HCl (20 mL) and brine (20 mL). The organic layer was dried over magnesium sulfate, filtered and concentrated in vacuo. The residue was purified using silica gel chromatography (Biotage 25-S silica gel column, gradient: 0 to 20% acetone in dichloromethane) to provide compound 16I (0.242 mmol; 71%) as a white solid. M.S. found for C25H23F2N3O5S: 516.02 (M+H)+.

Step 9:

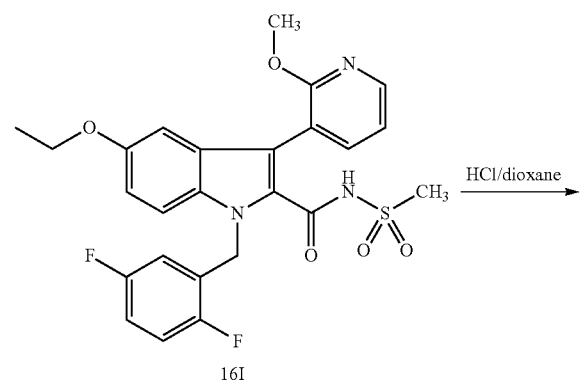

16I

A solution of 16G (530 mg; 1.136 mmol) in 12 mL of a 4:1:1 THF/water/methanol mixture was treated with lithium hydroxide monohydrate (5.0 eq, 238 mg). The mixture was heated to 60° C. for 5 hours. TLC (20% ethyl acetate in hexanes) showed complete consumption of the starting material. The mixture was diluted with aq 1M HCl (50 mL) and the product was taken into dichloromethane (3×40 mL). The combined organic layers were dried over magnesium sulfate, filtered and concentrated to provide compound 16H (0.912 mmol; 80%) as a white solid. MS found for C24H20F2N2O4: 439.02 (M+H)+.

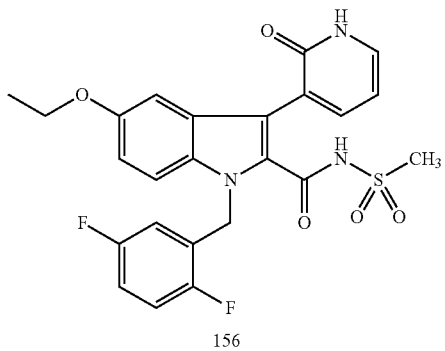

156

Compound 16I (115 mg, 0.230 mmol) was dissolved in 4 mL of 4M HCl soln in dioxane. Methanol was added (3 mL) and the solution was heated at 90° C. in a sealed tube for 3 hours. The reaction mixture was cooled and concentrated to provide the crude product as a white solid. HPLC separation was utilized to recover product. The fraction containing the product according to MS analysis was concentrated to provide compound 156 (0.175 mmol, 76%) as a white solid. $^1$H NMR (400 MHz, d$_6$-DMSO): δ7.82 (d, J=6.59 Hz, 11-1), 7.63 (bs, 1H), 7.51 (d, J=8.79 Hz, 1H), 7.31-7.25 (m, 1H), 7.17-7.11 (m, 1H), 7.00 (d, J=8.79 Hz, 1H), 6.82 (s, 1H), 6.60-6.54 (m, 2H), 5.68 (s, 2H), 3.69 (q, J=6.59 & 7.32 Hz, 2H), 3.24 (s, 3H), 1.29 (t, J=6.59 Hz, 3H). M.S. found for C24H21F2N3O5S: 502.04 (M+H)$^+$.

Example 17

Preparation of Compound 257

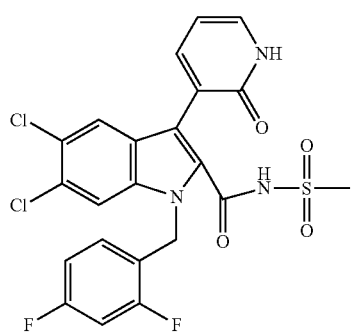

257

Step 1:

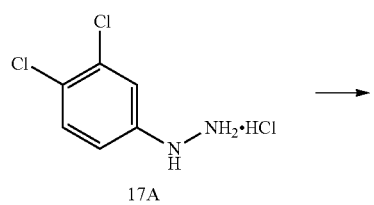

17A

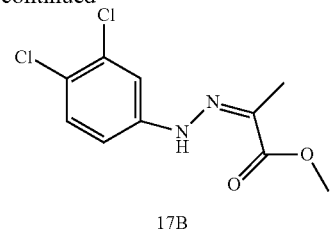

17B

Compound 17A (15.72 g, 90% purity, 67 mmol) was dissolved into ethanol (100 mL) at room temperature. To the solution were added ethyl pyruvate (11 mL) and acetic acid (1 mL). The reaction mixture was refluxed for 2 hours. After being cooled to room temperature, the mixture was concentrated under reduced pressure. The crude product was purified using silica gel chromatography (EtOAc/Hexane=1/10) to provide product 17B as a yellow solid (7.43 g). $^1$H NMR (500 MHz, d$_6$-DMSO): δ10.06 (s, 1H), 7.49 (d, J=8.79 Hz, 1H), 7.41 (d, J=2.20 Hz, 1H), 7.22 & 7.20 (dd, J=2.20 & 8.79 Hz, 1H), 4.18 (q, J=7.32 Hz, 2H), 2.04 (s, 3H), 1.24 (t, J=7.32 Hz, 3H).

Step 2:

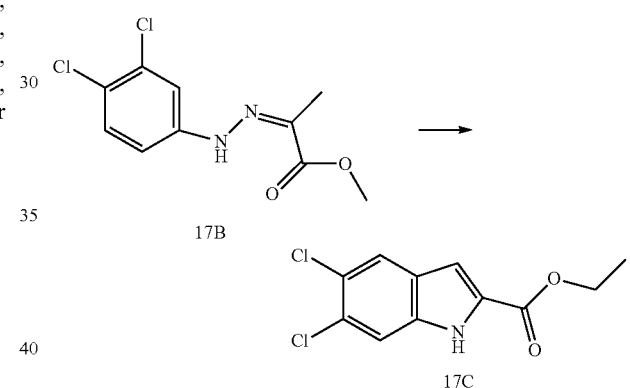

Compound 17B (7.22 g) was ground into a powder before being mixed with polyphosphoric acid (50 g). The biphasic mixture was vigorously stirred at 120° C. for 2 hours. After cooling to room temperature, the reaction mixture was partitioned between EtOAc and water. The combined organic layer was dried (magnesium sulfate), filtered and concentrated in vacuo. The crude product was purified using flash chromatography (0-50% EtOAc/hexane) to provide a mixture of 5,6-dichloroindole 17C and the undesired 4,5-dichloroindole. $^1$H NMR (500 MHz, d$_6$-DMSO): δ12.19 (s, 1H), 7.95 (s, 1H), 7.62 (s, 1H), 7.14 (s, 1H), 4.33 (q, J=7.32 Hz, 2H), 1.32 (t, J=7.32 Hz, 3H).

Step 3:

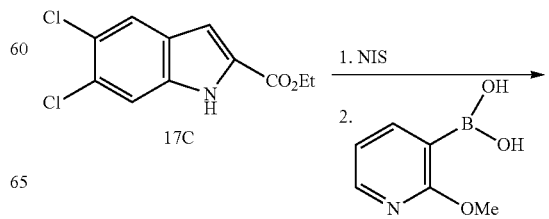

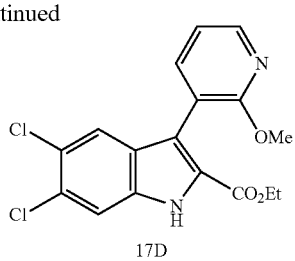

17D

The N-iodosuccinimide (0.5 g) was added to a stirred CH$_2$Cl$_2$ (10 mL) solution of the Indole 17C (0.57 g) at room temperature over night under an atmosphere of nitrogen. The reaction was partitioned between EtOAc and diluted aq. sodium thiosulfate. The organic phase was separated, washed with 10% aq. sodium bicarbonate, water, dried (MgSO$_4$) and concentrated to provide the desired crude iodoindole (0.828 g) which was added to the DME (4 mL). PdCl$_2$(dPPF)$_2$ (176 mg, 0.1 eq) was added to the mixture and was heated to 100° C. (oil bath temperature) for a period of 0.5 hour and a solution of the boronic acid (99 mg, 3 eq) and potassium carbonate (1.50 g, 5 eq) in H$_2$O/DME (1.5 mL/1.5 mL) was added dropwise. When the addition was complete the reaction mixture was heated to 100° C. (oil bath) for 3 hours. After cooling, 3% aq. sodium sulfate was added followed by EtOAc and filtered through celite. The filtrate was partitioned between water and CH$_2$Cl$_2$. The organic phase was separated and the aq. phase was further extracted with CH$_2$Cl$_2$. The combined organic phase was dried (MgSO$_4$) and concentrated. The residue was purified using silica gel chromatography (EtOAc:Hexane=3:7) to provide compound 17D as a yellow solid (0.522 g). M.S. found for C17H14Cl2N2O3: 365.10 (M+H)$^+$.

Step 4:

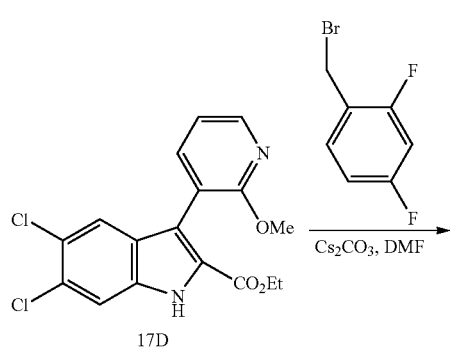

17D

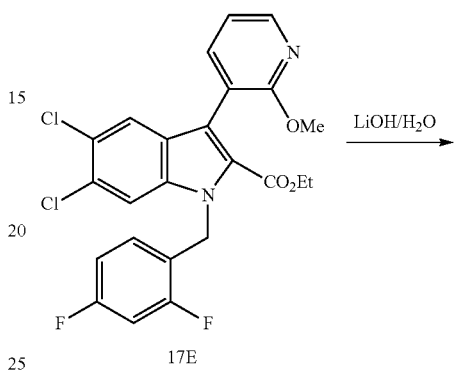

17E 2,4-difluorobenzylbromide (53 uL, 1.5 eq) was added drop wise to a stirred mixture of the indole 17D (100 mg, 1 eq) and Cs$_2$CO$_3$ (134 mg, 1.5 eq) in DMF at room temperature under an atmosphere of nitrogen. After 16 hours, the reaction mixture was partitioned between EtOAc and water. The aq. phase was separated, washed with water three times, dried (MgSO$_4$) and concentrated. The residue was purified using silica gel column chromatography (EtOAc:Hexane=1:10) to provide compound 17E (0.105 g) as a white solid. M.S. found for C24H18Cl2F2N2O3: 490.98 (M+H)$^+$.

Step 5:

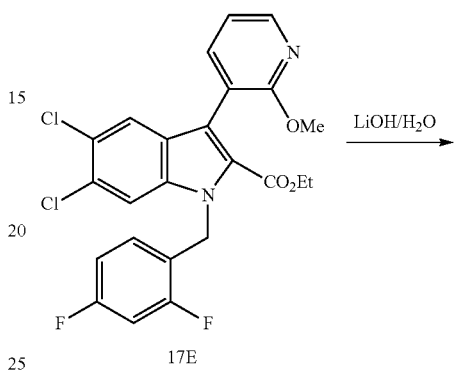

17E

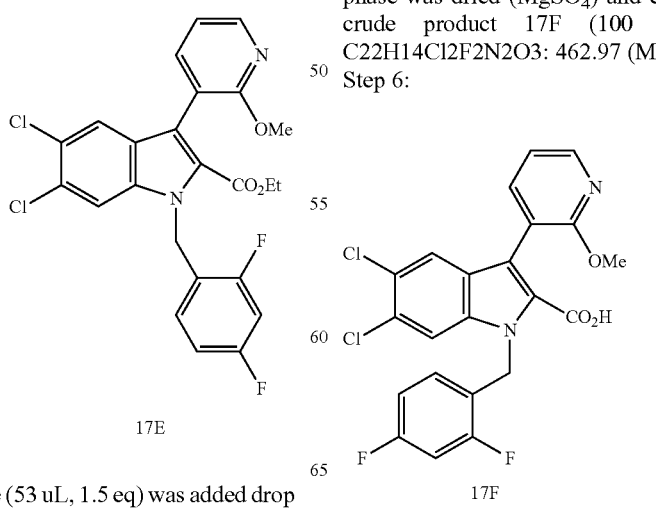

17F

Lithium hydroxide (26 mg, 3 eq) was added to a stirred solution of the ethylester 17E (100 mg, 1 eq) in THF/H$_2$O (7 mL/3 mL) under an atmosphere of nitrogen. The resulting reaction mixture was heated to reflux over night. After cooling, the reaction was partitioned between EtOAc and diluted aq. 1N HCl. The organic phases were separated. The organic phase was dried (MgSO$_4$) and concentrated to provide the crude product 17F (100 mg). M.S. found for C22H14Cl2F2N2O3: 462.97 (M+H)$^+$.

Step 6:

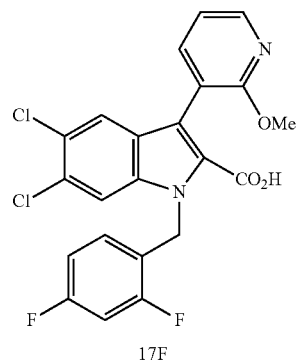

17F

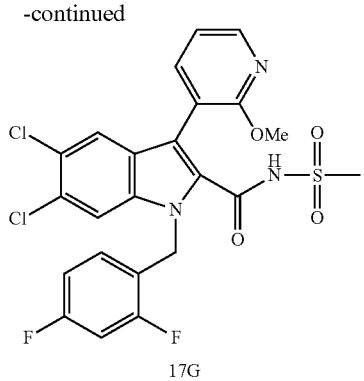

17G

A solution of acid 17F (58 mg, 1 eq) in THF (3 mL) was treated with carbonyldiimidazole (22 mg, 1.1 eq) and heated at reflux for 2 hours. The reaction mixture was cooled to room temperature and treated with methylsulfonamide (18 mg, 1.5 eq), and DBU (23 mg, 1.2 eq) and stirred overnight at room temperature. The mixture was concentrated and added EtOAc and washed with 1N HCl and water. The solvent was removed under reduced pressure and the crude material was purified using silica gel chromatography (MeOH/CH$_2$Cl$_2$=5%) to provide a pure colorless product 17G (9 mg). M.S. found for C23H17Cl2F2N3O4S: 540.24 (M)$^+$.

Step 7:

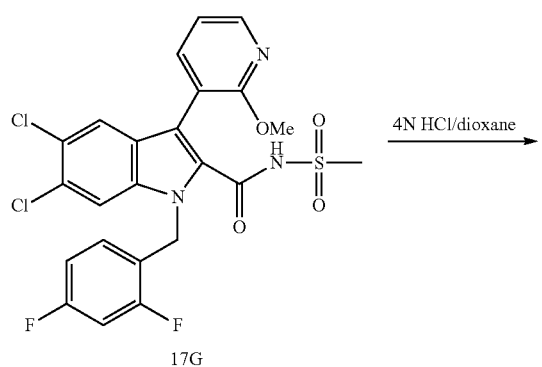

HCl (4N in dioxane, 2 mL) was added to 17G (9 mg) in a sealed tube and the resulting suspension was heated to 105° C. (oil bath) for 3 hours. After cooling, the solvent was removed under reduced pressure. Ether was added and the solid was collected to provide compound 257 (8 mg). M.S. found for C22H15Cl2F2N3O4S: 527.96 (M+H)$^+$.

Example 18

Preparation of Compound 498

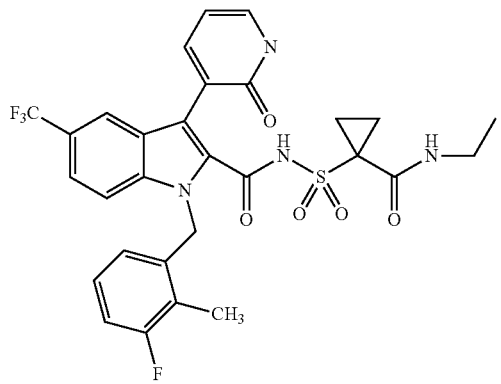

498

Step 1:

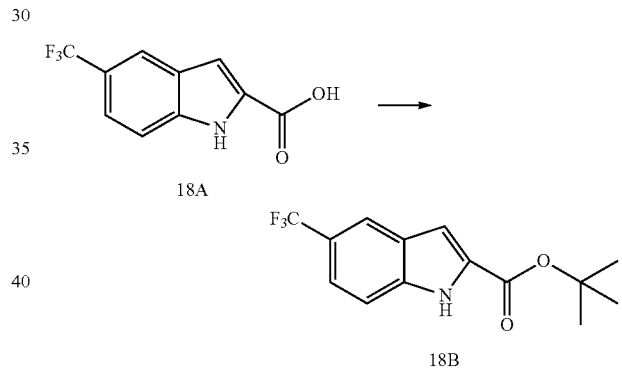

To a solution of the indole 18A (1.6 g, 6.9 mmol) in toluene (5.0 mL) was added N,N-dimethylformamide di-tert butyl acetal (5 mL), and heated to 90° C. for 12 h, cooled to room temperature, another aliquot of N,N-dimethylformamide di-tert butyl acetal (5 mL) was added and the reaction mixture was heated to 90° C. for 12 h, cooled to room temperature, diluted with ethyl acetate (10.0 mL), washed with water (2×10.0 mL), brine, dried over MgSO$_4$, filtered and concentrated to provide compound 18B (1.2 g, 60%) as a white solid. $^1$H NMR (400 MHz, CDCl3); δ9.17 (s, 1H), 7.97 (s, 1H), 7.51 (s, 21-1), 7.21 (s, 1H), 1.63 (s, 9H).

Step 2:

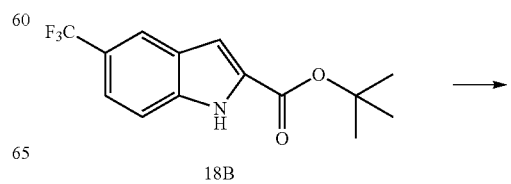

18B

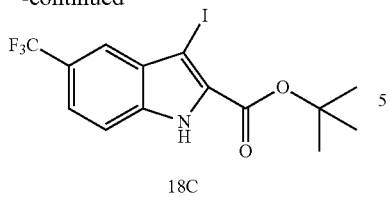

18C

To a solution of 18B (1.2 g, 4.2 mmol) in CHCl₃ (25 mL) was added N-iodosuccinimide (946 mg, 4.2 mmol) and the reaction allowed to stir at room temperature for 12 hours. The reaction mixture concentrated in vacuo, diluted with water and extracted in EtOAc (200 mL). The combined organic layers were dried (MgSO₄), filtered, and concentrated in vacuo. The brown residue was taken in minimum amount of CH₂Cl₂ and triturated with hexanes. Compound 18C was separated out as a brown solid which was filtered, and dried in vacuo. (1.23 g, 72% yield). $^1$H NMR (400 MHz, CDCl3); $\delta$9.34 (s, 1H), 7.87 (s, 1H), 7.57 (d, J=8.06 Hz, 1H), 7.49 (d, J=8.79 Hz, 1H), 1.68 (s, 9H).

Step 3:

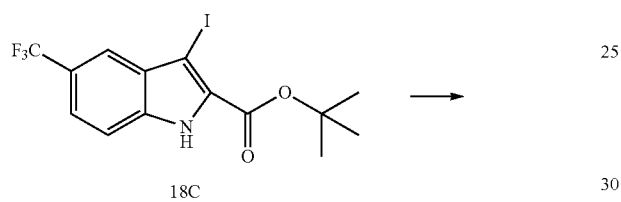

To a solution of compound 18C (1.23 g, 3.0 mmol) in DME (30 mL) under nitrogen atmosphere was added with 2-methoxy-3-pyridyl boronic acid (0.482 g, 3.15 mmol) and Pd(dppf)₂Cl₂ (245 mg, 0.3 mmol) and the resulting reaction was allowed to stir at room temperature under nitrogen for 0.5 hours. The reaction mixture was then treated with a solution of potassium carbonate (1.6 g, 12 mmol) in water (12 mL) and the resulting solution was heated to 90° C. and allowed to stir at this temperature for 1 hour. The reaction mixture was then diluted with EtOAc (200 mL) and the resulting solution was concentrated in vacuo to provide a crude residue which was purified using flash column chromatography (EtOAc/Hexanes, 0 to 30% EtOAc) to provide compound 18D as a solid (820.0 mg). M.S. found for C20H19F3N2O3: 393.2 (M+H)⁺.

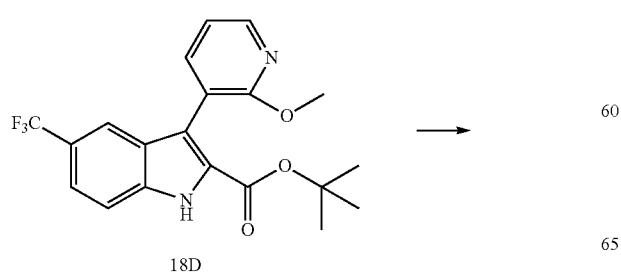

18D

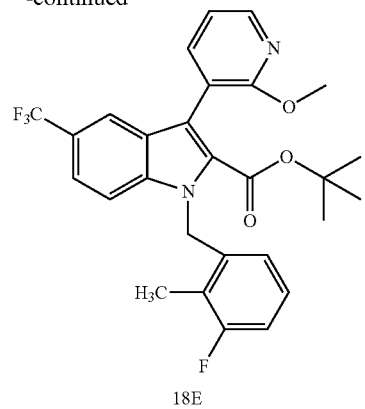

18E

Step 4:

To a solution of indole 18D (10.0 g, 25.4 mmol) in DMF (100 mL) was added cesium carbonate (9.93 g, 30.5 mmol) and 3-fluoro-3-methylbenzyl bromide (3.57 mL, 30.5 mmol) and allowed to stir at room temperature for 12 hours. The reaction mixture was diluted with EtOAc (500 mL), washed with water (3×100 mL) and with brine (2×100 mL). The combined organic layers were dried (MgSO₄), filtered, and concentrated in vacuo and purified using flash column chromatography on silica gel to provide compound 18E as a colorless solid.

Step 5:

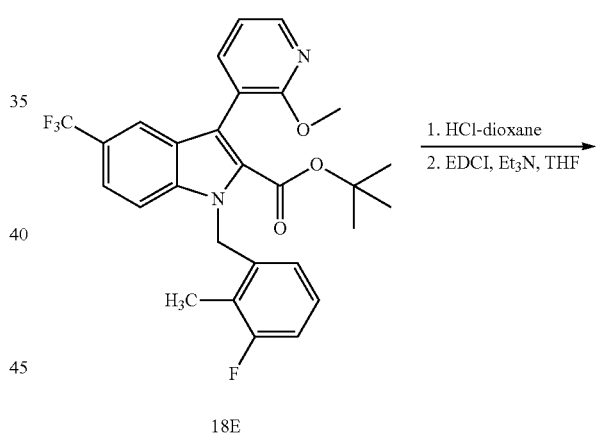

18E    1. HCl-dioxane    2. EDCI, Et₃N, THF

18F

A solution of compound 18E (1.0 g, 1.94 mmol) was dissolved in 4N HCl in dioxane (20 mL) and heated at 80° C.

overnight. After cooling the volatiles were removed under reduced pressure to provide the crude product, which was used directly in the next step. The residue from the first step was dissolved in anhydrous THF (10.0 mL) and EDCI (3.8 mmol, 746 mg) and Et₃N (2.55 mL, 19.0 mmol) were added to it. The reaction mixture was allowed to stir at room temperature for 12 hours, washed with 1N HCl and extracted with CH₂Cl₂ (3×20 mL). The combined organic layer was washed with brine and dried over MgSO₄, filtered and concentrated to provide compound 18F (724 mg). M.S. found for C23H14F4N2O2: 427.2 (M+H)⁺.

Step 6:

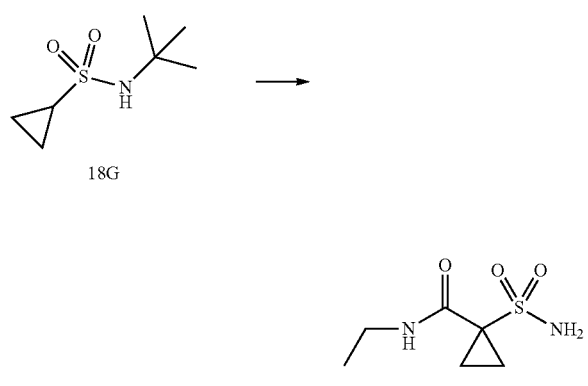

To a cooled solution of 18G (Prepared as described in International Publication No. WO 2004/043339) in THF (7.0 mL) was added BuLi (1.6 M in hexanes) dropwise. The reaction mixture was allowed to stir for 1 hour, ethyl isocyanate was added to it and then allowed to warm to room temperature overnight. The reaction mixture was acidified using 1N HCl and extracted with ethyl acetate (3×20 mL). The organic phase was washed with brine, dried over MgSO₄, filtered, and concentrated in vacuo and the resulting residue was purified using flash column chromatography on silica gel 10% EtOAc/Hexane (0 to 60%) to provide the intermediate as an oily residue (110.0 mg). The oily residue was stirred overnight in 4N HCl in dioxane, and then concentrated to provide compound 18H (46.0 mg).

Step 7:

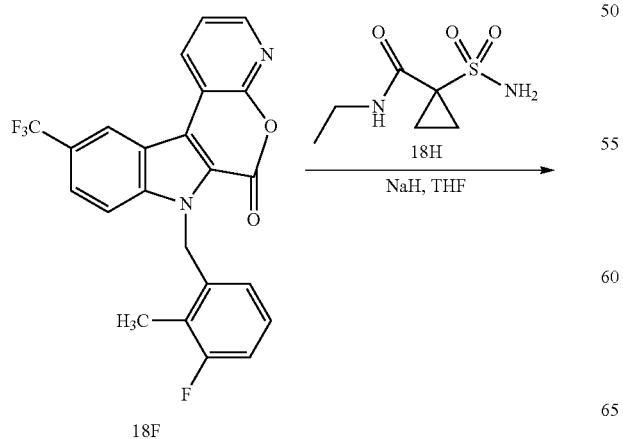

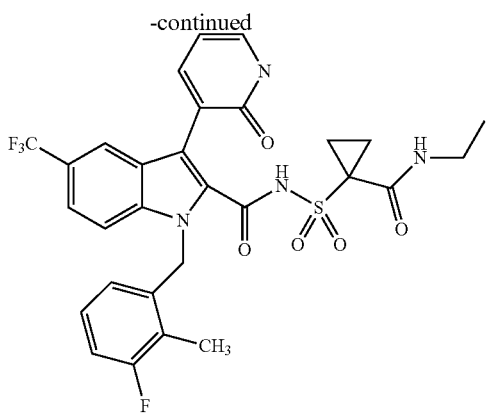

498

To a solution of compound 18F (25.0 mg, 0.06 mmol) in THF (2.0 mL) was added sulfonamide 18H and NaH (11.5 mg, 0.48 mg). The resulting reaction mixture was allowed to stir at room temperature for 30 minutes, then diluted with EtOAc (10 mL) and the resulting solution was washed with water and aqueous HCl (1N). The combined organic layers were dried (MgSO₄), filtered, and concentrated in vacuo and the resulting residue was purified using flash column chromatography on silica gel 10% MeOH/CH₂Cl₂ (0 to 90%) to provide compound 498 (20 mg). ¹H NMR (400 MHz, d₆-DMSO) δ8.30 (bs, 1H), 7.70 (s, 1H), 7.63-7.54 (m, 2H), 7.50-7.43 (m, 2H), 7.15 (t, J=7.56 Hz, 1H), 6.91 (t, J=7.56 Hz, 1H), 6.65 (t, J=7.56 Hz, 1H), 6.28 (s, 1H), 5.86 (s, 2H), 3.00 (t, J=6.94 Hz, 2H), 2.25 (s, 3H), 1.37-1.24 (m, 2H), 1.17-1.07 (m, 2H), 0.90 (t, J=6.94 Hz, 3H).

Example 19

Preparation of Compound 489

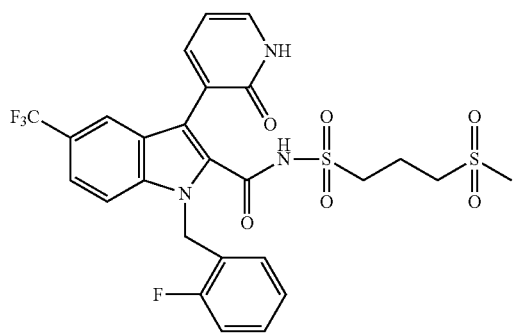

489

Step 1:

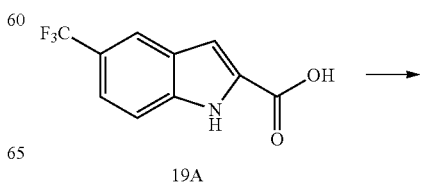

19A

-continued

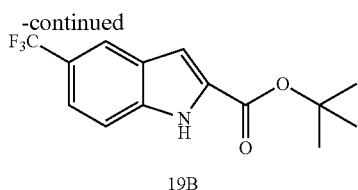
19B

To a solution of the indole 19A (1.6 g, 6.9 mmol) in toluene (5.0 mL) was added N,N-dimethylformamide di-tert butyl acetal (5 mL), and heated to 90° C. for 12 h, cooled to room temperature, another aliquot of N,N-dimethylformamide di-tert butyl acetal (5 mL) was added and the reaction mixture was heated to 90° C. for 12 h, cooled to room temperature, diluted with ethyl acetate (10.0 mL), washed with water (2×10.0 mL), brine, dried over MgSO₄, filtered and concentrated to provide compound 19B (1.2 g, 60%) as a white solid.
Step 2:

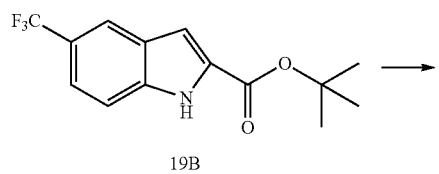
19B

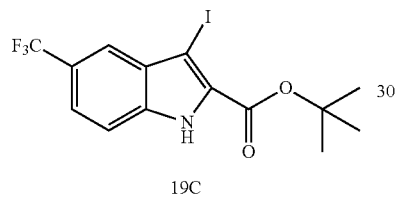
19C

To a solution of compound 19B (1.2 g, 4.2 mmol) in CHCl₃ (25 mL) was added N-iodosuccinimide (946 mg, 4.2 mmol) and the reaction allowed to stir at room temperature for 12 hours. The reaction mixture concentrated in vacuo, diluted with water and extracted in EtOAc (200 mL). The combined organic layers were dried (MgSO₄), filtered, and concentrated in vacuo. The brown residue was taken in minimum amount of CH₂Cl₂ and triturated with hexanes. The product 19C was separated out as a brown solid which was filtered, and dried in vacuo. (1.23 g, 72% yield)
Step 3:

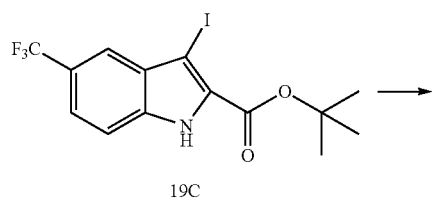
19C

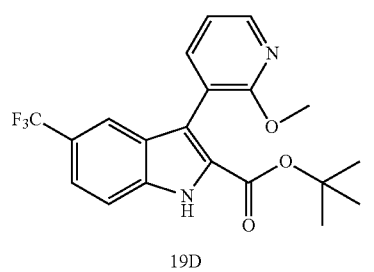
19D

To a solution of compound 19C (1.23 g, 3.0 mmol) in DME (30 mL) under nitrogen atmosphere was added with 2-methoxy-3-pyridyl boronic acid (0.482 g, 3.15 mmol) and Pd (dppf)₂Cl₂ (245 mg, 0.3 mmol) and the resulting reaction was allowed to stir at room temperature under nitrogen for 0.5 hours. The reaction mixture was then treated with a solution of potassium carbonate (1.6 g, 12 mmol) in water (12 mL) and the resulting solution was heated to 90° C. and allowed to stir at this temperature for 1 hour. The reaction mixture was then diluted with EtOAc (200 mL) and the resulting solution was concentrated in vacuo to provide a crude residue which was purified using flash column chromatography (EtOAc/Hexanes, 0 to 30% EtOAc) to provide compound 19D as a solid (820.0 mg).

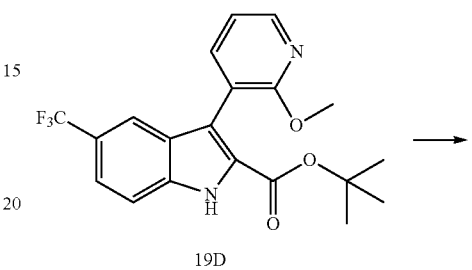
19D

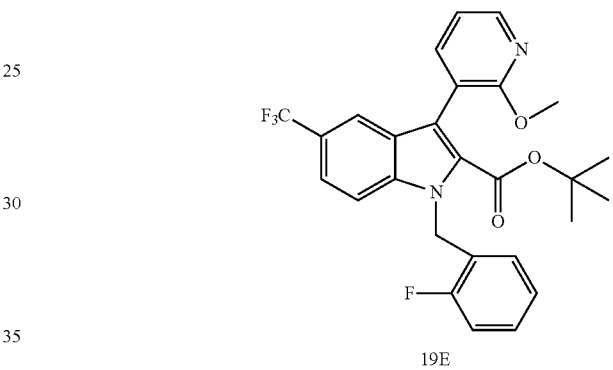
19E

Step 4:
To a solution of indole 19D (10.0 g, 25.4 mmol) in DMF (100 mL) was added cesium carbonate (9.93 g, 30.5 mmol) and 2-fluorobenzyl bromide (3.57 mL, 30.5 mmol) and allowed to stir at room temperature for 12 hours. The reaction mixture was diluted with EtOAc (500 mL), washed with water (3×100 mL) and with brine (2×100 mL). The combined organic layers were dried (MgSO₄), filtered, and concentrated in vacuo and purified using flash column chromatography on silica gel to provide compound 19E as a colorless solid.
Step 5:

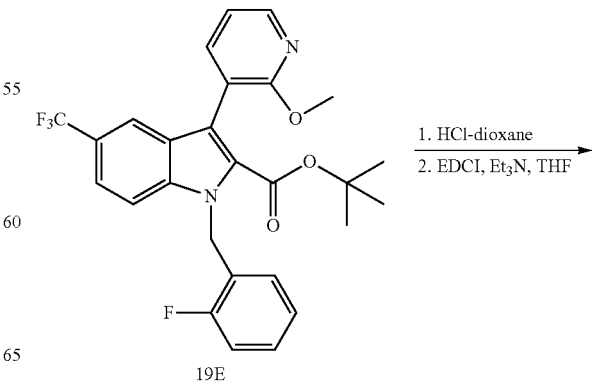
19E

1. HCl-dioxane
2. EDCI, Et₃N, THF

-continued

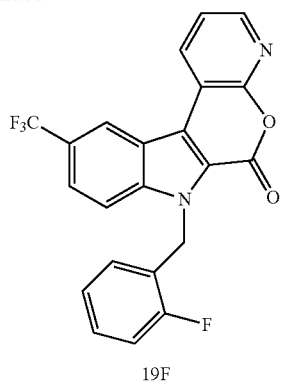

19F

4N HCl in dioxane (20 mL) was added to compound 19E (1.30 g) in a sealed tube and heated to 80° C. (oil bath) overnight. After cooling to room temperature, the solvents were removed under reduced pressure to provide a crude product which was dissolved in anhydrous THF (20 mL) and EDCI (1.15 g) followed by Et3N (4.10 mL) were added and the resulting reaction mixture was stirred overnight at room temperature. The reaction mixture was partitioned between diluted aq. HCl (~10%) and $CH_2Cl_2$. The organic phase was separated, extracted with $CH_2Cl_2$ two times. The combined organic phases were washed with water, dried ($MgSO_4$) and concentrated to provide the lactone 19F as a light brown solid (0.991 g). $^1$H NMR (400 MHz, $d_6$-DMSO) δ 9.13 & 9.11 (dd, J=1.46 & 8.06 Hz, 1H), 8.94 (s, 1H), 8.48 & 8.46 (dd, J=1.46 & 5.13 Hz, 1H), 7.99 (d, J=8.79 Hz, 1H), 7.89 (d, J=8.79 Hz, 1H), 7.57 (dd, J=4.39 & 8.06 Hz, 1H), 7.33-7.21 (m, 2H), 7.01 (t, J=7.32 Hz, 1H), 6.77 (t, J=7.32 Hz, 1H), 6.12 (s, 2H). M.S. found for C22H12F4N2O2: 412.93 (M+H)$^+$.

Step 6:

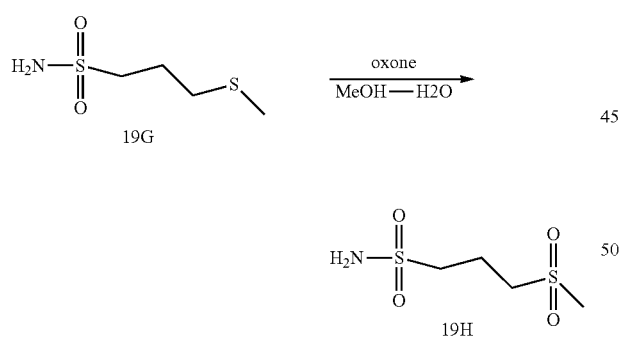

An aq. solution of oxone (1.82 g, 3 mL water) was added to the methanol (3 mL) solution of the sulfide 19G (0.1 g) at room temperature and the resulting reaction mixture was stirred overnight at room temperature. The methanol was removed under reduce pressure and the residue was partitioned between $CH_2Cl_2$ and water. The organic phases were washed with water, dried ($MgSO_4$) and concentrated to provide the sulfone 19H (25.6 mg). $^1$H NMR (400 MHz, $d_6$-DMSO) δ 6.90 (s, 2H), 3.25 (t, J=7.32 Hz, 2H), 3.10 (t, J=7.32 Hz, 2H), 2.97 (s, 3H), 2.13-2.05 (m, 2H).

Step 7:

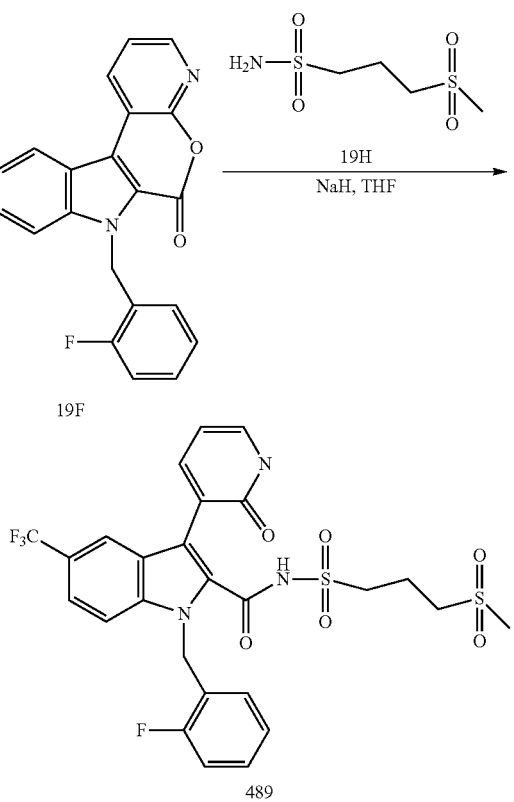

489

NaH (3.5 mg, 1.2 eq) was added in one portion to the stirred solution of the lactone 19F (50 mg, 0.12 mmol) and sulfonamide 19H (25 mg, 0.12 mmol) at room temperature under an atmosphere of nitrogen. The reaction mixture was allowed to stir for 4 hours at room temperature. The crude reaction product was purified using silica gel column chromatography ($CH_2Cl_2$/MeOH=99:1-20:1) to provide compound 489 (22.6 mg) as a white solid. $^1$H NMR (400 MHz, $d_6$-DMSO) δ 7.87 (d, J=8.30 Hz, 1H), 7.82 (d, J=6.35 Hz, 1H), 7.78 (s, 1H), 7.65-7.64 (m, 2H), 7.32 (q, J=6.35 Hz, 1H), 7.22 (t, J=8.79 Hz, 1H), 7.10 (t, J=7.32 Hz, 1H), 6.93 (t, J=7.32 Hz, 1H), 6.58 (bs, 1H), 5.83 (s, 2H), 3.54 (s, 2H), 3.26 (t, J=7.81 Hz, 2H), 2.97 (s, 3H), 2.06 (quintet, J=7.32 Hz, 2H). M.S. found for $C_{26}H_{23}F_4N_3O_6S_2$: 614.3 (M+H)$^+$.

Example 20

Preparation of Compound 71

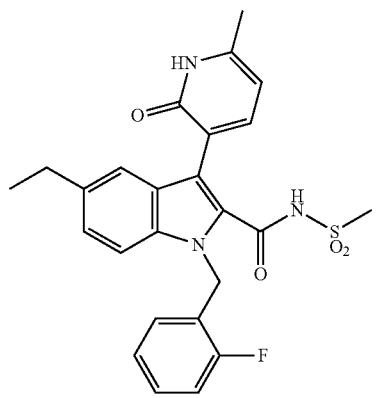

71

Step 1:

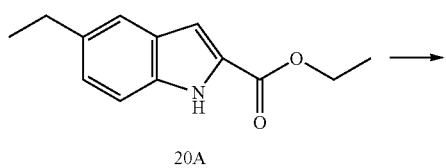

20A

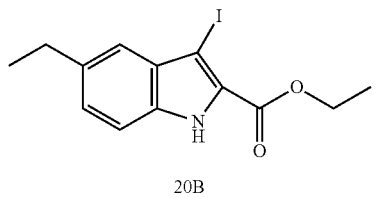

20B

The starting materials 20A (15.0 g, 69.04 mmol) and THF (100 mL) were added to a 1000 ml round-bottomed flask. The resulting solution was cooled with a water bath. To this stirring solution, MS (15.30 g, 68.80 mmol) was added slowly. The resulting solution was allowed to stir at room temperature for 5 hours before 700 ml of water was added. The resulting mixture was continued to stir at room temperature for 30 minutes and then filtered. The cake was washed with water (2×40 mL), air-dried, then dried under vacuum to provide compound 20B as an off-white solid (23.0 g, 97%). M.S. found for $C_{13}H_{14}INO_2$: 344.2 (M+H)$^+$.

Step 2:

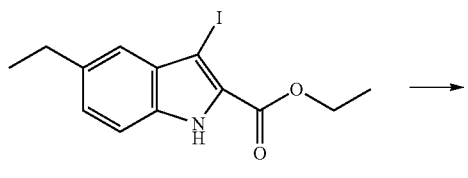

20B

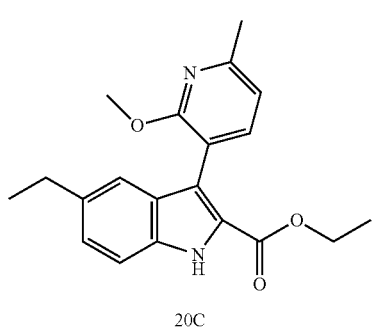

20C

A 200 ml round-bottomed flask was charged with 20B (2.45 g, 7.14 mmol), 6-methyl-2-methoxypyridine-3-boronic acid (0.98 g, 5.87 mmol), [1,1' bis(diphenylphosphino) ferrocene]dichloropalladium(II) complex with dichloromethane (1:1) (0.58 g, 0.71 mmol), and DME (50 mL). To the stirring solution, a solution of sodium carbonate (10 ml of 1.5 M, 15.0 mmol) was added via a syringe. The reaction mixture was maintained reflux for 4 hours before cooled to room temperature. After concentration, the residue was taken up with ethyl acetate (200 mL), washed with water (3×100 mL), and dried over sodium sulfate. The solvent was removed by distillation under reduced pressure and the residue was purified using Combiflash chromatography on silica gel using 0-10% ethyl acetate in hexanes as the solvent to provide compound 20C as a white solid (1.51 g, 76%). M.S. found for $C_{20}H_{22}N_2O_3$: 339.2 (M+H)$^+$.

Step 3:

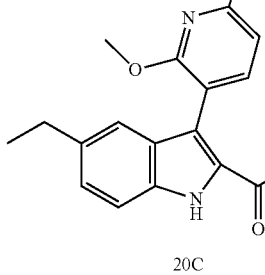

20C

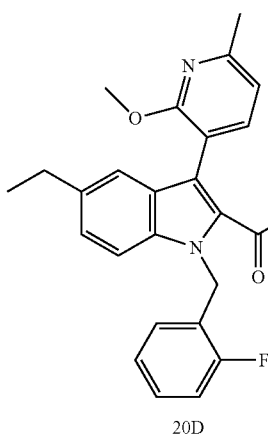

20D

The reaction materials 20C (200 mg, 0.59 mmol), 2-fluorobenzylchloride (170 mg, 1.76 mmol), cesium carbonate (700 mg, 2.16 mmol), and DMF (3 mL) were added to a 100 ml round-bottomed flask. The resulting suspension was allowed to stir at room temperature for 16 hours, diluted with ethyl acetate (100 mL), and washed with water (3×40 mL). The organic solution was dried over sodium sulfate and concentrated. The residue was purified using Combiflash chromatography on silica gel using 0-10% ethyl acetate in hexanes as the eluent to provide compound 20D as a gel (205 mg, 78%).

Step 4:

-continued

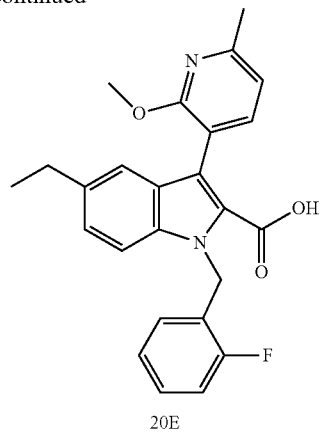

20E

To the stirring mixture of 20D (200 mg, 0.45 mmol) in THF (5 mL) in a 100 ml round-bottomed flask was added with a solution of lithium hydroxide (2.5 ml of 1 M, 2.5 mmol). The resulting solution was maintained at reflux for 4 days before cooled to room temperature. After concentration in vacuo, the residue was dissolved in methanol (5 mL), neutralized with 1.0 M HCl aqueous solution (2.5 mL, 2.5 mmol) and then concentrated again. The residue was extracted with ethyl acetate (3×40 mL). The combined organic solutions were concentrated and dried on house vacuum to provide compound 20E as a white wax (190 mg, ~100%). M.S. found for $C_{27}H_{25}ClFN_2O_3S$: 542.3 $(M+H)^+$.
Step 5:

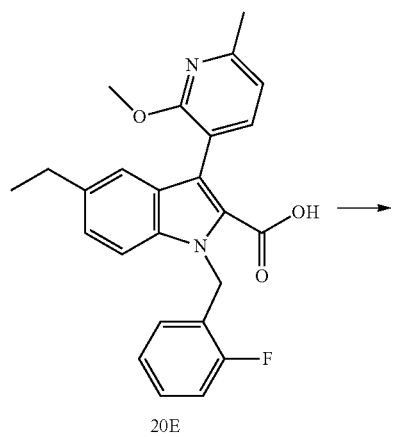

20E

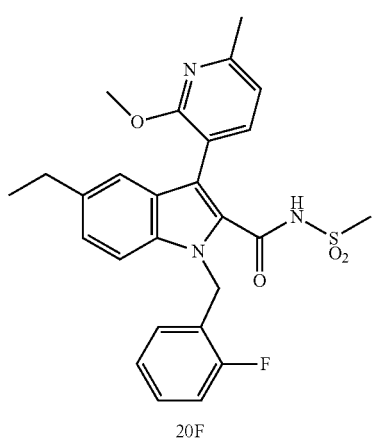

20F

A solution of 20E (65 mg, 0.16 mmol) and 1,1'-carbonyldiimidazole (37 mg, 0.23 mmol) in THF (5 mL) in a 50 ml round-bottomed flask was refluxed for 1 hour before cooled to room temperature. Methylsulfonamide (35 mg, 0.37 mmol) followed by DBU (55 mg, 0.36 mmol) were added. The resulting reaction mixture was allowed to reflux for 3 hours before cooled to room temperature and concentrated in vacuo. The residue was purified using Combiflash chromatography on silica gel using 0-2% methanol in dichloromethane as the eluent to provide compound 20F as a white wax (70 mg, 91%). M.S. found for $C_{26}H_{26}FN_3O_4S$: 496.3 $(M+H)^+$.
Step 6:

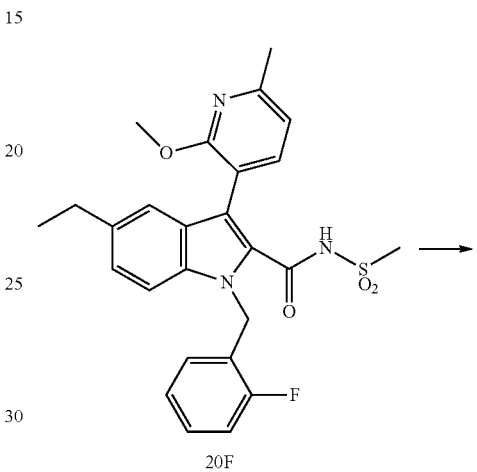

20F

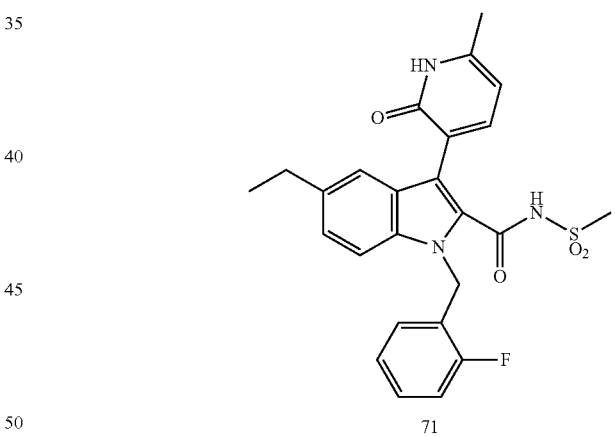

71

The starting material 20F (60 mg, 0.12 mmol) and 4.0 M HCl in 1,4-dioxane (3.0 mL, 12.0 mmol) were added to a 15 ml pressure vessel. The resulting solution was allowed to stir at 90° C. for 1 hour before cooled to room temperature. The mixture was transferred to a 25 ml round-bottomed flask and concentrated on rotavapor. The residue was purified using preparative TLC on silica gel with 5% methanol in dichloromethane as the developing solvent to provide compound 71 as a white solid (25 mg, 43%). $^1$H NMR (400 MHz, $d_6$-DMSO) δ7.72 (s, 1H), 7.33 (s, 1H), 7.30-7.25 (m, 1H), 7.25-7.18 (m, 1H), 7.18-7.11 (m, 1H), 7.09-7.05 (m, 1H), 7.00-6.94 (m, 1H), 6.94-6.84 (m, 1H), 6.33 (s, 1H), 5.78 (s, 2H), 2.95 (s, 3H), 2.72 (q, J=7.57 Hz, 2H), 2.26 (s, 3H), 1.26 (t, J=7.57 Hz, 3H). M.S. found for $C_{25}H_{24}FN_3O_4S$: 482.3 $(M+H)^+$.

Example 21

Preparation of Compound 263

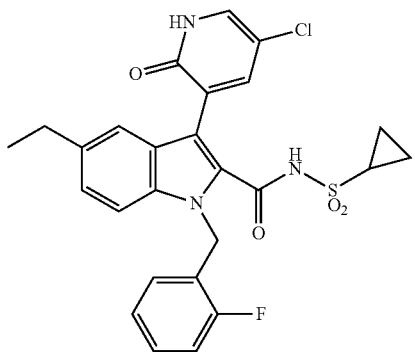

Step 1:

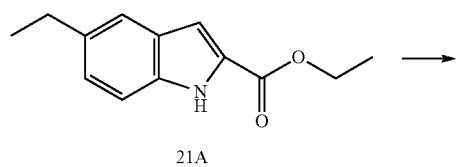

The starting materials 21A (15.0 g, 69.04 mmol) and THF (100 mL) were added to a 1000 ml round-bottomed flask. The resulting solution was cooled with a water bath. To this stirring solution, MS (15.30 g, 68.80 mmol) was added slowly. The resulting solution was allowed to stir at room temperature for 5 hours before 700 ml of water was added. The resulting mixture was continued to stir at room temperature for 30 min and then filtered. The cake was washed with water (2×40 mL), dried by air and then on house vacuum to provide compound 21B as an off-white solid (23.0 g, 97%). MS found 344.2 for $C_{13}H_{14}INO_2+H^+$.

Step 2:

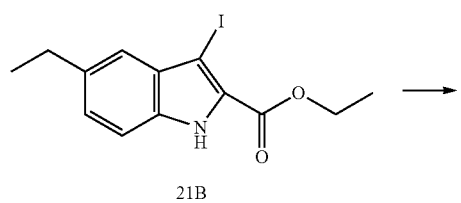

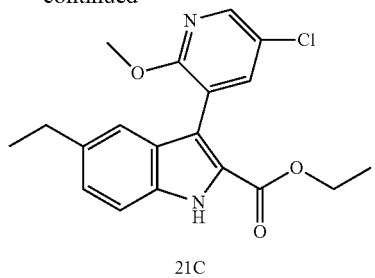

A 250 ml round-bottomed flask was charged with 21B (3.60 g, 10.49 mmol), 5-chloro-2-methoxypyridine-3-boronic acid (2.0 g, 10.67 mmol), [1,1'-bis(diphenylphosphino)ferrocene]dichloropalladium(II) complex with dichloromethane (1:1) (0.87 g, 1.06 mmol), and DME (50 mL). To the stirring solution, a solution of sodium carbonate (10 ml of 1.5 M, 15.0 mmol) was added via a syringe. The reaction mixture was maintained at reflux for 6 hours before cooled to room temperature. After concentration, the residue was taken up with ethyl acetate (200 mL), washed with water (100 mL), and dried over sodium sulfate. The solvent was removed by distillation under reduced pressure and the residue was purified using Combiflash chromatography on silica gel using 0-10% ethyl acetate in hexanes as the solvent to provide compound 21C as a white solid (2.4 g, 64%). M.S. found for $C_{19}ClN_2O_3$: 359.2 (M+H)+.

Step 3:

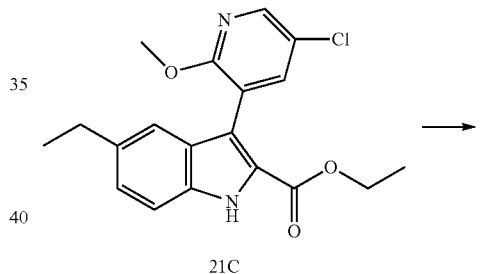

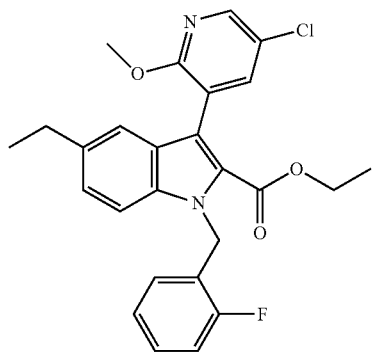

A suspension of 21C (280 mg, 0.78 mmol), 2-fluorobenzylchloride (300 mg, 2.07 mmol), cesium carbonate (400 mg, 1.23 mmol) and DMF (3 mL) was allowed to stir at room temperature for 19 hours, diluted with ethyl acetate (100 mL), and washed with water (3×50 mL). The organic solution was dried over sodium sulfate and concentrated. The residue was purified using Combiflash chromatography on silica gel using 0-5% ethyl acetate in hexanes as the eluent to provide compound 21D as a gel (318 mg, 87%).

Step 4:

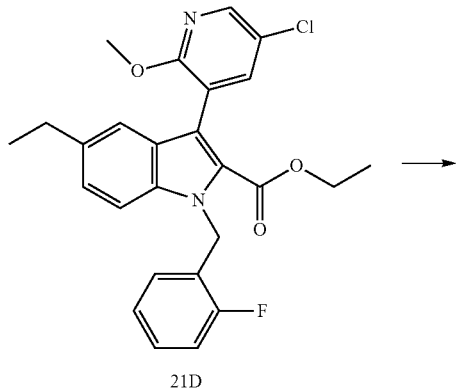

21D

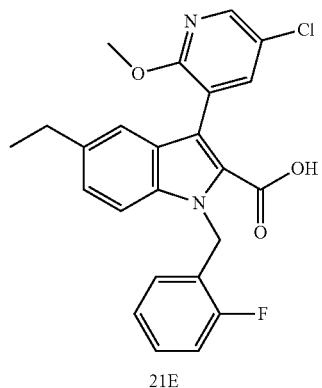

21E

To the stirring mixture of 21D (318 mg, 0.68 mmol) in THF (10 mL) in a 100 ml round-bottomed flask was added with a solution of lithium hydroxide (2.0 ml of 1 M, 2.0 mmol). The resulting solution was maintained at reflux for 5 days before cooled to room temperature. After concentration in vacuo, the residue was dissolved in methanol (5 mL), neutralized with 1.0 M HCl aqueous solution (2.0 mL, 2.0 mmol) and then concentrated again. The residue was extracted with ethyl acetate (3×40 mL). The combined organic solutions were concentrated and dried on house vacuum to provide compound 21E as a white solid (280 mg, 94%). M.S. found for $C_{24}H_{20}ClFN_2O_3$: 439.2 $(M+H)^+$.

Step 5:

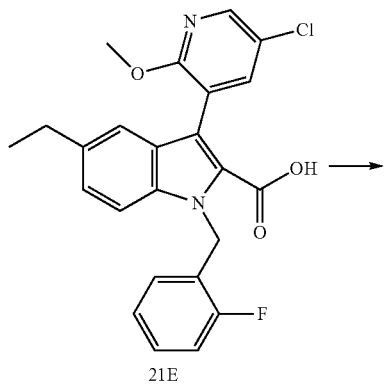

21E

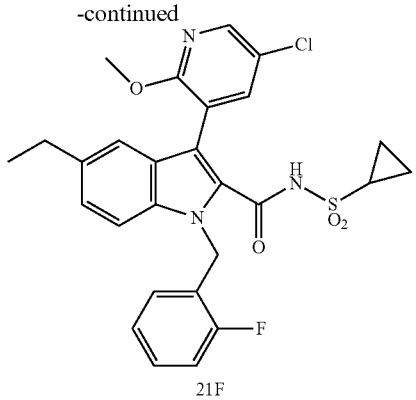

21F

A solution of 21E (70 mg, 0.16 mmol) and 1,1'-carbonyldiimidazole (40 mg, 0.25 mmol) in THF (3 mL) in a 50 ml round-bottomed flask was refluxed for 1.5 hour before cooled to room temperature. Cyclopropylsulfonamide (40 mg, 0.33 mmol) followed by DBU (80 mg, 0.53 mmol) were added. The resulting reaction mixture was allowed to reflux for 4 hours before cooled to room temperature and concentrated on rotavapor. The residue was purified using Combiflash chromatography on silica gel using 0-4% methanol in dichloromethane as the eluent to provide compound 21F as a gel (45 mg, 52%). M.S. found for $C_{27}H_{25}ClFN_3O_4S$: 542.3 $(M+H)^+$.

Step 6:

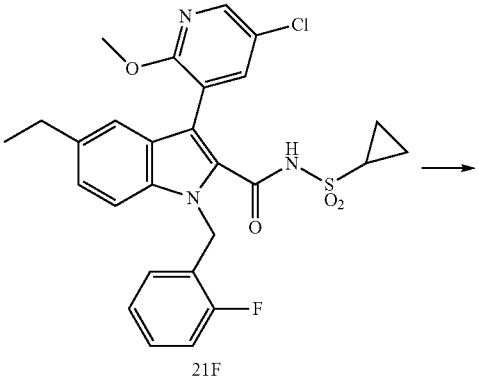

21F

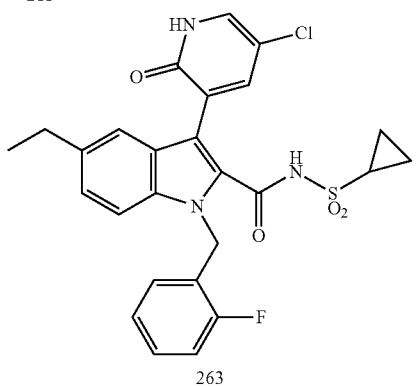

263

The starting material 21F (40 mg, 0.073 mmol) and 4.0 M HCl in 1,4-dioxane (5.0 mL, 20.0 mmol) were added to a 15 ml pressure vessel. The resulting solution was allowed to stir at 90° C. for 2 hours before cooled to room temperature. The mixture was transferred to a 25 ml round-bottomed flask and concentrated in vacuo. The residue was purified using preparative TLC on silica gel with 5% methanol in dichloromethane as the developing solvent to provide compound 263 as a white solid (25 mg, 65%). $^1$H NMR (400 MHz, d$_6$-DMSO) δ7.80 (s, 1H), 7.69 (s, 1H), 7.46 (d, J=8.51 Hz, 1H), 7.34 (s, 1H), 7.29-7.24 (m, 2H), 7.10 (t, J=9.14 Hz, 1H), 7.04 (t, J=7.25 Hz, 1H), 6.90 (t, J=6.62 Hz, 1H), 5.79 (s, 2H), 2.94 (bs, 1H), 2.74 (q, J=7.57 Hz, 2H), 1.26 (t, J=7.57 Hz, 3H), 1.16 (bs, 2H), 1.04 (bs, 2H). M.S. found for C26H23ClFN3O4S: 528.3 (M+H)$^+$.

Example 22

Preparation of Compound 213

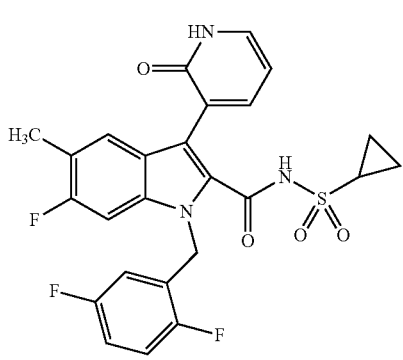

Using the method described in Example 1, Step 7, and substituting 2,5-difluorobenzyl bromide for 3-bromomethyl-4-fluoro-benzonitrile, compound 213 was prepared. M.S. found for C25H20F3N3O4S: 516.3 (M+H)$^+$.

Example 23

Preparation of Compound 317

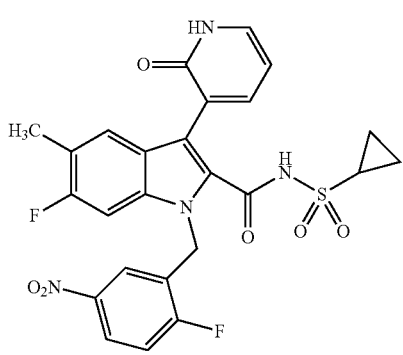

Using the method described in Example 1, Step 7, and substituting 3-bromomethyl-4-fluoro-nitrobenzene for 3-bromomethyl-4-fluoro-benzonitrile, compound 317 was prepared. M.S. found for C25H20F2N4O6S: 543.3 (M+H)$^+$.

Example 24

Preparation of Intermediate Compound 24G

Step A—Synthesis of Compound 24B

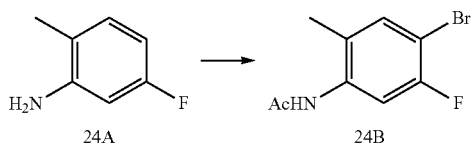

A solution of 5-fluoro-2-methylaniline (24A, 25 g, 200 mmol) in toluene (250 mL) was treated with acetic anhydride (25 mL. 226 mmol) heated at reflux for 1 hour. The reaction mixture was cooled when a colorless solid precipitated out which was filtered and washed with a mixture of ether and hexanes. The colorless solid was taken in acetic acid (150 mL) and treated dropwise with a solution of bromine (9.6 mL, 186 mmol) in acetic acid (20 mL) and stirred at room temperature. for 12 hours. The solution was diluted with water and the solid separating out was filtered and washed to provide N-(4-bromo-5-fluoro-2-methylphenyl)acetamide (24B, 40 g) as a colorless solid.

Step B—Synthesis of Compound 29C

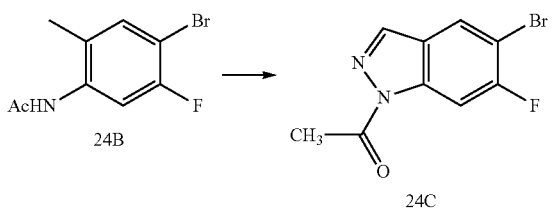

A solution of N-(4-bromo-5-fluoro-2-methylphenyl)acetamide (24B, 10.00 g, 40.64 mmol) in chloroform (100 mL) was treated with acetic anhydride (11.5 mL, 122.0 mmol), potassium acetate (8.00 g, 81.5 mmol), and 18-Crown-6 (540.00 mg, 2.0430 mmol) and then with isoamyl nitrite (12.3 mL, 871 mmol) and heated at 65° C. for 12 hours. The reaction mixture was cooled to room temperature and treated with EtOAc (500 mL), washed with water, dried (MgSO$_4$), filtered, and then concentrated in vacuo. A pale yellow solid of 1-(5-bromo-6-fluoro-1H-indazol-1-yl)ethanone (29C) precipitated out. The initial filtrate was concentrated and the residue was purified using chromatography (SiO$_2$, EtOAc/Hexanes) to provide more of product 24C.

Step C—Synthesis of Compound 24D

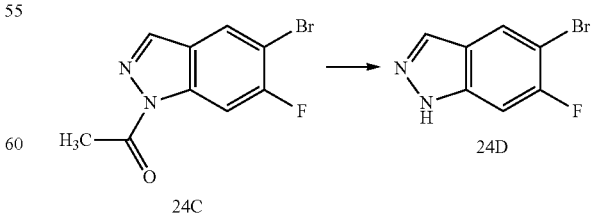

A solution of 1-(5-bromo-6-fluoro-1H-indazol-1-yl)ethanone (24C, 5.0 g, 19.5 mmol) was treated with aq HCl (3M soln., 100 mL) and methanol (20 mL) and heated at 90° C. for 3 h, when the reaction turns homogenous. The reaction mixture was cooled to room temperature and basified with aq. NaOH. A colorless solid precipitated out which was filtered and dried to provide 5-bromo-6-fluoro-1H-indazole (24D)

Step D—Synthesis of Compound 24E

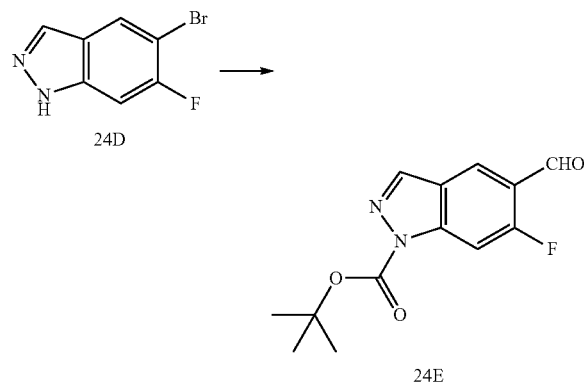

A solution of 5-bromo-6-fluoro-1H-indazole (24D, 3.50 g, 16.28 mmol) in tetrahydrofuran (200.00 mL) was treated with sodium hydride (60% in mineral oil, 1.172 g) at 0° C. and stirred at room temperature. for 20 minutes. The reaction mixture was cooled to −78° C. (dry ice and acetone) and treated with 2.5 M of n-butyl lithium in hexane (8.2 mL, 20.3 mmol) dropwise. The reaction mixture was allowed to stir at that temperature for 20 min and treated with DMF (5.06 mL, 65.11 mmol). The reaction mixture was slowly warmed to room temperature when the viscous solution turn fluidic and stirring was efficient. Analysis of TLC (40% EtOAc/Hexanes) indicated complete conversion of starting material to product. The reaction mixture was acidified with aq. HCl taken up in EtOAc (500 mL) washed with aq. HCl (100 mL), brine (100 mL), dried (MgSO$_4$), filtered, concentrated in vacuo and used as it is in next step. A solution of product 6-fluoro-1H-indazole-5-carbaldehyde (2.3 g) in THF (100 mL) was treated with di-tert-butyldicarbonate (3.56 g, 16.28 mmol) and DMAP (300 mg) and stirred at room temperature for 3 hours. The reaction mixture was concentrated in vacuo and the residue was purified using chromatography (SiO$_2$, EtOAc/Hexanes gradient 0-40%) to provide [2e] tert-butyl 6-fluoro-5-formyl-1H-indazole-1-carboxylate (24E, 3.5 g; Yield=81%) as a colorless solid.

Step E—Synthesis of Compound 24F

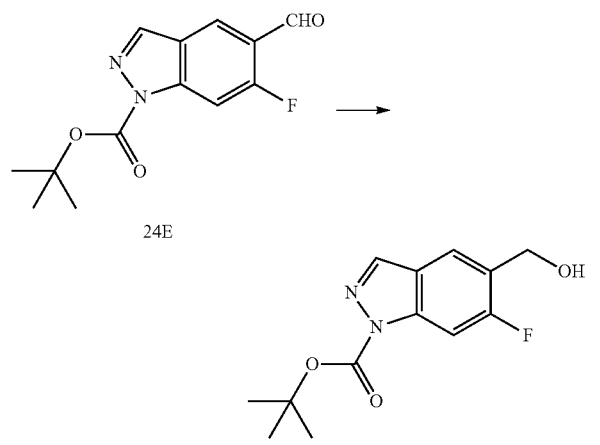

A solution of tert-butyl 6-fluoro-5-formyl-1H-indazole-1-carboxylate (29E, 3.55 g, 13.4 mmol) in methanol (50.00 mL) was treated with NaBH$_4$ (1.02 g, 26.9 mmol) at 0° C. and allowed to stir for 1 h. The reaction mixture was diluted with water and EtOAc (500 mL). The organic layer was separated and washed with aq. HCl (1M, 200 mL), aq. NaOH (1M, 200 mL) brine (200 mL) dried (MgSO$_4$), filtered, concentrated in vacuo and residue was purified using chromatography (SiO$_2$, EtOAc/hexanes) to provide tert-butyl 5-(hydroxymethyl)-6-fluoro-1H-indazole-1-carboxylate (29F, 3.00 g; Yield=83.9%) as a colorless solid.

Step F—Synthesis of Compound 24G

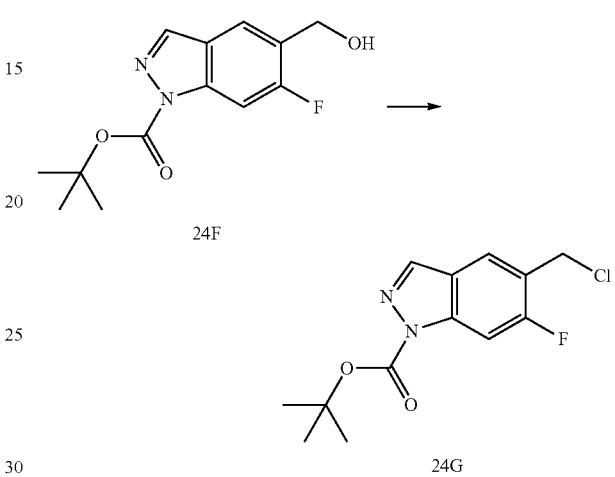

A solution of tert-butyl 5-(hydroxymethyl)-6-fluoro-1H-indazole-1-carboxylate (29F, 3.0 g, 11.27 mmol) in methylene chloride (50.00 mL, 780.0 mmol) at room temperature. was treated with pyridine (4.56 mL, 56.33 mmol) and methanesulfonyl chloride (1.31 mL) and stirred at room temperature for 16 hours. The reaction mixture was concentrated in vacuo and the residue was dissolved in EtOAc (300 mL) washed with aq HCl (100 mL), brine (100 mL), dried (MgSO$_4$), filtered, concentrated in vacuo, and purified using chromatography (SiO$_2$, EtOAc/Hexanes) to provide tert-butyl 5-(chloromethyl)-6-fluoro-1H-indazole-1-carboxylate (24G, 1.9 g; Yield=59%)

Example 25

Preparation of Intermediate Compound 25B

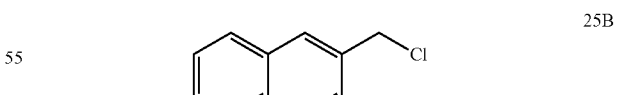

Step A—Synthesis of Compound 6A

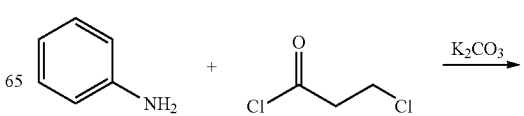

-continued

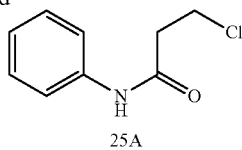
25A

A mixture of aniline (65.04 mL, 713.8 mmol), potassium carbonate (54.4 g, 394 mmol) and water (300 mL) were added to a 2000 mL flask. The resulting reaction was kept at room temperature using a room temperature water bath and stirred with a mechanic stirrer. 3-Chloro-propionyl chloride (75.18 mL, 787.6 mmol) was added dropwise via additional funnel and the resulting suspension was allowed to stir at room temperature for 3 hours. The reaction mixture was filtered and the collected solid was washed sequentially with water (300 mL), aq. HCl (1M, 2×300 mL), and water (300 mL), then dried to provide compound 25A, which was used without purification (114.5 g, 87%).

Step B—Synthesis of Compound 25B

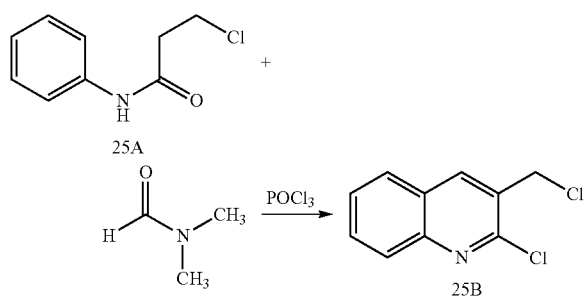

N,N-Dimethylformamide (53.7 mL, 694 mmol) was charged into a three necked flask and cooled to 0° C. and treated with phosphoryl chloride (177.7 mL, 1906 mmol) dropwise. The reaction was allowed to stir at that temperature for 10 min and treated with 3-Chloro-N-phenylpropanamide 25A (50.00 g, 272.3 mmol) and stirred at room temperature for 30 minutes. The reaction mixture was heated at 80° C. for 3 h and slowly poured into ice. The solid separating out was filtered and washed extensively with water (2×1000 mL), aq. saturated sodium bicarbonate (500 mL), and taken in EtOAc (1 L), The solution was dried (MgSO₄) filtered concentrated in vacuo and the residue obtained was recrystallized from boiling hexanes to provide compound 25B (20 g).

Example 26

Preparation of Intermediate Compounds 26E and 26F

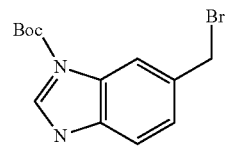
26F

Step A—Synthesis of Compound 26B

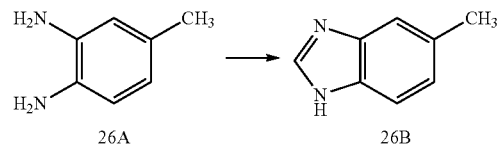

A solution of compound 26A (3 g, 24.5 mmol) in trimethyl orthoformate (15 mL) was treated with 2 drops conc. HCl and heated to 80° C. for 2 hours. The reaction mixture was cooled to room temperature and concentrated in vacuo to provide compound 26B (3.65 g), which was used without further purification. M.S. found for $C_8H_8N_2$: 133.2 $(M+H)^+$.

Step B—Synthesis of Compounds 26C and 26D

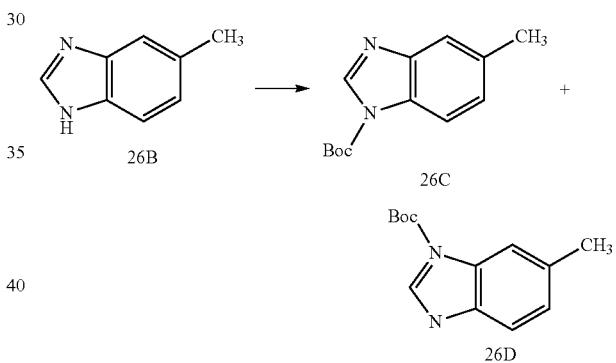

To a solution of compound 26B (24.5 mmol) in $CH_3CN$ (65 mL) was added di-tertbutyl dicarbonate (5.89 g, 27.0 mmol), triethylamine (3.76 mL, 27.0 mmol) and 4-dimethylamino pyridine (300 mg, 2.45 mmol) and the resulting reaction was heated to 80° C. and allowed to stir at this temperature for 1.5 hours. The reaction mixture was cooled to room temperature, concentrated in vacuo, and the residue obtained was purified using flash column chromatography (silica gel, EtOAc/Hexanes 5-20%) to provide a mixture of isomeric compounds 26C and 26D (5.38 g, 94.3% yield over steps A and B).

Step C—Synthesis of Compounds 26E and 26F

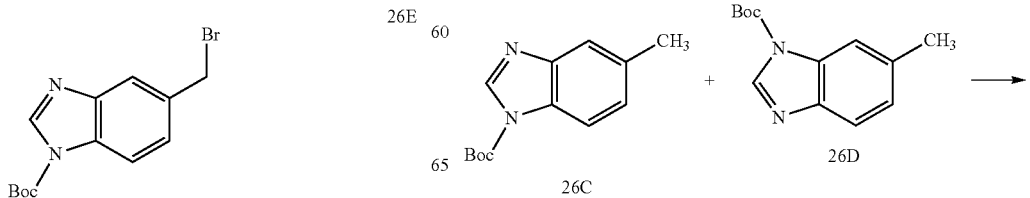

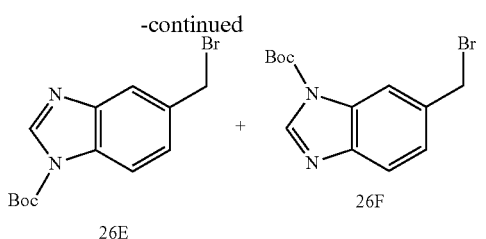

To a solution of compounds 26C and 26D (2 g, 8.61 mmol) in carbon tetrachloride (40 mL) was added N-bromosuccinimide (1.6 g, 9.04 mmol) and dibenzoyl peroxide (41.7 mg, 0.1722 mmol) and the resulting reaction was heated to 90° C. and allowed to stir at this temperature for 12 hours. The reaction was cooled to room temperature, solids were filtered off and the filtrate was washed with water, dried over sodium sulfate and concentrated in vacuo to provide compounds 26E and 26F (2.58 g) which was used without further purification. M.S. found for $C_{13}H_{15}BrN_2O_2$: 334.7 $(M+Na)^+$.

Example 27

Preparation of Intermediate Compound 27B

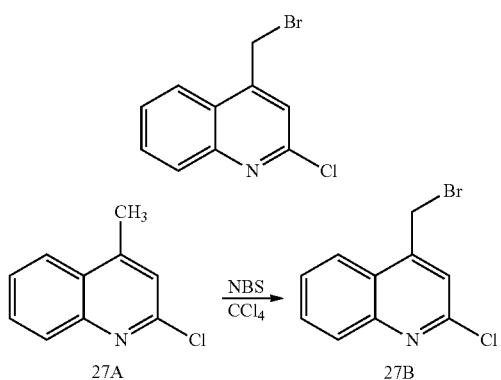

A mixture of compound 27A (1.5 g, 8.44 mmol), NBS (1.8 g, 10.11 mmol) in carbon tetrachloride (50 mL) was heated to reflux, then benzoyl peroxide (0.21 g, 0.866 mmol) was added. The resulting suspension was allowed to stir at reflux for 19 hours, then cooled to room temperature and filtered. The filtrate was washed with saturated sodium carbonate, dried over sodium sulfate and concentrated in vacuo to provide a mixture (1.7 g) which contains about 50% of compound 27B, and was used without further purification.

Example 28

Preparation of Intermediate Compound 28G

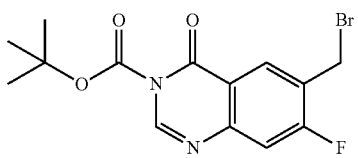

Step A—Synthesis of Compound 9B

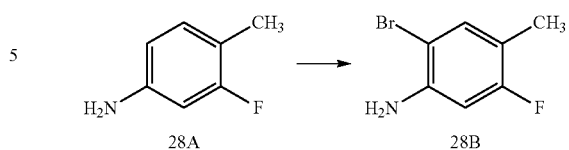

A mixture of compound 28A (6.00 g, 47.9 mmol) and anhydrous potassium carbonate (6.70 g, 48.5 mmol) in anhydrous dichloromethane (130 mL) was cooled to −15° C. in a salt-ice bath and then added dropwise to a solution of bromine (7.70 g, 48.2 mmol) in anhydrous dichloromethane (80 mL). After addition was complete, the reaction was allowed to stir at −15° C. for 1 hour. Ice water (100 mL) was added to the reaction mixture and the aqueous layer was extracted with dichloromethane (2×100 mL). The combined organic layers were dried over $MgSO_4$ and concentrated in vacuo to provide compound 28B (11.0 g, quant.), which was used without further purification.

Step B—Synthesis of Compound 28C

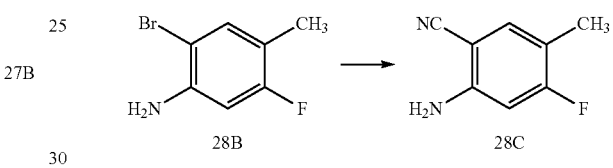

Compound 28B was dissolved in DMF (150 mL) and to this solution was added copper (I) cyanide (11.0 g, 123 mmol). The mixture was heated to 160° C. and allowed to stir at this temperature for 20 hours. After being cooled to room temperature, with water (200 mL), iron (II) chloride (42.0 g, 155 mmol) and concentrated hydrochloric acid (20 mL) were added to the reaction mixture and the resulting reaction was allowed to stir for 45 minutes. The reaction mixture was then basified to pH>10 using commercial ammonium hydroxide solution. The basic solution was then extracted with ethyl acetate (4×400 mL). The combined organic extracts were washed with water, dried over magnesium sulfate, filtered and concentrated in vacuo. The residue obtained was purified using flash chromatography to provide compound 28C (5.82 g, 81%). $^1$H NMR (400 MHz, $d_6$-DMSO): δ7.34 (d, J=8.4 Hz, 1H), 6.52 (d, J=12.4 Hz, 1H), 6.10 (s, 2H), 2.08 (s, 3H).

Step C—Synthesis of Compound 28D

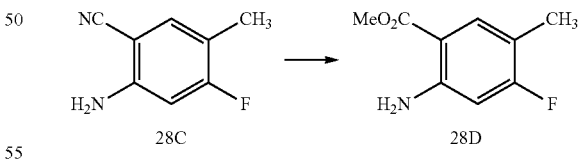

To a solution of 28C (2.0 g, 13.3 mmol) in anhydrous methanol (15 mL) at room temperature was added concentrated sulfuric acid (4.0 mL). The reaction mixture was heated to 70° C. and allowed to stir for four days. After cooled to room temperature, it was poured into with ice water. The mixture was then diluted with ethyl acetate (200 mL) and was made basic (pH>10) with commercial ammonium hydroxide solution. The layers were separated. The aqueous layer was extracted with ethyl acetate (2×100 mL). The combined organic solution was dried over $MgSO_4$ and concentrated in vacuo to provide the crude product which, was purified using flash chromatography to provide compound 28D (1.0 g, 41%) and some recovered 28C. $^1$H NMR (400 MHz, d$_6$-DMSO): δ7.61 (d, J=8.8 Hz, 1H), 6.69 (s, 2H), 6.51 (d, J=12.0 Hz, 1H), 3.77 (s, 3H), 2.06 (s, 3H).

Step D—Synthesis of Compound 28E

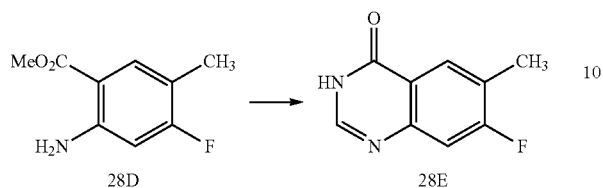

The solution of compound 28D (500 mg, 2.73 mmol) in formamide (6.0 mL) was heated to 150° C. in an oil bath and allowed to stir for 18 hours. After cooled to room temperature, ethyl acetate (100 mL) and water (100 mL) were added and the layers were separated. The organic solution was washed with water (2×60 mL), dried over MgSO$_4$ and concentrated in vacuo to provide the crude product 28E (0.50 g, quant.) which, was used without further purification. MS found for C$_9$H$_7$FN$_2$O: 179.0 (M+H)$^+$.

Step E—Synthesis of Compound 28F

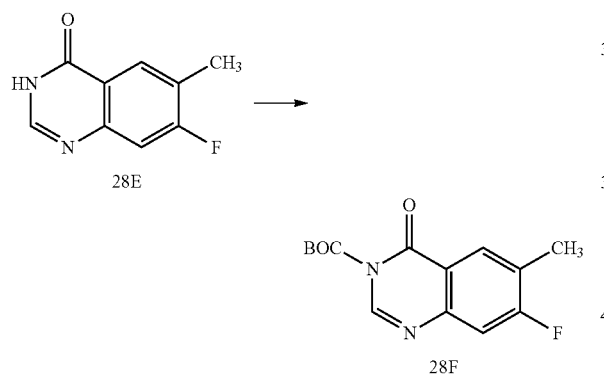

To a solution of 28E (from Step 4) in anhydrous THF (20 mL) at room temperature was added di-tert-butyl dicarbonate (1.84 g, 8.43 mmol), 4-dimethylaminopyridine (350 mg, 2.86 mmol) and triethyl amine (0.40 mL, 2.87 mmol). The reaction mixture was allowed to stir for 18 hours. Ethyl acetate (100 mL) and water (100 mL) were added and the layers were separated. The aqueous layer was extracted with ethyl acetate (2×50 mL). The combined organic solution was dried over MgSO$_4$ and concentrated in vacuo to provide the crude product which, was purified using flash chromatography to provide compound 28F (285 mg, 36%). MS found for C$_{14}$H$_{15}$FN$_2$O$_3$: 179.0 (M+H-100)$^+$.

Step F—Synthesis of Compound 28G

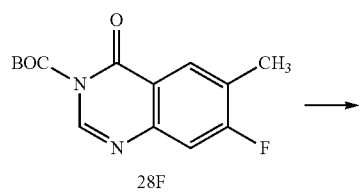

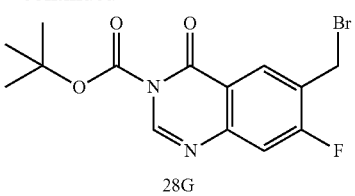

The mixture of 28F (282 mg, 1.01 mmol), NBS (253 mg, 1.42 mmol) and AIBN (58 mg, 0.353 mmol) in anhydrous carbon tetrachloride (60 mL) was heated to 90° C. in an oil bath and allowed to stir for 4 hours. After cooled to room temperature and concentrated in vacuo, the residue was dissolved in ethyl acetate (100 mL) and water (100 mL). The layers were separated. The organic solution was washed with water (100 mL), dried over MgSO$_4$ and concentrated in vacuo to provide the crude product 28G (453 mg, quant.) which, was used without further purification.

Example 29

Preparation of Intermediate Compound 29E

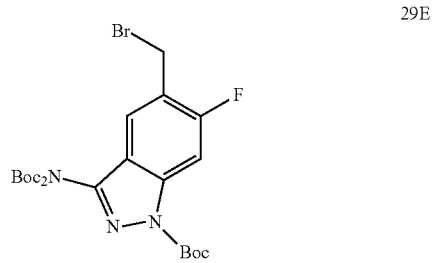

Step A—Synthesis of Compound 29A

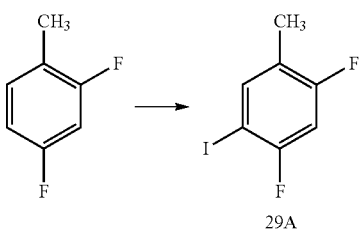

A solution of 2,4-difluorotoluene (4.72 g, 36.8 mmol) in trifluoroacetic acid (12.29 mL, 159.5 mmol) was cooled to 0° C., then N-Iodosuccinimide (9.59 g, 42.6 mmol) was added and the resulting reaction was allowed to stir at room temperature for about 15 hours. The reaction mixture was then concentrated in vacuo and the residue obtained was dissolved in hexanes (100 mL), washed with aqueous sodium thiosulfate (100 mL), brine (100 mL), then dried (MgSO$_4$), filtered and concentrated in vacuo. The resulting residue was purified using bulb-to-bulb distillation to provide compound 29A (7.2 g, 77%) as a colorless oil.

Step B—Synthesis of Compound 29B

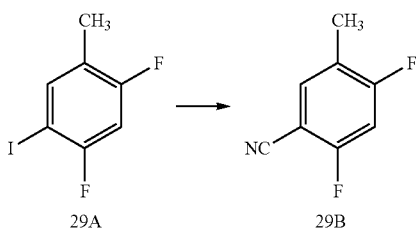

A solution of compound 29A (7.11 g, 28.0 mmol), zinc cyanide (1.97 g, 16.8 mmol) and tetrakis(triphenylphosphine) palladium(0) (3.23 g, 2.80 mmol) in DMF (30 mL) was heated to 90° C. and allowed to stir at this temperature for 1.5 hours. The reaction mixture was concentrated in vacuo and the residue obtained was taken up in water (400 mL) and extracted with ether (400 mL). The organic extract was washed with aqueous ammonium hydroxide solution (1N). The organic layer was dried ($MgSO_4$) filtered, concentrated in vacuo to provide a residue that was purified using flash column chromatography ($SiO_2$, EtOAc/Hexanes) to provide a mixture that contained product and triphenylphosphine. This mixture was further purified using sublimation at 1 mm/Hg at 45° C. to provide compound 29B (1.8 g; Yield=42%).

Step C—Synthesis of Compound 29C

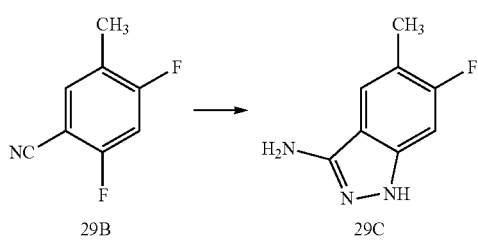

A solution of compound 29B (1.400 g, 9.154 mmol) and hydrazine (0.700 mL, 22.3 mmol) in isopropyl alcohol (50 mL, 653.1 mmol), was heated to reflux and allowed to stir at this temperature for 24 hours. The reaction mixture was cooled to room temperature, concentrated in vacuo and the residue obtained was purified using flash column chromatography ($SiO_2$, Acetone/Hexanes 0→50%) to provide compound 29C (330 mg, 22%).

Step D—Synthesis of Compound 29D

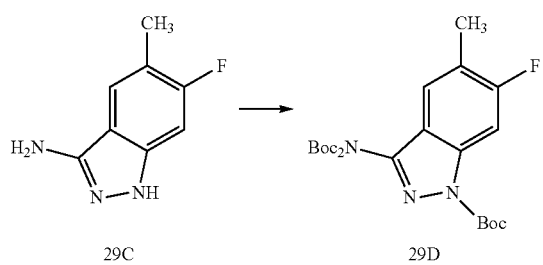

A solution of compound 29C (330.00 mg, 1.998 mmol), di-tert-butyldicarbonate (2.6163 g, 11.98 mmol) and 4-dimethylaminopyridine (48.817 mg, 0.39959 mmol) in acetonitrile (15 mL, 287.2 mmol) was heated to reflux and allowed to stir at this temperature for 2 hours. The reaction mixture was cooled to room temperature, concentrated in vacuo, and the resulting residue was purified using flash column chromatography ($SiO_2$, EtOAc/Hexanes 0-20%) to provide compound 29D (640.00 mg, 68%) as a colorless oil.

Step E—Synthesis of Compound 29E

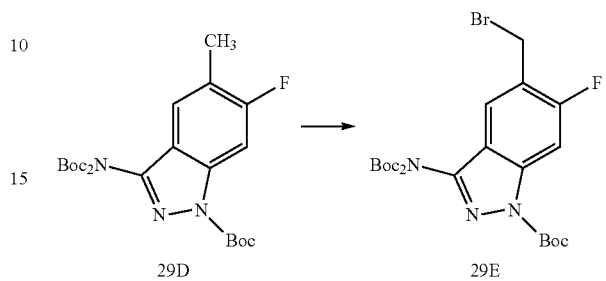

A solution of compound 29D (630.00 mg, 1.3533 mmol), N-bromosuccinimide (337.22 mg, 1.8947 mmol) and benzoyl peroxide (65.563 mg, 0.27067 mmol) in carbon tetrachloride (20 mL) was heated to reflux and allowed to stir at this temperature for 3 hours. The reaction mixture was cooled to room temperature, concentrated in vacuo and the residue obtained was dissolved in EtOAc (300 mL). The resulting solution was washed with aqueous sodium thiosulfate (100 mL), brine (100 mL), dried ($MgSO_4$), filtered, and concentrated in vacuo. The residue obtained was purified using flash column chromatography ($SiO_2$, EtOAc/Hexanes) to provide compound 29E as a colorless oil.

Example 30

Preparation of Intermediate Compounds 30E and 30F

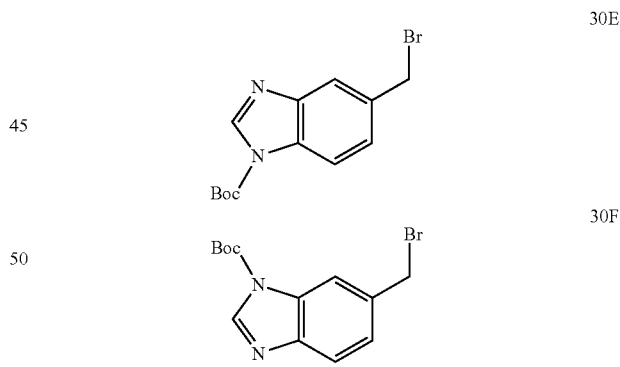

Step A—Synthesis of Compound 30B

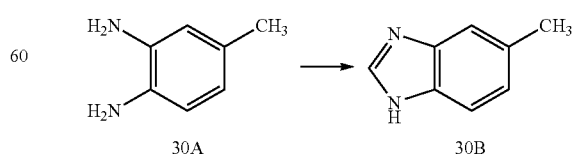

A solution of compound 8A (3 g, 24.5 mmol) in trimethyl orthoformate (15 mL) was treated with 2 drops conc. HCl and heated to 80° C. for 2 hours. The reaction mixture was cooled to room temperature and concentrated in vacuo to provide compound 8B (3.65 g), which was used without further purification. M.S. found for $C_8H_8N_2$: 133.2 $(M+H)^+$.

Step B—Synthesis of Compounds 30C and 30D

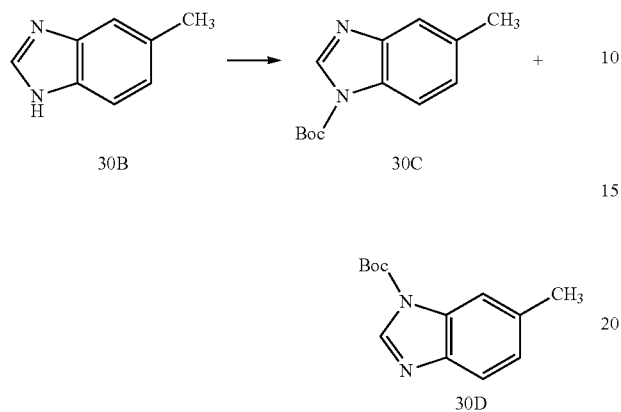

To a solution of compound 30B (24.5 mmol) in $CH_3CN$ (65 mL) was added di-tertbutyl dicarbonate (5.89 g, 27.0 mmol), triethylamine (3.76 mL, 27.0 mmol) and 4-dimethylamino pyridine (300 mg, 2.45 mmol) and the resulting reaction was heated to 80° C. and allowed to stir at this temperature for 1.5 hours. The reaction mixture was cooled to room temperature, concentrated in vacuo, and the residue obtained was purified using flash column chromatography (silica gel, EtOAc/Hexanes 5-20%) to provide a mixture of isomeric compounds 30C and 30D (5.38 g, 94.3% yield over steps A and B).

Step C—Synthesis of Compounds 30E and 30F

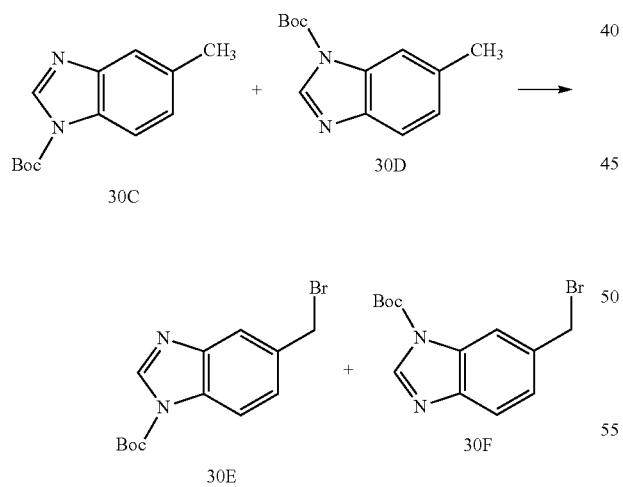

To a solution of compounds 30C and 30D (2 g, 8.61 mmol) in carbon tetrachloride (40 mL) was added N-bromosuccinimide (1.6 g, 9.04 mmol) and dibenzoyl peroxide (41.7 mg, 0.1722 mmol) and the resulting reaction was heated to 90° C. and allowed to stir at this temperature for 12 hours. The reaction was cooled to room temperature, solids were filtered off and the filtrate was washed with water, dried over sodium sulfate and concentrated in vacuo to provide compounds 30E and 30F (2.58 g) which was used without further purification. M.S. found for $C_{13}H_{15}BrN_2O_2$: 334.7 $(M+Na)^+$.

Example 31

Preparation of Intermediate Compound 31B

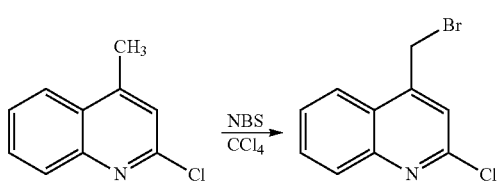

A mixture of compound 31A (1.5 g, 8.44 mmol), NBS (1.8 g, 10.11 mmol) in carbon tetrachloride (50 mL) was heated to reflux, then benzoyl peroxide (0.21 g, 0.866 mmol) was added. The resulting suspension was allowed to stir at reflux for 19 hours, then cooled to room temperature and filtered. The filtrate was washed with saturated sodium carbonate, dried over sodium sulfate and concentrated in vacuo to provide a mixture (1.7 g) which contains about 50% of compound 31B, and was used without further purification.

Example 32

Preparation of Intermediate Compound 32D

Step A—Synthesis of Compound 32B

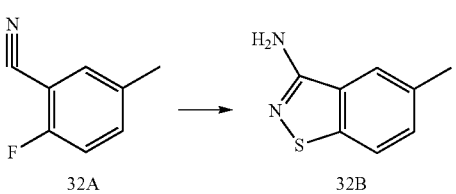

A mixture of 2-fluoro-5-methylbenzonitrile (32A, 2.0 g; 14.799 mmol) and sodium sulfide (1.0 eq, 1.15 g) was dissolved in 150 mL of DMSO and heated at 70° C. overnight. The mixture was placed in an ice-water bath and treated with concentrated aqueous ammonium hydroxide (20 mL) and aqueous sodium hypochlorite (20 mL). The reaction mixture was allowed to warm to room temperature and allowed to stir for 5 hours. The mixture was diluted with ethyl acetate (300 mL) and washed with water (2×60 mL) and brine (50 mL). The organic layer was dried over magnesium sulfate, filtered and concentrated in vacuo. The residue was adsorbed on silica gel and purified on a Biotage 40-M silica gel column (gradient: 0 to 30% acetone in hexanes) to provide compound 32B (860 mg; 36%) as a white solid. $^1$H-NMR ($CDCl_3$; 400 MHz): δ 7.68 (1H, d, J=8.54 Hz), 7.48 (1H, s), 7.33 (1H, d, J=8.54 Hz), 4.89 (2H, broad s), 2.50 (3H, s).

Step B—Synthesis of Compound 32C

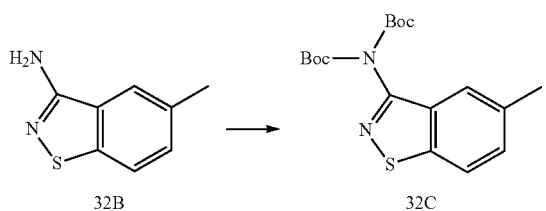

A solution of 5-methylbenzo[d]isothiazol-3-ylamine, (10B, 850 mg; 5.176 mmol) in dry acetonitrile (50 mL) was treated with Boc-anhydride (2.1 eq, 2.37 g) and heated to 50° C. All starting material had been consumed after 2 h and the mixture was concentrated in vacuo to one third of its volume. The residue was dissolved in ethyl acetate (100 mL) and washed with aqueous sodium hydrogen sulfate (20 mL), and brine (20 mL). The organic layer was dried over magnesium sulfate, filtered and concentrated in vacuo. The residue was adsorbed on silica gel and purified on a Biotage 40-M silica gel column (gradient: 0 to 10% ethyl acetate in hexanes) to provide compound 10C (1.7 g; 91%) as a white powder. $^1$H-NMR (CDCl$_3$; 400 MHz): δ 7.77 (1H, d, J=8.54 Hz), 7.55 (1H, s), 7.38 (1H, dd, J=1.83, 8.54 Hz), 2.51 (3H, s), 1.36 (18H, s). LR-MS (ESI): calcd for $C_{18}H_{25}N_2O_4S$ [M+H]$^+$ 365.15. found 365.23.

Step C—Synthesis of Compound 32D

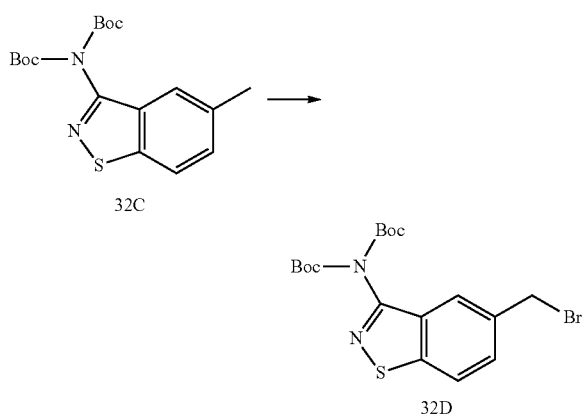

A solution of N,N-bis-Boc-5-methyl-benzo[d]isothiazol-3-ylamine (32D, 500 mg; 1.371 mmol) in 15 mL of carbon tetrachloride was treated N-bromosuccinimide (1.05 eq, 256 mg) and benzoyl peroxide (10 mol %; 33 mg). The solution was degassed (vacuum/argon flush) and then heated to 75° C. for 5 hours. The reaction mixture was concentrated to one third of its volume in vacuo and the residue was dissolved in ethyl acetate (50 mL). The solution was washed with aqueous saturated sodium bicarbonate soln (2×10 mL) and brine (10 mL). The organic layer was dried over magnesium sulfate, filtered and concentrated in vacuo. The residue was adsorbed on silica gel and purified on a Biotage 40-S silica gel column (gradient: hexanes then 0 to 10% ethyl acetate in hexanes) to provide compound 32D (396 mg; 69%) as a white solid. $^1$H-NMR (CDCl$_3$; 400 MHz): δ 7.87 (1H, d, J=8.54 Hz), 7.78 (1H, s), 7.58 (1H, dd, J=1.83, 8.54 Hz), 4.63 (2H, s), 1.37 (18H, s). LR-MS (ESI): calcd for $C_{18}H_{24}BrN_2O_4S$ [M+H]$^+$ 445.06. found 445.24.

Example 33

Preparation of Intermediate Compound 33D

Step A—Synthesis of Compound 33B

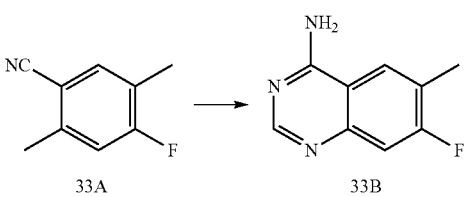

A solution of 33A (0.20 g, 1.33 mmol) in formamide (15 mL) was heated to 150° C. and allowed to stir for 18 hours. After cooled to room temperature, ethyl acetate (60 mL) and water (30 mL) were added and the layers were separated. The organic solution was washed with water (3×20 mL), dried (MgSO$_4$), filtered, and concentrated in vacuo to provide the crude product 33B (0.22 g, 93%). MS found for $C_9H_8FN_3$: 178.2 (M+H)$^+$.

Step B—Synthesis of Compound 11C

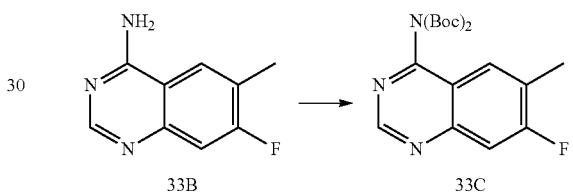

33B was treated with 3.0 equivalent of (Boc)$_2$O to provide 33C. MS found for $C_{19}H_{24}FN_3O_4$: 378.4 (M+H)$^+$.

Step C—Synthesis of Compound 33D

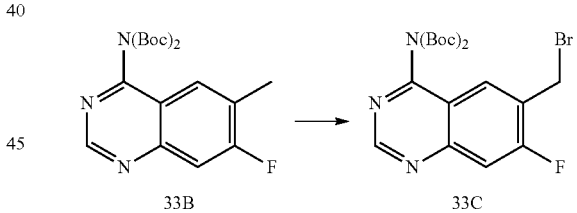

Bromination of 33C understandard N-bromo succinimide conditions afforded 33D. MS found for $C_{19}H_{23}BrFN_3O_4$: 458.3 (M+H)$^+$.

Example 34

Preparation of Intermediate Compound 34F

Step A—Synthesis of Compound 34B

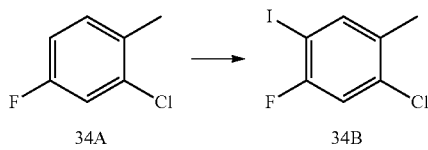

N-iodosuccinimide (1.1 eq; 17.1 g) was added to a solution of 2,4-difluoro toluene (34A, 10.0 g; 69.17 mmol; Alfa Aesar) in trifluoroacetic acid (46 mL). The reaction was set to stir for 12 hours. The volatiles were removed under reduced pressure; the remaining slurry was diluted with ether (400 mL) and washed with 5% aq sodium thiosulfate (5×40 mL), water (2×30 mL), and brine (40 mL). The organic layer was collected, dried over magnesium sulfate, filtered, and concentrated in vacuo. The reaction was purified via bulb to bulb distillation to provide product 34B as a colorless liquid (17 g; 91%)

Step B—Synthesis of Compound 34C

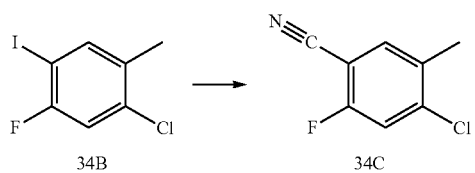

A solution of intermediate 34B (13.0 g; 48.06 mmol) and zinc cyanide (1 eq; 5.644 g) in N,N-dimethlyformamide (50 mL) was treated with tetrakis (triphenylphosphine) palladium (0) (0.1 eq; 5.55 g) and heated at 90° C. for 12 hours. The reaction mixture was diluted with ether (600 mL) and ammonium hydroxide (1:1 concentrated ammonium hydroxide:water 200 mL). The organic layer was separated and washed with water (100 mL) and brine (100 mL), dried over magnesium sulfate, filtered, concentrated under reduced pressure, and purified over silica gel first eluting with hexanes, then with 20% ethyl acetate/hexanes. Product 34C (4.48 g; 33%) was afforded as a clear oil.

Step C—Synthesis of Compound 34D

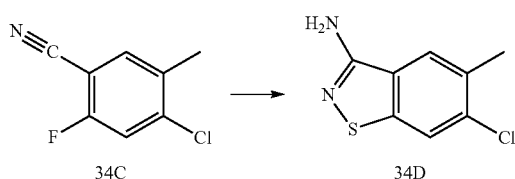

A solution of 34C (2.25 g; 13.27 mmol) and sodium sulfide (1 eq; 1.035 g) was prepared in DMSO (130 mL) and heated at 70° C. overnight. The mixture was placed in an ice water bath and treated with concentrated aqueous ammonium hydroxide (30 mL) and aqueous sodium hypochlorite (30 mL). The reaction mixture was allowed to stir for 5 h (temp from 0 to 25° C.). The mixture was diluted with ethyl acetate (400 mL) and washed with water (2×40 mL) and brine (50 mL). The organic layer was dried over magnesium sulfate, filtered and concentrated in vacuo. The residue was adsorbed on silica gel and purified on an ISCO 330G column (gradient: 0-30% acetone in hexanes), affording product 34D (800 mg; 30.3%) as a white solid.

Step D—Synthesis of Compound 34E

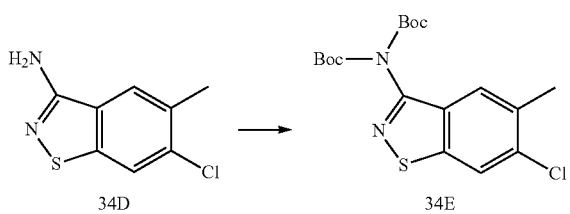

A solution of intermediate 34D (780 mg; 3.93 mmol) in dry acetonitrile (39 mL) was treated with Boc-anhydride (2.2 eq; 1.885 g) and heated to 50° C. All starting material had been consumed after 2 h and the mixture was concentrated in vacuo to one third of its volume. The residue was dissolved in ethyl acetate (100 mL) and washed with aqueous sodium hydrogen sulfate (20 mL) and brine (20 mL). The organic layer was dried over magnesium sulfate, filtered and concentrated in vacuo. The residue was adsorbed on silica gel and purified on a ISCO 80 gram column (gradient: 0 to 10% ethyl acetate in hexanes) to provide compound 34E (1.03 g; 66% yield) as a white solid.

Step E—Synthesis of Compound 34F

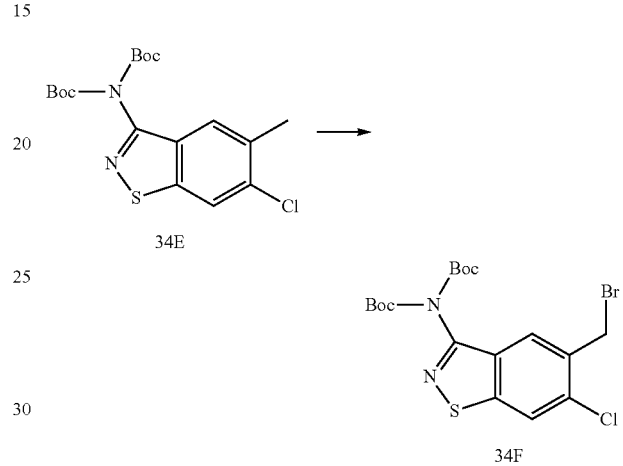

A solution of intermediate 34E (400 mg; 1.003 mmol), N-Bromosuccinimide (1.05 eq; 187.4 mg), and benzoyl peroxide (0.1 eq; 24.3 mg) in dry carbon tetrachloride (10 mL) was prepared and heated at reflux for 12 hours. TLC (30% ethyl acetate in hexanes) revealed the reaction had partially progressed. The reaction mixture was concentrated under reduced pressure, diluted with ethyl acetate (100 mL), washed with saturated aqueous sodium bicarbonate (25 mL) and brine (25 mL), dried over magnesium sulfate, filtered, and concentrated in vacuo. The residue was then diluted with dichloromethane, adsorbed onto silica gel, and purified on ISCO (25-M Column; 0-40% ethyl acetate in hexanes). The fractions containing product were concentrated under reduced pressure affording intermediate 34F (278 mg; 58%) as a clear yellow oil.

Example 35

Preparation of Intermediate Compound 35C

Step A—Synthesis of Compound 31A

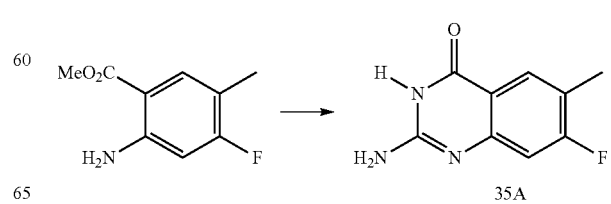

A solid mixture of methyl 2-amino-4-fluoro-5-methylbenzoate (2.66 g, 14.5 mmol), chloroformamidinium hydrochloride (2.6 g, 22.6 mmol) and methyl sulfone (8.5 g, 90.3 mmol) was heated to 150-160° C. in an oil bath with vigorous stirring. It became a clear solution after about 10 minutes. Heating was continued for a total of 2 hours. When cooled to room temperature, it became a solid. The material was taken up with water (200 mL), basified with commercial ammonium hydroxide. After stirred for 1 hour, the solid was collected through filtration. It was washed with water (20 mL) and dried under vacuum to provide crude product 35A (2.93 g, quant.). MS found for $C_9H_8FN_3O$: 194.2 $(M+H)^+$.

Step B—Synthesis of Compound 35B

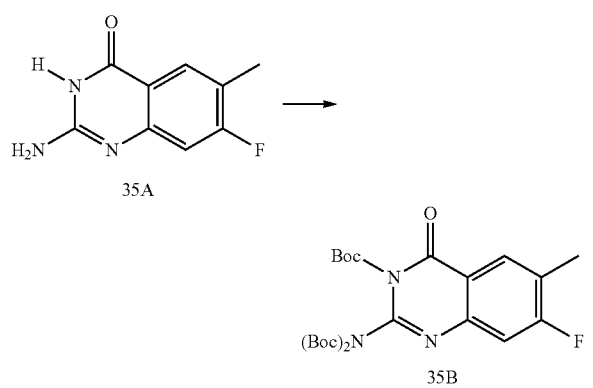

Compound 35B was prepared from 35A according the procedures described, and using 4 equivalents of $(Boc)_2O$. MS found for $C_{24}H_{32}FN_3O_7$: 394.3 $(M+H-100)^+$.

Step C—Synthesis of Compound 35C

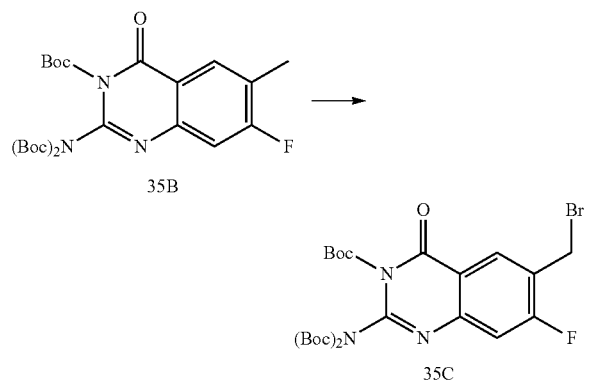

A solution of compound 35B (4.83 g, 9.8 mmol), N-bromosuccinimide (2.70 g, 15.2 mmol) and benzoyl peroxide (600 mg, 2.48 mmol) in carbon tetrachloride (300 mL) was heated to reflux and allowed to stir at this temperature for 18 hours. The reaction mixture was cooled to room temperature, concentrated in vacuo and the residue obtained was dissolved in EtOAc (300 mL). The resulting solution was washed with aqueous sodium thiosulfate (100 mL), brine (100 mL), dried ($MgSO_4$), filtered, and concentrated in vacuo to provide intermediate compound 35C, which was used without further purification. MS found for $C_{24}H_{31}BrFN_3O_7$: 472.3 $(M+H-100)^+$.

Example 36

Preparation of Intermediate Compound 36G

Step A—Synthesis of Compound 36B

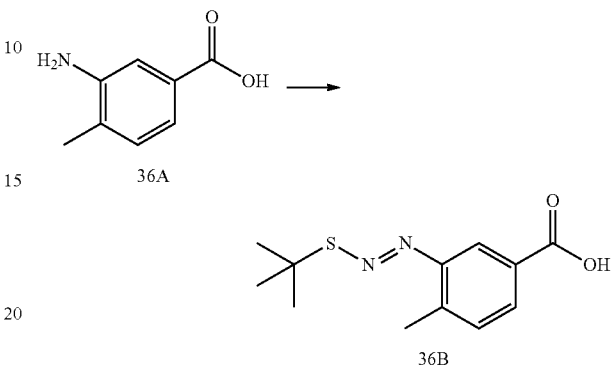

To a stirred solution of aqueous HCl (15 mL of conc HCl in 50 mL of water) was added 3-amino-4-methyl benzoic acid (36 A, 5.0 g; 33.0 mmol). The mixture was cooled in an ice-water bath followed by slow addition of a solution of sodium nitrite (1.1 eq, 2.50 g) in water (12 mL). The mixture was allowed to stir for 30 min at which point the mixture was a homogeneous dark solution. A saturated aqueous solution of sodium acetate was added until pH 6 was attained. Sodium t-butylthiolate (0.5 eq, 1.85 g) was added in one portion. The reaction was allowed to stir for 2 h and the resulting precipitate was collected by filtration (whatman #1), washed with water (20 mL) and dried under vacuum to provide compound 36B (2.7 g; 64%) as a tan solid.

Step B—Synthesis of Compound 36C

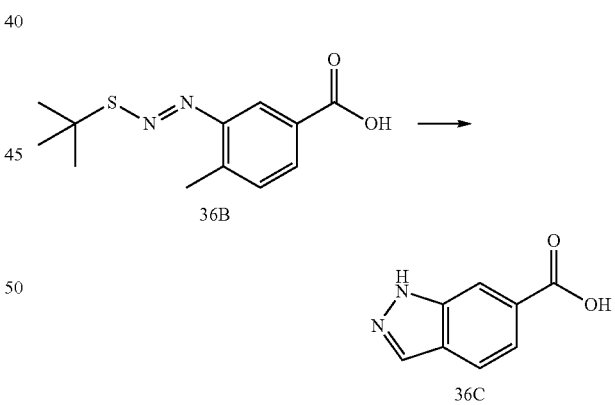

To a stirred solution of potassium tert-butoxide (10.0 eq, 12.0 g) in DMSO (50 mL) was added a solution of t-butyl-diazaenyl benzoic acid 36B (2.7 g; 10.70 mmol) in DMSO (30 mL). The mixture was allowed to stir for 6 h and then diluted with ice and acidified with aqueous 1 M HCl until pH 5-6 was attained. The mixture was extracted with ethyl acetate (3×50 mL) and the combined organic layers were washed with water (20 mL) and brine (20 mL). The organic layer was dried over magnesium sulfate, filtered and concentrated in vacuo to provide the crude product 36C as a slightly yellow solid which was used without further purification.

Step C—Synthesis of Compound 36D

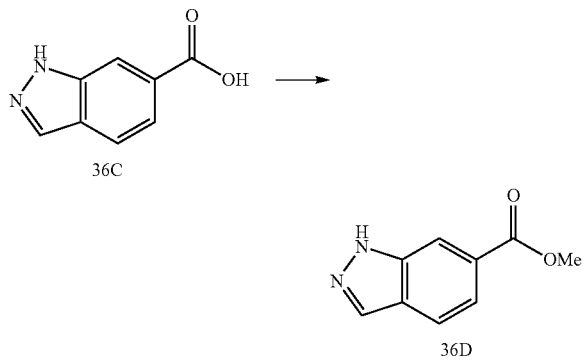

A solution of 1H-indazole-6-carboxylic acid 36C (1.73 g; 10.70 mmol) in toluene (80 mL) and methanol (30 mL) was treated with a solution of TMS-diazomethane (2 M soln in ether) until evolution of gas stopped. The reaction mixture was concentrated in vacuo and the residue was adsorbed on silica gel. The product was purified on a Biotage 40-M silica gel column (gradient: 0 to 20% acetone in hexanes) to provide compound 36D (950 mg; 50% for two steps) as a yellow solid. $^1$H-NMR (CDCl$_3$; 400 MHz): δ 8.28 (1H, s), 8.16 (1H, s), 7.86 (1H, d, J=8.54 Hz), 7.81 (1H, d, J=8.54 Hz), 3.98 (3H, s). LR-MS (ESI): calcd for C$_9$H$_9$N$_2$O$_2$ [M+H]$^+$ 177.07. found 177.20.

Step D—Synthesis of Compound 36E

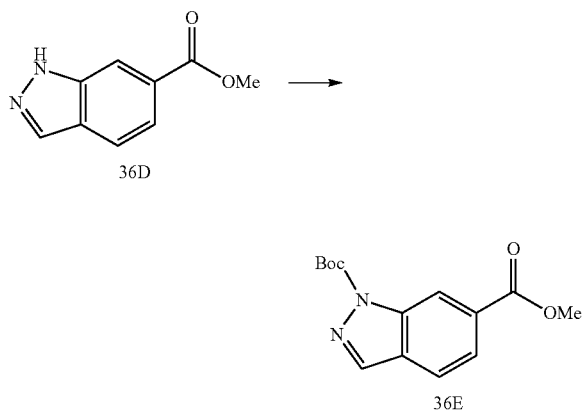

A solution of 1H-indazole-6-carboxylic acid methyl ester 36D (840 mg; 4.76 mmol) in 25 mL of acetonitrile was treated with Boc-anhydride (1.05 eq, 1.09 g) and a catalytic amount of DMAP (tip of spatula). The mixture was allowed to stir at 60° C. for 3 hours. The mixture was concentrated to half its volume in vacuo, then diluted with ethyl acetate (100 mL) and washed with aqueous saturated sodium bicarbonate (20 mL) and brine (20 mL). The organic layer was dried over magnesium sulfate, filtered and concentrated in vacuo. The residue was purified on a Biotage 40-M silica gel column (gradient: 0 to 20% ethyl acetate in hexanes) to provide compound 36E (1.2 g; 93%) as a colorless oil. $^1$H-NMR (CDCl$_3$; 400 MHz): δ 8.91 (1H, s), 8.22 (1H, s), 7.99 (1H, dd, J=1.22, 8.54 Hz), 7.78 (1H, d, J=8.54 Hz), 3.97 (3H, s), 1.74 (9H, s).

Step E—Synthesis of Compound 36F

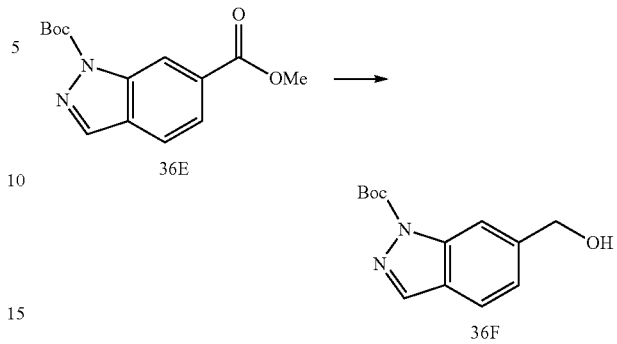

A solution of indazole 36E (460 mg; 1.66 mmol) in 16 mL of dry THF was cooled to −78° C. and treated with lithium triethylborohydride (2.5 eq, 4.15 mL of a 1 M soln in THF). The reaction mixture was allowed to stir at −78° C. and followed by TLC (25% ethyl acetate in hexanes). The reaction was completed in about 1 h and quenched by addition of aqueous saturated sodium hydrogen sulfate (3 mL). The mixture was extracted with ethyl acetate (100 mL) and washed with water (20 mL) and brine (20 mL). The organic layer was dried over magnesium sulfate, filtered and concentrated in vacuo to provide the crude product as a colorless oil. The residue was chromatographed on a Biotage 40-S silica gel column (0 to 40% ethyl acetate in hexanes) to provide compound 36F (160 mg; 40%). $^1$H-NMR (CDCl$_3$; 400 MHz): δ 8.19 (1H, s), 8.13 (1H, s), 7.67 (1H, d, J=7.93 Hz), 7.30 (1H, d, J=7.93 Hz), 5.13 (2H, s), 1.71 (9H, s).

Step F—Synthesis of Compound 36G

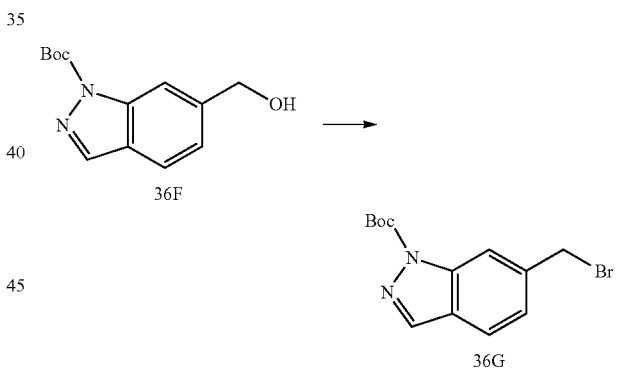

A solution of alcohol 36F (160 mg; 0.644 mmol) in dry chloroform (12 mL) was placed in an ice-water bath and treated with pyridine (4.0 eq, 0.208 mL, d 0.978) and a solution of thionyl bromide (1.2 eq, 0.060 mL, d 2.683) in 1 mL of chloroform. The ice-water bath was removed and the reaction mixture was allowed to stir at room temp for 30 minutes. TLC (30% ethyl acetate in hexanes) showed about 40% conversion and more thionyl bromide was added (0.2 eq). The mixture was heated to 70° C. for 10 minutes. Upon cooling the mixture was diluted with ethyl acetate (30 mL) and washed with aqueous saturated sodium bicarbonate (5 mL), aqueous sodium hydrogen sulfate (5 mL) and brine (5 mL). The organic layer was dried over magnesium sulfate, filtered and concentrated in vacuo. The residue was purified on a Biotage 25-S silica gel column (gradient: 0 to 40% ethyl acetate in hexanes) to provide compound 36G (76 mg; 38%) as a colorless oil along with unreacted starting material (25 mg; 24%). $^1$H-NMR (CDCl$_3$; 400 MHz): δ 8.23 (1H, s), 8.14 (1H, s), 7.72 (1H, d, J=8.54 Hz), 7.32 (1H, dd, J=1.22, 8.54 Hz), 5.21 (1H, d, J=12.20 Hz), 5.09 (1H, d, J=12.20 Hz), 1.71 (9H, s).

Example 37

Preparation of Intermediate Compound 37C

Step A—Synthesis of Compound 37B

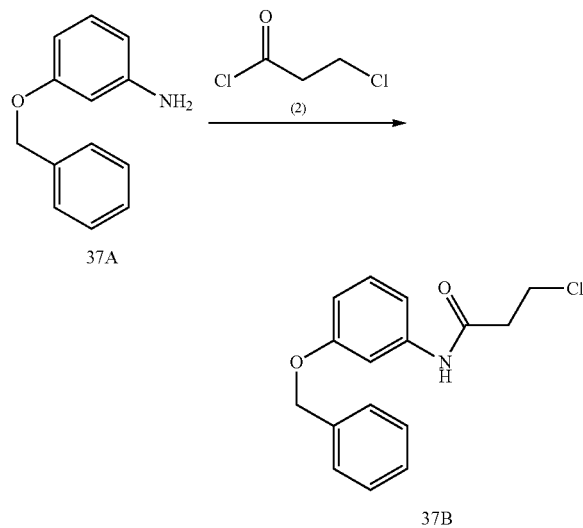

Compound 37A (commercially available) (10.0 g, 50.25 mmol) was dissolved in water at room temperature and to resulting suspension K$_2$CO$_3$ (3.8 g, 27.64 mmol) was added. 3-Chloro propionylchloride (7.0 g, 55.28 mmol) was added dropwise for 30 minutes and allowed to stir for 2 hours at room temperature. The precipitate was filtered and washed with water, 1 N HCl, dried at 50° C. under vacuum overnight to provide 7.2 g of compound 37B.

Step B—Synthesis of Compound 37C

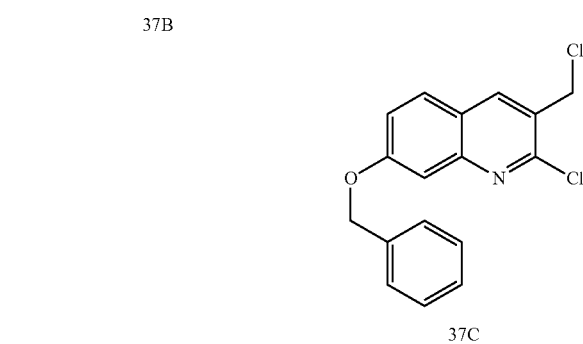

To N,N-Dimethylformamide (3.6 g, 49.66 mmol) at 0° C. was added drop wise POCl$_3$ (26.6 g, 173.8 mmol) and allowed to stir for 60 minutes, during which time a white precipitate was formed. The 7.2 g of the compound 37B was added by portion in reaction mixture and allowed to stir for 24 hours at room temperature. The reaction mixture was diluted with ethyl acetate and slowly added to a beaker with ice, after ice was melted, organic layer was separated and washed with 0.5 N NaOH and water, brine, dried over sodium sulfate, and concentrated in vacuo, purified using flash chromatography, to provide compound 37C (5.5 g, 34% after two steps). M.S. found: 318.04 (M+H)$^+$.

Example 38

Preparation of Intermediate Compound 38E

Step A—Synthesis of Compound 38B

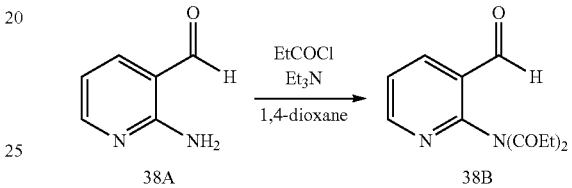

To a solution of 38A (7.2 g, 58.8 mmol) in 1,4-dioxane (39 mL) at 0° C. was added propionyl chloride (37.8 mL, 176.5 mmol) and Et$_3$N (24.6 mL, 176.5 mmol) with stirring. The reaction mixture was allowed to stir at room temperature for overnight. The solvent was removed under reduced pressure, and the resulting residue was taken up in EtOAc. The organic phase was washed with water, dried over MgSO$_4$, filtered, and concentrated in vacuo to compound 38B, which was used without further purification.

Step B—Synthesis of Compound 38C

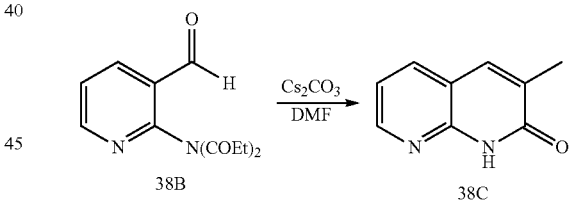

To a suspension of 38B (crude residue from above) in DMF (60 mL) was added cesium carbonate (38 g, 117.6 mmol), and the resulting mixture was heated at 65° C. for overnight. Reaction was cooled to room temperature, and the bulk of DMF was removed under reduced pressure. Water was then added to the crude residue and the mixture was filtered. The filter-cake was washed with water and EtOAc. 5.2 g of 38C was collected as a pale yellow solid.

Step C—Synthesis of Compound 38D

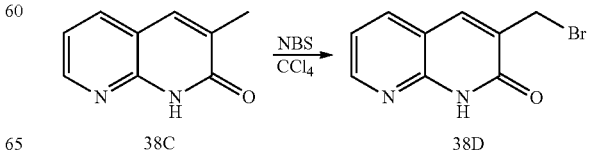

To a suspension of 38C (0.8 g, 5 mmol) in CCl$_4$ (25 mL) was added NBS (38 g, 117.6 mmol), and benzoyl peroxide (61 mg, 0.25 mmol), and the resulting mixture was then heated at 90° C. for 4 hours. Cooled the reaction to room temperature, and 300 mL of CH$_2$Cl$_2$ was added. The mixture was filtered, and filtrate was dried over MgSO$_4$, filtered, and concentrated in vacuo to provide 2 g of compound 38D, which was used without further purification.

Step D—Synthesis of Compound 38E

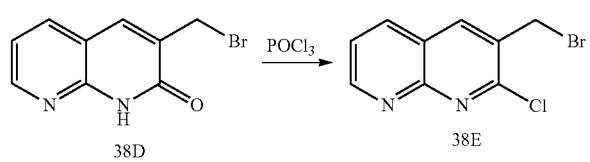

POCl$_3$ was added to a 100 mL round bottom flask containing crude 38D. The resulting suspension was then heated at 88° C. for 4 hours. Cooled the reaction to room temperature, and then poured into a 1 liter beaker containing ice. The resulting solution was neutralized to ph 8 using 6 N NaOH solution. Solid that precipitated from the solution was collected to provide 0.82 g of crude residue which was purified using column chromatography on silica gel (ISCO CombiFlash Rf; gradient: 5 to 50% ethyl acetate in hexanes) to provide 330 mg of compound 38E.

Example 39

Preparation of Intermediate Compound 39D

Step A—Synthesis of Compound 39B

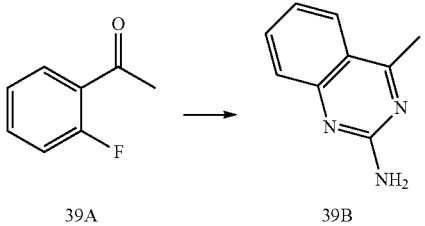

A mixture of ortho-fluoroacetophenone (39A, 3.45 g; 25 mmol) and guanidine carbonate (2 eq; 9.0 g) was prepared in 250 mL of N,N-dimethyl acetamide, set to stir, and heated at 135° C. under nitrogen purge overnight. The solvent was removed under reduced pressure and diluted with ethyl acetate (600 mL). The solution was washed with water (2×100 mL) and brine (40 mL). The organic layer was separated, dried over magnesium sulfate, filtered, and concentrated in vacuo. The solid was dissolved in methylene dichloride, loaded on silica gel and dried under reduced pressure. The material was purified on ISCO (80 g column; 0-70% THF in Hexanes). Fractions containing product were collected and concentrated in vacuo to provide product 39B as a créme colored solid (880 mg; 22%)

Step B—Synthesis of Compound 39C

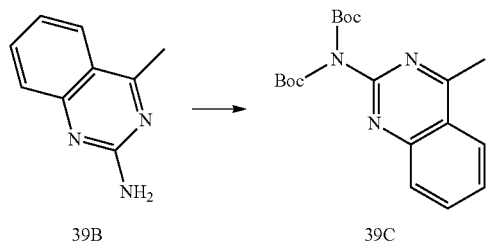

A solution of 4-Methyl-quinazolin-2-ylamine 39B (640 mg; 4.02 mmol) in 10 mL of dry acetonitrile was treated with a solution of Boc-anhydride (2.5 eq; 2.19 g) in 10.0 mL of dry acetonitrile. The resulting solution was treated with DMAP (0.2 eq; 98.2 mg). The mixture was set to stir overnight. TLC (50% THF in hexanes) showed a complete reaction. The mixture was diluted with ethyl acetate (500 mL) and washed with water (3×30 mL), and Brine (40 mL). The organic layer was dried over magnesium sulfate, filtered and concentrated in vacuo. The residue was adsorbed on silica gel and purified on an ISCO column (120 g) (0% to 60% THF in hexanes). The fractions with product were collected and concentrated in vacuo to provide product 39C as a light yellow-white solid (1.3 g; 90%).

Step C—Synthesis of Compound 39D

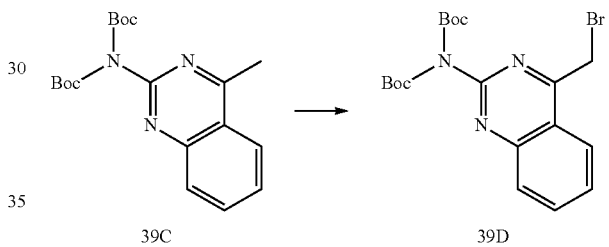

Intermediate 39C (1.11 g; 3.09 mmol), N-Bromosuccinimide (1.05 eq; 577 mg), and benzoyl peroxide (0.1 eq; 75 mg) were combined in round bottom and diluted with dry carbon tetrachloride (31 mL). The reaction was allowed to stir at room temperature for 10 minutes and then heated at reflux overnight. TLC (30% ethyl acetate in hexanes) revealed the reaction has partially progressed. The reaction mixture was concentrated under reduced pressure, diluted with ethyl acetate (300 mL), and washed with sat. aqueous sodium bicarbonate (40 mL) and brine (40 mL), dried over magnesium sulfate, filtered, concentrated under reduced pressure, diluted with methylene dichloride, adsorbed onto silica gel, and purified on ISCO (25-M Column; 0-40% ethyl acetate in hexanes). The fractions containing product were concentrated under reduced pressure and afforded product as a clear oil in a 2:1 mixture of compound 39D and starting material (Total: 440 mg; 33%).

Example 40

Preparation of Intermediate Compound 40C

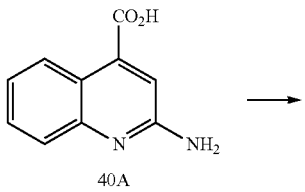

-continued

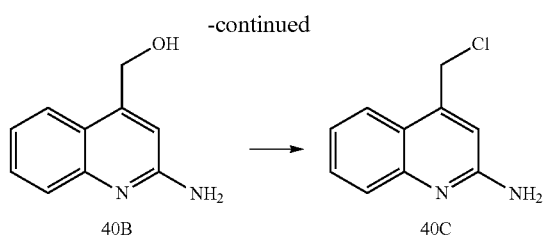

The starting materials 40A (2.0 g, 10.6 mmol), lithium aluminum hydride (2.0 g, 52.7 mmol), and THF (100 mL) were added to a 250 ml round-bottomed flask. The resulting suspension was allowed to stir at room temperature for 18 hours. The reaction was quenched with 10 ml of saturated ammonium chloride solution followed by 200 ml of ethyl acetate. After filtration, the organic layer was washed with brine (2×100 mL), dried over sodium sulfate, and concentrated under vacuum to provide 40B as a yellowish solid (1.05 g, 59%).

A 250 ml round-bottomed flask was charged with 40B (1.05 g, 6.03 mmol) and thionyl chloride (10 mL). The resulting mixture was allowed to stir at 60° C. for 4 hours before cooled to room temperature. After removal of excess of thionyl chloride, the residue was dried under vacuum to provide 40C as an orange solid (1.45 g). This crude material was used without further purification.

Example 41

HCV NS5B Polymerase Inhibition Assay

An in vitro transcribed heteropolymeric RNA known as D-RNA or DCoH has been shown to be an efficient template for HCV NS5B polymerase (S.-E. Behrens et al., *EMBO J.* 15:12-22 (1996); WO 96/37619). A chemically synthesized 75-mer version, designated DCoH75, whose sequence matches the 3'-end of D-RNA, and DCoH75ddC, where the 3'-terminal cytidine of DCoH75 is replaced by dideoxycytidine, were used for assaying the NS5B enzyme activity as described in Ferrari et al., *12th International Symposium on HCV and Related Viruses*, P-306 (2005). A soluble C-terminal 21-amino acid truncated NS5B enzyme form (NS5BDeltaCT21) was produced and purified from *Escherichia coli* as C-terminal polyhistidine-tagged fusion protein as described in Ferrari et al., *J. Virol.* 73:1649-1654 (1999). A typical assay contained 20 mM Hepes pH 7.3, 10 mM $MgCl_2$, 60 mM NaCl, 100 μg/ml BSA, 20 units/ml RNasin, 7.5 mM DTT, 0.1 μM ATP/GTP/UTP, 0.026 μM CTP, 0.25 mM GAU, 0.03 μM RNA template, 20 μCi/ml [$^{33}$P]-CTP, 2% DMSO, and 30 or 150 nM NS5B enzyme. Reactions were incubated at 22° C. for 2 hours, then stopped by adding 150 mM EDTA, washed in DE81 filter plate in 0.5M di-basic sodium phosphate buffer, pH 7.0, and counted using Packard TopCount after the addition of scintillation cocktail. Polynucleotide synthesis was monitored by the incorporation of radiolabeled CTP. The effect of the 2,3-Substituted Indole Derivatives on the polymerase activity was evaluated by adding various concentrations of a 2,3-Substituted Indole Derivative, typically in 10 serial 2-fold dilutions, to the assay mixture. The starting concentrations of the indole derivatives ranged from 200 μM to 1 μM. An $IC_{50}$ value for the inhibitor, defined as the compound concentration that provides 50% inhibition of polymerase activity, was determined by fitting the cpm data to the Hill equation $Y=100/(1+10^{((\text{Log } IC50-X)*\text{HillSlope})})$, where X is the logarithm of compound concentration, and Y is the % inhibition. Ferrari et al., *12th International Symposium on HCV and Related Viruses*, P-306 (2005) described in detail this assay procedure. It should be noted that such an assay as described is exemplary and not intended to limit the scope of the invention. The skilled practitioner can appreciate that modifications including but not limited to RNA template, primer, nucleotides, NS5B polymerase form, buffer composition, can be made to develop similar assays that yield the same result for the efficacy of the compounds and compositions described in the invention.

NS5B polymerase inhibition data for selected 2,3-Substituted Indole Derivatives of the present invention was obtained using the above method and calculated $IC_{50}$ values ranged from about 0.001 μM to about 14000 μM.

Example 42

Cell-Based HCV Replicon Assay

To measure cell-based anti-HCV activity of the 2,3-Substituted Indole Derivatives of the present invention, replicon cells were seeded at 5000 cells/well in 96-well collagen I-coated Nunc plates in the presence of the 2,3-Substituted Indole Derivative. Various concentrations of a 2,3-Substituted Indole Derivative, typically in 10 serial 2-fold dilutions, were added to the assay mixture, the starting concentration of the compound ranging from 250 μM to 1 μM. The final concentration of DMSO was 0.5%, fetal bovine serum was 5%, in the assay media. Cells were harvested on day 3 by the addition of 1× cell lysis buffer (Ambion cat #8721). The replicon RNA level was measured using real time PCR (Taqman assay). The amplicon was located in 5B. The PCR primers were: 5B.2F, ATGGACAGGCGCCCTGA; 5B.2R, TTGATGGGCAGCTTGGTTTC; the probe sequence was FAM-labeled CACGCCATGCGCTGCGG. GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM 7900HT Sequence Detection System using the following program: 48° C. for 30 minutes, 95° C. for 10 minutes, 40 cycles of 95° C. for 15 sec, 60° C. for 1 minute. The ACT values ($CT_{5B}$-$CT_{GAPDH}$) were plotted against the concentration of test compound and fitted to the sigmoid dose-response model using XLfit4 (MDL). $EC_{50}$ was defined as the concentration of inhibitor necessary to achieve ΔCT=1 over the projected baseline; $EC_{90}$ the concentration necessary to achieve ΔCT=3.2 over the baseline. Alternatively, to quantitate the absolute amount of replicon RNA, a standard curve was established by including serially diluted T7 transcripts of replicon RNA in the Taqman assay. All Taqman reagents were from PE Applied Biosystems. Such an assay procedure was described in detail in e.g. Malcolm et al., *Antimicrobial Agents and Chemotherapy* 50: 1013-1020 (2006).

HCV Replicon assay data for selected 2,3-Substituted Indole Derivatives of the present invention was obtained using the above method and calculated $EC_{50}$ values ranged from about 1 μM to about 14000 μM.

Uses of the 2,3-Substituted Indole Derivatives

The 2,3-Substituted Indole Derivatives are useful in human and veterinary medicine for treating or preventing a viral infection or a virus-related disorder in a patient. In accordance with the invention, the 2,3-Substituted Indole Derivatives can be administered to a patient in need of treatment or prevention of a viral infection or a virus-related disorder.

Accordingly, in one embodiment, the invention provides methods for treating a viral infection in a patient comprising administering to the patient an effective amount of at least one 2,3-Substituted Indole Derivative or a pharmaceutically acceptable salt, solvate, ester or prodrug thereof. In another embodiment, the invention provides methods for treating a virus-related disorder in a patient comprising administering to the patient an effective amount of at least one 2,3-Substituted Indole Derivative or a pharmaceutically acceptable salt, solvate, ester or prodrug thereof.

Treatment or Prevention of a Viral Infection

The 2,3-Substituted Indole Derivatives can be used to treat or prevent a viral infection. In one embodiment, the 2,3-Substituted Indole Derivatives can be inhibitors of viral replication. In a specific embodiment, the 2,3-Substituted Indole Derivatives can be inhibitors of HCV replication. Accordingly, the 2,3-Substituted Indole Derivatives are useful for treating viral diseases and disorders related to the activity of a virus, such as HCV polymerase.

Examples of viral infections that can be treated or prevented using the present methods, include but are not limited to, hepatitis A infection, hepatitis B infection and hepatitis C infection.

In one embodiment, the viral infection is hepatitis C(HCV) infection.

In one embodiment, the hepatitis C infection is acute hepatitis C. In another embodiment, the hepatitis C infection is chronic hepatitis C.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74 (Pt 11):2391-2399 (1993) is widely used and classifies isolates into six major genotypes, 1 through 6, with two or more related subtypes, e.g., 1a, 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al, *J Gen Virol*, 78 (Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Treatment or Prevention of a Virus-Related Disorder

The 2,3-Substituted Indole Derivatives can be used to treat or prevent a virus-related disorder. Accordingly, the 2,3-Substituted Indole Derivatives are useful for treating disorders related to the activity of a virus, such as liver inflammation or cirrhosis. Virus-related disorders include, but are not limited to, RNA-dependent polymerase-related disorders and disorders related to HCV infection.

Treatment or Prevention of a RNA-Dependent Polymerase-Related Disorder

The 2,3-Substituted Indole Derivatives are useful for treating or preventing a RNA dependent polymerase (RdRp) related disorder in a patient. Such disorders include viral infections wherein the infective virus contain a RdRp enzyme.

Accordingly, in one embodiment, the present invention provides a method for treating a RNA dependent polymerase-related disorder in a patient, comprising administering to the patient an effective amount of at least one 2,3-Substituted Indole Derivative or a pharmaceutically acceptable salt, solvate, ester or prodrug thereof.

Treatment or Prevention of a Disorder Related to HCV Infection

The 2,3-Substituted Indole Derivatives can also be useful for treating or preventing a disorder related to an HCV infection. Examples of such disorders include, but are not limited to, cirrhosis, portal hypertension, ascites, bone pain, varices, jaundice, hepatic encephalopathy, thyroiditis, porphyria cutanea tarda, cryoglobulinemia, glomerulonephritis, sicca syndrome, thrombocytopenia, lichen planus and diabetes mellitus.

Accordingly, in one embodiment, the invention provides methods for treating an HCV-related disorder in a patient, wherein the method comprises administering to the patient a therapeutically effective amount of at least one 2,3-Substituted Indole Derivative, or a pharmaceutically acceptable salt, solvate, ester or prodrug thereof.

Combination Therapy

In another embodiment, the present methods for treating or preventing a viral infection can further comprise the administration of one or more additional therapeutic agents which are not 2,3-Substituted Indole Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one 2,3-Substituted Indole Derivative, or a pharmaceutically acceptable salt, solvate, ester or prodrug thereof, and (ii) at least one other antiviral agent that is other than a 2,3-Substituted Indole Derivative, wherein the amounts administered are together effective to treat or prevent a viral infection.

When administering a combination therapy of the invention to a patient, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a 2,3-Substituted Indole Derivative and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

In one embodiment, the at least one 2,3-Substituted Indole Derivative is administered during at time when the additional antiviral agent(s) exert their prophylactic or therapeutic effect, or vice versa.

In another embodiment, the at least one 2,3-Substituted Indole Derivative and the additional antiviral agent(s) are administered in doses commonly employed when such agents are used as monotherapy for treating a viral infection.

In another embodiment, the at least one 2,3-Substituted Indole Derivative and the additional antiviral agent(s) are administered in doses lower than the doses commonly employed when such agents are used as monotherapy for treating a viral infection.

In still another embodiment, the at least one 2,3-Substituted Indole Derivative and the additional antiviral agent(s) act synergistically and are administered in doses lower than the doses commonly employed when such agents are used as monotherapy for treating a viral infection.

In one embodiment, the at least one 2,3-Substituted Indole Derivative and the additional antiviral agent(s) are present in the same composition. In one embodiment, this composition is suitable for oral administration. In another embodiment, this composition is suitable for intravenous administration.

Viral infections and virus-related disorders that can be treated or prevented using the combination therapy methods of the present invention include, but are not limited to, those listed above.

In one embodiment, the viral infection is HCV infection.

The at least one 2,3-Substituted Indole Derivative and the additional antiviral agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of at least one 2,3-Substituted Indole Derivative and the additional antiviral agent(s) may inhibit the resistance of a viral infection to these agents.

Non-limiting examples of other therapeutic agents useful in the present compositions and methods include an HCV polymerase inhibitor, an interferon, a nucleoside, a viral replication inhibitor, an antisense agent, a therapeutic vaccine, a viral protease inhibitor, a virion production inhibitor, an antibody therapy (monoclonal or polyclonal), and any agent useful for treating an RNA-dependent polymerase-related disorder.

In one embodiment, the other antiviral agent is a viral protease inhibitor.

In another embodiment, the other antiviral agent is an HCV protease inhibitor.

In another embodiment, the other antiviral agent is an interferon.

In still another embodiment, the other antiviral agent is a viral replication inhibitor.

In one embodiment, the other antiviral agent is a viral replication inhibitor, which is an HCV replicase inhibitor.

In another embodiment, the other antiviral agent is an antisense agent.

In another embodiment, the other antiviral agent is a therapeutic vaccine.

In a further embodiment, the other antiviral agent is an virion production inhibitor.

In another embodiment, the other antiviral agent is antibody therapy.

In another embodiment, the other antiviral agents comprise a protease inhibitor and a polymerase inhibitor.

In still another embodiment, the other antiviral agents comprise a protease inhibitor and an immunosuppressive agent.

In yet another embodiment, the other antiviral agents comprise a polymerase inhibitor and an immunosuppressive agent.

In a further embodiment, the other antiviral agents comprise a protease inhibitor, a polymerase inhibitor and an immunosuppressive agent.

In another embodiment the other agent is ribavirin.

HCV polymerase inhibitors useful in the present methods and compositions include, but are not limited to VP-19744 (Wyeth/ViroPharma), HCV-796 (Wyeth/ViroPharma), NM-283 (Idenix/Novartis), R-1626 (Roche), MK-0608 (Merck), A848837 (Abbott), GSK-71185 (Glaxo SmithKline), XTL-2125 (XTL Biopharmaceuticals), and those disclosed in Ni et al., *Current Opinion in Drug Discovery and Development*, 7(41:446 (2004); Tan et al., *Nature Reviews*, 1:867 (2002); and Beaulieu et al., *Current Opinion in Investigational Drugs*, 5:838 (2004).

Interferons useful in the present methods and compositions include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, Boehringer Ingelheim, Ingelheim, Germany), interferon alpha fusion polypeptides, or consensus interferon as defined by determination of a consensus sequence of naturally occurring interferon alphas (Infergen™, Amgen, Thousand Oaks, Calif.).

Antibody therapy agents useful in the present methods and compositions include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like). Viral protease inhibitors useful in the present methods and compositions include, but are not limited to, NS3 serine protease inhibitors (including, but not limited to, those disclosed in U.S. Pat. Nos. 7,012,066, 6,914,122, 6,911,428, 6,846,802, 6,838,475, 6,800,434, 5,017,380, 4,933,443, 4,812,561 and 4,634,697; and U.S. Patent Publication Nos. US20020160962, US20050176648 and US20050249702), HCV protease inhibitors (e.g., SCH503034 (Schering-Plough), VX-950 (Vertex), GS-9132 (Gilead/Achillion), ITMN-191 (InterMune/Roche)), amprenavir, atazanavir, fosemprenavir, indinavir, lopinavir, ritonavir, nelfinavir, saquinavir, tipranavir and TMC114.

Viral replication inhibitors useful in the present methods and compositions include, but are not limited to, HCV replicase inhibitors, NS3 helicase inhibitors, NS5A inhibitors, ribavirin, viramidine, A-831 (Arrow Therapeutics); an antisense agent or a therapeutic vaccine.

In one embodiment, viral replication inhibitors useful in the present methods and compositions include, but are not limited to, NS3 helicase inhibitors or NS5A inhibitors.

Examples of protease inhibitors useful in the present methods include, but are not limited to, an HCV protease inhibitor and a NS-3 serine protease inhibitor.

Examples of HCV protease inhibitors useful in the present methods include, but are not limited to, those disclosed in Landro et al., *Biochemistry*, 36(31):9340-9348 (1997); Ingallinella et al., *Biochemistry*, 37(25):8906-8914 (1998); Llinas-Brunet et al., *Bioorg Med Chem Lett*, 8(13):1713-1718 (1998); Martin et al., *Biochemistry*, 37(33):11459-11468 (1998); Dimasi et al., *J Virol*, 71(10):7461-7469 (1997); Martin et al., *Protein Eng*, 10(5):607-614 (1997); Elzouki et al., *J Hepat*, 27(1):42-48 (1997); *Bio World Today*, 9(217):4 (Nov. 10, 1998); U.S. Patent Publication Nos. US2005/0249702 and US 2007/0274951; and International Publication Nos. WO 98/14181; WO 98/17679, WO 98/17679, WO 98/22496 and WO 99/07734 and WO 05/087731.

Further examples of HCV protease inhibitors useful in the present methods include, but are not limited to, the following compounds:

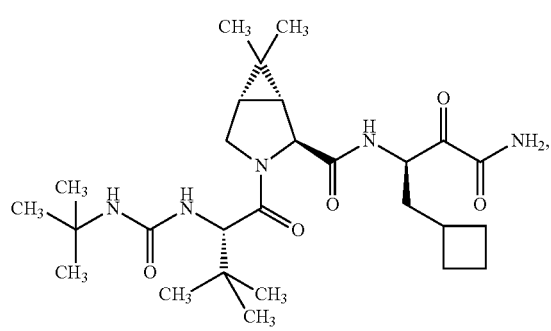

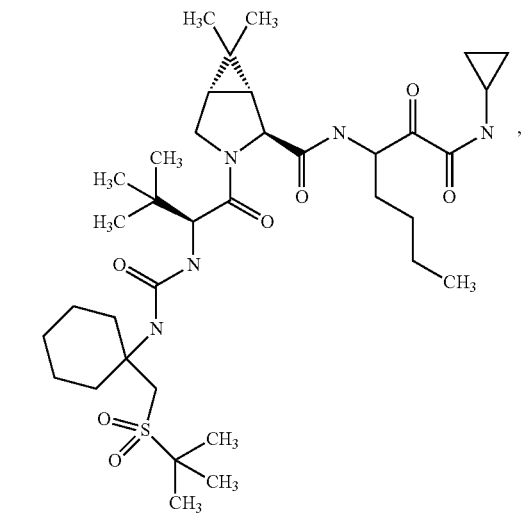

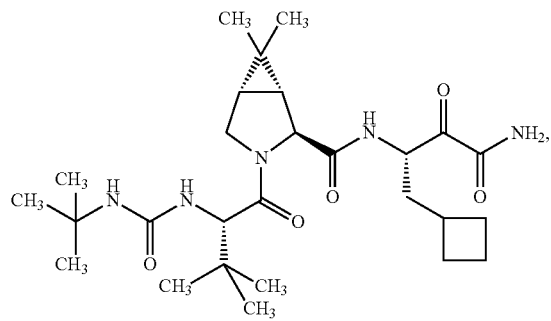

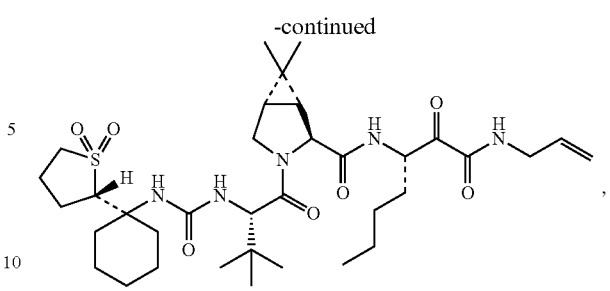

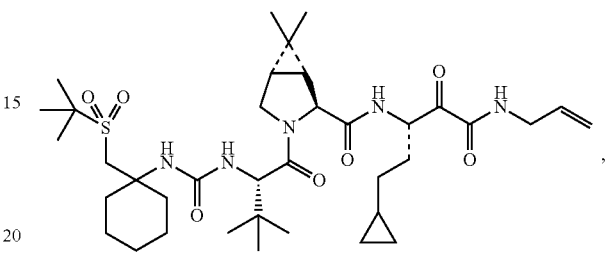

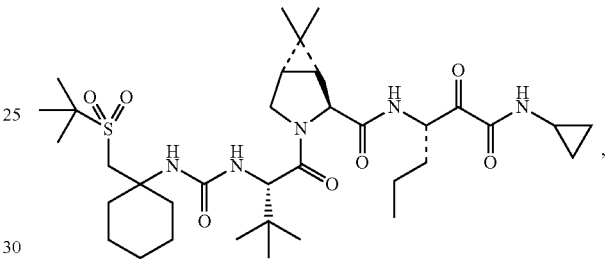

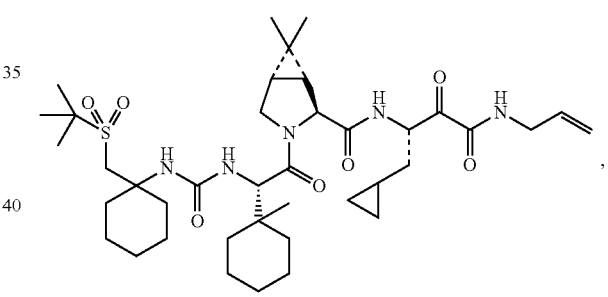

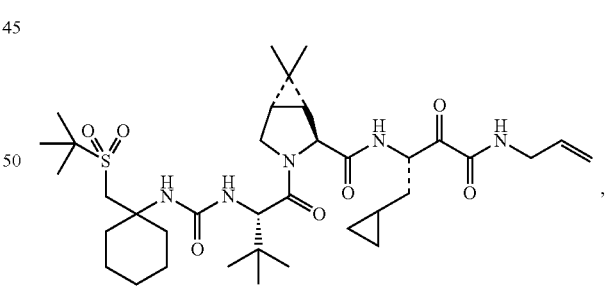

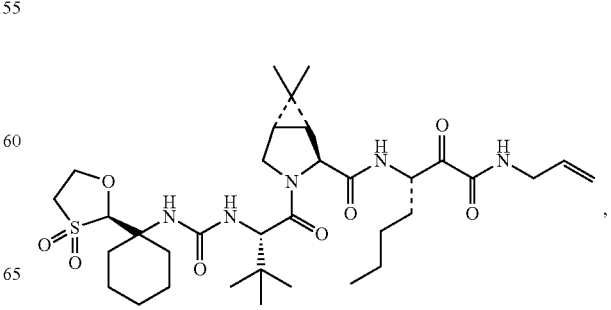

587
-continued
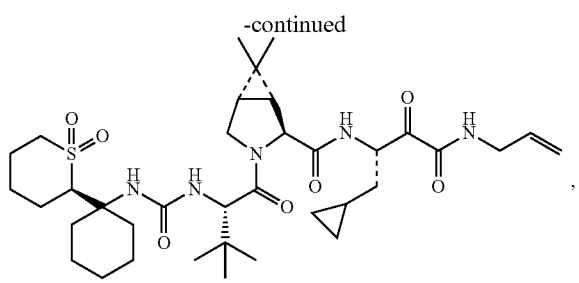
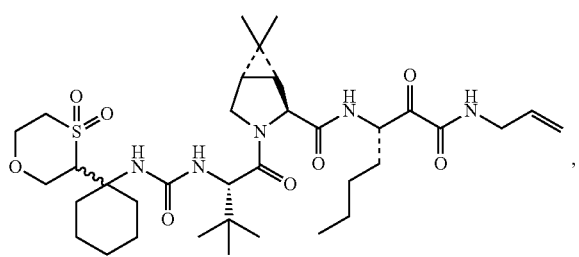
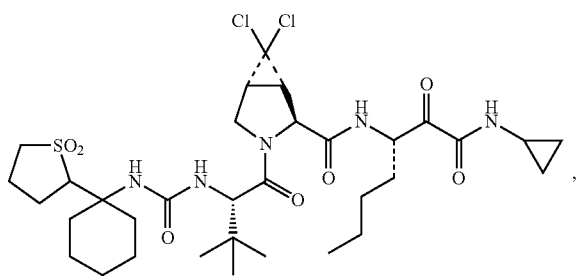
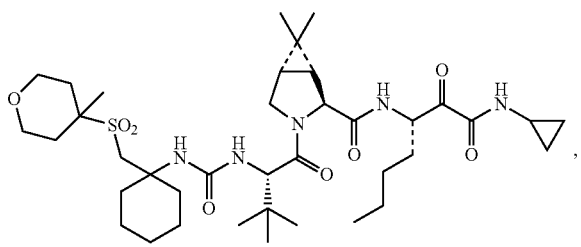
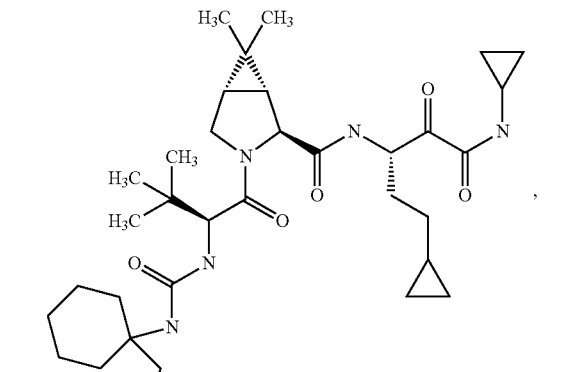
588
-continued
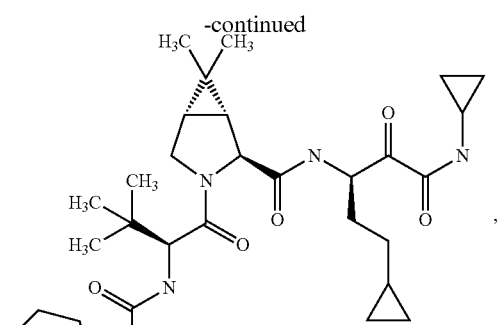
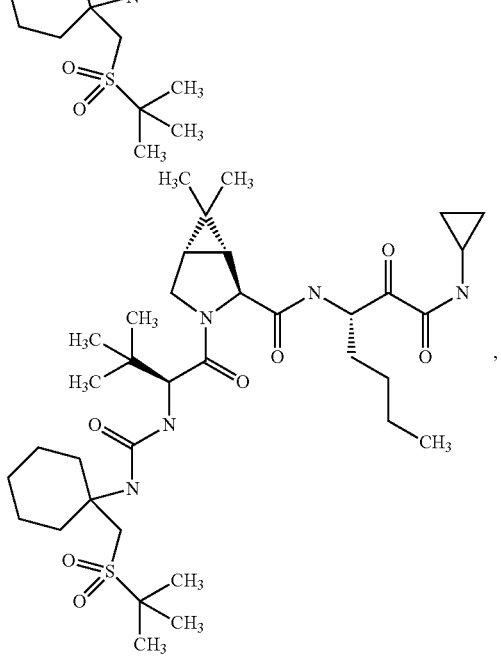
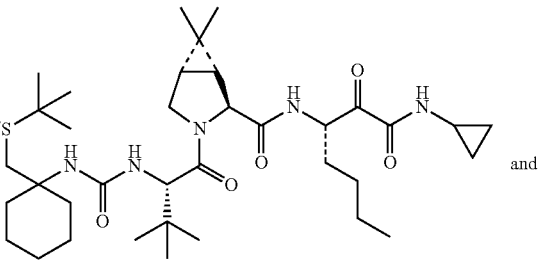
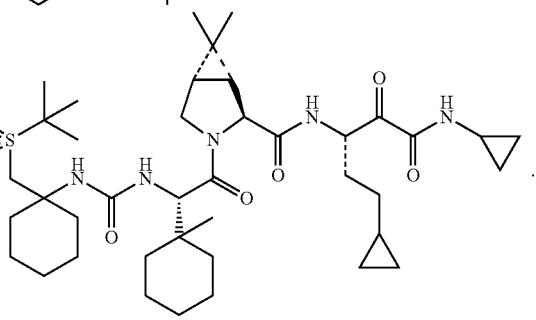
Additional examples of other therapeutic agents useful in the present methods include, but are not limited to, Levovirin™ (ICN Pharmaceuticals, Costa Mesa, Calif.), VP 50406 (Viropharma, Incorporated, Exton, Pa.), ISIS 14803™ (ISIS Pharmaceuticals, Carlsbad, Calif.), Heptazyme™ (Ribozyme Pharmaceuticals, Boulder, Colo.), VX-950™ (Vertex Pharmaceuticals, Cambridge, Mass.), Thymosin™ (SciClone Pharmaceuticals, San Mateo, Calif.), Maxamine™ (Maxim Pharmaceuticals, San Diego, Calif.), NKB-122 (JenKen Bioscience Inc., North Carolina), mycophenolate mofetil (Hoffman-LaRoche, Nutley, N.J.).

The doses and dosage regimen of the other agents used in the combination therapies of the present invention for the treatment or prevention of a viral infection can be determined by the attending clinician, taking into consideration the approved doses and dosage regimen in the package insert; the age, sex and general health of the patient; and the type and severity of the viral infection or related disease or disorder. When administered in combination, the 2,3-Substituted Indole Derivative(s) and the other agent(s) for treating diseases or conditions listed above can be administered simultaneously (i.e., in the same composition or in separate compositions one right after the other) or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the at least one 2,3-Substituted Indole Derivative and the additional antiviral agent(s), when administered as combination therapy, can range from about 0.1 to about 2000 mg per day, although variations will necessarily occur depending on the target of the therapy, the patient and the route of administration. In one embodiment, the dosage is from about 10 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the other therapeutic agent is INTRON-A interferon alpha 2b (commercially available from Schering-Plough Corp.), this agent is administered by subcutaneous injection at 3MIU (12 mcg)/0.5 mL/TIW is for 24 weeks or 48 weeks for first time treatment.

In another embodiment, when the other therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the other therapeutic agent is ROFERON A interferon alpha 2a (commercially available from Hoffmann-La Roche), this agent is administered by subcutaneous or intramuscular injection at 3MIU (11.1 mcg/mL)/TIW for at least 48 to 52 weeks, or alternatively 6MIU/TIW for 12 weeks followed by 3MIU/TIW for 36 weeks.

In still another embodiment, when the other therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the other therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the other therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

In one embodiment, one or more compounds of the present invention are adminstered with one or more additional therapeutic agents selected from an HCV protease inhibitor, an HCV replicase inhibitor, a nucleoside, an interferon, a pegylated interferon and ribavirin. The combination therapies can include any combination of these additional therapeutic agents.

In another embodiment, one or more compounds of the present invention are adminstered with one additional therapeutic agent selected from an HCV protease inhibitor, an HCV replicase inhibitor, a nucleoside, an interferon, a pegylated interferon and ribavirin.

In another embodiment, one or more compounds of the present invention are adminstered with two additional therapeutic agents selected from an HCV protease inhibitor, an HCV replicase inhibitor, a nucleoside, an interferon, a pegylated interferon and ribavirin.

In still another embodiment, one or more compounds of the present invention are adminstered with two additional therapeutic agents selected from an HCV protease inhibitor, an HCV replicase inhibitor, a nucleoside, an interferon, a pegylated interferon and ribavirin. In a specific embodiment, one or more compounds of the present invention are adminstered with an HCV protease inhibitor and ribavirin. In another specific embodiment, one or more compounds of the present invention are adminstered with a pegylated interferon and ribavirin.

In another embodiment, one or more compounds of the present invention are adminstered with three additional therapeutic agents selected from an HCV protease inhibitor, an HCV replicase inhibitor, a nucleoside, an interferon, a pegylated interferon and ribavirin.

In one embodiment, one or more compounds of the present invention are administered with one or more additional therapeutic agents selected from an HCV polymerase inhibitor, a viral protease inhibitor, a nucleoside, an interferon, and a viral replication inhibitor. In another embodiment, one or more compounds of the present invention are administered with one or more additional therapeutic agents selected from an HCV polymerase inhibitor, a viral protease inhibitor, a nucleoside, an interferon, and ribavirin. In one embodiment, one compound of the present invention is administered with one additional therapeutic agents selected from an HCV polymerase inhibitor, a viral protease inhibitor, a nucleoside, an interferon, and a viral replication inhibitor. In another embodiment, one compound of the present invention is administered with two additional therapeutic agents selected from an HCV polymerase inhibitor, a viral protease inhibitor, a nucleoside, an interferon, and a viral replication inhibitor. In another embodiment, one compound of the present invention is administered with ribavirin. In still another embodiment, one compound of the present invention is administered with ribavirin and another therapeutic agent. In still another embodiment, one compound of the present invention is administered with ribavirin and another therapeutic agent, wherein the other therapeutic agent is selected from an HCV polymerase inhibitor, a viral protease inhibitor, a nucleoside, an interferon, and a viral replication inhibitor.

Compositions and Administration

Due to their activity, the 2,3-Substituted Indole Derivatives are useful in veterinary and human medicine. As described above, the 2,3-Substituted Indole Derivatives are useful for treating or preventing a viral infection or a virus-related disorder in a patient in need thereof.

When administered to a patient, the IDs can be administered as a component of a composition that comprises a pharmaceutically acceptable carrier or vehicle. The present invention provides pharmaceutical compositions comprising an effective amount of at least one 2,3-Substituted Indole Derivative and a pharmaceutically acceptable carrier. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The 2,3-Substituted Indole Derivatives of the present invention may also be deliverable transdermally. The transdermal compositions can take the form of creams, lotions, aerosols and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize the therapeutic effects, i.e. anti-inflammatory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more 2,3-Substituted Indole Derivatives are administered orally.

In another embodiment, the one or more 2,3-Substituted Indole Derivatives are administered intravenously.

In another embodiment, the one or more 2,3-Substituted Indole Derivatives are administered topically.

In still another embodiment, the one or more 2,3-Substituted Indole Derivatives are administered sublingually.

In one embodiment, a pharmaceutical preparation comprising at least one 2,3-Substituted Indole Derivative is in unit dosage form. In such form, the preparation is subdivided into unit doses containing appropriate quantities of the active component, e.g., an effective amount to achieve the desired purpose.

Compositions can be prepared according to conventional mixing, granulating or coating methods, respectively, and the present compositions can contain, in one embodiment, from about 0.1% to about 99% of the 2,3-Substituted Indole Derivative(s) by weight or volume. In various embodiments, the present compositions can contain, in one embodiment, from about 1% to about 70% or from about 5% to about 60% of the 2,3-Substituted Indole Derivative(s) by weight or volume.

The quantity of 2,3-Substituted Indole Derivative in a unit dose of preparation may be varied or adjusted from about 0.1 mg to about 2000 mg. In various embodiment, the quantity is from about 1 mg to about 2000 mg, 100 mg to about 200 mg, 500 mg to about 2000 mg, 100 mg to about 1000 mg, and 1 mg to about 500 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the 2,3-Substituted Indole Derivatives will be regulated according to the judgment of the attending clinician considering such factors as age, condition and size of the patient as well as severity of the symptoms being treated. Generally, a total daily dosage of the 2,3-Substituted Indole Derivatives range from about 0.1 to about 2000 mg per day, although variations will necessarily occur depending on the target of the therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one 2,3-Substituted Indole Derivative or a pharmaceutically acceptable salt, solvate, ester or prodrug thereof; (ii) one or more additional therapeutic agents that are not a 2,3-Substituted Indole Derivative; and (iii) a pharmaceutically acceptable carrier, wherein the amounts in the composition are together effective to treat a viral infection or a virus-related disorder.

Kits

In one aspect, the present invention provides a kit comprising a therapeutically effective amount of at least one 2,3-Substituted Indole Derivative, or a pharmaceutically acceptable salt, solvate, ester or prodrug of said compound and a pharmaceutically acceptable carrier, vehicle or diluent.

In another aspect the present invention provides a kit comprising an amount of at least one 2,3-Substituted Indole Derivative, or a pharmaceutically acceptable salt, solvate, ester or prodrug of said compound and an amount of at least one additional therapeutic agent listed above, wherein the amounts of the two or more ingredients result in a desired therapeutic effect.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the formula:

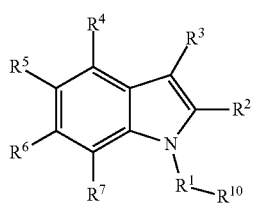

(I)

or a pharmaceutically acceptable salt thereof, wherein:
$R^1$ is a bond, $-[C(R^{12})_2]_r-$, $-[C(R^{12})_2]_r-O-[C(R^{12})_2]_q-$, $-[C(R^{12})_2]_r-N(R^9)-[C(R^{12})_2]_q-$, $-[C(R^{12})_2]_q-CH=CH-[C(R^{12})_2]_q-$, $-[C(R^{12})_2]_q-C\equiv C-[C(R^{12})_2]_q-$, or $-[C(R^{12})_2]_q-SO_2-[C(R^{12})_2]_q-$;
$R^2$ is $-[C(R^{12})_2]_q-C(O)N(R^9)SOR^{11}$, $-[C(R^{12})_2]_q-C(O)N(R^9)SO_2R^{11}$, $-[C(R^{12})_2]_q-C(O)N(R^9)SO_2N(R^9)_2$,

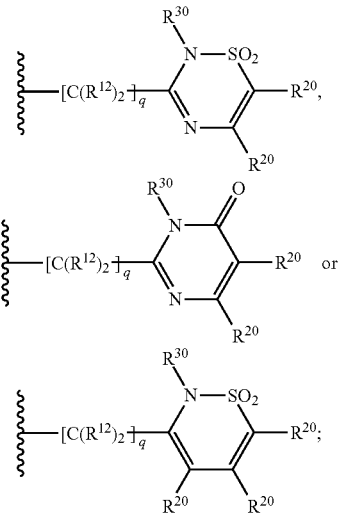

$R^3$ is:

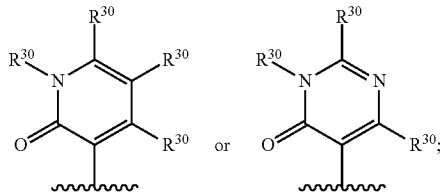

$R^4$, $R^5$, $R^6$ and $R^7$ are each, independently, H, alkyl, alkenyl, alkynyl phenyl, naphthyl, $-[C(R^{12})_2]_q-$(3 to 10-membered cycloalkyl), $-[C(R^{12})_2]_q-$(3 to 10-membered cycloalkenyl), $[C(R^{12})_2]_q-$(3 to 10-membered heterocycloalkyl), $-[C(R^{12})_2]_q-$(3 to 10-membered heterocycloalkenyl), $-[C(R^{12})_2]_q-$(5 to 10-membered heteroaryl), $-[C(R^{12})_2]_q-$haloalkyl, $-[C(R^{12})_2]_q-$hydroxyalkyl, halo, $-OH$, $-OR^9$, $-CN$, $-[C(R^{12})_2]_q-C(O)R^8$, $-[C(R^{12})_2]_q-C(O)OR^9$, $-[C(R^{12})_2]_q-C(O)N(R^9)_2$, $-[C(R^{12})_2]_q-OR^9$, $-[C(R^{12})_2]_q-N(R^9)_2$, $-[C(R^{12})_2]_q-NHC(O)R^8$, $-[C(R^{12})_2]_q-NR^8C(O)N(R^9)_2$, $-[C(R^{12})_2]_q-NHSO_2R^{11}$, $-[C(R^{12})_2]_q-S(O)_pR^{11}$, $-[C(R^{12})_2]_q-SO_2N(R^9)_2$ or $-SO_2N(R^9)C(O)N(R^9)_2$;
each occurrence of $R^8$ is independently H, alkenyl, alkynyl, $-[C(R^{12})_2]_q-$phenyl, $-[C(R^{12})_2]_q-$napthyl, $-[C(R^{12})_2]_q-$(3 to 10-membered cycloalkyl), $-[C(R^{12})_2]_q-$(3 to 10-membered cycloalkenyl), $[C(R^{12})_2]_q-$(3 to 10-membered heterocycloalkyl), $-[C(R^{12})_2]_q-$(3 to 10-membered heterocycloalkenyl), $-[C(R^{12})_2]_q-$(5 to 10-membered heteroaryl), haloalkyl or hydroxyalkyl;
each occurrence of $R^9$ is independently H, alkyl, alkenyl, alkynyl, $-[C(R^{12})_2]_q-$O-alkyl, $-[C(R^{12})_2]_q-$N(alkyl)$_2$, $-[C(R^{12})_2]_q-$phenyl, $-[C(R^{12})_2]_q-$napthyl, $-[C(R^{12})_2]_q-$(3 to 10-membered cycloalkyl), $-[C(R^{12})_2]_q-$(3 to 10-membered cycloalkenyl), $[C(R^{12})_2]_q-$(3 to 10-membered heterocycloalkyl), $-[C(R^{12})_2]_q-$(3 to 10-membered heterocycloalkenyl), $-[C(R^{12})_2]_q-$(5 to 10-membered heteroaryl), haloalkyl or hydroxyalkyl;
$R^{10}$ is H, 3 to 10-membered cycloalkyl, 3 to 10-membered cycloalkenyl; 3 to 10-membered heterocycloalkyl, 3 to 10-membered heterocycloalkenyl, phenyl, naphthyl, or 5 to 10-membered heteroaryl, wherein a 3 to 10-membered cycloalkyl, 3 to 10-membered cycloalkenyl, 3 to 10-membered heterocycloalkyl, heterocycloalkenyl, phenyl, naphthyl or 5 to 10-membered heteroaryl group can be optionally and independently substituted with up to 4 substituents, which are each independently selected from H, alkyl, alkenyl, alkynyl, phenyl, naphthyl, —[C(R$^{12}$)$_2$]$_q$-(3 to 10-membered cycloalkyl), —[C(R$^{12}$)$_2$]$_q$-(3 to 10-membered cycloalkenyl), —[C(R$^{12}$)$_2$]$_q$-(3 to 10-membered heterocycloalkyl), —[C(R$^{12}$)$_2$]$_q$-(3 to 10-membered heterocycloalkenyl), —[C(R$^{12}$)$_2$]$_q$-(5 to 10-membered heteroaryl), —[C(R$^{12}$)$_2$]$_q$-haloalkyl, —[C(R$^{12}$)$_2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$, such that when R$^1$ is a bond, R$^{10}$ is not H;

each occurrence of R$^{11}$ is independently alkyl, phenyl, naphthyl, 3 to 10-membered cycloalkyl, 3 to 10-membered cycloalkenyl, 3 to 10-membered heterocycloalkyl, heterocycloalkenyl, 5 to 10-membered heteroaryl, haloalkyl, hydroxy or hydroxyalkyl, wherein a 3 to 10-membered cycloalkyl, 3 to 10-membered cycloalkenyl, 3 to 10-membered heterocycloalkyl, 3 to 10-membered heterocycloalkenyl, phenyl, naphthyl or 5 to 10-membered heteroaryl group can be optionally and independently substituted with up to 4 substituents, which are each independently selected from —H, alkyl, alkenyl, alkynyl, phenyl, naphthyl, —[C(R$^{12}$)$_2$]$_q$-(3 to 10-membered cycloalkyl), —[C(R$^{12}$)$_2$]$_q$-(3 to 10-membered cycloalkenyl), —[C(R$^{12}$)$_2$]$_q$-(3 to 10-membered heterocycloalkyl), —[C(R$^{12}$)$_2$]$_q$-(3 to 10-membered heterocycloalkenyl), —[C(R$^{12}$)$_2$]$_q$-(5 to 10-membered heteroaryl), —[C(R$^{12}$)$_2$]$_q$-haloalkyl, —[C(R$^{12}$)$_2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$alkyl, —[C(R$^{12}$)$_2$]$_q$—NHSO$_2$-(3 to 10-membered cycloalkyl), —[C(R$^{12}$)$_2$]$_q$—NHSO$_2$aryl, —[C(R$^{12}$)$_2$]$_q$—SO$_2$N(R$^9$)$_2$ and —SO$_2$N(R$^9$)C(O)N(R)$_2$;

each occurrence of R$^{12}$ is independently H, halo, —N(R$^9$)$_2$, —OR$^9$, alkyl, 3 to 10-membered cycloalkyl, 3 to 10-membered cycloalkenyl, 3 to 10-membered heterocycloalkyl or heterocycloalkenyl, wherein a 3 to 10-membered cycloalkyl, 3 to 10-membered cycloalkenyl, 3 to 10-membered heterocycloalkyl or 3 to 10-membered heterocycloalkenyl group can be optionally and independently substituted with up to 4 substituents, which are each independently selected from alkyl, halo, haloalkyl, hydroxyalkyl, —OH, —CN, —C(O)alkyl, —C(O)Oalkyl, —C(O)NH-alkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two R$^{12}$ groups, together with the carbon atoms to which they are attached, join to form a 3 to 10-membered cycloalkyl, 3 to 10-membered heterocycloalkyl or C=O group;

each occurrence of R$^{20}$ is independently alkyl, phenyl, naphthyl, 3 to 10-membered cycloalkyl, 3 to 10-membered heterocycloalkyl or 5 to 10-membered heteroaryl, or both R$^{20}$ groups and the carbon atoms to which they are attached, join to form a 3 to 10-membered cycloalkyl, cycloheteroalkyl, phenyl, naphthyl or 5 to 10-membered heteroaryl group wherein a 3 to 10-membered cycloalkyl, cycloheteroalkyl, phenyl, naphthyl or 5 to 10-membered heteroaryl group can be substituted with up to 4 groups, which are each independently selected from alkyl, alkenyl, alkynyl, halo, —OH, —OR$^9$, —CN, —[C(R$^{12}$)$_2$]$_q$-(3 to 10-membered cycloalkyl), —[C(R$^{12}$)$_2$]$_q$-(3 to 10-membered cycloalkenyl), —[C(R$^{12}$)$_2$]$_q$-(3 to 10-membered heterocycloalkyl), —[C(R$^{12}$)$_2$]$_q$-(3 to 10-membered heterocycloalkenyl), —[C(R$^{12}$)$_2$]$_q$-haloalkyl, —[C(R$^{12}$)$_2$]$_q$-hydroxyalkyl, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$;

each occurrence of R$^{30}$ is independently H, alkyl, alkenyl, alkynyl, phenyl, naphthyl, —[C(R$^{12}$)$_2$]$_q$-(3 to 10-membered cycloalkyl), —[C(R$^{12}$)$_2$]$_q$-(3 to 10-membered cycloalkenyl), —[C(R$^{12}$)$_2$]$_q$-(3 to 10-membered heterocycloalkyl), —[C(R$^{12}$)$_2$]$_q$-(3 to 10-membered heterocycloalkenyl), —[C(R$^{12}$)$_2$]$_q$-(5 to 10-membered heteroaryl), —[C(R$^{12}$)$_2$]$_q$-haloalkyl, —[C(R$^{12}$)$_2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ or —SO$_2$N(R$^9$)C(O)N(R$^9$)$_2$, or two adjacent R$^{30}$ groups, together with the carbon atoms to which they are attached, join to form phenyl, naphthyl, a 3 to 7-membered cycloalkyl, a 5 or 6-membered heteroaryl group or a 3 to 7-membered heterocycloalkyl group;

each occurrence of p is independently 0, 1 or 2;

each occurrence of q is independently an integer ranging from 0 to 4; and each occurrence of r is independently an integer ranging from 1 to 4, wherein a 3 to 7-membered heterocycloalkyl group, a 3 to 10-membered heterocycloalkyl group, a 3 to 10-membered heterocycloalkenyl group, or a 5 to 10-membered heteroaryl group has from 1 to 4 ring heteroatoms, each independently selected from O, N and S, and any of said 3 to 7-membered heterocycloalkyl group, 3 to 10-membered heterocycloalkyl group, 3 to 10-membered heterocycloalkenyl group and 5 to 10-membered heteroaryl group can be joined to the rest of the compound via a ring carbon or ring nitrogen atom.

2. The compound of claim 1, wherein R$^2$ is —C(O)NHSO$_2$R$^{11}$ or —C(O)NHSO$_2$N(R$^9$)$_2$, wherein R$^9$ is H, alkyl, -alkyl-N(alkyl)$_2$, phenyl, naphthyl, 3 to 10-membered cycloalkyl, 5 to 10-membered heteroaryl or 3 to 10-membered heterocycloalkyl and R$^{11}$ is alkyl, -alkyl-N(alkyl)$_2$, phenyl, naphthyl, 3 to 10-membered cycloalkyl, haloalkyl, 5 to 10-membered heteroaryl, 3 to 10-membered heterocycloalkyl or hydroxyalkyl.

3. The compound of claim 2, wherein R$^3$ is:

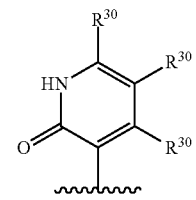

and R¹ is —CH₂—, —CH₂CH₂—, —CH(CH₃)— or

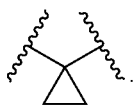

4. The compound of claim 1, wherein R¹⁰ is:

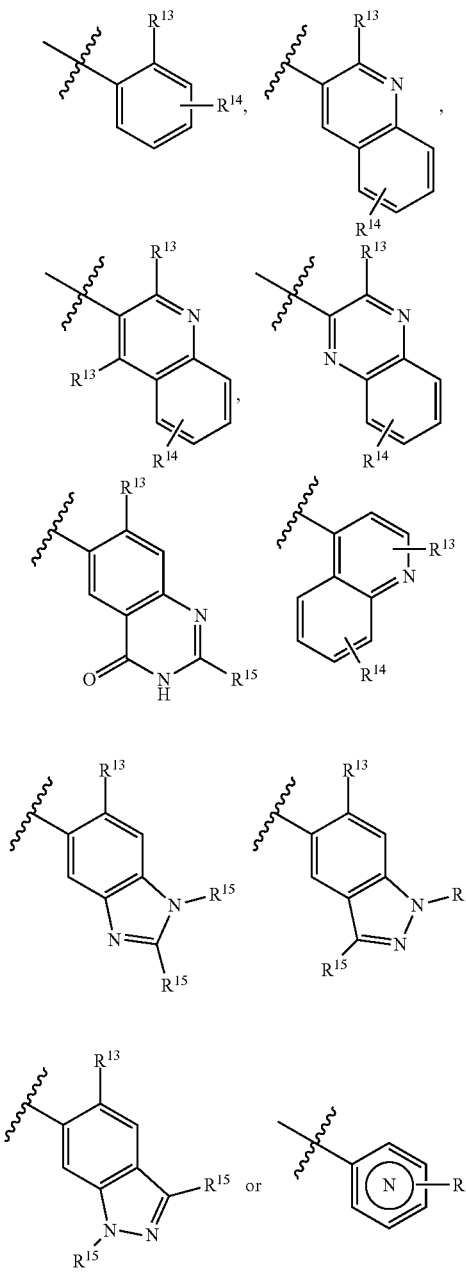

wherein R¹³ is H, F, Br or Cl; R¹⁴ represents up to 4 optional and additional substituents, each independently selected from alkyl, 3 to 10-membered cycloalkyl, CF₃, —CN, halo, —O-alkyl, —O-haloalkyl, —NHSO₂-alkyl, —NO₂, —C(O)NH₂, —C(O)NH-alkyl, —C(O)OH, —OH, —NH₂, —SO₂alkyl, —SO₂NH-alkyl, —S-alkyl, —CH₂NH₂, —CH₂OH, —SO₂NH₂, —NHC(O)-alkyl, —C(O)O-alkyl, —C(O)-(3 to 10-membered heterocycloalkyl) and 5 to 10-membered heteroaryl; each occurrence of R¹⁵ is independently alkyl, 3 to 10-membered cycloalkyl, CF₃, —CN, halo, —O-alkyl, —O-haloalkyl, —NHSO₂-alkyl, —NO₂, —C(O)NH₂, —C(O)NH-alkyl, —C(O)OH, —OH, —NH₂, —SO₂alkyl, —SO₂NH-alkyl, —S-alkyl, —CH₂NH₂, —CH₂OH, —SO₂NH₂, —NHC(O)-alkyl, —C(O)O-alkyl, —C(O)-(3 to 10-membered heterocycloalkyl) or 5 to 10-membered heteroaryl; and

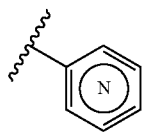

represents a pyridyl group, wherein the ring nitrogen atom can be at any of the five unsubstituted ring atom positions.

5. The compound of claim 1 having the formula:

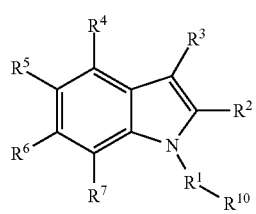

(Ia)

or a pharmaceutically acceptable salt thereof:
wherein:
R¹ is —CH₂—, —CH₂CH₂—, —CH(CH₃)— or

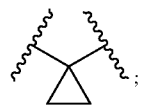

R² is —C(O)NHSO₂R¹¹, —C(O)NHSO₂N(R⁹)₂, —C(O)N(alkyl)SO₂R¹¹ or —C(O)N(alkyl)SO₂N(R⁹)₂;
R³ is:

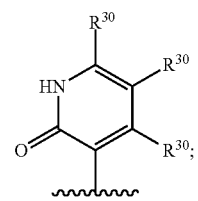

R⁴, R⁵, R⁶ and R⁷ are each, independently, H, alkyl, —[C(R¹²)₂]_q-(3 to 10-membered cycloalkyl), —[C(R¹²)₂]_q-(3 to 10-membered heterocycloalkyl), haloalkyl, halo, —OH, —OR⁹ or —N(R⁹)₂;

each occurrence of R⁹ is independently H, alkyl, alkyl-N(alkyl)₂, 3 to 10-membered cycloalkyl, 3 to 10-membered heterocycloalkyl, haloalkyl or hydroxyalkyl;

$R^{10}$ is:

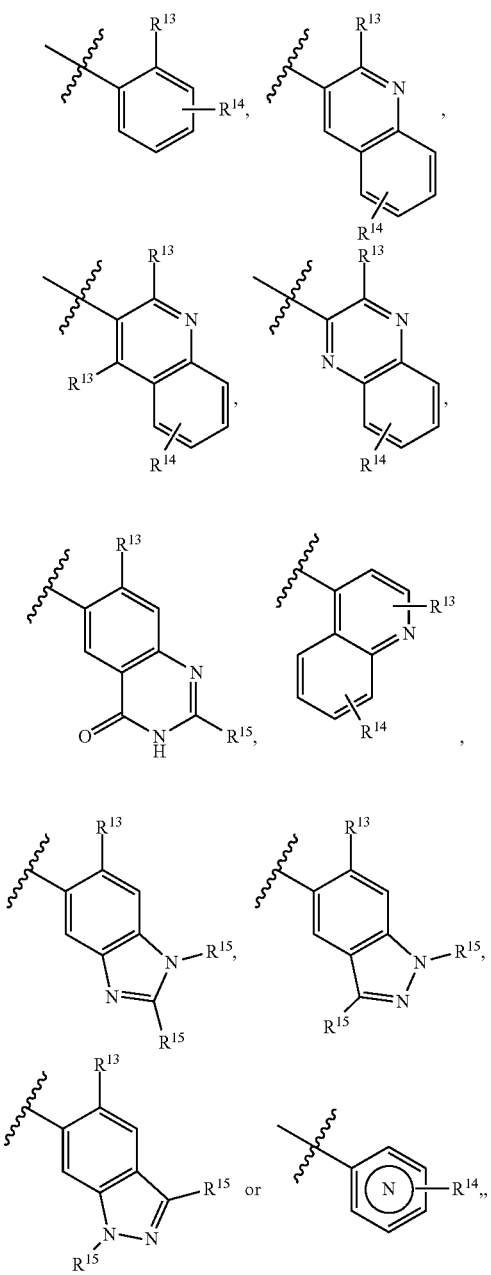

such that when $R^1$ is a bond, $R^{10}$ is not H;

each occurrence of $R^{11}$ is independently alkyl, -alkyl-N(alkyl)$_2$, phenyl, naphthyl, 3 to 10-membered cycloalkyl, haloalkyl, 5 to 10-membered heteroaryl, 3 to 10-membered heterocycloalkyl or hydroxyalkyl;

each occurrence of $R^{12}$ is independently H, halo, —N(alkyl)$_2$, —OH, —O-alkyl, alkyl, 3 to 10-membered cycloalkyl or 3 to 10-membered heterocycloalkyl, or two $R^{12}$ groups, together with the carbon atoms to which they are attached, join to form a 3 to 10-membered cycloalkyl, 3 to 10-membered heterocycloalkyl or C=O group;

$R^{13}$ is H, F, Br or Cl;

$R^{14}$ represents up to 4 optional and additional substituents, each independently selected from alkyl, 3 to 10-membered cycloalkyl, —CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-(3 to 10-membered heterocycloalkyl) and 5 to 10-membered heteroaryl;

each occurrence of $R^{15}$ is independently alkyl, 3 to 10-membered cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-(3 to 10-membered heterocycloalkyl) or 5 to 10-membered heteroaryl;

each occurrence of $R^{30}$ is independently, H, halo, —N(alkyl)$_2$, —OH, —O-alkyl, —O-haloalkyl, alkyl, 3 to 10-membered cycloalkyl or 3 to 10-membered heterocycloalkyl, or two adjacent $R^{30}$ groups, together with the carbon atoms to which they are attached, join to form phenyl, naphthyl, a 3 to 7-membered cycloalkyl group, a 5 or 6-membered heteroaryl group or a 3 to 7-membered heterocycloalkyl group;

each occurrence of q is independently an integer ranging from 0 to 4;

each occurrence of r is independently an integer ranging from 1 to 4; and

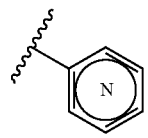

represents a pyridyl group, wherein the ring nitrogen atom can be at any of the five unsubstituted ring atom positions.

6. The compound of claim 5 wherein $R^1$ is CH$_2$—;

$R^2$ is —C(O)NHSO$_2$R$^{11}$ or —C(O)NHSO$_2$N(R$^9$)$_2$;

$R^3$ is:

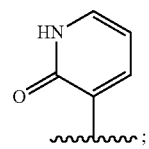

$R^4$, $R^5$, $R^6$ and $R^7$ are each independently H, alkyl, haloalkyl or halo;

each occurrence of $R^9$ is independently H, alkyl, 3 to 10-membered cycloalkyl, 3 to 10-membered heterocycloalkyl, haloalkyl or hydroxyalkyl; and each occurrence of $R^{11}$ is independently alkyl, phenyl, naphthyl or 3 to 10-membered cycloalkyl.

7. The compound of claim 6 wherein:

$R^4$, $R^5$, $R^6$ and $R^7$ are each independently H, alkyl, or halo;

each occurrence of $R^9$ is independently H, alkyl or 3 to 10-membered cycloalkyl; and $R^{10}$ is:
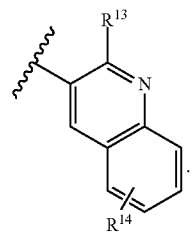
8. A compound having the structure:
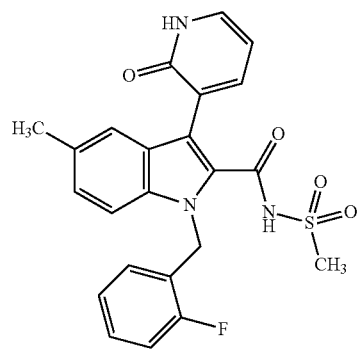
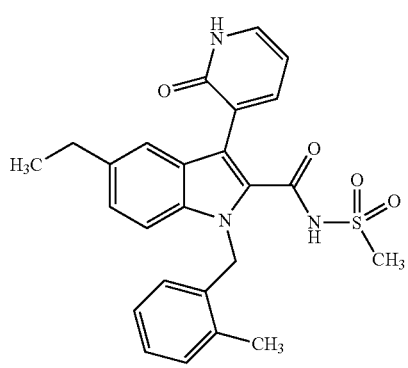
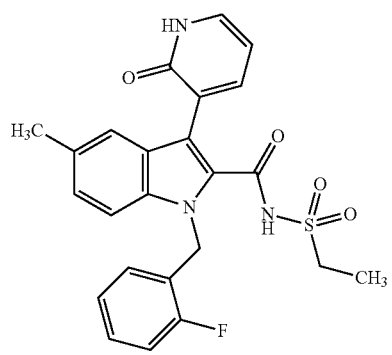
-continued
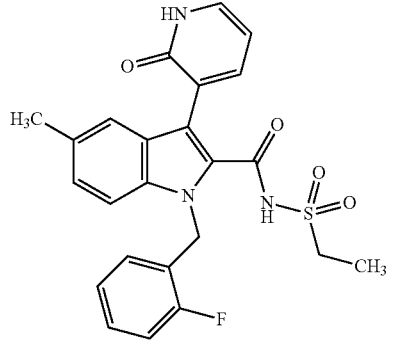
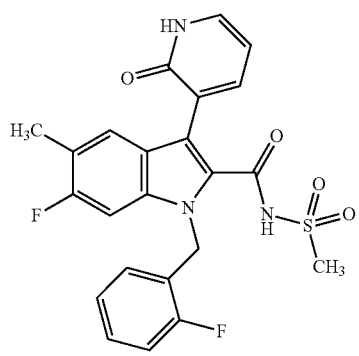
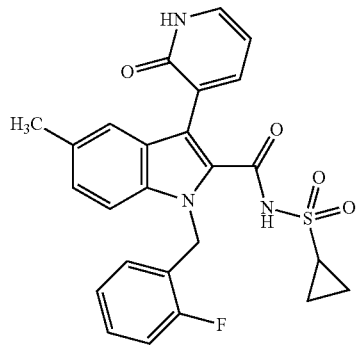
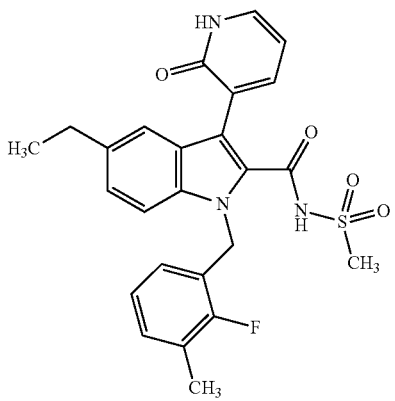

603
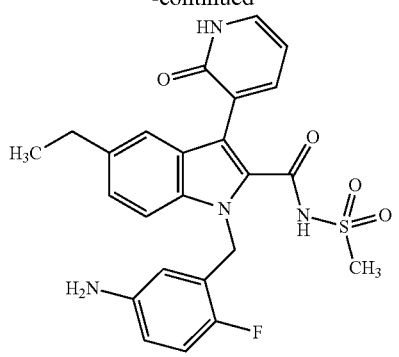
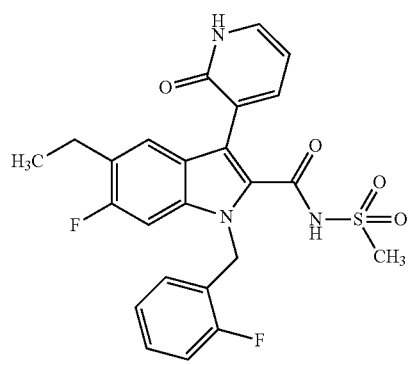
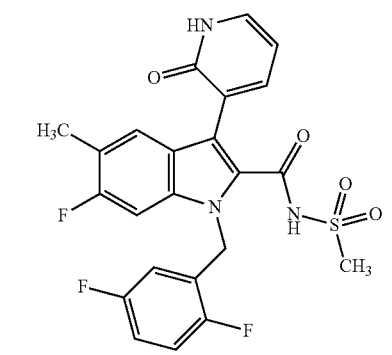
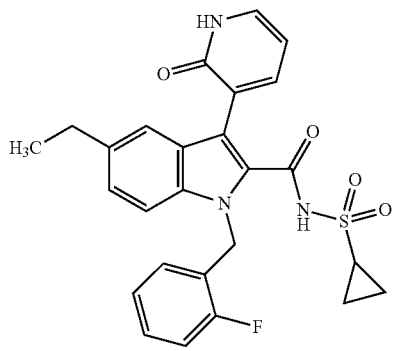
604
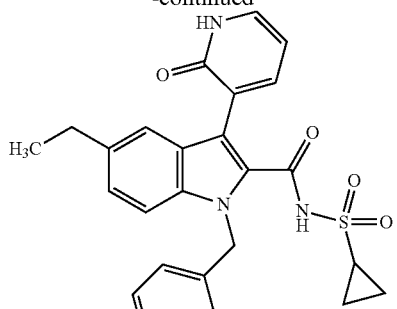
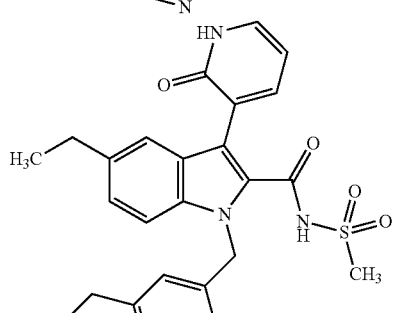
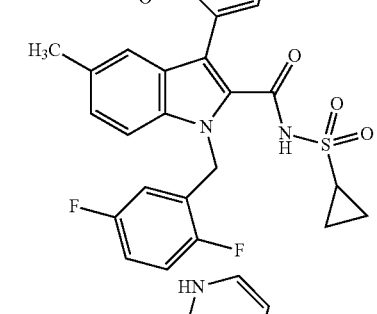
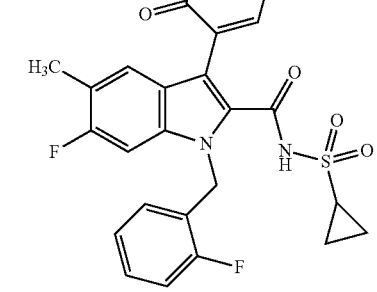
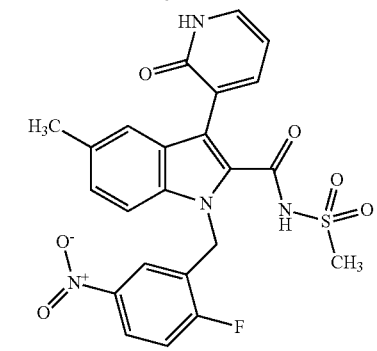

605
-continued
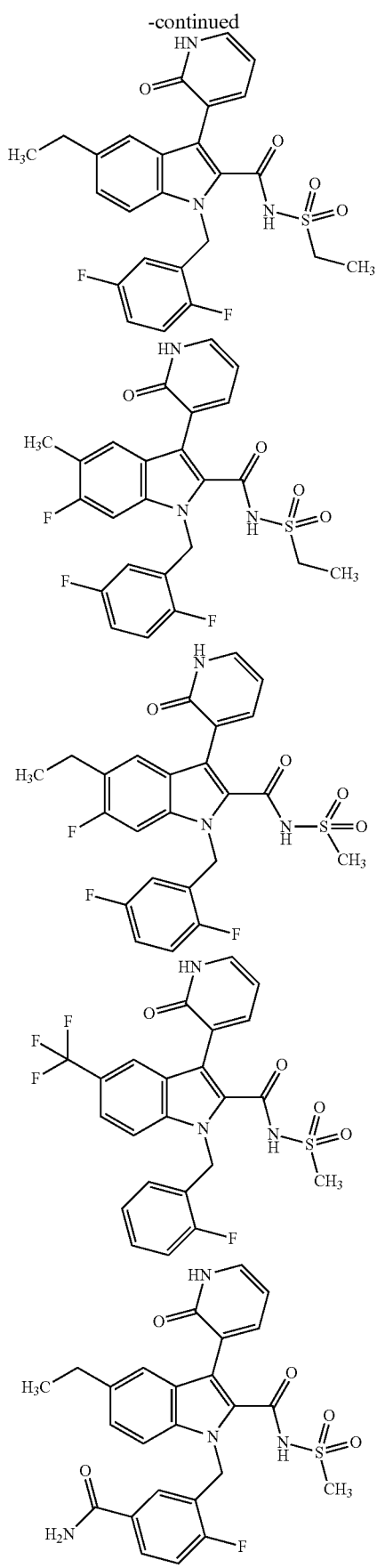
606
-continued
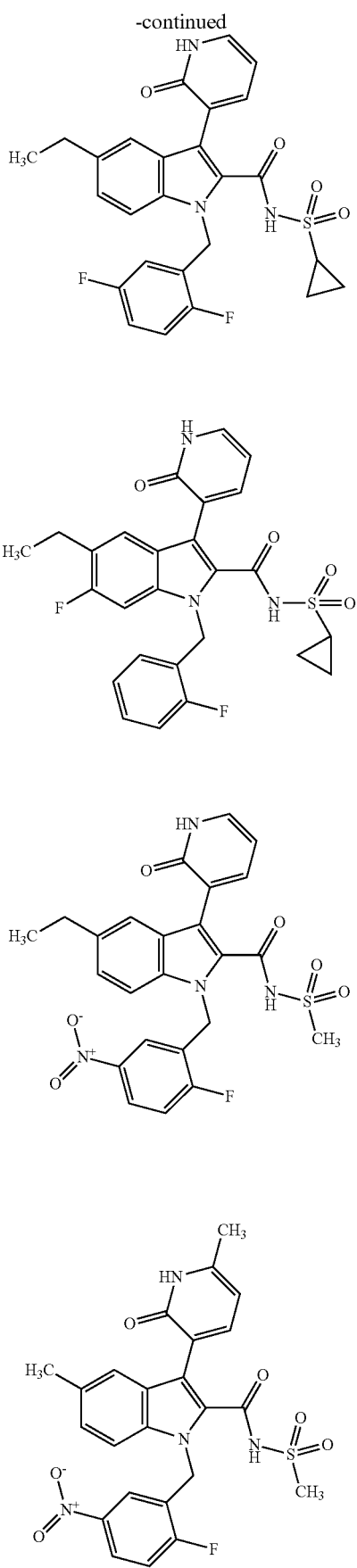

607
-continued
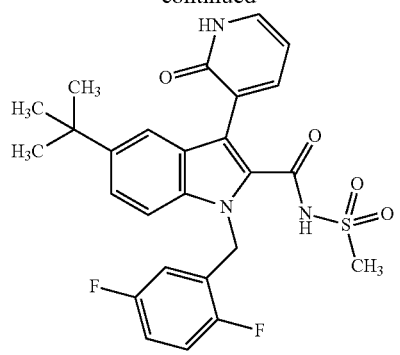
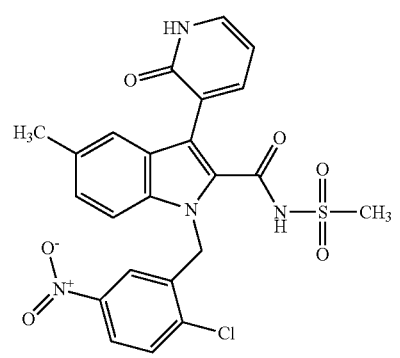
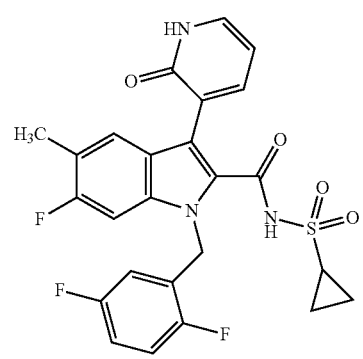
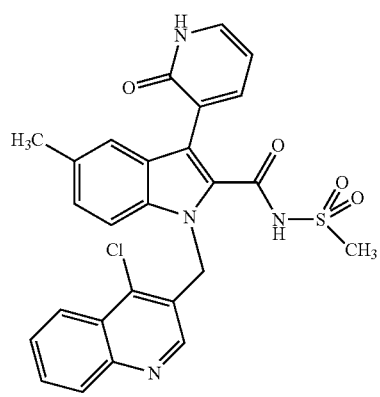
608
-continued
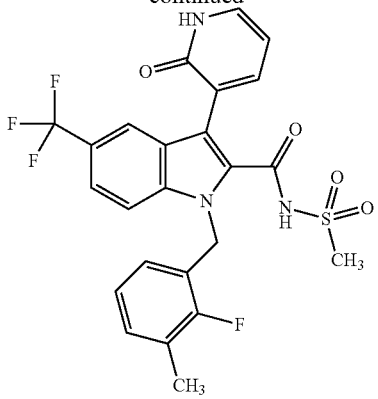
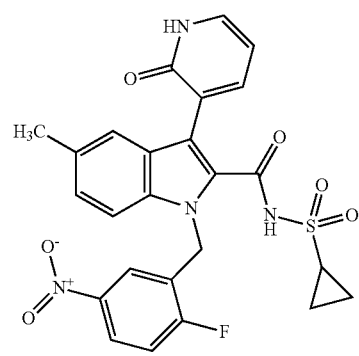
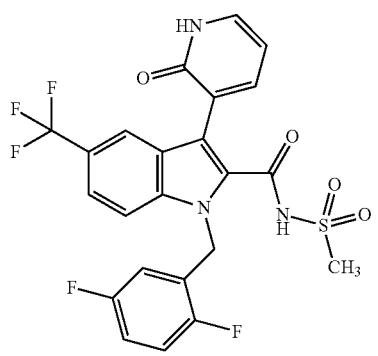
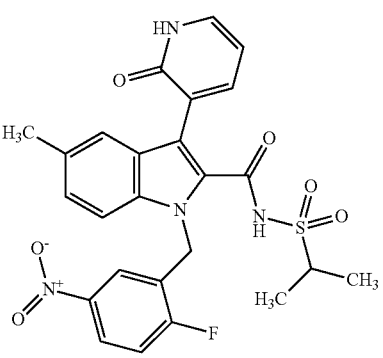

609
-continued
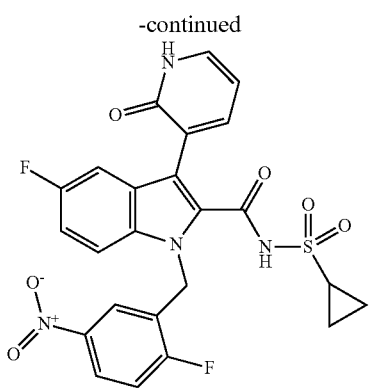
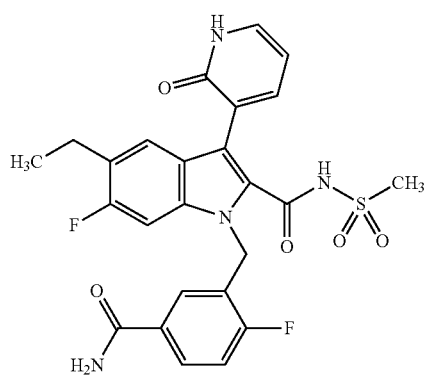
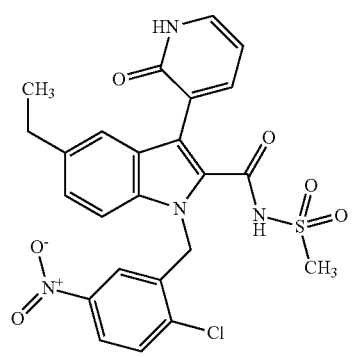
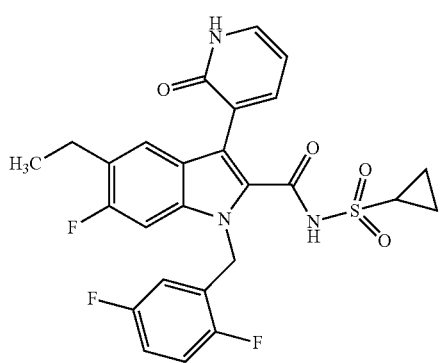
610
-continued
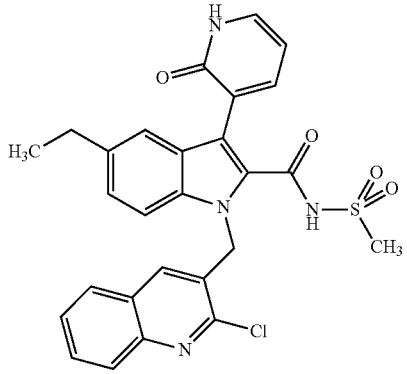
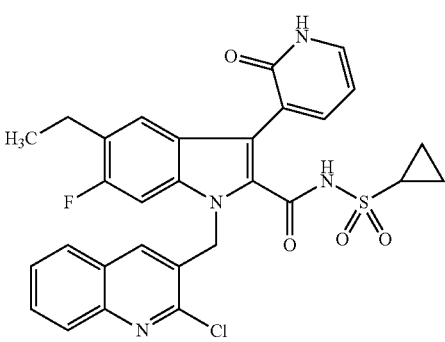
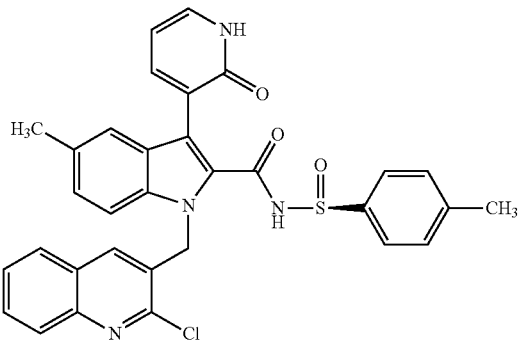
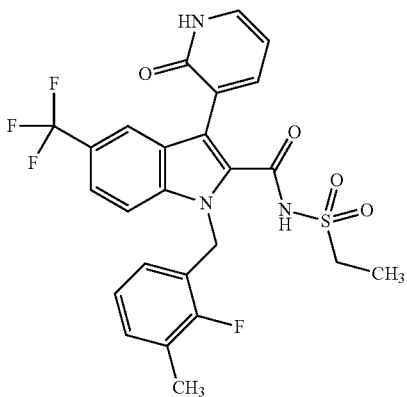

611
-continued
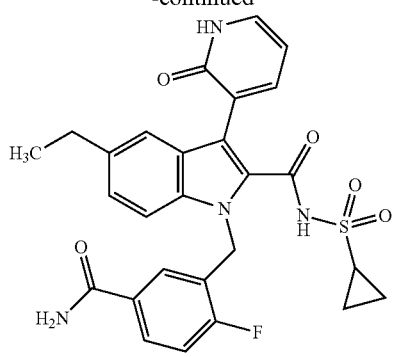
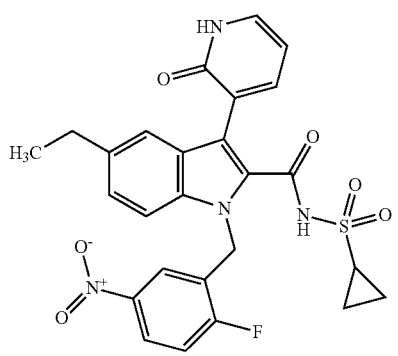
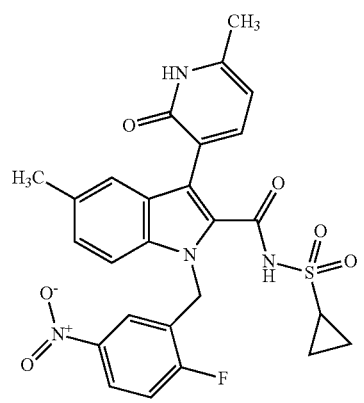
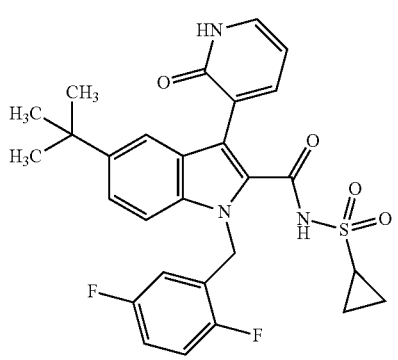
612
-continued
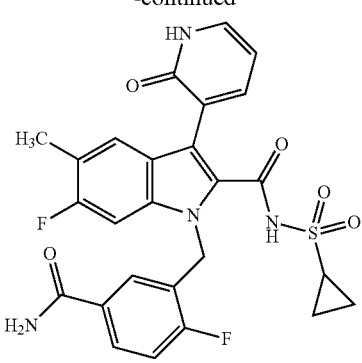
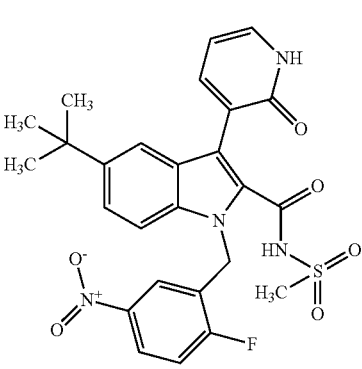
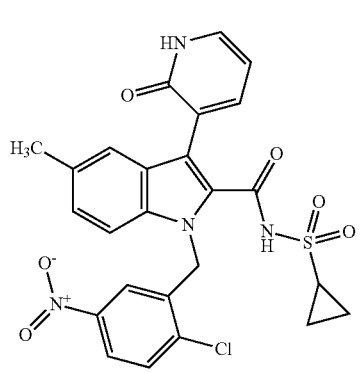
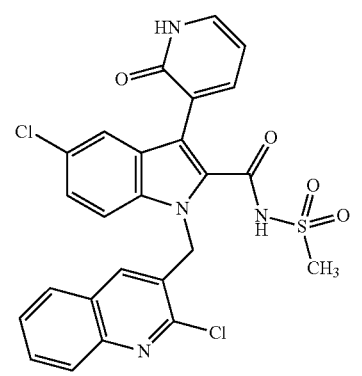

613
-continued
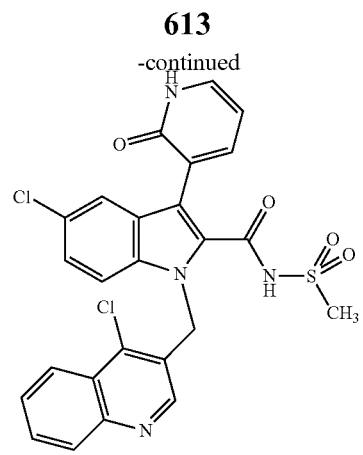
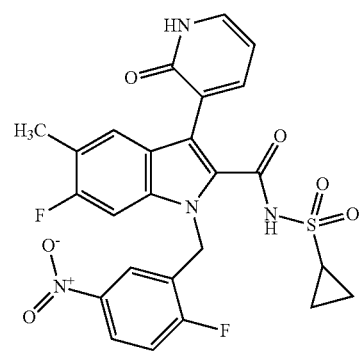
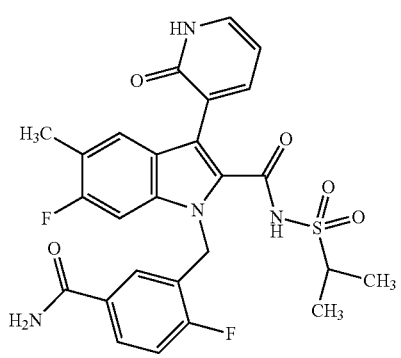
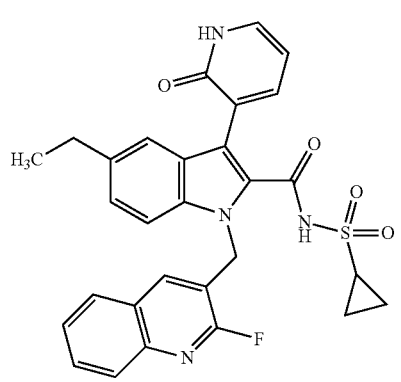
614
-continued
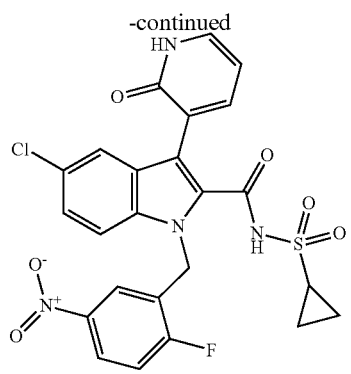
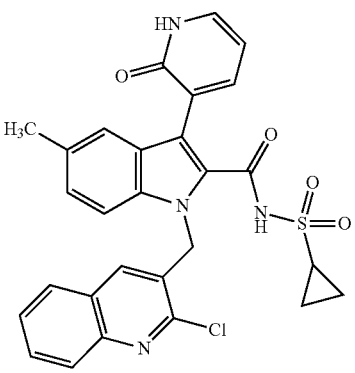
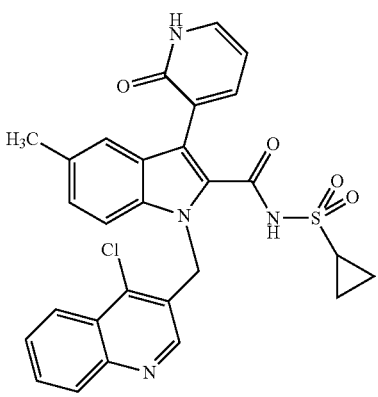
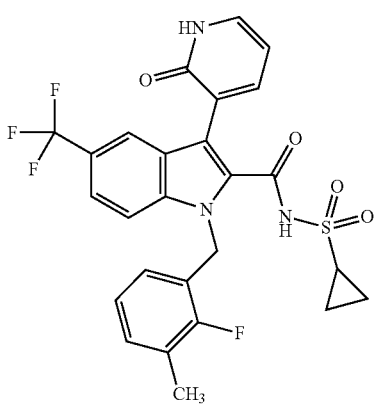

615
-continued
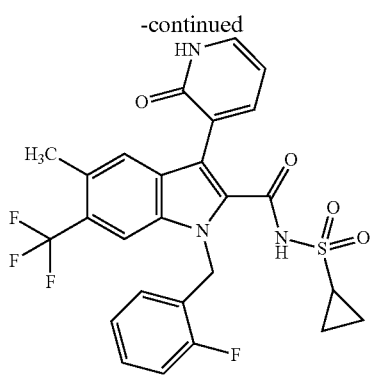
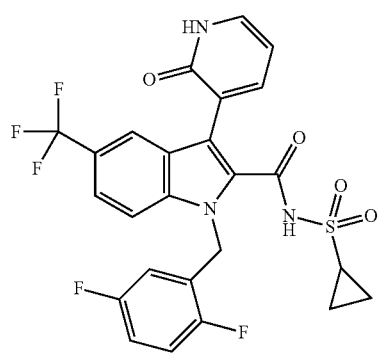
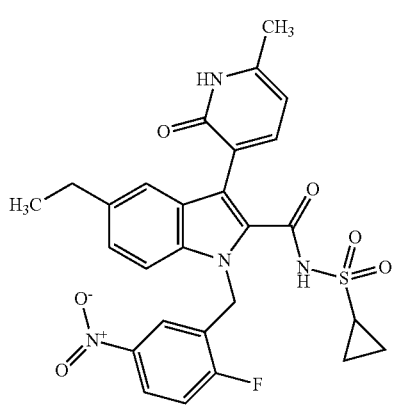
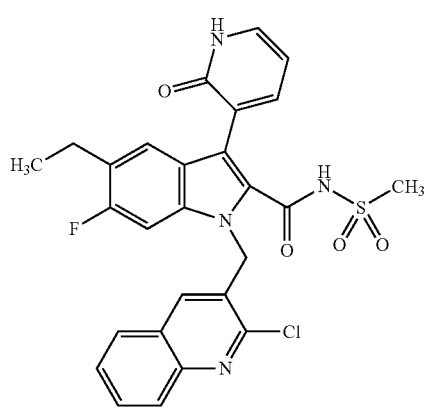
616
-continued
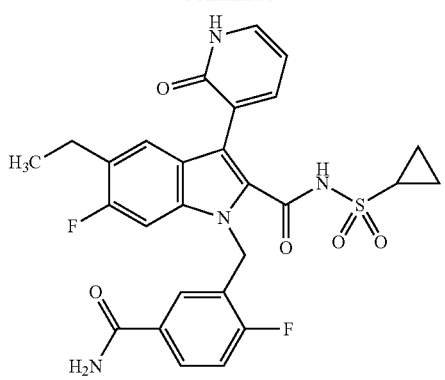
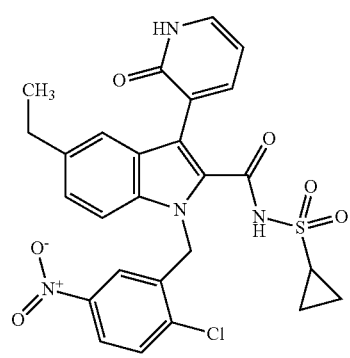
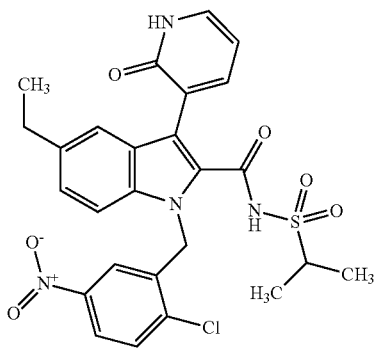
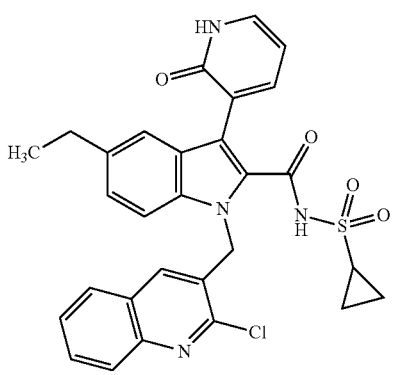

617
-continued
618
-continued
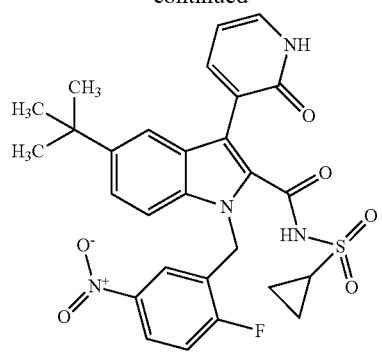
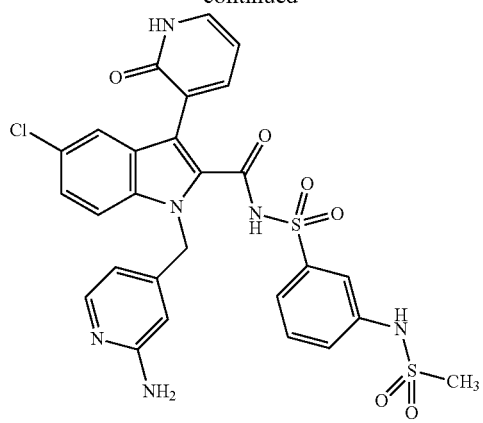
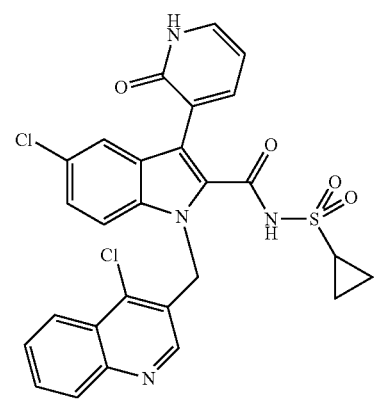
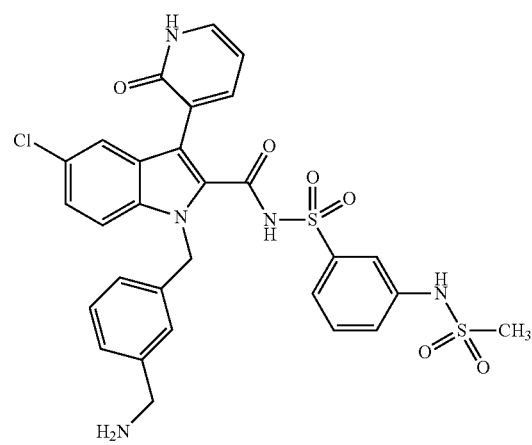
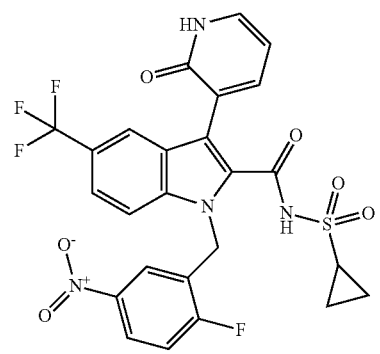
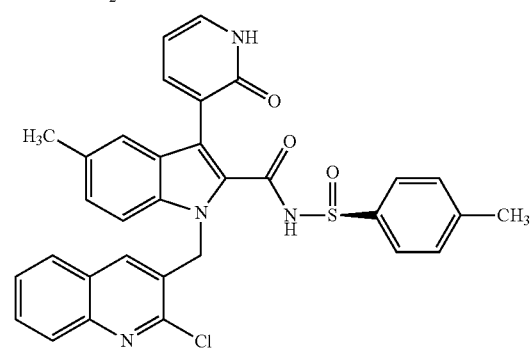
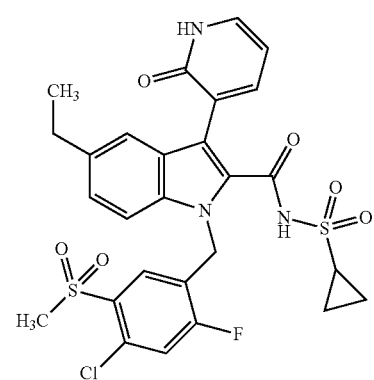
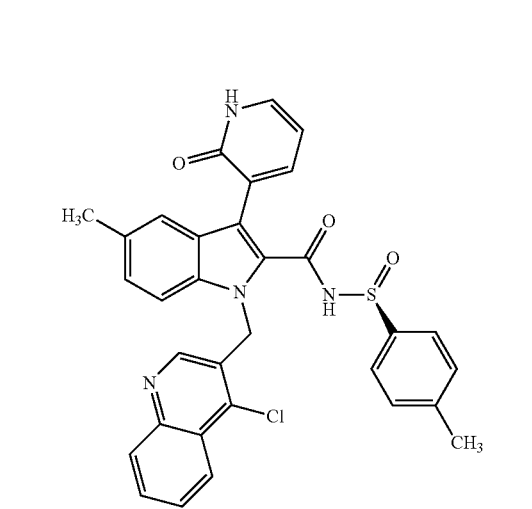

619
-continued
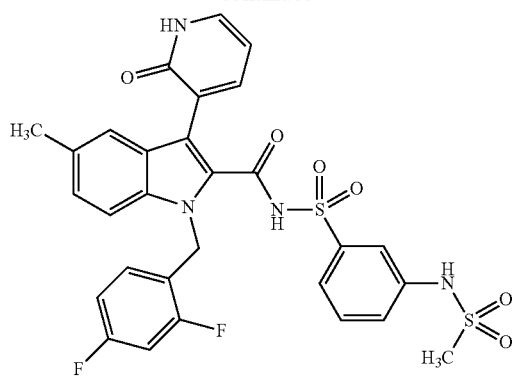
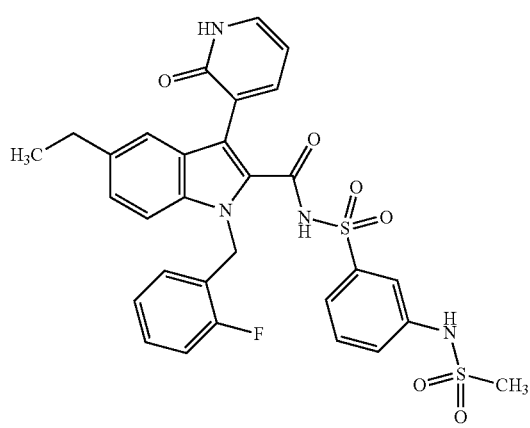
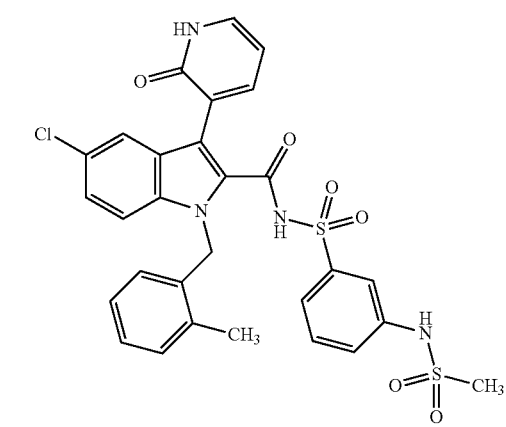
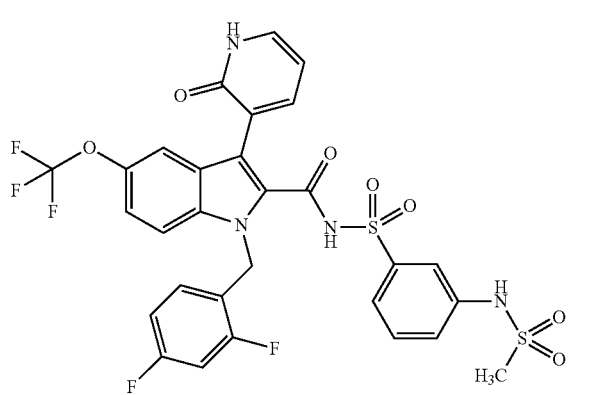
620
-continued
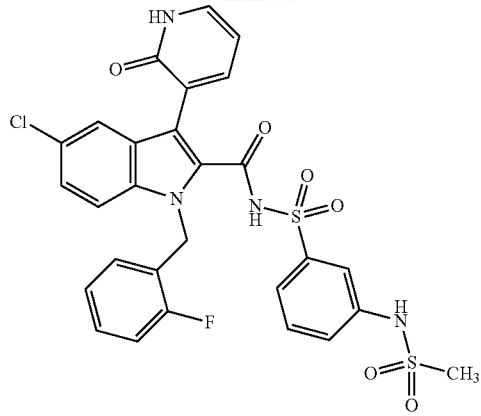
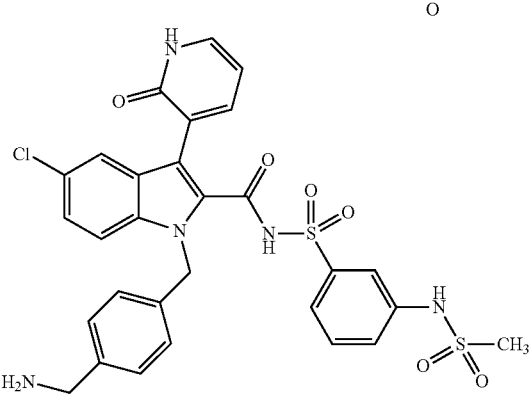
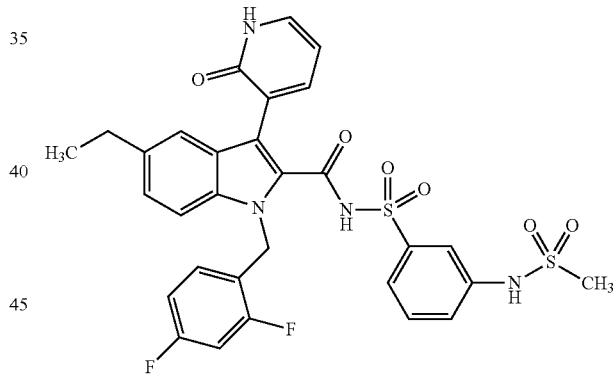
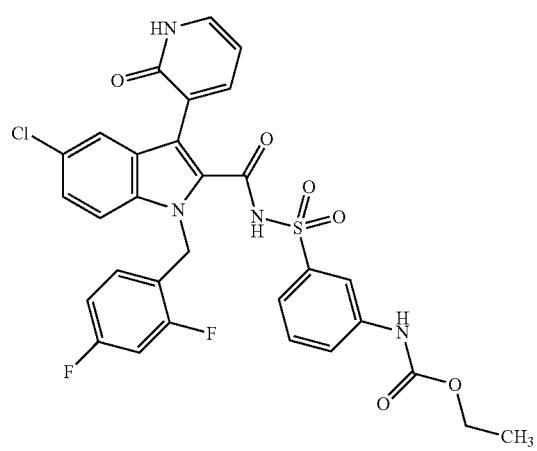

621
-continued
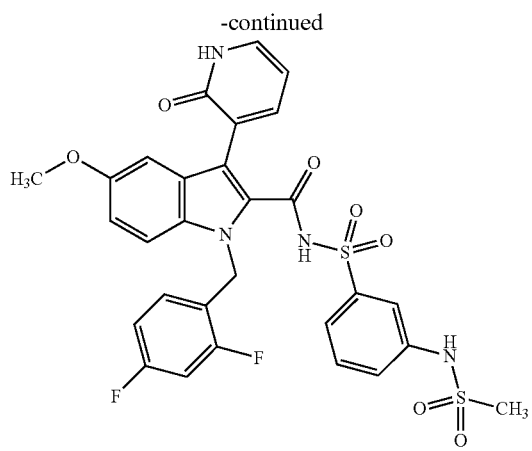
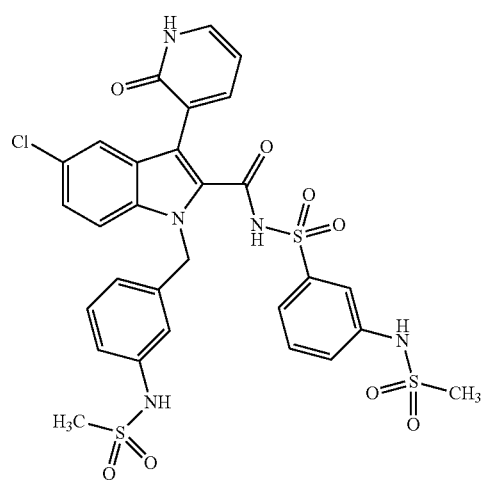
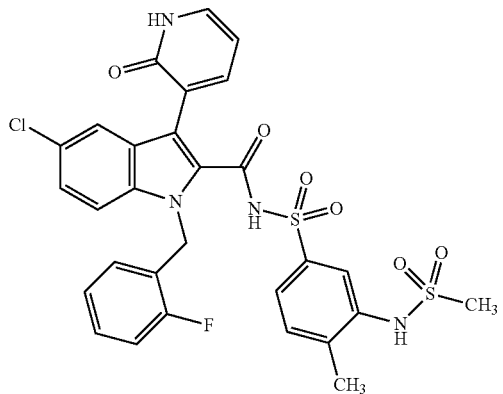
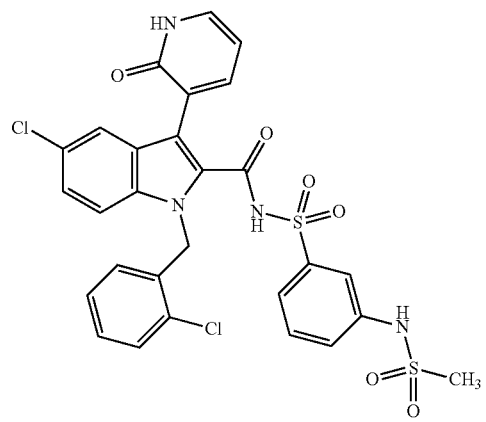
622
-continued
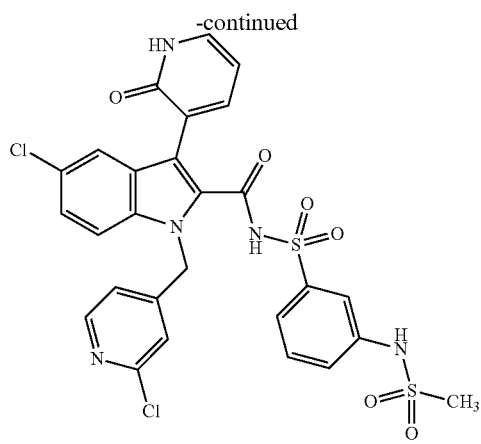
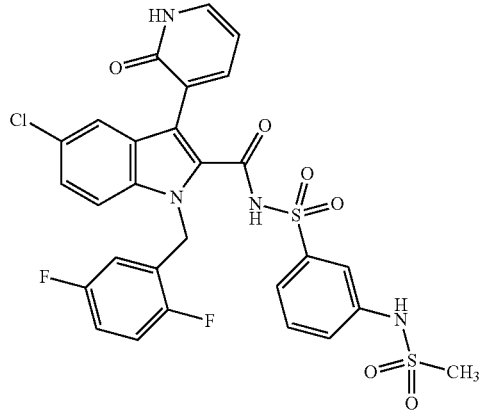
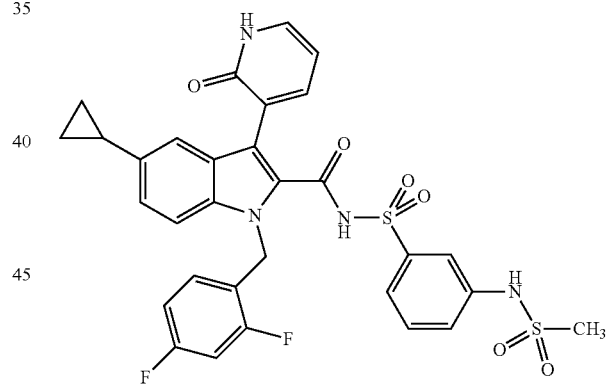
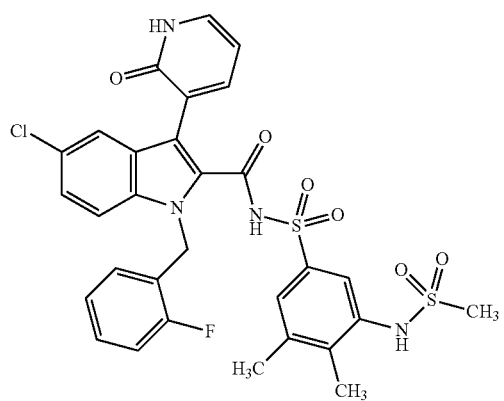

623
-continued
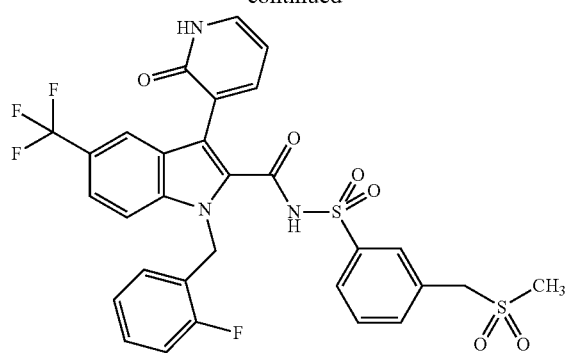
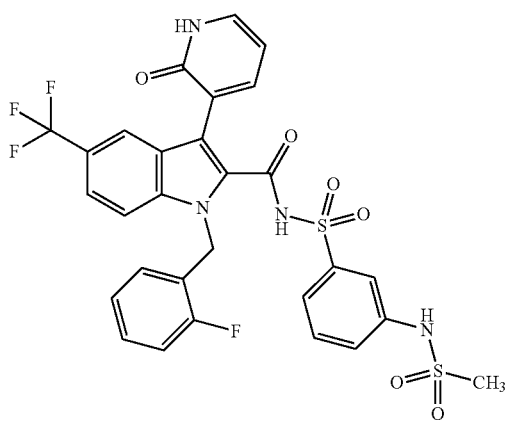
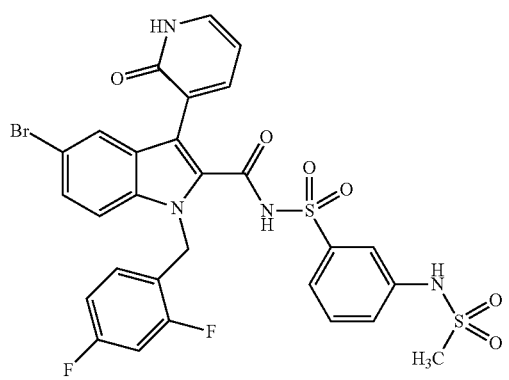
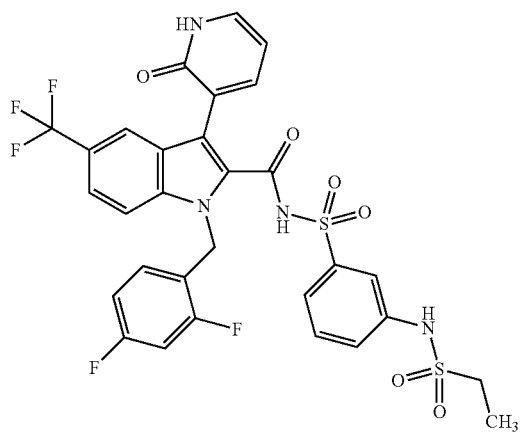
624
-continued
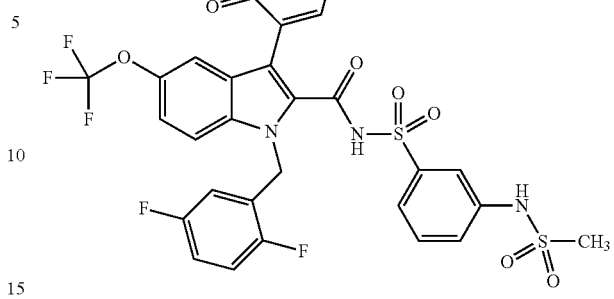
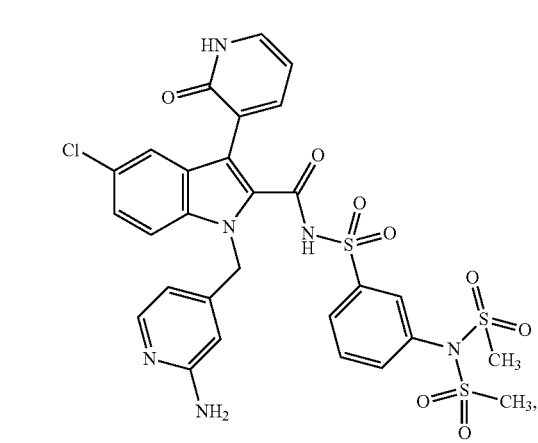
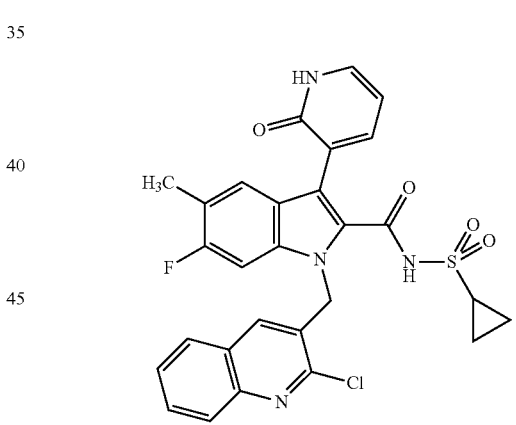
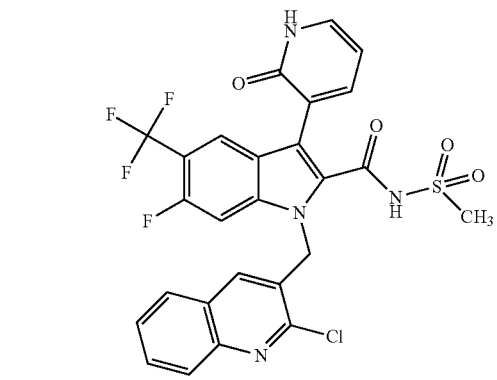

625
-continued
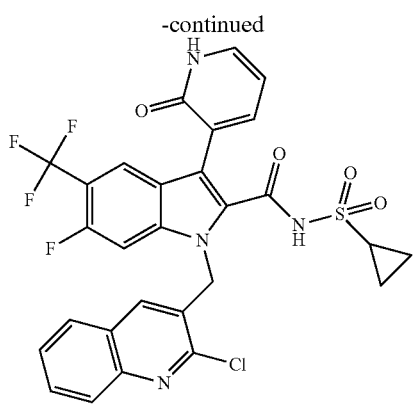
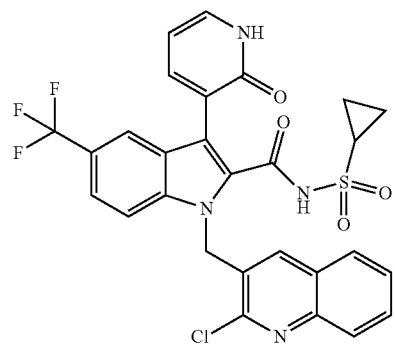
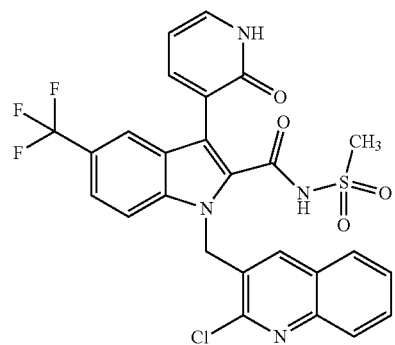
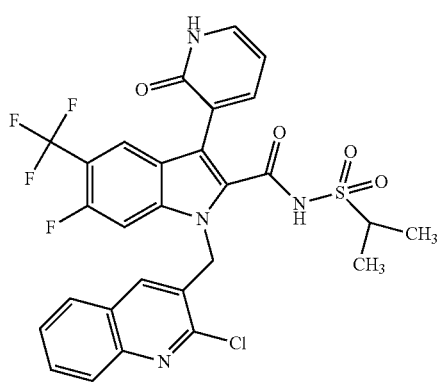
626
-continued
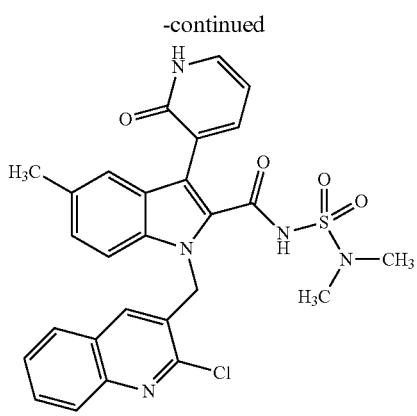
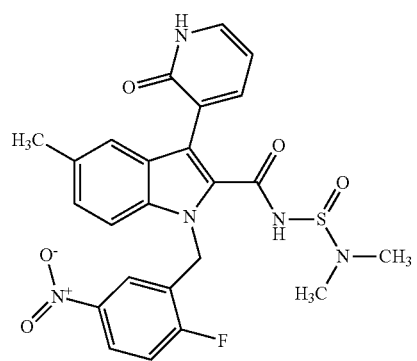
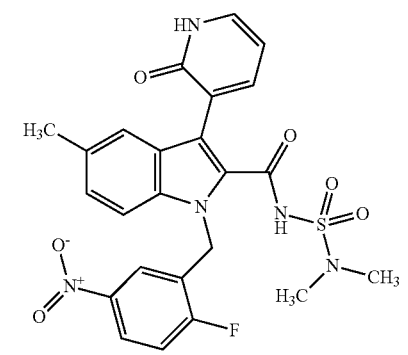
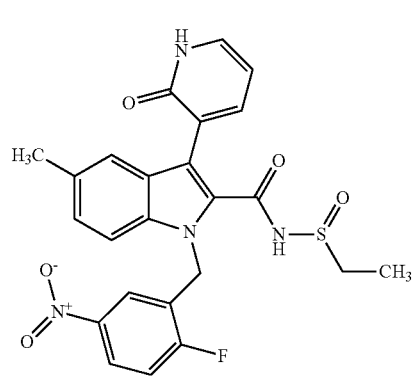

627
-continued
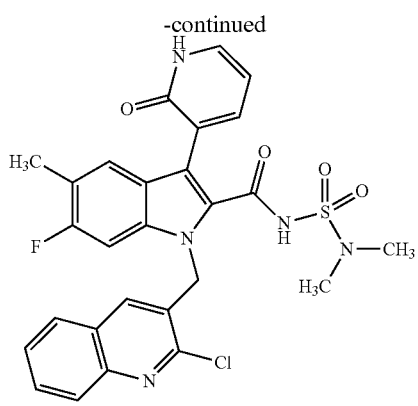
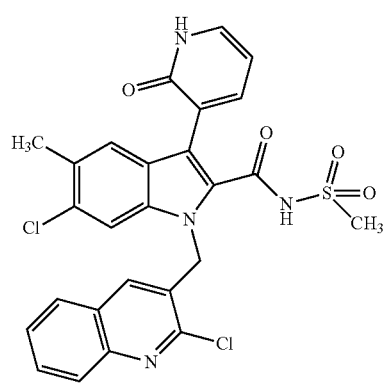
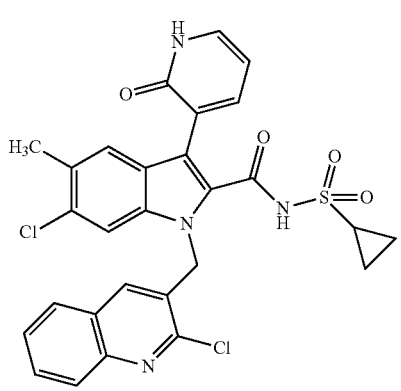
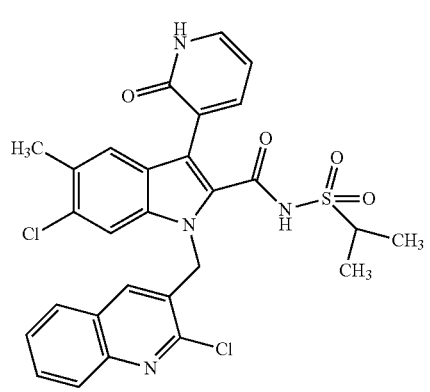
628
-continued
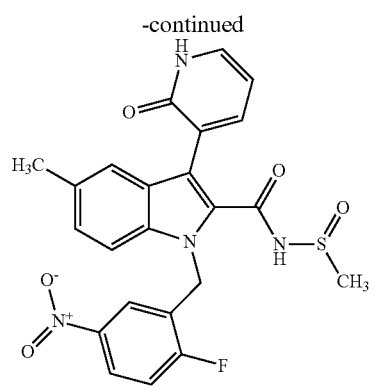
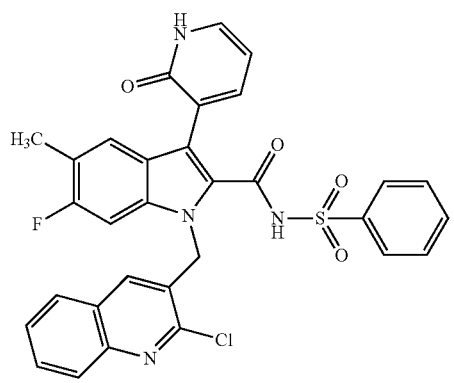
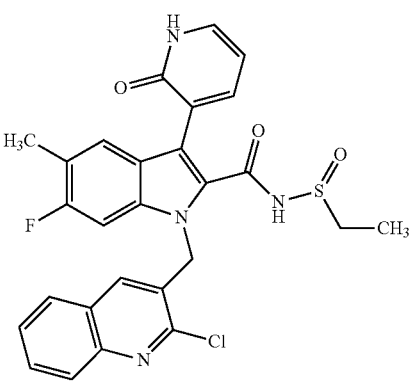
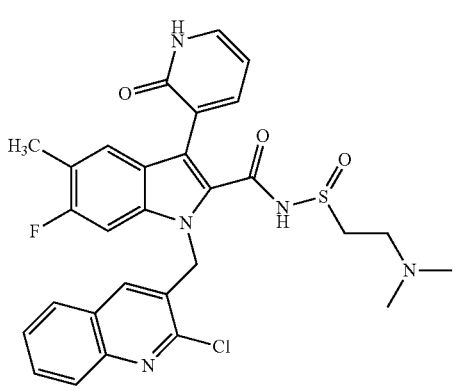

629
-continued
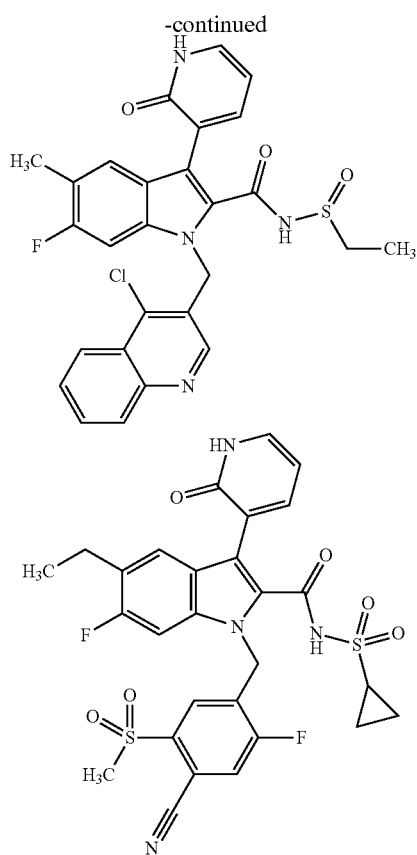
630
-continued
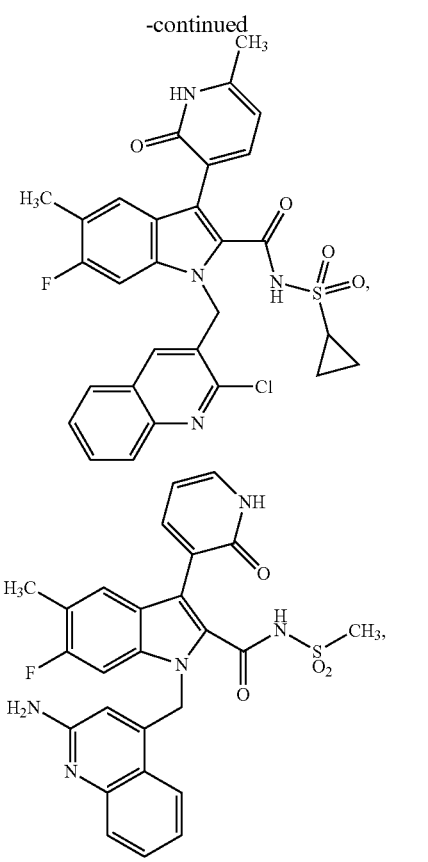
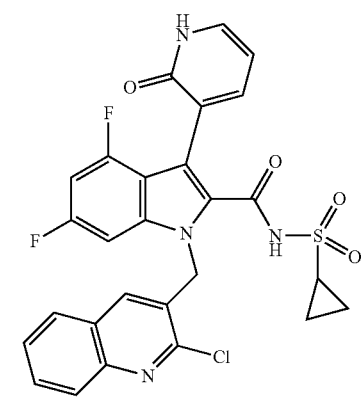
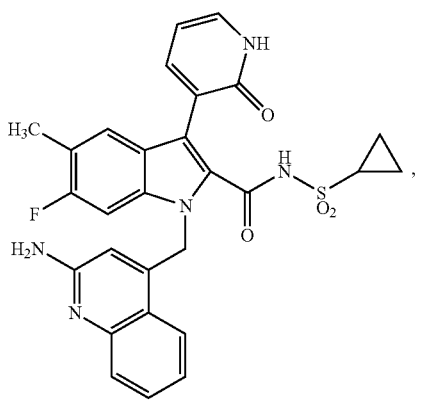
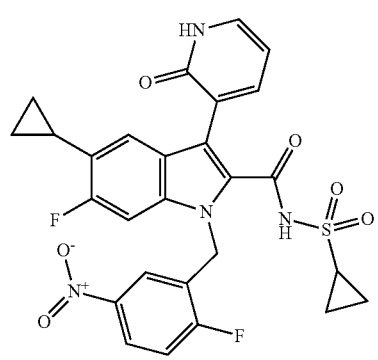
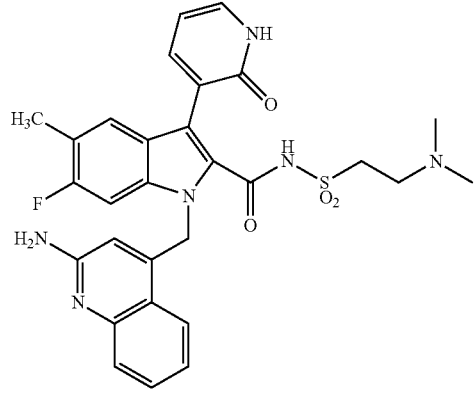

631
-continued
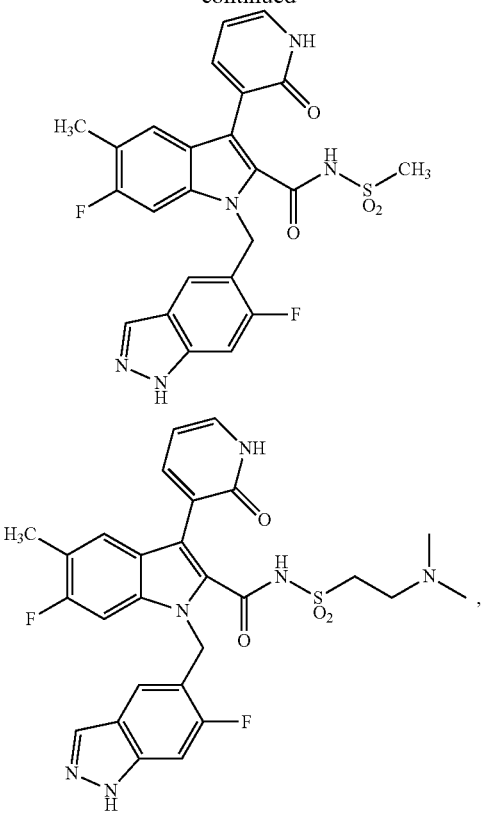
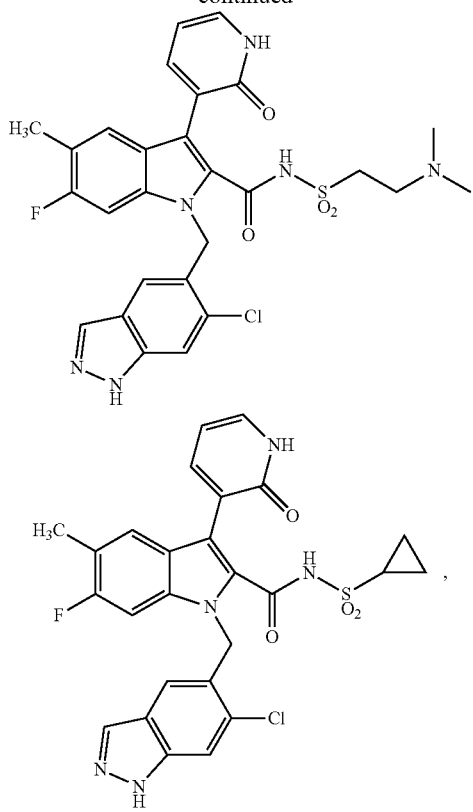
632
-continued
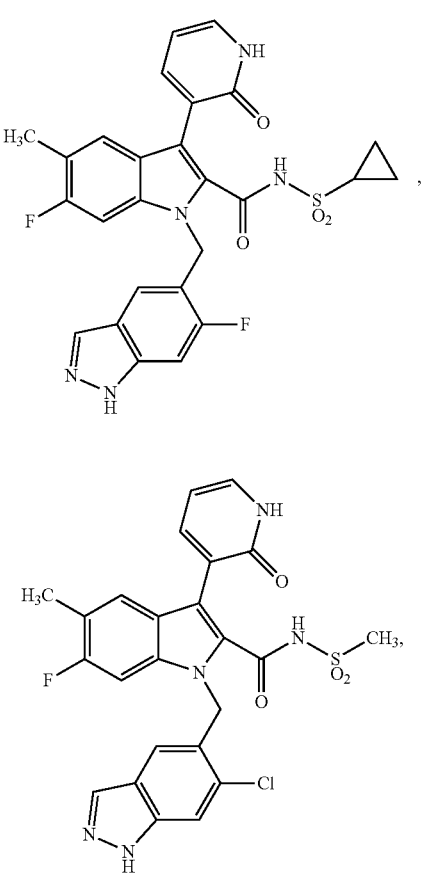
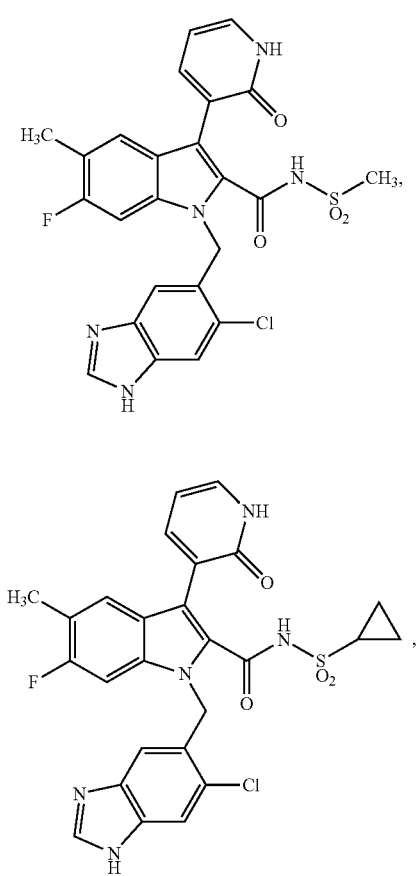

633
-continued
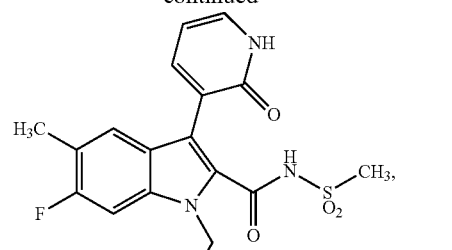
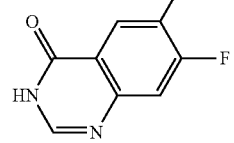
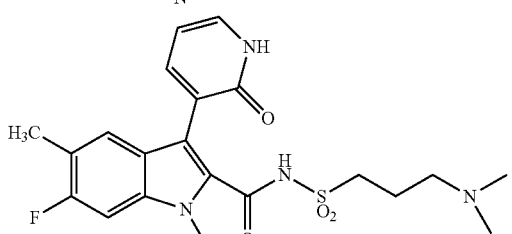
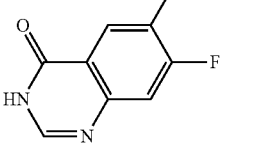
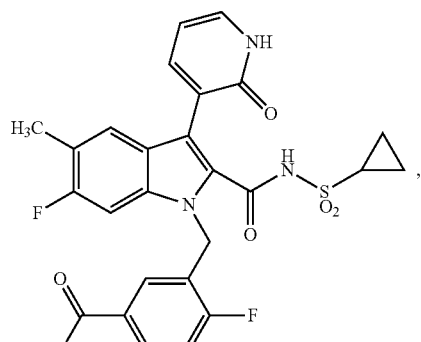
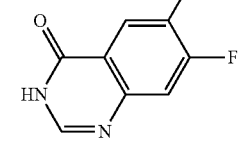
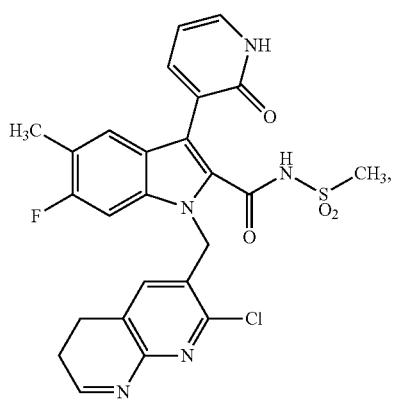
634
-continued
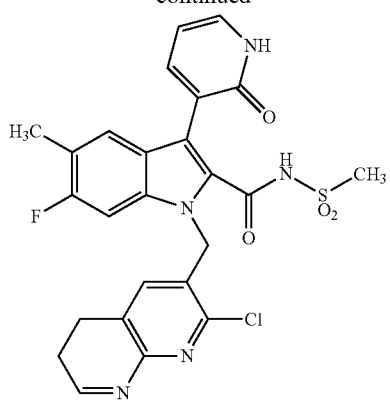
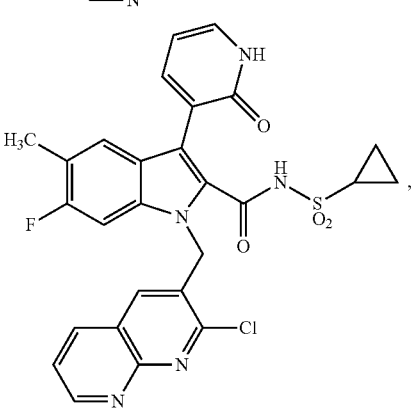
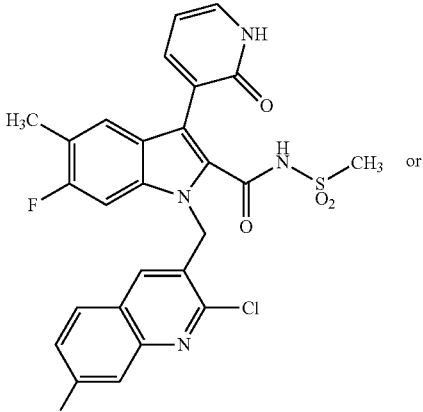, or
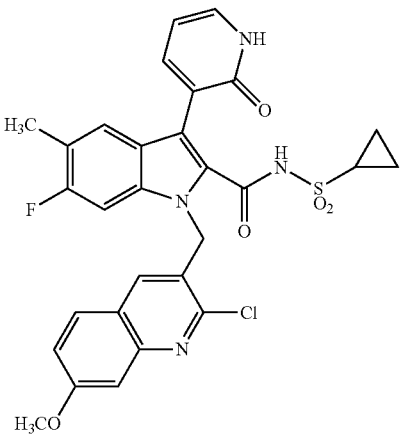
or a pharmaceutically acceptable salt thereof.

9. A pharmaceutical composition comprising at least one compound of claim 1 or a pharmaceutically acceptable salt thereof, and at least one pharmaceutically acceptable carrier.

10. The pharmaceutical composition of claim 9, further comprising at least one additional antiviral agent, wherein the additional agent is selected from an HCV polymerase inhibitor, an interferon, a viral replication inhibitor, a nucleoside, an antisense agent, a viral protease inhibitor, and a virion production inhibitor.

11. A method for treating HCV infection in a patient, the method comprising administering to the patient an effective amount of at least one compound of claim 1 or a pharmaceutically acceptable salt thereof.

12. The method of claim 11, further comprising administering to the patient at least one additional antiviral agent, wherein the additional agent is selected from an HCV polymerase inhibitor, an interferon, a viral replication inhibitor, a nucleoside, an antisense agent, a viral protease inhibitor, and a virion production inhibitor.

\* \* \* \* \*